US012383601B2

(12) United States Patent
Abujoub et al.

(10) Patent No.: US 12,383,601 B2
(45) Date of Patent: Aug. 12, 2025

(54) CHIMERIC ANTIGEN RECEPTORS AND USES THEREOF

(71) Applicant: Novartis AG, Basel (CH)

(72) Inventors: Aida Abujoub, Winchester, MA (US); John Blankenship, Acton, MA (US); Attilio Bondanza, Basel (CH); Jennifer Brogdon, Sudbury, MA (US); Dexiu Bu, Melrose, MA (US); Serena De Vita, Brookline, MA (US); Glenn Dranoff, Sudbury, MA (US); Boris Engels, Arlington, MA (US); Tony Fleming, Stow, MA (US); Brian Walter Granda, Salisbury, MA (US); Michael R. Greene, Groton, MA (US); Carla Patricia Guimaraes, Boston, MA (US); Anniesha Hack, East Hanover, MA (US); Brian Holmberg, Somerville, MA (US); Connie Hong, Somerville, MA (US); Lu Huang, West Roxbury, MA (US); Olja Kodrasi, Quincy, MA (US); Joni Waiee Lam, Somerville, MA (US); Hyungwook Lim, Cambridge, MA (US); Elizabeth Dorothy Pratico, East Boston, MA (US); Andrew Price, Cambridge, MA (US); Akash Sohoni, Cambridge, MA (US); Andrew Marc Stein, Cambridge, MA (US); Louise Treanor, Cambridge, MA (US); Chonghui Zhang, Cambridge, MA (US); Xu Zhu, Cambridge, MA (US)

(73) Assignee: Novartis AG, Basel (CH)

(*) Notice: Subject to any disclaimer, the term of this patent is extended or adjusted under 35 U.S.C. 154(b) by 454 days.

(21) Appl. No.: 17/104,983

(22) Filed: Nov. 25, 2020

(65) Prior Publication Data

US 2021/0220404 A1 Jul. 22, 2021

Related U.S. Application Data

(60) Provisional application No. 62/940,509, filed on Nov. 26, 2019.

(51) Int. Cl.

| | |
|---|---|
| ***A61K 35/17*** | (2015.01) |
| ***A61K 38/17*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***A61P 35/00*** | (2006.01) |
| ***C07K 14/705*** | (2006.01) |
| ***C07K 14/725*** | (2006.01) |
| ***C07K 16/28*** | (2006.01) |
| ***C12N 5/0783*** | (2010.01) |
| *A61K 39/00* | (2006.01) |

(52) U.S. Cl.

CPC ........ *A61K 38/177* (2013.01); *A61K 38/1774* (2013.01); *A61K 39/3955* (2013.01); *A61K 40/11* (2025.01); *A61K 40/31* (2025.01); *A61K 40/4211* (2025.01); *A61K 40/4215* (2025.01); *A61K 45/06* (2013.01); *A61P 35/00* (2018.01); *C07K 14/7051* (2013.01); *C07K 14/70521* (2013.01); *C07K 14/70578* (2013.01); *C07K 16/2803* (2013.01); *C07K 16/2878* (2013.01); *C12N 5/0636* (2013.01); *A61K 2039/505* (2013.01); *A61K 2239/29* (2023.05); *A61K 2239/38* (2023.05); *A61K 2239/48* (2023.05); *C07K 2317/53* (2013.01); *C07K 2317/565* (2013.01); *C07K 2317/622* (2013.01); *C07K 2319/02* (2013.01); *C07K 2319/03* (2013.01); *C07K 2319/30* (2013.01); *C07K 2319/33* (2013.01); *C12N 2501/2302* (2013.01); *C12N 2501/2306* (2013.01); *C12N 2501/2307* (2013.01); *C12N 2501/2315* (2013.01); *C12N 2501/2321* (2013.01)

(58) Field of Classification Search

None

See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,712,149 | A | 1/1998 | Roberts |
| 5,874,240 | A | 2/1999 | Ni et al. |
| 5,906,936 | A | 5/1999 | Eshhar et al. |
| 6,103,521 | A | 8/2000 | Capon et al. |
| 6,319,494 | B1 | 11/2001 | Capon et al. |

(Continued)

FOREIGN PATENT DOCUMENTS

| | | | |
|---|---|---|---|
| EP | 0574512 | A1 | 12/1993 |
| EP | 0871495 | A1 | 10/1998 |

(Continued)

OTHER PUBLICATIONS

Gussow et al (Methods in Enzymology. 1991; 203: 99-121).*

(Continued)

*Primary Examiner* — Brad Duffy

(74) *Attorney, Agent, or Firm* — K&L Gates LLP

(57) ABSTRACT

The invention provides immune effector cells (for example, T cells, NK cells) that express a chimeric antigen receptor (CAR), and compositions and methods thereof.

21 Claims, 55 Drawing Sheets

Specification includes a Sequence Listing.

(56) References Cited

U.S. PATENT DOCUMENTS

| | | | |
|---|---|---|---|
| 6,355,779 | B1 | 3/2002 | Goodwin et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,994,298 | B2 | 8/2011 | Zhang et al. |
| 8,211,422 | B2 | 7/2012 | Eshhar et al. |
| 8,252,914 | B2 | 8/2012 | Zhang et al. |
| 8,389,282 | B2 | 3/2013 | Sadelain et al. |
| 8,399,645 | B2 | 3/2013 | Campana et al. |
| 8,465,743 | B2 | 6/2013 | Rosenberg et al. |
| 8,637,307 | B2 | 1/2014 | June et al. |
| 8,722,400 | B2 | 5/2014 | Riley et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,394,368 | B2 | 7/2016 | Brogdon et al. |
| 9,573,988 | B2 | 2/2017 | Brogdon et al. |
| 9,745,368 | B2 | 8/2017 | Milone et al. |
| 9,777,061 | B2 | 10/2017 | Ebersbach et al. |
| 9,815,901 | B2 | 11/2017 | Brogdon et al. |
| 2003/0060444 | A1 | 3/2003 | Finney et al. |
| 2003/0077249 | A1 | 4/2003 | Bebbington et al. |
| 2003/0147869 | A1 | 8/2003 | Riley et al. |
| 2003/0148982 | A1 | 8/2003 | Brenner et al. |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2004/0101519 | A1 | 5/2004 | June et al. |
| 2004/0110290 | A1 | 6/2004 | June et al. |
| 2005/0113564 | A1 | 5/2005 | Campana et al. |
| 2005/0129671 | A1 | 6/2005 | Cooper et al. |
| 2006/0034810 | A1 | 2/2006 | Riley et al. |
| 2007/0036773 | A1 | 2/2007 | Cooper et al. |
| 2008/0131415 | A1 | 6/2008 | Riddell et al. |
| 2009/0257994 | A1 | 10/2009 | Jensen |
| 2010/0261269 | A1 | 10/2010 | June et al. |
| 2011/0052554 | A1 | 3/2011 | Zakrzewski et al. |
| 2011/0262467 | A1 | 10/2011 | Riley et al. |
| 2012/0148552 | A1 | 6/2012 | Jensen |
| 2012/0321667 | A1 | 12/2012 | Sentman |
| 2013/0071409 | A1 | 3/2013 | Riley et al. |
| 2013/0071414 | A1 | 3/2013 | Dotti et al. |
| 2013/0149337 | A1 | 6/2013 | Cooper et al. |
| 2013/0155909 | A1 | 6/2013 | Jackson et al. |
| 2013/0287748 | A1 | 10/2013 | June et al. |
| 2013/0288368 | A1 | 10/2013 | June et al. |
| 2013/0309258 | A1 | 11/2013 | June et al. |
| 2014/0050708 | A1 | 2/2014 | Powell et al. |
| 2014/0099309 | A1 | 4/2014 | Powell, Jr. et al. |
| 2014/0099340 | A1 | 4/2014 | June et al. |
| 2014/0106449 | A1 | 4/2014 | June et al. |
| 2014/0186947 | A1 | 7/2014 | June et al. |
| 2014/0212446 | A1 | 7/2014 | Riley et al. |
| 2014/0219975 | A1 | 8/2014 | June et al. |
| 2014/0227237 | A1 | 8/2014 | June et al. |
| 2014/0271635 | A1 | 9/2014 | Brogdon et al. |
| 2014/0322169 | A1 | 10/2014 | Harper et al. |
| 2014/0322183 | A1 | 10/2014 | Milone et al. |
| 2014/0322212 | A1 | 10/2014 | Brogdon et al. |
| 2014/0322275 | A1 | 10/2014 | Brogdon et al. |
| 2014/0370017 | A1 | 12/2014 | June et al. |
| 2014/0370045 | A1 | 12/2014 | June et al. |
| 2015/0017141 | A1 | 1/2015 | June et al. |
| 2015/0024482 | A1 | 1/2015 | Frigault et al. |
| 2015/0050729 | A1 | 2/2015 | June et al. |
| 2015/0093822 | A1 | 4/2015 | June et al. |
| 2015/0099299 | A1 | 4/2015 | June et al. |
| 2015/0118202 | A1 | 4/2015 | June et al. |
| 2015/0140019 | A1 | 5/2015 | June et al. |
| 2015/0190428 | A1 | 7/2015 | June et al. |
| 2015/0202286 | A1 | 7/2015 | June et al. |
| 2015/0283178 | A1 | 10/2015 | June et al. |
| 2015/0290244 | A1 | 10/2015 | June et al. |
| 2015/0342994 | A1 | 12/2015 | Riley et al. |
| 2016/0046724 | A1 | 2/2016 | Brogdon et al. |
| 2016/0051651 | A1 | 2/2016 | Brogdon et al. |
| 2016/0068601 | A1 | 3/2016 | Brogdon et al. |
| 2016/0096892 | A1 | 4/2016 | Brogdon et al. |
| 2016/0185861 | A1 | 6/2016 | Bedoya et al. |
| 2016/0311907 | A1 | 10/2016 | Brogdon et al. |
| 2016/0311917 | A1 | 10/2016 | Beatty et al. |
| 2016/0340406 | A1 | 11/2016 | Zhao et al. |
| 2016/0362472 | A1 | 12/2016 | Bitter et al. |
| 2017/0008963 | A1 | 1/2017 | Brogdon et al. |
| 2017/0081411 | A1 | 3/2017 | Engels et al. |
| 2017/0137783 | A1 | 5/2017 | Bedoya et al. |
| 2017/0183415 | A1 | 6/2017 | Brogdon et al. |
| 2017/0209492 | A1 | 7/2017 | June et al. |
| 2017/0211055 | A1 | 7/2017 | Brogdon et al. |
| 2017/0226495 | A1 | 8/2017 | Guimaraes |
| 2017/0239294 | A1 | 8/2017 | Thomas-Tikhonenko et al. |
| 2017/0260268 | A1 | 9/2017 | Beatty et al. |
| 2017/0274014 | A1 | 9/2017 | Brogdon et al. |
| 2017/0306416 | A1 | 10/2017 | Bedoya et al. |
| 2017/0335281 | A1 | 11/2017 | Loew et al. |
| 2018/0022795 | A1 | 1/2018 | Milone et al. |
| 2018/0044423 | A1 | 2/2018 | Ebersbach et al. |
| 2018/0044424 | A1 | 2/2018 | June et al. |
| 2018/0118834 | A1 | 5/2018 | Brogdon et al. |
| 2018/0125892 | A1 | 5/2018 | Brannetti et al. |
| 2018/0133296 | A1 | 5/2018 | Barrett et al. |
| 2018/0140602 | A1 | 5/2018 | Angst et al. |
| 2018/0230193 | A1 | 8/2018 | Loew et al. |
| 2018/0252727 | A1 | 9/2018 | Garfall et al. |
| 2018/0258149 | A1 | 9/2018 | Motz et al. |
| 2018/0298068 | A1 | 10/2018 | Albelda |
| 2018/0312595 | A1 | 11/2018 | Brogdon et al. |
| 2019/0000880 | A1 | 1/2019 | Motz et al. |
| 2019/0000944 | A1 | 1/2019 | Brogdon et al. |
| 2019/0135940 | A1 | 5/2019 | Brogdon et al. |
| 2019/0151365 | A1 | 5/2019 | Anak et al. |
| 2019/0153061 | A1 | 5/2019 | Brogdon et al. |
| 2019/0161542 | A1 | 5/2019 | Gill et al. |
| 2019/0263914 | A1 | 8/2019 | Brogdon et al. |
| 2019/0269727 | A1 | 9/2019 | Fachin et al. |
| 2019/0292238 | A1 | 9/2019 | Bitter et al. |
| 2019/0292257 | A1 | 9/2019 | Bedoya et al. |
| 2019/0298715 | A1 | 10/2019 | Motz et al. |
| 2019/0330356 | A1 | 10/2019 | Brogdon et al. |
| 2019/0336504 | A1 | 11/2019 | Gill et al. |
| 2019/0375815 | A1 | 12/2019 | Engels et al. |
| 2019/0382500 | A1 | 12/2019 | Abujoub et al. |
| 2019/0388471 | A1 | 12/2019 | June et al. |
| 2019/0389928 | A1 | 12/2019 | Posey et al. |
| 2020/0048359 | A1 | 2/2020 | Albelda et al. |
| 2020/0055948 | A1 | 2/2020 | Daley et al. |
| 2020/0061113 | A1 | 2/2020 | Kassim et al. |
| 2020/0085869 | A1 | 3/2020 | Schuster et al. |
| 2020/0087376 | A1 | 3/2020 | Fraietta et al. |
| 2020/0113941 | A1 | 4/2020 | Brannetti et al. |
| 2020/0179511 | A1 | 6/2020 | Daley et al. |
| 2020/0215171 | A1 | 7/2020 | Brogdon et al. |
| 2020/0281973 | A1 | 9/2020 | Dranoff |
| 2020/0283729 | A1 | 9/2020 | Loew et al. |
| 2020/0291354 | A1 | 9/2020 | Johnson et al. |
| 2020/0339704 | A1 | 10/2020 | Bradner et al. |
| 2020/0360431 | A1 | 11/2020 | Garfall et al. |
| 2020/0368268 | A1 | 11/2020 | Johnson et al. |

(56) References Cited

U.S. PATENT DOCUMENTS

| | | | |
|---|---|---|---|
| 2020/0370012 | A1 | 11/2020 | Fraietta et al. |
| 2020/0371091 | A1 | 11/2020 | Pruteanu-Malinici et al. |
| 2020/0399383 | A1 | 12/2020 | Scholler et al. |
| 2021/0002377 | A1 | 1/2021 | Brogdon et al. |
| 2021/0047405 | A1 | 2/2021 | Nobles et al. |
| 2021/0079073 | A1 | 3/2021 | Milone et al. |
| 2021/0087279 | A1 | 3/2021 | Engels et al. |
| 2021/0139595 | A1 | 5/2021 | Ebersbach et al. |
| 2021/0171909 | A1 | 6/2021 | Golovina |
| 2021/0172020 | A1 | 6/2021 | Bedoya et al. |
| 2021/0177896 | A1 | 6/2021 | Porter et al. |
| 2021/0177900 | A1 | 6/2021 | Engels et al. |
| 2021/0213063 | A1 | 7/2021 | Isaacs et al. |
| 2021/0220404 | A1 | 7/2021 | Abujoub et al. |
| 2021/0246423 | A1 | 8/2021 | Bedoya et al. |
| 2021/0284752 | A1 | 9/2021 | Brogdon et al. |
| 2021/0317183 | A1 | 10/2021 | Zhao et al. |
| 2021/0347851 | A1 | 11/2021 | Isaacs et al. |
| 2021/0396739 | A1 | 12/2021 | Pruteanu-Malinici et al. |
| 2022/0047633 | A1 | 2/2022 | Grupp |
| 2022/0064316 | A1 | 3/2022 | Brogdon et al. |
| 2022/0089750 | A1 | 3/2022 | June et al. |
| 2022/0152150 | A1 | 5/2022 | Koshy et al. |
| 2022/0168389 | A1 | 6/2022 | Ghassemi et al. |
| 2022/0195010 | A1 | 6/2022 | Bitter et al. |
| 2022/0251152 | A1 | 8/2022 | Carbonneau et al. |
| 2022/0364055 | A1 | 11/2022 | Treanor et al. |
| 2022/0387486 | A1 | 12/2022 | Brannetti et al. |
| 2023/0026049 | A1 | 1/2023 | Brogdon et al. |
| 2023/0071283 | A1 | 3/2023 | Golosov et al. |
| 2023/0074800 | A1 | 3/2023 | Berger et al. |
| 2023/0111593 | A1 | 4/2023 | Schuster et al. |
| 2023/0139800 | A1 | 5/2023 | Motz et al. |
| 2023/0174933 | A1 | 6/2023 | Brogdon et al. |
| 2023/0183368 | A1 | 6/2023 | Abujoub et al. |
| 2023/0220090 | A1 | 7/2023 | Brogdon et al. |
| 2023/0250179 | A1 | 8/2023 | Abujoub et al. |
| 2023/0256017 | A1 | 8/2023 | Brogdon et al. |
| 2023/0295296 | A1 | 9/2023 | Bedoya et al. |
| 2023/0302155 | A1 | 9/2023 | Koshy et al. |
| 2023/0312677 | A1 | 10/2023 | Posey et al. |
| 2023/0332104 | A1 | 10/2023 | Estevez Silva et al. |
| 2023/0357717 | A1 | 11/2023 | Johnson et al. |
| 2023/0374105 | A1 | 11/2023 | Bitter et al. |
| 2023/0416390 | A1 | 12/2023 | Abujoub et al. |
| 2024/0024360 | A1 | 1/2024 | Fachin et al. |
| 2024/0033358 | A1 | 2/2024 | Chadbourne et al. |
| 2024/0083968 | A1 | 3/2024 | Loew et al. |
| 2024/0139244 | A1 | 5/2024 | Dranoff |
| 2024/0238396 | A1 | 7/2024 | Brogdon et al. |
| 2024/0252538 | A1 | 8/2024 | Brannetti et al. |
| 2024/0288444 | A1 | 8/2024 | Garfall et al. |

FOREIGN PATENT DOCUMENTS

| | | | | | |
|---|---|---|---|---|---|
| EP | 1226244 | A2 | | 7/2002 | |
| JP | 6359520 | B2 | | 7/2018 | |
| JP | 2018518974 | A | | 7/2018 | |
| RU | 2706582 | C2 | | 11/2019 | |
| WO | 1992015322 | A1 | | 9/1992 | |
| WO | 199530014 | A1 | | 11/1995 | |
| WO | 9623814 | A1 | | 8/1996 | |
| WO | 9624671 | A1 | | 8/1996 | |
| WO | 1997015669 | A1 | | 5/1997 | |
| WO | 9723613 | A2 | | 7/1997 | |
| WO | 9818809 | A1 | | 5/1998 | |
| WO | 9900494 | A2 | | 1/1999 | |
| WO | 9957268 | A1 | | 11/1999 | |
| WO | 0014257 | A1 | | 3/2000 | |
| WO | 2002033101 | A1 | | 4/2002 | |
| WO | 02077029 | A2 | | 10/2002 | |
| WO | 02088334 | A1 | | 11/2002 | |
| WO | 2003057171 | A2 | | 7/2003 | |
| WO | 2005019429 | A2 | | 3/2005 | |
| WO | 2005044996 | A2 | | 5/2005 | |
| WO | 2005/118788 | A2 | | 12/2005 | |
| WO | 2006060878 | A1 | | 6/2006 | |
| WO | 2008045437 | A2 | | 4/2008 | |
| WO | 2009091826 | A2 | | 7/2009 | |
| WO | 2010085660 | A2 | | 7/2010 | |
| WO | 2010095031 | A2 | | 8/2010 | |
| WO | 2010104949 | A2 | | 9/2010 | |
| WO | 2011059836 | A2 | | 5/2011 | |
| WO | 2011097477 | A1 | | 8/2011 | |
| WO | 2012058460 | A2 | | 5/2012 | |
| WO | 2012079000 | A1 | | 6/2012 | |
| WO | 2012082841 | A2 | | 6/2012 | |
| WO | 2012/099973 | A2 | | 7/2012 | |
| WO | 2012127464 | A2 | | 9/2012 | |
| WO | 2012129514 | A1 | | 9/2012 | |
| WO | 2012135854 | A2 | | 10/2012 | |
| WO | 2012138858 | A1 | | 10/2012 | |
| WO | 2013019615 | A2 | | 2/2013 | |
| WO | 2013033626 | A2 | | 3/2013 | |
| WO | 2013040371 | A2 | | 3/2013 | |
| WO | 2013040557 | A2 | | 3/2013 | |
| WO | 2013059593 | A1 | | 4/2013 | |
| WO | 2013/126712 | A1 | | 8/2013 | |
| WO | 2013126729 | A1 | | 8/2013 | |
| WO | 2013126733 | A1 | | 8/2013 | |
| WO | 2013154760 | A1 | | 10/2013 | |
| WO | 2014/011984 | A1 | | 1/2014 | |
| WO | 2014/011987 | A1 | | 1/2014 | |
| WO | 2014/011993 | A2 | | 1/2014 | |
| WO | 2014/012001 | A2 | | 1/2014 | |
| WO | 2014011988 | A2 | | 1/2014 | |
| WO | 2014011996 | A1 | | 1/2014 | |
| WO | 2014031687 | A1 | | 2/2014 | |
| WO | 2014039513 | A2 | | 3/2014 | |
| WO | 2014/055442 | A2 | | 4/2014 | |
| WO | 2014055657 | A1 | | 4/2014 | |
| WO | 2014130635 | A1 | | 8/2014 | |
| WO | 2014/145252 | A2 | | 9/2014 | |
| WO | 2014153270 | A1 | | 9/2014 | |
| WO | 2015090229 | A1 | | 6/2015 | |
| WO | 2015090230 | A1 | | 6/2015 | |
| WO | 2015112626 | A1 | | 7/2015 | |
| WO | 2015/142661 | A1 | | 9/2015 | |
| WO | 2015142675 | A2 | | 9/2015 | |
| WO | 2015157252 | A1 | | 10/2015 | |
| WO | 2016014501 | A1 | | 1/2016 | |
| WO | 2016014530 | A1 | | 1/2016 | |
| WO | 2016014535 | A1 | | 1/2016 | |
| WO | 2016014553 | A1 | | 1/2016 | |
| WO | 2016014565 | A2 | | 1/2016 | |
| WO | 2016014576 | A1 | | 1/2016 | |
| WO | 2016019300 | A1 | | 2/2016 | |
| WO | 2016025880 | A1 | | 2/2016 | |
| WO | 2016028896 | A1 | | 2/2016 | |
| WO | 2016044605 | A1 | | 3/2016 | |
| WO | 2016090320 | A1 | | 6/2016 | |
| WO | 2016094304 | A2 | | 6/2016 | |
| WO | 2016102965 | A1 | | 6/2016 | |
| WO | 2016130598 | A1 | | 8/2016 | |
| WO | 2016166630 | A1 | | 10/2016 | |
| WO | 2017130223 | A2 | | 8/2017 | |
| WO | WO-2017149515 | A1 | * | 9/2017 | ............. A61K 35/17 |
| WO | 2018237022 | A1 | | 12/2018 | |
| WO | 2019089798 | A1 | | 5/2019 | |
| WO | 2019108900 | A1 | | 6/2019 | |
| WO | 2019241426 | A1 | | 12/2019 | |
| WO | 2020047452 | A2 | | 3/2020 | |

OTHER PUBLICATIONS

Winkler et al (J. Imm., 265:4505-4514, 2000).*

Lloyd et al (Protein Engineering, Design & Selection, 22:159-168, 2009.*

Edwards et al (J Mol Biol, 14;334(1):103-118, 2003).*

Sermer et al (BR, 57:1-11, 2023).*

Xing et al (Cancers, 15:1-15, 2023).*

(56) References Cited

OTHER PUBLICATIONS

Zufferey et al., "Multiply attenuated lentiviral vector achieves efficient gene delivery in vivo" Nature Biotechnology (1997) vol. 15 pp. 871-876.

International Search Report and Written Opinion issued in PCT/US2020/062357, mailed May 25, 2021, 26 pages.

Kang et al., "Characterization of novel dual tandem CD19/BCMA chimeric antigen receptor T cells to potentially treat multiple myeloma," Biomarker Research (2020) vol. 8, Article 14, 11 pages.

Yan et al., "A combination of humanised anti-CD19 and anti-BCMA Car T cells in patients with relapsed or refractory multiple myeloma: a single-arm phase 2 trial," The Lancet Haematology (2019) vol. 6, No. 10, pp. e521-e529.

Baeksgaard & Sorensen, "Acute tumor lysis syndrome in solid tumors—a case report and review of the literature" Cancer Chemotherapy Pharmacology (2003) vol. 51 pp. 187-192.

Bondanza et al. "Suicide gene therapy of graft-versus-host disease induced by central memory human T lymphocytes" Blood (2006) vol. 107 No. 5 pp. 1828-1836.

Brentjens et al. "Genetically Targeted T Cells Eradicate Systemic Acute Lymphoblastic Leukemia Xenografts", Clinical Cancer Research(2007) vol. 13, No. 18, pp. 5426-5435.

Brentjens et al. "Novel cellular therapies for leukemia: CAR-modified T cells targeted to the CD19 antigen" Hematology (2012) pp. 143-151.

Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.

Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.

Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).

Brentjens et al., "Eradication of systemic B-cell tumors by genetically targeted human T lymphocytes co-stimulated by CD80 and interleukin-15" Nature Medicine (2003) vol. 9 No. 3 pp. 279-286.

Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.

Brocker and Karjalainen, "Signals through T Cell Receptor-Chain alone Are Insufficient to Prime Resting T Lymphocytes" J. Exp. Med. (1995) vol. 181 pp. 1653-1659.

Call & Wucherpfennig, "The T Cell Receptor: Critical Role of the Membrane Environment in Receptor Assembly and Function" Annu. Rev. Immunol. (2005) vol. 23 pp. 101-125.

Carpenito et al. "Control of large, established tumor xenografts with genetically retargeted human T cells containing CD28 and CD137 domains", Proc Natl Acad Sci USA (2009) vol. 106 pp. 3360-3365.

Carpenter et al. "B-cell Maturation Antigen Is a Promising Target for Adoptive T-cell Therapy of Multiple Myeloma" Clinical Cancer Research (2013) vol. 19, No. 8, pp. 2048-2060.

Cartellieri et al., "Chimeric Antigen Receptor-Engineered T Cells for Immunotherapy of Cancer," Journal of Biomedicine and Biotechnology (2010) vol. 2010, Article 956304, 13 pages.

Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.

Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.

Dropulic and June, "Gene-Based Immunotherapy for Human Immunodeficiency Virus Infection and Acquired Immunodeficiency Syndrome" Human Gene Therapy (2006) vol. 17 pp. 577-588.

Dull et al, "A Third-Generation Lentivirus Vector with a Conditional Packaging System" Journal of Virology (1998) vol. 72 No. 11 pp. 8463-8471.

Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).

Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).

Finney et al., "Chimeric receptors providing both primary and costimulatory signaling in T cells from a single gene product," J. Immunol. 161: 2791-2797 (1998).

Frey, N. "Genetically Engineered Lymphocyte Therapy in Treating Patients With B-Cell Leukemia or Lymphoma That is Resistant or Refractory to Chemotherapy" (2015) Clinical Trial NCT01029366.

Friedmann-Morvinski et al., "Redirected primary T cells harboring a chimeric receptor require costimulation for their antigen-specific activation," Blood 105: 3087-3093 (2005).

Geiger & Jyothi, "Development and Application of Receptor-Modified T Lymphocytes for Adoptive Immunotherapy" Transfusion Medicine Reviews (2001) vol. 15 No. 1 pp. 21-34.

Geiger et al., "Integrated src kinase and constimulatory activity enhances signal transduction through single-chain chimeric receptors in T lymphocytes," Blood 98(8): 2364-2371 (2001).

GenBank Accession No. NP_000725.1 accessed on Jan. 7, 2016 from http://www.ncbi.nlm.nih.gov/protein/NP_000725.

GenBank Accession No. NP_932170.1 accessed Jan. 7, 2016 from http://www.ncbi.nlm.nih.gov/protein/NP_932170.

Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.

Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.

Gribben et al., "Stem cell transplantation for indolent lymphoma and chronic lymphocytic leukemia" Biol Blood Marrow Transplant (2011) vol. 17 (1 Suppl): S63-S70.

Griffin, "Development and applications of surface-linked single chain antibodies against T-cell antigens" Journal of Immunological Methods (2001) vol. 248 pp. 77-90.

Gross et al., "Endowing T cells with antibody specificity using chimeric T cell receptors," The FASEB Journal 6: 3370-3378 (1992).

Grupp et al. "Chimeric Antigen Receptor-Modified T Cells for Acute Lymphoid Leukemia", New England Journal of Medicine (2013) vol. 368 No. 16 pp. 1509-1518.

Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.

Hekele et al., "Growth Retardation of Tumors by Adoptive Transfer of Cytotoxic T Lymphocytes Reprogrammed by CD44V6-Specific SCFV:zeta-Chimera" Int J. Cancer (1996) vol. 68 pp. 232-238.

Ho et al., "Adoptive immunotherapy: Engineering T cell responses as biological weapons for tumor mass destruction" Cancer Cell (2003) vol. 3 pp. 431-437.

Hollyman et al. "Manufacturing validation of biologically functional T cells targeted to CD19 antigen for autologous adoptive cell therapy" J Immunother (2009) vol. 32 No. 2 pp. 169-180.

Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).

Imai et al., "Chimeric receptors with 4-1BB signaling capacity provoke potent cytotoxicity against acute lymphoblastic leukemia," Leukemia 18: 676-684 (2004).

(56) References Cited

OTHER PUBLICATIONS

Imai et al., "Genetic modification of primary natural killer cells overcomes inhibitory signals and induces specific killing of leukemic cells" Blood (2005) vol. 106 No. 1 pp. 376-383.
International Search Report and Written Opinion for International Application No. PCT/US2014/029943 dated Jul. 17, 2014.
International Search Report and Written Opinion for International Application No. PCT/US2015/041378 dated Jan. 21, 2016.
International Search Report and Written Opinion for International Application No. PCT/US2019/036830 dated Oct. 18, 2019.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH); Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 689-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Macallan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
Maus et al. "Antibody-modified T cells: CARs take the front seat for hematologic malignancies" Blood (2014) vol. 123, No. 17, pp. 2625-2635.
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.

(56) References Cited

OTHER PUBLICATIONS

Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Ryan et al. "Antibody targeting of B-cell maturation antigen on malignant plasma cells" Mol Cancer Ther (2007) vol. 6, No. 11, pp. 3009-3018.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Terakura et al. "Generation of CD19-chimeric antigen receptor modified CD8+ T cells derived from virus-specific central memory T cells" Blood (2012) vol. 119, No. 1, pp. 72-82.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Vinay & Kwon, "Role of 4-1BB in immune responses" Immunology (1998) vol. 10 pp. 481-489.
Willemsen et al., "Genetic Engineering of T Cell Specificity for Immunotherapy of Cancer" Human Immunology (2003) vol. 64 pp. 56-68.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Badri et al., "Optimization of radiation dosing schedules for proneural glioblastoma," J Math Biol (2016) vol. 72, pp. 1301-1336.
Baylot et al., "TCTP Has a Crucial Role in the Different Stages of Prostate Cancer Malignant Progression," Chapter 13 in Results and Problems in Cell Differentiation, vol. 64, Eds. Kubiak et al., TCTP/tpt1—Remodeling Signaling from Stem Cell Disease, Telerman et al., Eds., (2017) Springer International Publishing AG, Cham Switzerland, pp. 255-261.
Brunner et al., "Cytotoxic T cells: Double-barreled shot guns," Nature Medicine , 1999, vol. 5, No. 1, Abstract.
Kussie et al., "A single engineered amino acid substitution changes antibody fine specificity," J Immunol (1994) vol. 152, No. 1, pp. 146-152.
Muller et al., "Spliceosomal Peptide P140 for Immunotherapy of Systemic Lupus Erythematosus," Arthritis & Rheumatism (2008) vol. 58, No. 12, pp. 3873-3883.
Roitt, et al., "Immunology," Moscow, Mir, 2000, pp. 4-6.
Rudikoff et al. "Single amino acid substitution altering antigen-binding specificity" PNAS (1982) vol. 79, pp. 1979-1983.
Zabel et al., "The making and function of CAR cells," Immunol Lett (2019) vol. 212, pp. 53-69.
Ghassemi et al., "Reducing Ex Vivo Culture Improves the Antileukemic Activity of Chimeric Antigen Receptor (CAR) T Cells," Cancer Immunology Research (2018) vol. 6, No. 9, pp. 1100-1109.
Liu et al., "First-in-Human Trial of BCMA-CD19 Compound CAR with Remarkable Donor-Specific Antibody Reduction," Blood (2019) vol. 134, Supp. 1, No. 38, 3 pages.
Zhang et al., "A BCMA and CD19 Bispecific CAR-T for Relapsed and Refractory Multiple Myeloma," Blood (2019) vol. 134, Supp. 1, No. 3147, 3 pages.

* cited by examiner

FIG. 4A

| constructs | %CD19 CAR | %BCMA CAR | %Double Positive | CD19 CAR Only | BCMA CAR Only |
|---|---|---|---|---|---|
| UTD | 0.01 | 0.01 | 0.00 | 0.01 | 0.01 |
| 234 | 7.43 | 3.47 | 3.73 | 3.62 | 0.06 |
| 235 | 1.35 | 1.35 | 1.21 | 0.13 | 0.18 |
| 236 | 10.10 | 10.30 | 9.62 | 0.35 | 0.77 |
| 237 | 10.40 | 9.61 | 9.31 | 0.96 | 0.59 |
| 238 | 12.10 | 9.89 | 9.74 | 2.12 | 0.47 |
| 244 | 31.60 | 0.04 | 0.04 | 31.40 | 0.01 |

FIG. 6A
FIG. 6B
CD19 CAR normalization
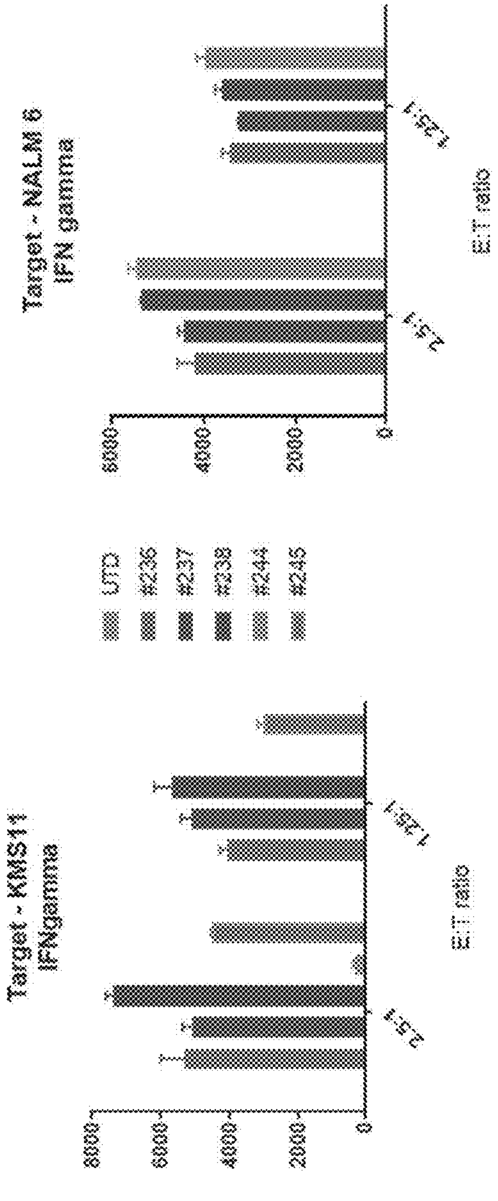
FIG. 6C
FIG. 6D
BCMA CAR normalization
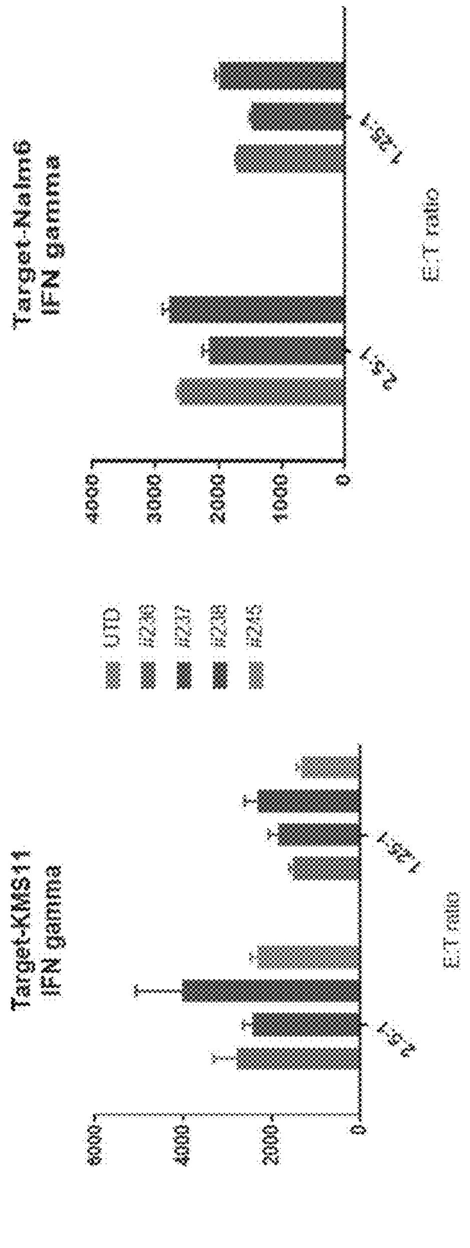

Medians:
D1: -0.062
D9: 0.14
Input: -0.081

Medians:
D1: 0.019
D9: 0.11
Input: -0.096

Medians:
D1: 0.066
D9: 0.11
Input: -0.09

SEQUENCE LISTING

```
<160> NUMBER OF SEQ ID NOS: 417

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 1

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 3
<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205
```

```
Val Met His Glu Ala Leu His Asn His Tyr Thr Gln Lys Ser Leu Ser
    210                 215                 220

Leu Ser Leu Gly Lys Met
225                 230
```

<210> SEQ ID NO 4
<211> LENGTH: 282
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Gly Gly Gly Gly Ser Gly Gly Gly Gly Ser
1 5 10

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 7
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 8
<211> LENGTH: 48
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Gln Arg Arg Lys Tyr Arg Ser Asn Lys Gly Glu Ser Pro Val Glu Pro
1 5 10 15

Ala Glu Pro Cys Arg Tyr Ser Cys Pro Arg Glu Glu Glu Gly Ser Thr
20 25 30

Ile Pro Ile Gln Glu Asp Tyr Arg Lys Pro Glu Pro Ala Cys Ser Pro
35 40 45

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr

```
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 11
<211> LENGTH: 1184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

cgtgaggctc cggtgcccgt cagtgggcag agcgcacatc gcccacagtc cccgagaagt      60

tggggggagg ggtcggcaat tgaaccggtg cctagagaag gtggcgcggg gtaaactggg     120

aaagtgatgt cgtgtactgg ctccgccttt ttcccgaggg tgggggagaa ccgtatataa     180

gtgcagtagt cgccgtgaac gttctttttc gcaacgggtt tgccgccaga acacaggtaa     240

gtgccgtgtg tggttcccgc gggcctggcc tctttacggg ttatggccct tgcgtgcctt     300

gaattacttc cacctggctg cagtacgtga ttcttgatcc cgagcttcgg gttggaagtg     360

ggtgggagag ttcgaggcct tgcgcttaag gagccccttc gcctcgtgct tgagttgagg     420

cctggcctgg gcgctggggc cgccgcgtgc gaatctggtg gcaccttcgc gcctgtctcg     480

ctgctttcga taagtctcta gccatttaaa atttttgatg acctgctgcg acgctttttt     540

tctggcaaga tagtcttgta aatgcgggcc aagatctgca cactggtatt tcggtttttg     600

gggccgcggg cggcgacggg gcccgtgcgt cccagcgcac atgttcggcg aggcggggcc     660
```

tgcgagcgcg gccaccgaga atcggacggg ggtagtctca agctggccgg cctgctctgg 720
tgcctggcct cgcgccgccg tgtatcgccc cgccctgggc ggcaaggctg gcccggtcgg 780
caccagttgc gtgagcggaa agatggccgc ttcccggccc tgctgcaggg agctcaaaat 840
ggaggacgcg gcgctcggga gagcgggcgg gtgagtcacc cacacaaagg aaaagggcct 900
ttccgtcctc agccgtcgct tcatgtgact ccacggagta ccgggcgccg tccaggcacc 960
tcgattagtt ctcgagcttt tggagtacgt cgtctttagg ttggggggag gggttttatg 1020
cgatggagtt tccccacact gagtgggtgg agactgaagt taggccagct tggcacttga 1080
tgtaattctc cttggaattt gcccttttttg agtttggatc ttggttcatt ctcaagcctc 1140
agacagtggt tcaaagtttt tttcttccat ttcaggtgtc gtga 1184

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
atggccctgc ctgtgacagc cctgctgctg cctctggctc tgctgctgca tgccgctaga 60
ccc 63

<210> SEQ ID NO 13
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gtgat 135

<210> SEQ ID NO 14
<211> LENGTH: 690
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
gagagcaagt acggccctcc ctgcccccct tgccctgccc ccgagttcct gggcggaccc 60
agcgtgttcc tgttcccccc caagcccaag gacaccctga tgatcagccg gacccccgag 120
gtgacctgtg tggtggtgga cgtgtcccag gaggaccccg aggtccagtt caactggtac 180
gtggacggcg tggaggtgca caacgccaag accaagcccc gggaggagca gttcaatagc 240
acctaccggg tggtgtccgt gctgaccgtg ctgcaccagg actggctgaa cggcaaggaa 300
tacaagtgta aggtgtccaa caagggcctg cccagcagca tcgagaaaac catcagcaag 360
gccaagggcc agcctcggga gccccaggtg tacaccctgc cccctagcca agaggagatg 420
accaagaacc aggtgtccct gacctgcctg gtgaagggct tctaccccag cgacatcgcc 480
gtggagtggg agagcaacgg ccagcccgag aacaactaca agaccacccc ccctgtgctg 540
gacagcgacg gcagcttctt cctgtacagc cggctgaccg tggacaagag ccggtggcag 600
gagggcaacg tctttagctg ctccgtgatg cacgaggccc tgcacaacca ctacacccag 660
aagagcctga gcctgtccct gggcaagatg 690

<210> SEQ ID NO 15
<211> LENGTH: 847
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
aggtggcccg aaagtcccaa ggcccaggca tctagtgttc ctactgcaca gccccaggca 60
gaaggcagcc tagccaaagc tactactgca cctgccacta cgcgcaatac tggccgtggc 120
ggggaggaga agaaaaagga gaaagagaaa gaagaacagg aagagaggga gaccaagacc 180
cctgaatgtc catcccatac ccagccgctg ggcgtctatc tcttgactcc cgcagtacag 240
gacttgtggc ttagagataa ggccaccttt acatgtttcg tcgtgggctc tgacctgaag 300
gatgcccatt tgacttggga ggttgccgga aaggtaccca caggggggt tgaggaaggg 360 ttgctggagc gccattccaa tggctctcag agccagcact caagactcac ccttccgaga 420
tccctgtgga acgccgggac ctctgtcaca tgtactctaa atcatcctag cctgcccca 480 cagcgtctga tggcccttag agagccagcc gcccaggcac cagttaagct tagcctgaat 540
ctgctcgcca gtagtgatcc cccagaggcc gccagctggc tcttatgcga agtgtccggc 600
tttagcccgc ccaacatctt gctcatgtgg ctggaggacc agcgagaagt gaacaccagc 660
ggcttcgctc cagcccggcc cccaccccag ccgggttcta ccacattctg ggcctggagt 720
gtcttaaggg tcccagcacc acctagcccc cagccagcca catacacctg tgttgtgtcc 780
catgaagata gcaggaccct gctaaatgct tctaggagtc tggaggtttc ctacgtgact 840
gaccatt 847

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 16
ggtggcggag gttctggagg tggaggttcc 30

<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
atctacatct gggcgccctt ggccgggact tgtggggtcc ttctcctgtc actggttatc 60
accctttact gc 72

<210> SEQ ID NO 18
<211> LENGTH: 126
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 18
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 19
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
agagtgaagt tcagcaggag cgcagacgcc cccgcgtaca agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

<210> SEQ ID NO 21
<211> LENGTH: 336
<212> TYPE: DNA
<213> ORGANISM: Homo sapiens

<400> SEQUENCE: 21
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

<210> SEQ ID NO 22
<211> LENGTH: 373
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 22

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370
```

<210> SEQ ID NO 23

<211> LENGTH: 1182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atggccctcc ctgtcactgc cctgcttctc cccctcgcac tcctgctcca cgccgctaga     60

ccacccggat ggtttctgga ctctccggat cgcccgtgga atccccccaac cttctcaccg    120

gcactcttgg ttgtgactga gggcgataat gcgaccttca cgtgctcgtt ctccaacacc    180

tccgaatcat tcgtgctgaa ctggtaccgc atgagcccgt caaaccagac cgacaagctc    240

gccgcgtttc cggaagatcg gtcgcaaccg ggacaggatt gtcggttccg cgtgactcaa    300

ctgccgaatg gcagagactt ccacatgagc gtggtccgcg ctaggcgaaa cgactccggg    360

acctacctgt gcggagccat ctcgctggcg cctaaggccc aaatcaaaga gagcttgagg    420

gccgaactga gagtgaccga gcgcagagct gaggtgccaa ctgcacatcc atccccatcg    480

cctcggcctg cggggcagtt tcagaccctg gtcacgacca ctccggcgcc gcgcccaccg    540

actccggccc caactatcgc gagccagccc ctgtcgctga ggccggaagc atgccgccct    600

gccgccggag gtgctgtgca tacccgggga ttggacttcg catgcgacat ctacatttgg    660

gctcctctcg ccggaacttg tggcgtgctc cttctgtccc tggtcatcac cctgtactgc    720

aagcggggtc ggaaaaagct tctgtacatt ttcaagcagc ccttcatgag gcccgtgcaa    780

accacccagg aggaggacgg ttgctcctgc cggttccccg aagaggaaga aggaggttgc    840

gagctgcgcg tgaagttctc ccggagcgcc gacgcccccg cctataagca gggccagaac    900

cagctgtaca acgaactgaa cctgggacgg cgggaagagt acgatgtgct ggacaagcgg    960

cgcggccggg accccgaaat gggcgggaag cctagaagaa agaaccctca ggaaggcctg   1020

tataacgagc tgcagaagga caagatggcc gaggcctact ccgaaattgg gatgaaggga   1080

gagcggcgga ggggaaaggg gcacgacggc ctgtaccaag gactgtccac cgccaccaag   1140

gacacatacg atgccctgca catgcaggcc cttccccctc gc                      1182
```

<210> SEQ ID NO 24
<211> LENGTH: 394
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Ala Leu Pro Val Thr Ala Leu Leu Leu Pro Leu Ala Leu Leu Leu
1               5                   10                  15

His Ala Ala Arg Pro Pro Gly Trp Phe Leu Asp Ser Pro Asp Arg Pro
            20                  25                  30

Trp Asn Pro Pro Thr Phe Ser Pro Ala Leu Leu Val Val Thr Glu Gly
        35                  40                  45

Asp Asn Ala Thr Phe Thr Cys Ser Phe Ser Asn Thr Ser Glu Ser Phe
    50                  55                  60

Val Leu Asn Trp Tyr Arg Met Ser Pro Ser Asn Gln Thr Asp Lys Leu
65                  70                  75                  80

Ala Ala Phe Pro Glu Asp Arg Ser Gln Pro Gly Gln Asp Cys Arg Phe
                85                  90                  95

Arg Val Thr Gln Leu Pro Asn Gly Arg Asp Phe His Met Ser Val Val
```

-continued

```
            100                 105                 110

Arg Ala Arg Arg Asn Asp Ser Gly Thr Tyr Leu Cys Gly Ala Ile Ser
        115                 120                 125

Leu Ala Pro Lys Ala Gln Ile Lys Glu Ser Leu Arg Ala Glu Leu Arg
    130                 135                 140

Val Thr Glu Arg Arg Ala Glu Val Pro Thr Ala His Pro Ser Pro Ser
145                 150                 155                 160

Pro Arg Pro Ala Gly Gln Phe Gln Thr Leu Val Thr Thr Thr Pro Ala
                165                 170                 175

Pro Arg Pro Pro Thr Pro Ala Pro Thr Ile Ala Ser Gln Pro Leu Ser
            180                 185                 190

Leu Arg Pro Glu Ala Cys Arg Pro Ala Ala Gly Gly Ala Val His Thr
        195                 200                 205

Arg Gly Leu Asp Phe Ala Cys Asp Ile Tyr Ile Trp Ala Pro Leu Ala
    210                 215                 220

Gly Thr Cys Gly Val Leu Leu Leu Ser Leu Val Ile Thr Leu Tyr Cys
225                 230                 235                 240

Lys Arg Gly Arg Lys Lys Leu Leu Tyr Ile Phe Lys Gln Pro Phe Met
                245                 250                 255

Arg Pro Val Gln Thr Thr Gln Glu Glu Asp Gly Cys Ser Cys Arg Phe
            260                 265                 270

Pro Glu Glu Glu Glu Gly Gly Cys Glu Leu Arg Val Lys Phe Ser Arg
        275                 280                 285

Ser Ala Asp Ala Pro Ala Tyr Lys Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390


<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Gly Gly Ser
1               5


<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MISC_FEATURE
<222> LOCATION: (1)..(30)
<223> OTHER INFORMATION: This sequence may encompass 1-6 "Gly Gly Gly Gly Ser" repeating units
<220> FEATURE:
<223> OTHER INFORMATION: See specification as filed for detailed description of substitutions and preferred embodiments

<400> SEQUENCE: 26

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gly Gly Gly Gly Ser Gly Gly Gly Gly Ser Gly Gly Gly Gly Ser Gly
1 5 10 15

Gly Gly Gly Ser
20

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Gly Gly Gly Gly Ser Gly Gly Gly Gly Ser Gly Gly Gly Gly Ser
1 5 10 15

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Gly Gly Gly Ser
1

<210> SEQ ID NO 30
<211> LENGTH: 5000
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(5000)
<223> OTHER INFORMATION: This sequence may encompass 50-5000 nucleotides

<400> SEQUENCE: 30
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120

-continued

```
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaaaa aaaaaaaaaa    480
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
```

-continued

```
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaaaaaaaa aaaaaaaaaa aaaaaaaaaa aaaaaaaaaa   2940
aaaaaaaaaa aaaaaaaaaa aaaaaaaaaa aaaaaaaaaa aaaaaaaaaa aaaaaaaaaa   3000
aaaaaaaaaa aaaaaaaaaa aaaaaaaaaa aaaaaaaaaa aaaaaaaaaa aaaaaaaaaa   3060
aaaaaaaaaa aaaaaaaaaa aaaaaaaaaa aaaaaaaaaa aaaaaaaaaa aaaaaaaaaa   3120
aaaaaaaaaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaaa aaaaaaaaaa aaaaaaaaaa aaaaaaaaaa   3300
aaaaaaaaaa aaaaaaaaaa aaaaaaaaaa aaaaaaaaaa aaaaaaaaaa aaaaaaaaaa   3360
aaaaaaaaaa aaaaaaaaaa aaaaaaaaaa aaaaaaaaaa aaaaaaaaaa aaaaaaaaaa   3420
aaaaaaaaaa aaaaaaaaaa aaaaaaaaaa aaaaaaaaaa aaaaaaaaaa aaaaaaaaaa   3480
aaaaaaaaaa aaaaaaaaaa aaaaaaaaaa aaaaaaaaaa aaaaaaaaaa aaaaaaaaaa   3540
aaaaaaaaaa aaaaaaaaaa aaaaaaaaaa aaaaaaaaaa aaaaaaaaaa aaaaaaaaaa   3600
aaaaaaaaaa aaaaaaaaaa aaaaaaaaaa aaaaaaaaaa aaaaaaaaaa aaaaaaaaaa   3660
aaaaaaaaaa aaaaaaaaaa aaaaaaaaaa aaaaaaaaaa aaaaaaaaaa aaaaaaaaaa   3720
aaaaaaaaaa aaaaaaaaaa aaaaaaaaaa aaaaaaaaaa aaaaaaaaaa aaaaaaaaaa   3780
aaaaaaaaaa aaaaaaaaaa aaaaaaaaaa aaaaaaaaaa aaaaaaaaaa aaaaaaaaaa   3840
aaaaaaaaaa aaaaaaaaaa aaaaaaaaaa aaaaaaaaaa aaaaaaaaaa aaaaaaaaaa   3900
aaaaaaaaaa aaaaaaaaaa aaaaaaaaaa aaaaaaaaaa aaaaaaaaaa aaaaaaaaaa   3960
aaaaaaaaaa aaaaaaaaaa aaaaaaaaaa aaaaaaaaaa aaaaaaaaaa aaaaaaaaaa   4020
aaaaaaaaaa aaaaaaaaaa aaaaaaaaaa aaaaaaaaaa aaaaaaaaaa aaaaaaaaaa   4080
aaaaaaaaaa aaaaaaaaaa aaaaaaaaaa aaaaaaaaaa aaaaaaaaaa aaaaaaaaaa   4140
aaaaaaaaaa aaaaaaaaaa aaaaaaaaaa aaaaaaaaaa aaaaaaaaaa aaaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaaaa   4320
aaaaaaaaaa aaaaaaaaaa aaaaaaaaaa aaaaaaaaaa aaaaaaaaaa aaaaaaaaaa   4380
aaaaaaaaaa aaaaaaaaaa aaaaaaaaaa aaaaaaaaaa aaaaaaaaaa aaaaaaaaaa   4440
aaaaaaaaaa aaaaaaaaaa aaaaaaaaaa aaaaaaaaaa aaaaaaaaaa aaaaaaaaaa   4500
aaaaaaaaaa aaaaaaaaaa aaaaaaaaaa aaaaaaaaaa aaaaaaaaaa aaaaaaaaaa   4560
aaaaaaaaaa aaaaaaaaaa aaaaaaaaaa aaaaaaaaaa aaaaaaaaaa aaaaaaaaaa   4620
aaaaaaaaaa aaaaaaaaaa aaaaaaaaaa aaaaaaaaaa aaaaaaaaaa aaaaaaaaaa   4680
aaaaaaaaaa aaaaaaaaaa aaaaaaaaaa aaaaaaaaaa aaaaaaaaaa aaaaaaaaaa   4740
aaaaaaaaaa aaaaaaaaaa aaaaaaaaaa aaaaaaaaaa aaaaaaaaaa aaaaaaaaaa   4800
aaaaaaaaaa aaaaaaaaaa aaaaaaaaaa aaaaaaaaaa aaaaaaaaaa aaaaaaaaaa   4860
```

```
aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000


<210> SEQ ID NO 31
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

tttttttttt tttttttttt tttttttttt tttttttttt tttttttttt tttttttttt     60

tttttttttt tttttttttt tttttttttt tttttttttt                          100


<210> SEQ ID NO 32
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass 50-5000 nucleotides

<400> SEQUENCE: 32

tttttttttt tttttttttt tttttttttt tttttttttt tttttttttt tttttttttt     60

tttttttttt tttttttttt tttttttttt tttttttttt tttttttttt tttttttttt    120

tttttttttt tttttttttt tttttttttt tttttttttt tttttttttt tttttttttt    180

tttttttttt tttttttttt tttttttttt tttttttttt tttttttttt tttttttttt    240

tttttttttt tttttttttt tttttttttt tttttttttt tttttttttt tttttttttt    300

tttttttttt tttttttttt tttttttttt tttttttttt tttttttttt tttttttttt    360

tttttttttt tttttttttt tttttttttt tttttttttt tttttttttt tttttttttt    420

tttttttttt tttttttttt tttttttttt tttttttttt tttttttttt tttttttttt    480

tttttttttt tttttttttt tttttttttt tttttttttt tttttttttt tttttttttt    540

tttttttttt tttttttttt tttttttttt tttttttttt tttttttttt tttttttttt    600

tttttttttt tttttttttt tttttttttt tttttttttt tttttttttt tttttttttt    660

tttttttttt tttttttttt tttttttttt tttttttttt tttttttttt tttttttttt    720

tttttttttt tttttttttt tttttttttt tttttttttt tttttttttt tttttttttt    780

tttttttttt tttttttttt tttttttttt tttttttttt tttttttttt tttttttttt    840

tttttttttt tttttttttt tttttttttt tttttttttt tttttttttt tttttttttt    900

tttttttttt tttttttttt tttttttttt tttttttttt tttttttttt tttttttttt    960

tttttttttt tttttttttt tttttttttt tttttttttt tttttttttt tttttttttt   1020

tttttttttt tttttttttt tttttttttt tttttttttt tttttttttt tttttttttt   1080

tttttttttt tttttttttt tttttttttt tttttttttt tttttttttt tttttttttt   1140

tttttttttt tttttttttt tttttttttt tttttttttt tttttttttt tttttttttt   1200

tttttttttt tttttttttt tttttttttt tttttttttt tttttttttt tttttttttt   1260
```

-continued

```
tttttttttt tttttttttt tttttttttt tttttttttt tttttttttt tttttttttt   1320
tttttttttt tttttttttt tttttttttt tttttttttt tttttttttt tttttttttt   1380
tttttttttt tttttttttt tttttttttt tttttttttt tttttttttt tttttttttt   1440
tttttttttt tttttttttt tttttttttt tttttttttt tttttttttt tttttttttt   1500
tttttttttt tttttttttt tttttttttt tttttttttt tttttttttt tttttttttt   1560
tttttttttt tttttttttt tttttttttt tttttttttt tttttttttt tttttttttt   1620
tttttttttt tttttttttt tttttttttt tttttttttt tttttttttt tttttttttt   1680
tttttttttt tttttttttt tttttttttt tttttttttt tttttttttt tttttttttt   1740
tttttttttt tttttttttt tttttttttt tttttttttt tttttttttt tttttttttt   1800
tttttttttt tttttttttt tttttttttt tttttttttt tttttttttt tttttttttt   1860
tttttttttt tttttttttt tttttttttt tttttttttt tttttttttt tttttttttt   1920
tttttttttt tttttttttt tttttttttt tttttttttt tttttttttt tttttttttt   1980
tttttttttt tttttttttt tttttttttt tttttttttt tttttttttt tttttttttt   2040
tttttttttt tttttttttt tttttttttt tttttttttt tttttttttt tttttttttt   2100
tttttttttt tttttttttt tttttttttt tttttttttt tttttttttt tttttttttt   2160
tttttttttt tttttttttt tttttttttt tttttttttt tttttttttt tttttttttt   2220
tttttttttt tttttttttt tttttttttt tttttttttt tttttttttt tttttttttt   2280
tttttttttt tttttttttt tttttttttt tttttttttt tttttttttt tttttttttt   2340
tttttttttt tttttttttt tttttttttt tttttttttt tttttttttt tttttttttt   2400
tttttttttt tttttttttt tttttttttt tttttttttt tttttttttt tttttttttt   2460
tttttttttt tttttttttt tttttttttt tttttttttt tttttttttt tttttttttt   2520
tttttttttt tttttttttt tttttttttt tttttttttt tttttttttt tttttttttt   2580
tttttttttt tttttttttt tttttttttt tttttttttt tttttttttt tttttttttt   2640
tttttttttt tttttttttt tttttttttt tttttttttt tttttttttt tttttttttt   2700
tttttttttt tttttttttt tttttttttt tttttttttt tttttttttt tttttttttt   2760
tttttttttt tttttttttt tttttttttt tttttttttt tttttttttt tttttttttt   2820
tttttttttt tttttttttt tttttttttt tttttttttt tttttttttt tttttttttt   2880
tttttttttt tttttttttt tttttttttt tttttttttt tttttttttt tttttttttt   2940
tttttttttt tttttttttt tttttttttt tttttttttt tttttttttt tttttttttt   3000
tttttttttt tttttttttt tttttttttt tttttttttt tttttttttt tttttttttt   3060
tttttttttt tttttttttt tttttttttt tttttttttt tttttttttt tttttttttt   3120
tttttttttt tttttttttt tttttttttt tttttttttt tttttttttt tttttttttt   3180
tttttttttt tttttttttt tttttttttt tttttttttt tttttttttt tttttttttt   3240
tttttttttt tttttttttt tttttttttt tttttttttt tttttttttt tttttttttt   3300
tttttttttt tttttttttt tttttttttt tttttttttt tttttttttt tttttttttt   3360
tttttttttt tttttttttt tttttttttt tttttttttt tttttttttt tttttttttt   3420
tttttttttt tttttttttt tttttttttt tttttttttt tttttttttt tttttttttt   3480
tttttttttt tttttttttt tttttttttt tttttttttt tttttttttt tttttttttt   3540
tttttttttt tttttttttt tttttttttt tttttttttt tttttttttt tttttttttt   3600
tttttttttt tttttttttt tttttttttt tttttttttt tttttttttt tttttttttt   3660
```

tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 33
<211> LENGTH: 5000
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (1)..(5000)
<223> OTHER INFORMATION: This sequence may encompass 100-5000
nucleotides

<400> SEQUENCE: 33
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480

-continued

```
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
```

aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa 5000

<210> SEQ ID NO 34
<211> LENGTH: 400
<212> TYPE: RNA
<213> ORGANISM: Artificial Sequence
<220> FEATURE:

<223> OTHER INFORMATION: Description of Artificial Sequence: Synthetic
      polynucleotide
<220> FEATURE:
<221> NAME/KEY: misc_feature
<222> LOCATION: (1)..(400)
<223> OTHER INFORMATION: This sequence may encompass 100-400 nucleotides

<400> SEQUENCE: 34
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa 400

<210> SEQ ID NO 35
<211> LENGTH: 2000
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(2000)
<223> OTHER INFORMATION: This sequence may encompass 50-2000 nucleotides

<400> SEQUENCE: 35
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260

```
aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaaaaaaa aaaaaaaaaa   1500

aaaaaaaaaa aaaaaaaaaa aaaaaaaaaa aaaaaaaaaa aaaaaaaaaa aaaaaaaaaa   1560

aaaaaaaaaa aaaaaaaaaa aaaaaaaaaa aaaaaaaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaaaaaa aaaaaaaaaa aaaaaaaaaa   1740

aaaaaaaaaa aaaaaaaaaa aaaaaaaaaa aaaaaaaaaa aaaaaaaaaa aaaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaaa aaaaaaaaaa                                               2000


<210> SEQ ID NO 36
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 37
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123


<210> SEQ ID NO 38
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
```

```
            20                  25                  30

Val Thr Leu
        35


<210> SEQ ID NO 39
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

acaaaaaaga agtattcatc cagtgtgcac gaccctaacg gtgaatacat gttcatgaga     60

gcagtgaaca cagccaaaaa atccagactc acagatgtga cccta                    105


<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

ggtggcggag gttctggagg tgggggttcc                                      30


<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Ser
1


<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 42

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 43

Gly Ser Thr Ser Gly Ser Gly Lys Pro Gly Ser Gly Glu Gly Ser Thr
1 5 10 15

Lys Gly

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Ser Tyr Ala Met Ser
1 5

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Ala Ile Ser Gly Ser Gly Gly Ser Thr Tyr Tyr Ala Asp Ser Val Lys
1 5 10 15

Gly

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Arg Glu Trp Val Pro Tyr Asp Val Ser Trp Tyr Phe Asp Tyr
1 5 10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gly Phe Thr Phe Ser Ser Tyr
1 5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Ser Gly Ser Gly Gly Ser

-continued

```
1               5


<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Ser Ser Tyr Ala
1               5


<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Ser Gly Ser Gly Gly Ser Thr
1               5


<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Arg Glu Trp Val Pro Tyr Asp Val Ser Trp Tyr Phe Asp Tyr
1               5                   10                  15


<210> SEQ ID NO 52
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Val Pro Tyr Asp Val Ser Trp Tyr Phe Asp Tyr
            100                 105                 110

Trp Gly Gln Gly Thr Leu Val Thr Val Ser Ser
        115                 120
```

<210> SEQ ID NO 53
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53
gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tgggtgccct acgatgtcag ctggtacttc gactactggg gacagggcac tctcgtgact 360
gtgtcctcc 369

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Arg Ala Ser Gln Ser Ile Ser Ser Tyr Leu Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Ala Ala Ser Ser Leu Gln Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Gln Gln Ser Tyr Ser Thr Pro Leu Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Ser Gln Ser Ile Ser Ser Tyr 1 5

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Ala Ala Ser
1

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ser Tyr Ser Thr Pro Leu
1 5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Gln Ser Ile Ser Ser Tyr
1 5

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gln Gly Thr Lys Val Glu Ile Lys
100 105

<210> SEQ ID NO 62
<211> LENGTH: 321

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gacattcaaa tgactcagtc cccgtcctcc ctctccgcct ccgtgggaga tcgcgtcacg      60

atcacgtgca gggccagcca gagcatctcc agctacctga actggtacca gcagaagcca     120

gggaaggcac cgaagctcct gatctacgcc gctagctcgc tgcagtccgg cgtcccttca     180

cggttctcgg gatcgggctc aggcaccgac ttcaccctga ccattagcag cctgcagccg     240

gaggacttcg cgacatacta ctgtcagcag tcatactcca cccctctgac cttcggccaa     300

gggaccaaag tggagatcaa g                                               321
```

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 64
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Val Pro Tyr Asp Val Ser Trp Tyr Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
```

```
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gln Gly Thr Lys Val Glu Ile Lys
                245                 250
```

<210> SEQ ID NO 65
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
gaagtgcagt tgctggagtc aggcggagga ctggtgcagc ccggaggatc gcttcgcttg      60

agctgcgcag cctcaggctt taccttctcc tcctacgcca tgtcctgggt cagacaggct     120

cccgggaagg gactggaatg ggtgtccgcc attagcggtt ccggcggaag cacttactat     180

gccgactctg tgaagggccg cttcactatc tcccgggaca actccaagaa caccctgtat     240

ctccaaatga attccctgag ggccgaagat accgcggtgt actactgcgc tagacgggag     300

tgggtgccct acgatgtcag ctggtacttc gactactggg gacagggcac tctcgtgact     360

gtgtcctccg gtggtggtgg atcggggggt ggtggttcgg gcggaggagg atctggagga     420

ggagggtcgg acattcaaat gactcagtcc ccgtcctccc tctccgcctc cgtgggagat     480

cgcgtcacga tcacgtgcag ggccagccag agcatctcca gctacctgaa ctggtaccag     540

cagaagccag ggaaggcacc gaagctcctg atctacgccg ctagctcgct gcagtccggc     600

gtcccttcac ggttctcggg atcgggctca ggcaccgact tcaccctgac cattagcagc     660

ctgcagccgg aggacttcgc gacatactac tgtcagcagt catactccac ccctctgacc     720

ttcggccaag ggaccaaagt ggagatcaag                                      750
```

<210> SEQ ID NO 66
<211> LENGTH: 473
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Arg Glu Trp Val Pro Tyr Asp Val Ser Trp Tyr Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gln Gly Thr Lys Val Glu Ile Lys Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470
```

<210> SEQ ID NO 67
<211> LENGTH: 1419

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tgggtgccct acgatgtcag ctggtacttc gactactggg gacagggcac tctcgtgact 360
gtgtcctccg gtggtggtgg atcgggggt ggtggttcgg gcggaggagg atctggagga 420
ggagggtcgg acattcaaat gactcagtcc ccgtcctccc tctccgcctc cgtgggagat 480
cgcgtcacga tcacgtgcag ggccagccag agcatctcca gctacctgaa ctggtaccag 540
cagaagccag ggaaggcacc gaagctcctg atctacgccg ctagctcgct gcagtccggc 600
gtcccttcac ggttctcggg atcgggctca ggcaccgact tcaccctgac cattagcagc 660
ctgcagccgg aggacttcgc gacatactac tgtcagcagt catactccac ccctctgacc 720
ttcggccaag ggaccaaagt ggagatcaag accactaccc cagcaccgag gccacccacc 780
ccggctccta ccatcgcctc ccagcctctg tccctgcgtc cggaggcatg tagacccgca 840
gctggtgggg ccgtgcatac ccggggtctt gacttcgcct gcgatatcta catttgggcc 900
cctctggctg gtacttgcgg ggtcctgctg ctttcactcg tgatcactct ttactgtaag 960
cgcggtcgga agaagctgct gtacatcttt aagcaaccct tcatgaggcc tgtgcagact 1020
actcaagagg aggacggctg ttcatgccgg ttcccagagg aggaggaagg cggctgcgaa 1080
ctgcgcgtga aattcagccg cagcgcagat gctccagcct accagcaggg gcagaaccag 1140
ctctacaacg aactcaatct tggtcggaga gaggagtacg acgtgctgga caagcggaga 1200
ggacgggacc cagaaatggg cgggaagccg cgcagaaaga atccccaaga gggcctgtac 1260
aacgagctcc aaaaggataa gatggcagaa gcctatagcg agattggtat gaaaggggaa 1320
cgcagaagag gcaaaggcca cgacggactg taccagggac tcagcaccgc caccaaggac 1380
acctatgacg ctcttcacat gcaggccctg ccgcctcgg 1419

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Arg Glu Trp Trp Tyr Asp Asp Trp Tyr Leu Asp Tyr
1 5 10

<210> SEQ ID NO 69
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ala Arg Arg Glu Trp Trp Tyr Asp Asp Trp Tyr Leu Asp Tyr
1               5                   10

<210> SEQ ID NO 70
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Tyr Asp Asp Trp Tyr Leu Asp Tyr Trp Gly
            100                 105                 110

Gln Gly Thr Leu Val Thr Val Ser Ser
        115                 120

<210> SEQ ID NO 71
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gaagtgcagt tgctggagtc aggcggagga ctggtgcagc ccggaggatc gcttcgcttg     60
agctgcgcag cctcaggctt taccttctcc tcctacgcca tgtcctgggt cagacaggct    120
cccgggaagg gactggaatg ggtgtccgcc attagcggtt ccggcggaag cacttactat    180
gccgactctg tgaagggccg cttcactatc tcccgggaca actccaagaa caccctgtat    240
ctccaaatga attccctgag ggccgaagat accgcggtgt actactgcgc tagacgggag    300
tggtggtacg acgattggta cctggactac tggggacagg gcactctcgt gactgtgtcc    360
tcc                                                                  363

<210> SEQ ID NO 72
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Tyr Asp Asp Trp Tyr Leu Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys
                245
```

<210> SEQ ID NO 73
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
gaagtgcagt tgctggagtc aggcggagga ctggtgcagc ccggaggatc gcttcgcttg     60

agctgcgcag cctcaggctt taccttctcc tcctacgcca tgtcctgggt cagacaggct    120

cccgggaagg gactggaatg ggtgtccgcc attagcggtt ccggcggaag cacttactat    180

gccgactctg tgaagggccg cttcactatc tcccgggaca actccaagaa caccctgtat    240

ctccaaatga attccctgag ggccgaagat accgcggtgt actactgcgc tagacgggag    300

tggtggtacg acgattggta cctggactac tggggacagg gcactctcgt gactgtgtcc    360

tccggtggtg gtggatcggg gggtggtggt tcgggcggag gaggatctgg aggaggaggg    420

tcggacattc aaatgactca gtccccgtcc tccctctccg cctccgtggg agatcgcgtc    480

acgatcacgt gcagggccag ccagagcatc tccagctacc tgaactggta ccagcagaag    540

ccagggaagg caccgaagct cctgatctac gccgctagct cgctgcagtc cggcgtccct    600

tcacggttct cgggatcggg ctcaggcacc gacttcaccc tgaccattag cagcctgcag    660

ccggaggact tcgcgacata ctactgtcag cagtcatact ccacccctct gaccttcggc    720
```

caagggacca aagtggagat caag 744

<210> SEQ ID NO 74
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Glu Trp Trp Tyr Asp Asp Trp Tyr Leu Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Asp Ile Gln
130 135 140

Met Thr Gln Ser Pro Ser Ser Leu Ser Ala Ser Val Gly Asp Arg Val
145 150 155 160

Thr Ile Thr Cys Arg Ala Ser Gln Ser Ile Ser Ser Tyr Leu Asn Trp
165 170 175

Tyr Gln Gln Lys Pro Gly Lys Ala Pro Lys Leu Leu Ile Tyr Ala Ala
180 185 190

Ser Ser Leu Gln Ser Gly Val Pro Ser Arg Phe Ser Gly Ser Gly Ser
195 200 205

Gly Thr Asp Phe Thr Leu Thr Ile Ser Ser Leu Gln Pro Glu Asp Phe
210 215 220

Ala Thr Tyr Tyr Cys Gln Gln Ser Tyr Ser Thr Pro Leu Thr Phe Gly
225 230 235 240

Gln Gly Thr Lys Val Glu Ile Lys Thr Thr Thr Pro Ala Pro Arg Pro
245 250 255

Pro Thr Pro Ala Pro Thr Ile Ala Ser Gln Pro Leu Ser Leu Arg Pro
260 265 270

Glu Ala Cys Arg Pro Ala Ala Gly Gly Ala Val His Thr Arg Gly Leu
275 280 285

Asp Phe Ala Cys Asp Ile Tyr Ile Trp Ala Pro Leu Ala Gly Thr Cys
290 295 300

Gly Val Leu Leu Leu Ser Leu Val Ile Thr Leu Tyr Cys Lys Arg Gly
305 310 315 320

Arg Lys Lys Leu Leu Tyr Ile Phe Lys Gln Pro Phe Met Arg Pro Val
325 330 335

Gln Thr Thr Gln Glu Glu Asp Gly Cys Ser Cys Arg Phe Pro Glu Glu
340 345 350

```
Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470
```

<210> SEQ ID NO 75
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
gaagtgcagt tgctggagtc aggcggagga ctggtgcagc ccggaggatc gcttcgcttg     60

agctgcgcag cctcaggctt taccttctcc tcctacgcca tgtcctgggt cagacaggct    120

cccgggaagg gactggaatg ggtgtccgcc attagcggtt ccggcggaag cacttactat    180

gccgactctg tgaagggccg cttcactatc tcccgggaca actccaagaa caccctgtat    240

ctccaaatga attccctgag ggccgaagat accgcggtgt actactgcgc tagacgggag    300

tggtggtacg acgattggta cctggactac tggggacagg gcactctcgt gactgtgtcc    360

tccggtggtg gtggatcggg gggtggtggt tcgggcggag gaggatctgg aggaggaggg    420

tcggacattc aaatgactca gtccccgtcc tccctctccg cctccgtggg agatcgcgtc    480

acgatcacgt gcagggccag ccagagcatc tccagctacc tgaactggta ccagcagaag    540

ccagggaagg caccgaagct cctgatctac gccgctagct cgctgcagtc cggcgtccct    600

tcacggttct cgggatcggg ctcaggcacc gacttcaccc tgaccattag cagcctgcag    660

ccggaggact tcgcgacata ctactgtcag cagtcatact ccacccctct gaccttcggc    720

caagggacca aagtggagat caagaccact accccagcac cgaggccacc caccccggct    780

cctaccatcg cctcccagcc tctgtccctg cgtccggagg catgtagacc cgcagctggt    840

ggggccgtgc atacccgggg tcttgacttc gcctgcgata tctacatttg ggcccctctg    900

gctggtactt gcggggtcct gctgctttca ctcgtgatca ctctttactg taagcgcggt    960

cggaagaagc tgctgtacat ctttaagcaa cccttcatga ggcctgtgca gactactcaa   1020

gaggaggacg gctgttcatg ccggttccca gaggaggagg aaggcggctg cgaactgcgc   1080

gtgaaattca gccgcagcgc agatgctcca gcctaccagc aggggcagaa ccagctctac   1140

aacgaactca atcttggtcg gagagaggag tacgacgtgc tggacaagcg gagaggacgg   1200

gacccagaaa tgggcgggaa gccgcgcaga aagaatcccc aagagggcct gtacaacgag   1260

ctccaaaagg ataagatggc agaagcctat agcgagattg gtatgaaagg ggaacgcaga   1320
```

agaggcaaag gccacgacgg actgtaccag ggactcagca ccgccaccaa ggacacctat 1380
gacgctcttc acatgcaggc cctgccgcct cgg 1413

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Arg Glu Trp Trp Gly Glu Ser Trp Leu Phe Asp Tyr
1 5 10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Ala Arg Arg Glu Trp Trp Gly Glu Ser Trp Leu Phe Asp Tyr
1 5 10

<210> SEQ ID NO 78
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Glu Trp Trp Gly Glu Ser Trp Leu Phe Asp Tyr Trp Gly
100 105 110

Gln Gly Thr Leu Val Thr Val Ser Ser
115 120

<210> SEQ ID NO 79
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79

-continued gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tggtggggag aaagctggct gttcgactac tggggacagg gcactctcgt gactgtgtcc 360
tcc 363

<210> SEQ ID NO 80
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Glu Trp Trp Gly Glu Ser Trp Leu Phe Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Asp Ile Gln
130 135 140

Met Thr Gln Ser Pro Ser Ser Leu Ser Ala Ser Val Gly Asp Arg Val
145 150 155 160

Thr Ile Thr Cys Arg Ala Ser Gln Ser Ile Ser Ser Tyr Leu Asn Trp
165 170 175

Tyr Gln Gln Lys Pro Gly Lys Ala Pro Lys Leu Leu Ile Tyr Ala Ala
180 185 190

Ser Ser Leu Gln Ser Gly Val Pro Ser Arg Phe Ser Gly Ser Gly Ser
195 200 205

Gly Thr Asp Phe Thr Leu Thr Ile Ser Ser Leu Gln Pro Glu Asp Phe
210 215 220

Ala Thr Tyr Tyr Cys Gln Gln Ser Tyr Ser Thr Pro Leu Thr Phe Gly
225 230 235 240

Gln Gly Thr Lys Val Glu Ile Lys
245

<210> SEQ ID NO 81
<211> LENGTH: 744
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 81
gaagtgcagt tgctggagtc aggcggagga ctggtgcagc ccggaggatc gcttcgcttg 60
agctgcgcag cctcaggctt taccttctcc tcctacgcca tgtcctgggt cagacaggct 120
cccgggaagg gactggaatg ggtgtccgcc attagcggtt ccggcggaag cacttactat 180
gccgactctg tgaagggccg cttcactatc tcccgggaca actccaagaa caccctgtat 240
ctccaaatga attccctgag ggccgaagat accgcggtgt actactgcgc tagacgggag 300
tggtggggag aaagctggct gttcgactac tggggacagg gcactctcgt gactgtgtcc 360
tccggtggtg gtggatcggg gggtggtggt tcgggcggag gaggatctgg aggaggaggg 420
tcggacattc aaatgactca gtccccgtcc tccctctccg cctccgtggg agatcgcgtc 480
acgatcacgt gcagggccag ccagagcatc tccagctacc tgaactggta ccagcagaag 540
ccagggaagg caccgaagct cctgatctac gccgctagct cgctgcagtc cggcgtccct 600
tcacggttct cgggatcggg ctcaggcacc gacttcaccc tgaccattag cagcctgcag 660
ccggaggact tcgcgacata ctactgtcag cagtcatact ccacccctct gaccttcggc 720
caagggacca aagtggagat caag 744

<210> SEQ ID NO 82
<211> LENGTH: 471
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Arg Glu Trp Trp Gly Glu Ser Trp Leu Phe Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Asp Ile Gln
130 135 140

Met Thr Gln Ser Pro Ser Ser Leu Ser Ala Ser Val Gly Asp Arg Val
145 150 155 160

Thr Ile Thr Cys Arg Ala Ser Gln Ser Ile Ser Ser Tyr Leu Asn Trp
165 170 175

Tyr Gln Gln Lys Pro Gly Lys Ala Pro Lys Leu Leu Ile Tyr Ala Ala
180 185 190

Ser Ser Leu Gln Ser Gly Val Pro Ser Arg Phe Ser Gly Ser Gly Ser

```
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470


<210> SEQ ID NO 83
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

gaagtgcagt tgctggagtc aggcggagga ctggtgcagc ccggaggatc gcttcgcttg      60

agctgcgcag cctcaggctt taccttctcc tcctacgcca tgtcctgggt cagacaggct     120

cccgggaagg gactggaatg ggtgtccgcc attagcggtt ccggcggaag cacttactat     180

gccgactctg tgaagggccg cttcactatc tcccgggaca actccaagaa caccctgtat     240

ctccaaatga attccctgag ggccgaagat accgcggtgt actactgcgc tagacgggag     300

tggtggggag aaagctggct gttcgactac tggggacagg gcactctcgt gactgtgtcc     360

tccggtggtg gtggatcggg gggtggtggt tcgggcggag gaggatctgg aggaggaggg     420

tcggacattc aaatgactca gtccccgtcc tccctctccg cctccgtggg agatcgcgtc     480
```

-continued

```
acgatcacgt gcagggccag ccagagcatc tccagctacc tgaactggta ccagcagaag    540
ccagggaagg caccgaagct cctgatctac gccgctagct cgctgcagtc cggcgtccct    600
tcacggttct cgggatcggg ctcaggcacc gacttcaccc tgaccattag cagcctgcag    660
ccggaggact tcgcgacata ctactgtcag cagtcatact ccacccctct gaccttcggc    720
caagggacca aagtggagat caagaccact accccagcac cgaggccacc caccccggct    780
cctaccatcg cctcccagcc tctgtccctg cgtccggagg catgtagacc cgcagctggt    840
ggggccgtgc atacccgggg tcttgacttc gcctgcgata tctacatttg ggcccctctg    900
gctggtactt gcggggtcct gctgctttca ctcgtgatca ctctttactg taagcgcggt    960
cggaagaagc tgctgtacat ctttaagcaa cccttcatga ggcctgtgca gactactcaa   1020
gaggaggacg gctgttcatg ccggttccca gaggaggagg aaggcggctg cgaactgcgc   1080
gtgaaattca gccgcagcgc agatgctcca gcctaccagc aggggcagaa ccagctctac   1140
aacgaactca atcttggtcg gagagaggag tacgacgtgc tggacaagcg gagaggacgg   1200
gacccagaaa tgggcgggaa gccgcgcaga aagaatcccc aagagggcct gtacaacgag   1260
ctccaaaagg ataagatggc agaagcctat agcgagattg gtatgaaagg ggaacgcaga   1320
agaggcaaag gccacgacgg actgtaccag ggactcagca ccgccaccaa ggacacctat   1380
gacgctcttc acatgcaggc cctgccgcct cgg                                1413
```

```
<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: V or absent
<220> FEATURE:
<221> NAME/KEY: MOD_RES
<222> LOCATION: (5)..(5)
<223> OTHER INFORMATION: P or absent
<220> FEATURE:
<221> NAME/KEY: MOD_RES
<222> LOCATION: (6)..(6)
<223> OTHER INFORMATION: W or Y
<220> FEATURE:
<221> NAME/KEY: MOD_RES
<222> LOCATION: (7)..(7)
<223> OTHER INFORMATION: G, Y, or D
<220> FEATURE:
<221> NAME/KEY: MOD_RES
<222> LOCATION: (8)..(8)
<223> OTHER INFORMATION: E, D, or V
<220> FEATURE:
<221> NAME/KEY: MOD_RES
<222> LOCATION: (9)..(9)
<223> OTHER INFORMATION: S or D
<220> FEATURE:
<221> NAME/KEY: MOD_RES
<222> LOCATION: (11)..(11)
<223> OTHER INFORMATION: L or Y
<220> FEATURE:
<221> NAME/KEY: MOD_RES
<222> LOCATION: (12)..(12)
<223> OTHER INFORMATION: F or L

<400> SEQUENCE: 84

Arg Glu Trp Xaa Xaa Xaa Xaa Xaa Xaa Trp Xaa Xaa Asp Tyr
1               5                   10
```

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: V or absent
<220> FEATURE:
<221> NAME/KEY: MOD_RES
<222> LOCATION: (7)..(7)
<223> OTHER INFORMATION: P or absent
<220> FEATURE:
<221> NAME/KEY: MOD_RES
<222> LOCATION: (8)..(8)
<223> OTHER INFORMATION: W or Y
<220> FEATURE:
<221> NAME/KEY: MOD_RES
<222> LOCATION: (9)..(9)
<223> OTHER INFORMATION: G, Y, or D
<220> FEATURE:
<221> NAME/KEY: MOD_RES
<222> LOCATION: (10)..(10)
<223> OTHER INFORMATION: E, D, or V
<220> FEATURE:
<221> NAME/KEY: MOD_RES
<222> LOCATION: (11)..(11)
<223> OTHER INFORMATION: S or D
<220> FEATURE:
<221> NAME/KEY: MOD_RES
<222> LOCATION: (13)..(13)
<223> OTHER INFORMATION: L or Y
<220> FEATURE:
<221> NAME/KEY: MOD_RES
<222> LOCATION: (14)..(14)
<223> OTHER INFORMATION: F or L

<400> SEQUENCE: 85

Ala Arg Arg Glu Trp Xaa Xaa Xaa Xaa Xaa Xaa Trp Xaa Xaa Asp Tyr
1               5                   10                  15

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Gly Met His
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ile Ser Tyr Asp Gly Ser Asn Lys Tyr Tyr Ala Asp Ser Val Lys
1               5                   10                  15

Gly

<210> SEQ ID NO 88
<211> LENGTH: 14

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Ser Gly Tyr Ala Leu His Asp Asp Tyr Tyr Gly Leu Asp Val
1 5 10

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Ser Tyr Asp Gly Ser Asn
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Gly Phe Thr Phe Ser Ser Tyr Gly
1 5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Ile Ser Tyr Asp Gly Ser Asn Lys
1 5

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Gly Gly Ser Gly Tyr Ala Leu His Asp Asp Tyr Tyr Gly Leu Asp Val
1 5 10 15

<210> SEQ ID NO 93
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 93

Gln Val Gln Leu Gln Glu Ser Gly Gly Gly Val Val Gln Pro Gly Arg

```
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser
        115                 120
```

```
<210> SEQ ID NO 94
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

caagtgcagc tgcaggaatc cggtggcgga gtcgtgcagc ctggaaggag cctgagactc     60

tcatgcgccg cgtcagggtt caccttttcc tcctacggga tgcattgggt cagacaggcc    120

cccggaaagg gactcgaatg ggtggctgtg atcagctacg acggctccaa caagtactac    180

gccgactccg tgaaaggccg gttcactatc tcccgggaca actccaagaa cacgctgtat    240

ctgcaaatga attcactgcg cgcggaggat accgctgtgt actactgcgg tggctccggt    300

tacgccctgc acgatgacta ttacggcctt gacgtctggg gccagggaac cctcgtgact    360

gtgtccagc                                                            369


<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Gly Thr Ser Ser Asp Val Gly Gly Tyr Asn Tyr Val Ser
1               5                   10


<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Val Ser Asn Arg Pro Ser
1               5


<210> SEQ ID NO 97
<211> LENGTH: 11
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Ser Ser Tyr Thr Ser Ser Ser Thr Leu Tyr Val
1 5 10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Thr Ser Ser Asp Val Gly Gly Tyr Asn Tyr
1 5 10

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Asp Val Ser
1

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Tyr Thr Ser Ser Ser Thr Leu Tyr
1 5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Ser Ser Asp Val Gly Gly Tyr Asn Tyr
1 5

<210> SEQ ID NO 102
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Gln Ser Ala Leu Thr Gln Pro Ala Ser Val Ser Gly Ser Pro Gly Gln

```
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Ser Gly Thr Lys Val Thr Val Leu
            100                 105                 110
```

<210> SEQ ID NO 103
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103

```
cagagcgcac tgactcagcc ggcatccgtg tccggtagcc ccggacagtc gattaccatc     60

tcctgtaccg gcacctcctc cgacgtggga gggtacaact acgtgtcgtg gtaccagcag    120

cacccaggaa aggcccctaa gttgatgatc tacgatgtgt caaaccgccc gtctggagtc    180

tccaaccggt tctccggctc caagtccggc aacaccgcca gcctgaccat tagcgggctg    240

caagccgagg atgaggccga ctactactgc tcgagctaca catcctcgag caccctctac    300

gtgttcggct cggggactaa ggtcaccgtg ctg                                 333
```

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

```
Gly Gly Gly Gly Ser Gly Gly Gly Gly Ser Gly Gly Gly Gly Ser
1               5                   10                  15
```

<210> SEQ ID NO 105
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gln Ser Ala Leu Thr Gln
    130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Asp Val Ser
            180                 185                 190

Asn Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Ser Ser Ser Thr Leu Tyr Val Phe
225                 230                 235                 240

Gly Ser Gly Thr Lys Val Thr Val Leu
                245
```

<210> SEQ ID NO 106
<211> LENGTH: 747
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106

```
caagtgcagc tgcaggaatc cggtggcgga gtcgtgcagc ctggaaggag cctgagactc     60

tcatgcgccg cgtcagggtt caccttttcc tcctacggga tgcattgggt cagacaggcc    120

cccggaaagg gactcgaatg ggtggctgtg atcagctacg acggctccaa caagtactac    180

gccgactccg tgaaaggccg gttcactatc tcccgggaca actccaagaa cacgctgtat    240

ctgcaaatga attcactgcg cgcggaggat accgctgtgt actactgcgg tggctccggt    300

tacgccctgc acgatgacta ttacggcctt gacgtctggg gccagggaac cctcgtgact    360

gtgtccagcg gtggaggagg ttcgggcgga ggaggatcag gagggggtgg atcgcagagc    420

gcactgactc agccggcatc cgtgtccggt agccccggac agtcgattac catctcctgt    480

accggcacct cctccgacgt gggagggtac aactacgtgt cgtggtacca gcagcaccca    540

ggaaaggccc ctaagttgat gatctacgat gtgtcaaacc gcccgtctgg agtctccaac    600

cggttctccg gctccaagtc cggcaacacc gccagcctga ccattagcgg gctgcaagcc    660

gaggatgagg ccgactacta ctgctcgagc tacacatcct cgagcaccct ctacgtgttc    720

ggctcgggga ctaaggtcac cgtgctg                                        747
```

<210> SEQ ID NO 107
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gln Ser Ala Leu Thr Gln
    130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Asp Val Ser
            180                 185                 190

Asn Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Ser Ser Ser Thr Leu Tyr Val Phe
225                 230                 235                 240

Gly Ser Gly Thr Lys Val Thr Val Leu Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
```

385 390 395 400

Arg Asp Pro Glu Met Gly Gly Lys Pro Arg Arg Lys Asn Pro Gln Glu
405 410 415

Gly Leu Tyr Asn Glu Leu Gln Lys Asp Lys Met Ala Glu Ala Tyr Ser
420 425 430

Glu Ile Gly Met Lys Gly Glu Arg Arg Arg Gly Lys Gly His Asp Gly
435 440 445

Leu Tyr Gln Gly Leu Ser Thr Ala Thr Lys Asp Thr Tyr Asp Ala Leu
450 455 460

His Met Gln Ala Leu Pro Pro Arg
465 470

<210> SEQ ID NO 108
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
caagtgcagc tgcaggaatc cggtggcgga gtcgtgcagc ctggaaggag cctgagactc 60
tcatgcgccg cgtcagggtt caccttttcc tcctacggga tgcattgggt cagacaggcc 120
cccggaaagg gactcgaatg ggtggctgtg atcagctacg acggctccaa caagtactac 180
gccgactccg tgaaaggccg gttcactatc tcccgggaca actccaagaa cacgctgtat 240
ctgcaaatga attcactgcg cgcggaggat accgctgtgt actactgcgg tggctccggt 300
tacgccctgc acgatgacta ttacggcctt gacgtctggg gccagggaac cctcgtgact 360
gtgtccagcg gtggaggagg ttcgggcgga ggaggatcag gagggggtgg atcgcagagc 420
gcactgactc agccggcatc cgtgtccggt agccccggac agtcgattac catctcctgt 480
accggcacct cctccgacgt gggagggtac aactacgtgt cgtggtacca gcagcaccca 540
ggaaaggccc ctaagttgat gatctacgat gtgtcaaacc gcccgtctgg agtctccaac 600
cggttctccg gctccaagtc cggcaacacc gccagcctga ccattagcgg gctgcaagcc 660
gaggatgagg ccgactacta ctgctcgagc tacacatcct cgagcaccct ctacgtgttc 720
ggctcgggga ctaaggtcac cgtgctgacc actaccccag caccgaggcc acccaccccg 780
gctcctacca tcgcctccca gcctctgtcc ctgcgtccgg aggcatgtag acccgcagct 840
ggtggggccg tgcatacccg gggtcttgac ttcgcctgcg atatctacat ttgggcccct 900
ctggctggta cttgcggggt cctgctgctt tcactcgtga tcactcttta ctgtaagcgc 960
ggtcggaaga agctgctgta catctttaag caacccttca tgaggcctgt gcagactact 1020
caagaggagg acggctgttc atgccggttc ccagaggagg aggaaggcgg ctgcgaactg 1080
cgcgtgaaat tcagccgcag cgcagatgct ccagcctacc agcaggggca gaaccagctc 1140
tacaacgaac tcaatcttgg tcggagagag gagtacgacg tgctggacaa gcggagagga 1200
cgggacccag aaatgggcgg gaagccgcgc agaaagaatc cccaagaggg cctgtacaac 1260
gagctccaaa aggataagat ggcagaagcc tatagcgaga ttggtatgaa aggggaacgc 1320
agaagaggca aaggccacga cggactgtac cagggactca gcaccgccac caaggacacc 1380
tatgacgctc ttcacatgca ggccctgccg cctcgg 1416

<210> SEQ ID NO 109
<211> LENGTH: 17

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Val Ile Ser Tyr Lys Gly Ser Asn Lys Tyr Tyr Ala Asp Ser Val Lys
1 5 10 15

Gly

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Ser Tyr Lys Gly Ser Asn
1 5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Ile Ser Tyr Lys Gly Ser Asn Lys
1 5

<210> SEQ ID NO 112
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 112

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Lys Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Gly Gly Ser Gly Tyr Ala Leu His Asp Asp Tyr Tyr Gly Leu Asp Val
100 105 110

Trp Gly Gln Gly Thr Leu Val Thr Val Ser Ser
115 120

<210> SEQ ID NO 113
<211> LENGTH: 369

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
caagtgcagc ttgtcgaatc gggaggcgga gtggtgcagc ctggacgatc gctccggctc 60
tcatgtgccg cgagcggatt caccttctcg agctacggca tgcactgggt cagacaagcc 120
ccaggaaagg gcctggaatg ggtggctgtc atctcgtaca agggctcaaa caagtactac 180
gccgactccg tgaagggccg gttcaccatc tcccgcgata actccaagaa taccctctat 240
ctgcaaatga acagcctgag ggccgaggat actgcagtgt actactgcgg gggttcaggc 300
tacgcgctgc acgacgacta ctacggattg gacgtctggg gccaaggaac tcttgtgacc 360
gtgtcctct 369

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Glu Val Ser Asn Arg Leu Arg
1               5

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Ser Tyr Thr Ser Ser Ser Ala Leu Tyr Val
1               5                   10

<210> SEQ ID NO 116
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Val Ser
1

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Tyr Thr Ser Ser Ser Ala Leu Tyr
1               5

<210> SEQ ID NO 118
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Leu Arg Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ala Leu Tyr Val Phe Gly Ser Gly Thr Lys Val Thr Val Leu
            100                 105                 110
```

<210> SEQ ID NO 119
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119

```
cagagcgcgc tgactcagcc tgcctccgtg agcggttcgc cgggacagtc cattaccatt     60

tcgtgcaccg ggacctcctc cgacgtggga ggctacaact acgtgtcctg gtaccagcag    120

catcccggaa aggccccgaa gctgatgatc tacgaagtgt cgaacagact gcggggagtc    180

tccaaccgct tttccgggtc caagtccggc aacaccgcca gcctgaccat cagcgggctc    240

caggcagaag atgaggctga ctattactgc tcctcctaca cgtcaagctc cgccctctac    300

gtgttcgggt ccgggaccaa agtcactgtg ctg                                 333
```

<210> SEQ ID NO 120
<211> LENGTH: 254
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
85 90 95

Gly Gly Ser Gly Tyr Ala Leu His Asp Asp Tyr Tyr Gly Leu Asp Val
100 105 110

Trp Gly Gln Gly Thr Leu Val Thr Val Ser Ser Gly Gly Gly Gly Ser
115 120 125

Gly Gly Gly Gly Ser Gly Gly Gly Gly Ser Gly Gly Gly Gly Ser Gln
130 135 140

Ser Ala Leu Thr Gln Pro Ala Ser Val Ser Gly Ser Pro Gly Gln Ser
145 150 155 160

Ile Thr Ile Ser Cys Thr Gly Thr Ser Ser Asp Val Gly Gly Tyr Asn
165 170 175

Tyr Val Ser Trp Tyr Gln Gln His Pro Gly Lys Ala Pro Lys Leu Met
180 185 190

Ile Tyr Glu Val Ser Asn Arg Leu Arg Gly Val Ser Asn Arg Phe Ser
195 200 205

Gly Ser Lys Ser Gly Asn Thr Ala Ser Leu Thr Ile Ser Gly Leu Gln
210 215 220

Ala Glu Asp Glu Ala Asp Tyr Tyr Cys Ser Ser Tyr Thr Ser Ser Ser
225 230 235 240

Ala Leu Tyr Val Phe Gly Ser Gly Thr Lys Val Thr Val Leu
245 250

<210> SEQ ID NO 121
<211> LENGTH: 762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121
caagtgcagc ttgtcgaatc gggaggcgga gtggtgcagc ctggacgatc gctccggctc 60
tcatgtgccg cgagcggatt caccttctcg agctacggca tgcactgggt cagacaagcc 120
ccaggaaagg gcctggaatg ggtggctgtc atctcgtaca agggctcaaa caagtactac 180
gccgactccg tgaagggccg gttcaccatc tcccgcgata actccaagaa taccctctat 240
ctgcaaatga acagcctgag ggccgaggat actgcagtgt actactgcgg gggttcaggc 300
tacgcgctgc acgacgacta ctacggattg gacgtctggg gccaaggaac tcttgtgacc 360
gtgtcctctg gtggaggcgg atcagggggt ggcggatctg gggggtggtgg ttccggggga 420 ggaggatcgc agagcgcgct gactcagcct gcctccgtga gcggttcgcc gggacagtcc 480
attaccattt cgtgcaccgg gacctcctcc gacgtgggag gctacaacta cgtgtcctgg 540
taccagcagc atcccggaaa ggccccgaag ctgatgatct acgaagtgtc gaacagactg 600
cggggagtct ccaaccgctt ttccgggtcc aagtccggca acaccgccag cctgaccatc 660
agcgggctcc aggcagaaga tgaggctgac tattactgct cctcctacac gtcaagctcc 720
gccctctacg tgttcgggtc cgggaccaaa gtcactgtgc tg 762

<210> SEQ ID NO 122
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Ala Leu Tyr Val Phe Gly Ser Gly Thr Lys Val Thr Val Leu Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Ile Tyr Ile Trp Ala
    290                 295                 300

Pro Leu Ala Gly Thr Cys Gly Val Leu Leu Leu Ser Leu Val Ile Thr
305                 310                 315                 320

Leu Tyr Cys Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg

-continued

```
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475
```

<210> SEQ ID NO 123
<211> LENGTH: 1431
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
caagtgcagc ttgtcgaatc gggaggcgga gtggtgcagc ctggacgatc gctccggctc     60

tcatgtgccg cgagcggatt caccttctcg agctacggca tgcactgggt cagacaagcc    120

ccaggaaagg gcctggaatg ggtggctgtc atctcgtaca agggctcaaa caagtactac    180

gccgactccg tgaagggccg gttcaccatc tcccgcgata actccaagaa taccctctat    240

ctgcaaatga acagcctgag ggccgaggat actgcagtgt actactgcgg gggttcaggc    300

tacgcgctgc acgacgacta ctacggattg gacgtctggg gccaaggaac tcttgtgacc    360

gtgtcctctg gtggaggcgg atcagggggt ggcggatctg gggtggtgg ttccgggga     420

ggaggatcgc agagcgcgct gactcagcct gcctccgtga gcggttcgcc gggacagtcc    480

attaccattt cgtgcaccgg gacctcctcc gacgtgggag gctacaacta cgtgtcctgg    540

taccagcagc atcccggaaa ggccccgaag ctgatgatct acgaagtgtc gaacagactg    600

cggggagtct ccaaccgctt ttccgggtcc aagtccggca acaccgccag cctgaccatc    660

agcgggctcc aggcagaaga tgaggctgac tattactgct cctcctacac gtcaagctcc    720

gccctctacg tgttcgggtc cgggaccaaa gtcactgtgc tgaccactac cccagcaccg    780

aggccaccca ccccggctcc taccatcgcc tcccagcctc tgtccctgcg tccggaggca    840

tgtagacccg cagctggtgg ggccgtgcat acccggggtc ttgacttcgc ctgcgatatc    900

tacatttggg cccctctggc tggtacttgc ggggtcctgc tgctttcact cgtgatcact    960

ctttactgta agcgcggtcg gaagaagctg ctgtacatct ttaagcaacc cttcatgagg   1020

cctgtgcaga ctactcaaga ggaggacggc tgttcatgcc ggttcccaga ggaggaggaa   1080

ggcggctgcg aactgcgcgt gaaattcagc cgcagcgcag atgctccagc ctaccagcag   1140

gggcagaacc agctctacaa cgaactcaat cttggtcgga gagaggagta cgacgtgctg   1200

gacaagcgga gaggacggga cccagaaatg ggcgggaagc cgcgcagaaa gaatccccaa   1260

gagggcctgt acaacgagct ccaaaaggat aagatggcag aagcctatag cgagattggt   1320

atgaaagggg aacgcagaag aggcaaaggc cacgacggac tgtaccaggg actcagcacc   1380

gccaccaagg acacctatga cgctcttcac atgcaggccc tgccgcctcg g            1431
```

<210> SEQ ID NO 124
<211> LENGTH: 111
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 124

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Glu Val Ser Asn Arg Leu Arg Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu Tyr Val Phe Gly Ser Gly Thr Lys Val Thr Val Leu
100 105 110

<210> SEQ ID NO 125
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 125
cagagcgcgc tgactcagcc tgcctccgtg agcggttcgc cgggacagtc cattaccatt 60
tcgtgcaccg ggacctcctc cgacgtggga ggctacaact acgtgtcctg gtaccagcag 120
catcccggaa aggccccgaa gctgatgatc tacgaagtgt cgaacagact gcggggagtc 180
tccaaccgct tttccgggtc caagtccggc aacaccgcca gcctgaccat cagcgggctc 240
caggcagaag atgaggctga ctattactgc tcctcctaca cgtcaagctc caccctctac 300
gtgttcgggt ccgggaccaa agtcactgtg ctg 333

<210> SEQ ID NO 126
<211> LENGTH: 254
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 126

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Lys Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Gly Gly Ser Gly Tyr Ala Leu His Asp Asp Tyr Tyr Gly Leu Asp Val

```
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Thr Leu Tyr Val Phe Gly Ser Gly Thr Lys Val Thr Val Leu
                245                 250
```

<210> SEQ ID NO 127
<211> LENGTH: 762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
caagtgcagc ttgtcgaatc gggaggcgga gtggtgcagc ctggacgatc gctccggctc     60

tcatgtgccg cgagcggatt caccttctcg agctacggca tgcactgggt cagacaagcc    120

ccaggaaagg gcctggaatg ggtggctgtc atctcgtaca agggctcaaa caagtactac    180

gccgactccg tgaagggccg gttcaccatc tcccgcgata actccaagaa taccctctat    240

ctgcaaatga acagcctgag ggccgaggat actgcagtgt actactgcgg gggttcaggc    300

tacgcgctgc acgacgacta ctacggattg gacgtctggg gccaaggaac tcttgtgacc    360

gtgtcctctg gtggaggcgg atcagggggt ggcggatctg gggggtggtgg ttccgggggga    420

ggaggatcgc agagcgcgct gactcagcct gcctccgtga gcggttcgcc gggacagtcc    480

attaccattt cgtgcaccgg gacctcctcc gacgtgggag gctacaacta cgtgtcctgg    540

taccagcagc atcccggaaa ggccccgaag ctgatgatct acgaagtgtc gaacagactg    600

cggggagtct ccaaccgctt ttccgggtcc aagtccggca acaccgccag cctgaccatc    660

agcgggctcc aggcagaaga tgaggctgac tattactgct cctcctacac gtcaagctcc    720

accctctacg tgttcgggtc cgggaccaaa gtcactgtgc tg                       762
```

<210> SEQ ID NO 128
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

```
Gln Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Lys Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Gln
    130                 135                 140

Ser Ala Leu Thr Gln Pro Ala Ser Val Ser Gly Ser Pro Gly Gln Ser
145                 150                 155                 160

Ile Thr Ile Ser Cys Thr Gly Thr Ser Ser Asp Val Gly Gly Tyr Asn
                165                 170                 175

Tyr Val Ser Trp Tyr Gln Gln His Pro Gly Lys Ala Pro Lys Leu Met
            180                 185                 190

Ile Tyr Glu Val Ser Asn Arg Leu Arg Gly Val Ser Asn Arg Phe Ser
        195                 200                 205

Gly Ser Lys Ser Gly Asn Thr Ala Ser Leu Thr Ile Ser Gly Leu Gln
    210                 215                 220

Ala Glu Asp Glu Ala Asp Tyr Tyr Cys Ser Ser Tyr Thr Ser Ser Ser
225                 230                 235                 240

Thr Leu Tyr Val Phe Gly Ser Gly Thr Lys Val Thr Val Leu Thr Thr
                245                 250                 255

Thr Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Ile Tyr Ile Trp Ala
    290                 295                 300

Pro Leu Ala Gly Thr Cys Gly Val Leu Leu Leu Ser Leu Val Ile Thr
305                 310                 315                 320

Leu Tyr Cys Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430
```

-continued

```
Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475
```

<210> SEQ ID NO 129
<211> LENGTH: 1431
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
caagtgcagc ttgtcgaatc gggaggcgga gtggtgcagc ctggacgatc gctccggctc     60

tcatgtgccg cgagcggatt caccttctcg agctacggca tgcactgggt cagacaagcc    120

ccaggaaagg gcctggaatg ggtggctgtc atctcgtaca agggctcaaa caagtactac    180

gccgactccg tgaagggccg gttcaccatc tcccgcgata actccaagaa taccctctat    240

ctgcaaatga acagcctgag ggccgaggat actgcagtgt actactgcgg gggttcaggc    300

tacgcgctgc acgacgacta ctacggattg gacgtctggg gccaaggaac tcttgtgacc    360

gtgtcctctg gtggaggcgg atcagggggt ggcggatctg gggggtggtgg ttccggggga    420

ggaggatcgc agagcgcgct gactcagcct gcctccgtga gcggttcgcc gggacagtcc    480

attaccattt cgtgcaccgg gacctcctcc gacgtgggag gctacaacta cgtgtcctgg    540

taccagcagc atcccggaaa ggccccgaag ctgatgatct acgaagtgtc gaacagactg    600

cggggagtct ccaaccgctt ttccgggtcc aagtccggca acaccgccag cctgaccatc    660

agcgggctcc aggcagaaga tgaggctgac tattactgct cctcctacac gtcaagctcc    720

accctctacg tgttcgggtc cgggaccaaa gtcactgtgc tgaccactac cccagcaccg    780

aggccaccca ccccggctcc taccatcgcc tcccagcctc tgtccctgcg tccggaggca    840

tgtagacccg cagctggtgg ggccgtgcat acccggggtc ttgacttcgc ctgcgatatc    900

tacatttggg cccctctggc tggtacttgc ggggtcctgc tgctttcact cgtgatcact    960

ctttactgta agcgcggtcg gaagaagctg ctgtacatct ttaagcaacc cttcatgagg   1020

cctgtgcaga ctactcaaga ggaggacggc tgttcatgcc ggttcccaga ggaggaggaa   1080

ggcggctgcg aactgcgcgt gaaattcagc cgcagcgcag atgctccagc ctaccagcag   1140

gggcagaacc agctctacaa cgaactcaat cttggtcgga gagaggagta cgacgtgctg   1200

gacaagcgga gaggacggga cccagaaatg ggcgggaagc cgcgcagaaa gaatccccaa   1260

gagggcctgt acaacgagct ccaaaaggat aagatggcag aagcctatag cgagattggt   1320

atgaaagggg aacgcagaag aggcaaaggc cacgacggac tgtaccaggg actcagcacc   1380

gccaccaagg acacctatga cgctcttcac atgcaggccc tgccgcctcg g            1431
```

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)

<223> OTHER INFORMATION: D or K

<400> SEQUENCE: 130

Val Ile Ser Tyr Xaa Gly Ser Asn Lys Tyr Tyr Ala Asp Ser Val Lys
1 5 10 15

Gly

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: D or E
<220> FEATURE:
<221> NAME/KEY: MOD_RES
<222> LOCATION: (6)..(6)
<223> OTHER INFORMATION: P or L
<220> FEATURE:
<221> NAME/KEY: MOD_RES
<222> LOCATION: (7)..(7)
<223> OTHER INFORMATION: S or R

<400> SEQUENCE: 131

Xaa Val Ser Asn Arg Xaa Xaa
1 5

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: T or A

<400> SEQUENCE: 132

Ser Ser Tyr Thr Ser Ser Ser Xaa Leu Tyr Val
1 5 10

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: D or K

<400> SEQUENCE: 133

Ser Tyr Xaa Gly Ser Asn
1 5

<210> SEQ ID NO 134
<211> LENGTH: 3
<212> TYPE: PRT
<213> ORGANISM: Artificial Sequence
<220> FEATURE:
<223> OTHER INFORMATION: Description of Artificial Sequence: Synthetic
peptide <220> FEATURE:
<221> NAME/KEY: MOD_RES
<222> LOCATION: (1)..(1)
<223> OTHER INFORMATION: D or E

<400> SEQUENCE: 134

Xaa Val Ser
1

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (6)..(6)
<223> OTHER INFORMATION: T or A

<400> SEQUENCE: 135

Tyr Thr Ser Ser Ser Xaa Leu Tyr
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: D or K

<400> SEQUENCE: 136

Ile Ser Tyr Xaa Gly Ser Asn Lys
1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Gly Phe Trp Met Ser
1               5

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Asn Ile Lys Gln Asp Gly Ser Glu Lys Tyr Tyr Val Asp Ser Val Arg
1               5                   10                  15

Gly

<210> SEQ ID NO 139
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Ala Leu Asp Tyr Tyr Gly Met Asp Val
1 5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Gly Phe Thr Phe Ser Gly Phe
1 5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Lys Gln Asp Gly Ser Glu
1 5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Gly Phe Thr Phe Ser Gly Phe Trp
1 5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Ile Lys Gln Asp Gly Ser Glu Lys
1 5

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Ala Arg Ala Leu Asp Tyr Tyr Gly Met Asp Val

-continued

```
1               5                   10


<210> SEQ ID NO 145
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Tyr Tyr Gly Met Asp Val Trp Gly Gln Gly Thr
            100                 105                 110

Thr Val Thr Val Ser Ser
        115


<210> SEQ ID NO 146
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

gaagtgcaac tggtggagag cggtggaggg cttgtccagc ccggaggatc gctgcggctg      60

tcctgtgctg cgtccgggtt caccttctcc ggcttctgga tgtcctgggt cagacaggca     120

ccgggaaagg gcctcgaatg ggtggccaac atcaagcagg atggctccga gaagtactac     180

gtcgactccg tgagaggccg cttcaccatc tcccgggaca acgccaagaa ctcgctgtac     240

ctccaaatga atagcctcag ggcggaagat actgctgtgt attactgcgc acgcgccctt     300

gactactacg gcatggacgt ctggggccaa gggaccactg tgaccgtgtc tagc           354


<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Arg Ser Ser Gln Ser Leu Leu Asp Ser Asp Asp Gly Asn Thr Tyr Leu
1               5                   10                  15

Asp


<210> SEQ ID NO 148
<211> LENGTH: 7
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Thr Leu Ser Tyr Arg Ala Ser
1 5

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Thr Gln Arg Leu Glu Phe Pro Ser Ile Thr
1 5 10

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Ser Gln Ser Leu Leu Asp Ser Asp Asp Gly Asn Thr Tyr
1 5 10

<210> SEQ ID NO 151
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Thr Leu Ser
1

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Arg Leu Glu Phe Pro Ser Ile
1 5

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Gln Ser Leu Leu Asp Ser Asp Asp Gly Asn Thr Tyr 1 5 10

<210> SEQ ID NO 154
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Leu Asp Ser
20 25 30

Asp Asp Gly Asn Thr Tyr Leu Asp Trp Tyr Leu Gln Lys Pro Gly Gln
35 40 45

Ser Pro Arg Leu Leu Ile Tyr Thr Leu Ser Tyr Arg Ala Ser Gly Val
50 55 60

Pro Asp Arg Phe Ser Gly Ser Gly Ser Gly Thr Asp Phe Thr Leu Lys
65 70 75 80

Ile Ser Arg Val Glu Ala Glu Asp Val Gly Leu Tyr Tyr Cys Thr Gln
85 90 95

Arg Leu Glu Phe Pro Ser Ile Thr Phe Gly Gln Gly Thr Arg Leu Glu
100 105 110

Ile Lys

<210> SEQ ID NO 155
<211> LENGTH: 342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
gatatcgtga tgacccagac tcccctgtcc ctgcctgtga ctcccggaga accagcctcc 60
atttcctgcc ggtcctccca gtccctgctg gacagcgacg acggcaacac ttacctggac 120
tggtacttgc agaagccggg ccaatcgcct cgcctgctga tctataccct gtcataccgg 180
gcctcaggag tgcctgaccg cttctcggga tcagggagcg ggaccgattt caccctgaaa 240
atttcccgag tggaagccga ggacgtcgga ctgtactact gcacccagcg cctcgaattc 300
ccgtcgatta cgtttggaca gggtacccgg cttgagatca ag 342

<210> SEQ ID NO 156
<211> LENGTH: 252
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Gly Phe
20 25 30

Trp Met Ser Trp Val Arg Gln Ala Pro Gly Lys Gly Leu Glu Trp Val
35 40 45

```
Ala Asn Ile Lys Gln Asp Gly Ser Glu Lys Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Tyr Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Arg Leu Leu Ile
            180                 185                 190

Tyr Thr Leu Ser Tyr Arg Ala Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Leu Tyr Tyr Cys Thr Gln Arg Leu Glu Phe Pro Ser
225                 230                 235                 240

Ile Thr Phe Gly Gln Gly Thr Arg Leu Glu Ile Lys
                245                 250


<210> SEQ ID NO 157
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157

gaagtgcaac tggtggagag cggtggaggg cttgtccagc ccggaggatc gctgcggctg      60

tcctgtgctg cgtccgggtt caccttctcc ggcttctgga tgtcctgggt cagacaggca     120

ccgggaaagg gcctcgaatg ggtggccaac atcaagcagg atggctccga gaagtactac     180

gtcgactccg tgagaggccg cttcaccatc tcccgggaca acgccaagaa ctcgctgtac     240

ctccaaatga atagcctcag ggcggaagat actgctgtgt attactgcgc acgcgccctt     300

gactactacg gcatggacgt ctggggccaa gggaccactg tgaccgtgtc tagcggaggc     360

ggaggttcag gggcggtgg atcaggcgga ggaggatcgg ggggtggtgg atcggatatc     420

gtgatgaccc agactcccct gtccctgcct gtgactcccg gagaaccagc ctccatttcc     480

tgccggtcct cccagtccct gctggacagc gacgacggca acacttacct ggactggtac     540

ttgcagaagc cgggccaatc gcctcgcctg ctgatctata ccctgtcata ccgggcctca     600

ggagtgcctg accgcttctc gggatcaggg agcgggaccg atttcaccct gaaaatttcc     660

cgagtggaag ccgaggacgt cggactgtac tactgcaccc agcgcctcga attcccgtcg     720

attacgtttg gacagggtac ccggcttgag atcaag                               756


<210> SEQ ID NO 158
<211> LENGTH: 475
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Asp Tyr Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Arg Leu Leu Ile
            180                 185                 190

Tyr Thr Leu Ser Tyr Arg Ala Ser Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Leu Tyr Tyr Cys Thr Gln Arg Leu Glu Phe Pro Ser
225                 230                 235                 240

Ile Thr Phe Gly Gln Gly Thr Arg Leu Glu Ile Lys Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Lys Arg Gly Arg Lys Lys Leu Leu Tyr Ile Phe Lys Gln Pro Phe
                325                 330                 335

Met Arg Pro Val Gln Thr Thr Gln Glu Glu Asp Gly Cys Ser Cys Arg
            340                 345                 350

Phe Pro Glu Glu Glu Glu Gly Gly Cys Glu Leu Arg Val Lys Phe Ser
        355                 360                 365

Arg Ser Ala Asp Ala Pro Ala Tyr Gln Gln Gly Gln Asn Gln Leu Tyr
    370                 375                 380
```

```
Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475


<210> SEQ ID NO 159
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

gaagtgcaac tggtggagag cggtggaggg cttgtccagc ccggaggatc gctgcggctg      60

tcctgtgctg cgtccgggtt caccttctcc ggcttctgga tgtcctgggt cagacaggca     120

ccgggaaagg gcctcgaatg ggtggccaac atcaagcagg atggctccga gaagtactac     180

gtcgactccg tgagaggccg cttcaccatc tcccgggaca acgccaagaa ctcgctgtac     240

ctccaaatga atagcctcag ggcggaagat actgctgtgt attactgcgc acgcgccctt     300

gactactacg gcatggacgt ctggggccaa gggaccactg tgaccgtgtc tagcggaggc     360

ggaggttcag gggcggtgg atcaggcgga ggaggatcgg ggggtggtgg atcggatatc     420

gtgatgaccc agactcccct gtccctgcct gtgactcccg gagaaccagc ctccatttcc     480

tgccggtcct cccagtccct gctggacagc gacgacggca acacttacct ggactggtac     540

ttgcagaagc cgggccaatc gcctcgcctg ctgatctata ccctgtcata ccgggcctca     600

ggagtgcctg accgcttctc gggatcaggg agcgggaccg atttcaccct gaaaatttcc     660

cgagtggaag ccgaggacgt cggactgtac tactgcaccc agcgcctcga attcccgtcg     720

attacgtttg gacagggtac ccggcttgag atcaagacca ctaccccagc accgaggcca     780

cccaccccgg ctcctaccat cgcctcccag cctctgtccc tgcgtccgga ggcatgtaga     840

cccgcagctg gtggggccgt gcatacccgg ggtcttgact tcgcctgcga tatctacatt     900

tgggcccctc tggctggtac ttgcggggtc ctgctgcttt cactcgtgat cactctttac     960

tgtaagcgcg gtcggaagaa gctgctgtac atctttaagc aacccttcat gaggcctgtg    1020

cagactactc aagaggagga cggctgttca tgccggttcc cagaggagga ggaaggcggc    1080

tgcgaactgc gcgtgaaatt cagccgcagc gcagatgctc cagcctacca gcaggggcag    1140

aaccagctct acaacgaact caatcttggt cggagagagg agtacgacgt gctggacaag    1200

cggagaggac gggacccaga aatgggcggg aagccgcgca gaaagaatcc ccaagagggc    1260

ctgtacaacg agctccaaaa ggataagatg gcagaagcct atagcgagat tggtatgaaa    1320

ggggaacgca gaagaggcaa aggccacgac ggactgtacc agggactcag caccgccacc    1380

aaggacacct atgacgctct tcacatgcag gccctgccgc ctcgg                    1425
```

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Ser Phe Arg Met Asn
1 5

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Ser Ile Ser Ser Ser Ser Ser Tyr Ile Tyr Tyr Ala Asp Ser Val Lys
1 5 10 15

Gly

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Trp Leu Ser Tyr Tyr Gly Met Asp Val
1 5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Gly Phe Thr Phe Ser Ser Phe
1 5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Ser Ser Ser Ser Ser Tyr
1 5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Gly Phe Thr Phe Ser Ser Phe Arg
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Ile Ser Ser Ser Ser Ser Tyr Ile
1               5

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Ala Arg Trp Leu Ser Tyr Tyr Gly Met Asp Val
1               5                   10

<210> SEQ ID NO 168
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Leu Ser Tyr Tyr Gly Met Asp Val Trp Gly Gln Gly Thr
            100                 105                 110

Thr Val Thr Val Ser Ser
        115

<210> SEQ ID NO 169
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169

```
gaagtgcaac tggtggagag cggtggaggg cttgtcaagc ccggaggatc gctgcggctg     60

tcctgtgctg cgtccgggtt caccttctcc tcgttccgca tgaactgggt cagacaggca    120

ccgggaaagg gcctcgaatg ggtgtcctca atctcatcgt cctcgtccta catctactac    180

gccgactccg tgaaaggccg cttcaccatc tcccgggaca acgccaagaa ctcgctgtac    240

ctccaaatga atagcctcag ggcggaagat actgctgtgt attactgcgc acgctggctt    300

tcctactacg gcatggacgt ctggggccaa gggaccactg tgaccgtgtc tagc          354


<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Thr Leu Ser Phe Arg Ala Ser
1               5


<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Met Gln Arg Ile Gly Phe Pro Ile Thr
1               5


<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Ile Gly Phe Pro Ile
1               5


<210> SEQ ID NO 173
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Phe Arg Ala Ser Gly Val
    50                  55                  60

Pro Asp Arg Phe Ser Gly Ser Gly Ser Gly Thr Asp Phe Thr Leu Lys
```

65 70 75 80

Ile Arg Arg Val Glu Ala Glu Asp Val Gly Val Tyr Tyr Cys Met Gln
85 90 95

Arg Ile Gly Phe Pro Ile Thr Phe Gly Gln Gly Thr Arg Leu Glu Ile
100 105 110

Lys

<210> SEQ ID NO 174
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 174
gatatcgtga tgacccagac tcccctgtcc ctgcctgtga ctcccggaga accagcctcc 60
atttcctgcc ggtcctccca gtccctgctg gacagcgacg acggcaacac ttacctggac 120
tggtacttgc agaagccggg ccaatcgcct cagctgctga tctataccct gtcattccgg 180
gcctcaggag tgcctgaccg cttctcggga tcagggagcg ggaccgattt caccctgaaa 240
attaggcgag tggaagccga ggacgtcgga gtgtactact gcatgcagcg catcggcttc 300
ccgattacgt ttggacaggg tacccggctt gagatcaag 339

<210> SEQ ID NO 175
<211> LENGTH: 251
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 175

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Phe
20 25 30

Arg Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Trp Leu Ser Tyr Tyr Gly Met Asp Val Trp Gly Gln Gly Thr
100 105 110

Thr Val Thr Val Ser Ser Gly Gly Gly Gly Ser Gly Gly Gly Gly Ser
115 120 125

Gly Gly Gly Gly Ser Gly Gly Gly Gly Ser Asp Ile Val Met Thr Gln
130 135 140

Thr Pro Leu Ser Leu Pro Val Thr Pro Gly Glu Pro Ala Ser Ile Ser
145 150 155 160

Cys Arg Ser Ser Gln Ser Leu Leu Asp Ser Asp Asp Gly Asn Thr Tyr
165 170 175

Leu Asp Trp Tyr Leu Gln Lys Pro Gly Gln Ser Pro Gln Leu Leu Ile
180 185 190

```
Tyr Thr Leu Ser Phe Arg Ala Ser Gly Val Pro Asp Arg Phe Ser Gly
        195                 200                 205

Ser Gly Ser Gly Thr Asp Phe Thr Leu Lys Ile Arg Arg Val Glu Ala
    210                 215                 220

Glu Asp Val Gly Val Tyr Tyr Cys Met Gln Arg Ile Gly Phe Pro Ile
225                 230                 235                 240

Thr Phe Gly Gln Gly Thr Arg Leu Glu Ile Lys
                245                 250
```

```
<210> SEQ ID NO 176
<211> LENGTH: 753
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176

gaagtgcaac tggtggagag cggtggaggg cttgtcaagc ccggaggatc gctgcggctg      60

tcctgtgctg cgtccgggtt caccttctcc tcgttccgca tgaactgggt cagacaggca     120

ccgggaaagg gcctcgaatg ggtgtcctca atctcatcgt cctcgtccta catctactac     180

gccgactccg tgaaaggccg cttcaccatc tcccgggaca acgccaagaa ctcgctgtac     240

ctccaaatga atagcctcag ggcggaagat actgctgtgt attactgcgc acgctggctt     300

tcctactacg gcatggacgt ctggggccaa gggaccactg tgaccgtgtc tagcggaggc     360

ggaggttcag gggcggtgg atcaggcgga ggaggatcgg ggggtggtgg atcggatatc     420

gtgatgaccc agactcccct gtccctgcct gtgactcccg gagaaccagc ctccatttcc     480

tgccggtcct cccagtccct gctggacagc gacgacggca acacttacct ggactggtac     540

ttgcagaagc cgggccaatc gcctcagctg ctgatctata ccctgtcatt ccgggcctca     600

ggagtgcctg accgcttctc gggatcaggg agcgggaccg atttcaccct gaaaattagg     660

cgagtggaag ccgaggacgt cggagtgtac tactgcatgc agcgcatcgg cttcccgatt     720

acgtttggac agggtacccg gcttgagatc aag                                  753
```

```
<210> SEQ ID NO 177
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Phe
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Trp Leu Ser Tyr Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Met Thr Gln
    130                 135                 140

Thr Pro Leu Ser Leu Pro Val Thr Pro Gly Glu Pro Ala Ser Ile Ser
145                 150                 155                 160

Cys Arg Ser Ser Gln Ser Leu Leu Asp Ser Asp Asp Gly Asn Thr Tyr
                165                 170                 175

Leu Asp Trp Tyr Leu Gln Lys Pro Gly Gln Ser Pro Gln Leu Leu Ile
            180                 185                 190

Tyr Thr Leu Ser Phe Arg Ala Ser Gly Val Pro Asp Arg Phe Ser Gly
        195                 200                 205

Ser Gly Ser Gly Thr Asp Phe Thr Leu Lys Ile Arg Arg Val Glu Ala
    210                 215                 220

Glu Asp Val Gly Val Tyr Tyr Cys Met Gln Arg Ile Gly Phe Pro Ile
225                 230                 235                 240

Thr Phe Gly Gln Gly Thr Arg Leu Glu Ile Lys Thr Thr Thr Pro Ala
                245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
        275                 280                 285

Arg Gly Leu Asp Phe Ala Cys Asp Ile Tyr Ile Trp Ala Pro Leu Ala
    290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470
```

<210> SEQ ID NO 178
<211> LENGTH: 1422
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 178
gaagtgcaac tggtggagag cggtggaggg cttgtcaagc ccggaggatc gctgcggctg 60
tcctgtgctg cgtccgggtt caccttctcc tcgttccgca tgaactgggt cagacaggca 120
ccgggaaagg gcctcgaatg ggtgtcctca atctcatcgt cctcgtccta catctactac 180
gccgactccg tgaaaggccg cttcaccatc tcccgggaca acgccaagaa ctcgctgtac 240
ctccaaatga atagcctcag ggcggaagat actgctgtgt attactgcgc acgctggctt 300
tcctactacg gcatggacgt ctggggccaa gggaccactg tgaccgtgtc tagcggaggc 360
ggaggttcag gggcggtgg atcaggcgga ggaggatcgg ggggtggtgg atcggatatc 420
gtgatgaccc agactcccct gtccctgcct gtgactcccg gagaaccagc ctccatttcc 480
tgccggtcct cccagtccct gctggacagc gacgacggca acacttacct ggactggtac 540
ttgcagaagc cgggccaatc gcctcagctg ctgatctata ccctgtcatt ccgggcctca 600
ggagtgcctg accgcttctc gggatcaggg agcgggaccg atttcaccct gaaaattagg 660
cgagtggaag ccgaggacgt cggagtgtac tactgcatgc agcgcatcgg cttcccgatt 720
acgtttggac agggtacccg gcttgagatc aagaccacta ccccagcacc gaggccaccc 780
accccggctc ctaccatcgc ctcccagcct ctgtccctgc gtccggaggc atgtagaccc 840
gcagctggtg gggccgtgca tacccggggt cttgacttcg cctgcgatat ctacatttgg 900
gcccctctgg ctggtacttg cggggtcctg ctgctttcac tcgtgatcac tctttactgt 960
aagcgcggtc ggaagaagct gctgtacatc tttaagcaac ccttcatgag gcctgtgcag 1020
actactcaag aggaggacgg ctgttcatgc cggttcccag aggaggagga aggcggctgc 1080
gaactgcgcg tgaaattcag ccgcagcgca gatgctccag cctaccagca ggggcagaac 1140
cagctctaca acgaactcaa tcttggtcgg agagaggagt acgacgtgct ggacaagcgg 1200
agaggacggg acccagaaat gggcgggaag ccgcgcagaa agaatcccca agagggcctg 1260
tacaacgagc tccaaaagga taagatggca gaagcctata gcgagattgg tatgaaaggg 1320
gaacgcagaa gaggcaaagg ccacgacgga ctgtaccagg gactcagcac cgccaccaag 1380
gacacctatg acgctcttca catgcaggcc ctgccgcctc gg 1422

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: G or S
<220> FEATURE:
<221> NAME/KEY: MOD_RES
<222> LOCATION: (3)..(3)
<223> OTHER INFORMATION: W or R
<220> FEATURE:
<221> NAME/KEY: MOD_RES
<222> LOCATION: (5)..(5)
<223> OTHER INFORMATION: S or N

<400> SEQUENCE: 179

Xaa Phe Xaa Met Xaa
1 5

```
<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N or S
<220> FEATURE:
<221> NAME/KEY: MOD_RES
<222> LOCATION: (3)..(3)
<223> OTHER INFORMATION: K or S
<220> FEATURE:
<221> NAME/KEY: MOD_RES
<222> LOCATION: (4)..(4)
<223> OTHER INFORMATION: Q or S
<220> FEATURE:
<221> NAME/KEY: MOD_RES
<222> LOCATION: (5)..(5)
<223> OTHER INFORMATION: D or S
<220> FEATURE:
<221> NAME/KEY: MOD_RES
<222> LOCATION: (6)..(6)
<223> OTHER INFORMATION: G or S
<220> FEATURE:
<221> NAME/KEY: MOD_RES
<222> LOCATION: (8)..(8)
<223> OTHER INFORMATION: E or Y
<220> FEATURE:
<221> NAME/KEY: MOD_RES
<222> LOCATION: (9)..(9)
<223> OTHER INFORMATION: K or I
<220> FEATURE:
<221> NAME/KEY: MOD_RES
<222> LOCATION: (12)..(12)
<223> OTHER INFORMATION: V or A
<220> FEATURE:
<221> NAME/KEY: MOD_RES
<222> LOCATION: (16)..(16)
<223> OTHER INFORMATION: R or K

<400> SEQUENCE: 180

Xaa Ile Xaa Xaa Xaa Xaa Ser Xaa Xaa Tyr Tyr Xaa Asp Ser Val Xaa
1               5                   10                  15

Gly


<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or W
<220> FEATURE:
<221> NAME/KEY: MOD_RES
<222> LOCATION: (3)..(3)
<223> OTHER INFORMATION: D or S

<400> SEQUENCE: 181

Xaa Leu Xaa Tyr Tyr Gly Met Asp Val
1               5


<210> SEQ ID NO 182
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Y or F

<400> SEQUENCE: 182

Thr Leu Ser Xaa Arg Ala Ser
1               5


<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: T or M
<220> FEATURE:
<221> NAME/KEY: MOD_RES
<222> LOCATION: (4)..(4)
<223> OTHER INFORMATION: L or I
<220> FEATURE:
<221> NAME/KEY: MOD_RES
<222> LOCATION: (5)..(5)
<223> OTHER INFORMATION: E or G
<220> FEATURE:
<221> NAME/KEY: MOD_RES
<222> LOCATION: (8)..(8)
<223> OTHER INFORMATION: S or absent

<400> SEQUENCE: 183

Xaa Gln Arg Xaa Xaa Phe Pro Xaa Ile Thr
1               5                   10


<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: G or S

<400> SEQUENCE: 184

Gly Phe Thr Phe Ser Xaa Phe
1               5


<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: K or S
<220> FEATURE:
<221> NAME/KEY: MOD_RES
<222> LOCATION: (2)..(2)
<223> OTHER INFORMATION: Q or S
<220> FEATURE:
<221> NAME/KEY: MOD_RES
<222> LOCATION: (3)..(3)
```

<223> OTHER INFORMATION: D or S
<220> FEATURE:
<221> NAME/KEY: MOD_RES
<222> LOCATION: (4)..(4)
<223> OTHER INFORMATION: G or S
<220> FEATURE:
<221> NAME/KEY: MOD_RES
<222> LOCATION: (6)..(6)
<223> OTHER INFORMATION: E or Y

<400> SEQUENCE: 185

Xaa Xaa Xaa Xaa Ser Xaa
1 5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: L or I
<220> FEATURE:
<221> NAME/KEY: MOD_RES
<222> LOCATION: (3)..(3)
<223> OTHER INFORMATION: E or G
<220> FEATURE:
<221> NAME/KEY: MOD_RES
<222> LOCATION: (6)..(6)
<223> OTHER INFORMATION: S or absent

<400> SEQUENCE: 186

Arg Xaa Xaa Phe Pro Xaa Ile
1 5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (6)..(6)
<223> OTHER INFORMATION: G or S
<220> FEATURE:
<221> NAME/KEY: MOD_RES
<222> LOCATION: (8)..(8)
<223> OTHER INFORMATION: W or R

<400> SEQUENCE: 187

Gly Phe Thr Phe Ser Xaa Phe Xaa
1 5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: K or S
<220> FEATURE:
<221> NAME/KEY: MOD_RES
<222> LOCATION: (3)..(3)
<223> OTHER INFORMATION: Q or S
<220> FEATURE:
<221> NAME/KEY: MOD_RES
<222> LOCATION: (4)..(4)
<223> OTHER INFORMATION: D or S
<220> FEATURE:
<221> NAME/KEY: MOD_RES
<222> LOCATION: (5)..(5)
<223> OTHER INFORMATION: G or S
<220> FEATURE:
<221> NAME/KEY: MOD_RES
<222> LOCATION: (7)..(7)
<223> OTHER INFORMATION: E or Y
<220> FEATURE:
<221> NAME/KEY: MOD_RES
<222> LOCATION: (8)..(8)
<223> OTHER INFORMATION: K or I

<400> SEQUENCE: 188

Ile Xaa Xaa Xaa Xaa Ser Xaa Xaa
1 5

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: A or W
<220> FEATURE:
<221> NAME/KEY: MOD_RES
<222> LOCATION: (5)..(5)
<223> OTHER INFORMATION: D or S

<400> SEQUENCE: 189

Ala Arg Xaa Leu Xaa Tyr Tyr Gly Met Asp Val
1 5 10

<210> SEQ ID NO 190
<211> LENGTH: 521
<212> TYPE: DNA
<213> ORGANISM: Unknown
<220> FEATURE:
<223> OTHER INFORMATION: Description of Unknown:
PGK Promoter sequence

<400> SEQUENCE: 190
acccctctct ccagccacta agccagttgc tccctcggct gacggctgca cgcgaggcct 60
ccgaacgtct tacgccttgt ggcgcgcccg tccttgtccc gggtgtgatg gcggggtgtg 120
gggcggaggg cgtggcgggg aagggccggc gacgagagcc gcgcgggacg actcgtcggc 180
gataaccggt gtcgggtagc gccagccgcg cgacggtaac gagggaccgc gacaggcaga 240
cgctcccatg atcactctgc acgccgaagg caaatagtgc aggccgtgcg gcgcttggcg 300
ttccttggaa gggctgaatc cccgcctcgt ccttcgcagc ggccccccgg gtgttcccat 360
cgccgcttct aggcccactg cgacgcttgc ctgcacttct tacacgctct gggtcccagc 420
cgcggcgacg caaagggcct tggtgcgggt ctcgtcggcg cagggacgcg tttgggtccc 480
gacggaacct tttccgcgtt ggggttgggg caccataagc t 521

<210> SEQ ID NO 191
<211> LENGTH: 221
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 191
acccctctct ccagccacta agccagttgc tccctcggct gacggctgca cgcgaggcct     60
ccgaacgtct tacgccttgt ggcgcgcccg tccttgtccc gggtgtgatg gcggggtgtg    120
gggcggaggg cgtggcgggg aagggccggc gacgagagcc gcgcgggacg actcgtcggc    180
gataaccggt gtcgggtagc gccagccgcg cgacggtaac g                        221

<210> SEQ ID NO 192
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
acccctctct ccagccacta agccagttgc tccctcggct gacggctgca cgcgaggcct     60
ccgaacgtct tacgccttgt ggcgcgcccg tccttgtccc gggtgtgatg gcggggtgtg    120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga    240
cgctcccatg atcactctgc acgccgaagg caaatagtgc aggccgtgcg gcgcttggcg    300
ttccttggaa gggctgaatc cccg                                           324

<210> SEQ ID NO 193
<211> LENGTH: 422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
acccctctct ccagccacta agccagttgc tccctcggct gacggctgca cgcgaggcct     60
ccgaacgtct tacgccttgt ggcgcgcccg tccttgtccc gggtgtgatg gcggggtgtg    120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga    240
cgctcccatg atcactctgc acgccgaagg caaatagtgc aggccgtgcg gcgcttggcg    300
ttccttggaa gggctgaatc cccgcctcgt ccttcgcagc ggccccccgg gtgttcccat    360
cgccgcttct aggcccactg cgacgcttgc ctgcacttct tacacgctct gggtcccagc    420
cg                                                                   422

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198
<211> LENGTH: 118
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198
acccctctct ccagccacta agccagttgc tccctcggct gacggctgca cgcgaggcct 60
ccgaacgtct tacgccttgt ggcgcgcccg tccttgtccc gggtgtgatg gcggggtg 118

<210> SEQ ID NO 199
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 199
atggccctcc ctgtcaccgc cctgctgctt ccgctggctc ttctgctcca cgccgctcgg 60
ccc 63

<210> SEQ ID NO 200
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

Glu Val Gln Leu Val Glu Ser Gly Gly Gly Leu Val Gln Pro Gly Gly
1 5 10 15

Ser Leu Arg Leu Ser Cys Ala Val Ser Gly Phe Ala Leu Ser Asn His
20 25 30

Gly Met Ser Trp Val Arg Arg Ala Pro Gly Lys Gly Leu Glu Trp Val
35 40 45

Ser Gly Ile Val Tyr Ser Gly Ser Thr Tyr Tyr Ala Ala Ser Val Lys
50 55 60

Gly Arg Phe Thr Ile Ser Arg Asp Asn Ser Arg Asn Thr Leu Tyr Leu
65 70 75 80

Gln Met Asn Ser Leu Arg Pro Glu Asp Thr Ala Ile Tyr Tyr Cys Ser
85 90 95

Ala His Gly Gly Glu Ser Asp Val Trp Gly Gln Gly Thr Thr Val Thr
100 105 110

Val Ser Ser Ala Ser Gly Gly Gly Gly Ser Gly Gly Gly Gly Ser Gly
115 120 125

Gly Gly Gly Ser Asp Ile Gln Leu Thr Gln Ser Pro Ser Ser Leu Ser
130 135 140

```
Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Thr Phe Gly Gln Gly Thr Lys Val Glu Ile Lys
225                 230                 235


<210> SEQ ID NO 201
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

gaagtgcaat tggtggaatc agggggagga cttgtgcagc ctggaggatc gctgagactg      60

tcatgtgccg tgtccggctt tgccctgtcc aaccacggga tgtcctgggt ccgccgcgcg     120

cctggaaagg gcctcgaatg ggtgtcgggt attgtgtaca gcggtagcac ctactatgcc     180

gcatccgtga aggggagatt caccatcagc cgggacaact ccaggaacac tctgtacctc     240

caaatgaatt cgctgaggcc agaggacact gccatctact actgctccgc gcatggcgga     300

gagtccgacg tctggggaca ggggaccacc gtgaccgtgt ctagcgcgtc cggcggaggc     360

ggcagcgggg gtggtggttc agggggcggc ggatcggaca tccagctcac ccagtccccg     420

agctcgctgt ccgcctccgt gggagatcgg gtcaccatca cgtgccgcgc cagccagtcg     480

atttcctcct acctgaactg gtaccaacag aagcccggaa aagccccgaa gcttctcatc     540

tacgccgcct cgagcctgca gtcaggagtg ccctcacggt tctccggctc cggttccggt     600

actgatttca ccctgaccat ttcctccctg caaccggagg acttcgctac ttactactgc     660

cagcagtcgt actccacccc ctacactttc ggacaaggca ccaaggtcga aatcaag        717


<210> SEQ ID NO 202
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65
```

<210> SEQ ID NO 203
<211> LENGTH: 207
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203
accactaccc cagcaccgag gccacccacc ccggctccta ccatcgcctc ccagcctctg 60
tccctgcgtc cggaggcatg tagacccgca gctggtgggg ccgtgcatac ccggggtctt 120
gacttcgcct gcgatatcta catttgggcc cctctggctg gtacttgcgg ggtcctgctg 180
ctttcactcg tgatcactct ttactgt 207

<210> SEQ ID NO 204
<211> LENGTH: 126
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 204
aagcgcggtc ggaagaagct gctgtacatc tttaagcaac ccttcatgag gcctgtgcag 60
actactcaag aggaggacgg ctgttcatgc cggttcccag aggaggagga aggcggctgc 120
gaactg 126

<210> SEQ ID NO 205
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
cgcgtgaaat tcagccgcag cgcagatgct ccagcctacc agcaggggca gaaccagctc 60
tacaacgaac tcaatcttgg tcggagagag gagtacgacg tgctggacaa gcggagagga 120
cgggacccag aaatgggcgg gaagccgcgc agaaagaatc cccaagaggg cctgtacaac 180
gagctccaaa aggataagat ggcagaagcc tatagcgaga ttggtatgaa aggggaacgc 240
agaagaggca aaggccacga cggactgtac cagggactca gcaccgccac caaggacacc 300
tatgacgctc ttcacatgca ggccctgccg cctcgg 336

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Gly Ser Gly
1

<210> SEQ ID NO 207
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207 ggaagcgga 9

<210> SEQ ID NO 208
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Thr Asn Phe Ser Leu Leu Lys Gln Ala Gly Asp Val Glu Glu Asn
1               5                   10                  15

Pro Gly Pro

<210> SEQ ID NO 209
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gctactaact tcagcctgct gaagcaggct ggagacgtgg aggagaaccc tggacct 57

<210> SEQ ID NO 210
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
atggccttac cagtgaccgc cttgctcctg ccgctggcct tgctgctcca cgccgccagg 60
ccg 63

<210> SEQ ID NO 211
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr

-continued

```
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser
```

<210> SEQ ID NO 212
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212

```
gaaattgtga tgacccagtc acccgccact cttagccttt cacccggtga gcgcgcaacc     60

ctgtcttgca gagcctccca agacatctca aaatacctta attggtatca acagaagccc    120

ggacaggctc ctcgccttct gatctaccac accagccggc tccattctgg aatccctgcc    180

aggttcagcg gtagcggatc tgggaccgac tacaccctca ctatcagctc actgcagcca    240

gaggacttcg ctgtctattt ctgtcagcaa gggaacaccc tgccctacac ctttggacag    300

ggcaccaagc tcgagattaa aggtggaggt ggcagcggag gaggtgggtc cggcggtgga    360

ggaagccagg tccaactcca agaaagcgga ccgggtcttg tgaagccatc agaaactctt    420

tcactgactt gtactgtgag cggagtgtct ctccccgatt acggggtgtc ttggatcaga    480

cagccaccgg ggaagggtct ggaatggatt ggagtgattt ggggctctga gactacttac    540

taccaatcat ccctcaagtc acgcgtcacc atctcaaagg acaactctaa gaatcaggtg    600

tcactgaaac tgtcatctgt gaccgcagcc gacaccgccg tgtactattg cgctaagcat    660

tactattatg gcgggagcta cgcaatggat tactggggac agggtactct ggtcaccgtg    720

tccagc                                                               726
```

<210> SEQ ID NO 213
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213

-continued

```
accacgacgc cagcgccgcg accaccaaca ccggcgccca ccatcgcgtc gcagcccctg     60

tccctgcgcc cagaggcgtg ccggccagcg gcgggggcg cagtgcacac gagggggctg     120

gacttcgcct gtgatatcta catctgggcg cccttggccg ggacttgtgg ggtccttctc    180

ctgtcactgg ttatcaccct ttactgc                                        207
```

<210> SEQ ID NO 214
<211> LENGTH: 1000
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Arg Glu Trp Trp Gly Glu Ser Trp Leu
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
        195                 200                 205

Leu Ile Tyr Ala Ala Ser Ser Leu Gln Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
                245                 250                 255

Pro Leu Thr Phe Gly Gln Gly Thr Lys Val Glu Ile Lys Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320
```

-continued

```
Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg Gly Ser Gly Ala
                485                 490                 495

Thr Asn Phe Ser Leu Leu Lys Gln Ala Gly Asp Val Glu Glu Asn Pro
            500                 505                 510

Gly Pro Met Ala Leu Pro Val Thr Ala Leu Leu Leu Pro Leu Ala Leu
        515                 520                 525

Leu Leu His Ala Ala Arg Pro Glu Ile Val Met Thr Gln Ser Pro Ala
    530                 535                 540

Thr Leu Ser Leu Ser Pro Gly Glu Arg Ala Thr Leu Ser Cys Arg Ala
545                 550                 555                 560

Ser Gln Asp Ile Ser Lys Tyr Leu Asn Trp Tyr Gln Gln Lys Pro Gly
                565                 570                 575

Gln Ala Pro Arg Leu Leu Ile Tyr His Thr Ser Arg Leu His Ser Gly
            580                 585                 590

Ile Pro Ala Arg Phe Ser Gly Ser Gly Ser Gly Thr Asp Tyr Thr Leu
        595                 600                 605

Thr Ile Ser Ser Leu Gln Pro Glu Asp Phe Ala Val Tyr Phe Cys Gln
    610                 615                 620

Gln Gly Asn Thr Leu Pro Tyr Thr Phe Gly Gln Gly Thr Lys Leu Glu
625                 630                 635                 640

Ile Lys Gly Gly Gly Gly Ser Gly Gly Gly Gly Ser Gly Gly Gly Gly
                645                 650                 655

Ser Gln Val Gln Leu Gln Glu Ser Gly Pro Gly Leu Val Lys Pro Ser
            660                 665                 670

Glu Thr Leu Ser Leu Thr Cys Thr Val Ser Gly Val Ser Leu Pro Asp
        675                 680                 685

Tyr Gly Val Ser Trp Ile Arg Gln Pro Pro Gly Lys Gly Leu Glu Trp
    690                 695                 700

Ile Gly Val Ile Trp Gly Ser Glu Thr Thr Tyr Tyr Gln Ser Ser Leu
705                 710                 715                 720

Lys Ser Arg Val Thr Ile Ser Lys Asp Asn Ser Lys Asn Gln Val Ser
                725                 730                 735

Leu Lys Leu Ser Ser Val Thr Ala Ala Asp Thr Ala Val Tyr Tyr Cys
```

-continued

```
            740                 745                 750

Ala Lys His Tyr Tyr Tyr Gly Gly Ser Tyr Ala Met Asp Tyr Trp Gly
        755                 760                 765

Gln Gly Thr Leu Val Thr Val Ser Ser Thr Thr Thr Pro Ala Pro Arg
    770                 775                 780

Pro Pro Thr Pro Ala Pro Thr Ile Ala Ser Gln Pro Leu Ser Leu Arg
785                 790                 795                 800

Pro Glu Ala Cys Arg Pro Ala Ala Gly Gly Ala Val His Thr Arg Gly
                805                 810                 815

Leu Asp Phe Ala Cys Asp Ile Tyr Ile Trp Ala Pro Leu Ala Gly Thr
            820                 825                 830

Cys Gly Val Leu Leu Leu Ser Leu Val Ile Thr Leu Tyr Cys Lys Arg
        835                 840                 845

Gly Arg Lys Lys Leu Leu Tyr Ile Phe Lys Gln Pro Phe Met Arg Pro
    850                 855                 860

Val Gln Thr Thr Gln Glu Glu Asp Gly Cys Ser Cys Arg Phe Pro Glu
865                 870                 875                 880

Glu Glu Glu Gly Gly Cys Glu Leu Arg Val Lys Phe Ser Arg Ser Ala
                885                 890                 895

Asp Ala Pro Ala Tyr Gln Gln Gly Gln Asn Gln Leu Tyr Asn Glu Leu
            900                 905                 910

Asn Leu Gly Arg Arg Glu Glu Tyr Asp Val Leu Asp Lys Arg Arg Gly
        915                 920                 925

Arg Asp Pro Glu Met Gly Gly Lys Pro Arg Arg Lys Asn Pro Gln Glu
    930                 935                 940

Gly Leu Tyr Asn Glu Leu Gln Lys Asp Lys Met Ala Glu Ala Tyr Ser
945                 950                 955                 960

Glu Ile Gly Met Lys Gly Glu Arg Arg Arg Gly Lys Gly His Asp Gly
                965                 970                 975

Leu Tyr Gln Gly Leu Ser Thr Ala Thr Lys Asp Thr Tyr Asp Ala Leu
            980                 985                 990

His Met Gln Ala Leu Pro Pro Arg
        995                 1000
```

<210> SEQ ID NO 215
<211> LENGTH: 3000
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 215

```
atggccctcc ctgtcaccgc cctgctgctt ccgctggctc ttctgctcca cgccgctcgg     60

cccgaagtgc agttgctgga gtcaggcgga ggactggtgc agcccggagg atcgcttcgc    120

ttgagctgcg cagcctcagg ctttaccttc tcctcctacg ccatgtcctg ggtcagacag    180

gctcccggga agggactgga atgggtgtcc gccattagcg gttccggcgg aagcacttac    240

tatgccgact ctgtgaaggg ccgcttcact atctcccggg acaactccaa gaacaccctg    300

tatctccaaa tgaattccct gagggccgaa gataccgcgg tgtactactg cgctagacgg    360

gagtggtggg gagaaagctg gctgttcgac tactggggac agggcactct cgtgactgtg    420

tcctccggtg gtggtggatc ggggggtggt ggttcgggcg gaggaggatc tggaggagga    480

gggtcggaca ttcaaatgac tcagtccccg tcctccctct ccgcctccgt gggagatcgc    540
```

-continued

```
gtcacgatca cgtgcagggc cagccagagc atctccagct acctgaactg gtaccagcag    600
aagccaggga aggcaccgaa gctcctgatc tacgccgcta gctcgctgca gtccggcgtc    660
ccttcacggt tctcgggatc gggctcaggc accgacttca ccctgaccat tagcagcctg    720
cagccggagg acttcgcgac atactactgt cagcagtcat actccacccc tctgaccttc    780
ggccaaggga ccaaagtgga gatcaagacc actaccccag caccgaggcc acccaccccg    840
gctcctacca tcgcctccca gcctctgtcc ctgcgtccgg aggcatgtag acccgcagct    900
ggtggggccg tgcatacccg ggtcttgac ttcgcctgcg atatctacat ttgggcccct    960
ctggctggta cttgcggggt cctgctgctt tcactcgtga tcactcttta ctgtaagcgc   1020
ggtcggaaga agctgctgta catctttaag caacccttca tgaggcctgt gcagactact   1080
caagaggagg acggctgttc atgccggttc ccagaggagg aggaaggcgg ctgcgaactg   1140
cgcgtgaaat tcagccgcag cgcagatgct ccagcctacc agcaggggca gaaccagctc   1200
tacaacgaac tcaatcttgg tcggagagag gagtacgacg tgctggacaa gcggagagga   1260
cgggacccag aaatgggcgg gaagccgcgc agaaagaatc cccaagaggg cctgtacaac   1320
gagctccaaa aggataagat ggcagaagcc tatagcgaga ttggtatgaa aggggaacgc   1380
agaagaggca aaggccacga cggactgtac cagggactca gcaccgccac caaggacacc   1440
tatgacgctc ttcacatgca ggccctgccg cctcggggaa gcggagctac taacttcagc   1500
ctgctgaagc aggctggaga cgtggaggag aaccctggac ctatggcctt accagtgacc   1560
gccttgctcc tgccgctggc cttgctgctc cacgccgcca ggccggaaat tgtgatgacc   1620
cagtcacccg ccactcttag cctttcaccc ggtgagcgcg caaccctgtc ttgcagagcc   1680
tcccaagaca tctcaaaata ccttaattgg tatcaacaga agcccggaca ggctcctcgc   1740
cttctgatct accacaccag ccggctccat tctggaatcc ctgccaggtt cagcggtagc   1800
ggatctggga ccgactacac cctcactatc agctcactgc agccagagga cttcgctgtc   1860
tatttctgtc agcaagggaa caccctgccc tacaccttttg gacagggcac caagctcgag   1920
attaaaggtg gaggtggcag cggaggaggt gggtccggcg gtggaggaag ccaggtccaa   1980
ctccaagaaa gcggaccggg tcttgtgaag ccatcagaaa ctctttcact gacttgtact   2040
gtgagcggag tgtctctccc cgattacggg gtgtcttgga tcagacagcc accggggaag   2100
ggtctggaat ggattggagt gatttggggc tctgagacta cttactacca atcatccctc   2160
aagtcacgcg tcaccatctc aaaggacaac tctaagaatc aggtgtcact gaaactgtca   2220
tctgtgaccg cagccgacac cgccgtgtac tattgcgcta agcattacta ttatggcggg   2280
agctacgcaa tggattactg ggacagggt actctggtca ccgtgtccag caccacgacg   2340
ccagcgccgc gaccaccaac accggcgccc accatcgcgt cgcagcccct gtccctgcgc   2400
ccagaggcgt gccggccagc ggcgggggggc gcagtgcaca cgagggggct ggacttcgcc   2460
tgtgatatct acatctgggc gcccttggcc gggacttgtg gggtccttct cctgtcactg   2520
gttatcaccc tttactgcaa acggggcaga aagaaactcc tgtatatatt caaacaacca   2580
tttatgagac cagtacaaac tactcaagag gaagatggct gtagctgccg atttccagaa   2640
gaagaagaag gaggatgtga actgagagtg aagttcagca ggagcgcaga cgcccccgcg   2700
taccagcagg gccagaacca gctctataac gagctcaatc taggacgaag agaggagtac   2760
gatgttttgg acaagagacg tggccgggac cctgagatgg ggggaaagcc gagaaggaag   2820
aaccctcagg aaggcctgta caatgaactg cagaaagata agatggcgga ggcctacagt   2880
gagattggga tgaaaggcga gcgccggagg ggcaaggggc acgatggcct ttaccagggt   2940
```

ctcagtacag ccaccaagga cacctacgac gcccttcaca tgcaggccct gccccctcgc 3000

<210> SEQ ID NO 216
<211> LENGTH: 1001
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 216

Met Ala Leu Pro Val Thr Ala Leu Leu Leu Pro Leu Ala Leu Leu Leu
1 5 10 15

His Ala Ala Arg Pro Gln Val Gln Leu Gln Glu Ser Gly Gly Gly Val
20 25 30

Val Gln Pro Gly Arg Ser Leu Arg Leu Ser Cys Ala Ala Ser Gly Phe
35 40 45

Thr Phe Ser Ser Tyr Gly Met His Trp Val Arg Gln Ala Pro Gly Lys
50 55 60

Gly Leu Glu Trp Val Ala Val Ile Ser Tyr Asp Gly Ser Asn Lys Tyr
65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Gly Gly Ser Gly Tyr Ala Leu His Asp Asp Tyr
115 120 125

Tyr Gly Leu Asp Val Trp Gly Gln Gly Thr Leu Val Thr Val Ser Ser
130 135 140

Gly Gly Gly Gly Ser Gly Gly Gly Gly Ser Gly Gly Gly Gly Ser Gln
145 150 155 160

Ser Ala Leu Thr Gln Pro Ala Ser Val Ser Gly Ser Pro Gly Gln Ser
165 170 175

Ile Thr Ile Ser Cys Thr Gly Thr Ser Ser Asp Val Gly Gly Tyr Asn
180 185 190

Tyr Val Ser Trp Tyr Gln Gln His Pro Gly Lys Ala Pro Lys Leu Met
195 200 205

Ile Tyr Asp Val Ser Asn Arg Pro Ser Gly Val Ser Asn Arg Phe Ser
210 215 220

Gly Ser Lys Ser Gly Asn Thr Ala Ser Leu Thr Ile Ser Gly Leu Gln
225 230 235 240

Ala Glu Asp Glu Ala Asp Tyr Tyr Cys Ser Ser Tyr Thr Ser Ser Ser
245 250 255

Thr Leu Tyr Val Phe Gly Ser Gly Thr Lys Val Thr Val Leu Thr Thr
260 265 270

Thr Pro Ala Pro Arg Pro Pro Thr Pro Ala Pro Thr Ile Ala Ser Gln
275 280 285

Pro Leu Ser Leu Arg Pro Glu Ala Cys Arg Pro Ala Ala Gly Gly Ala
290 295 300

Val His Thr Arg Gly Leu Asp Phe Ala Cys Asp Ile Tyr Ile Trp Ala
305 310 315 320

Pro Leu Ala Gly Thr Cys Gly Val Leu Leu Leu Ser Leu Val Ile Thr
325 330 335

Leu Tyr Cys Lys Arg Gly Arg Lys Lys Leu Leu Tyr Ile Phe Lys Gln
340 345 350

-continued

```
Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Ser Gly
                485                 490                 495

Ala Thr Asn Phe Ser Leu Leu Lys Gln Ala Gly Asp Val Glu Glu Asn
            500                 505                 510

Pro Gly Pro Met Ala Leu Pro Val Thr Ala Leu Leu Leu Pro Leu Ala
        515                 520                 525

Leu Leu Leu His Ala Ala Arg Pro Glu Ile Val Met Thr Gln Ser Pro
    530                 535                 540

Ala Thr Leu Ser Leu Ser Pro Gly Glu Arg Ala Thr Leu Ser Cys Arg
545                 550                 555                 560

Ala Ser Gln Asp Ile Ser Lys Tyr Leu Asn Trp Tyr Gln Gln Lys Pro
                565                 570                 575

Gly Gln Ala Pro Arg Leu Leu Ile Tyr His Thr Ser Arg Leu His Ser
            580                 585                 590

Gly Ile Pro Ala Arg Phe Ser Gly Ser Gly Ser Gly Thr Asp Tyr Thr
        595                 600                 605

Leu Thr Ile Ser Ser Leu Gln Pro Glu Asp Phe Ala Val Tyr Phe Cys
    610                 615                 620

Gln Gln Gly Asn Thr Leu Pro Tyr Thr Phe Gly Gln Gly Thr Lys Leu
625                 630                 635                 640

Glu Ile Lys Gly Gly Gly Gly Ser Gly Gly Gly Gly Ser Gly Gly Gly
                645                 650                 655

Gly Ser Gln Val Gln Leu Gln Glu Ser Gly Pro Gly Leu Val Lys Pro
            660                 665                 670

Ser Glu Thr Leu Ser Leu Thr Cys Thr Val Ser Gly Val Ser Leu Pro
        675                 680                 685

Asp Tyr Gly Val Ser Trp Ile Arg Gln Pro Pro Gly Lys Gly Leu Glu
    690                 695                 700

Trp Ile Gly Val Ile Trp Gly Ser Glu Thr Thr Tyr Tyr Gln Ser Ser
705                 710                 715                 720

Leu Lys Ser Arg Val Thr Ile Ser Lys Asp Asn Ser Lys Asn Gln Val
                725                 730                 735

Ser Leu Lys Leu Ser Ser Val Thr Ala Ala Asp Thr Ala Val Tyr Tyr
            740                 745                 750

Cys Ala Lys His Tyr Tyr Tyr Gly Gly Ser Tyr Ala Met Asp Tyr Trp
        755                 760                 765
```

-continued

```
Gly Gln Gly Thr Leu Val Thr Val Ser Ser Thr Thr Thr Pro Ala Pro
    770                 775                 780

Arg Pro Pro Thr Pro Ala Pro Thr Ile Ala Ser Gln Pro Leu Ser Leu
785                 790                 795                 800

Arg Pro Glu Ala Cys Arg Pro Ala Ala Gly Gly Ala Val His Thr Arg
                805                 810                 815

Gly Leu Asp Phe Ala Cys Asp Ile Tyr Ile Trp Ala Pro Leu Ala Gly
            820                 825                 830

Thr Cys Gly Val Leu Leu Leu Ser Leu Val Ile Thr Leu Tyr Cys Lys
        835                 840                 845

Arg Gly Arg Lys Lys Leu Leu Tyr Ile Phe Lys Gln Pro Phe Met Arg
    850                 855                 860

Pro Val Gln Thr Thr Gln Glu Glu Asp Gly Cys Ser Cys Arg Phe Pro
865                 870                 875                 880

Glu Glu Glu Glu Gly Gly Cys Glu Leu Arg Val Lys Phe Ser Arg Ser
                885                 890                 895

Ala Asp Ala Pro Ala Tyr Gln Gln Gly Gln Asn Gln Leu Tyr Asn Glu
            900                 905                 910

Leu Asn Leu Gly Arg Arg Glu Glu Tyr Asp Val Leu Asp Lys Arg Arg
        915                 920                 925

Gly Arg Asp Pro Glu Met Gly Gly Lys Pro Arg Arg Lys Asn Pro Gln
    930                 935                 940

Glu Gly Leu Tyr Asn Glu Leu Gln Lys Asp Lys Met Ala Glu Ala Tyr
945                 950                 955                 960

Ser Glu Ile Gly Met Lys Gly Glu Arg Arg Arg Gly Lys Gly His Asp
                965                 970                 975

Gly Leu Tyr Gln Gly Leu Ser Thr Ala Thr Lys Asp Thr Tyr Asp Ala
            980                 985                 990

Leu His Met Gln Ala Leu Pro Pro  Arg
        995                 1000
```

```
<210> SEQ ID NO 217
<211> LENGTH: 3003
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217

atggccctcc ctgtcaccgc cctgctgctt ccgctggctc ttctgctcca cgccgctcgg      60

ccccaagtgc agctgcagga atccggtggc ggagtcgtgc agcctggaag gagcctgaga     120

ctctcatgcg ccgcgtcagg gttcaccttt tcctcctacg ggatgcattg ggtcagacag     180

gcccccggaa agggactcga atgggtggct gtgatcagct acgacggctc caacaagtac     240

tacgccgact ccgtgaaagg ccggttcact atctcccggg acaactccaa gaacacgctg     300

tatctgcaaa tgaattcact gcgcgcggag gataccgctg tgtactactg cggtggctcc     360

ggttacgccc tgcacgatga ctattacggc cttgacgtct ggggccaggg aaccctcgtg     420

actgtgtcca gcggtggagg aggttcgggc ggaggaggat caggaggggg tggatcgcag     480

agcgcactga ctcagccggc atccgtgtcc ggtagccccg gacagtcgat taccatctcc     540

tgtaccggca cctcctccga cgtgggaggg tacaactacg tgtcgtggta ccagcagcac     600

ccaggaaagg cccctaagtt gatgatctac gatgtgtcaa accgcccgtc tggagtctcc     660

aaccggttct ccggctccaa gtccggcaac accgccagcc tgaccattag cgggctgcaa     720
```

```
gccgaggatg aggccgacta ctactgctcg agctacacat cctcgagcac cctctacgtg    780
ttcggctcgg ggactaaggt caccgtgctg accactaccc cagcaccgag gccacccacc    840
ccggctccta ccatcgcctc ccagcctctg tccctgcgtc cggaggcatg tagacccgca    900
gctggtgggg ccgtgcatac ccggggtctt gacttcgcct gcgatatcta catttgggcc    960
cctctggctg gtacttgcgg ggtcctgctg ctttcactcg tgatcactct ttactgtaag   1020
cgcggtcgga agaagctgct gtacatcttt aagcaaccct tcatgaggcc tgtgcagact   1080
actcaagagg aggacggctg ttcatgccgg ttcccagagg aggaggaagg cggctgcgaa   1140
ctgcgcgtga aattcagccg cagcgcagat gctccagcct accagcaggg gcagaaccag   1200
ctctacaacg aactcaatct tggtcggaga gaggagtacg acgtgctgga caagcggaga   1260
ggacgggacc cagaaatggg cgggaagccg cgcagaaaga atccccaaga gggcctgtac   1320
aacgagctcc aaaaggataa gatggcagaa gcctatagcg agattggtat gaaaggggaa   1380
cgcagaagag gcaaaggcca cgacggactg taccagggac tcagcaccgc caccaaggac   1440
acctatgacg ctcttcacat gcaggccctg ccgcctcggg gaagcggagc tactaacttc   1500
agcctgctga agcaggctgg agacgtggag gagaaccctg gacctatggc cttaccagtg   1560
accgccttgc tcctgccgct ggccttgctg ctccacgccg ccaggccgga aattgtgatg   1620
acccagtcac ccgccactct tagcctttca cccggtgagc gcgcaaccct gtcttgcaga   1680
gcctcccaag acatctcaaa ataccttaat tggtatcaac agaagcccgg acaggctcct   1740
cgccttctga tctaccacac cagccggctc cattctggaa tccctgccag gttcagcggt   1800
agcggatctg ggaccgacta caccctcact atcagctcac tgcagccaga ggacttcgct   1860
gtctatttct gtcagcaagg gaacaccctg ccctacacct ttggacaggg caccaagctc   1920
gagattaaag gtggaggtgg cagcggagga ggtgggtccg gcggtggagg aagccaggtc   1980
caactccaag aaagcggacc gggtcttgtg aagccatcag aaactctttc actgacttgt   2040
actgtgagcg gagtgtctct ccccgattac ggggtgtctt ggatcagaca gccaccgggg   2100
aagggtctgg aatggattgg agtgatttgg ggctctgaga ctacttacta ccaatcatcc   2160
ctcaagtcac gcgtcaccat ctcaaaggac aactctaaga atcaggtgtc actgaaactg   2220
tcatctgtga ccgcagccga caccgccgtg tactattgcg ctaagcatta ctattatggc   2280
gggagctacg caatggatta ctggggacag ggtactctgg tcaccgtgtc cagcaccacg   2340
acgccagcgc cgcgaccacc aacaccggcg cccaccatcg cgtcgcagcc cctgtccctg   2400
cgcccagagg cgtgccggcc agcggcgggg ggcgcagtgc acacgagggg gctggacttc   2460
gcctgtgata tctacatctg ggcgcccttg gccgggactt gtggggtcct tctcctgtca   2520
ctggttatca ccctttactg caaacggggc agaaagaaac tcctgtatat attcaaacaa   2580
ccatttatga gaccagtaca aactactcaa gaggaagatg gctgtagctg ccgatttcca   2640
gaagaagaag aaggaggatg tgaactgaga gtgaagttca gcaggagcgc agacgccccc   2700
gcgtaccagc agggccagaa ccagctctat aacgagctca atctaggacg aagagaggag   2760
tacgatgttt tggacaagag acgtggccgg gaccctgaga tggggggaaa gccgagaagg   2820
aagaaccctc aggaaggcct gtacaatgaa ctgcagaaag ataagatggc ggaggcctac   2880
agtgagattg ggatgaaagg cgagcgccgg aggggcaagg ggcacgatgg cctttaccag   2940
ggtctcagta cagccaccaa ggacacctac gacgcccttc acatgcaggc cctgcccct    3000
cgc                                                                 3003
```

<210> SEQ ID NO 218
<211> LENGTH: 1002
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 218

Met Ala Leu Pro Val Thr Ala Leu Leu Leu Pro Leu Ala Leu Leu Leu
1 5 10 15

His Ala Ala Arg Pro Glu Val Gln Leu Leu Glu Ser Gly Gly Gly Leu
20 25 30

Val Gln Pro Gly Gly Ser Leu Arg Leu Ser Cys Ala Ala Ser Gly Phe
35 40 45

Thr Phe Ser Ser Tyr Ala Met Ser Trp Val Arg Gln Ala Pro Gly Lys
50 55 60

Gly Leu Glu Trp Val Ser Ala Ile Ser Gly Ser Gly Gly Ser Thr Tyr
65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Ala Arg Arg Glu Trp Val Pro Tyr Asp Val Ser
115 120 125

Trp Tyr Phe Asp Tyr Trp Gly Gln Gly Thr Leu Val Thr Val Ser Ser
130 135 140

Gly Gly Gly Gly Ser Gly Gly Gly Gly Ser Gly Gly Gly Gly Ser Gly
145 150 155 160

Gly Gly Gly Ser Asp Ile Gln Met Thr Gln Ser Pro Ser Ser Leu Ser
165 170 175

Ala Ser Val Gly Asp Arg Val Thr Ile Thr Cys Arg Ala Ser Gln Ser
180 185 190

Ile Ser Ser Tyr Leu Asn Trp Tyr Gln Gln Lys Pro Gly Lys Ala Pro
195 200 205

Lys Leu Leu Ile Tyr Ala Ala Ser Ser Leu Gln Ser Gly Val Pro Ser
210 215 220

Arg Phe Ser Gly Ser Gly Ser Gly Thr Asp Phe Thr Leu Thr Ile Ser
225 230 235 240

Ser Leu Gln Pro Glu Asp Phe Ala Thr Tyr Tyr Cys Gln Gln Ser Tyr
245 250 255

Ser Thr Pro Leu Thr Phe Gly Gln Gly Thr Lys Val Glu Ile Lys Thr
260 265 270

Thr Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

Ala Pro Leu Ala Gly Thr Cys Gly Val Leu Leu Leu Ser Leu Val Ile
325 330 335

Thr Leu Tyr Cys Lys Arg Gly Arg Lys Lys Leu Leu Tyr Ile Phe Lys
340 345 350

Gln Pro Phe Met Arg Pro Val Gln Thr Thr Gln Glu Glu Asp Gly Cys
355 360 365

-continued

```
Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg Gly Ser
                485                 490                 495

Gly Ala Thr Asn Phe Ser Leu Leu Lys Gln Ala Gly Asp Val Glu Glu
            500                 505                 510

Asn Pro Gly Pro Met Ala Leu Pro Val Thr Ala Leu Leu Leu Pro Leu
        515                 520                 525

Ala Leu Leu Leu His Ala Ala Arg Pro Glu Ile Val Met Thr Gln Ser
    530                 535                 540

Pro Ala Thr Leu Ser Leu Ser Pro Gly Glu Arg Ala Thr Leu Ser Cys
545                 550                 555                 560

Arg Ala Ser Gln Asp Ile Ser Lys Tyr Leu Asn Trp Tyr Gln Gln Lys
                565                 570                 575

Pro Gly Gln Ala Pro Arg Leu Leu Ile Tyr His Thr Ser Arg Leu His
            580                 585                 590

Ser Gly Ile Pro Ala Arg Phe Ser Gly Ser Gly Ser Gly Thr Asp Tyr
        595                 600                 605

Thr Leu Thr Ile Ser Ser Leu Gln Pro Glu Asp Phe Ala Val Tyr Phe
    610                 615                 620

Cys Gln Gln Gly Asn Thr Leu Pro Tyr Thr Phe Gly Gln Gly Thr Lys
625                 630                 635                 640

Leu Glu Ile Lys Gly Gly Gly Gly Ser Gly Gly Gly Gly Ser Gly Gly
                645                 650                 655

Gly Gly Ser Gln Val Gln Leu Gln Glu Ser Gly Pro Gly Leu Val Lys
            660                 665                 670

Pro Ser Glu Thr Leu Ser Leu Thr Cys Thr Val Ser Gly Val Ser Leu
        675                 680                 685

Pro Asp Tyr Gly Val Ser Trp Ile Arg Gln Pro Pro Gly Lys Gly Leu
    690                 695                 700

Glu Trp Ile Gly Val Ile Trp Gly Ser Glu Thr Thr Tyr Tyr Gln Ser
705                 710                 715                 720

Ser Leu Lys Ser Arg Val Thr Ile Ser Lys Asp Asn Ser Lys Asn Gln
                725                 730                 735

Val Ser Leu Lys Leu Ser Ser Val Thr Ala Ala Asp Thr Ala Val Tyr
            740                 745                 750

Tyr Cys Ala Lys His Tyr Tyr Tyr Gly Gly Ser Tyr Ala Met Asp Tyr
        755                 760                 765

Trp Gly Gln Gly Thr Leu Val Thr Val Ser Ser Thr Thr Thr Pro Ala
    770                 775                 780
```

-continued

```
Pro Arg Pro Pro Thr Pro Ala Pro Thr Ile Ala Ser Gln Pro Leu Ser
785                 790                 795                 800

Leu Arg Pro Glu Ala Cys Arg Pro Ala Ala Gly Gly Ala Val His Thr
                805                 810                 815

Arg Gly Leu Asp Phe Ala Cys Asp Ile Tyr Ile Trp Ala Pro Leu Ala
            820                 825                 830

Gly Thr Cys Gly Val Leu Leu Leu Ser Leu Val Ile Thr Leu Tyr Cys
        835                 840                 845

Lys Arg Gly Arg Lys Lys Leu Leu Tyr Ile Phe Lys Gln Pro Phe Met
    850                 855                 860

Arg Pro Val Gln Thr Thr Gln Glu Glu Asp Gly Cys Ser Cys Arg Phe
865                 870                 875                 880

Pro Glu Glu Glu Glu Gly Gly Cys Glu Leu Arg Val Lys Phe Ser Arg
                885                 890                 895

Ser Ala Asp Ala Pro Ala Tyr Gln Gln Gly Gln Asn Gln Leu Tyr Asn
            900                 905                 910

Glu Leu Asn Leu Gly Arg Arg Glu Glu Tyr Asp Val Leu Asp Lys Arg
        915                 920                 925

Arg Gly Arg Asp Pro Glu Met Gly Gly Lys Pro Arg Arg Lys Asn Pro
    930                 935                 940

Gln Glu Gly Leu Tyr Asn Glu Leu Gln Lys Asp Lys Met Ala Glu Ala
945                 950                 955                 960

Tyr Ser Glu Ile Gly Met Lys Gly Glu Arg Arg Arg Gly Lys Gly His
                965                 970                 975

Asp Gly Leu Tyr Gln Gly Leu Ser Thr Ala Thr Lys Asp Thr Tyr Asp
            980                 985                 990

Ala Leu His Met Gln Ala Leu Pro  Pro Arg
        995                 1000
```

<210> SEQ ID NO 219
<211> LENGTH: 3006
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 219

```
atggccctcc ctgtcaccgc cctgctgctt ccgctggctc ttctgctcca cgccgctcgg     60

cccgaagtgc agttgctgga gtcaggcgga ggactggtgc agcccggagg atcgcttcgc    120

ttgagctgcg cagcctcagg ctttaccttc tcctcctacg ccatgtcctg ggtcagacag    180

gctcccggga agggactgga atgggtgtcc gccattagcg gttccggcgg aagcacttac    240

tatgccgact ctgtgaaggg ccgcttcact atctcccggg acaactccaa gaacaccctg    300

tatctccaaa tgaattccct gagggccgaa gataccgcgg tgtactactg cgctagacgg    360

gagtgggtgc cctacgatgt cagctggtac ttcgactact ggggacaggg cactctcgtg    420

actgtgtcct ccggtggtgg tggatcgggg ggtggtggtt cgggcggagg aggatctgga    480

ggaggagggt cggacattca aatgactcag tccccgtcct ccctctccgc ctccgtggga    540

gatcgcgtca cgatcacgtg cagggccagc cagagcatct ccagctacct gaactggtac    600

cagcagaagc cagggaaggc accgaagctc ctgatctacg ccgctagctc gctgcagtcc    660

ggcgtccctt cacggttctc gggatcgggc tcaggcaccg acttcaccct gaccattagc    720

agcctgcagc cggaggactt cgcgacatac tactgtcagc agtcatactc cacccctctg    780
```

```
accttcggcc aagggaccaa agtggagatc aagaccacta ccccagcacc gaggccaccc    840
accccggctc ctaccatcgc ctcccagcct ctgtccctgc gtccggaggc atgtagaccc    900
gcagctggtg ggccgtgca tacccggggt cttgacttcg cctgcgatat ctacatttgg    960
gcccctctgg ctggtacttg cggggtcctg ctgctttcac tcgtgatcac tctttactgt   1020
aagcgcggtc ggaagaagct gctgtacatc tttaagcaac ccttcatgag gcctgtgcag   1080
actactcaag aggaggacgg ctgttcatgc cggttcccag aggaggagga aggcggctgc   1140
gaactgcgcg tgaaattcag ccgcagcgca gatgctccag cctaccagca ggggcagaac   1200
cagctctaca acgaactcaa tcttggtcgg agagaggagt acgacgtgct ggacaagcgg   1260
agaggacggg acccagaaat gggcgggaag ccgcgcagaa agaatcccca agagggcctg   1320
tacaacgagc tccaaaagga taagatggca gaagcctata gcgagattgg tatgaaaggg   1380
gaacgcagaa gaggcaaagg ccacgacgga ctgtaccagg gactcagcac cgccaccaag   1440
gacacctatg acgctcttca catgcaggcc ctgccgcctc ggggaagcgg agctactaac   1500
ttcagcctgc tgaagcaggc tggagacgtg gaggagaacc ctggacctat ggccttacca   1560
gtgaccgcct tgctcctgcc gctggccttg ctgctccacg ccgccaggcc ggaaattgtg   1620
atgacccagt cacccgccac tcttagcctt tcacccggtg agcgcgcaac cctgtcttgc   1680
agagcctccc aagacatctc aaaatacctt aattggtatc aacagaagcc cggacaggct   1740
cctcgccttc tgatctacca caccagccgg ctccattctg gaatccctgc caggttcagc   1800
ggtagcggat ctgggaccga ctacaccctc actatcagct cactgcagcc agaggacttc   1860
gctgtctatt tctgtcagca agggaacacc ctgccctaca cctttggaca gggcaccaag   1920
ctcgagatta aaggtggagg tggcagcgga ggaggtgggt ccggcggtgg aggaagccag   1980
gtccaactcc aagaaagcgg accgggtctt gtgaagccat cagaaactct ttcactgact   2040
tgtactgtga gcggagtgtc tctccccgat tacggggtgt cttggatcag acagccaccg   2100
gggaagggtc tggaatggat tggagtgatt tggggctctg agactactta ctaccaatca   2160
tccctcaagt cacgcgtcac catctcaaag gacaactcta agaatcaggt gtcactgaaa   2220
ctgtcatctg tgaccgcagc cgacaccgcc gtgtactatt gcgctaagca ttactattat   2280
ggcgggagct acgcaatgga ttactgggga cagggtactc tggtcaccgt gtccagcacc   2340
acgacgccag cgccgcgacc accaacaccg gcgcccacca tcgcgtcgca gcccctgtcc   2400
ctgcgcccag aggcgtgccg gccagcggcg gggggcgcag tgcacacgag ggggctggac   2460
ttcgcctgtg atatctacat ctgggcgccc ttggccggga cttgtggggt ccttctcctg   2520
tcactggtta tcacccttta ctgcaaacgg ggcagaaaga aactcctgta tatattcaaa   2580
caaccattta tgagaccagt acaaactact caagaggaag atggctgtag ctgccgattt   2640
ccagaagaag aagaaggagg atgtgaactg agagtgaagt tcagcaggag cgcagacgcc   2700
cccgcgtacc agcagggcca gaaccagctc tataacgagc tcaatctagg acgaagagag   2760
gagtacgatg ttttggacaa gagacgtggc cgggaccctg agatgggggg aaagccgaga   2820
aggaagaacc ctcaggaagg cctgtacaat gaactgcaga aagataagat ggcggaggcc   2880
tacagtgaga ttgggatgaa aggcgagcgc cggaggggca aggggcacga tggcctttac   2940
cagggtctca gtacagccac caaggacacc tacgacgccc ttcacatgca ggccctgccc   3000
cctcgc                                                              3006
```

<210> SEQ ID NO 220
<211> LENGTH: 991

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 220

Met Ala Leu Pro Val Thr Ala Leu Leu Leu Pro Leu Ala Leu Leu Leu
1 5 10 15

His Ala Ala Arg Pro Glu Val Gln Leu Val Glu Ser Gly Gly Gly Leu
20 25 30

Val Gln Pro Gly Gly Ser Leu Arg Leu Ser Cys Ala Val Ser Gly Phe
35 40 45

Ala Leu Ser Asn His Gly Met Ser Trp Val Arg Arg Ala Pro Gly Lys
50 55 60

Gly Leu Glu Trp Val Ser Gly Ile Val Tyr Ser Gly Ser Thr Tyr Tyr
65 70 75 80

Ala Ala Ser Val Lys Gly Arg Phe Thr Ile Ser Arg Asp Asn Ser Arg
85 90 95

Asn Thr Leu Tyr Leu Gln Met Asn Ser Leu Arg Pro Glu Asp Thr Ala
100 105 110

Ile Tyr Tyr Cys Ser Ala His Gly Gly Glu Ser Asp Val Trp Gly Gln
115 120 125

Gly Thr Thr Val Thr Val Ser Ser Ala Ser Gly Gly Gly Gly Ser Gly
130 135 140

Gly Gly Gly Ser Gly Gly Gly Gly Ser Asp Ile Gln Leu Thr Gln Ser
145 150 155 160

Pro Ser Ser Leu Ser Ala Ser Val Gly Asp Arg Val Thr Ile Thr Cys
165 170 175

Arg Ala Ser Gln Ser Ile Ser Ser Tyr Leu Asn Trp Tyr Gln Gln Lys
180 185 190

Pro Gly Lys Ala Pro Lys Leu Leu Ile Tyr Ala Ala Ser Ser Leu Gln
195 200 205

Ser Gly Val Pro Ser Arg Phe Ser Gly Ser Gly Ser Gly Thr Asp Phe
210 215 220

Thr Leu Thr Ile Ser Ser Leu Gln Pro Glu Asp Phe Ala Thr Tyr Tyr
225 230 235 240

Cys Gln Gln Ser Tyr Ser Thr Pro Tyr Thr Phe Gly Gln Gly Thr Lys
245 250 255

Val Glu Ile Lys Thr Thr Thr Pro Ala Pro Arg Pro Pro Thr Pro Ala
260 265 270

Pro Thr Ile Ala Ser Gln Pro Leu Ser Leu Arg Pro Glu Ala Cys Arg
275 280 285

Pro Ala Ala Gly Gly Ala Val His Thr Arg Gly Leu Asp Phe Ala Cys
290 295 300

Asp Ile Tyr Ile Trp Ala Pro Leu Ala Gly Thr Cys Gly Val Leu Leu
305 310 315 320

Leu Ser Leu Val Ile Thr Leu Tyr Cys Lys Arg Gly Arg Lys Lys Leu
325 330 335

Leu Tyr Ile Phe Lys Gln Pro Phe Met Arg Pro Val Gln Thr Thr Gln
340 345 350

Glu Glu Asp Gly Cys Ser Cys Arg Phe Pro Glu Glu Glu Glu Gly Gly
355 360 365

Cys Glu Leu Arg Val Lys Phe Ser Arg Ser Ala Asp Ala Pro Ala Tyr
370 375 380

-continued

```
Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg Gly Ser Gly Ala Thr Asn Phe Ser Leu Leu Lys Gln Ala
                485                 490                 495

Gly Asp Val Glu Glu Asn Pro Gly Pro Met Ala Leu Pro Val Thr Ala
            500                 505                 510

Leu Leu Leu Pro Leu Ala Leu Leu Leu His Ala Ala Arg Pro Glu Ile
        515                 520                 525

Val Met Thr Gln Ser Pro Ala Thr Leu Ser Leu Ser Pro Gly Glu Arg
    530                 535                 540

Ala Thr Leu Ser Cys Arg Ala Ser Gln Asp Ile Ser Lys Tyr Leu Asn
545                 550                 555                 560

Trp Tyr Gln Gln Lys Pro Gly Gln Ala Pro Arg Leu Leu Ile Tyr His
                565                 570                 575

Thr Ser Arg Leu His Ser Gly Ile Pro Ala Arg Phe Ser Gly Ser Gly
            580                 585                 590

Ser Gly Thr Asp Tyr Thr Leu Thr Ile Ser Ser Leu Gln Pro Glu Asp
        595                 600                 605

Phe Ala Val Tyr Phe Cys Gln Gln Gly Asn Thr Leu Pro Tyr Thr Phe
    610                 615                 620

Gly Gln Gly Thr Lys Leu Glu Ile Lys Gly Gly Gly Gly Ser Gly Gly
625                 630                 635                 640

Gly Gly Ser Gly Gly Gly Gly Ser Gln Val Gln Leu Gln Glu Ser Gly
                645                 650                 655

Pro Gly Leu Val Lys Pro Ser Glu Thr Leu Ser Leu Thr Cys Thr Val
            660                 665                 670

Ser Gly Val Ser Leu Pro Asp Tyr Gly Val Ser Trp Ile Arg Gln Pro
        675                 680                 685

Pro Gly Lys Gly Leu Glu Trp Ile Gly Val Ile Trp Gly Ser Glu Thr
    690                 695                 700

Thr Tyr Tyr Gln Ser Ser Leu Lys Ser Arg Val Thr Ile Ser Lys Asp
705                 710                 715                 720

Asn Ser Lys Asn Gln Val Ser Leu Lys Leu Ser Ser Val Thr Ala Ala
                725                 730                 735

Asp Thr Ala Val Tyr Tyr Cys Ala Lys His Tyr Tyr Tyr Gly Gly Ser
            740                 745                 750

Tyr Ala Met Asp Tyr Trp Gly Gln Gly Thr Leu Val Thr Val Ser Ser
        755                 760                 765

Thr Thr Thr Pro Ala Pro Arg Pro Pro Thr Pro Ala Pro Thr Ile Ala
    770                 775                 780

Ser Gln Pro Leu Ser Leu Arg Pro Glu Ala Cys Arg Pro Ala Ala Gly
785                 790                 795                 800
```

```
Gly Ala Val His Thr Arg Gly Leu Asp Phe Ala Cys Asp Ile Tyr Ile
                805                 810                 815

Trp Ala Pro Leu Ala Gly Thr Cys Gly Val Leu Leu Leu Ser Leu Val
            820                 825                 830

Ile Thr Leu Tyr Cys Lys Arg Gly Arg Lys Lys Leu Leu Tyr Ile Phe
        835                 840                 845

Lys Gln Pro Phe Met Arg Pro Val Gln Thr Thr Gln Glu Glu Asp Gly
    850                 855                 860

Cys Ser Cys Arg Phe Pro Glu Glu Glu Glu Gly Gly Cys Glu Leu Arg
865                 870                 875                 880

Val Lys Phe Ser Arg Ser Ala Asp Ala Pro Ala Tyr Gln Gln Gly Gln
                885                 890                 895

Asn Gln Leu Tyr Asn Glu Leu Asn Leu Gly Arg Arg Glu Glu Tyr Asp
            900                 905                 910

Val Leu Asp Lys Arg Arg Gly Arg Asp Pro Glu Met Gly Gly Lys Pro
        915                 920                 925

Arg Arg Lys Asn Pro Gln Glu Gly Leu Tyr Asn Glu Leu Gln Lys Asp
    930                 935                 940

Lys Met Ala Glu Ala Tyr Ser Glu Ile Gly Met Lys Gly Glu Arg Arg
945                 950                 955                 960

Arg Gly Lys Gly His Asp Gly Leu Tyr Gln Gly Leu Ser Thr Ala Thr
                965                 970                 975

Lys Asp Thr Tyr Asp Ala Leu His Met Gln Ala Leu Pro Pro Arg
            980                 985                 990


<210> SEQ ID NO 221
<211> LENGTH: 2973
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221

atggccctcc ctgtcaccgc cctgctgctt ccgctggctc ttctgctcca cgccgctcgg      60

cccgaagtgc aattggtgga atcaggggga ggacttgtgc agcctggagg atcgctgaga     120

ctgtcatgtg ccgtgtccgg ctttgccctg tccaaccacg ggatgtcctg ggtccgccgc     180

gcgcctggaa agggcctcga atgggtgtcg ggtattgtgt acagcggtag cacctactat     240

gccgcatccg tgaaggggag attcaccatc agccgggaca actccaggaa cactctgtac     300

ctccaaatga attcgctgag gccagaggac actgccatct actactgctc cgcgcatggc     360

ggagagtccg acgtctgggg acaggggacc accgtgaccg tgtctagcgc gtccggcgga     420

ggcggcagcg gggtggtgg ttcagggggc ggcggatcgg acatccagct cacccagtcc     480

ccgagctcgc tgtccgcctc cgtgggagat cgggtcacca tcacgtgccg cgccagccag     540

tcgatttcct cctacctgaa ctggtaccaa cagaagcccg gaaaagcccc gaagcttctc     600

atctacgccg cctcgagcct gcagtcagga gtgccctcac ggttctccgg ctccggttcc     660

ggtactgatt tcaccctgac catttcctcc ctgcaaccgg aggacttcgc tacttactac     720

tgccagcagt cgtactccac cccctacact ttcggacaag gcaccaaggt cgaaatcaag     780

accactaccc cagcaccgag gccacccacc ccggctccta ccatcgcctc ccagcctctg     840

tccctgcgtc cggaggcatg tagacccgca gctggtgggg ccgtgcatac ccggggtctt     900

gacttcgcct gcgatatcta catttgggcc cctctggctg gtacttgcgg ggtcctgctg     960
```

ctttcactcg tgatcactct ttactgtaag cgcggtcgga agaagctgct gtacatcttt 1020
aagcaaccct tcatgaggcc tgtgcagact actcaagagg aggacggctg ttcatgccgg 1080
ttcccagagg aggaggaagg cggctgcgaa ctgcgcgtga aattcagccg cagcgcagat 1140
gctccagcct accagcaggg gcagaaccag ctctacaacg aactcaatct tggtcggaga 1200
gaggagtacg acgtgctgga caagcggaga ggacgggacc cagaaatggg cgggaagccg 1260
cgcagaaaga atccccaaga gggcctgtac aacgagctcc aaaaggataa gatggcagaa 1320
gcctatagcg agattggtat gaaaggggaa cgcagaagag gcaaaggcca cgacggactg 1380
taccagggac tcagcaccgc caccaaggac acctatgacg ctcttcacat gcaggccctg 1440
ccgcctcggg gaagcggagc tactaacttc agcctgctga agcaggctgg agacgtggag 1500
gagaaccctg gacctatggc cttaccagtg accgccttgc tcctgccgct ggccttgctg 1560
ctccacgccg ccaggccgga aattgtgatg acccagtcac ccgccactct tagcctttca 1620
cccggtgagc gcgcaaccct gtcttgcaga gcctcccaag acatctcaaa ataccttaat 1680
tggtatcaac agaagcccgg acaggctcct cgccttctga tctaccacac cagccggctc 1740
cattctggaa tccctgccag gttcagcggt agcggatctg ggaccgacta caccctcact 1800
atcagctcac tgcagccaga ggacttcgct gtctatttct gtcagcaagg gaacaccctg 1860
ccctacacct ttggacaggg caccaagctc gagattaaag gtggaggtgg cagcggagga 1920
ggtgggtccg gcggtggagg aagccaggtc caactccaag aaagcggacc gggtcttgtg 1980
aagccatcag aaactctttc actgacttgt actgtgagcg gagtgtctct ccccgattac 2040
ggggtgtctt ggatcagaca gccaccgggg aagggtctgg aatggattgg agtgatttgg 2100
ggctctgaga ctacttacta ccaatcatcc ctcaagtcac gcgtcaccat ctcaaaggac 2160
aactctaaga atcaggtgtc actgaaactg tcatctgtga ccgcagccga caccgccgtg 2220
tactattgcg ctaagcatta ctattatggc gggagctacg caatggatta ctggggacag 2280
ggtactctgg tcaccgtgtc cagcaccacg acgccagcgc cgcgaccacc aacaccggcg 2340
cccaccatcg cgtcgcagcc cctgtccctg cgcccagagg cgtgccggcc agcggcgggg 2400
ggcgcagtgc acacgagggg gctggacttc gcctgtgata tctacatctg ggcgcccttg 2460
gccgggactt gtggggtcct tctcctgtca ctggttatca ccctttactg caaacggggc 2520
agaaagaaac tcctgtatat attcaaacaa ccatttatga gaccagtaca aactactcaa 2580
gaggaagatg gctgtagctg ccgatttcca gaagaagaag aaggaggatg tgaactgaga 2640
gtgaagttca gcaggagcgc agacgccccc gcgtaccagc agggccagaa ccagctctat 2700
aacgagctca atctaggacg aagagaggag tacgatgttt tggacaagag acgtggccgg 2760
gaccctgaga tgggggggaaa gccgagaagg aagaaccctc aggaaggcct gtacaatgaa 2820
ctgcagaaag ataagatggc ggaggcctac agtgagattg ggatgaaagg cgagcgccgg 2880
aggggcaagg ggcacgatgg cctttaccag ggtctcagta cagccaccaa ggacacctac 2940
gacgcccttc acatgcaggc cctgcccccct cgc 2973

<210> SEQ ID NO 222
<211> LENGTH: 991
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 222

-continued

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
```

-continued

```
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Gly Ala Thr Asn Phe Ser Leu Leu
                485                 490                 495

Lys Gln Ala Gly Asp Val Glu Glu Asn Pro Gly Pro Met Ala Leu Pro
            500                 505                 510

Val Thr Ala Leu Leu Leu Pro Leu Ala Leu Leu Leu His Ala Ala Arg
        515                 520                 525

Pro Glu Val Gln Leu Val Glu Ser Gly Gly Gly Leu Val Gln Pro Gly
    530                 535                 540

Gly Ser Leu Arg Leu Ser Cys Ala Val Ser Gly Phe Ala Leu Ser Asn
545                 550                 555                 560

His Gly Met Ser Trp Val Arg Arg Ala Pro Gly Lys Gly Leu Glu Trp
                565                 570                 575

Val Ser Gly Ile Val Tyr Ser Gly Ser Thr Tyr Tyr Ala Ala Ser Val
            580                 585                 590

Lys Gly Arg Phe Thr Ile Ser Arg Asp Asn Ser Arg Asn Thr Leu Tyr
        595                 600                 605

Leu Gln Met Asn Ser Leu Arg Pro Glu Asp Thr Ala Ile Tyr Tyr Cys
    610                 615                 620

Ser Ala His Gly Gly Glu Ser Asp Val Trp Gly Gln Gly Thr Thr Val
625                 630                 635                 640

Thr Val Ser Ser Ala Ser Gly Gly Gly Gly Ser Gly Gly Gly Gly Ser
                645                 650                 655

Gly Gly Gly Gly Ser Asp Ile Gln Leu Thr Gln Ser Pro Ser Ser Leu
            660                 665                 670

Ser Ala Ser Val Gly Asp Arg Val Thr Ile Thr Cys Arg Ala Ser Gln
        675                 680                 685

Ser Ile Ser Ser Tyr Leu Asn Trp Tyr Gln Gln Lys Pro Gly Lys Ala
    690                 695                 700

Pro Lys Leu Leu Ile Tyr Ala Ala Ser Ser Leu Gln Ser Gly Val Pro
705                 710                 715                 720

Ser Arg Phe Ser Gly Ser Gly Ser Gly Thr Asp Phe Thr Leu Thr Ile
                725                 730                 735

Ser Ser Leu Gln Pro Glu Asp Phe Ala Thr Tyr Tyr Cys Gln Gln Ser
            740                 745                 750

Tyr Ser Thr Pro Tyr Thr Phe Gly Gln Gly Thr Lys Val Glu Ile Lys
        755                 760                 765

Thr Thr Thr Pro Ala Pro Arg Pro Pro Thr Pro Ala Pro Thr Ile Ala
    770                 775                 780

Ser Gln Pro Leu Ser Leu Arg Pro Glu Ala Cys Arg Pro Ala Ala Gly
785                 790                 795                 800

Gly Ala Val His Thr Arg Gly Leu Asp Phe Ala Cys Asp Ile Tyr Ile
                805                 810                 815

Trp Ala Pro Leu Ala Gly Thr Cys Gly Val Leu Leu Leu Ser Leu Val
            820                 825                 830

Ile Thr Leu Tyr Cys Lys Arg Gly Arg Lys Lys Leu Leu Tyr Ile Phe
        835                 840                 845
```

Lys Gln Pro Phe Met Arg Pro Val Gln Thr Thr Gln Glu Glu Asp Gly
    850                 855                 860

Cys Ser Cys Arg Phe Pro Glu Glu Glu Glu Gly Gly Cys Glu Leu Arg
865                 870                 875                 880

Val Lys Phe Ser Arg Ser Ala Asp Ala Pro Ala Tyr Gln Gln Gly Gln
                885                 890                 895

Asn Gln Leu Tyr Asn Glu Leu Asn Leu Gly Arg Arg Glu Glu Tyr Asp
            900                 905                 910

Val Leu Asp Lys Arg Arg Gly Arg Asp Pro Glu Met Gly Gly Lys Pro
        915                 920                 925

Arg Arg Lys Asn Pro Gln Glu Gly Leu Tyr Asn Glu Leu Gln Lys Asp
    930                 935                 940

Lys Met Ala Glu Ala Tyr Ser Glu Ile Gly Met Lys Gly Glu Arg Arg
945                 950                 955                 960

Arg Gly Lys Gly His Asp Gly Leu Tyr Gln Gly Leu Ser Thr Ala Thr
                965                 970                 975

Lys Asp Thr Tyr Asp Ala Leu His Met Gln Ala Leu Pro Pro Arg
            980                 985                 990

<210> SEQ ID NO 223
<211> LENGTH: 2973
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
atggccttac cagtgaccgc cttgctcctg ccgctggcct tgctgctcca cgccgccagg 60
ccggaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactaccaat catccctcaa gtcacgcgtc accatctcaa aggacaactc taagaatcag 660
gtgtcactga aactgtcatc tgtgaccgca gccgacaccg ccgtgtacta ttgcgctaag 720
cattactatt atggcgggag ctacgcaatg gattactggg gacagggtac tctggtcacc 780
gtgtccagca ccacgacgcc agcgccgcga ccaccaacac cggcgcccac catcgcgtcg 840
cagcccctgt ccctgcgccc agaggcgtgc cggccagcgg cggggggcgc agtgcacacg 900
agggggctgg acttcgcctg tgatatctac atctgggcgc ccttggccgg gacttgtggg 960
gtccttctcc tgtcactggt tatcaccctt tactgcaaac ggggcagaaa gaaactcctg 1020
tatatattca aacaaccatt tatgagacca gtacaaacta ctcaagagga agatggctgt 1080
agctgccgat ttccagaaga agaagaagga ggatgtgaac tgagagtgaa gttcagcagg 1140
agcgcagacg cccccgcgta ccagcagggc cagaaccagc tctataacga gctcaatcta 1200

```
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgcgg aagcggagct actaacttca gcctgctgaa gcaggctgga   1500
gacgtggagg agaaccctgg acctatggcc ctccctgtca ccgccctgct gcttccgctg   1560
gctcttctgc tccacgccgc tcggcccgaa gtgcaattgg tggaatcagg gggaggactt   1620
gtgcagcctg gaggatcgct gagactgtca tgtgccgtgt ccggctttgc cctgtccaac   1680
cacgggatgt cctgggtccg ccgcgcgcct ggaaagggcc tcgaatgggt gtcgggtatt   1740
gtgtacagcg gtagcaccta ctatgccgca tccgtgaagg ggagattcac catcagccgg   1800
gacaactcca ggaacactct gtacctccaa atgaattcgc tgaggccaga ggacactgcc   1860
atctactact gctccgcgca tggcggagag tccgacgtct ggggacaggg gaccaccgtg   1920
accgtgtcta gcgcgtccgg cggaggcggc agcgggggtg gtggttcagg gggcggcgga   1980
tcggacatcc agctcaccca gtccccgagc tcgctgtccg cctccgtggg agatcgggtc   2040
accatcacgt gccgcgccag ccagtcgatt tcctcctacc tgaactggta ccaacagaag   2100
cccggaaaag ccccgaagct tctcatctac gccgcctcga gcctgcagtc aggagtgccc   2160
tcacggttct ccggctccgg ttccggtact gatttcaccc tgaccatttc ctccctgcaa   2220
ccggaggact tcgctactta ctactgccag cagtcgtact ccacccccta cactttcgga   2280
caaggcacca aggtcgaaat caagaccact accccagcac cgaggccacc caccccggct   2340
cctaccatcg cctcccagcc tctgtccctg cgtccggagg catgtagacc cgcagctggt   2400
ggggccgtgc atacccgggg tcttgacttc gcctgcgata tctacatttg ggcccctctg   2460
gctggtactt gcggggtcct gctgctttca ctcgtgatca ctctttactg taagcgcggt   2520
cggaagaagc tgctgtacat ctttaagcaa cccttcatga ggcctgtgca gactactcaa   2580
gaggaggacg gctgttcatg ccggttccca gaggaggagg aaggcggctg cgaactgcgc   2640
gtgaaattca gccgcagcgc agatgctcca gcctaccagc aggggcagaa ccagctctac   2700
aacgaactca atcttggtcg gagagaggag tacgacgtgc tggacaagcg gagaggacgg   2760
gacccagaaa tgggcgggaa gccgcgcaga aagaatcccc aagagggcct gtacaacgag   2820
ctccaaaagg ataagatggc agaagcctat agcgagattg gtatgaaagg ggaacgcaga   2880
agaggcaaag gccacgacgg actgtaccag ggactcagca ccgccaccaa ggacacctat   2940
gacgctcttc acatgcaggc cctgccgcct cgg                                2973
```

<210> SEQ ID NO 224
<211> LENGTH: 492
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

-continued

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Gly Glu Ser Trp Leu Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Leu Thr Phe Gly
225                 230                 235                 240

Gln Gly Thr Lys Val Glu Ile Lys Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460
```

Met Gln Ala Leu Pro Pro Arg Gly Ser Gly Ala Thr Asn Phe Ser Leu
465 470 475 480

Leu Lys Gln Ala Gly Asp Val Glu Glu Asn Pro Gly
485 490

<210> SEQ ID NO 225
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 225

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Pro Gly Leu Val Lys Pro Ser Glu Thr Leu Ser Leu Thr Cys
130 135 140

Thr Val Ser Gly Val Ser Leu Pro Asp Tyr Gly Val Ser Trp Ile Arg
145 150 155 160

Gln Pro Pro Gly Lys Gly Leu Glu Trp Ile Gly Val Ile Trp Gly Ser
165 170 175

Glu Thr Thr Tyr Tyr Gln Ser Ser Leu Lys Ser Arg Val Thr Ile Ser
180 185 190

Lys Asp Asn Ser Lys Asn Gln Val Ser Leu Lys Leu Ser Ser Val Thr
195 200 205

Ala Ala Asp Thr Ala Val Tyr Tyr Cys Ala Lys His Tyr Tyr Tyr Gly
210 215 220

Gly Ser Tyr Ala Met Asp Tyr Trp Gly Gln Gly Thr Leu Val Thr Val
225 230 235 240

Ser Ser Thr Thr Thr Pro Ala Pro Arg Pro Pro Thr Pro Ala Pro Thr
245 250 255

Ile Ala Ser Gln Pro Leu Ser Leu Arg Pro Glu Ala Cys Arg Pro Ala
260 265 270

Ala Gly Gly Ala Val His Thr Arg Gly Leu Asp Phe Ala Cys Asp Ile
275 280 285

Tyr Ile Trp Ala Pro Leu Ala Gly Thr Cys Gly Val Leu Leu Leu Ser
290 295 300

Leu Val Ile Thr Leu Tyr Cys Lys Arg Gly Arg Lys Lys Leu Leu Tyr
305 310 315 320

Ile Phe Lys Gln Pro Phe Met Arg Pro Val Gln Thr Thr Gln Glu Glu
325 330 335

```
Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465


<210> SEQ ID NO 226
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gln Ser Ala Leu Thr Gln
    130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Asp Val Ser
            180                 185                 190

Asn Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
```

```
    210                 215                 220

Asp Tyr Tyr Cys Ser Ser Tyr Thr Ser Ser Ser Thr Leu Tyr Val Phe
225                 230                 235                 240

Gly Ser Gly Thr Lys Val Thr Val Leu Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg Gly Ser Gly Ala Thr Asn Phe Ser
465                 470                 475                 480

Leu Leu Lys Gln Ala Gly Asp Val Glu Glu Asn Pro Gly
                485                 490
```

<210> SEQ ID NO 227
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 227

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Arg Arg Glu Trp Val Pro Tyr Asp Val Ser Trp Tyr Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gln Gly Thr Lys Val Glu Ile Lys Thr Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg Gly Ser Gly Ala Thr Asn Phe
465                 470                 475                 480

Ser Leu Leu Lys Gln Ala Gly Asp Val Glu Glu Asn Pro Gly
                485                 490
```

<210> SEQ ID NO 228
<211> LENGTH: 483
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Gly Gly Ser Gly
        115                 120                 125

Gly Gly Gly Ser Asp Ile Gln Leu Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Thr Phe Gly Gln Gly Thr Lys Val Glu Ile Lys Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Ile Tyr Ile Trp
        275                 280                 285

Ala Pro Leu Ala Gly Thr Cys Gly Val Leu Leu Leu Ser Leu Val Ile
    290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
            340                 345                 350

Lys Phe Ser Arg Ser Ala Asp Ala Pro Ala Tyr Gln Gln Gly Gln Asn
        355                 360                 365
```

Gln Leu Tyr Asn Glu Leu Asn Leu Gly Arg Arg Glu Glu Tyr Asp Val
370 375 380

Leu Asp Lys Arg Arg Gly Arg Asp Pro Glu Met Gly Gly Lys Pro Arg
385 390 395 400

Arg Lys Asn Pro Gln Glu Gly Leu Tyr Asn Glu Leu Gln Lys Asp Lys
405 410 415

Met Ala Glu Ala Tyr Ser Glu Ile Gly Met Lys Gly Glu Arg Arg Arg
420 425 430

Gly Lys Gly His Asp Gly Leu Tyr Gln Gly Leu Ser Thr Ala Thr Lys
435 440 445

Asp Thr Tyr Asp Ala Leu His Met Gln Ala Leu Pro Pro Arg Gly Ser
450 455 460

Gly Ala Thr Asn Phe Ser Leu Leu Lys Gln Ala Gly Asp Val Glu Glu
465 470 475 480

Asn Pro Gly

<210> SEQ ID NO 229
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Pro Gly Leu Val Lys Pro Ser Glu Thr Leu Ser Leu Thr Cys
130 135 140

Thr Val Ser Gly Val Ser Leu Pro Asp Tyr Gly Val Ser Trp Ile Arg
145 150 155 160

Gln Pro Pro Gly Lys Gly Leu Glu Trp Ile Gly Val Ile Trp Gly Ser
165 170 175

Glu Thr Thr Tyr Tyr Gln Ser Ser Leu Lys Ser Arg Val Thr Ile Ser
180 185 190

Lys Asp Asn Ser Lys Asn Gln Val Ser Leu Lys Leu Ser Ser Val Thr
195 200 205

Ala Ala Asp Thr Ala Val Tyr Tyr Cys Ala Lys His Tyr Tyr Tyr Gly
210 215 220

Gly Ser Tyr Ala Met Asp Tyr Trp Gly Gln Gly Thr Leu Val Thr Val
225 230 235 240

```
Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg Gly Ser Gly Ala Thr Asn Phe Ser Leu Leu Lys Gln Ala Gly Asp
465                 470                 475                 480

Val Glu Glu Asn Pro Gly
                485
```

<210> SEQ ID NO 230
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 230

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110
```

```
Val Ser Ser Ala Ser Gly Gly Gly Gly Ser Gly Gly Gly Gly Ser Gly
        115                 120                 125

Gly Gly Gly Ser Asp Ile Gln Leu Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Thr Phe Gly Gln Gly Thr Lys Val Glu Ile Lys Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Ile Tyr Ile Trp
        275                 280                 285

Ala Pro Leu Ala Gly Thr Cys Gly Val Leu Leu Leu Ser Leu Val Ile
    290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460
```

```
<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asn His Gly Met Ser
```

1 5

<210> SEQ ID NO 232
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Gly Ile Val Tyr Ser Gly Ser Thr Tyr Tyr Ala Ala Ser Val Lys Gly
1 5 10 15

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

His Gly Gly Glu Ser Asp Val
1 5

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Gly Phe Ala Leu Ser Asn His
1 5

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Val Tyr Ser Gly Ser
1 5

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Gly Phe Ala Leu Ser Asn His Gly
1 5

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Ile Val Tyr Ser Gly Ser Thr
1 5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Ser Ala His Gly Gly Glu Ser Asp Val
1 5

<210> SEQ ID NO 239
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

Glu Val Gln Leu Val Glu Ser Gly Gly Gly Leu Val Gln Pro Gly Gly
1 5 10 15

Ser Leu Arg Leu Ser Cys Ala Val Ser Gly Phe Ala Leu Ser Asn His
20 25 30

Gly Met Ser Trp Val Arg Arg Ala Pro Gly Lys Gly Leu Glu Trp Val
35 40 45

Ser Gly Ile Val Tyr Ser Gly Ser Thr Tyr Tyr Ala Ala Ser Val Lys
50 55 60

Gly Arg Phe Thr Ile Ser Arg Asp Asn Ser Arg Asn Thr Leu Tyr Leu
65 70 75 80

Gln Met Asn Ser Leu Arg Pro Glu Asp Thr Ala Ile Tyr Tyr Cys Ser
85 90 95

Ala His Gly Gly Glu Ser Asp Val Trp Gly Gln Gly Thr Thr Val Thr
100 105 110

Val Ser Ser
115

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Gln Gln Ser Tyr Ser Thr Pro Tyr Thr
1 5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Ser Tyr Ser Thr Pro Tyr
1 5

<210> SEQ ID NO 242
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Tyr
85 90 95

Thr Phe Gly Gln Gly Thr Lys Val Glu Ile Lys
100 105

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Ala Ser Gly Gly Gly Gly Ser Gly Gly Gly Gly Ser Gly Gly Gly Gly
1 5 10 15

Ser

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Gly Val Ser Leu Pro Asp Tyr Gly Val Ser
1 5 10

<210> SEQ ID NO 245
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

Val Ile Trp Gly Ser Glu Thr Thr Tyr Tyr Gln Ser Ser Leu Lys Ser 1 5 10 15

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

His Tyr Tyr Tyr Gly Gly Ser Tyr Ala Met Asp Tyr
1 5 10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 247

Arg Ala Ser Gln Asp Ile Ser Lys Tyr Leu Asn
1 5 10

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

His Thr Ser Arg Leu His Ser
1 5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Gln Gln Gly Asn Thr Leu Pro Tyr Thr
1 5

<210> SEQ ID NO 250
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Gly Leu Glu Trp Ile
35 40 45

Gly Val Ile Trp Gly Ser Glu Thr Thr Tyr Tyr Gln Ser Ser Leu Lys 50 55 60

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser
115 120

<210> SEQ ID NO 251
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 251

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys
100 105

<210> SEQ ID NO 252
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 252
atggccctcc ctgtcaccgc tctgttgctg ccgcttgctc tgctgctcca cgcagcgcga 60
ccg 63

<210> SEQ ID NO 253
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 253
caggtacaat tgcaggagtc tggaggcggt gtggtgcaac ccggtcgcag cttgcgcctg 60
agttgtgctg cgtctggatt tacattttca tcttacggaa tgcattgggt acgccaggca 120
ccggggaaag gccttgaatg ggtggctgta atttcatacg atggttccaa caaatactat 180
gctgactcag tcaagggtcg atttacaatt agtcgggaca actccaagaa caccctttat 240
cttcaaatga attcccttag agcagaggat acggcggtct attactgtgg tggcagtggt 300
tatgcacttc atgatgatta ctatggcttg gatgtctggg ggcaagggac gcttgtaact 360
gtatcctctg gtggtggtgg tagtggtggg ggaggctccg gcggtggcgg ctctcaatct 420
gctctgactc aaccagcaag cgtatcaggg tcaccgggac agagtattac cataagttgc 480
acggggacct ctagcgatgt aggggggtat aattatgtat cttggtatca acaacacccc 540
gggaaagccc ctaaattgat gatctacgac gtgagcaatc gacctagtgg cgtatcaaat 600
cgcttctctg gtagcaagag tgggaatacg gcgtccctta ctattagcgg attgcaagca 660
gaagatgagg ccgattacta ctgcagctcc tatactagct cttctacatt gtacgtcttt 720
gggagcggaa caaaagtaac agtactc 747

<210> SEQ ID NO 254
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
acaacaacac ctgccccgag accgcctaca ccagccccga ctattgccag ccagcctctg 60
agcctcaggc ctgaggcctg taggcccgca gcgggcggcg cagttcatac acggggcttg 120
gatttcgctt gtgatattta tatttgggct cctttggcgg ggacatgtgg cgtgctgctt 180
ctgtcacttg ttattacact gtactgt 207

<210> SEQ ID NO 255
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
aaacgcgggc gaaaaaaatt gctgtatatt tttaagcagc catttatgag gcccgttcag 60
acgacgcagg aggaggacgg ttgctcttgc aggttcccag aagaggaaga agggggctgt 120
gaattg 126

<210> SEQ ID NO 256
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256
cgggttaaat tttcaagatc cgcagacgct ccagcatacc aacagggaca aaaccaactc 60
tataacgagc tgaatcttgg aagaagggag gaatatgatg tgctggataa acggcgcggt 120
agagatccgg agatgggcgg aaaaccaagg cgaaaaaacc ctcaggaggg actctacaac 180
gaactgcaga aagacaaaat ggcggaggct tattccgaaa taggcatgaa gggcgagcgg 240
aggcgaggga aagggcacga cggactgtat caaggcctct caaccgcgac taaggatacg 300
tacgacgccc tgcacatgca ggccctgcct ccgaga 336

```
<210> SEQ ID NO 257
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Gly Gly Ser Gly Tyr Ala Leu His Asp Asp Tyr
        115                 120                 125

Tyr Gly Leu Asp Val Trp Gly Gln Gly Thr Leu Val Thr Val Ser Ser
    130                 135                 140

Gly Gly Gly Gly Ser Gly Gly Gly Gly Ser Gly Gly Gly Gly Ser Gln
145                 150                 155                 160

Ser Ala Leu Thr Gln Pro Ala Ser Val Ser Gly Ser Pro Gly Gln Ser
                165                 170                 175

Ile Thr Ile Ser Cys Thr Gly Thr Ser Ser Asp Val Gly Gly Tyr Asn
            180                 185                 190

Tyr Val Ser Trp Tyr Gln Gln His Pro Gly Lys Ala Pro Lys Leu Met
        195                 200                 205

Ile Tyr Asp Val Ser Asn Arg Pro Ser Gly Val Ser Asn Arg Phe Ser
    210                 215                 220

Gly Ser Lys Ser Gly Asn Thr Ala Ser Leu Thr Ile Ser Gly Leu Gln
225                 230                 235                 240

Ala Glu Asp Glu Ala Asp Tyr Tyr Cys Ser Ser Tyr Thr Ser Ser Ser
                245                 250                 255

Thr Leu Tyr Val Phe Gly Ser Gly Thr Lys Val Thr Val Leu Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365
```

```
Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 258
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258

atggccctcc ctgtcaccgc tctgttgctg ccgcttgctc tgctgctcca cgcagcgcga     60

ccgcaggtac aattgcagga gtctggaggc ggtgtggtgc aacccggtcg cagcttgcgc    120

ctgagttgtg ctgcgtctgg atttacattt tcatcttacg gaatgcattg ggtacgccag    180

gcaccgggga aaggccttga atgggtggct gtaatttcat acgatggttc caacaaatac    240

tatgctgact cagtcaaggg tcgatttaca attagtcggg acaactccaa gaacaccctt    300

tatcttcaaa tgaattccct tagagcagag gatacggcgg tctattactg tggtggcagt    360

ggttatgcac ttcatgatga ttactatggc ttggatgtct gggggcaagg gacgcttgta    420

actgtatcct ctggtggtgg tggtagtggt gggggaggct ccggcggtgg cggctctcaa    480

tctgctctga ctcaaccagc aagcgtatca gggtcaccgg gacagagtat taccataagt    540

tgcacgggga cctctagcga tgtagggggg tataattatg tatcttggta tcaacaacac    600

cccgggaaag cccctaaatt gatgatctac gacgtgagca atcgacctag tggcgtatca    660

aatcgcttct ctggtagcaa gagtgggaat acggcgtccc ttactattag cggattgcaa    720

gcagaagatg aggccgatta ctactgcagc tcctatacta gctcttctac attgtacgtc    780

tttgggagcg gaacaaaagt aacagtactc acaacaacac ctgccccgag accgcctaca    840

ccagccccga ctattgccag ccagcctctg agcctcaggc ctgaggcctg taggcccgca    900

gcgggcggcg cagttcatac acggggcttg gatttcgctt gtgatattta tatttgggct    960

cctttggcgg ggacatgtgg cgtgctgctt ctgtcacttg ttattacact gtactgtaaa   1020

cgcgggcgaa aaaaattgct gtatattttt aagcagccat ttatgaggcc cgttcagacg   1080

acgcaggagg aggacggttg ctcttgcagg ttcccagaag aggaagaagg gggctgtgaa   1140

ttgcgggtta aattttcaag atccgcagac gctccagcat accaacaggg acaaaaccaa   1200

ctctataacg agctgaatct tggaagaagg gaggaatatg atgtgctgga taaacggcgc   1260

ggtagagatc cggagatggg cggaaaacca aggcgaaaaa accctcagga gggactctac   1320
```

aacgaactgc agaaagacaa aatggcggag gcttattccg aaataggcat gaagggcgag 1380
cggaggcgag ggaaagggca cgacggactg tatcaaggcc tctcaaccgc gactaaggat 1440
acgtacgacg ccctgcacat gcaggccctg cctccgaga 1479

<210> SEQ ID NO 259
<211> LENGTH: 1416
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 259
caggtacaat tgcaggagtc tggaggcggt gtggtgcaac ccggtcgcag cttgcgcctg 60
agttgtgctg cgtctggatt tacattttca tcttacggaa tgcattgggt acgccaggca 120
ccggggaaag gccttgaatg ggtggctgta atttcatacg atggttccaa caaatactat 180
gctgactcag tcaagggtcg atttacaatt agtcgggaca actccaagaa caccctttat 240
cttcaaatga attcccttag agcagaggat acggcggtct attactgtgg tggcagtggt 300
tatgcacttc atgatgatta ctatggcttg gatgtctggg ggcaagggac gcttgtaact 360
gtatcctctg gtggtggtgg tagtggtggg ggaggctccg gcggtggcgg ctctcaatct 420
gctctgactc aaccagcaag cgtatcaggg tcaccgggac agagtattac cataagttgc 480
acggggacct ctagcgatgt agggggggtat aattatgtat cttggtatca acaacacccc 540
gggaaagccc ctaaattgat gatctacgac gtgagcaatc gacctagtgg cgtatcaaat 600
cgcttctctg gtagcaagag tgggaatacg gcgtccctta ctattagcgg attgcaagca 660
gaagatgagg ccgattacta ctgcagctcc tatactagct cttctacatt gtacgtcttt 720
gggagcggaa caaaagtaac agtactcaca acaacacctg ccccgagacc gcctacacca 780
gccccgacta ttgccagcca gcctctgagc ctcaggcctg aggcctgtag gcccgcagcg 840
ggcggcgcag ttcatacacg ggcttggat ttcgcttgtg atatttatat ttgggctcct 900
ttggcgggga catgtggcgt gctgcttctg tcacttgtta ttacactgta ctgtaaacgc 960
gggcgaaaaa aattgctgta tatttttaag cagccattta tgaggcccgt tcagacgacg 1020
caggaggagg acggttgctc ttgcaggttc ccagaagagg aagaaggggg ctgtgaattg 1080
cgggttaaat tttcaagatc cgcagacgct ccagcatacc aacagggaca aaaccaactc 1140
tataacgagc tgaatcttgg aagaagggag gaatatgatg tgctggataa acggcgcggt 1200
agagatccgg agatgggcgg aaaaccaagg cgaaaaaacc ctcaggaggg actctacaac 1260
gaactgcaga aagacaaaat ggcggaggct tattccgaaa taggcatgaa gggcgagcgg 1320
aggcgaggga aagggcacga cggactgtat caaggcctct caaccgcgac taaggatacg 1380
tacgacgccc tgcacatgca ggccctgcct ccgaga 1416

<210> SEQ ID NO 260
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 260
caggtacaat tgcaggagtc tggaggcggt gtggtgcaac ccggtcgcag cttgcgcctg 60
agttgtgctg cgtctggatt tacattttca tcttacggaa tgcattgggt acgccaggca 120

```
ccggggaaag gccttgaatg ggtggctgta atttcatacg atggttccaa caaatactat    180

gctgactcag tcaagggtcg atttacaatt agtcgggaca actccaagaa caccctttat    240

cttcaaatga attcccttag agcagaggat acggcggtct attactgtgg tggcagtggt    300

tatgcacttc atgatgatta ctatggcttg gatgtctggg ggcaagggac gcttgtaact    360

gtatcctct                                                            369
```

<210> SEQ ID NO 261
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261

```
caatctgctc tgactcaacc agcaagcgta tcagggtcac cgggacagag tattaccata     60

agttgcacgg ggacctctag cgatgtaggg ggtataatt  atgtatcttg gtatcaacaa    120

caccccggga aagcccctaa attgatgatc tacgacgtga gcaatcgacc tagtggcgta    180

tcaaatcgct tctctggtag caagagtggg aatacggcgt cccttactat tagcggattg    240

caagcagaag atgaggccga ttactactgc agctcctata ctagctcttc tacattgtac    300

gtctttggga gcggaacaaa agtaacagta ctc                                 333
```

<210> SEQ ID NO 262
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 262

```
gaagtgcaat tggtggaatc aggggggagga cttgtgcagc ctggaggatc gctgagactg     60

tcatgtgccg tgtccggctt tgccctgtcc aaccacggga tgtcctgggt ccgccgcgcg    120

cctggaaagg gcctcgaatg ggtgtcgggt attgtgtaca gcggtagcac ctactatgcc    180

gcatccgtga aggggagatt caccatcagc cgggacaact ccaggaacac tctgtacctc    240

caaatgaatt cgctgaggcc agaggacact gccatctact actgctccgc gcatggcgga    300

gagtccgacg tctggggaca ggggaccacc gtgaccgtgt ctagc                    345
```

<210> SEQ ID NO 263
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 263

```
gacatccagc tcacccagtc cccgagctcg ctgtccgcct ccgtgggaga tcgggtcacc     60

atcacgtgcc gcgccagcca gtcgatttcc tcctacctga actggtacca acagaagccc    120

ggaaaagccc cgaagcttct catctacgcc gcctcgagcc tgcagtcagg agtgccctca    180

cggttctccg gctccggttc cggtactgat ttcaccctga ccatttcctc cctgcaaccg    240

gaggacttcg ctacttacta ctgccagcag tcgtactcca ccccctacac tttcggacaa    300

ggcaccaagg tcgaaatcaa g                                              321
```

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 275

```
Asp Val Pro Asp Tyr Ala Ser Leu Gly Gly Pro Ser Ser Pro Lys Lys
1               5                   10                  15

Lys Arg Lys Val Ser Arg Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Thr Ser Tyr
    130
```

<210> SEQ ID NO 276
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 276

```
Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80

Tyr Gly Ala Thr Gly His Pro Gly Ile Ile Pro Pro His Ala Thr Leu
                85                  90                  95

Val Phe Asp Val Glu Leu Leu Lys Leu Glu Thr Ser
            100                 105
```

<210> SEQ ID NO 277
<211> LENGTH: 93
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 277

```
Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys
                85                  90


<210> SEQ ID NO 278
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Ile Leu Trp His Glu Met Trp His Glu Gly Leu Ile Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95


<210> SEQ ID NO 279
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Ile Leu Trp His Glu Met Trp His Glu Gly Leu Leu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Thr Gln Ala
65                  70                  75                  80

Trp Asp Leu Tyr Tyr His Val Phe Arg Arg Ile Ser Lys Thr Ser
                85                  90                  95


<210> SEQ ID NO 280
```

<211> LENGTH: 95
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 280

Ile Leu Trp His Glu Met Trp His Glu Gly Leu Glu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Leu Gln Ala
65 70 75 80

Trp Asp Leu Tyr Tyr His Val Phe Arg Arg Ile Ser Lys Thr Ser
85 90 95

<210> SEQ ID NO 281
<211> LENGTH: 95
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (78)..(78)
<223> OTHER INFORMATION: Any amino acid

<400> SEQUENCE: 281

Ile Leu Trp His Glu Met Trp His Glu Gly Leu Xaa Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Xaa Gln Ala
65 70 75 80

Trp Asp Leu Tyr Tyr His Val Phe Arg Arg Ile Ser Lys Thr Ser
85 90 95

<210> SEQ ID NO 282
<211> LENGTH: 95
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 282

Ile Leu Trp His Glu Met Trp His Glu Gly Leu Ile Glu Ala Ser Arg
1 5 10 15

Leu Tyr Phe Gly Glu Arg Asn Val Lys Gly Met Phe Glu Val Leu Glu 20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Leu Gln Ala
65 70 75 80

Trp Asp Leu Tyr Tyr His Val Phe Arg Arg Ile Ser Lys Thr Ser
85 90 95

<210> SEQ ID NO 283
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 283

Ile Leu Trp His Glu Met Trp His Glu Gly Leu Leu Glu Ala Ser Arg
1 5 10 15

Leu Tyr Phe Gly Glu Arg Asn Val Lys Gly Met Phe Glu Val Leu Glu
20 25 30

Pro Leu His Ala Met Met Glu Arg Gly Pro Gln Thr Leu Lys Glu Thr
35 40 45

Ser Phe Asn Gln Ala Tyr Gly Arg Asp Leu Met Glu Ala Gln Glu Trp
50 55 60

Cys Arg Lys Tyr Met Lys Ser Gly Asn Val Lys Asp Leu Leu Gln Ala
65 70 75 80

Trp Asp Leu Tyr Tyr His Val Phe Arg Arg Ile Ser Lys Thr Ser
85 90 95

<210> SEQ ID NO 284
<211> LENGTH: 1132
<212> TYPE: PRT
<213> ORGANISM: Homo sapiens

<400> SEQUENCE: 284

Met Pro Arg Ala Pro Arg Cys Arg Ala Val Arg Ser Leu Leu Arg Ser
1 5 10 15

His Tyr Arg Glu Val Leu Pro Leu Ala Thr Phe Val Arg Arg Leu Gly
20 25 30

Pro Gln Gly Trp Arg Leu Val Gln Arg Gly Asp Pro Ala Ala Phe Arg
35 40 45

Ala Leu Val Ala Gln Cys Leu Val Cys Val Pro Trp Asp Ala Arg Pro
50 55 60

Pro Pro Ala Ala Pro Ser Phe Arg Gln Val Ser Cys Leu Lys Glu Leu
65 70 75 80

Val Ala Arg Val Leu Gln Arg Leu Cys Glu Arg Gly Ala Lys Asn Val
85 90 95

Leu Ala Phe Gly Phe Ala Leu Leu Asp Gly Ala Arg Gly Gly Pro Pro
100 105 110

Glu Ala Phe Thr Thr Ser Val Arg Ser Tyr Leu Pro Asn Thr Val Thr
115 120 125

Asp Ala Leu Arg Gly Ser Gly Ala Trp Gly Leu Leu Leu Arg Arg Val
130 135 140

Gly Asp Asp Val Leu Val His Leu Leu Ala Arg Cys Ala Leu Phe Val

-continued

```
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Gly Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575
```

-continued

```
Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990
```

-continued

```
Ser Leu Gln Thr Val Cys Thr Asn  Ile Tyr Lys Ile Leu  Leu Leu Gln
        995                 1000                 1005

Ala Tyr  Arg Phe His Ala Cys  Val Leu Gln Leu Pro  Phe His Gln
    1010                 1015                 1020

Gln Val  Trp Lys Asn Pro Thr  Phe Phe Leu Arg Val  Ile Ser Asp
    1025                 1030                 1035

Thr Ala  Ser Leu Cys Tyr Ser  Ile Leu Lys Ala Lys  Asn Ala Gly
    1040                 1045                 1050

Met Ser  Leu Gly Ala Lys Gly  Ala Ala Gly Pro Leu  Pro Ser Glu
    1055                 1060                 1065

Ala Val  Gln Trp Leu Cys His  Gln Ala Phe Leu Leu  Lys Leu Thr
    1070                 1075                 1080

Arg His  Arg Val Thr Tyr Val  Pro Leu Leu Gly Ser  Leu Arg Thr
    1085                 1090                 1095

Ala Gln  Thr Gln Leu Ser Arg  Lys Leu Pro Gly Thr  Thr Leu Thr
    1100                 1105                 1110

Ala Leu  Glu Ala Ala Ala Asn  Pro Ala Leu Pro Ser  Asp Phe Lys
    1115                 1120                 1125

Thr Ile  Leu Asp
    1130


<210> SEQ ID NO 285
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Met Leu Ser Asn
            20                  25                  30

Ser Asp Thr Trp Asn Trp Ile Arg Gln Ser Pro Ser Arg Gly Leu Glu
        35                  40                  45

Trp Leu Gly Arg Thr Tyr His Arg Ser Thr Trp Tyr Asp Asp Tyr Ala
    50                  55                  60

Ser Ser Val Arg Gly Arg Val Ser Ile Asn Val Asp Thr Ser Lys Asn
65                  70                  75                  80

Gln Tyr Ser Leu Gln Leu Asn Ala Val Thr Pro Glu Asp Thr Gly Val
                85                  90                  95

Tyr Tyr Cys Ala Arg Val Arg Leu Gln Asp Gly Asn Ser Trp Ser Asp
            100                 105                 110

Ala Phe Asp Val Trp Gly Gln Gly Thr Met Val Thr Val Ser Ser Gly
        115                 120                 125

Gly Gly Gly Ser Gly Gly Gly Gly Ser Gly Gly Gly Gly Ser Gln Ser
    130                 135                 140

Ala Leu Thr Gln Pro Ala Ser Ala Ser Gly Ser Pro Gly Gln Ser Val
145                 150                 155                 160

Thr Ile Ser Cys Thr Gly Thr Ser Ser Asp Val Gly Gly Tyr Asn Tyr
                165                 170                 175

Val Ser Trp Tyr Gln Gln His Pro Gly Lys Ala Pro Lys Leu Met Ile
            180                 185                 190

Tyr Asp Val Ser Asn Arg Pro Ser Gly Val Ser Asn Arg Phe Ser Gly
        195                 200                 205
```

```
Ser Lys Ser Gly Asn Thr Ala Ser Leu Thr Ile Ser Gly Leu Gln Ala
    210                 215                 220

Glu Asp Glu Ala Asp Tyr Tyr Cys Ser Ser Tyr Thr Ser Ser Ser Thr
225                 230                 235                 240

Leu Tyr Val Phe Gly Thr Gly Thr Gln Leu Thr Val Leu
                245                 250


<210> SEQ ID NO 286
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Met Leu Ser Asn
            20                  25                  30

Ser Asp Thr Trp Asn Trp Ile Arg Gln Ser Pro Ser Arg Gly Leu Glu
        35                  40                  45

Trp Leu Gly Arg Thr Tyr His Arg Ser Thr Trp Tyr Asp Asp Tyr Ala
    50                  55                  60

Ser Ser Val Arg Gly Arg Val Ser Ile Asn Val Asp Thr Ser Lys Asn
65                  70                  75                  80

Gln Tyr Ser Leu Gln Leu Asn Ala Val Thr Pro Glu Asp Thr Gly Val
                85                  90                  95

Tyr Tyr Cys Ala Arg Val Arg Leu Gln Asp Gly Asn Ser Trp Ser Asp
            100                 105                 110

Ala Phe Asp Val Trp Gly Gln Gly Thr Met Val Thr Val Ser Ser
        115                 120                 125


<210> SEQ ID NO 287
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Gln Ser Ala Leu Thr Gln Pro Ala Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Thr Gly Thr Gln Leu Thr Val Leu
            100                 105                 110


<210> SEQ ID NO 288
```

<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 288

Gly Asp Ser Met Leu Ser Asn Ser Asp Thr Trp Asn
1 5 10

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

Ser Asn Ser Asp Thr Trp Asn
1 5

<210> SEQ ID NO 290
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

Arg Thr Tyr His Arg Ser Thr Trp Tyr Asp Asp Tyr Ala Ser Ser Val
1 5 10 15

Arg Gly

<210> SEQ ID NO 291
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 291

Val Arg Leu Gln Asp Gly Asn Ser Trp Ser Asp Ala Phe Asp Val
1 5 10 15

<210> SEQ ID NO 292
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 292

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

-continued

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Glu Val Lys Leu Gln Glu
115 120 125

Ser Gly Pro Gly Leu Val Ala Pro Ser Gln Ser Leu Ser Val Thr Cys
130 135 140

Thr Val Ser Gly Val Ser Leu Pro Asp Tyr Gly Val Ser Trp Ile Arg
145 150 155 160

Gln Pro Pro Arg Lys Gly Leu Glu Trp Leu Gly Val Ile Trp Gly Ser
165 170 175

Glu Thr Thr Tyr Tyr Asn Ser Ala Leu Lys Ser Arg Leu Thr Ile Ile
180 185 190

Lys Asp Asn Ser Lys Ser Gln Val Phe Leu Lys Met Asn Ser Leu Gln
195 200 205

Thr Asp Asp Thr Ala Ile Tyr Tyr Cys Ala Lys His Tyr Tyr Tyr Gly
210 215 220

Gly Ser Tyr Ala Met Asp Tyr Trp Gly Gln Gly Thr Ser Val Thr Val
225 230 235 240

Ser Ser Thr Thr Thr Pro Ala Pro Arg Pro Pro Thr Pro Ala Pro Thr
245 250 255

Ile Ala Ser Gln Pro Leu Ser Leu Arg Pro Glu Ala Cys Arg Pro Ala
260 265 270

Ala Gly Gly Ala Val His Thr Arg Gly Leu Asp Phe Ala Cys Asp Ile
275 280 285

Tyr Ile Trp Ala Pro Leu Ala Gly Thr Cys Gly Val Leu Leu Leu Ser
290 295 300

Leu Val Ile Thr Leu Tyr Cys Lys Arg Gly Arg Lys Lys Leu Leu Tyr
305 310 315 320

Ile Phe Lys Gln Pro Phe Met Arg Pro Val Gln Thr Thr Gln Glu Glu
325 330 335

Asp Gly Cys Ser Cys Arg Phe Pro Glu Glu Glu Glu Gly Gly Cys Glu
340 345 350

Leu Arg Val Lys Phe Ser Arg Ser Ala Asp Ala Pro Ala Tyr Lys Gln
355 360 365

Gly Gln Asn Gln Leu Tyr Asn Glu Leu Asn Leu Gly Arg Arg Glu Glu
370 375 380

Tyr Asp Val Leu Asp Lys Arg Arg Gly Arg Asp Pro Glu Met Gly Gly
385 390 395 400

Lys Pro Arg Arg Lys Asn Pro Gln Glu Gly Leu Tyr Asn Glu Leu Gln
405 410 415

Lys Asp Lys Met Ala Glu Ala Tyr Ser Glu Ile Gly Met Lys Gly Glu
420 425 430

Arg Arg Arg Gly Lys Gly His Asp Gly Leu Tyr Gln Gly Leu Ser Thr
435 440 445

Ala Thr Lys Asp Thr Tyr Asp Ala Leu His Met Gln Ala Leu Pro Pro
450 455 460

Arg
465

<210> SEQ ID NO 293
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 293

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser
```

<210> SEQ ID NO 294
<211> LENGTH: 465
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 294

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60
```

-continued

```
Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465
```

-continued

<210> SEQ ID NO 295
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Asp Tyr Gly Val Ser
1               5

<210> SEQ ID NO 296
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Val Ile Trp Gly Ser Glu Thr Thr Tyr Tyr Asn Ser Ala Leu Lys Ser
1               5                   10                  15

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

His Tyr Tyr Tyr Gly Gly Ser Tyr Ala Met Asp Tyr
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Arg Ala Ser Gln Asp Ile Ser Lys Tyr Leu Asn
1               5                   10

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

His Thr Ser Arg Leu His Ser
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln Gln Gly Asn Thr Leu Pro Tyr Thr
1               5

<210> SEQ ID NO 301
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

-continued

```
Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 302
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302

atggccttac cagtgaccgc cttgctcctg ccgctggcct tgctgctcca cgccgccagg     60

ccggacatcc agatgacaca gactacatcc tccctgtctg cctctctggg agacagagtc    120

accatcagtt gcagggcaag tcaggacatt agtaaatatt taaattggta tcagcagaaa    180

ccagatggaa ctgttaaact cctgatctac catacatcaa gattacactc aggagtccca    240

tcaaggttca gtggcagtgg gtctggaaca gattattctc tcaccattag caacctggag    300

caagaagata ttgccactta cttttgccaa cagggtaata cgcttccgta cacgttcgga    360

ggggggacca agctggagat cacaggtggc ggtggctcgg gcggtggtgg gtcgggtggc    420

ggcggatctg aggtgaaact gcaggagtca ggacctggcc tggtggcgcc ctcacagagc    480

ctgtccgtca catgcactgt ctcaggggtc tcattacccg actatggtgt aagctggatt    540

cgccagcctc cacgaaaggg tctggagtgg ctgggagtaa tatggggtag tgaaaccaca    600

tactataatt cagctctcaa atccagactg accatcatca aggacaactc caagagccaa    660

gttttcttaa aaatgaacag tctgcaaact gatgacacag ccatttacta ctgtgccaaa    720

cattattact acggtggtag ctatgctatg gactactggg gccaaggaac ctcagtcacc    780

gtctcctcaa ccacgacgcc agcgccgcga ccaccaacac cggcgcccac catcgcgtcg    840

cagcccctgt ccctgcgccc agaggcgtgc cggccagcgg cggggggcgc agtgcacacg    900

agggggctgg acttcgcctg tgatatctac atctgggcgc ccttggccgg gacttgtggg    960

gtccttctcc tgtcactggt tatcaccctt tactgcaaac ggggcagaaa gaaactcctg   1020

tatatattca aacaaccatt tatgagacca gtacaaacta ctcaagagga agatggctgt   1080

agctgccgat ttccagaaga agaagaagga ggatgtgaac tgagagtgaa gttcagcagg   1140
```

agcgcagacg cccccgcgta caagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgc 1458

<210> SEQ ID NO 303
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 303

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Glu Val Lys Leu Gln Glu
115 120 125

Ser Gly Pro Gly Leu Val Ala Pro Ser Gln Ser Leu Ser Val Thr Cys
130 135 140

Thr Val Ser Gly Val Ser Leu Pro Asp Tyr Gly Val Ser Trp Ile Arg
145 150 155 160

Gln Pro Pro Arg Lys Gly Leu Glu Trp Leu Gly Val Ile Trp Gly Ser
165 170 175

Glu Thr Thr Tyr Tyr Asn Ser Ala Leu Lys Ser Arg Leu Thr Ile Ile
180 185 190

Lys Asp Asn Ser Lys Ser Gln Val Phe Leu Lys Met Asn Ser Leu Gln
195 200 205

Thr Asp Asp Thr Ala Ile Tyr Tyr Cys Ala Lys His Tyr Tyr Tyr Gly
210 215 220

Gly Ser Tyr Ala Met Asp Tyr Trp Gly Gln Gly Thr Ser Val Thr Val
225 230 235 240

Ser Ser

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Val Ile Trp Gly Ser Glu Thr Thr Tyr Tyr Gln Ser Ser Leu Lys Ser
1 5 10 15

<210> SEQ ID NO 305
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 305
gaaattgtga tgacccagtc acccgccact cttagccttt cacccggtga gcgcgcaacc 60
ctgtcttgca gagcctccca agacatctca aaatacctta attggtatca acagaagccc 120
ggacaggctc ctcgccttct gatctaccac accagccggc tccattctgg aatccctgcc 180
aggttcagcg gtagcggatc tgggaccgac tacaccctca ctatcagctc actgcagcca 240
gaggacttcg ctgtctattt ctgtcagcaa gggaacaccc tgccctacac ctttggacag 300
ggcaccaagc tcgagattaa aggtggaggt ggcagcggag gaggtgggtc cggcggtgga 360
ggaagccagg tccaactcca agaaagcgga ccgggtcttg tgaagccatc agaaactctt 420
tcactgactt gtactgtgag cggagtgtct ctccccgatt acggggtgtc ttggatcaga 480
cagccaccgg ggaagggtct ggaatggatt ggagtgattt ggggctctga gactacttac 540
taccaatcat ccctcaagtc acgcgtcacc atctcaaagg acaactctaa gaatcaggtg 600
tcactgaaac tgtcatctgt gaccgcagcc gacaccgccg tgtactattg cgctaagcat 660
tactattatg gcgggagcta cgcaatggat tactggggac agggtactct ggtcaccgtg 720
tccagc 726

<210> SEQ ID NO 306
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 306

Met Ala Leu Pro Val Thr Ala Leu Leu Leu Pro Leu Ala Leu Leu Leu
1 5 10 15

His Ala Ala Arg Pro Glu Ile Val Met Thr Gln Ser Pro Ala Thr Leu
20 25 30

Ser Leu Ser Pro Gly Glu Arg Ala Thr Leu Ser Cys Arg Ala Ser Gln
35 40 45

Asp Ile Ser Lys Tyr Leu Asn Trp Tyr Gln Gln Lys Pro Gly Gln Ala
50 55 60

Pro Arg Leu Leu Ile Tyr His Thr Ser Arg Leu His Ser Gly Ile Pro
65 70 75 80

Ala Arg Phe Ser Gly Ser Gly Ser Gly Thr Asp Tyr Thr Leu Thr Ile
85 90 95

Ser Ser Leu Gln Pro Glu Asp Phe Ala Val Tyr Phe Cys Gln Gln Gly
100 105 110

Asn Thr Leu Pro Tyr Thr Phe Gly Gln Gly Thr Lys Leu Glu Ile Lys
115 120 125

Gly Gly Gly Gly Ser Gly Gly Gly Gly Ser Gly Gly Gly Gly Ser Gln
130 135 140

```
Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 307
<211> LENGTH: 1458
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 307

```
atggccctcc ctgtcaccgc cctgctgctt ccgctggctc ttctgctcca cgccgctcgg     60
```

```
cccgaaattg tgatgaccca gtcacccgcc actcttagcc tttcacccgg tgagcgcgca    120

accctgtctt gcagagcctc ccaagacatc tcaaaatacc ttaattggta tcaacagaag    180

cccggacagg ctcctcgcct tctgatctac cacaccagcc ggctccattc tggaatccct    240

gccaggttca gcggtagcgg atctgggacc gactacaccc tcactatcag ctcactgcag    300

ccagaggact tcgctgtcta tttctgtcag caagggaaca ccctgcccta cacctttgga    360

cagggcacca agctcgagat taaaggtgga ggtggcagcg gaggaggtgg gtccggcggt    420

ggaggaagcc aggtccaact ccaagaaagc ggaccgggtc ttgtgaagcc atcagaaact    480

ctttcactga cttgtactgt gagcggagtg tctctccccg attacggggt gtcttggatc    540

agacagccac cggggaaggg tctggaatgg attggagtga tttggggctc tgagactact    600

tactaccaat catccctcaa gtcacgcgtc accatctcaa aggacaactc taagaatcag    660

gtgtcactga aactgtcatc tgtgaccgca gccgacaccg ccgtgtacta ttgcgctaag    720

cattactatt atggcgggag ctacgcaatg gattactggg gacagggtac tctggtcacc    780

gtgtccagca ccactacccc agcaccgagg ccacccaccc cggctcctac catcgcctcc    840

cagcctctgt ccctgcgtcc ggaggcatgt agacccgcag ctggtggggc cgtgcatacc    900

cggggtcttg acttcgcctg cgatatctac atttgggccc ctctggctgg tacttgcggg    960

gtcctgctgc tttcactcgt gatcactctt tactgtaagc gcggtcggaa gaagctgctg   1020

tacatcttta agcaaccctt catgaggcct gtgcagacta ctcaagagga ggacggctgt   1080

tcatgccggt tcccagagga ggaggaaggc ggctgcgaac tgcgcgtgaa attcagccgc   1140

agcgcagatg ctccagccta caagcagggg cagaaccagc tctacaacga actcaatctt   1200

ggtcggagag aggagtacga cgtgctggac aagcggagag gacgggaccc agaaatgggc   1260

gggaagccgc gcagaaagaa tccccaagag ggcctgtaca acgagctcca aaaggataag   1320

atggcagaag cctatagcga gattggtatg aaaggggaac gcagaagagg caaaggccac   1380

gacggactgt accagggact cagcaccgcc accaaggaca cctatgacgc tcttcacatg   1440

caggccctgc cgcctcgg                                                 1458
```

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

```
Leu Ala Glu Ala Ala Ala Lys
1               5
```

<210> SEQ ID NO 309
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 309

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ile Thr Cys Pro Pro Pro Met Ser Val Glu His Ala Asp Ile
        115                 120                 125

Trp Val Lys Ser Tyr Ser Leu Tyr Ser Arg Glu Arg Tyr Ile Cys Asn
    130                 135                 140

Ser Gly Phe Lys Arg Lys Ala Gly Thr Ser Ser Leu Thr Glu Cys Val
145                 150                 155                 160

Leu Asn Lys Ala Thr Asn Val Ala His Trp Thr Thr Pro Ser Leu Lys
                165                 170                 175

Cys Ile Arg Asp Pro Ala Leu Val His Gln Arg Pro Ala Pro Pro Ser
            180                 185                 190

Thr Val Thr Thr Ala Gly Val Thr Pro Gln Pro Glu Ser Leu Ser Pro
        195                 200                 205

Ser Gly Lys Glu Pro Ala Ala Ser Ser Pro Ser Ser Asn Asn Thr Ala
    210                 215                 220

Ala Thr Thr Ala Ala Ile Val Pro Gly Ser Gln Leu Met Pro Ser Lys
225                 230                 235                 240

Ser Pro Ser Thr Gly Thr Thr Glu Ile Ser Ser His Glu Ser Ser His
                245                 250                 255

Gly Thr Pro Ser Gln Thr Thr Ala Lys Asn Trp Glu Leu Thr Ala Ser
            260                 265                 270

Ala Ser His Gln Pro Pro Gly Val Tyr Pro Gln Gly
        275                 280


<210> SEQ ID NO 310
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Val Ser Leu Pro Asp Tyr
1               5


<210> SEQ ID NO 311
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Trp Gly Ser Glu Thr
1               5


<210> SEQ ID NO 312
```

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 312

Gly Val Ser Leu Pro Asp Tyr Gly
1 5

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Ile Trp Gly Ser Glu Thr Thr
1 5

<210> SEQ ID NO 314
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

Ala Lys His Tyr Tyr Tyr Gly Gly Ser Tyr Ala Met Asp Tyr
1 5 10

<210> SEQ ID NO 315
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 315
caggtccaac tccaagaaag cggaccgggt cttgtgaagc catcagaaac tctttcactg 60
acttgtactg tgagcggagt gtctctcccc gattacgggg tgtcttggat cagacagcca 120
ccggggaagg gtctggaatg gattggagtg atttggggct ctgagactac ttactaccaa 180
tcatccctca agtcacgcgt caccatctca aaggacaact ctaagaatca ggtgtcactg 240
aaactgtcat ctgtgaccgc agccgacacc gccgtgtact attgcgctaa gcattactat 300
tatggcggga gctacgcaat ggattactgg ggacagggta ctctggtcac cgtgtccagc 360

<210> SEQ ID NO 316
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Ser Gln Asp Ile Ser Lys Tyr
1 5

<210> SEQ ID NO 317

<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 317

His Thr Ser
1

<210> SEQ ID NO 318
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 318

Gly Asn Thr Leu Pro Tyr
1 5

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 319

Gln Asp Ile Ser Lys Tyr
1 5

<210> SEQ ID NO 320
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 320
gaaattgtga tgacccagtc acccgccact cttagccttt cacccggtga gcgcgcaacc 60
ctgtcttgca gagcctccca agacatctca aaatacctta attggtatca acagaagccc 120
ggacaggctc ctcgccttct gatctaccac accagccggc tccattctgg aatccctgcc 180
aggttcagcg gtagcggatc tgggaccgac tacaccctca ctatcagctc actgcagcca 240
gaggacttcg ctgtctattt ctgtcagcaa gggaacaccc tgccctacac ctttggacag 300
ggcaccaagc tcgagattaa a 321

<210> SEQ ID NO 321
<211> LENGTH: 491
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 321

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

-continued

```
Gly Val Ser Trp Ile Arg Gln Pro Pro Gly Lys Cys Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gln Ser Ala
        115                 120                 125

Leu Thr Gln Pro Ala Ser Val Ser Gly Ser Pro Gly Gln Ser Ile Thr
    130                 135                 140

Ile Ser Cys Thr Gly Thr Ser Ser Asp Val Gly Gly Tyr Asn Tyr Val
145                 150                 155                 160

Ser Trp Tyr Gln Gln His Pro Gly Lys Ala Pro Lys Leu Met Ile Tyr
                165                 170                 175

Asp Val Ser Asn Arg Pro Ser Gly Val Ser Asn Arg Phe Ser Gly Ser
            180                 185                 190

Lys Ser Gly Asn Thr Ala Ser Leu Thr Ile Ser Gly Leu Gln Ala Glu
        195                 200                 205

Asp Glu Ala Asp Tyr Tyr Cys Ser Ser Tyr Thr Ser Ser Ser Thr Leu
    210                 215                 220

Tyr Val Phe Gly Ser Gly Thr Lys Val Thr Val Leu Gly Gly Gly Gly
225                 230                 235                 240

Ser Gly Gly Gly Gly Ser Gly Gly Gly Gly Ser Gly Gly Gly Gly Ser
                245                 250                 255

Gln Val Gln Leu Gln Glu Ser Gly Gly Gly Val Val Gln Pro Gly Arg
            260                 265                 270

Ser Leu Arg Leu Ser Cys Ala Ala Ser Gly Phe Thr Phe Ser Ser Tyr
        275                 280                 285

Gly Met His Trp Val Arg Gln Ala Pro Gly Lys Gly Leu Glu Trp Val
    290                 295                 300

Ala Val Ile Ser Tyr Asp Gly Ser Asn Lys Tyr Tyr Ala Asp Ser Val
305                 310                 315                 320

Lys Gly Arg Phe Thr Ile Ser Arg Asp Asn Ser Lys Asn Thr Leu Tyr
                325                 330                 335

Leu Gln Met Asn Ser Leu Arg Ala Glu Asp Thr Ala Val Tyr Tyr Cys
            340                 345                 350

Gly Gly Ser Gly Tyr Ala Leu His Asp Asp Tyr Tyr Gly Leu Asp Val
        355                 360                 365

Trp Gly Gln Gly Thr Leu Val Thr Val Ser Ser Gly Gly Gly Gly Ser
    370                 375                 380

Glu Ile Val Met Thr Gln Ser Pro Ala Thr Leu Ser Leu Ser Pro Gly
385                 390                 395                 400

Glu Arg Ala Thr Leu Ser Cys Arg Ala Ser Gln Asp Ile Ser Lys Tyr
                405                 410                 415

Leu Asn Trp Tyr Gln Gln Lys Pro Gly Gln Ala Pro Arg Leu Leu Ile
            420                 425                 430

Tyr His Thr Ser Arg Leu His Ser Gly Ile Pro Ala Arg Phe Ser Gly
        435                 440                 445
```

```
Ser Gly Ser Gly Thr Asp Tyr Thr Leu Thr Ile Ser Ser Leu Gln Pro
    450                 455                 460

Glu Asp Phe Ala Val Tyr Phe Cys Gln Gln Gly Asn Thr Leu Pro Tyr
465                 470                 475                 480

Thr Phe Gly Cys Gly Thr Lys Leu Glu Ile Lys
                485                 490


<210> SEQ ID NO 322
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Cys Gly Thr Lys Leu Glu Ile Lys Gly Gly Gly Gly Ser
            100                 105                 110

Gln Val Gln Leu Gln Glu Ser Gly Gly Gly Val Val Gln Pro Gly Arg
        115                 120                 125

Ser Leu Arg Leu Ser Cys Ala Ala Ser Gly Phe Thr Phe Ser Ser Tyr
    130                 135                 140

Gly Met His Trp Val Arg Gln Ala Pro Gly Lys Gly Leu Glu Trp Val
145                 150                 155                 160

Ala Val Ile Ser Tyr Asp Gly Ser Asn Lys Tyr Tyr Ala Asp Ser Val
                165                 170                 175

Lys Gly Arg Phe Thr Ile Ser Arg Asp Asn Ser Lys Asn Thr Leu Tyr
            180                 185                 190

Leu Gln Met Asn Ser Leu Arg Ala Glu Asp Thr Ala Val Tyr Tyr Cys
        195                 200                 205

Gly Gly Ser Gly Tyr Ala Leu His Asp Asp Tyr Tyr Gly Leu Asp Val
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Gln
                245                 250                 255

Ser Ala Leu Thr Gln Pro Ala Ser Val Ser Gly Ser Pro Gly Gln Ser
            260                 265                 270

Ile Thr Ile Ser Cys Thr Gly Thr Ser Ser Asp Val Gly Gly Tyr Asn
        275                 280                 285

Tyr Val Ser Trp Tyr Gln Gln His Pro Gly Lys Ala Pro Lys Leu Met
    290                 295                 300

Ile Tyr Asp Val Ser Asn Arg Pro Ser Gly Val Ser Asn Arg Phe Ser
305                 310                 315                 320
```

```
Gly Ser Lys Ser Gly Asn Thr Ala Ser Leu Thr Ile Ser Gly Leu Gln
                325                 330                 335

Ala Glu Asp Glu Ala Asp Tyr Tyr Cys Ser Ser Tyr Thr Ser Ser Ser
            340                 345                 350

Thr Leu Tyr Val Phe Gly Ser Gly Thr Lys Val Thr Val Leu Gly Gly
        355                 360                 365

Gly Gly Ser Gln Val Gln Leu Gln Glu Ser Gly Pro Gly Leu Val Lys
    370                 375                 380

Pro Ser Glu Thr Leu Ser Leu Thr Cys Thr Val Ser Gly Val Ser Leu
385                 390                 395                 400

Pro Asp Tyr Gly Val Ser Trp Ile Arg Gln Pro Pro Gly Lys Cys Leu
                405                 410                 415

Glu Trp Ile Gly Val Ile Trp Gly Ser Glu Thr Thr Tyr Tyr Gln Ser
            420                 425                 430

Ser Leu Lys Ser Arg Val Thr Ile Ser Lys Asp Asn Ser Lys Asn Gln
        435                 440                 445

Val Ser Leu Lys Leu Ser Ser Val Thr Ala Ala Asp Thr Ala Val Tyr
    450                 455                 460

Tyr Cys Ala Lys His Tyr Tyr Tyr Gly Gly Ser Tyr Ala Met Asp Tyr
465                 470                 475                 480

Trp Gly Gln Gly Thr Leu Val Thr Val Ser Ser
                485                 490


<210> SEQ ID NO 323
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Cys Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gln Val Gln
        115                 120                 125

Leu Gln Glu Ser Gly Gly Gly Val Val Gln Pro Gly Arg Ser Leu Arg
    130                 135                 140

Leu Ser Cys Ala Ala Ser Gly Phe Thr Phe Ser Ser Tyr Gly Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Ala Asp Ser Val Lys Gly Arg
```

```
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Gly Gly Ser
    210                 215                 220

Gly Tyr Ala Leu His Asp Asp Tyr Tyr Gly Leu Asp Val Trp Gly Gln
225                 230                 235                 240

Gly Thr Leu Val Thr Val Ser Ser Gly Gly Gly Gly Ser Gly Gly Gly
                245                 250                 255

Gly Ser Gly Gly Gly Gly Ser Gly Gly Gly Gly Ser Gln Ser Ala Leu
            260                 265                 270

Thr Gln Pro Ala Ser Val Ser Gly Ser Pro Gly Gln Ser Ile Thr Ile
        275                 280                 285

Ser Cys Thr Gly Thr Ser Ser Asp Val Gly Gly Tyr Asn Tyr Val Ser
    290                 295                 300

Trp Tyr Gln Gln His Pro Gly Lys Ala Pro Lys Leu Met Ile Tyr Asp
305                 310                 315                 320

Val Ser Asn Arg Pro Ser Gly Val Ser Asn Arg Phe Ser Gly Ser Lys
                325                 330                 335

Ser Gly Asn Thr Ala Ser Leu Thr Ile Ser Gly Leu Gln Ala Glu Asp
            340                 345                 350

Glu Ala Asp Tyr Tyr Cys Ser Ser Tyr Thr Ser Ser Ser Thr Leu Tyr
        355                 360                 365

Val Phe Gly Ser Gly Thr Lys Val Thr Val Leu Gly Gly Gly Gly Ser
    370                 375                 380

Glu Ile Val Met Thr Gln Ser Pro Ala Thr Leu Ser Leu Ser Pro Gly
385                 390                 395                 400

Glu Arg Ala Thr Leu Ser Cys Arg Ala Ser Gln Asp Ile Ser Lys Tyr
                405                 410                 415

Leu Asn Trp Tyr Gln Gln Lys Pro Gly Gln Ala Pro Arg Leu Leu Ile
            420                 425                 430

Tyr His Thr Ser Arg Leu His Ser Gly Ile Pro Ala Arg Phe Ser Gly
        435                 440                 445

Ser Gly Ser Gly Thr Asp Tyr Thr Leu Thr Ile Ser Ser Leu Gln Pro
    450                 455                 460

Glu Asp Phe Ala Val Tyr Phe Cys Gln Gln Gly Asn Thr Leu Pro Tyr
465                 470                 475                 480

Thr Phe Gly Cys Gly Thr Lys Leu Glu Ile Lys
                485                 490
```

<210> SEQ ID NO 324
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 324

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45
```

-continued

```
Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Cys Gly Thr Lys Leu Glu Ile Lys Gly Gly Gly Gly Ser
            100                 105                 110

Gln Ser Ala Leu Thr Gln Pro Ala Ser Val Ser Gly Ser Pro Gly Gln
        115                 120                 125

Ser Ile Thr Ile Ser Cys Thr Gly Thr Ser Ser Asp Val Gly Gly Tyr
    130                 135                 140

Asn Tyr Val Ser Trp Tyr Gln Gln His Pro Gly Lys Ala Pro Lys Leu
145                 150                 155                 160

Met Ile Tyr Asp Val Ser Asn Arg Pro Ser Gly Val Ser Asn Arg Phe
                165                 170                 175

Ser Gly Ser Lys Ser Gly Asn Thr Ala Ser Leu Thr Ile Ser Gly Leu
            180                 185                 190

Gln Ala Glu Asp Glu Ala Asp Tyr Tyr Cys Ser Ser Tyr Thr Ser Ser
        195                 200                 205

Ser Thr Leu Tyr Val Phe Gly Ser Gly Thr Lys Val Thr Val Leu Gly
    210                 215                 220

Gly Gly Gly Ser Gly Gly Gly Gly Ser Gly Gly Gly Gly Ser Gly Gly
225                 230                 235                 240

Gly Gly Ser Gln Val Gln Leu Gln Glu Ser Gly Gly Gly Val Val Gln
                245                 250                 255

Pro Gly Arg Ser Leu Arg Leu Ser Cys Ala Ala Ser Gly Phe Thr Phe
            260                 265                 270

Ser Ser Tyr Gly Met His Trp Val Arg Gln Ala Pro Gly Lys Gly Leu
        275                 280                 285

Glu Trp Val Ala Val Ile Ser Tyr Asp Gly Ser Asn Lys Tyr Tyr Ala
    290                 295                 300

Asp Ser Val Lys Gly Arg Phe Thr Ile Ser Arg Asp Asn Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Gly Gly Ser Gly Tyr Ala Leu His Asp Asp Tyr Tyr Gly
            340                 345                 350

Leu Asp Val Trp Gly Gln Gly Thr Leu Val Thr Val Ser Ser Gly Gly
        355                 360                 365

Gly Gly Ser Gln Val Gln Leu Gln Glu Ser Gly Pro Gly Leu Val Lys
    370                 375                 380

Pro Ser Glu Thr Leu Ser Leu Thr Cys Thr Val Ser Gly Val Ser Leu
385                 390                 395                 400

Pro Asp Tyr Gly Val Ser Trp Ile Arg Gln Pro Pro Gly Lys Cys Leu
                405                 410                 415

Glu Trp Ile Gly Val Ile Trp Gly Ser Glu Thr Thr Tyr Tyr Gln Ser
            420                 425                 430

Ser Leu Lys Ser Arg Val Thr Ile Ser Lys Asp Asn Ser Lys Asn Gln
        435                 440                 445

Val Ser Leu Lys Leu Ser Ser Val Thr Ala Ala Asp Thr Ala Val Tyr
    450                 455                 460

Tyr Cys Ala Lys His Tyr Tyr Tyr Gly Gly Ser Tyr Ala Met Asp Tyr
```

```
465                 470                 475                 480

Trp Gly Gln Gly Thr Leu Val Thr Val Ser Ser
                485                 490


<210> SEQ ID NO 325
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Glu Ile Val Met Thr Gln Ser Pro Ala Thr Leu Ser Leu Ser Pro Gly
    130                 135                 140

Glu Arg Ala Thr Leu Ser Cys Arg Ala Ser Gln Asp Ile Ser Lys Tyr
145                 150                 155                 160

Leu Asn Trp Tyr Gln Gln Lys Pro Gly Gln Ala Pro Arg Leu Leu Ile
                165                 170                 175

Tyr His Thr Ser Arg Leu His Ser Gly Ile Pro Ala Arg Phe Ser Gly
            180                 185                 190

Ser Gly Ser Gly Thr Asp Tyr Thr Leu Thr Ile Ser Ser Leu Gln Pro
        195                 200                 205

Glu Asp Phe Ala Val Tyr Phe Cys Gln Gln Gly Asn Thr Leu Pro Tyr
    210                 215                 220

Thr Phe Gly Gln Gly Thr Lys Leu Glu Ile Lys Gly Gly Gly Gly Ser
225                 230                 235                 240

Gly Gly Gly Gly Ser Gly Gly Gly Gly Ser Gly Gly Gly Gly Ser Gln
                245                 250                 255

Val Gln Leu Gln Glu Ser Gly Pro Gly Leu Val Lys Pro Ser Glu Thr
            260                 265                 270

Leu Ser Leu Thr Cys Thr Val Ser Gly Val Ser Leu Pro Asp Tyr Gly
        275                 280                 285

Val Ser Trp Ile Arg Gln Pro Pro Gly Lys Gly Leu Glu Trp Ile Gly
    290                 295                 300

Val Ile Trp Gly Ser Glu Thr Thr Tyr Tyr Gln Ser Ser Leu Lys Ser
305                 310                 315                 320

Arg Val Thr Ile Ser Lys Asp Asn Ser Lys Asn Gln Val Ser Leu Lys
                325                 330                 335
```

```
Leu Ser Ser Val Thr Ala Ala Asp Thr Ala Val Tyr Tyr Cys Ala Lys
            340                 345                 350

His Tyr Tyr Tyr Gly Gly Ser Tyr Ala Met Asp Tyr Trp Gly Gln Gly
        355                 360                 365

Thr Leu Val Thr Val Ser Ser Gly Gly Gly Gly Ser Gln Ser Ala Leu
    370                 375                 380

Thr Gln Pro Ala Ser Val Ser Gly Ser Pro Gly Gln Ser Ile Thr Ile
385                 390                 395                 400

Ser Cys Thr Gly Thr Ser Ser Asp Val Gly Gly Tyr Asn Tyr Val Ser
                405                 410                 415

Trp Tyr Gln Gln His Pro Gly Lys Ala Pro Lys Leu Met Ile Tyr Asp
            420                 425                 430

Val Ser Asn Arg Pro Ser Gly Val Ser Asn Arg Phe Ser Gly Ser Lys
        435                 440                 445

Ser Gly Asn Thr Ala Ser Leu Thr Ile Ser Gly Leu Gln Ala Glu Asp
    450                 455                 460

Glu Ala Asp Tyr Tyr Cys Ser Ser Tyr Thr Ser Ser Ser Thr Leu Tyr
465                 470                 475                 480

Val Phe Gly Cys Gly Thr Lys Val Thr Val Leu
                485                 490


<210> SEQ ID NO 326
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Cys Gly Thr Lys Val Thr Val Leu Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Thr Val Ser Gly Val Ser
    130                 135                 140

Leu Pro Asp Tyr Gly Val Ser Trp Ile Arg Gln Pro Pro Gly Lys Gly
145                 150                 155                 160

Leu Glu Trp Ile Gly Val Ile Trp Gly Ser Glu Thr Thr Tyr Tyr Gln
                165                 170                 175

Ser Ser Leu Lys Ser Arg Val Thr Ile Ser Lys Asp Asn Ser Lys Asn
            180                 185                 190

Gln Val Ser Leu Lys Leu Ser Ser Val Thr Ala Ala Asp Thr Ala Val
        195                 200                 205
```

```
Tyr Tyr Cys Ala Lys His Tyr Tyr Tyr Gly Gly Ser Tyr Ala Met Asp
    210                 215                 220

Tyr Trp Gly Gln Gly Thr Leu Val Thr Val Ser Ser Gly Gly Gly Gly
225                 230                 235                 240

Ser Gly Gly Gly Gly Ser Gly Gly Gly Gly Ser Gly Gly Gly Gly Ser
                245                 250                 255

Glu Ile Val Met Thr Gln Ser Pro Ala Thr Leu Ser Leu Ser Pro Gly
            260                 265                 270

Glu Arg Ala Thr Leu Ser Cys Arg Ala Ser Gln Asp Ile Ser Lys Tyr
        275                 280                 285

Leu Asn Trp Tyr Gln Gln Lys Pro Gly Gln Ala Pro Arg Leu Leu Ile
    290                 295                 300

Tyr His Thr Ser Arg Leu His Ser Gly Ile Pro Ala Arg Phe Ser Gly
305                 310                 315                 320

Ser Gly Ser Gly Thr Asp Tyr Thr Leu Thr Ile Ser Ser Leu Gln Pro
                325                 330                 335

Glu Asp Phe Ala Val Tyr Phe Cys Gln Gln Gly Asn Thr Leu Pro Tyr
            340                 345                 350

Thr Phe Gly Gln Gly Thr Lys Leu Glu Ile Lys Gly Gly Gly Gly Ser
        355                 360                 365

Gln Val Gln Leu Gln Glu Ser Gly Gly Gly Val Val Gln Pro Gly Arg
    370                 375                 380

Ser Leu Arg Leu Ser Cys Ala Ala Ser Gly Phe Thr Phe Ser Ser Tyr
385                 390                 395                 400

Gly Met His Trp Val Arg Gln Ala Pro Gly Lys Cys Leu Glu Trp Val
                405                 410                 415

Ala Val Ile Ser Tyr Asp Gly Ser Asn Lys Tyr Tyr Ala Asp Ser Val
            420                 425                 430

Lys Gly Arg Phe Thr Ile Ser Arg Asp Asn Ser Lys Asn Thr Leu Tyr
        435                 440                 445

Leu Gln Met Asn Ser Leu Arg Ala Glu Asp Thr Ala Val Tyr Tyr Cys
    450                 455                 460

Gly Gly Ser Gly Tyr Ala Leu His Asp Asp Tyr Tyr Gly Leu Asp Val
465                 470                 475                 480

Trp Gly Gln Gly Thr Leu Val Thr Val Ser Ser
                485                 490
```

<210> SEQ ID NO 327
<211> LENGTH: 491
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 327

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
```

-continued

```
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Gln Val Gln Leu Gln Glu Ser Gly Pro Gly Leu Val Lys Pro Ser Glu
    130                 135                 140

Thr Leu Ser Leu Thr Cys Thr Val Ser Gly Val Ser Leu Pro Asp Tyr
145                 150                 155                 160

Gly Val Ser Trp Ile Arg Gln Pro Pro Gly Lys Gly Leu Glu Trp Ile
                165                 170                 175

Gly Val Ile Trp Gly Ser Glu Thr Thr Tyr Tyr Gln Ser Ser Leu Lys
            180                 185                 190

Ser Arg Val Thr Ile Ser Lys Asp Asn Ser Lys Asn Gln Val Ser Leu
        195                 200                 205

Lys Leu Ser Ser Val Thr Ala Ala Asp Thr Ala Val Tyr Tyr Cys Ala
    210                 215                 220

Lys His Tyr Tyr Tyr Gly Gly Ser Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Gly Gly Gly Gly Ser Gly Gly Gly Gly Ser Glu Ile Val Met
            260                 265                 270

Thr Gln Ser Pro Ala Thr Leu Ser Leu Ser Pro Gly Glu Arg Ala Thr
        275                 280                 285

Leu Ser Cys Arg Ala Ser Gln Asp Ile Ser Lys Tyr Leu Asn Trp Tyr
    290                 295                 300

Gln Gln Lys Pro Gly Gln Ala Pro Arg Leu Leu Ile Tyr His Thr Ser
305                 310                 315                 320

Arg Leu His Ser Gly Ile Pro Ala Arg Phe Ser Gly Ser Gly Ser Gly
                325                 330                 335

Thr Asp Tyr Thr Leu Thr Ile Ser Ser Leu Gln Pro Glu Asp Phe Ala
            340                 345                 350

Val Tyr Phe Cys Gln Gln Gly Asn Thr Leu Pro Tyr Thr Phe Gly Gln
        355                 360                 365

Gly Thr Lys Leu Glu Ile Lys Gly Gly Gly Gly Ser Gln Ser Ala Leu
    370                 375                 380

Thr Gln Pro Ala Ser Val Ser Gly Ser Pro Gly Gln Ser Ile Thr Ile
385                 390                 395                 400

Ser Cys Thr Gly Thr Ser Ser Asp Val Gly Gly Tyr Asn Tyr Val Ser
                405                 410                 415

Trp Tyr Gln Gln His Pro Gly Lys Ala Pro Lys Leu Met Ile Tyr Asp
            420                 425                 430

Val Ser Asn Arg Pro Ser Gly Val Ser Asn Arg Phe Ser Gly Ser Lys
        435                 440                 445

Ser Gly Asn Thr Ala Ser Leu Thr Ile Ser Gly Leu Gln Ala Glu Asp
    450                 455                 460

Glu Ala Asp Tyr Tyr Cys Ser Ser Tyr Thr Ser Ser Ser Thr Leu Tyr
465                 470                 475                 480

Val Phe Gly Cys Gly Thr Lys Val Thr Val Leu
                485                 490
```

<210> SEQ ID NO 328
<211> LENGTH: 491
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 328

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Cys Gly Thr Lys Val Thr Val Leu Gly
            100                 105                 110

Gly Gly Gly Ser Glu Ile Val Met Thr Gln Ser Pro Ala Thr Leu Ser
        115                 120                 125

Leu Ser Pro Gly Glu Arg Ala Thr Leu Ser Cys Arg Ala Ser Gln Asp
    130                 135                 140

Ile Ser Lys Tyr Leu Asn Trp Tyr Gln Gln Lys Pro Gly Gln Ala Pro
145                 150                 155                 160

Arg Leu Leu Ile Tyr His Thr Ser Arg Leu His Ser Gly Ile Pro Ala
                165                 170                 175

Arg Phe Ser Gly Ser Gly Ser Gly Thr Asp Tyr Thr Leu Thr Ile Ser
            180                 185                 190

Ser Leu Gln Pro Glu Asp Phe Ala Val Tyr Phe Cys Gln Gln Gly Asn
        195                 200                 205

Thr Leu Pro Tyr Thr Phe Gly Gln Gly Thr Lys Leu Glu Ile Lys Gly
    210                 215                 220

Gly Gly Gly Ser Gly Gly Gly Gly Ser Gly Gly Gly Gly Ser Gly Gly
225                 230                 235                 240

Gly Gly Ser Gln Val Gln Leu Gln Glu Ser Gly Pro Gly Leu Val Lys
                245                 250                 255

Pro Ser Glu Thr Leu Ser Leu Thr Cys Thr Val Ser Gly Val Ser Leu
            260                 265                 270

Pro Asp Tyr Gly Val Ser Trp Ile Arg Gln Pro Pro Gly Lys Gly Leu
        275                 280                 285

Glu Trp Ile Gly Val Ile Trp Gly Ser Glu Thr Thr Tyr Tyr Gln Ser
    290                 295                 300

Ser Leu Lys Ser Arg Val Thr Ile Ser Lys Asp Asn Ser Lys Asn Gln
305                 310                 315                 320

Val Ser Leu Lys Leu Ser Ser Val Thr Ala Ala Asp Thr Ala Val Tyr
                325                 330                 335

Tyr Cys Ala Lys His Tyr Tyr Tyr Gly Gly Ser Tyr Ala Met Asp Tyr
            340                 345                 350

Trp Gly Gln Gly Thr Leu Val Thr Val Ser Ser Gly Gly Gly Gly Ser
```

```
        355                 360                 365

Gln Val Gln Leu Gln Glu Ser Gly Gly Gly Val Val Gln Pro Gly Arg
    370                 375                 380

Ser Leu Arg Leu Ser Cys Ala Ala Ser Gly Phe Thr Phe Ser Ser Tyr
385                 390                 395                 400

Gly Met His Trp Val Arg Gln Ala Pro Gly Lys Cys Leu Glu Trp Val
                405                 410                 415

Ala Val Ile Ser Tyr Asp Gly Ser Asn Lys Tyr Tyr Ala Asp Ser Val
            420                 425                 430

Lys Gly Arg Phe Thr Ile Ser Arg Asp Asn Ser Lys Asn Thr Leu Tyr
        435                 440                 445

Leu Gln Met Asn Ser Leu Arg Ala Glu Asp Thr Ala Val Tyr Tyr Cys
    450                 455                 460

Gly Gly Ser Gly Tyr Ala Leu His Asp Asp Tyr Tyr Gly Leu Asp Val
465                 470                 475                 480

Trp Gly Gln Gly Thr Leu Val Thr Val Ser Ser
                485                 490


<210> SEQ ID NO 329
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Cys Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Asp Ile Gln
        115                 120                 125

Met Thr Gln Ser Pro Ser Ser Leu Ser Ala Ser Val Gly Asp Arg Val
    130                 135                 140

Thr Ile Thr Cys Arg Ala Ser Gln Ser Ile Ser Ser Tyr Leu Asn Trp
145                 150                 155                 160

Tyr Gln Gln Lys Pro Gly Lys Ala Pro Lys Leu Leu Ile Tyr Ala Ala
                165                 170                 175

Ser Ser Leu Gln Ser Gly Val Pro Ser Arg Phe Ser Gly Ser Gly Ser
            180                 185                 190

Gly Thr Asp Phe Thr Leu Thr Ile Ser Ser Leu Gln Pro Glu Asp Phe
        195                 200                 205

Ala Thr Tyr Tyr Cys Gln Gln Ser Tyr Ser Thr Pro Leu Thr Phe Gly
    210                 215                 220
```

Gln Gly Thr Lys Val Glu Ile Lys Gly Gly Gly Gly Ser Gly Gly Gly
225 230 235 240

Gly Ser Gly Gly Gly Gly Ser Gly Gly Gly Gly Ser Glu Val Gln Leu
245 250 255

Leu Glu Ser Gly Gly Gly Leu Val Gln Pro Gly Gly Ser Leu Arg Leu
260 265 270

Ser Cys Ala Ala Ser Gly Phe Thr Phe Ser Ser Tyr Ala Met Ser Trp
275 280 285

Val Arg Gln Ala Pro Gly Lys Gly Leu Glu Trp Val Ser Ala Ile Ser
290 295 300

Gly Ser Gly Gly Ser Thr Tyr Tyr Ala Asp Ser Val Lys Gly Arg Phe
305 310 315 320

Thr Ile Ser Arg Asp Asn Ser Lys Asn Thr Leu Tyr Leu Gln Met Asn
325 330 335

Ser Leu Arg Ala Glu Asp Thr Ala Val Tyr Tyr Cys Ala Arg Arg Glu
340 345 350

Trp Trp Gly Glu Ser Trp Leu Phe Asp Tyr Trp Gly Gln Gly Thr Leu
355 360 365

Val Thr Val Ser Ser Gly Gly Gly Gly Ser Glu Ile Val Met Thr Gln
370 375 380

Ser Pro Ala Thr Leu Ser Leu Ser Pro Gly Glu Arg Ala Thr Leu Ser
385 390 395 400

Cys Arg Ala Ser Gln Asp Ile Ser Lys Tyr Leu Asn Trp Tyr Gln Gln
405 410 415

Lys Pro Gly Gln Ala Pro Arg Leu Leu Ile Tyr His Thr Ser Arg Leu
420 425 430

His Ser Gly Ile Pro Ala Arg Phe Ser Gly Ser Gly Ser Gly Thr Asp
435 440 445

Tyr Thr Leu Thr Ile Ser Ser Leu Gln Pro Glu Asp Phe Ala Val Tyr
450 455 460

Phe Cys Gln Gln Gly Asn Thr Leu Pro Tyr Thr Phe Gly Cys Gly Thr
465 470 475 480

Lys Leu Glu Ile Lys
485

<210> SEQ ID NO 330
<211> LENGTH: 485
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 330

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Cys Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Arg Arg Glu Trp Trp Gly Glu Ser Trp Leu Phe Asp Tyr Trp Gly
            100                 105                 110

Gln Gly Thr Leu Val Thr Val Ser Ser Gly Gly Gly Gly Ser Glu Ile
        115                 120                 125

Val Met Thr Gln Ser Pro Ala Thr Leu Ser Leu Ser Pro Gly Glu Arg
    130                 135                 140

Ala Thr Leu Ser Cys Arg Ala Ser Gln Asp Ile Ser Lys Tyr Leu Asn
145                 150                 155                 160

Trp Tyr Gln Gln Lys Pro Gly Gln Ala Pro Arg Leu Leu Ile Tyr His
                165                 170                 175

Thr Ser Arg Leu His Ser Gly Ile Pro Ala Arg Phe Ser Gly Ser Gly
            180                 185                 190

Ser Gly Thr Asp Tyr Thr Leu Thr Ile Ser Ser Leu Gln Pro Glu Asp
        195                 200                 205

Phe Ala Val Tyr Phe Cys Gln Gln Gly Asn Thr Leu Pro Tyr Thr Phe
    210                 215                 220

Gly Gln Gly Thr Lys Leu Glu Ile Lys Gly Gly Gly Gly Ser Gly Gly
225                 230                 235                 240

Gly Gly Ser Gly Gly Gly Gly Ser Gly Gly Gly Gly Ser Gln Val Gln
                245                 250                 255

Leu Gln Glu Ser Gly Pro Gly Leu Val Lys Pro Ser Glu Thr Leu Ser
            260                 265                 270

Leu Thr Cys Thr Val Ser Gly Val Ser Leu Pro Asp Tyr Gly Val Ser
        275                 280                 285

Trp Ile Arg Gln Pro Pro Gly Lys Gly Leu Glu Trp Ile Gly Val Ile
    290                 295                 300

Trp Gly Ser Glu Thr Thr Tyr Tyr Gln Ser Ser Leu Lys Ser Arg Val
305                 310                 315                 320

Thr Ile Ser Lys Asp Asn Ser Lys Asn Gln Val Ser Leu Lys Leu Ser
                325                 330                 335

Ser Val Thr Ala Ala Asp Thr Ala Val Tyr Tyr Cys Ala Lys His Tyr
            340                 345                 350

Tyr Tyr Gly Gly Ser Tyr Ala Met Asp Tyr Trp Gly Gln Gly Thr Leu
        355                 360                 365

Val Thr Val Ser Ser Gly Gly Gly Gly Ser Asp Ile Gln Met Thr Gln
    370                 375                 380

Ser Pro Ser Ser Leu Ser Ala Ser Val Gly Asp Arg Val Thr Ile Thr
385                 390                 395                 400

Cys Arg Ala Ser Gln Ser Ile Ser Ser Tyr Leu Asn Trp Tyr Gln Gln
                405                 410                 415

Lys Pro Gly Lys Ala Pro Lys Leu Leu Ile Tyr Ala Ala Ser Ser Leu
            420                 425                 430

Gln Ser Gly Val Pro Ser Arg Phe Ser Gly Ser Gly Ser Gly Thr Asp
        435                 440                 445

Phe Thr Leu Thr Ile Ser Ser Leu Gln Pro Glu Asp Phe Ala Thr Tyr
    450                 455                 460

Tyr Cys Gln Gln Ser Tyr Ser Thr Pro Leu Thr Phe Gly Cys Gly Thr
465                 470                 475                 480

Lys Val Glu Ile Lys
                485
```

<210> SEQ ID NO 331
<211> LENGTH: 120

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Cys Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120


<210> SEQ ID NO 332
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Cys Gly Thr Lys Leu Glu Ile Lys
            100                 105


<210> SEQ ID NO 333
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
            20                  25                  30

Gly Met His Trp Val Arg Gln Ala Pro Gly Lys Cys Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser
        115                 120


<210> SEQ ID NO 334
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Cys Gly Thr Lys Val Thr Val Leu
            100                 105                 110


<210> SEQ ID NO 335
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95

Ala Arg Arg Glu Trp Trp Gly Glu Ser Trp Leu Phe Asp Tyr Trp Gly
            100                 105                 110

Gln Gly Thr Leu Val Thr Val Ser Ser
        115                 120
```

<210> SEQ ID NO 336
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 336

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Cys Gly Thr Lys Val Glu Ile Lys
            100                 105
```

<210> SEQ ID NO 337
<211> LENGTH: 135
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 337

```
accactaccc cagcaccgag gccacccacc ccggctccta ccatcgcctc ccagcctctg      60

tccctgcgtc cggaggcatg tagacccgca gctggtgggg ccgtgcatac ccggggtctt     120

gacttcgcct gcgat                                                      135
```

<210> SEQ ID NO 338
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 338

```
atctacattt gggcccctct ggctggtact tgcggggtcc tgctgctttc actcgtgatc      60

actctttact gt                                                          72
```

<210> SEQ ID NO 339
<211> LENGTH: 714
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 339

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Cys Leu Glu Trp Ile
35 40 45

Gly Val Ile Trp Gly Ser Glu Thr Thr Tyr Tyr Gln Ser Ser Leu Lys
50 55 60

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser Gly Gly Gly Gly Ser Gln Ser Ala
115 120 125

Leu Thr Gln Pro Ala Ser Val Ser Gly Ser Pro Gly Gln Ser Ile Thr
130 135 140

Ile Ser Cys Thr Gly Thr Ser Ser Asp Val Gly Gly Tyr Asn Tyr Val
145 150 155 160

Ser Trp Tyr Gln Gln His Pro Gly Lys Ala Pro Lys Leu Met Ile Tyr
165 170 175

Asp Val Ser Asn Arg Pro Ser Gly Val Ser Asn Arg Phe Ser Gly Ser
180 185 190

Lys Ser Gly Asn Thr Ala Ser Leu Thr Ile Ser Gly Leu Gln Ala Glu
195 200 205

Asp Glu Ala Asp Tyr Tyr Cys Ser Ser Tyr Thr Ser Ser Ser Thr Leu
210 215 220

Tyr Val Phe Gly Ser Gly Thr Lys Val Thr Val Leu Gly Gly Gly Gly
225 230 235 240

Ser Gly Gly Gly Gly Ser Gly Gly Gly Gly Ser Gly Gly Gly Gly Ser
245 250 255

Gln Val Gln Leu Gln Glu Ser Gly Gly Gly Val Val Gln Pro Gly Arg
260 265 270

Ser Leu Arg Leu Ser Cys Ala Ala Ser Gly Phe Thr Phe Ser Ser Tyr
275 280 285

Gly Met His Trp Val Arg Gln Ala Pro Gly Lys Gly Leu Glu Trp Val
290 295 300

Ala Val Ile Ser Tyr Asp Gly Ser Asn Lys Tyr Tyr Ala Asp Ser Val
305 310 315 320

Lys Gly Arg Phe Thr Ile Ser Arg Asp Asn Ser Lys Asn Thr Leu Tyr
325 330 335

Leu Gln Met Asn Ser Leu Arg Ala Glu Asp Thr Ala Val Tyr Tyr Cys
340 345 350

Gly Gly Ser Gly Tyr Ala Leu His Asp Asp Tyr Tyr Gly Leu Asp Val
355 360 365

Trp Gly Gln Gly Thr Leu Val Thr Val Ser Ser Gly Gly Gly Gly Ser
370 375 380

Glu Ile Val Met Thr Gln Ser Pro Ala Thr Leu Ser Leu Ser Pro Gly
385 390 395 400

-continued

Glu Arg Ala Thr Leu Ser Cys Arg Ala Ser Gln Asp Ile Ser Lys Tyr
405 410 415

Leu Asn Trp Tyr Gln Gln Lys Pro Gly Gln Ala Pro Arg Leu Leu Ile
420 425 430

Tyr His Thr Ser Arg Leu His Ser Gly Ile Pro Ala Arg Phe Ser Gly
435 440 445

Ser Gly Ser Gly Thr Asp Tyr Thr Leu Thr Ile Ser Ser Leu Gln Pro
450 455 460

Glu Asp Phe Ala Val Tyr Phe Cys Gln Gln Gly Asn Thr Leu Pro Tyr
465 470 475 480

Thr Phe Gly Cys Gly Thr Lys Leu Glu Ile Lys Thr Thr Thr Pro Ala
485 490 495

Pro Arg Pro Pro Thr Pro Ala Pro Thr Ile Ala Ser Gln Pro Leu Ser
500 505 510

Leu Arg Pro Glu Ala Cys Arg Pro Ala Ala Gly Gly Ala Val His Thr
515 520 525

Arg Gly Leu Asp Phe Ala Cys Asp Ile Tyr Ile Trp Ala Pro Leu Ala
530 535 540

Gly Thr Cys Gly Val Leu Leu Leu Ser Leu Val Ile Thr Leu Tyr Cys
545 550 555 560

Lys Arg Gly Arg Lys Lys Leu Leu Tyr Ile Phe Lys Gln Pro Phe Met
565 570 575

Arg Pro Val Gln Thr Thr Gln Glu Glu Asp Gly Cys Ser Cys Arg Phe
580 585 590

Pro Glu Glu Glu Glu Gly Gly Cys Glu Leu Arg Val Lys Phe Ser Arg
595 600 605

Ser Ala Asp Ala Pro Ala Tyr Lys Gln Gly Gln Asn Gln Leu Tyr Asn
610 615 620

Glu Leu Asn Leu Gly Arg Arg Glu Glu Tyr Asp Val Leu Asp Lys Arg
625 630 635 640

Arg Gly Arg Asp Pro Glu Met Gly Gly Lys Pro Arg Arg Lys Asn Pro
645 650 655

Gln Glu Gly Leu Tyr Asn Glu Leu Gln Lys Asp Lys Met Ala Glu Ala
660 665 670

Tyr Ser Glu Ile Gly Met Lys Gly Glu Arg Arg Arg Gly Lys Gly His
675 680 685

Asp Gly Leu Tyr Gln Gly Leu Ser Thr Ala Thr Lys Asp Thr Tyr Asp
690 695 700

Ala Leu His Met Gln Ala Leu Pro Pro Arg
705 710

<210> SEQ ID NO 340
<211> LENGTH: 714
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 340

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

-continued

```
Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Cys Gly Thr Lys Leu Glu Ile Lys Gly Gly Gly Gly Ser
            100                 105                 110

Gln Val Gln Leu Gln Glu Ser Gly Gly Gly Val Val Gln Pro Gly Arg
        115                 120                 125

Ser Leu Arg Leu Ser Cys Ala Ala Ser Gly Phe Thr Phe Ser Ser Tyr
    130                 135                 140

Gly Met His Trp Val Arg Gln Ala Pro Gly Lys Gly Leu Glu Trp Val
145                 150                 155                 160

Ala Val Ile Ser Tyr Asp Gly Ser Asn Lys Tyr Tyr Ala Asp Ser Val
                165                 170                 175

Lys Gly Arg Phe Thr Ile Ser Arg Asp Asn Ser Lys Asn Thr Leu Tyr
            180                 185                 190

Leu Gln Met Asn Ser Leu Arg Ala Glu Asp Thr Ala Val Tyr Tyr Cys
        195                 200                 205

Gly Gly Ser Gly Tyr Ala Leu His Asp Asp Tyr Tyr Gly Leu Asp Val
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Gln
                245                 250                 255

Ser Ala Leu Thr Gln Pro Ala Ser Val Ser Gly Ser Pro Gly Gln Ser
            260                 265                 270

Ile Thr Ile Ser Cys Thr Gly Thr Ser Ser Asp Val Gly Gly Tyr Asn
        275                 280                 285

Tyr Val Ser Trp Tyr Gln Gln His Pro Gly Lys Ala Pro Lys Leu Met
    290                 295                 300

Ile Tyr Asp Val Ser Asn Arg Pro Ser Gly Val Ser Asn Arg Phe Ser
305                 310                 315                 320

Gly Ser Lys Ser Gly Asn Thr Ala Ser Leu Thr Ile Ser Gly Leu Gln
                325                 330                 335

Ala Glu Asp Glu Ala Asp Tyr Tyr Cys Ser Ser Tyr Thr Ser Ser Ser
            340                 345                 350

Thr Leu Tyr Val Phe Gly Ser Gly Thr Lys Val Thr Val Leu Gly Gly
        355                 360                 365

Gly Gly Ser Gln Val Gln Leu Gln Glu Ser Gly Pro Gly Leu Val Lys
    370                 375                 380

Pro Ser Glu Thr Leu Ser Leu Thr Cys Thr Val Ser Gly Val Ser Leu
385                 390                 395                 400

Pro Asp Tyr Gly Val Ser Trp Ile Arg Gln Pro Pro Gly Lys Cys Leu
                405                 410                 415

Glu Trp Ile Gly Val Ile Trp Gly Ser Glu Thr Thr Tyr Tyr Gln Ser
            420                 425                 430

Ser Leu Lys Ser Arg Val Thr Ile Ser Lys Asp Asn Ser Lys Asn Gln
        435                 440                 445

Val Ser Leu Lys Leu Ser Ser Val Thr Ala Ala Asp Thr Ala Val Tyr
    450                 455                 460
```

-continued

```
Tyr Cys Ala Lys His Tyr Tyr Tyr Gly Gly Ser Tyr Ala Met Asp Tyr
465                 470                 475                 480

Trp Gly Gln Gly Thr Leu Val Thr Val Ser Ser Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525

Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590

Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
        675                 680                 685

Asp Gly Leu Tyr Gln Gly Leu Ser Thr Ala Thr Lys Asp Thr Tyr Asp
    690                 695                 700

Ala Leu His Met Gln Ala Leu Pro Pro Arg
705                 710


<210> SEQ ID NO 341
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Cys Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110
```

```
Gly Thr Leu Val Thr Val Ser Ser Gly Gly Gly Gly Ser Gln Val Gln
        115                 120                 125

Leu Gln Glu Ser Gly Gly Gly Val Val Gln Pro Gly Arg Ser Leu Arg
    130                 135                 140

Leu Ser Cys Ala Ala Ser Gly Phe Thr Phe Ser Ser Tyr Gly Met His
145                 150                 155                 160

Trp Val Arg Gln Ala Pro Gly Lys Gly Leu Glu Trp Val Ala Val Ile
                165                 170                 175

Ser Tyr Asp Gly Ser Asn Lys Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Gly Gly Ser
    210                 215                 220

Gly Tyr Ala Leu His Asp Asp Tyr Tyr Gly Leu Asp Val Trp Gly Gln
225                 230                 235                 240

Gly Thr Leu Val Thr Val Ser Ser Gly Gly Gly Gly Ser Gly Gly Gly
                245                 250                 255

Gly Ser Gly Gly Gly Gly Ser Gly Gly Gly Gly Ser Gln Ser Ala Leu
            260                 265                 270

Thr Gln Pro Ala Ser Val Ser Gly Ser Pro Gly Gln Ser Ile Thr Ile
        275                 280                 285

Ser Cys Thr Gly Thr Ser Ser Asp Val Gly Gly Tyr Asn Tyr Val Ser
    290                 295                 300

Trp Tyr Gln Gln His Pro Gly Lys Ala Pro Lys Leu Met Ile Tyr Asp
305                 310                 315                 320

Val Ser Asn Arg Pro Ser Gly Val Ser Asn Arg Phe Ser Gly Ser Lys
                325                 330                 335

Ser Gly Asn Thr Ala Ser Leu Thr Ile Ser Gly Leu Gln Ala Glu Asp
            340                 345                 350

Glu Ala Asp Tyr Tyr Cys Ser Ser Tyr Thr Ser Ser Ser Thr Leu Tyr
        355                 360                 365

Val Phe Gly Ser Gly Thr Lys Val Thr Val Leu Gly Gly Gly Gly Ser
    370                 375                 380

Glu Ile Val Met Thr Gln Ser Pro Ala Thr Leu Ser Leu Ser Pro Gly
385                 390                 395                 400

Glu Arg Ala Thr Leu Ser Cys Arg Ala Ser Gln Asp Ile Ser Lys Tyr
                405                 410                 415

Leu Asn Trp Tyr Gln Gln Lys Pro Gly Gln Ala Pro Arg Leu Leu Ile
            420                 425                 430

Tyr His Thr Ser Arg Leu His Ser Gly Ile Pro Ala Arg Phe Ser Gly
        435                 440                 445

Ser Gly Ser Gly Thr Asp Tyr Thr Leu Thr Ile Ser Ser Leu Gln Pro
    450                 455                 460

Glu Asp Phe Ala Val Tyr Phe Cys Gln Gln Gly Asn Thr Leu Pro Tyr
465                 470                 475                 480

Thr Phe Gly Cys Gly Thr Lys Leu Glu Ile Lys Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525
```

```
Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590

Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
        675                 680                 685

Asp Gly Leu Tyr Gln Gly Leu Ser Thr Ala Thr Lys Asp Thr Tyr Asp
    690                 695                 700

Ala Leu His Met Gln Ala Leu Pro Pro Arg
705                 710


<210> SEQ ID NO 342
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Cys Gly Thr Lys Leu Glu Ile Lys Gly Gly Gly Gly Ser
            100                 105                 110

Gln Ser Ala Leu Thr Gln Pro Ala Ser Val Ser Gly Ser Pro Gly Gln
        115                 120                 125

Ser Ile Thr Ile Ser Cys Thr Gly Thr Ser Ser Asp Val Gly Gly Tyr
    130                 135                 140

Asn Tyr Val Ser Trp Tyr Gln Gln His Pro Gly Lys Ala Pro Lys Leu
145                 150                 155                 160

Met Ile Tyr Asp Val Ser Asn Arg Pro Ser Gly Val Ser Asn Arg Phe
                165                 170                 175
```

-continued

```
Ser Gly Ser Lys Ser Gly Asn Thr Ala Ser Leu Thr Ile Ser Gly Leu
            180                 185                 190

Gln Ala Glu Asp Glu Ala Asp Tyr Tyr Cys Ser Ser Tyr Thr Ser Ser
        195                 200                 205

Ser Thr Leu Tyr Val Phe Gly Ser Gly Thr Lys Val Thr Val Leu Gly
    210                 215                 220

Gly Gly Gly Ser Gly Gly Gly Gly Ser Gly Gly Gly Gly Ser Gly Gly
225                 230                 235                 240

Gly Gly Ser Gln Val Gln Leu Gln Glu Ser Gly Gly Gly Val Val Gln
                245                 250                 255

Pro Gly Arg Ser Leu Arg Leu Ser Cys Ala Ala Ser Gly Phe Thr Phe
            260                 265                 270

Ser Ser Tyr Gly Met His Trp Val Arg Gln Ala Pro Gly Lys Gly Leu
        275                 280                 285

Glu Trp Val Ala Val Ile Ser Tyr Asp Gly Ser Asn Lys Tyr Tyr Ala
    290                 295                 300

Asp Ser Val Lys Gly Arg Phe Thr Ile Ser Arg Asp Asn Ser Lys Asn
305                 310                 315                 320

Thr Leu Tyr Leu Gln Met Asn Ser Leu Arg Ala Glu Asp Thr Ala Val
                325                 330                 335

Tyr Tyr Cys Gly Gly Ser Gly Tyr Ala Leu His Asp Asp Tyr Tyr Gly
            340                 345                 350

Leu Asp Val Trp Gly Gln Gly Thr Leu Val Thr Val Ser Ser Gly Gly
        355                 360                 365

Gly Gly Ser Gln Val Gln Leu Gln Glu Ser Gly Pro Gly Leu Val Lys
    370                 375                 380

Pro Ser Glu Thr Leu Ser Leu Thr Cys Thr Val Ser Gly Val Ser Leu
385                 390                 395                 400

Pro Asp Tyr Gly Val Ser Trp Ile Arg Gln Pro Pro Gly Lys Cys Leu
                405                 410                 415

Glu Trp Ile Gly Val Ile Trp Gly Ser Glu Thr Thr Tyr Tyr Gln Ser
            420                 425                 430

Ser Leu Lys Ser Arg Val Thr Ile Ser Lys Asp Asn Ser Lys Asn Gln
        435                 440                 445

Val Ser Leu Lys Leu Ser Ser Val Thr Ala Ala Asp Thr Ala Val Tyr
    450                 455                 460

Tyr Cys Ala Lys His Tyr Tyr Tyr Gly Gly Ser Tyr Ala Met Asp Tyr
465                 470                 475                 480

Trp Gly Gln Gly Thr Leu Val Thr Val Ser Ser Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525

Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590
```

```
Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
        675                 680                 685

Asp Gly Leu Tyr Gln Gly Leu Ser Thr Ala Thr Lys Asp Thr Tyr Asp
    690                 695                 700

Ala Leu His Met Gln Ala Leu Pro Pro Arg
705                 710
```

<210> SEQ ID NO 343
<211> LENGTH: 714
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

```
Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Cys Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Gly Ser Gly Tyr Ala Leu His Asp Asp Tyr Tyr Gly Leu Asp Val
            100                 105                 110

Trp Gly Gln Gly Thr Leu Val Thr Val Ser Ser Gly Gly Gly Gly Ser
        115                 120                 125

Glu Ile Val Met Thr Gln Ser Pro Ala Thr Leu Ser Leu Ser Pro Gly
    130                 135                 140

Glu Arg Ala Thr Leu Ser Cys Arg Ala Ser Gln Asp Ile Ser Lys Tyr
145                 150                 155                 160

Leu Asn Trp Tyr Gln Gln Lys Pro Gly Gln Ala Pro Arg Leu Leu Ile
                165                 170                 175

Tyr His Thr Ser Arg Leu His Ser Gly Ile Pro Ala Arg Phe Ser Gly
            180                 185                 190

Ser Gly Ser Gly Thr Asp Tyr Thr Leu Thr Ile Ser Ser Leu Gln Pro
        195                 200                 205

Glu Asp Phe Ala Val Tyr Phe Cys Gln Gln Gly Asn Thr Leu Pro Tyr
    210                 215                 220

Thr Phe Gly Gln Gly Thr Lys Leu Glu Ile Lys Gly Gly Gly Gly Ser
225                 230                 235                 240
```

```
Gly Gly Gly Gly Ser Gly Gly Gly Gly Ser Gly Gly Gly Gly Ser Gln
                245                 250                 255

Val Gln Leu Gln Glu Ser Gly Pro Gly Leu Val Lys Pro Ser Glu Thr
            260                 265                 270

Leu Ser Leu Thr Cys Thr Val Ser Gly Val Ser Leu Pro Asp Tyr Gly
        275                 280                 285

Val Ser Trp Ile Arg Gln Pro Pro Gly Lys Gly Leu Glu Trp Ile Gly
    290                 295                 300

Val Ile Trp Gly Ser Glu Thr Thr Tyr Tyr Gln Ser Ser Leu Lys Ser
305                 310                 315                 320

Arg Val Thr Ile Ser Lys Asp Asn Ser Lys Asn Gln Val Ser Leu Lys
                325                 330                 335

Leu Ser Ser Val Thr Ala Ala Asp Thr Ala Val Tyr Tyr Cys Ala Lys
            340                 345                 350

His Tyr Tyr Tyr Gly Gly Ser Tyr Ala Met Asp Tyr Trp Gly Gln Gly
        355                 360                 365

Thr Leu Val Thr Val Ser Ser Gly Gly Gly Gly Ser Gln Ser Ala Leu
    370                 375                 380

Thr Gln Pro Ala Ser Val Ser Gly Ser Pro Gly Gln Ser Ile Thr Ile
385                 390                 395                 400

Ser Cys Thr Gly Thr Ser Ser Asp Val Gly Gly Tyr Asn Tyr Val Ser
                405                 410                 415

Trp Tyr Gln Gln His Pro Gly Lys Ala Pro Lys Leu Met Ile Tyr Asp
            420                 425                 430

Val Ser Asn Arg Pro Ser Gly Val Ser Asn Arg Phe Ser Gly Ser Lys
        435                 440                 445

Ser Gly Asn Thr Ala Ser Leu Thr Ile Ser Gly Leu Gln Ala Glu Asp
    450                 455                 460

Glu Ala Asp Tyr Tyr Cys Ser Ser Tyr Thr Ser Ser Ser Thr Leu Tyr
465                 470                 475                 480

Val Phe Gly Cys Gly Thr Lys Val Thr Val Leu Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525

Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590

Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655
```

Gln Glu Gly Leu Tyr Asn Glu Leu Gln Lys Asp Lys Met Ala Glu Ala
660 665 670

Tyr Ser Glu Ile Gly Met Lys Gly Glu Arg Arg Arg Gly Lys Gly His
675 680 685

Asp Gly Leu Tyr Gln Gly Leu Ser Thr Ala Thr Lys Asp Thr Tyr Asp
690 695 700

Ala Leu His Met Gln Ala Leu Pro Pro Arg
705 710

<210> SEQ ID NO 344
<211> LENGTH: 714
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 344

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu
35 40 45

Met Ile Tyr Asp Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Tyr Thr Ser Ser
85 90 95

Ser Thr Leu Tyr Val Phe Gly Cys Gly Thr Lys Val Thr Val Leu Gly
100 105 110

Gly Gly Gly Ser Gln Val Gln Leu Gln Glu Ser Gly Pro Gly Leu Val
115 120 125

Lys Pro Ser Glu Thr Leu Ser Leu Thr Cys Thr Val Ser Gly Val Ser
130 135 140

Leu Pro Asp Tyr Gly Val Ser Trp Ile Arg Gln Pro Pro Gly Lys Gly
145 150 155 160

Leu Glu Trp Ile Gly Val Ile Trp Gly Ser Glu Thr Thr Tyr Tyr Gln
165 170 175

Ser Ser Leu Lys Ser Arg Val Thr Ile Ser Lys Asp Asn Ser Lys Asn
180 185 190

Gln Val Ser Leu Lys Leu Ser Ser Val Thr Ala Ala Asp Thr Ala Val
195 200 205

Tyr Tyr Cys Ala Lys His Tyr Tyr Tyr Gly Gly Ser Tyr Ala Met Asp
210 215 220

Tyr Trp Gly Gln Gly Thr Leu Val Thr Val Ser Ser Gly Gly Gly Gly
225 230 235 240

Ser Gly Gly Gly Gly Ser Gly Gly Gly Gly Ser Gly Gly Gly Gly Ser
245 250 255

Glu Ile Val Met Thr Gln Ser Pro Ala Thr Leu Ser Leu Ser Pro Gly
260 265 270

Glu Arg Ala Thr Leu Ser Cys Arg Ala Ser Gln Asp Ile Ser Lys Tyr
275 280 285

Leu Asn Trp Tyr Gln Gln Lys Pro Gly Gln Ala Pro Arg Leu Leu Ile
290 295 300

-continued

```
Tyr His Thr Ser Arg Leu His Ser Gly Ile Pro Ala Arg Phe Ser Gly
305                 310                 315                 320

Ser Gly Ser Gly Thr Asp Tyr Thr Leu Thr Ile Ser Ser Leu Gln Pro
                325                 330                 335

Glu Asp Phe Ala Val Tyr Phe Cys Gln Gln Gly Asn Thr Leu Pro Tyr
            340                 345                 350

Thr Phe Gly Gln Gly Thr Lys Leu Glu Ile Lys Gly Gly Gly Gly Ser
        355                 360                 365

Gln Val Gln Leu Gln Glu Ser Gly Gly Gly Val Val Gln Pro Gly Arg
    370                 375                 380

Ser Leu Arg Leu Ser Cys Ala Ala Ser Gly Phe Thr Phe Ser Ser Tyr
385                 390                 395                 400

Gly Met His Trp Val Arg Gln Ala Pro Gly Lys Cys Leu Glu Trp Val
                405                 410                 415

Ala Val Ile Ser Tyr Asp Gly Ser Asn Lys Tyr Tyr Ala Asp Ser Val
            420                 425                 430

Lys Gly Arg Phe Thr Ile Ser Arg Asp Asn Ser Lys Asn Thr Leu Tyr
        435                 440                 445

Leu Gln Met Asn Ser Leu Arg Ala Glu Asp Thr Ala Val Tyr Tyr Cys
    450                 455                 460

Gly Gly Ser Gly Tyr Ala Leu His Asp Asp Tyr Tyr Gly Leu Asp Val
465                 470                 475                 480

Trp Gly Gln Gly Thr Leu Val Thr Val Ser Ser Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525

Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590

Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
        675                 680                 685

Asp Gly Leu Tyr Gln Gly Leu Ser Thr Ala Thr Lys Asp Thr Tyr Asp
    690                 695                 700

Ala Leu His Met Gln Ala Leu Pro Pro Arg
705                 710
```

<210> SEQ ID NO 345
<211> LENGTH: 714
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 345

Gln Val Gln Leu Gln Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Cys Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Gly Gly Ser Gly Tyr Ala Leu His Asp Asp Tyr Tyr Gly Leu Asp Val
100 105 110

Trp Gly Gln Gly Thr Leu Val Thr Val Ser Ser Gly Gly Gly Gly Ser
115 120 125

Gln Val Gln Leu Gln Glu Ser Gly Pro Gly Leu Val Lys Pro Ser Glu
130 135 140

Thr Leu Ser Leu Thr Cys Thr Val Ser Gly Val Ser Leu Pro Asp Tyr
145 150 155 160

Gly Val Ser Trp Ile Arg Gln Pro Pro Gly Lys Gly Leu Glu Trp Ile
165 170 175

Gly Val Ile Trp Gly Ser Glu Thr Thr Tyr Tyr Gln Ser Ser Leu Lys
180 185 190

Ser Arg Val Thr Ile Ser Lys Asp Asn Ser Lys Asn Gln Val Ser Leu
195 200 205

Lys Leu Ser Ser Val Thr Ala Ala Asp Thr Ala Val Tyr Tyr Cys Ala
210 215 220

Lys His Tyr Tyr Tyr Gly Gly Ser Tyr Ala Met Asp Tyr Trp Gly Gln
225 230 235 240

Gly Thr Leu Val Thr Val Ser Ser Gly Gly Gly Gly Ser Gly Gly Gly
245 250 255

Gly Ser Gly Gly Gly Gly Ser Gly Gly Gly Gly Ser Glu Ile Val Met
260 265 270

Thr Gln Ser Pro Ala Thr Leu Ser Leu Ser Pro Gly Glu Arg Ala Thr
275 280 285

Leu Ser Cys Arg Ala Ser Gln Asp Ile Ser Lys Tyr Leu Asn Trp Tyr
290 295 300

Gln Gln Lys Pro Gly Gln Ala Pro Arg Leu Leu Ile Tyr His Thr Ser
305 310 315 320

Arg Leu His Ser Gly Ile Pro Ala Arg Phe Ser Gly Ser Gly Ser Gly
325 330 335

Thr Asp Tyr Thr Leu Thr Ile Ser Ser Leu Gln Pro Glu Asp Phe Ala
340 345 350

Val Tyr Phe Cys Gln Gln Gly Asn Thr Leu Pro Tyr Thr Phe Gly Gln
355 360 365

```
Gly Thr Lys Leu Glu Ile Lys Gly Gly Gly Gly Ser Gln Ser Ala Leu
    370                 375                 380

Thr Gln Pro Ala Ser Val Ser Gly Ser Pro Gly Gln Ser Ile Thr Ile
385                 390                 395                 400

Ser Cys Thr Gly Thr Ser Ser Asp Val Gly Gly Tyr Asn Tyr Val Ser
                405                 410                 415

Trp Tyr Gln Gln His Pro Gly Lys Ala Pro Lys Leu Met Ile Tyr Asp
            420                 425                 430

Val Ser Asn Arg Pro Ser Gly Val Ser Asn Arg Phe Ser Gly Ser Lys
        435                 440                 445

Ser Gly Asn Thr Ala Ser Leu Thr Ile Ser Gly Leu Gln Ala Glu Asp
    450                 455                 460

Glu Ala Asp Tyr Tyr Cys Ser Ser Tyr Thr Ser Ser Ser Thr Leu Tyr
465                 470                 475                 480

Val Phe Gly Cys Gly Thr Lys Val Thr Val Leu Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525

Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590

Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
        675                 680                 685

Asp Gly Leu Tyr Gln Gly Leu Ser Thr Ala Thr Lys Asp Thr Tyr Asp
    690                 695                 700

Ala Leu His Met Gln Ala Leu Pro Pro Arg
705                 710
```

<210> SEQ ID NO 346
<211> LENGTH: 714
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 346

```
Gln Ser Ala Leu Thr Gln Pro Ala Ser Val Ser Gly Ser Pro Gly Gln
```

-continued

```
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Tyr Val Phe Gly Cys Gly Thr Lys Val Thr Val Leu Gly
            100                 105                 110

Gly Gly Gly Ser Glu Ile Val Met Thr Gln Ser Pro Ala Thr Leu Ser
        115                 120                 125

Leu Ser Pro Gly Glu Arg Ala Thr Leu Ser Cys Arg Ala Ser Gln Asp
    130                 135                 140

Ile Ser Lys Tyr Leu Asn Trp Tyr Gln Gln Lys Pro Gly Gln Ala Pro
145                 150                 155                 160

Arg Leu Leu Ile Tyr His Thr Ser Arg Leu His Ser Gly Ile Pro Ala
                165                 170                 175

Arg Phe Ser Gly Ser Gly Ser Gly Thr Asp Tyr Thr Leu Thr Ile Ser
            180                 185                 190

Ser Leu Gln Pro Glu Asp Phe Ala Val Tyr Phe Cys Gln Gln Gly Asn
        195                 200                 205

Thr Leu Pro Tyr Thr Phe Gly Gln Gly Thr Lys Leu Glu Ile Lys Gly
    210                 215                 220

Gly Gly Gly Ser Gly Gly Gly Gly Ser Gly Gly Gly Gly Ser Gly Gly
225                 230                 235                 240

Gly Gly Ser Gln Val Gln Leu Gln Glu Ser Gly Pro Gly Leu Val Lys
                245                 250                 255

Pro Ser Glu Thr Leu Ser Leu Thr Cys Thr Val Ser Gly Val Ser Leu
            260                 265                 270

Pro Asp Tyr Gly Val Ser Trp Ile Arg Gln Pro Pro Gly Lys Gly Leu
        275                 280                 285

Glu Trp Ile Gly Val Ile Trp Gly Ser Glu Thr Thr Tyr Tyr Gln Ser
    290                 295                 300

Ser Leu Lys Ser Arg Val Thr Ile Ser Lys Asp Asn Ser Lys Asn Gln
305                 310                 315                 320

Val Ser Leu Lys Leu Ser Ser Val Thr Ala Ala Asp Thr Ala Val Tyr
                325                 330                 335

Tyr Cys Ala Lys His Tyr Tyr Tyr Gly Gly Ser Tyr Ala Met Asp Tyr
            340                 345                 350

Trp Gly Gln Gly Thr Leu Val Thr Val Ser Ser Gly Gly Gly Gly Ser
        355                 360                 365

Gln Val Gln Leu Gln Glu Ser Gly Gly Gly Val Val Gln Pro Gly Arg
    370                 375                 380

Ser Leu Arg Leu Ser Cys Ala Ala Ser Gly Phe Thr Phe Ser Ser Tyr
385                 390                 395                 400

Gly Met His Trp Val Arg Gln Ala Pro Gly Lys Cys Leu Glu Trp Val
                405                 410                 415

Ala Val Ile Ser Tyr Asp Gly Ser Asn Lys Tyr Tyr Ala Asp Ser Val
            420                 425                 430
```

```
Lys Gly Arg Phe Thr Ile Ser Arg Asp Asn Ser Lys Asn Thr Leu Tyr
        435                 440                 445

Leu Gln Met Asn Ser Leu Arg Ala Glu Asp Thr Ala Val Tyr Tyr Cys
    450                 455                 460

Gly Gly Ser Gly Tyr Ala Leu His Asp Asp Tyr Tyr Gly Leu Asp Val
465                 470                 475                 480

Trp Gly Gln Gly Thr Leu Val Thr Val Ser Ser Thr Thr Thr Pro Ala
                485                 490                 495

Pro Arg Pro Pro Thr Pro Ala Pro Thr Ile Ala Ser Gln Pro Leu Ser
            500                 505                 510

Leu Arg Pro Glu Ala Cys Arg Pro Ala Ala Gly Gly Ala Val His Thr
        515                 520                 525

Arg Gly Leu Asp Phe Ala Cys Asp Ile Tyr Ile Trp Ala Pro Leu Ala
    530                 535                 540

Gly Thr Cys Gly Val Leu Leu Leu Ser Leu Val Ile Thr Leu Tyr Cys
545                 550                 555                 560

Lys Arg Gly Arg Lys Lys Leu Leu Tyr Ile Phe Lys Gln Pro Phe Met
                565                 570                 575

Arg Pro Val Gln Thr Thr Gln Glu Glu Asp Gly Cys Ser Cys Arg Phe
            580                 585                 590

Pro Glu Glu Glu Glu Gly Gly Cys Glu Leu Arg Val Lys Phe Ser Arg
        595                 600                 605

Ser Ala Asp Ala Pro Ala Tyr Lys Gln Gly Gln Asn Gln Leu Tyr Asn
    610                 615                 620

Glu Leu Asn Leu Gly Arg Arg Glu Glu Tyr Asp Val Leu Asp Lys Arg
625                 630                 635                 640

Arg Gly Arg Asp Pro Glu Met Gly Gly Lys Pro Arg Arg Lys Asn Pro
                645                 650                 655

Gln Glu Gly Leu Tyr Asn Glu Leu Gln Lys Asp Lys Met Ala Glu Ala
            660                 665                 670

Tyr Ser Glu Ile Gly Met Lys Gly Glu Arg Arg Arg Gly Lys Gly His
        675                 680                 685

Asp Gly Leu Tyr Gln Gly Leu Ser Thr Ala Thr Lys Asp Thr Tyr Asp
    690                 695                 700

Ala Leu His Met Gln Ala Leu Pro Pro Arg
705                 710
```

<210> SEQ ID NO 347
<211> LENGTH: 708
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 347

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Cys Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
```

-continued

```
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Asp Ile Gln
        115                 120                 125

Met Thr Gln Ser Pro Ser Ser Leu Ser Ala Ser Val Gly Asp Arg Val
    130                 135                 140

Thr Ile Thr Cys Arg Ala Ser Gln Ser Ile Ser Ser Tyr Leu Asn Trp
145                 150                 155                 160

Tyr Gln Gln Lys Pro Gly Lys Ala Pro Lys Leu Leu Ile Tyr Ala Ala
                165                 170                 175

Ser Ser Leu Gln Ser Gly Val Pro Ser Arg Phe Ser Gly Ser Gly Ser
            180                 185                 190

Gly Thr Asp Phe Thr Leu Thr Ile Ser Ser Leu Gln Pro Glu Asp Phe
        195                 200                 205

Ala Thr Tyr Tyr Cys Gln Gln Ser Tyr Ser Thr Pro Leu Thr Phe Gly
    210                 215                 220

Gln Gly Thr Lys Val Glu Ile Lys Gly Gly Gly Gly Ser Gly Gly Gly
225                 230                 235                 240

Gly Ser Gly Gly Gly Gly Ser Gly Gly Gly Gly Ser Glu Val Gln Leu
                245                 250                 255

Leu Glu Ser Gly Gly Gly Leu Val Gln Pro Gly Gly Ser Leu Arg Leu
            260                 265                 270

Ser Cys Ala Ala Ser Gly Phe Thr Phe Ser Ser Tyr Ala Met Ser Trp
        275                 280                 285

Val Arg Gln Ala Pro Gly Lys Gly Leu Glu Trp Val Ser Ala Ile Ser
    290                 295                 300

Gly Ser Gly Gly Ser Thr Tyr Tyr Ala Asp Ser Val Lys Gly Arg Phe
305                 310                 315                 320

Thr Ile Ser Arg Asp Asn Ser Lys Asn Thr Leu Tyr Leu Gln Met Asn
                325                 330                 335

Ser Leu Arg Ala Glu Asp Thr Ala Val Tyr Tyr Cys Ala Arg Arg Glu
            340                 345                 350

Trp Trp Gly Glu Ser Trp Leu Phe Asp Tyr Trp Gly Gln Gly Thr Leu
        355                 360                 365

Val Thr Val Ser Ser Gly Gly Gly Gly Ser Glu Ile Val Met Thr Gln
    370                 375                 380

Ser Pro Ala Thr Leu Ser Leu Ser Pro Gly Glu Arg Ala Thr Leu Ser
385                 390                 395                 400

Cys Arg Ala Ser Gln Asp Ile Ser Lys Tyr Leu Asn Trp Tyr Gln Gln
                405                 410                 415

Lys Pro Gly Gln Ala Pro Arg Leu Leu Ile Tyr His Thr Ser Arg Leu
            420                 425                 430

His Ser Gly Ile Pro Ala Arg Phe Ser Gly Ser Gly Ser Gly Thr Asp
        435                 440                 445

Tyr Thr Leu Thr Ile Ser Ser Leu Gln Pro Glu Asp Phe Ala Val Tyr
    450                 455                 460

Phe Cys Gln Gln Gly Asn Thr Leu Pro Tyr Thr Phe Gly Cys Gly Thr
465                 470                 475                 480

Lys Leu Glu Ile Lys Thr Thr Thr Pro Ala Pro Arg Pro Pro Thr Pro
                485                 490                 495
```

```
Ala Pro Thr Ile Ala Ser Gln Pro Leu Ser Leu Arg Pro Glu Ala Cys
            500                 505                 510

Arg Pro Ala Ala Gly Gly Ala Val His Thr Arg Gly Leu Asp Phe Ala
        515                 520                 525

Cys Asp Ile Tyr Ile Trp Ala Pro Leu Ala Gly Thr Cys Gly Val Leu
    530                 535                 540

Leu Leu Ser Leu Val Ile Thr Leu Tyr Cys Lys Arg Gly Arg Lys Lys
545                 550                 555                 560

Leu Leu Tyr Ile Phe Lys Gln Pro Phe Met Arg Pro Val Gln Thr Thr
                565                 570                 575

Gln Glu Glu Asp Gly Cys Ser Cys Arg Phe Pro Glu Glu Glu Glu Gly
            580                 585                 590

Gly Cys Glu Leu Arg Val Lys Phe Ser Arg Ser Ala Asp Ala Pro Ala
        595                 600                 605

Tyr Lys Gln Gly Gln Asn Gln Leu Tyr Asn Glu Leu Asn Leu Gly Arg
    610                 615                 620

Arg Glu Glu Tyr Asp Val Leu Asp Lys Arg Arg Gly Arg Asp Pro Glu
625                 630                 635                 640

Met Gly Gly Lys Pro Arg Arg Lys Asn Pro Gln Glu Gly Leu Tyr Asn
                645                 650                 655

Glu Leu Gln Lys Asp Lys Met Ala Glu Ala Tyr Ser Glu Ile Gly Met
            660                 665                 670

Lys Gly Glu Arg Arg Arg Gly Lys Gly His Asp Gly Leu Tyr Gln Gly
        675                 680                 685

Leu Ser Thr Ala Thr Lys Asp Thr Tyr Asp Ala Leu His Met Gln Ala
    690                 695                 700

Leu Pro Pro Arg
705


<210> SEQ ID NO 348
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Glu Trp Trp Gly Glu Ser Trp Leu Phe Asp Tyr Trp Gly
            100                 105                 110

Gln Gly Thr Leu Val Thr Val Ser Ser Gly Gly Gly Gly Ser Glu Ile
        115                 120                 125

Val Met Thr Gln Ser Pro Ala Thr Leu Ser Leu Ser Pro Gly Glu Arg
```

```
    130                 135                 140

Ala Thr Leu Ser Cys Arg Ala Ser Gln Asp Ile Ser Lys Tyr Leu Asn
145                 150                 155                 160

Trp Tyr Gln Gln Lys Pro Gly Gln Ala Pro Arg Leu Leu Ile Tyr His
                165                 170                 175

Thr Ser Arg Leu His Ser Gly Ile Pro Ala Arg Phe Ser Gly Ser Gly
            180                 185                 190

Ser Gly Thr Asp Tyr Thr Leu Thr Ile Ser Ser Leu Gln Pro Glu Asp
        195                 200                 205

Phe Ala Val Tyr Phe Cys Gln Gln Gly Asn Thr Leu Pro Tyr Thr Phe
    210                 215                 220

Gly Gln Gly Thr Lys Leu Glu Ile Lys Gly Gly Gly Gly Ser Gly Gly
225                 230                 235                 240

Gly Gly Ser Gly Gly Gly Gly Ser Gly Gly Gly Gly Ser Gln Val Gln
                245                 250                 255

Leu Gln Glu Ser Gly Pro Gly Leu Val Lys Pro Ser Glu Thr Leu Ser
            260                 265                 270

Leu Thr Cys Thr Val Ser Gly Val Ser Leu Pro Asp Tyr Gly Val Ser
        275                 280                 285

Trp Ile Arg Gln Pro Pro Gly Lys Gly Leu Glu Trp Ile Gly Val Ile
    290                 295                 300

Trp Gly Ser Glu Thr Thr Tyr Tyr Gln Ser Ser Leu Lys Ser Arg Val
305                 310                 315                 320

Thr Ile Ser Lys Asp Asn Ser Lys Asn Gln Val Ser Leu Lys Leu Ser
                325                 330                 335

Ser Val Thr Ala Ala Asp Thr Ala Val Tyr Tyr Cys Ala Lys His Tyr
            340                 345                 350

Tyr Tyr Gly Gly Ser Tyr Ala Met Asp Tyr Trp Gly Gln Gly Thr Leu
        355                 360                 365

Val Thr Val Ser Ser Gly Gly Gly Gly Ser Asp Ile Gln Met Thr Gln
    370                 375                 380

Ser Pro Ser Ser Leu Ser Ala Ser Val Gly Asp Arg Val Thr Ile Thr
385                 390                 395                 400

Cys Arg Ala Ser Gln Ser Ile Ser Ser Tyr Leu Asn Trp Tyr Gln Gln
                405                 410                 415

Lys Pro Gly Lys Ala Pro Lys Leu Leu Ile Tyr Ala Ala Ser Ser Leu
            420                 425                 430

Gln Ser Gly Val Pro Ser Arg Phe Ser Gly Ser Gly Ser Gly Thr Asp
        435                 440                 445

Phe Thr Leu Thr Ile Ser Ser Leu Gln Pro Glu Asp Phe Ala Thr Tyr
    450                 455                 460

Tyr Cys Gln Gln Ser Tyr Ser Thr Pro Leu Thr Phe Gly Cys Gly Thr
465                 470                 475                 480

Lys Val Glu Ile Lys Thr Thr Thr Pro Ala Pro Arg Pro Pro Thr Pro
                485                 490                 495

Ala Pro Thr Ile Ala Ser Gln Pro Leu Ser Leu Arg Pro Glu Ala Cys
            500                 505                 510

Arg Pro Ala Ala Gly Gly Ala Val His Thr Arg Gly Leu Asp Phe Ala
        515                 520                 525

Cys Asp Ile Tyr Ile Trp Ala Pro Leu Ala Gly Thr Cys Gly Val Leu
    530                 535                 540

Leu Leu Ser Leu Val Ile Thr Leu Tyr Cys Lys Arg Gly Arg Lys Lys
545                 550                 555                 560
```

```
Leu Leu Tyr Ile Phe Lys Gln Pro Phe Met Arg Pro Val Gln Thr Thr
                565                 570                 575

Gln Glu Glu Asp Gly Cys Ser Cys Arg Phe Pro Glu Glu Glu Glu Gly
            580                 585                 590

Gly Cys Glu Leu Arg Val Lys Phe Ser Arg Ser Ala Asp Ala Pro Ala
        595                 600                 605

Tyr Lys Gln Gly Gln Asn Gln Leu Tyr Asn Glu Leu Asn Leu Gly Arg
    610                 615                 620

Arg Glu Glu Tyr Asp Val Leu Asp Lys Arg Arg Gly Arg Asp Pro Glu
625                 630                 635                 640

Met Gly Gly Lys Pro Arg Arg Lys Asn Pro Gln Glu Gly Leu Tyr Asn
                645                 650                 655

Glu Leu Gln Lys Asp Lys Met Ala Glu Ala Tyr Ser Glu Ile Gly Met
            660                 665                 670

Lys Gly Glu Arg Arg Arg Gly Lys Gly His Asp Gly Leu Tyr Gln Gly
        675                 680                 685

Leu Ser Thr Ala Thr Lys Asp Thr Tyr Asp Ala Leu His Met Gln Ala
    690                 695                 700

Leu Pro Pro Arg
705
```

<210> SEQ ID NO 349
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 349

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Asp Ile Ser Lys Tyr Leu Asn Trp Tyr Gln Gln Lys Pro Gly Gln Ala
    50                  55                  60

Pro Arg Leu Leu Ile Tyr His Thr Ser Arg Leu His Ser Gly Ile Pro
65                  70                  75                  80

Ala Arg Phe Ser Gly Ser Gly Ser Gly Thr Asp Tyr Thr Leu Thr Ile
                85                  90                  95

Ser Ser Leu Gln Pro Glu Asp Phe Ala Val Tyr Phe Cys Gln Gln Gly
            100                 105                 110

Asn Thr Leu Pro Tyr Thr Phe Gly Gln Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Glu Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
            180                 185                 190

Val Ile Trp Gly Ser Glu Thr Thr Tyr Tyr Gln Ser Ser Leu Lys Ser
```

```
        195                 200                 205

Arg Val Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Leu Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485


<210> SEQ ID NO 350
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60
```

-continued

```
Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465
```

<210> SEQ ID NO 351
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Met Leu Leu Leu Val Thr Ser Leu Leu Leu Cys Glu Leu Pro His Pro
1 5 10 15

Ala Phe Leu Leu Ile Pro
20

<210> SEQ ID NO 352
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
atgcttctcc tggtgacaag ccttctgctc tgtgagttac cacacccagc attcctcctg 60
atccca 66

<210> SEQ ID NO 353
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
atgctgctgc tggtgaccag cctgctgctg tgcgagctgc cccaccccgc ctttctgctg 60
atcccc 66

<210> SEQ ID NO 354
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 354
atggccctcc ctgtcaccgc cctgctgctt ccgctggctc ttctgctcca cgccgctcgg 60
cccgaaattg tgatgaccca gtcacccgcc actcttagcc tttcacccgg tgagcgcgca 120
accctgtctt gcagagcctc ccaagacatc tcaaaatacc ttaattggta tcaacagaag 180
cccggacagg ctcctcgcct tctgatctac cacaccagcc ggctccattc tggaatccct 240
gccaggttca gcggtagcgg atctgggacc gactacaccc tcactatcag ctcactgcag 300
ccagaggact tcgctgtcta tttctgtcag caagggaaca ccctgcccta cacctttgga 360
cagggcacca agctcgagat taaaggtgga ggtggcagcg gaggaggtgg gtccggcggt 420
ggaggaagcc aggtccaact ccaagaaagc ggaccgggtc ttgtgaagcc atcagaaact 480
ctttcactga cttgtactgt gagcggagtg tctctccccg attacggggt gtcttggatc 540
agacagccac cggggaaggg tctggaatgg attggagtga tttggggctc tgagactact 600
tactaccaat catccctcaa gtcacgcgtc accatctcaa aggacaactc taagaatcag 660

-continued

```
gtgtcactga aactgtcatc tgtgaccgca gccgacaccg ccgtgtacta ttgcgctaag    720

cattactatt atggcgggag ctacgcaatg gattactggg gacagggtac tctggtcacc    780

gtgtccagca ccactacccc agcaccgagg ccacccaccc cggctcctac catcgcctcc    840

cagcctctgt ccctgcgtcc ggaggcatgt agacccgcag ctggtggggc cgtgcatacc    900

cggggtcttg acttcgcctg cgatatctac atttgggccc ctctggctgg tacttgcggg    960

gtcctgctgc tttcactcgt gatcactctt tactgtaagc gcggtcggaa gaagctgctg   1020

tacatcttta agcaaccctt catgaggcct gtgcagacta ctcaagagga ggacggctgt   1080

tcatgccggt tcccagagga ggaggaaggc ggctgcgaac tgcgcgtgaa attcagccgc   1140

agcgcagatg ctccagccta ccagcagggg cagaaccagc tctacaacga actcaatctt   1200

ggtcggagag aggagtacga cgtgctggac aagcggagag gacgggaccc agaaatgggc   1260

gggaagccgc gcagaaagaa tccccaagag ggcctgtaca acgagctcca aaaggataag   1320

atggcagaag cctatagcga gattggtatg aaaggggaac gcagaagagg caaaggccac   1380

gacggactgt accagggact cagcaccgcc accaaggaca cctatgacgc tcttcacatg   1440

caggccctgc cgcctcggta a                                             1461
```

```
<210> SEQ ID NO 355
<211> LENGTH: 1458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355

atggccctcc ctgtcaccgc cctgctgctt ccgctggctc ttctgctcca cgccgctcgg     60

cccgaaattg tgatgaccca gtcacccgcc actcttagcc tttcacccgg tgagcgcgca    120

accctgtctt gcagagcctc ccaagacatc tcaaaatacc ttaattggta tcaacagaag    180

cccggacagg ctcctcgcct tctgatctac cacaccagcc ggctccattc tggaatccct    240

gccaggttca gcggtagcgg atctgggacc gactacaccc tcactatcag ctcactgcag    300

ccagaggact tcgctgtcta tttctgtcag caagggaaca ccctgcccta cacctttgga    360

cagggcacca agctcgagat taaaggtgga ggtggcagcg gaggaggtgg gtccggcggt    420

ggaggaagcc aggtccaact ccaagaaagc ggaccgggtc ttgtgaagcc atcagaaact    480

ctttcactga cttgtactgt gagcggagtg tctctccccg attacggggt gtcttggatc    540

agacagccac cggggaaggg tctggaatgg attggagtga tttggggctc tgagactact    600

tactaccaat catccctcaa gtcacgcgtc accatctcaa aggacaactc taagaatcag    660

gtgtcactga aactgtcatc tgtgaccgca gccgacaccg ccgtgtacta ttgcgctaag    720

cattactatt atggcgggag ctacgcaatg gattactggg gacagggtac tctggtcacc    780

gtgtccagca ccactacccc agcaccgagg ccacccaccc cggctcctac catcgcctcc    840

cagcctctgt ccctgcgtcc ggaggcatgt agacccgcag ctggtggggc cgtgcatacc    900

cggggtcttg acttcgcctg cgatatctac atttgggccc ctctggctgg tacttgcggg    960

gtcctgctgc tttcactcgt gatcactctt tactgtaagc gcggtcggaa gaagctgctg   1020

tacatcttta agcaaccctt catgaggcct gtgcagacta ctcaagagga ggacggctgt   1080

tcatgccggt tcccagagga ggaggaaggc ggctgcgaac tgcgcgtgaa attcagccgc   1140

agcgcagatg ctccagccta ccagcagggg cagaaccagc tctacaacga actcaatctt   1200
```

-continued ggtcggagag aggagtacga cgtgctggac aagcggagag gacgggaccc agaaatgggc 1260
gggaagccgc gcagaaagaa tccccaagag ggcctgtaca acgagctcca aaaggataag 1320
atggcagaag cctatagcga gattggtatg aaaggggaac gcagaagagg caaaggccac 1380
gacggactgt accagggact cagcaccgcc accaaggaca cctatgacgc tcttcacatg 1440
caggccctgc cgcctcgg 1458

<210> SEQ ID NO 356
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 356
gaaattgtga tgacccagtc acccgccact cttagccttt cacccggtga gcgcgcaacc 60
ctgtcttgca gagcctccca agacatctca aaatacctta attggtatca acagaagccc 120
ggacaggctc ctcgccttct gatctaccac accagccggc tccattctgg aatccctgcc 180
aggttcagcg gtagcggatc tgggaccgac tacaccctca ctatcagctc actgcagcca 240
gaggacttcg ctgtctattt ctgtcagcaa gggaacaccc tgccctacac ctttggacag 300
ggcaccaagc tcgagattaa aggtggaggt ggcagcggag gaggtgggtc cggcggtgga 360
ggaagccagg tccaactcca agaaagcgga ccgggtcttg tgaagccatc agaaactctt 420
tcactgactt gtactgtgag cggagtgtct ctccccgatt acggggtgtc ttggatcaga 480
cagccaccgg ggaagggtct ggaatggatt ggagtgattt ggggctctga gactacttac 540
taccaatcat ccctcaagtc acgcgtcacc atctcaaagg acaactctaa gaatcaggtg 600
tcactgaaac tgtcatctgt gaccgcagcc gacaccgccg tgtactattg cgctaagcat 660
tactattatg gcgggagcta cgcaatggat tactggggac agggtactct ggtcaccgtg 720
tccagcacca ctaccccagc accgaggcca cccaccccgg ctcctaccat cgcctcccag 780
cctctgtccc tgcgtccgga ggcatgtaga cccgcagctg gtggggccgt gcatacccgg 840
ggtcttgact tcgcctgcga tatctacatt tgggcccctc tggctggtac ttgcggggtc 900
ctgctgcttt cactcgtgat cactctttac tgtaagcgcg gtcggaagaa gctgctgtac 960
atctttaagc aacccttcat gaggcctgtg cagactactc aagaggagga cggctgttca 1020
tgccggttcc cagaggagga ggaaggcggc tgcgaactgc gcgtgaaatt cagccgcagc 1080
gcagatgctc cagcctacca gcaggggcag aaccagctct acaacgaact caatcttggt 1140
cggagagagg agtacgacgt gctggacaag cggagaggac gggacccaga aatgggcggg 1200
aagccgcgca gaaagaatcc ccaagagggc ctgtacaacg agctccaaaa ggataagatg 1260
gcagaagcct atagcgagat tggtatgaaa ggggaacgca gaagaggcaa aggccacgac 1320
ggactgtacc agggactcag caccgccacc aaggacacct atgacgctct tcacatgcag 1380
gccctgccgc ctcggtaa 1398

<210> SEQ ID NO 357
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 357

-continued caggtccagc tgcaggaatc aggaccaggg ctggtgaaac ctagcgaaac tctgagtctg 60
acttgtaccg tctccggggt gtctctgcca gactacggcg tgagctggat cagacagccc 120
cctggcaagt gcctggagtg gatcggcgtg atctggggct ccgagaccac atactatcag 180
agctccctga agtctcgggt gaccatctcc aaggacaact ctaagaatca ggtgagcctg 240
aagctgtcta gcgtgaccgc cgccgataca gccgtgtact attgtgccaa gcactactat 300
tacggcggct cctatgccat ggattactgg ggccagggca ccctggtgac agtgtcctct 360

<210> SEQ ID NO 358
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 358
caggtccagc tgcaggaatc cggcccagga ctggtgaagc ctagcgagac cctgtccctg 60
acctgcacag tgagcggcgt gtccctgccc gattacggcg tgagctggat cagacagccc 120
cctggcaagt gtctggagtg gatcggcgtg atctggggct ctgagaccac atactatcag 180
tcctctctga agagcagggt gaccatctct aaggacaaca gcaagaatca ggtgtccctg 240
aagctgagct ccgtgaccgc agcagataca gccgtgtact attgcgccaa gcactactat 300
tacggcggct cctatgctat ggattattgg gggcagggca ctctggtcac tgtctcatca 360

<210> SEQ ID NO 359
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 359
caggtgcagc tgcaggaatc tggacccgga ctggtgaaac ctagtgaaac tctgtctctg 60
acttgtaccg tctcaggggt ctcactgcca gactacggcg tgtcctggat cagacagccc 120
cctggcaagt gcctggagtg gatcggcgtg atctggggct ctgagaccac atactatcag 180
agctccctga agagccgggt gaccatctcc aaggacaact ctaagaatca ggtgtccctg 240
aagctgtcta gcgtgaccgc cgccgataca gccgtgtact attgtgccaa gcactactat 300
tacggcggca gctatgccat ggattactgg ggccagggca ccctggtgac agtgtcctct 360

<210> SEQ ID NO 360
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 360
caggtccagc tgcaggaaag cggcccagga ctggtgaagc ctagcgagac cctgtccctg 60
acctgcacag tgagcggcgt gtccctgcct gattacggcg tgtcctggat cagacagccc 120
cctggcaagt gtctggagtg gatcggcgtg atctggggct ccgagaccac atactatcag 180
tcctctctga agtctagggt gacaatctct aaggacaaca gcaagaatca ggtgagcctg 240
aagctgagct ccgtgaccgc agcagataca gccgtgtact attgtgccaa gcactactat 300
tacggcggct cttatgctat ggattattgg gggcagggca ctctggtcac tgtctcaagc 360

<210> SEQ ID NO 361
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 361
caggtgcagc tgcaggagag cggcccagga ctggtgaagc cttccgagac actgtctctg 60
acctgtacag tgagcggcgt gtccctgccc gactacggcg tgtcctggat cagacagcca 120
cctggcaagg gactggagtg gatcggcgtg atctggggca gcgagaccac atactatcag 180
agctccctga agtccagggt gaccatcagc aaggacaact ccaagaatca ggtgagcctg 240
aagctgtcta gcgtgaccgc cgccgataca gccgtgtact attgcgccaa gcactactat 300
tacggcggct cctatgccat ggattactgg ggccagggca ccctggtcac agtgtcctct 360

<210> SEQ ID NO 362
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 362
caggtgcagc tgcaggagtc tggcccagga ctggtgaagc cttctgagac cctgagcctg 60
acctgcacag tgtccggcgt gtctctgccc gattacggcg tgtcctggat cagacagcca 120
cctggcaagg gactggagtg gatcggcgtg atctggggct ctgagaccac atactatcag 180
tctagcctga agagccgggt gacaatctcc aaggacaact ctaagaatca ggtgtccctg 240
aagctgtcct ctgtgaccgc cgccgataca gccgtgtact attgtgccaa gcactactat 300
tacggcggca gctatgccat ggactactgg ggccagggca ccctggtgac agtgagctcc 360

<210> SEQ ID NO 363
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 363
caggtgcagc tgcaggagtc tggcccagga ctggtgaagc cttctgagac cctgagcctg 60
acctgcacag tgagcggcgt gtccctgccc gattacggcg tgtcctggat cagacagcca 120
cctggcaagg gactggagtg gatcggcgtg atctggggca gcgagaccac atactatcag 180
tcctctctga agtccagggt gacaatctcc aaggacaact ctaagaatca ggtgagcctg 240
aagctgagct ccgtgaccgc agcagataca gccgtgtact attgcgccaa gcactactat 300
tacggcggct cctatgccat ggactactgg ggccagggca ccctggtcac agtgtctagc 360

<210> SEQ ID NO 364
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 364
caggtgcagc tgcaggagtc cggcccagga ctggtgaagc cttccgagac actgtctctg 60
acctgtacag tgtccggcgt gtctctgccc gactacggcg tgagctggat cagacagcca 120
cctggcaagg gactggagtg gatcggcgtg atctggggct ctgagaccac atactatcag 180
tcctctctga agagccgggt gaccatcagc aaggacaact ccaagaatca ggtgtccctg 240
aagctgagct ccgtgaccgc agcagataca gccgtgtact attgcgccaa gcactactat 300
tacggcggca gctatgccat ggattactgg ggccagggca ccctggtgac agtgtctagc 360

<210> SEQ ID NO 365
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 365
gagatcgtga tgacccagag cccagccaca ctgagcctgt ccccaggaga gagggccaca 60
ctgtcttgta gagccagcca ggatatctcc aagtatctga actggtacca gcagaagcct 120
ggacaggcac caaggctgct gatctaccac acctctagac tgcacagcgg catccctgcc 180
aggttttctg gcagcggctc cggcacagac tataccctga caatctctag cctgcagcca 240
gaggatttcg ccgtgtactt ttgtcagcag ggcaatactc tgccatacac ctttggatgc 300
ggaactaaac tggaaatcaa g 321

<210> SEQ ID NO 366
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 366
gaaattgtga tgacccagtc ccccgctact ctgtctctgt cccccggaga acgggctact 60
ctgtcttgtc gcgcttccca ggatattagc aagtacctga actggtatca gcagaagcca 120
ggacaggcac caaggctgct gatctaccac acctctcgcc tgcacagcgg catccctgca 180
cggttctctg gcagcggctc cggcacagac tacaccctga caatcagctc cctgcagcct 240
gaggatttcg ccgtgtactt ttgccagcag ggcaataccc tgccatatac atttggctgt 300
ggcaccaagc tggagatcaa g 321

<210> SEQ ID NO 367
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 367
gagatcgtga tgacccagtc cccagccaca ctgagcctgt ccccaggaga gagggccacc 60
ctgtcttgta gagccagcca ggatatctcc aagtatctga actggtacca gcagaagcct 120
ggacaggcac caaggctgct gatctaccac acctctagac tgcacagcgg catccctgcc 180
aggttttctg gcagcggctc cggcacagac tataccctga caatctctag cctgcagcca 240
gaggatttcg ccgtgtactt ttgtcagcag ggaaatactc tgccatacac ctttggatgc 300
ggaactaaac tggaaatcaa g 321

<210> SEQ ID NO 368
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 368
gagattgtga tgacccagtc ccccgccacc ctgagtctga gccccggaga acgagctacc 60
ctgagttgcc gagcttccca ggacatttcc aagtacctga actggtatca gcagaagcca 120
ggacaggcac caaggctgct gatctaccac acctctcgcc tgcacagcgg catcccagca 180
cggttctctg gcagcggctc cggcacagac tacaccctga caatcagctc cctgcagcct 240
gaggatttcg ccgtgtactt ttgccagcag ggcaataccc tgccatatac atttggctgt 300
ggcaccaagc tggagatcaa g 321

<210> SEQ ID NO 369
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 369
gagatcgtga tgacccagtc tccagccaca ctgtctctga gcccaggaga gagggccacc 60
ctgtcttgcc gcgccagcca ggatatctcc aagtatctga actggtacca gcagaagcca 120
ggacaggcac caaggctgct gatctaccac acctctcgcc tgcacagcgg catcccagca 180
cggttctccg gctctggcag cggcacagac tacaccctga caatctcctc tctgcagccc 240
gaggatttcg ccgtgtattt ttgccagcag ggcaataccc tgccttacac atttggccag 300
ggcaccaagc tggagatcaa g 321

<210> SEQ ID NO 370
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 370
gagatcgtga tgacccagag cccagccaca ctgagcctgt ccccaggaga gagggccacc 60
ctgagctgca gagcctccca ggatatctct aagtatctga actggtacca gcagaagcct 120
ggacaggcac caaggctgct gatctaccac accagcagac tgcactccgg catccctgca 180
aggttctctg gcagcggctc cggcacagac tacaccctga caatctctag cctgcagcct 240
gaggatttcg ccgtgtattt ttgtcagcag ggcaataccc tgccatacac atttggccag 300
ggcaccaagc tggagatcaa g 321

<210> SEQ ID NO 371
<211> LENGTH: 321
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 371
gagatcgtga tgacccagag cccagccaca ctgtctctga gcccaggaga gagggccacc     60
ctgagctgtc gcgcctccca ggatatctct aagtatctga actggtacca gcagaagcca    120
ggacaggcac caaggctgct gatctaccac accagccgcc tgcactccgg catcccagca    180
cggttctccg gctctggcag cggcacagac tacaccctga caatctcctc tctgcagccc    240
gaggatttcg ccgtgtattt ttgccagcag ggcaataccc tgccttacac atttggccag    300
ggcaccaagc tggagatcaa g                                              321

<210> SEQ ID NO 372
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372
gagatcgtga tgacccagtc tccagccaca ctgagcctgt ccccaggaga gagggccacc     60
ctgtcttgca gagccagcca ggatatctcc aagtatctga actggtacca gcagaagcct    120
ggacaggcac caaggctgct gatctaccac acctctagac tgcacagcgg catcccagca    180
aggttctctg gcagcggctc cggcacagac tacaccctga caatctctag cctgcagcct    240
gaggatttcg ccgtgtattt ttgccagcag ggcaataccc tgccatacac atttggccag    300
ggcaccaagc tggagatcaa g                                              321

<210> SEQ ID NO 373
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

-continued

Thr Val Ser Gly Val Ser Leu Pro Asp Tyr Gly Val Ser Trp Ile Arg
145 150 155 160

Gln Pro Pro Gly Lys Gly Leu Glu Trp Ile Gly Val Ile Trp Gly Ser
165 170 175

Glu Thr Thr Tyr Tyr Ser Ser Ser Leu Lys Ser Arg Val Thr Ile Ser
180 185 190

Lys Asp Asn Ser Lys Asn Gln Val Ser Leu Lys Leu Ser Ser Val Thr
195 200 205

Ala Ala Asp Thr Ala Val Tyr Tyr Cys Ala Lys His Tyr Tyr Tyr Gly
210 215 220

Gly Ser Tyr Ala Met Asp Tyr Trp Gly Gln Gly Thr Leu Val Thr Val
225 230 235 240

Ser Ser

<210> SEQ ID NO 374
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 374

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Gly Leu Glu Trp Ile
35 40 45

Gly Val Ile Trp Gly Ser Glu Thr Thr Tyr Tyr Ser Ser Ser Leu Lys
50 55 60

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Glu Ile Val Met Thr Gln Ser Pro Ala
130 135 140

Thr Leu Ser Leu Ser Pro Gly Glu Arg Ala Thr Leu Ser Cys Arg Ala
145 150 155 160

Ser Gln Asp Ile Ser Lys Tyr Leu Asn Trp Tyr Gln Gln Lys Pro Gly
165 170 175

Gln Ala Pro Arg Leu Leu Ile Tyr His Thr Ser Arg Leu His Ser Gly
180 185 190

Ile Pro Ala Arg Phe Ser Gly Ser Gly Ser Gly Thr Asp Tyr Thr Leu
195 200 205

Thr Ile Ser Ser Leu Gln Pro Glu Asp Phe Ala Val Tyr Phe Cys Gln
210 215 220

Gln Gly Asn Thr Leu Pro Tyr Thr Phe Gly Gln Gly Thr Lys Leu Glu
225 230 235 240

Ile Lys

<210> SEQ ID NO 375
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 375

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys

<210> SEQ ID NO 376
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 376

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly

-continued

```
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245


<210> SEQ ID NO 377
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160
```

```
Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245


<210> SEQ ID NO 378
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245


<210> SEQ ID NO 379
```

<211> LENGTH: 247
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 379

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Gly Leu Glu Trp Ile
35 40 45

Gly Val Ile Trp Gly Ser Glu Thr Thr Tyr Tyr Gln Ser Ser Leu Lys
50 55 60

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Glu Ile Val Met
130 135 140

Thr Gln Ser Pro Ala Thr Leu Ser Leu Ser Pro Gly Glu Arg Ala Thr
145 150 155 160

Leu Ser Cys Arg Ala Ser Gln Asp Ile Ser Lys Tyr Leu Asn Trp Tyr
165 170 175

Gln Gln Lys Pro Gly Gln Ala Pro Arg Leu Leu Ile Tyr His Thr Ser
180 185 190

Arg Leu His Ser Gly Ile Pro Ala Arg Phe Ser Gly Ser Gly Ser Gly
195 200 205

Thr Asp Tyr Thr Leu Thr Ile Ser Ser Leu Gln Pro Glu Asp Phe Ala
210 215 220

Val Tyr Phe Cys Gln Gln Gly Asn Thr Leu Pro Tyr Thr Phe Gly Gln
225 230 235 240

Gly Thr Lys Leu Glu Ile Lys
245

<210> SEQ ID NO 380
<211> LENGTH: 247
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 380

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gly Gly Gly Gly Ser Gln
115 120 125

Val Gln Leu Gln Glu Ser Gly Pro Gly Leu Val Lys Pro Ser Glu Thr
130 135 140

Leu Ser Leu Thr Cys Thr Val Ser Gly Val Ser Leu Pro Asp Tyr Gly
145 150 155 160

Val Ser Trp Ile Arg Gln Pro Pro Gly Lys Gly Leu Glu Trp Ile Gly
165 170 175

Val Ile Trp Gly Ser Glu Thr Thr Tyr Tyr Asn Ser Ser Leu Lys Ser
180 185 190

Arg Val Thr Ile Ser Lys Asp Asn Ser Lys Asn Gln Val Ser Leu Lys
195 200 205

Leu Ser Ser Val Thr Ala Ala Asp Thr Ala Val Tyr Tyr Cys Ala Lys
210 215 220

His Tyr Tyr Tyr Gly Gly Ser Tyr Ala Met Asp Tyr Trp Gly Gln Gly
225 230 235 240

Thr Leu Val Thr Val Ser Ser
245

<210> SEQ ID NO 381
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 381

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Leu Pro Asp Tyr
20 25 30

Gly Val Ser Trp Ile Arg Gln Pro Pro Gly Lys Gly Leu Glu Trp Ile
35 40 45

Gly Val Ile Trp Gly Ser Glu Thr Thr Tyr Tyr Asn Ser Ser Leu Lys
50 55 60

Ser Arg Val Thr Ile Ser Lys Asp Asn Ser Lys Asn Gln Val Ser Leu
65 70 75 80

Lys Leu Ser Ser Val Thr Ala Ala Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Gly Gly Gly Gly Ser Glu Ile Val Met
130 135 140

Thr Gln Ser Pro Ala Thr Leu Ser Leu Ser Pro Gly Glu Arg Ala Thr
145 150 155 160

Leu Ser Cys Arg Ala Ser Gln Asp Ile Ser Lys Tyr Leu Asn Trp Tyr

-continued

```
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245
```

<210> SEQ ID NO 382
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 382

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser
```

<210> SEQ ID NO 383
<211> LENGTH: 242
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 383

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys
```

<210> SEQ ID NO 384
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 384

```
atgcttctcc tggtgacaag ccttctgctc tgtgagttac cacacccagc attcctcctg      60

atcccagaca tccagatgac acagactaca tcctccctgt ctgcctctct gggagacaga     120

gtcaccatca gttgcagggc aagtcaggac attagtaaat atttaaattg gtatcagcag     180

aaaccagatg gaactgttaa actcctgatc taccatacat caagattaca ctcaggagtc     240

ccatcaaggt tcagtggcag tgggtctgga acagattatt ctctcaccat tagcaacctg     300

gagcaagaag atattgccac ttacttttgc caacagggta atacgcttcc gtacacgttc     360

ggagggggga ctaagttgga aataacaggc tccacctctg gatccggcaa gcccggatct     420
```

-continued

```
ggcgagggat ccaccaaggg cgaggtgaaa ctgcaggagt caggacctgg cctggtggcg    480

ccctcacaga gcctgtccgt cacatgcact gtctcagggg tctcattacc cgactatggt    540

gtaagctgga ttcgccagcc tccacgaaag ggtctggagt ggctgggagt aatatggggt    600

agtgaaacca catactataa ttcagctctc aaatccagac tgaccatcat caaggacaac    660

tccaagagcc aagttttctt aaaaatgaac agtctgcaaa ctgatgacac agccatttac    720

tactgtgcca aacattatta ctacggtggt agctatgcta tggactactg gggtcaagga    780

acctcagtca ccgtctcctc agcggccgca attgaagtta tgtatcctcc tccttaccta    840

gacaatgaga agagcaatgg aaccattatc catgtgaaag ggaaacacct ttgtccaagt    900

cccctatttc ccggaccttc taagcccttt tgggtgctgg tggtggttgg gggagtcctg    960

gcttgctata gcttgctagt aacagtggcc tttattattt tctgggtgag gagtaagagg   1020

agcaggctcc tgcacagtga ctacatgaac atgactcccc gccgccccgg gcccacccgc   1080

aagcattacc agccctatgc cccaccacgc gacttcgcag cctatcgctc cagagtgaag   1140

ttcagcagga gcgcagacgc ccccgcgtac cagcagggcc agaaccagct ctataacgag   1200

ctcaatctag gacgaagaga ggagtacgat gttttggaca agagacgtgg ccgggaccct   1260

gagatggggg gaaagccgag aaggaagaac cctcaggaag gcctgtacaa tgaactgcag   1320

aaagataaga tggcggaggc ctacagtgag attgggatga aaggcgagcg ccggaggggc   1380

aaggggcacg atggccttta ccagggtctc agtacagcca ccaaggacac ctacgacgcc   1440

cttcacatgc aggccctgcc ccctcgc                                       1467
```

```
<210> SEQ ID NO 385
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175
```

```
Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Ile Glu
            260                 265                 270

Val Met Tyr Pro Pro Pro Tyr Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 386
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 386

```
atgcttctcc tggtgacaag ccttctgctc tgtgagttac cacacccagc attcctcctg      60

atcccagaca tccagatgac acagactaca tcctccctgt ctgcctctct gggagacaga     120

gtcaccatca gttgcagggc aagtcaggac attagtaaat atttaaattg gtatcagcag     180

aaaccagatg gaactgttaa actcctgatc taccatacat caagattaca ctcaggagtc     240
```

```
ccatcaaggt tcagtggcag tgggtctgga acagattatt ctctcaccat tagcaacctg    300

gagcaagaag atattgccac ttacttttgc caacagggta atacgcttcc gtacacgttc    360

ggagggggga ctaagttgga aataacaggc tccacctctg gatccggcaa gcccggatct    420

ggcgagggat ccaccaaggg cgaggtgaaa ctgcaggagt caggacctgg cctggtggcg    480

ccctcacaga gcctgtccgt cacatgcact gtctcagggg tctcattacc cgactatggt    540

gtaagctgga ttcgccagcc tccacgaaag ggtctggagt ggctgggagt aatatggggt    600

agtgaaacca catactataa ttcagctctc aaatccagac tgaccatcat caaggacaac    660

tccaagagcc aagttttctt aaaaatgaac agtctgcaaa ctgatgacac agccatttac    720

tactgtgcca aacattatta ctacggtggt agctatgcta tggactactg gggtcaagga    780

acctcagtca ccgtctcctc a                                              801
```

<210> SEQ ID NO 387
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255
```

Trp Gly Gln Gly Thr Ser Val Thr Val Ser
260 265

<210> SEQ ID NO 388
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 388
gacatccaga tgacacagac tacatcctcc ctgtctgcct ctctgggaga cagagtcacc 60
atcagttgca gggcaagtca ggacattagt aaatatttaa attggtatca gcagaaacca 120
gatggaactg ttaaactcct gatctaccat acatcaagat tacactcagg agtcccatca 180
aggttcagtg gcagtgggtc tggaacagat tattctctca ccattagcaa cctggagcaa 240
gaagatattg ccacttactt ttgccaacag ggtaatacgc ttccgtacac gttcggaggg 300
gggactaagt tggaaataac aggctccacc tctggatccg gcaagcccgg atctggcgag 360
ggatccacca agggcgaggt gaaactgcag gagtcaggac ctggcctggt ggcgccctca 420
cagagcctgt ccgtcacatg cactgtctca ggggtctcat tacccgacta tggtgtaagc 480
tggattcgcc agcctccacg aaagggtctg gagtggctgg gagtaatatg gggtagtgaa 540
accacatact ataattcagc tctcaaatcc agactgacca tcatcaagga caactccaag 600
agccaagttt tcttaaaaat gaacagtctg caaactgatg acacagccat ttactactgt 660
gccaaacatt attactacgg tggtagctat gctatggact actggggtca aggaacctca 720
gtcaccgtct cctcagcggc cgcaattgaa gttatgtatc ctcctcctta cctagacaat 780
gagaagagca atggaaccat tatccatgtg aaagggaaac acctttgtcc aagtccccta 840
tttcccggac cttctaagcc cttttgggtg ctggtggtgg ttgggggagt cctggcttgc 900
tatagcttgc tagtaacagt ggcctttatt attttctggg tgaggagtaa gaggagcagg 960
ctcctgcaca gtgactacat gaacatgact ccccgccgcc ccgggcccac ccgcaagcat 1020
taccagccct atgccccacc acgcgacttc gcagcctatc gctccagagt gaagttcagc 1080
aggagcgcag acgcccccgc gtaccagcag ggccagaacc agctctataa cgagctcaat 1140
ctaggacgaa gagaggagta cgatgttttg gacaagagac gtggccggga ccctgagatg 1200
gggggaaagc cgagaaggaa gaaccctcag gaaggcctgt acaatgaact gcagaaagat 1260
aagatggcgg aggcctacag tgagattggg atgaaaggcg agcgccggag gggcaagggg 1320
cacgatggcc tttaccaggg tctcagtaca gccaccaagg acacctacga cgcccttcac 1380
atgcaggccc tgccccctcg c 1401

<210> SEQ ID NO 389
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 389

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

-continued

```
Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Ala Ala Ala Ile Glu Val Met Tyr Pro Pro Pro
                245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445
```

```
Ser Thr Ala Thr Lys Asp Thr Tyr Asp Ala Leu His Met Gln Ala Leu
    450                 455                 460

Pro Pro Arg
465
```

<210> SEQ ID NO 390
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 390

```
gacatccaga tgacacagac tacatcctcc ctgtctgcct ctctgggaga cagagtcacc      60

atcagttgca gggcaagtca ggacattagt aaatatttaa attggtatca gcagaaacca     120

gatggaactg ttaaactcct gatctaccat acatcaagat tacactcagg agtcccatca     180

aggttcagtg gcagtgggtc tggaacagat tattctctca ccattagcaa cctggagcaa     240

gaagatattg ccacttactt ttgccaacag ggtaatacgc ttccgtacac gttcggaggg     300

gggactaagt tggaaataac aggctccacc tctggatccg gcaagcccgg atctggcgag     360

ggatccacca agggcgaggt gaaactgcag gagtcaggac ctggcctggt ggcgccctca     420

cagagcctgt ccgtcacatg cactgtctca ggggtctcat tacccgacta tggtgtaagc     480

tggattcgcc agcctccacg aaagggtctg gagtggctgg gagtaatatg gggtagtgaa     540

accacatact ataattcagc tctcaaatcc agactgacca tcatcaagga caactccaag     600

agccaagttt tcttaaaaat gaacagtctg caaactgatg acacagccat ttactactgt     660

gccaaacatt attactacgg tggtagctat gctatggact actggggtca aggaacctca     720

gtcaccgtct cctca                                                      735
```

<210> SEQ ID NO 391
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 391

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
```

```
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 392
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 392

atgctgctgc tggtgaccag cctgctgctg tgcgagctgc cccaccccgc ctttctgctg     60

atccccgaca tccagatgac ccagaccacc tccagcctga gcgccagcct gggcgaccgg    120

gtgaccatca gctgccgggc cagccaggac atcagcaagt acctgaactg gtatcagcag    180

aagcccgacg gcaccgtcaa gctgctgatc taccacacca gccggctgca cagcggcgtg    240

cccagccggt ttagcggcag cggctccggc accgactaca gcctgaccat ctccaacctg    300

gaacaggaag atatcgccac ctacttttgc cagcagggca acacactgcc ctacaccttt    360

ggcggcggaa caaagctgga aatcaccggc agcacctccg gcagcggcaa gcctggcagc    420

ggcgagggca gcaccaaggg cgaggtgaag ctgcaggaaa gcggccctgg cctggtggcc    480

cccagccaga gcctgagcgt gacctgcacc gtgagcggcg tgagcctgcc cgactacggc    540

gtgagctgga tccggcagcc ccccaggaag ggcctggaat ggctgggcgt gatctggggc    600

agcgagacca cctactacaa cagcgccctg aagagccggc tgaccatcat caaggacaac    660

agcaagagcc aggtgttcct gaagatgaac agcctgcaga ccgacgacac cgccatctac    720

tactgcgcca agcactacta ctacggcggc agctacgcca tggactactg gggccagggc    780

accagcgtga ccgtgagcag cgaatctaag tacggaccgc cctgcccccc ttgccctatg    840

ttctgggtgc tggtggtggt cggaggcgtg ctggcctgct acagcctgct ggtcaccgtg    900

gccttcatca tcttttgggt gaaacggggc agaaagaaac tcctgtatat attcaaacaa    960

ccatttatga gaccagtaca aactactcaa gaggaagatg gctgtagctg ccgatttcca   1020

gaagaagaag aaggaggatg tgaactgcgg gtgaagttca gcagaagcgc cgacgcccct   1080

gcctaccagc agggccagaa tcagctgtac aacgagctga acctgggcag aagggaagag   1140

tacgacgtcc tggataagcg gagaggccgg gaccctgaga tgggcggcaa gcctcggcgg   1200

aagaaccccc aggaaggcct gtataacgaa ctgcagaaag acaagatggc cgaggcctac   1260

agcgagatcg gcatgaaggg cgagcggagg cggggcaagg gccacgacgg cctgtatcag   1320

ggcctgtcca ccgccaccaa ggatacctac gacgccctgc acatgcaggc cctgcccccca   1380
```

agg 1383

<210> SEQ ID NO 393
<211> LENGTH: 461
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 393

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Thr Thr Ser Ser
20 25 30

Leu Ser Ala Ser Leu Gly Asp Arg Val Thr Ile Ser Cys Arg Ala Ser
35 40 45

Gln Asp Ile Ser Lys Tyr Leu Asn Trp Tyr Gln Gln Lys Pro Asp Gly
50 55 60

Thr Val Lys Leu Leu Ile Tyr His Thr Ser Arg Leu His Ser Gly Val
65 70 75 80

Pro Ser Arg Phe Ser Gly Ser Gly Ser Gly Thr Asp Tyr Ser Leu Thr
85 90 95

Ile Ser Asn Leu Glu Gln Glu Asp Ile Ala Thr Tyr Phe Cys Gln Gln
100 105 110

Gly Asn Thr Leu Pro Tyr Thr Phe Gly Gly Gly Thr Lys Leu Glu Ile
115 120 125

Thr Gly Ser Thr Ser Gly Ser Gly Lys Pro Gly Ser Gly Glu Gly Ser
130 135 140

Thr Lys Gly Glu Val Lys Leu Gln Glu Ser Gly Pro Gly Leu Val Ala
145 150 155 160

Pro Ser Gln Ser Leu Ser Val Thr Cys Thr Val Ser Gly Val Ser Leu
165 170 175

Pro Asp Tyr Gly Val Ser Trp Ile Arg Gln Pro Pro Arg Lys Gly Leu
180 185 190

Glu Trp Leu Gly Val Ile Trp Gly Ser Glu Thr Thr Tyr Tyr Asn Ser
195 200 205

Ala Leu Lys Ser Arg Leu Thr Ile Ile Lys Asp Asn Ser Lys Ser Gln
210 215 220

Val Phe Leu Lys Met Asn Ser Leu Gln Thr Asp Asp Thr Ala Ile Tyr
225 230 235 240

Tyr Cys Ala Lys His Tyr Tyr Tyr Gly Gly Ser Tyr Ala Met Asp Tyr
245 250 255

Trp Gly Gln Gly Thr Ser Val Thr Val Ser Ser Glu Ser Lys Tyr Gly
260 265 270

Pro Pro Cys Pro Pro Cys Pro Met Phe Trp Val Leu Val Val Val Gly
275 280 285

Gly Val Leu Ala Cys Tyr Ser Leu Leu Val Thr Val Ala Phe Ile Ile
290 295 300

Phe Trp Val Lys Arg Gly Arg Lys Lys Leu Leu Tyr Ile Phe Lys Gln
305 310 315 320

Pro Phe Met Arg Pro Val Gln Thr Thr Gln Glu Glu Asp Gly Cys Ser
325 330 335

Cys Arg Phe Pro Glu Glu Glu Glu Gly Gly Cys Glu Leu Arg Val Lys
340 345 350

```
Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460


<210> SEQ ID NO 394
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 394

atgctgctgc tggtgaccag cctgctgctg tgcgagctgc cccaccccgc ctttctgctg      60

atccccgaca tccagatgac ccagaccacc tccagcctga gcgccagcct gggcgaccgg     120

gtgaccatca gctgccgggc cagccaggac atcagcaagt acctgaactg gtatcagcag     180

aagcccgacg gcaccgtcaa gctgctgatc taccacacca gccggctgca cagcggcgtg     240

cccagccggt ttagcggcag cggctccggc accgactaca gcctgaccat ctccaacctg     300

gaacaggaag atatcgccac ctacttttgc cagcagggca acacactgcc ctacaccttt     360

ggcggcggaa caaagctgga aatcaccggc agcacctccg gcagcggcaa gcctggcagc     420

ggcgagggca gcaccaaggg cgaggtgaag ctgcaggaaa gcggccctgg cctggtggcc     480

cccagccaga gcctgagcgt gacctgcacc gtgagcggcg tgagcctgcc cgactacggc     540

gtgagctgga tccggcagcc ccccaggaag ggcctggaat ggctgggcgt gatctggggc     600

agcgagacca cctactacaa cagcgccctg aagagccggc tgaccatcat caaggacaac     660

agcaagagcc aggtgttcct gaagatgaac agcctgcaga ccgacgacac cgccatctac     720

tactgcgcca agcactacta ctacggcggc agctacgcca tggactactg gggccagggc     780

accagcgtga ccgtgagcag c                                               801


<210> SEQ ID NO 395
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
```

```
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265
```

```
<210> SEQ ID NO 396
<211> LENGTH: 1317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396

gacatccaga tgacccagac cacctccagc ctgagcgcca gcctgggcga ccgggtgacc     60

atcagctgcc gggccagcca ggacatcagc aagtacctga actggtatca gcagaagccc    120

gacggcaccg tcaagctgct gatctaccac accagccggc tgcacagcgg cgtgcccagc    180

cggtttagcg gcagcggctc cggcaccgac tacagcctga ccatctccaa cctggaacag    240

gaagatatcg ccacctactt ttgccagcag ggcaacacac tgccctacac ctttggcggc    300

ggaacaaagc tggaaatcac cggcagcacc tccggcagcg gcaagcctgg cagcggcgag    360

ggcagcacca agggcgaggt gaagctgcag gaaagcggcc ctggcctggt ggcccccagc    420

cagagcctga gcgtgacctg caccgtgagc ggcgtgagcc tgcccgacta cggcgtgagc    480

tggatccggc agcccccag gaagggcctg gaatggctgg gcgtgatctg gggcagcgag     540

accacctact acaacagcgc cctgaagagc cggctgacca tcatcaagga caacagcaag    600

agccaggtgt tcctgaagat gaacagcctg cagaccgacg acaccgccat ctactactgc    660

gccaagcact actactacgg cggcagctac gccatggact actggggcca gggcaccagc    720
```

-continued

```
gtgaccgtga gcagcgaatc taagtacgga ccgccctgcc ccccttgccc tatgttctgg    780

gtgctggtgg tggtcggagg cgtgctggcc tgctacagcc tgctggtcac cgtggccttc    840

atcatctttt gggtgaaacg gggcagaaag aaactcctgt atatattcaa acaaccattt    900

atgagaccag tacaaactac tcaagaggaa gatggctgta gctgccgatt tccagaagaa    960

gaagaaggag gatgtgaact gcgggtgaag ttcagcagaa gcgccgacgc ccctgcctac   1020

cagcagggcc agaatcagct gtacaacgag ctgaacctgg gcagaaggga agagtacgac   1080

gtcctggata agcggagagg ccgggaccct gagatgggcg gcaagcctcg gcggaagaac   1140

ccccaggaag gcctgtataa cgaactgcag aaagacaaga tggccgaggc ctacagcgag   1200

atcggcatga agggcgagcg gaggcggggc aagggccacg acggcctgta tcagggcctg   1260

tccaccgcca ccaaggatac ctacgacgcc ctgcacatgc aggccctgcc cccaagg      1317
```

```
<210> SEQ ID NO 397
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Glu Ser Lys Tyr Gly Pro Pro Cys Pro Pro Cys
                245                 250                 255
```

-continued

```
Pro Met Phe Trp Val Leu Val Val Val Gly Gly Val Leu Ala Cys Tyr
            260                 265                 270

Ser Leu Leu Val Thr Val Ala Phe Ile Ile Phe Trp Val Lys Arg Gly
        275                 280                 285

Arg Lys Lys Leu Leu Tyr Ile Phe Lys Gln Pro Phe Met Arg Pro Val
    290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Arg Val Lys Phe Ser Arg Ser Ala Asp
                325                 330                 335

Ala Pro Ala Tyr Gln Gln Gly Gln Asn Gln Leu Tyr Asn Glu Leu Asn
            340                 345                 350

Leu Gly Arg Arg Glu Glu Tyr Asp Val Leu Asp Lys Arg Arg Gly Arg
        355                 360                 365

Asp Pro Glu Met Gly Gly Lys Pro Arg Arg Lys Asn Pro Gln Glu Gly
    370                 375                 380

Leu Tyr Asn Glu Leu Gln Lys Asp Lys Met Ala Glu Ala Tyr Ser Glu
385                 390                 395                 400

Ile Gly Met Lys Gly Glu Arg Arg Arg Gly Lys Gly His Asp Gly Leu
                405                 410                 415

Tyr Gln Gly Leu Ser Thr Ala Thr Lys Asp Thr Tyr Asp Ala Leu His
            420                 425                 430

Met Gln Ala Leu Pro Pro Arg
        435
```

<210> SEQ ID NO 398
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 398

```
gacatccaga tgacccagac cacctccagc ctgagcgcca gcctgggcga ccgggtgacc     60

atcagctgcc gggccagcca ggacatcagc aagtacctga actggtatca gcagaagccc    120

gacggcaccg tcaagctgct gatctaccac accagccggc tgcacagcgg cgtgcccagc    180

cggtttagcg gcagcggctc cggcaccgac tacagcctga ccatctccaa cctggaacag    240

gaagatatcg ccacctactt ttgccagcag ggcaacacac tgccctacac ctttggcggc    300

ggaacaaagc tggaaatcac cggcagcacc tccggcagcg gcaagcctgg cagcggcgag    360

ggcagcacca agggcgaggt gaagctgcag gaaagcggcc ctggcctggt ggcccccagc    420

cagagcctga gcgtgacctg caccgtgagc ggcgtgagcc tgcccgacta cggcgtgagc    480

tggatccggc agccccccag gaagggcctg gaatggctgg gcgtgatctg gggcagcgag    540

accacctact acaacagcgc cctgaagagc cggctgacca tcatcaagga caacagcaag    600

agccaggtgt tcctgaagat gaacagcctg cagaccgacg acaccgccat ctactactgc    660

gccaagcact actactacgg cggcagctac gccatggact actggggcca gggcaccagc    720

gtgaccgtga gcagc                                                     735
```

<210> SEQ ID NO 399
<211> LENGTH: 245
<212> TYPE: PRT
<213> ORGANISM: Artificial Sequence
<220> FEATURE:

-continued

<223> OTHER INFORMATION: Description of Artificial Sequence: Synthetic
polypeptide

<400> SEQUENCE: 399

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245
```

<210> SEQ ID NO 400
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 400

```
caggtgcagc tgcaggagtc cggcggcggc gtggtgcagc caggccggtc cctgagactg     60

tcttgtgccg ccagcggctt caccttttcc tcttatggca tgcactgggt gagacaggca    120

cctggcaagg gactggagtg ggtggccgtg atctcctacg acggctctaa caagtattac    180

gccgatagcg tgaagggcag gttcaccatc agccgcgaca actccaagaa tacactgtat    240

ctgcagatga atagcctgcg ggccgaggat accgccgtgt attactgcgg aggctccggc    300

tacgcactgc acgacgatta ttacggactg gacgtgtggg gacagggcac cctggtcaca    360

gtgagctcc                                                            369
```

<210> SEQ ID NO 401
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 401
caggtgcagc tgcaggagtc tggcggagga gtggtgcagc caggccggtc cctgagactg 60
tcttgcgccg ccagcggctt cacattttct agctacggaa tgcactgggt gcgccaggca 120
cctggcaagg gactggagtg ggtggccgtg atctcctatg acggctctaa caagtactat 180
gccgattccg tgaagggcag gttcaccatc agccgcgaca actccaagaa tacactgtac 240
ctgcagatga attccctgcg ggccgaggat accgccgtgt actattgtgg cggctctggc 300
tatgccctgc acgacgatta ctatggactg gacgtgtggg gacagggcac cctggtgaca 360
gtgtcctct 369

<210> SEQ ID NO 402
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 402
caggtgcagc tgcaggagtc tggcggagga gtggtgcagc caggccggag cctgagactg 60
tcctgcgccg cctctggctt cacctttagc tcctatggca tgcactgggt gagacaggca 120
cctggcaagg gactggagtg ggtggccgtg atcagctacg acggctccaa caagtattac 180
gccgatagcg tgaagggcag gttcaccatc tctcgcgaca acagcaagaa tacactgtat 240
ctgcagatga attccctgcg ggccgaggat acagccgtgt attactgcgg aggcagcggc 300
tacgcactgc acgacgatta ttacggactg gacgtgtggg gacagggcac cctggtcaca 360
gtgtctagc 369

<210> SEQ ID NO 403
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 403
caggtgcagc tgcaggagag cggcggcggc gtggtgcagc ccggccggtc tctgagactg 60
agctgtgccg cctccggctt cacctttagc tcctacggaa tgcactgggt gcgccaggca 120
cctggcaagg gactggagtg ggtggccgtg atctcttatg acggcagcaa caagtactat 180
gccgatagcg tgaagggcag gttcaccatc tcccgcgaca actctaagaa tacactgtac 240
ctgcagatga atagcctgcg ggccgaggat accgccgtgt actattgcgg aggctccggc 300
tatgcactgc acgacgatta ctatggactg gacgtgtggg gacagggcac cctggtgaca 360
gtgtctagc 369

<210> SEQ ID NO 404
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 404
caggtccagc tgcaggagag tggggggggg gtcgtccagc ccggaagaag cctgagactg 60
tcatgtgccg catctgggtt tacttttagc tcctatggaa tgcactgggt gcgccaggca 120
cctggcaagt gcctggagtg ggtggccgtg atctcctacg acggctctaa caagtactat 180
gccgatagcg tgaagggccg gttcaccatc agcagagaca actccaagaa tacactgtat 240
ctgcagatga attctctgcg ggccgaggat accgccgtgt actattgtgg aggctccggc 300
tacgcactgc acgacgatta ctatggactg gacgtgtggg gacagggcac cctggtgaca 360
gtgtctagc 369

<210> SEQ ID NO 405
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 405
caggtccagc tgcaggaatc cggcggagga gtggtgcagc caggccggtc tctgagactg 60
agctgcgccg cctccggctt cacattttcc tcttatggca tgcactgggt gagacaggcc 120
cctggcaagt gtctggagtg ggtggccgtg atctcttacg acggcagcaa caagtattac 180
gccgatagcg tgaagggcag gttcaccatc tcccgcgaca actctaagaa tacactgtat 240
ctgcagatga attccctgcg ggccgaggat accgccgtgt attactgcgg cggctctggc 300
tacgccctgc acgacgacta ctatggactg gatgtctggg ggcagggcac actggtcact 360
gtctcttca 369

<210> SEQ ID NO 406
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 406
caggtccagc tgcaggaatc aggggggggg gtcgtccagc ccggaagaag tctgagactg 60
tcatgtgccg catcagggtt tacctttagc tcctatggaa tgcactgggt gcgccaggca 120
cctggcaagt gcctggagtg ggtggccgtg atctcctacg acggctctaa caagtactat 180
gccgatagcg tgaagggccg gttcaccatc agcagagaca actccaagaa tacactgtat 240
ctgcagatga attctctgcg ggccgaggat accgccgtgt actattgtgg aggctccggc 300
tacgcactgc acgacgatta ctatggactg gacgtgtggg gacagggcac cctggtgaca 360
gtgtctagc 369

<210> SEQ ID NO 407
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 407
caggtccagc tgcaggaatc cggcggagga gtggtgcagc caggccggtc tctgagactg 60
agctgcgccg cctccggctt caccttttcc tcttatggca tgcactgggt gagacaggcc 120
cctggcaagt gtctggagtg ggtggccgtg atctcttacg acggcagcaa caagtattac 180
gccgatagcg tgaagggcag gttcaccatc tcccgcgaca actctaagaa tacactgtat 240
ctgcagatga attccctgcg ggccgaggat acagccgtgt attactgtgg cggctctggc 300
tacgccctgc atgatgatta ttatggactg gatgtctggg ggcagggcac actggtcact 360
gtctcttcc 369

<210> SEQ ID NO 408
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 408
cagtctgccc tgacccagcc agcaagcgtg tccggctctc ctggccagag catcacaatc 60
tcctgcaccg gcacaagctc cgacgtggga ggctataact acgtgagctg gtatcagcag 120
cacccaggca aggcccccaa gctgatgatc tacgacgtga gcaacaggcc ttctggcgtg 180
agcaatcgct tcagcggctc caagtctggc aataccgcct ctctgacaat cagcggcctg 240
caggcagagg acgaggcaga ttattactgc tctagctata cctcctctag cacactgtac 300
gtgtttggca gcggcaccaa ggtgacagtg ctg 333

<210> SEQ ID NO 409
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409
cagagcgccc tgacccagcc agcatccgtg tctggcagcc caggccagtc tatcacaatc 60
agctgcaccg gcacaagctc cgacgtggga ggctacaact atgtgagctg gtaccagcag 120
caccctggca aggccccaaa gctgatgatc tatgacgtga gcaaccggcc atccggcgtg 180
tctaatagat tctccggctc taagagcggc aataccgcct ccctgacaat ctctggcctg 240
caggcagagg acgaggcaga ttactattgt tctagctaca cctcctctag cacactgtac 300
gtgttcggca gcggcaccaa ggtgacagtg ctg 333

<210> SEQ ID NO 410
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 410
cagtctgccc tgacccagcc agcaagcgtg tccggctctc ctggccagtc catcacaatc 60
tcttgtaccg gcacatcctc tgacgtgggc ggctataact acgtgtcctg gtatcagcag 120
cacccaggca aggcccccaa gctgatgatc tacgatgtga gcaacaggcc ttctggcgtg 180

-continued agcaatcgct tcagcggctc caagtctggc aataccgcca gcctgacaat ctccggcctg 240
caggcagagg acgaggcaga ttattactgc agctcctata cctctagctc cacactgtac 300
gtgtttggca gcggcaccaa ggtgacagtg ctg 333

<210> SEQ ID NO 411
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 411
cagagcgccc tgacccagcc agcatccgtg tctggcagcc caggccagtc catcacaatc 60
tcttgcaccg gcacatctag cgacgtgggc ggctacaact acgtgagctg gtaccagcag 120
caccctggca aggccccaaa gctgatgatc tatgatgtga gcaaccggcc ctccggcgtg 180
tctaatagat tctccggctc taagagcggc aataccgcca gcctgacaat ctccggcctg 240
caggcagagg acgaggcaga ttactattgc tcctcttaca ccagctcctc tacactgtac 300
gtgttcggct ccggcaccaa ggtgacagtg ctg 333

<210> SEQ ID NO 412
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 412
cagtctgccc tgacccagcc tgcaagcgtg tccggctctc caggccagtc tatcacaatc 60
agctgtaccg gcacaagctc cgacgtgggc ggctataact acgtgagctg gtatcagcag 120
caccctggca aggccccaaa gctgatgatc tacgacgtga gcaaccggcc ctctggcgtg 180
agcaatcggt tcagcggcag caagtctggc aataccgcct ccctgacaat ctctggcctg 240
caggcagagg acgaggcaga ttattactgt agcagttata cttcaagctc aaccctgtac 300
gtgtttggat gcggcactaa ggtcaccgtc ctg 333

<210> SEQ ID NO 413
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 413
cagtctgctc tgacccagcc cgcttccgtc tcagggtctc caggacagtc aattaccatt 60
agttgcacag gcacctcatc cgatgtgggc ggctataact acgtgtcctg gtatcagcag 120
cacccaggca aggcccccaa gctgatgatc tacgacgtga gcaacaggcc atctggcgtg 180
agcaatcgct tcagcggctc caagtctggc aataccgcca gcctgacaat ctccggcctg 240
caggcagagg acgaggcaga ttactattgc agctcctata cctctagctc cacactgtac 300
gtgtttggct gtggcaccaa ggtgacagtg ctg 333

<210> SEQ ID NO 414
<211> LENGTH: 333
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 414
cagtctgccc tgacccagcc tgcaagcgtg tccggctctc caggccagtc tatcacaatc 60
agctgtaccg gcacaagctc cgacgtgggc ggctataact acgtgagctg gtatcagcag 120
caccctggca aggccccaaa gctgatgatc tacgacgtga gcaaccggcc ctctggcgtg 180
agcaatcggt tcagcggcag caagtctggc aataccgcct ccctgacaat ctctggcctg 240
caggcagagg acgaggcaga ttattactgt agctcctaca cttcttcaag cacactgtat 300
gtctttggat gcggaactaa ggtcactgtc ctg 333

<210> SEQ ID NO 415
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 415
cagtctgctc tgacccagcc cgcttccgtc tcaggatctc caggacagtc tattacaatt 60
agttgcacag gaacctcttc cgatgtgggc ggctataact acgtgtcctg gtatcagcag 120
cacccaggca aggcccccaa gctgatgatc tacgacgtga gcaacaggcc ttctggcgtg 180
agcaatcgct tcagcggctc caagtctggc aataccgcca gcctgacaat ctccggcctg 240
caggcagagg acgaggcaga ttactattgc agctcctata cctctagctc cacactgtac 300
gtgtttggct gtggcaccaa ggtgacagtg ctg 333

<210> SEQ ID NO 416
<211> LENGTH: 1485
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 416
atggccctcc ctgtcaccgc tctgttgctg ccgcttgctc tgctgctcca cgcagcgcga 60
ccgcaggtac aattgcagga gtctggaggc ggtgtggtgc aacccggtcg cagcttgcgc 120
ctgagttgtg ctgcgtctgg atttacattt tcatcttacg gaatgcattg ggtacgccag 180
gcaccgggga aaggccttga atgggtggct gtaatttcat acgatggttc caacaaatac 240
tatgctgact cagtcaaggg tcgatttaca attagtcggg acaactccaa gaacaccctt 300
tatcttcaaa tgaattccct tagagcagag gatacggcgg tctattactg tggtggcagt 360
ggttatgcac ttcatgatga ttactatggc ttggatgtct gggggcaagg gacgcttgta 420
actgtatcct ctggtggtgg tggtagtggt gggggaggct ccggcggtgg cggctctcaa 480
tctgctctga ctcaaccagc aagcgtatca gggtcaccgg gacagagtat taccataagt 540
tgcacgggga cctctagcga tgtagggggg tataattatg tatcttggta tcaacaacac 600
cccgggaaag cccctaaatt gatgatctac gacgtgagca atcgacctag tggcgtatca 660
aatcgcttct ctggtagcaa gagtgggaat acggcgtccc ttactattag cggattgcaa 720
gcagaagatg aggccgatta ctactgcagc tcctatacta gctcttctac attgtacgtc 780
tttgggagcg gaacaaaagt aacagtactc acaacaacac ctgccccgag accgcctaca 840
ccagccccga ctattgccag ccagcctctg agcctcaggc ctgaggcctg taggcccgca 900
gcgggcggcg cagttcatac acggggcttg gatttcgctt gtgatattta tatttgggct 960
cctttggcgg ggacatgtgg cgtgctgctt ctgtcacttg ttattacact gtactgtaaa 1020
cgcgggcgaa aaaaattgct gtatattttt aagcagccat ttatgaggcc cgttcagacg 1080
acgcaggagg aggacggttg ctcttgcagg ttcccagaag aggaagaagg gggctgtgaa 1140
ttgcgggtta aattttcaag atccgcagac gctccagcat accaacaggg acaaaaccaa 1200
ctctataacg agctgaatct tggaagaagg gaggaatatg atgtgctgga taaacggcgc 1260
ggtagagatc cggagatggg cggaaaacca aggcgaaaaa accctcagga gggactctac 1320
aacgaactgc agaaagacaa aatggcggag gcttattccg aaataggcat gaagggcgag 1380
cggaggcgag ggaaagggca cgacggactg tatcaaggcc tctcaaccgc gactaaggat 1440
acgtacgacg ccctgcacat gcaggccctg cctccgagat gataa 1485

<210> SEQ ID NO 417
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 417
gaaattgtga tgacccagtc acccgccact cttagccttt cacccggtga gcgcgcaacc 60
ctgtcttgca gagcctccca agacatctca aaatacctta attggtatca acagaagccc 120
ggacaggctc ctcgccttct gatctaccac accagccggc tccattctgg aatccctgcc 180
aggttcagcg gtagcggatc tgggaccgac tacaccctca ctatcagctc actgcagcca 240
gaggacttcg ctgtctattt ctgtcagcaa gggaacaccc tgccctacac ctttggacag 300
ggcaccaagc tcgagattaa aggtggaggt ggcagcggag gaggtgggtc cggcggtgga 360
ggaagccagg tccaactcca agaaagcgga ccgggtcttg tgaagccatc agaaactctt 420
tcactgactt gtactgtgag cggagtgtct ctccccgatt acggggtgtc ttggatcaga 480
cagccaccgg ggaagggtct ggaatggatt ggagtgattt ggggctctga gactacttac 540
taccaatcat ccctcaagtc acgcgtcacc atctcaaagg acaactctaa gaatcaggtg 600
tcactgaaac tgtcatctgt gaccgcagcc gacaccgccg tgtactattg cgctaagcat 660
tactattatg gcgggagcta cgcaatggat tactggggac agggtactct ggtcaccgtg 720
tccagcacca ctaccccagc accgaggcca cccaccccgg ctcctaccat cgcctcccag 780
cctctgtccc tgcgtccgga ggcatgtaga cccgcagctg gtggggccgt gcatacccgg 840
ggtcttgact tcgcctgcga tatctacatt tgggcccctc tggctggtac ttgcggggtc 900
ctgctgcttt cactcgtgat cactctttac tgtaagcgcg gtcggaagaa gctgctgtac 960
atctttaagc aacccttcat gaggcctgtg cagactactc aagaggagga cggctgttca 1020
tgccggttcc cagaggagga ggaaggcggc tgcgaactgc gcgtgaaatt cagccgcagc 1080
gcagatgctc cagcctacca gcaggggcag aaccagctct acaacgaact caatcttggt 1140

-continued

```
cggagagagg agtacgacgt gctggacaag cggagaggac gggacccaga aatgggcggg   1200

aagccgcgca gaaagaatcc ccaagagggc ctgtacaacg agctccaaaa ggataagatg   1260

gcagaagcct atagcgagat tggtatgaaa ggggaacgca gaagaggcaa aggccacgac   1320

ggactgtacc agggactcag caccgccacc aaggacacct atgacgctct tcacatgcag   1380

gccctgccgc ctcgg                                                    1395
```

CHIMERIC ANTIGEN RECEPTORS AND USES THEREOF

CROSS-REFERENCE TO RELATED APPLICATIONS

This application claims priority to U.S. Ser. No. 62/940,509, filed on Nov. 26, 2019, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Nov. 24, 2020, is named N2067-716610_SL.txt and is 585,242 bytes in size.

FIELD OF THE INVENTION

The present invention relates generally to immune effector cells (for example, T cells or NK cells) engineered to express a Chimeric Antigen Receptor (CAR), and compositions and uses thereof.

BACKGROUND OF THE INVENTION

Adoptive cell transfer (ACT) therapy with T cells, especially with T cells transduced with Chimeric Antigen Receptors (CARs), has shown promise in several hematologic cancer trials. There exists a need for methods and processes to improve production of the CAR-expressing cell therapy product, enhance product quality, and maximize the therapeutic efficacy of the product.

SUMMARY OF THE INVENTION

In one aspect, this invention features a cell, e.g., an immune cell, e.g., a T cell or NK cell, comprising a first antigen-binding domain and a second antigen-binding domain. In some embodiments, the first antigen-binding domain is an anti-BCMA binding domain. In some embodiments, the anti-BCMA binding domain comprises an anti-BCMA binding sequence disclosed herein, e.g., a CDR, VH, VL, or scFv sequence disclosed in Tables 3-15, 19, 20, 22, 26 and 31. In some embodiments, the second antigen-binding domain is an anti-CD19 binding domain. In some embodiments, the anti-CD19 binding domain comprises an anti-CD19 binding sequence disclosed herein, e.g., a CDR, VH, VL, or scFv sequence disclosed in Tables 2, 19, 22, and 31.

In some embodiments, the present invention provides a cell comprising (a) a first antigen-binding domain which is an anti-BCMA binding domain, wherein the anti-BCMA binding domain comprises a heavy chain variable region (VH) comprising a heavy chain complementary determining region 1 (HC CDR1), a heavy chain complementary determining region 2 (HC CDR2), and a heavy chain complementary determining region 3 (HC CDR3), and a light chain variable region (VL) comprising a light chain complementary determining region 1 (LC CDR1), a light chain complementary determining region 2 (LC CDR2), and a light chain complementary determining region 3 (LC CDR3), wherein the HC CDR1, HC CDR2, HC CDR3, LC CDR1, LC CDR2, and LC CDR3 comprise the amino acid sequences of: (i) SEQ ID NOs: 86, 130, 88, 95, 131, and 132, respectively; (ii) SEQ ID NOs: 44, 45, 84, 54, 55, and 56, respectively; or (iii) SEQ ID NOs: 179, 180, 181, 147, 182, and 183, respectively; and (b) a second antigen-binding domain. In some embodiments, the first antigen-binding domain and the second antigen-binding domain are disposed in two chimeric antigen receptor (CARs). In some embodiments, the first antigen-binding domain and the second antigen-binding domain are disposed in one CAR.

In some embodiments, the HC CDR1, HC CDR2, HC CDR3, LC CDR1, LC CDR2, and LC CDR3 comprise the amino acid sequences of SEQ ID NOs: 86, 130, 88, 95, 131, and 132, respectively. In some embodiments, the HC CDR1, HC CDR2, HC CDR3, LC CDR1, LC CDR2, and LC CDR3 comprise the amino acid sequences of SEQ ID NOs: 86, 87, 88, 95, 96, and 97, respectively. In some embodiments, the HC CDR1, HC CDR2, HC CDR3, LC CDR1, LC CDR2, and LC CDR3 comprise the amino acid sequences of SEQ ID NOs: 86, 109, 88, 95, 114, and 115, respectively. In some embodiments, the HC CDR1, HC CDR2, HC CDR3, LC CDR1, LC CDR2, and LC CDR3 comprise the amino acid sequences of SEQ ID NOs: 86, 109, 88, 95, 114, and 97, respectively. In some embodiments, the VH comprises the amino acid sequence of SEQ ID NO: 93 or 112, or an amino acid sequence having at least about 85%, 90%, 95%, or 99% sequence identity thereto. In some embodiments, the VH is encoded by the nucleic acid sequence of SEQ ID NO: 260, 94 or 113, or a nucleic acid sequence having at least about 85%, 90%, 95%, or 99% sequence identity thereto. In some embodiments, the VL comprises the amino acid sequence of SEQ ID NO: 102, 118, or 124, or an amino acid sequence having at least about 85%, 90%, 95%, or 99% sequence identity thereto. In some embodiments, the VL is encoded by the nucleic acid sequence of SEQ ID NO: 261, 103, 119, or 125, or a nucleic acid sequence having at least about 85%, 90%, 95%, or 99% sequence identity thereto. In some embodiments, the VH and VL comprise the amino acid sequences of SEQ ID NOs: 93 and 102, respectively. In some embodiments, the VH and VL comprise the amino acid sequences of SEQ ID NOs: 112 and 118, respectively. In some embodiments, the VH and VL comprise the amino acid sequences of SEQ ID NOs: 112 and 124, respectively. In some embodiments, the first antigen-binding domain comprises a single-chain fragment variable (scFv) comprising the amino acid sequence of SEQ ID NO: 105, 120, or 126, or an amino acid sequence having at least about 85%, 90%, 95%, or 99% sequence identity thereto. In some embodiments, the first antigen-binding domain is encoded by the nucleic acid sequence of SEQ ID NO: 253, 106, 121, or 127, or a nucleic acid sequence having at least about 85%, 90%, 95%, or 99% sequence identity thereto. In some embodiments, the first antigen-binding domain is disposed in a first CAR. In some embodiments, the first CAR comprises the amino acid sequence of SEQ ID NO: 107, 226, 122, or 128, or an amino acid sequence having at least about 85%, 90%, 95%, or 99% sequence identity thereto. In some embodiments, the first CAR is encoded by the nucleic acid sequence of SEQ ID NO: 259, 258, 108, 123, or 129, or a nucleic acid sequence having at least about 85%, 90%, 95%, or 99% sequence identity thereto.

In some embodiments, the HC CDR1, HC CDR2, HC CDR3, LC CDR1, LC CDR2, and LC CDR3 comprise the amino acid sequences of SEQ ID NOs: 44, 45, 84, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 76, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 46, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 68, 54, 55, and 56, respectively. In some embodiments, the VH comprises the amino acid sequence of SEQ ID NO: 78, 52, or 70, or an amino acid sequence having at least about 85%, 90%, 95%, or 99% sequence identity thereto. In some embodiments, the VH is encoded by the nucleic acid sequence of SEQ ID NO: 79, 53, or 71, or a nucleic acid sequence having at least about 85%, 90%, 95%, or 99% sequence identity thereto. In some embodiments, the VL comprises the amino acid sequence of SEQ ID NO: 61, or an amino acid sequence having at least about 85%, 90%, 95%, or 99% sequence identity thereto. In some embodiments, the VL is encoded by the nucleic acid sequence of SEQ ID NO: 62, or a nucleic acid sequence having at least about 85%, 90%, 95%, or 99% sequence identity thereto. In some embodiments, the VH and VL comprise the amino acid sequences of SEQ ID NOs: 78 and 61, respectively. In some embodiments, the VH and VL comprise the amino acid sequences of SEQ ID NOs: 52 and 61, respectively. In some embodiments, the VH and VL comprise the amino acid sequences of SEQ ID NOs: 70 and 61, respectively. In some embodiments, the first antigen-binding domain comprises a single-chain fragment variable (scFv) comprising the amino acid sequence of SEQ ID NO: 80, 64, or 72, or an amino acid sequence having at least about 85%, 90%, 95%, or 99% sequence identity thereto. In some embodiments, the first antigen-binding domain is encoded by the nucleic acid sequence of SEQ ID NO: 81, 65, or 73, or a nucleic acid sequence having at least about 85%, 90%, 95%, or 99% sequence identity thereto. In some embodiments, the first antigen-binding domain is disposed in a first CAR. In some embodiments, the first CAR comprises the amino acid sequence of SEQ ID NO: 224, 82, 66, or 74, or an amino acid sequence having at least about 85%, 90%, 95%, or 99% sequence identity thereto. In some embodiments, the first CAR is encoded by the nucleic acid sequence of SEQ ID NO: 83, 67, or 75, or a nucleic acid sequence having at least about 85%, 90%, 95%, or 99% sequence identity thereto.

In some embodiments, the HC CDR1, HC CDR2, HC CDR3, LC CDR1, LC CDR2, and LC CDR3 comprise the amino acid sequences of SEQ ID NOs: 179, 180, 181, 147, 182, and 183, respectively. In some embodiments, the HC CDR1, HC CDR2, HC CDR3, LC CDR1, LC CDR2, and LC CDR3 comprise the amino acid sequences of SEQ ID NOs: 137, 138, 139, 147, 148, and 149, respectively. In some embodiments, the HC CDR1, HC CDR2, HC CDR3, LC CDR1, LC CDR2, and LC CDR3 comprise the amino acid sequences of SEQ ID NOs: 160, 161, 162, 147, 170, and 171, respectively. In some embodiments, the VH comprises the amino acid sequence of SEQ ID NO: 145 or 168, or an amino acid sequence having at least about 85%, 90%, 95%, or 99% sequence identity thereto. In some embodiments, the VH is encoded by the nucleic acid sequence of SEQ ID NO: 146 or 169, or a nucleic acid sequence having at least about 85%, 90%, 95%, or 99% sequence identity thereto. In some embodiments, the VL comprises the amino acid sequence of SEQ ID NO: 154 or 173, or an amino acid sequence having at least about 85%, 90%, 95%, or 99% sequence identity thereto. In some embodiments, the VL is encoded by the nucleic acid sequence of SEQ ID NO: 155 or 174, or a nucleic acid sequence having at least about 85%, 90%, 95%, or 99% sequence identity thereto. In some embodiments, the VH and VL comprise the amino acid sequences of SEQ ID NOs: 145 and 154, respectively. In some embodiments, the VH and VL comprise the amino acid sequences of SEQ ID NOs: 168 and 173, respectively. In some embodiments, the first antigen-binding domain comprises a single-chain fragment variable (scFv) comprising the amino acid sequence of SEQ ID NO: 156 or 175, or an amino acid sequence having at least about 85%, 90%, 95%, or 99% sequence identity thereto. In some embodiments, the first antigen-binding domain is encoded by the nucleic acid sequence of SEQ ID NO: 157 or 176, or a nucleic acid sequence having at least about 85%, 90%, 95%, or 99% sequence identity thereto. In some embodiments, the first antigen-binding domain is disposed in a first CAR. In some embodiments, the first CAR comprises the amino acid sequence of SEQ ID NO: 158 or 177, or an amino acid sequence having at least about 85%, 90%, 95%, or 99% sequence identity thereto. In some embodiments, the first CAR is encoded by the nucleic acid sequence of SEQ ID NO: 159 or 178, or a nucleic acid sequence having at least about 85%, 90%, 95%, or 99% sequence identity thereto.

In some embodiments, provided herein is a cell comprising: (a) a first antigen-binding domain which is an anti-BCMA binding domain, wherein the anti-BCMA binding domain comprises: (i) a VH comprising a HC CDR1, HC CDR2, and HC CDR3 of an anti-BCMA sequence listed in Table 20 or 26 and a VL comprising a LC CDR1, LC CDR2, and LC CDR3 of an anti-BCMA sequence listed in Table 20 or 26, wherein the VH and VL are connected by a linker comprising the amino acid sequence of SEQ ID NO: 243; (ii) a VH and VL comprising the amino acid sequences of SEQ ID NOs: 239 and 242, respectively, wherein the VH and VL are connected by a linker comprising the amino acid sequence of SEQ ID NO: 243; or (iii) an scFv comprising the amino acid sequence of SEQ ID NO: 200; and (b) a second antigen-binding domain. In some embodiments, the first antigen-binding domain and the second antigen-binding domain are disposed in two chimeric antigen receptor (CARs). In some embodiments, the first antigen-binding domain and the second antigen-binding domain are disposed in one CAR. In some embodiments, the second antigen-binding domain binds to an antigen chosen from: CD19, CD5, CD10, CD20, CD21, CD22, CD23, CD24, CD25, CD27, CD30, CD34, CD37, CD38, CD40, CD53, CD69, CD72, CD73, CD74, CD75, CD77, CD79a, CD79b, CD80, CD81, CD82, CD83, CD84, CD85, CD86, CD123, CD135, CD138, CD179, CD269, Flt3, ROR1, FcRn5, FcRn2, CS-1, CXCR4, 5, 7, IL-7/3R, IL7/4/3R, or IL4R, optionally wherein the B cell antigen is chosen from CD19, CD20, CD22, FcRn5, FcRn2, CS-1, CD138, CD123, CD33, CD34, CLL-1, folate receptor beta, or FLT3. In some embodiments, the second antigen-binding domain binds to CD19. In some embodiments, the second antigen-binding domain binds to an antigen chosen from: EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC.

In some embodiments, the second antigen-binding domain binds to CD19. In some embodiments, the second antigen-binding domain comprises a HC CDR1, HC CDR2, HC CDR3, LC CDR1, LC CDR2, and/or LC CDR3 of an anti-CD19 sequence listed in Table 19 or Table 22, for example, a HC CDR1, HC CDR2, HC CDR3, LC CDR1, LC CDR2, and LC CDR3 comprising the amino acid sequences of SEQ ID NOs: 295 and 245-249, respectively. In some embodiments, the second antigen-binding domain comprises a VH and/or VL of an anti-CD19 sequence listed in Table 19 or Table 22, for example, a VH and VL comprising the amino acid sequences of SEQ ID NOs: 250 and 251, respectively, or an amino acid sequence having at least about 85%, 90%, 95%, or 99% sequence identity thereto. In some embodiments, the second antigen-binding domain comprises a scFv of an anti-CD19 sequence listed in Table 19 or Table 22, for example, a scFv comprising the amino acid sequence of SEQ ID NO: 211, or an amino acid sequence having at least about 85%, 90%, 95%, or 99% sequence identity thereto. In some embodiments, the second antigen-binding domain is disposed in a second CAR, wherein the CAR comprises a CAR of an anti-CD19 sequence listed in Table 19 or Table 22, for example, a CAR comprising the amino acid sequence of SEQ ID NO: 225 or 229, or an amino acid sequence having at least about 85%, 90%, 95%, or 99% sequence identity thereto.

In some embodiments, the first antigen-binding domain comprises a HC CDR1, HC CDR2, HC CDR3, LC CDR1, LC CDR2, and LC CDR comprising the amino acid sequences of (a) SEQ ID NOs: 86, 87, 88, 95, 96, and 97, respectively; (b) SEQ ID NOs: 44, 45, 76, 54, 55, and 56, respectively; or (c) SEQ ID NOs: 44, 45, 46, 54, 55, and 56, respectively. In some embodiments, the second antigen-binding domain comprises a HC CDR1, HC CDR2, HC CDR3, LC CDR1, LC CDR2, and LC CDR3 comprising the amino acid sequences of SEQ ID NOs: 295 and 245-249, respectively. In some embodiments, the first antigen-binding domain comprises a VH and VL comprising the amino acid sequences of: (a) SEQ ID NOs: 93 and 102, respectively; (b) SEQ ID NOs: 78 and 61, respectively; or (c) SEQ ID NOs: 52 and 61, respectively. In some embodiments, the second antigen-binding domain comprises a VH and VL comprising the amino acid sequences of SEQ ID NOs: 250 and 251, respectively. In some embodiments, the first antigen-binding domain comprises a scFv comprising the amino acid sequence of SEQ ID NO: 105, 80, or 64. In some embodiments, the second antigen-binding domain comprises a scFv comprising the amino acid sequence of SEQ ID NO: 211. In some embodiments, the first antigen-binding domain is encoded by the nucleic acid sequence of SEQ ID NO: 253, 106, 81, or 65. In some embodiments, the second antigen-binding domain is encoded by the nucleic acid sequence of SEQ ID NO: 212.

In some embodiments, the first antigen-binding domain is disposed in a first CAR and the second antigen-binding domain is disposed in a second CAR. In some embodiments, the first CAR further comprises a first transmembrane domain and a first intracellular signaling domain. In some embodiments, the second CAR further comprises a second transmembrane domain and a second intracellular signaling domain.

In some embodiments, the first CAR is encoded by a first nucleic acid sequence and the second CAR is encoded by a second nucleic acid sequence, wherein the first and second nucleic acid sequences are disposed on separate nucleic acid molecules.

In some embodiments, the first CAR is encoded by a first nucleic acid sequence and the second CAR is encoded by a second nucleic acid sequence, wherein the first and second nucleic acid sequences are disposed on a single nucleic acid molecule. In some embodiments, the single nucleic acid molecule comprises the following configuration in a 5' to 3' orientation: a nucleic acid sequence encoding the first antigen-binding domain-a nucleic acid sequence encoding a first transmembrane domain-a nucleic acid sequence encoding a first intracellular signaling domain-a nucleic acid sequence encoding a linker-a nucleic acid sequence encoding the second antigen-binding domain-a nucleic acid sequence encoding a second transmembrane domain-a nucleic acid sequence encoding a second intracellular signaling domain. In some embodiments, the single nucleic acid molecule comprises the following configuration in a 5' to 3' orientation: a nucleic acid sequence encoding the second antigen-binding domain-a nucleic acid sequence encoding a second transmembrane domain-a nucleic acid sequence encoding a second intracellular signaling domain-a nucleic acid sequence encoding a linker-a nucleic acid sequence encoding the first antigen-binding domain-a nucleic acid sequence encoding a first transmembrane domain-a nucleic acid sequence encoding a first intracellular signaling domain.

In some embodiments, the linker comprises a self-cleavage site. In some embodiments, the linker comprises a P2A site, a T2A site, an E2A site, or an F2A site. In some embodiments, the linker comprises a P2A site. In some embodiments, the linker is encoded by the nucleic acid sequence of SEQ ID NO: 209, or a nucleic acid sequence having at least about 85%, 90%, 95%, or 99% sequence identity thereto. In some embodiments, the linker comprises the amino acid sequence of SEQ ID NO: 208, or an amino acid sequence having at least about 85%, 90%, 95%, or 99% sequence identity thereto. In some embodiments, the single nucleic acid molecule comprises the nucleic acid sequence of SEQ ID NO: 215, 217, 219, 221, or 223, or a nucleic acid sequence having at least about 85%, 90%, 95%, or 99% sequence identity thereto. In some embodiments, the single nucleic acid molecule encodes the amino acid sequence of SEQ ID NO: 214, 216, 218, 220, or 222, or an amino acid sequence having at least about 85%, 90%, 95%, or 99% sequence identity thereto.

In some embodiments, the first antigen-binding domain and the second antigen-binding domain are disposed in one CAR, wherein the CAR further comprises a transmembrane domain and an intracellular signaling domain. In some embodiments, the first antigen-binding domain comprises a first VH (VH1) and a first VL (VL1) and the second antigen-binding domain comprises a second VH (VH2) and a second VL (VL2). In some embodiments, the VH1, VL1, VH2, and VL2 are arranged in the following configuration from the N-terminus to the C-terminus: VH2-optionally linker 1 ("L1")-VL1 optionally linker 2 ("L2")-VH1-optionally linker 3 ("L3")-VL2. In some embodiments, the VH1, VL1, VH2, and VL2 are arranged in the following configuration from the N-terminus to the C-terminus: VH1-optionally L1-VH2-optionally L2-VL2-optionally L3-VL1. In some embodiments, the VH1, VL1, VH2, and VL2 are arranged in the following configuration from the N-terminus to the C-terminus: VL2-optionally L1-VL1-optionally L2-VH1-optionally L3-VH2. In some embodiments, the VH1, VL1, VH2, and VL2 are arranged in the following configuration from the N-terminus to the C-terminus: VL2- optionally L1-VH1-optionally L2-VL1-optionally L3-VH2. In some embodiments, the VH1, VL1, VH2, and VL2 are arranged in the following configuration from the N-terminus to the C-terminus: VH2-optionally L1-VH1-optionally L2-VL1-optionally L3-VL2. In some embodiments, the VH1, VL1, VH2, and VL2 are arranged in the following configuration from the N-terminus to the C-terminus: VL1-optionally L1-VH2-optionally L2-VL2-optionally L3-VH1. In some embodiments, the VH1, VL1, VH2, and VL2 are arranged in the following configuration from the N-terminus to the C-terminus: VL1-optionally L1-VL2-optionally L2-VH2-optionally L3-VH1. In some embodiments, the VH1, VL1, VH2, and VL2 are arranged in the following configuration from the N-terminus to the C-terminus: VH1-optionally L1-VL2-optionally L2-VH2-optionally L3-VL1. In some embodiments, the VH1 and VL1 comprise the amino acid sequences of SEQ ID NOs: 93 and 102, respectively (or an amino acid sequence having at least about 85%, 90%, 95%, or 99% sequence identity thereto). In some embodiments, the VH1 and VL1 comprise the amino acid sequences of SEQ ID NOs: 333 and 334, respectively (or an amino acid sequence having at least about 85%, 90%, 95%, or 99% sequence identity thereto). In some embodiments, the VH1 and VL1 comprise the amino acid sequences of SEQ ID NOs: 78 and 61, respectively (or an amino acid sequence having at least about 85%, 90%, 95%, or 99% sequence identity thereto). In some embodiments, the VH1 and VL1 comprise the amino acid sequences of SEQ ID NOs: 335 and 336, respectively (or an amino acid sequence having at least about 85%, 90%, 95%, or 99% sequence identity thereto). In some embodiments, the VH2 and VL2 comprise the amino acid sequences of SEQ ID NOs: 250 and 251, respectively (or an amino acid sequence having at least about 85%, 90%, 95%, or 99% sequence identity thereto). In some embodiments, the VH2 and VL2 comprise the amino acid sequences of SEQ ID NOs: 331 and 332, respectively (or an amino acid sequence having at least about 85%, 90%, 95%, or 99% sequence identity thereto). In some embodiments, L1 or L3 comprises the amino acid sequence of SEQ ID NO: 5 (or an amino acid sequence having at least about 85%, 90%, 95%, or 99% sequence identity thereto). In some embodiments, L2 comprises the amino acid sequence of SEQ ID NO: 63 (or an amino acid sequence having at least about 85%, 90%, 95%, or 99% sequence identity thereto). In some embodiments, the CAR comprises an amino acid sequence selected from the group consisting of SEQ ID NOs: 321-330, or an amino acid sequence having at least 80, 85, 90, 95, or 99% identity thereto. In some embodiments, the CAR comprises an amino acid sequence selected from the group consisting of SEQ ID NOs: 339-348, or an amino acid sequence having at least 80, 85, 90, 95, or 99% identity thereto.

In some embodiments, the CAR is encoded by a nucleic acid molecule comprising the following configuration in a 5' to 3' orientation: a nucleic acid sequence encoding the first antigen-binding domain-optionally a nucleic acid sequence encoding a linker-a nucleic acid sequence encoding the second antigen-binding domain-a nucleic acid sequence encoding a transmembrane domain-a nucleic acid sequence encoding an intracellular signaling domain. In some embodiments, the CAR is encoded by a nucleic acid molecule comprising the following configuration in a 5' to 3' orientation: a nucleic acid sequence encoding the second antigen-binding domain-optionally a nucleic acid sequence encoding a linker-a nucleic acid sequence encoding the first antigen-binding domain-a nucleic acid sequence encoding a transmembrane domain-a nucleic acid sequence encoding an intracellular signaling domain.

In some embodiments, the CAR comprises the following configuration in an N- to C-orientation: the first antigen-binding domain-optionally a linker-the second antigen-binding domain-a transmembrane domain-an intracellular signaling domain. In some embodiments, the CAR comprises the following configuration in an N- to C-orientation: the second antigen-binding domain-optionally a linker-the first antigen-binding domain-a transmembrane domain-an intracellular signaling domain.

In some embodiments, the first antigen-binding domain or second antigen-binding domain comprises a VH and a VL. In some embodiments, the VH and VL are connected by a linker. In some embodiments, the linker comprises the amino acid sequence of SEQ ID NO: 5, 63, 104, or 243, or an amino acid sequence having at least about 85%, 90%, 95%, or 99% sequence identity thereto.

In some embodiments, the transmembrane domain, first transmembrane domain, or second transmembrane domain comprises a transmembrane domain of a protein chosen from the alpha, beta or zeta chain of T-cell receptor, CD28, CD3 epsilon, CD45, CD4, CD5, CD8, CD9, CD16, CD22, CD33, CD37, CD64, CD80, CD86, CD134, CD137 or CD154. In some embodiments, the transmembrane domain, first transmembrane domain, or second transmembrane domain comprises the amino acid sequence of SEQ ID NO: 6, or an amino acid sequence having at least about 85%, 90%, 95%, or 99% sequence identity thereto. In some embodiments, the transmembrane domain, first transmembrane domain, or second transmembrane domain is encoded by the nucleic acid sequence of SEQ ID NO: 17, or a nucleic acid sequence having at least about 85%, 90%, 95%, or 99% sequence identity thereto.

In some embodiments, the first antigen-binding domain or second antigen-binding domain is connected to the transmembrane domain, first transmembrane domain, or second transmembrane domain by a hinge region (e.g., a first or second hinge region). In some embodiments, the hinge region comprises the amino acid sequence of SEQ ID NO: 2, 3, or 4, or an amino acid sequence having at least about 85%, 90%, 95%, or 99% sequence identity thereto. In some embodiments, the hinge region is encoded by the nucleic acid sequence of SEQ ID NO: 13, 14, or 15, or a nucleic acid sequence having at least about 85%, 90%, 95%, or 99% sequence identity thereto. In some embodiments, the hinge region and the transmembrane domain comprise the amino acid sequence of SEQ ID NO: 202, or an amino acid sequence having at least about 85%, 90%, 95%, or 99% sequence identity thereto. In some embodiments, the hinge region and the transmembrane domain are encoded by the nucleic acid sequence of SEQ ID NO: 203 or 213, or a nucleic acid sequence having at least about 85%, 90%, 95%, or 99% sequence identity thereto.

In some embodiments, the intracellular signaling domain, first intracellular signaling domain, or second intracellular signaling domain comprises a primary signaling domain (e.g., a first or second primary signaling domain). In some embodiments, the primary signaling domain comprises a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d. In some embodiments, the primary signaling domain comprises the amino acid sequence of SEQ ID NO: 9 or 10, or an amino acid sequence having at least about 85%, 90%, 95%, or 99% sequence identity thereto. In some embodiments, the primary signaling domain is encoded by the nucleic acid sequence of SEQ ID NO: 20, 21, or 205, or a nucleic acid sequence having at least about 85%, 90%, 95%, or 99% sequence identity thereto. In some embodiments, the intracellular signaling domain, first intracellular signaling domain, or second intracellular signaling domain comprises a costimulatory signaling domain (e.g., a first or second costimulatory signaling domain). In some embodiments, the costimulatory signaling domain comprises a functional signaling domain derived from a MHC class I molecule, a TNF receptor protein, an Immunoglobulin-like protein, a cytokine receptor, an integrin, a signalling lymphocytic activation molecule (SLAM protein), an activating NK cell receptor, BTLA, a Toll ligand receptor, OX40, CD2, CD7, CD27, CD28, CD30, CD40, CDS, ICAM-1, 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, or a ligand that specifically binds with CD83. In some embodiments, the costimulatory signaling domain comprises the amino acid sequence of SEQ ID NO: 7, or an amino acid sequence having at least about 85%, 90%, 95%, or 99% sequence identity thereto. In some embodiments, the costimulatory signaling domain is encoded by the nucleic acid sequence of SEQ ID NO: 18 or 204, or a nucleic acid sequence having at least about 85%, 90%, 95%, or 99% sequence identity thereto. In some embodiments, the intracellular signaling domain, first intracellular signaling domain, or second intracellular signaling domain comprises a functional signaling domain derived from 4-1BB and a functional signaling domain derived from CD3 zeta. In some embodiments, the intracellular signaling domain, first intracellular signaling domain, or second intracellular signaling domain comprises the amino acid sequence of SEQ ID NO: 7 (or an amino acid sequence having at least about 85%, 90%, 95%, or 99% sequence identity thereto) and the amino acid sequence of SEQ ID NO: 9 or 10 (or an amino acid sequence having at least about 85%, 90%, 95%, or 99% sequence identity thereto). In some embodiments, the intracellular signaling domain, first intracellular signaling domain, or second intracellular signaling domain comprises the amino acid sequence of SEQ ID NO: 7 and the amino acid sequence of SEQ ID NO: 9 or 10.

In some embodiments, the CAR, first CAR, or second CAR further comprises a leader sequence (e.g., a first or second leader sequence). In some embodiments, the leader sequence comprises the amino acid sequence of SEQ ID NO: 1, or an amino acid sequence having at least about 85%, 90%, 95%, or 99% sequence identity thereto. In some embodiments, the leader sequence is encoded by the nucleic acid sequence of SEQ ID NO: 199 or 210, or a nucleic acid sequence having at least about 85%, 90%, 95%, or 99% sequence identity thereto.

In some embodiments, the first leader sequence and the second leader sequence are encoded by different nucleic acid sequences (e.g., differ by at least 5%, 10%, 20%, 30%, 40%, 50%, 60%, 70%, 80%, 85%, 90%, 95%, or 100%). In some embodiments, the first hinge region and the second hinge region are encoded by different nucleic acid sequences (e.g., differ by at least 5%, 10%, 20%, 30%, 40%, 50%, 60%, 70%, 80%, 85%, 90%, 95%, or 100%). In some embodiments, the first transmembrane domain and the second transmembrane domain are encoded by different nucleic acid sequences (e.g., differ by at least 5%, 10%, 20%, 30%, 40%, 50%, 60%, 70%, 80%, 85%, 90%, 95%, or 100%). In some embodiments, the first intracellular signaling domain and the second intracellular signaling domain are encoded by different nucleic acid sequences (e.g., differ by at least 5%, 10%, 20%, 30%, 40%, 50%, 60%, 70%, 80%, 85%, 90%, 95%, or 100%). In some embodiments, the first primary signaling domain and the second primary signaling domain are encoded by different nucleic acid sequences (e.g., differ by at least 5%, 10%, 20%, 30%, 40%, 50%, 60%, 70%, 80%, 85%, 90%, 95%, or 100%). In some embodiments, the first costimulatory signaling domain and the second costimulatory signaling domain are encoded by different nucleic acid sequences (e.g., differ by at least 5%, 10%, 20%, 30%, 40%, 50%, 60%, 70%, 80%, 85%, 90%, 95%, or 100%). In some embodiments, the first leader sequence and the second leader sequence comprise the same amino acid sequence (e.g., the first leader sequence and the second leader sequence comprise the amino acid sequence of SEQ ID NO: 1, or an amino acid sequence having at least about 85%, 90%, 95%, or 99% sequence identity thereto). In some embodiments, the first leader sequence and the second leader sequence comprise different amino acid sequences. In some embodiments, the first hinge region and the second hinge region comprise the same amino acid sequence (e.g., the first hinge region and the second hinge region comprise the amino acid sequence of SEQ ID NO: 2, or an amino acid sequence having at least about 85%, 90%, 95%, or 99% sequence identity thereto). In some embodiments, the first hinge region and the second hinge region comprise different amino acid sequences. In some embodiments, the first transmembrane domain and the second transmembrane domain comprise the same amino acid sequence (e.g., the first transmembrane domain and the second transmembrane domain comprise the amino acid sequence of SEQ ID NO: 6, or an amino acid sequence having at least about 85%, 90%, 95%, or 99% sequence identity thereto). In some embodiments, the first transmembrane domain and the second transmembrane domain comprise different amino acid sequences. In some embodiments, the first intracellular signaling domain and the second intracellular signaling domain comprise the same amino acid sequence. In some embodiments, the first intracellular signaling domain and the second intracellular signaling domain comprise different amino acid sequences. In some embodiments, the first primary signaling domain and the second primary signaling domain comprise the same amino acid sequence (e.g., the first primary signaling domain and the second primary signaling domain comprise the amino acid sequence of SEQ ID NO: 10, or an amino acid sequence having at least about 85%, 90%, 95%, or 99% sequence identity thereto). In some embodiments, the first primary signaling domain and the second primary signaling domain comprise different amino acid sequences. In some embodiments, the first costimulatory signaling domain and the second costimulatory signaling domain comprise the same amino acid sequence (e.g., the first costimulatory signaling domain and the second costimulatory signaling domain comprise the amino acid sequence of SEQ ID NO: 7, or an amino acid sequence having at least about 85%, 90%, 95%, or 99% sequence identity thereto). In some embodiments, the first costimulatory signaling domain and the second costimulatory signaling domain comprise different amino acid sequences (e.g., the first and second costimulatory signaling domains comprise a 4-1BB costimulatory domain sequence and a CD28 costimulatory domain sequence, respectively; or comprise a CD28 costimulatory domain sequence and a 4-1BB costimulatory domain sequence, respectively). In some embodiments, the first leader sequence and the second leader sequence are encoded by nucleic acid sequences comprising SEQ ID NOs: 199 and 210, respectively (or a nucleic acid sequence having at least about 85%, 90%, 95%, or 99% sequence identity thereto). In some embodiments, the first leader sequence and the second leader sequence are encoded by nucleic acid sequences comprising SEQ ID NOs: 210 and 199, respectively (or a nucleic acid sequence having at least about 85%, 90%, 95%, or 99% sequence identity thereto). In some embodiments, the first hinge region and the second hinge region are encoded by nucleic acid sequences comprising SEQ ID NOs: 337 and 13, respectively (or a nucleic acid sequence having at least about 85%, 90%, 95%, or 99% sequence identity thereto). In some embodiments, the first hinge region and the second hinge region are encoded by nucleic acid sequences comprising SEQ ID NOs: 13 and 337, respectively (or a nucleic acid sequence having at least about 85%, 90%, 95%, or 99% sequence identity thereto). In some embodiments, the first transmembrane domain and the second transmembrane domain are encoded by nucleic acid sequences comprising SEQ ID NOs: 338 and 17, respectively (or a nucleic acid sequence having at least about 85%, 90%, 95%, or 99% sequence identity thereto). In some embodiments, the first transmembrane domain and the second transmembrane domain are encoded by nucleic acid sequences comprising SEQ ID NOs: 17 and 338, respectively (or a nucleic acid sequence having at least about 85%, 90%, 95%, or 99% sequence identity thereto). In some embodiments, the first costimulatory signaling domain and the second costimulatory signaling domain are encoded by nucleic acid sequences comprising SEQ ID NOs: 204 and 18, respectively (or a nucleic acid sequence having at least about 85%, 90%, 95%, or 99% sequence identity thereto). In some embodiments, the first costimulatory signaling domain and the second costimulatory signaling domain are encoded by nucleic acid sequences SEQ ID NOs: 18 and 204, respectively (or a nucleic acid sequence having at least about 85%, 90%, 95%, or 99% sequence identity thereto). In some embodiments, the first primary signaling domain and the second primary signaling domain are encoded by nucleic acid sequences comprising SEQ ID NOs: 205 and 21, respectively (or a nucleic acid sequence having at least about 85%, 90%, 95%, or 99% sequence identity thereto). In some embodiments, the first primary signaling domain and the second primary signaling domain are encoded by nucleic acid sequences comprising SEQ ID NOs: 21 and 205, respectively (or a nucleic acid sequence having at least about 85%, 90%, 95%, or 99% sequence identity thereto).

In some embodiments, the CAR, first CAR, or second CAR is encoded by a nucleic acid molecule comprising a woodchuck hepatitis post-transcriptional regulatory element (WPRE).

In some embodiments, provided herein is a nucleic acid molecule comprising: (a) a first nucleic acid sequence encoding a first antigen-binding domain which is an anti-BCMA binding domain, wherein the anti-BCMA binding domain comprises a heavy chain variable region (VH) comprising a heavy chain complementary determining region 1 (HC CDR1), a heavy chain complementary determining region 2 (HC CDR2), and a heavy chain complementary determining region 3 (HC CDR3), and a light chain variable region (VL) comprising a light chain complementary determining region 1 (LC CDR1), a light chain complementary determining region 2 (LC CDR2), and a light chain complementary determining region 3 (LC CDR3), wherein the HC CDR1, HC CDR2, HC CDR3, LC CDR1, LC CDR2, and LC CDR3 comprise the amino acid sequences of: (i) SEQ ID NOs: 86, 130, 88, 95, 131, and 132, respectively; (ii) SEQ ID NOs: 44, 45, 84, 54, 55, and 56, respectively; or (iii) SEQ ID NOs: 179, 180, 181, 147, 182, and 183, respectively; and (b) a second nucleic acid sequence encoding a second antigen-binding domain.

In some embodiments, the isolated nucleic acid molecule comprises a first nucleic acid molecule and a second nucleic acid molecule, which are separate nucleic acid molecules, and wherein the first nucleic acid sequence is disposed on the first nucleic acid molecule and the second nucleic acid sequence is disposed on the second nucleic acid molecule.

In some embodiments, provided herein is a nucleic acid molecule comprising: (a) a first nucleic acid sequence encoding a first antigen-binding domain which is an anti-BCMA binding domain, wherein the anti-BCMA binding domain comprises: (i) a VH comprising a HC CDR1, HC CDR2, and HC CDR3 of an anti-BCMA sequence listed in Table 20 or 26 and a VL comprising a LC CDR1, LC CDR2, and LC CDR3 of an anti-BCMA sequence listed in Table 20 or 26, wherein the VH and VL are connected by a linker comprising the amino acid sequence of SEQ ID NO: 243; (ii) a VH and VL comprising the amino acid sequences of SEQ ID NOs: 239 and 242, respectively, wherein the VH and VL are connected by a linker comprising the amino acid sequence of SEQ ID NO: 243; or (iii) an scFv comprising the amino acid sequence of SEQ ID NO: 200; and (b) a second nucleic acid sequence encoding a second antigen-binding domain.

In some embodiments, provided herein is a nucleic acid molecule comprising a first nucleic acid sequence encoding a first CAR and a second nucleic acid sequence encoding a second CAR, wherein the first CAR comprises a first antigen-binding domain which is an anti-BCMA binding domain, a first transmembrane domain, and a first intracellular signaling domain, and wherein the second CAR comprises a second antigen-binding domain which is an anti-CD19 binding domain, a second transmembrane domain, and a second intracellular signaling domain, wherein (i) the first antigen-binding domain comprises a HC CDR1, HC CDR2, HC CDR3, LC CDR1, LC CDR2, and LC CDR comprising the amino acid sequences of SEQ ID NOs: 86, 87, 88, 95, 96, and 97, respectively, and the second antigen-binding domain comprises a HC CDR1, HC CDR2, HC CDR3, LC CDR1, LC CDR2, and LC CDR comprising the amino acid sequences of SEQ ID NOs: 295 and 245-249, respectively; (ii) the first antigen-binding domain comprises a VH and VL comprising the amino acid sequences of SEQ ID NOs: 93 and 102, respectively, and the second antigen-binding domain comprises a VH and VL comprising the amino acid sequences of SEQ ID NOs: 250 and 251, respectively; (iii) the first antigen-binding domain comprises an scFv comprising the amino acid sequence of SEQ ID NO: 105, and the second antigen-binding domain comprises an scFv comprising the amino acid sequence of SEQ ID NO: 211; (iv) the first CAR comprises the amino acid sequence of SEQ ID NO: 107 or 226 and the second CAR comprises the amino acid sequence of SEQ ID NO: 225 or 229; or (v) the isolated nucleic acid molecule comprises the nucleic acid sequence of SEQ ID NO: 271.

In some embodiments, provided herein is a nucleic acid molecule comprising a first nucleic acid sequence encoding a first CAR and a second nucleic acid sequence encoding a second CAR, wherein the first CAR comprises a first antigen-binding domain which is an anti-BCMA binding domain, a first transmembrane domain, and a first intracellular signaling domain, and wherein the second CAR comprises a second antigen-binding domain which is an anti-CD19 binding domain, a second transmembrane domain, and a second intracellular signaling domain, wherein: (i) the first antigen-binding domain comprises a HC CDR1, HC CDR2, HC CDR3, LC CDR1, LC CDR2, and LC CDR comprising the amino acid sequences of SEQ ID NOs: 44, 45, 76, 54, 55, and 56, respectively, the second antigen-binding domain comprises a HC CDR1, HC CDR2, HC CDR3, LC CDR1, LC CDR2, and LC CDR3 comprising the amino acid sequences of SEQ ID NOs: 295 and 245-249, respectively; (ii) the first antigen-binding domain comprises a VH and VL comprising the amino acid sequences of SEQ ID NOs: 78 and 61, respectively, and the second antigen-binding domain comprises a VH and VL comprising the amino acid sequences of SEQ ID NOs: 250 and 251, respectively; (iii) the first antigen-binding domain comprises an scFv comprising the amino acid sequence of SEQ ID NO: 80, and the second antigen-binding domain comprises an scFv comprising the amino acid sequence of SEQ ID NO: 211; (iv) the first CAR comprises the amino acid sequence of SEQ ID NO: 82 or 224 and the second CAR comprises the amino acid sequence of SEQ ID NO: 225 or 229; or (v) the isolated nucleic acid molecule comprises the nucleic acid sequence of SEQ ID NO: 215.

In some embodiments, provided herein is a polypeptide molecule encoded by a nucleic acid molecule disclosed herein.

In some embodiments, provided herein is a CAR, wherein the CAR comprises: (a) a first antigen-binding domain which is an anti-BCMA binding domain, wherein the anti-BCMA binding domain comprises a heavy chain variable region (VH) comprising a heavy chain complementary determining region 1 (HC CDR1), a heavy chain complementary determining region 2 (HC CDR2), and a heavy chain complementary determining region 3 (HC CDR3), and a light chain variable region (VL) comprising a light chain complementary determining region 1 (LC CDR1), a light chain complementary determining region 2 (LC CDR2), and a light chain complementary determining region 3 (LC CDR3), wherein the HC CDR1, HC CDR2, HC CDR3, LC CDR1, LC CDR2, and LC CDR3 comprise the amino acid sequences of: (i) SEQ ID NOs: 86, 130, 88, 95, 131, and 132, respectively; (ii) SEQ ID NOs: 44, 45, 84, 54, 55, and 56, respectively; or (iii) SEQ ID NOs: 179, 180, 181, 147, 182, and 183, respectively; and (b) a second antigen-binding domain.

In some embodiments, provided herein is a CAR, wherein the CAR comprises: (a) a first antigen-binding domain which is an anti-BCMA binding domain, wherein the anti-BCMA binding domain comprises: (i) a VH comprising a HC CDR1, HC CDR2, and HC CDR3 of an anti-BCMA sequence listed in Table 20 or 26 and a VL comprising a LC CDR1, LC CDR2, and LC CDR3 of an anti-BCMA sequence listed in Table 20 or 26, wherein the VH and VL are connected by a linker comprising the amino acid sequence of SEQ ID NO: 243; (ii) a VH and VL comprising the amino acid sequences of SEQ ID NOs: 239 and 242, respectively, wherein the VH and VL are connected by a linker comprising the amino acid sequence of SEQ ID NO: 243; or (iii) an scFv comprising the amino acid sequence of SEQ ID NO: 200; and (b) a second antigen-binding domain.

In some embodiments, provided herein is a vector comprising a nucleic acid molecule disclosed herein or a nucleic acid molecule encoding a CAR disclosed herein. In some embodiments, the vector is chosen from a DNA vector, a RNA vector, a plasmid, a lentivirus vector, an adenoviral vector, or a retrovirus vector. In some embodiments, the vector comprises an EF-1 promoter comprising the nucleic acid sequence of SEQ ID NO: 11.

In some embodiments, provided herein is a cell comprising a nucleic acid molecule disclosed herein, a nucleic acid molecule encoding a CAR disclosed herein, a polypeptide disclosed herein, a CAR disclosed herein, or a vector disclosed herein. In some embodiments, the cell is a T cell or an NK cell.

In some embodiments, disclosed herein is a method of making a cell comprising transducing a cell with a vector disclosed herein, optionally wherein the cell is a T cell or NK cell. In some embodiments, disclosed herein is a method of making an RNA-engineered cell comprising introducing an in vitro transcribed RNA or synthetic RNA into a cell, wherein the RNA comprises a nucleic acid molecule disclosed herein, a nucleic acid molecule encoding a CAR disclosed herein. In some embodiments, the cell is a T cell or NK cell.

In some embodiments, disclosed herein is a method of making a population of cells (for example, T cells) that express a chimeric antigen receptor (CAR), the method comprising: (i) contacting (for example, binding) a population of cells (for example, T cells, for example, T cells isolated from a frozen or fresh leukapheresis product) with an agent that stimulates a CD3/TCR complex and/or an agent that stimulates a costimulatory molecule on the surface of the cells; (ii) contacting the population of cells (for example, T cells) with a nucleic acid molecule disclosed herein, or a nucleic acid molecule encoding a CAR disclosed herein, thereby providing a population of cells (for example, T cells) comprising the nucleic acid molecule, and (iii) harvesting the population of cells (for example, T cells) for storage (for example, reformulating the population of cells in cryopreservation media) or administration, wherein:

(a) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 (for example, 26) hours after the beginning of step (i), for example, no later than 22, 23, 24, 25, 26, 27, 28, 29, or 30 hours after the beginning of step (i), for example, no later than 24 hours after the beginning of step (i), (b) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 hours after the beginning of step (ii), for example, no later than 22, 23, 24, 25, 26, 27, 28, 29, or 30 hours after the beginning of step (ii), or (c) the population of cells from step (iii) are not expanded, or expanded by no more than 5, 10, 15, 20, 25, 30, 35, or 40%, for example, no more than 10%, for example, as assessed by the number of living cells, compared to the population of cells at the beginning of step (i), optionally wherein the nucleic acid molecule in step (ii) is on a viral vector, optionally wherein the nucleic acid molecule in step (ii) is an RNA molecule on a viral vector, optionally wherein step (ii) comprises transducing the population of cells (for example, T cells) with a viral vector comprising a nucleic acid molecule encoding the CAR.

In some embodiments, disclosed herein is a method of making a population of cells (for example, T cells) that express a chimeric antigen receptor (CAR), the method comprising: (1) contacting a population of cells (for example, T cells, for example, T cells isolated from a frozen leukapheresis product) with a cytokine chosen from IL-2, IL-7, IL-15 (for example, hetIL-15 (IL15/sIL-15Ra)), IL-21, IL-6 (for example, IL-6/sIL-6Ra), or a combination thereof, (2) contacting the population of cells (for example, T cells) with a nucleic acid molecule disclosed herein, or a nucleic acid molecule encoding a CAR disclosed herein, thereby providing a population of cells (for example, T cells) comprising the nucleic acid molecule, and (3) harvesting the population of cells (for example, T cells) for storage (for example, reformulating the population of cells in cryopreservation media) or administration, wherein:

(a) step (2) is performed together with step (1) or no later than 5 hours after the beginning of step (1), for example, no later than 1, 2, 3, 4, or 5 hours after the beginning of step (1), and
  step (3) is performed no later than 26 hours after the beginning of step (1), for example, no later than 22, 23, or 24 hours after the beginning of step (1), for example, no later than 24 hours after the beginning of step (1), or
(b) the population of cells from step (3) are not expanded, or expanded by no more than 5, 10, 15, 20, 25, 30, 35, or 40%, for example, no more than 10%, for example, as assessed by the number of living cells, compared to the population of cells at the beginning of step (1), optionally wherein the nucleic acid molecule in step (2) is on a viral vector, optionally wherein the nucleic acid molecule in step (ii) is an RNA molecule on a viral vector, optionally wherein step (ii) comprises transducing the population of cells (for example, T cells) with a viral vector comprising a nucleic acid molecule encoding the CAR.

In some embodiments, disclosed herein is a population of cells engineered to express a CAR ("a population of CAR-expressing cells"), said population comprising: (a) about the same percentage of naïve cells, for example, naïve T cells, for example, CD45RO− CCR7+ T cells, as compared to the percentage of naïve cells, for example, naïve T cells, for example, CD45RO− CCR7+ cells, in the same population of cells prior to being engineered to express the CAR; (b) a change within about 5% to about 10% of naïve cells, for example, naïve T cells, for example, CD45RO− CCR7+ T cells, for example, as compared to the percentage of naïve cells, for example, naïve T cells, for example, CD45RO− CCR7+ cells, in the same population of cells prior to being engineered to express the CAR; (c) an increased percentage of naïve cells, for example, naïve T cells, for example, CD45RO− CCR7+ T cells, for example, increased by at least 1.2, 1.4, 1.6, 1.8, 2.0, 2.2, 2.4, 2.6, 2.8, or 3-fold, as compared to the percentage of naïve cells, for example, naïve T cells, for example, CD45RO− CCR7+ cells, in the same population of cells prior to being engineered to express the CAR; (d) about the same percentage of central memory cells, for example, central memory T cells, for example, CCR7+CD45RO+ T cells, as compared to the percentage of central memory cells, for example, central memory T cells, for example, CCR7+CD45RO+ T cells, in the same population of cells prior to being engineered to express the CAR; (e) a change within about 5% to about 10% of central memory cells, for example, central memory T cells, for example, CCR7+CD45RO+ T cells, as compared to the percentage of central memory cells, for example, central memory T cells, for example, CCR7+CD45RO+ T cells, in the same population of cells prior to being engineered to express the CAR; (f) a decreased percentage of central memory cells, for example, central memory T cells, for example, CCR7+CD45RO+ T cells, for example, decreased by at least 20, 25, 30, 35, 40, 45, or 50%, as compared to the percentage of central memory cells, for example, central memory T cells, for example, CCR7+CD45RO+ T cells, in the same population of cells prior to being engineered to express the CAR; (g) about the same percentage of stem memory T cells, for example, CD45RA+CD95+IL-2 receptor β+CCR7+CD62L+ T cells, as compared to the percentage of stem memory T cells, for example, CD45RA+CD95+ IL-2 receptor β+CCR7+CD62L+ T cells, in the same population of cells prior to being engineered to express the CAR; (h) a change within about 5% to about 10% of stem memory T cells, for example, CD45RA+CD95+IL-2 receptor β+CCR7+CD62L+ T cells, as compared to the percentage of stem memory T cells, for example, CD45RA+CD95+ IL-2 receptor β+CCR7+CD62L+ T cells, in the same population of cells prior to being engineered to express the CAR; or (i) an increased percentage of stem memory T cells, for example, CD45RA+CD95+IL-2 receptor β+CCR7+ CD62L+ T cells, as compared to the percentage of stem memory T cells, for example, CD45RA+CD95+IL-2 receptor β+CCR7+CD62L+ T cells, in the same population of cells prior to being engineered to express the CAR. In some embodiments, the population comprises a cell disclosed herein. In some embodiments, the population comprises a cell comprising a dual CAR or diabody CAR disclosed herein. In some embodiments, the population comprises a cell comprising (a) a first antigen-binding domain which is an anti-BCMA binding domain, wherein the anti-BCMA binding domain comprises a heavy chain variable region (VH) comprising a heavy chain complementary determining region 1 (HC CDR1), a heavy chain complementary determining region 2 (HC CDR2), and a heavy chain complementary determining region 3 (HC CDR3), and a light chain variable region (VL) comprising a light chain complementary determining region 1 (LC CDR1), a light chain complementary determining region 2 (LC CDR2), and a light chain complementary determining region 3 (LC CDR3), wherein the HC CDR1, HC CDR2, HC CDR3, LC CDR1, LC CDR2, and LC CDR3 comprise the amino acid sequences of: (i) SEQ ID NOs: 86, 130, 88, 95, 131, and 132, respectively; (ii) SEQ ID NOs: 44, 45, 84, 54, 55, and 56, respectively; or (iii) SEQ ID NOs: 179, 180, 181, 147, 182, and 183, respectively; and (b) a second antigen-binding domain.

In some embodiments, disclosed herein is a pharmaceutical composition comprising a cell disclosed herein or a population of cells disclosed herein, and a pharmaceutically acceptable carrier.

In some embodiments, the population of cells is made by a method disclosed herein. In some embodiments, the population comprises:

(a) a first population of cells comprising an anti-BCMA CAR but not an anti-CD19 CAR;
(b) a second population of cells comprising an anti-CD19 CAR but not an anti-BCMA CAR; and (c) a third population of cells comprising both an anti-BCMA CAR and an anti-CD19 CAR.

In some embodiments:

(i) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined;

(ii) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined; and/or (iii) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the population.

In some embodiments, the population further comprises a fourth population of cells that do not comprise a CAR.

In some embodiments:

(i) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined;

(ii) the total number of viable cells in the second population is less than or equal to: about 45% to about 50% (e.g., about 47%); about 50 to about 55% (e.g., about 53%); about 60% to about 65% (e.g., about 63%); or about 80 to about 85% (e.g., about 82%) of the total number of viable cells in the first and third populations combined.

In some embodiments, disclosed herein is a method of providing an anti-tumor immunity in a subject comprising administering to the subject an effective amount of a cell disclosed herein, a population of cells disclosed herein, or a pharmaceutical composition disclosed herein. In some embodiments, disclosed herein is a method of treating a subject having a disease associated with expression of BCMA comprising administering to the subject an effective amount of a cell disclosed herein, a population of cells disclosed herein, or a pharmaceutical composition disclosed herein. In some embodiments, the disease associated with BCMA expression is: (i) a cancer or malignancy, or a precancerous condition chosen from one or more of a myelodysplasia, a myelodysplastic syndrome or a preleukemia, or (ii) a non-cancer related indication associated with expression of BCMA. In some embodiments, the disease is a hematologic cancer or a solid cancer. In some embodiments, the disease is chosen from: acute leukemia, B-cell acute lymphoid leukemia ("BALL"), T-cell acute lymphoid leukemia ("TALL"), acute lymphoid leukemia (ALL), chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell- or large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, prostate cancer (e.g., castrate-resistant or therapy-resistant prostate cancer, or metastatic prostate cancer), pancreatic cancer, lung cancer, a plasma cell proliferative disorder (e.g., asymptomatic myeloma (smoldering multiple myeloma or indolent myeloma), monoclonal gammapathy of undetermined significance (MGUS), Waldenstrom's macroglobulinemia, plasmacytoma (e.g., plasma cell dyscrasia, solitary myeloma, solitary plasmacytoma, extramedullary plasmacytoma, and multiple plasmacytoma), systemic amyloid light chain amyloidosis, or POEMS syndrome (also known as Crow-Fukase syndrome, Takatsuki disease, and PEP syndrome)), or a combination thereof. In some embodiments, the disease is multiple myeloma.

In some embodiments, the population of cells or pharmaceutical composition is administered to the subject at a dose of about $1\times10^6$ to about $1\times10^8$ (e.g., about $2\times10^6$ to about $5\times10^7$, about $5\times10^6$ to about $2\times10^7$, about $1\times10^6$ to about $1\times10^7$, about $1\times10^7$ to about $1\times10^8$, about $1\times10^6$ to about $3\times10^6$, about $2\times10^6$ to about $4\times10^6$, about $3\times10^6$ to about $5\times10^6$, about $4\times10^6$ to about $6\times10^6$, about $5\times10^6$ to about $7\times10^6$, about $6\times10^6$ to about $8\times10^6$, about $7\times10^6$ to about $9\times10^6$, about $8\times10^6$ to about $1\times10^7$, about $9\times10^6$ to about $2\times10^7$, about $1\times10^7$ to about $3\times10^7$, about $2\times10^7$ to about $4\times10^7$, about $3\times10^7$ to about $5\times10^7$, about $4\times10^7$ to about $6\times10^7$, about $5\times10^7$ to about $7\times10^7$, about $6\times10^7$ to about $8\times10^7$, about $7\times10^7$ to about $9\times10^7$, about $8\times10^7$ to about $1\times10^8$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$) CAR-positive viable cells (e.g., BCMA CAR+ T cells). In some embodiments, the population of cells or pharmaceutical composition is administered to the subject at a dose of about $5\times10^6$ to about $2\times10^7$ CAR-positive viable cells (e.g., BCMA CAR+ T cells).

In some embodiments, the population of cells or pharmaceutical composition is administered to the subject in one or more (e.g., 2, 3, 4, or more) doses. In some embodiments, the population of cells or pharmaceutical composition is administered to the subject in two doses. In some embodiments, the one or more doses comprises a first dose and a second dose, wherein the number of CAR-positive viable cells (e.g., BCMA CAR+ T cells) in the first dose is greater than, equal to, or less than the number of CAR-positive viable cells (e.g., BCMA CAR+ T cells) in the second dose.

In some embodiments, the one or more doses comprise a first dose and a second dose, wherein:

(a) the first dose comprises about $1\times10^6$ to about $1\times10^7$ (e.g., about $2\times10^6$ to about $8\times10^6$, about $4\times10^6$ to about $6\times10^6$, about $1\times10^6$ to about $5\times10^6$, about $5\times10^6$ to about $1\times10^7$, about $1\times10^6$ to about $3\times10^6$, about $2\times10^6$ to about $4\times10^6$, about $3\times10^6$ to about $5\times10^6$, about $4\times10^6$ to about $6\times10^6$, about $5\times10^6$ to about $7\times10^6$, about $6\times10^6$ to about $8\times10^6$, about $7\times10^6$ to about $9\times10^6$, about $8\times10^6$ to about $1\times10^7$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$) viable CAR-positive cells (e.g., BCMA CAR+ T cells);

(b) the second dose comprises about $1\times10^7$ to about $1\times10^8$ (e.g., about $2\times10^7$ to about $8\times10^7$, about $4\times10^7$ to about $6\times10^7$, about $1\times10^7$ to about $5\times10^7$, about $5\times10^7$ to about $1\times10^8$, about $1\times10^7$ to about $3\times10^7$, about $2\times10^7$ to about $4\times10^7$, about $3\times10^7$ to about $5\times10^7$, about $4\times10^7$ to about $6\times10^7$, about $5\times10^7$ to about $7\times10^7$, about $6\times10^7$ to about $8\times10^7$, about $7\times10^7$ to about $9\times10^7$, about $8\times10^7$ to about $1\times10^8$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$) CAR-positive viable cells (e.g., BCMA CAR+ T cells);

(c) the number of CAR-positive viable cells (e.g., BCMA CAR+ T cells) in the first dose is no more than 1/X, wherein X is 1, 2, 3, 4, 5, 6, 7, 8, 9, 10, 20, 30, 40, 50, 60, 70, 80, 90, or 100, of the number of CAR-positive viable cells (e.g., BCMA CAR+ T cells) in the second dose; and/or (d) the number of CAR-positive viable cells (e.g., BCMA CAR+ T cells) in the first dose is between about 1% and 100% (e.g., between about 10% and about 90%, between about 20% and about 80%, between about 30% and about 70%, between about 40% and about 60%, between about 10% and about 50%, between about 50% and about 90%, between about 10% and about 30%, between about 20% and about 40%, between about 30% and about 50%, between about 50% and about 70%, between about 60% and about 80%, or between about 70% and about 90%) of the number of CAR-positive viable cells (e.g., BCMA CAR+ T cells) in the second dose.

In some embodiments, the first dose comprises about $5\times10^6$ viable CAR-positive cells (e.g., BCMA CAR+ T cells). In some embodiments, the second dose comprises about $1\times10^7$ or about $2\times10^7$ viable CAR-positive cells (e.g., BCMA CAR+ T cells).

In some embodiments, the method further comprises administering to the subject a second therapeutic agent. In some embodiments, the second therapeutic agent is chosen from: (i) a PD-1 inhibitor, optionally wherein the PD-1 inhibitor is selected from the group consisting of PDR001, Nivolumab, Pembrolizumab, Pidilizumab, MEDIO680, REGN2810, TSR-042, PF-06801591, and AMP-224; (ii) a PD-L1 inhibitor, optionally wherein the PD-L1 inhibitor is selected from the group consisting of FAZ053, Atezolizumab, Avelumab, Durvalumab, and BMS-936559; (iii) a LAG-3 inhibitor, optionally wherein the LAG-3 inhibitor is selected from the group consisting of LAG525, BMS-986016, TSR-033, MK-4280 and REGN3767; (iv) a TIM-3 inhibitor, optionally wherein the TIM-3 inhibitor is selected from the group consisting of MBG453, TSR-022, and LY3321367; (v) a CTLA-4 inhibitor, optionally wherein the CTLA-4 inhibitor is Ipilimumab or Tremelimumab; (vi) an interleukin-15 (IL-15) polypeptide, an interleukin-15 receptor alpha (IL-15Ra) polypeptide, or a combination of both an IL-15 polypeptide and an IL-15Ra polypeptide, e.g., hetIL-15; (vii) an interleukin-12 (IL-12) polypeptide; or (viii) an mTOR inhibitor, optionally wherein the mTOR inhibitor is RAD001 or rapamycin.

In some embodiments, provided herein is a cell comprising: (a) a first CAR comprising a first antigen-binding domain that binds to a first antigen, a first transmembrane domain, and a first intracellular signaling domain (e.g., a first primary signaling domain and/or a first costimulatory signaling domain), optionally wherein the first CAR further comprises a first leader sequence and/or a first hinge region; and (b) a second CAR comprising a second antigen-binding domain that binds to a second antigen, a second transmembrane domain, and a second intracellular signaling domain (e.g., a second primary signaling domain and/or a second costimulatory signaling domain), optionally wherein the second CAR further comprises a second leader sequence and/or a second hinge region, wherein: (i) the first leader sequence and the second leader sequence are encoded by different nucleic acid sequences (e.g., differ by at least 5%, 10%, 20%, 30%, 40%, 50%, 60%, 70%, 80%, 85%, 90%, 95%, or 100%), optionally wherein the first and second leader sequences comprise the same amino acid sequence; (ii) the first hinge region and the second hinge region are encoded by different nucleic acid sequences (e.g., differ by at least 5%, 10%, 20%, 30%, 40%, 50%, 60%, 70%, 80%, 85%, 90%, 95%, or 100%), optionally wherein the first and second hinge regions comprise the same amino acid sequence; (iii) the first transmembrane domain and the second transmembrane domain are encoded by different nucleic acid sequences (e.g., differ by at least 5%, 10%, 20%, 30%, 40%, 50%, 60%, 70%, 80%, 85%, 90%, 95%, or 100%), optionally wherein the first and second transmembrane domains comprise the same amino acid sequence; and/or (iv) the first intracellular signaling domain and the second intracellular signaling domain are encoded by different nucleic acid sequences (e.g., differ by at least 5%, 10%, 20%, 30%, 40%, 50%, 60%, 70%, 80%, 85%, 90%, 95%, or 100%), optionally wherein the first primary signaling domain and the second primary signaling domain are encoded by different nucleic acid sequences (e.g., differ by at least 5%, 10%, 20%, 30%, 40%, 50%, 60%, 70%, 80%, 85%, 90%, 95%, or 100%), and/or the first costimulatory signaling domain and the second costimulatory signaling domain are encoded by different nucleic acid sequences (e.g., differ by at least 5%, 10%, 20%, 30%, 40%, 50%, 60%, 70%, 80%, 85%, 90%, 95%, or 100%).

In some embodiments, provided herein is a nucleic acid molecule comprising: (a) a first nucleic acid sequence encoding a first CAR, wherein the first CAR comprises a first antigen-binding domain that binds to a first antigen, a first transmembrane domain, and a first intracellular signaling domain (e.g., a first primary signaling domain and/or a first costimulatory signaling domain), optionally wherein the first CAR further comprises a first leader sequence and/or a first hinge region; and (b) a second nucleic acid sequence encoding a second CAR, wherein the second CAR comprises a second antigen-binding domain that binds to a second antigen, a second transmembrane domain, and a second intracellular signaling domain (e.g., a second primary signaling domain and/or a second costimulatory signaling domain), optionally wherein the second CAR further comprises a second leader sequence and/or a second hinge region, wherein: (i) the first leader sequence and the second leader sequence are encoded by different nucleic acid sequences (e.g., differ by at least 5%, 10%, 20%, 30%, 40%, 50%, 60%, 70%, 80%, 85%, 90%, 95%, or 100%), optionally wherein the first and second leader sequences comprise the same amino acid sequence; (ii) the first hinge region and the second hinge region are encoded by different nucleic acid sequences (e.g., differ by at least 5%, 10%, 20%, 30%, 40%, 50%, 60%, 70%, 80%, 85%, 90%, 95%, or 100%), optionally wherein the first and second hinge regions comprise the same amino acid sequence; (iii) the first transmembrane domain and the second transmembrane domain are encoded by different nucleic acid sequences (e.g., differ by at least 5%, 10%, 20%, 30%, 40%, 50%, 60%, 70%, 80%, 85%, 90%, 95%, or 100%), optionally wherein the first and second transmembrane domains comprise the same amino acid sequence; and/or (iv) the first intracellular signaling domain and the second intracellular signaling domain are encoded by different nucleic acid sequences (e.g., differ by at least 5%, 10%, 20%, 30%, 40%, 50%, 60%, 70%, 80%, 85%, 90%, 95%, or 100%), optionally wherein the first intracellular signaling domain and the second intracellular signaling domain comprise the same amino acid sequence.

In some embodiments, the first and second leader sequences comprise the same amino acid sequence. Without wishing to be bound by theory, such a nucleic acid molecule exhibits less recombination than an otherwise similar nucleic acid molecule in which the first leader sequence and the second leader sequence are encoded by the same nucleic acid sequence.

In some embodiments, the first and second hinge regions comprise the same amino acid sequence. Without wishing to be bound by theory, such a nucleic acid molecule exhibits less recombination than an otherwise similar nucleic acid molecule in which the first hinge region and the second hinge region are encoded by the same nucleic acid sequence.

In some embodiments, the first and second transmembrane domains comprise the same amino acid sequence. Without wishing to be bound by theory, such a nucleic acid molecule exhibits less recombination than an otherwise similar nucleic acid molecule in which the first transmembrane domain and the second transmembrane domain are encoded by the same nucleic acid sequence.

In some embodiments, the first intracellular signaling domain and the second intracellular signaling domain comprise the same amino acid sequence. Without wishing to be bound by theory, such a nucleic acid molecule exhibits less recombination than an otherwise similar nucleic acid molecule in which the first intracellular signaling domain and the second intracellular signaling domain are encoded by the same nucleic acid sequence.

In some embodiments, the first primary signaling domain and the second primary signaling domain comprise the same amino acid sequence. Without wishing to be bound by theory, such a nucleic acid molecule exhibits less recombination than an otherwise similar nucleic acid molecule in which the first primary signaling domain and the second primary signaling domain are encoded by the same nucleic acid sequence.

In some embodiments, the first primary signaling domain and the second primary signaling domain comprise different amino acid sequences.

In some embodiments, the first costimulatory signaling domain and the second costimulatory signaling domain comprise the same amino acid sequence. Without wishing to be bound by theory, such a nucleic acid molecule exhibits less recombination than an otherwise similar nucleic acid molecule in which the first costimulatory signaling domain and the second costimulatory signaling domain are encoded by the same nucleic acid sequence.

In some embodiments, the first costimulatory signaling domain and the second costimulatory signaling domain comprise different amino acid sequences (e.g., the first and second costimulatory signaling domains comprise a 4-1BB costimulatory domain sequence and a CD28 costimulatory domain sequence, respectively; or comprise a CD28 costimulatory domain sequence and a 4-1BB costimulatory domain sequence, respectively).

In some embodiments, the first leader sequence and the second leader sequence comprise the amino acid sequence of SEQ ID NO: 1, or an amino acid sequence having at least about 85%, 90%, 95%, or 99% sequence identity thereto. In some embodiments, the first leader sequence and the second leader sequence are encoded by nucleic acid sequences comprising SEQ ID NOs: 199 and 210, respectively (or a nucleic acid sequence having at least about 85%, 90%, 95%, or 99% sequence identity thereto), or SEQ ID NOs: 210 and 199, respectively (or a nucleic acid sequence having at least about 85%, 90%, 95%, or 99% sequence identity thereto).

In some embodiments, the first hinge region and the second hinge region comprise the amino acid sequence of SEQ ID NO: 2, or an amino acid sequence having at least about 85%, 90%, 95%, or 99% sequence identity thereto. In some embodiments, the first hinge region and the second hinge region are encoded by nucleic acid sequences comprising SEQ ID NOs: 337 and 13, respectively (or a nucleic acid sequence having at least about 85%, 90%, 95%, or 99% sequence identity thereto); or SEQ ID NOs: 13 and 337, respectively (or a nucleic acid sequence having at least about 85%, 90%, 95%, or 99% sequence identity thereto).

In some embodiments, the first transmembrane domain and the second transmembrane domain comprise the amino acid sequence of SEQ ID NO: 6, or an amino acid sequence having at least about 85%, 90%, 95%, or 99% sequence identity thereto. In some embodiments, the first transmembrane domain and the second transmembrane domain are encoded by nucleic acid sequences comprising SEQ ID NOs: 338 and 17, respectively (or a nucleic acid sequence having at least about 85%, 90%, 95%, or 99% sequence identity thereto); or SEQ ID NOs: 17 and 338, respectively (or a nucleic acid sequence having at least about 85%, 90%, 95%, or 99% sequence identity thereto).

In some embodiments, the first costimulatory signaling domain and the second costimulatory signaling domain comprise the amino acid sequence of SEQ ID NO: 7, or an amino acid sequence having at least about 85%, 90%, 95%, or 99% sequence identity thereto. In some embodiments, the first costimulatory signaling domain and the second costimulatory signaling domain are encoded by nucleic acid sequences comprising SEQ ID NOs: 204 and 18, respectively (or a nucleic acid sequence having at least about 85%, 90%, 95%, or 99% sequence identity thereto); or SEQ ID NOs: 18 and 204, respectively (or a nucleic acid sequence having at least about 85%, 90%, 95%, or 99% sequence identity thereto).

In some embodiments, the first primary signaling domain and the second primary signaling domain comprise the amino acid sequence of SEQ ID NO: 10, or an amino acid sequence having at least about 85%, 90%, 95%, or 99% sequence identity thereto. In some embodiments, the first primary signaling domain and the second primary signaling domain are encoded by nucleic acid sequences comprising SEQ ID NOs: 205 and 21, respectively (or a nucleic acid sequence having at least about 85%, 90%, 95%, or 99% sequence identity thereto); or SEQ ID NOs: 21 and 205, respectively (or a nucleic acid sequence having at least about 85%, 90%, 95%, or 99% sequence identity thereto).

In some embodiments, the first and second antigens are different. In some embodiments, the first or second antigen is chosen from: BCMA, CD19, CDS, CD10, CD20, CD21, CD22, CD23, CD24, CD25, CD27, CD30, CD34, CD37, CD38, CD40, CD53, CD69, CD72, CD73, CD74, CD75, CD77, CD79a, CD79b, CD80, CD81, CD82, CD83, CD84, CD85, CD86, CD123, CD135, CD138, CD179, CD269, Flt3, ROR1, FcRn5, FcRn2, CS-1, CXCR4, 5, 7, IL-7/3R, IL7/4/3R, or IL4R, optionally wherein the B cell antigen is chosen from CD19, CD20, CD22, FcRn5, FcRn2, CS-1, CD138, CD123, CD33, CD34, CLL-1, folate receptor beta, FLT3, EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In some embodiments, the first or second antigen-binding domain comprises a CDR, VH, VL, or scFv disclosed herein, or an amino acid sequence having at least about 85%, 90%, 95%, or 99% sequence identity thereto.

In some embodiments, provided herein is a CAR comprising a first VH (VH1), a first VL (VL1), a second VH (VH2), a second VL (VL2), a transmembrane domain, and an intracellular signaling domain, wherein the VH1 ad VL1 bind to a first antigen and the VH2 and VL2 bind to a second antigen. In some embodiments, the VH1, VL1, VH2, and VL2 are arranged in the following configuration from the N-terminus to the C-terminus: VH1-optionally linker 1 ("L1")-VH2-optionally linker 2 ("L2")-VL2-optionally linker 3 ("L3")-VL1. In some embodiments, the VH1, VL1, VH2, and VL2 are arranged in the following configuration from the N-terminus to the C-terminus: VH1-optionally L1-VL2-optionally L2-VH2-optionally L3-VL1. In some embodiments, the VH1, VL1, VH2, and VL2 are arranged in the following configuration from the N-terminus to the C-terminus: VL1-optionally L1-VH2-optionally L2-VL2-optionally L3-VH1. In some embodiments, the VH1, VL1, VH2, and VL2 are arranged in the following configuration from the N-terminus to the C-terminus: VL1-optionally L1-VL2-optionally L2-VH2-optionally L3-VH1. In some embodiments, the VH1, VL1, VH2, and VL2 are arranged in the following configuration from the N-terminus to the C-terminus: VH2-optionally L1-VH1-optionally L2-VL1-optionally L3-VL2. In some embodiments, the VH1, VL1, VH2, and VL2 are arranged in the following configuration from the N-terminus to the C-terminus: VH2-optionally L1-VL1-optionally L2-VH1-optionally L3-VL2. In some embodiments, the VH1, VL1, VH2, and VL2 are arranged in the following configuration from the N-terminus to the C-terminus: VL2-optionally L1-VH1-optionally L2-VL1-optionally L3-VH2. In some embodiments, the VH1, VL1, VH2, and VL2 are arranged in the following configuration from the N-terminus to the C-terminus: VL2-optionally L1-VL1-optionally L2-VH1-optionally L3-VH2. In some embodiments, the VH1, VL1, VH2, and VL2 are arranged in the following configuration from the N-terminus to the C-terminus: VH1-linker 1 ("L1")-VH2-linker 2 ("L2")-VL2-linker 3 ("L3")-VL1. In some embodiments, the VH1, VL1, VH2, and VL2 are arranged in the following configuration from the N-terminus to the C-terminus: VH1-L1-VL2-L2-VH2-L3-VL1. In some embodiments, the VH1, VL1, VH2, and VL2 are arranged in the following configuration from the N-terminus to the C-terminus: VL1-L1-VH2-L2-VL2-L3-VH1. In some embodiments, the VH1, VL1, VH2, and VL2 are arranged in the following configuration from the N-terminus to the C-terminus: VL1-L1-VL2-L2-VH2-L3-VH1. In some embodiments, the VH1, VL1, VH2, and VL2 are arranged in the following configuration from the N-terminus to the C-terminus: VH2-L1-VH1-L2-VL1-L3-VL2. In some embodiments, the VH1, VL1, VH2, and VL2 are arranged in the following configuration from the N-terminus to the C-terminus: VH2-L1-VL1-L2-VH1-L3-VL2. In some embodiments, the VH1, VL1, VH2, and VL2 are arranged in the following configuration from the N-terminus to the C-terminus: VL2-L1-VH1-L2-VL1-L3-VH2. In some embodiments, the VH1, VL1, VH2, and VL2 are arranged in the following configuration from the N-terminus to the C-terminus: VL2-L1-VL1-L2-VH1-L3-VH2. In some embodiments, the L1 or L3 comprises the amino acid sequence of SEQ ID NO: 5, or an amino acid sequence having at least about 85%, 90%, 95%, or 99% sequence identity thereto. In some embodiments, the L2 comprises the amino acid sequence of SEQ ID NO: 63, or an amino acid sequence having at least about 85%, 90%, 95%, or 99% sequence identity thereto. In some embodiments, the CAR comprises the following configuration from the N-terminus to the C-terminus: (i) VH1-optionally linker 1 ("L1")-VH2-optionally linker 2 ("L2")-VL2-optionally linker 3 ("L3")-VL1-optionally a hinge region-transmembrane domain-intracellular signaling domain; (ii) VH1-optionally L1-VL2-optionally L2-VH2-optionally L3-VL1-optionally a hinge region-transmembrane domain-intracellular signaling domain; (iii) VL1-optionally L1-VH2-optionally L2-VL2-optionally L3-VH1-optionally a hinge region-transmembrane domain-intracellular signaling domain; (iv) VL1-optionally L1-VL2-optionally L2-VH2-optionally L3-VH1-optionally a hinge region-transmembrane domain-intracellular signaling domain; (v) VH2-optionally L1-VH1-optionally L2-VL1-optionally L3-VL2-optionally a hinge region-transmembrane domain-intracellular signaling domain; (vi) VH2-optionally L1-VL1-optionally L2-VH1-optionally L3-VL2-optionally a hinge region-transmembrane domain-intracellular signaling domain; (vii) VL2-optionally L1-VH1-optionally L2-VL1-optionally L3-VH2-optionally a hinge region-transmembrane domain-intracellular signaling domain; or (viii) VL2-optionally L1-VL1-optionally L2-VH1-optionally L3-VH2-optionally a hinge region-transmembrane domain-intracellular signaling domain. In some embodiments, the first and second antigens are different. In some embodiments, the first or second antigen is chosen from: BCMA, CD19, CD5, CD10, CD20, CD21, CD22, CD23, CD24, CD25, CD27, CD30, CD34, CD37, CD38, CD40, CD53, CD69, CD72, CD73, CD74, CD75, CD77, CD79a, CD79b, CD80, CD81, CD82, CD83, CD84, CD85, CD86, CD123, CD135, CD138, CD179, CD269, Flt3, ROR1, FcRn5, FcRn2, CS-1, CXCR4, 5, 7, IL-7/3R, IL7/4/3R, or IL4R, optionally wherein the B cell antigen is chosen from CD19, CD20, CD22, FcRn5, FcRn2, CS-1, CD138, CD123, CD33, CD34, CLL-1, folate receptor beta, FLT3, EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In some embodiments, the VH1, VL1, VH2, or VL2 comprises a CDR, VH, or VL sequence disclosed herein, or an amino acid sequence having at least about 85%, 90%, 95%, or 99% sequence identity thereto. In some embodiments, the hinge region, transmembrane domain, or intracellular signaling domain (e.g., a primary signaling domain and/or a costimulatory signaling domain) comprises a hinge region sequence, transmembrane domain sequence, or intracellular signaling domain sequence (e.g., a primary signaling domain sequence and/or a costimulatory signaling domain sequence) disclosed herein, or an amino acid sequence having at least about 85%, 90%, 95%, or 99% sequence identity thereto.

In some embodiments, provided herein is a nucleic acid molecule encoding a diabody CAR disclosed herein. In some embodiments, provided herein is a vector comprising a nucleic acid molecule encoding a diabody CAR disclosed herein. In some embodiments, provided herein is a cell comprising a CAR disclosed herein, a nucleic acid molecule encoding a diabody CAR disclosed herein, or a vector comprising a nucleic acid molecule encoding a diabody CAR disclosed herein. In some embodiments, provided herein is a pharmaceutical composition comprising a cell comprising a diabody CAR disclosed herein and a pharmaceutically acceptable carrier. In some embodiments, disclosed herein is a method of making a cell comprising a diabody CAR disclosed herein. In some embodiments, disclosed herein is a method of treating a subject, e.g., a subject having cancer, using a cell comprising a diabody CAR disclosed herein.

In some embodiments, the present disclosure pertains to methods of making immune effector cells (for example, T cells or NK cells) engineered to express a CAR, and compositions generated using such methods. The methods disclosed herein (e.g., the ARM process or the cytokine process disclosed herein) can be used to make cells expressing dual CARs or diabody CARs disclosed herein. Also disclosed are methods of using such compositions for treating a disease, for example, cancer, in a subject.

In some embodiments, this invention features a method of making a population of cells (for example, T cells) that express a chimeric antigen receptor (CAR), the method comprising: (i) contacting (for example, binding) a population of cells (for example, T cells, for example, T cells isolated from a frozen or fresh leukapheresis product) with an agent that stimulates a CD3/TCR complex and/or an agent that stimulates a costimulatory molecule on the surface of the cells; (ii) contacting the population of cells (for example, T cells) with a nucleic acid molecule (for example, a DNA or RNA molecule) encoding the CAR, thereby providing a population of cells (for example, T cells) comprising the nucleic acid molecule, and (iii) harvesting the population of cells (for example, T cells) for storage (for example, reformulating the population of cells in cryopreservation media) or administration, wherein: (a) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 26 hours after the beginning of step (i), for example, no later than 22, 23, 24, or 25 hours after the beginning of step (i), for example, no later than 24 hours after the beginning of step (i); (b) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 hours after the beginning of step (ii), for example, no later than 22, 23, 24, 25, 26, 27, 28, 29, or 30 hours after the beginning of step (ii); or (c) the population of cells from step (iii) are not expanded, or expanded by no more than 5, 6, 7, 8, 9, 10, 11, 12, 13, 14, 15, 16, 17, 18, 19, 20, 25, 30, 35, or 40%, for example, no more than 10%, for example, as assessed by the number of living cells, compared to the population of cells at the beginning of step (i). In some embodiments, the nucleic acid molecule in step (ii) is a DNA molecule. In some embodiments, the nucleic acid molecule in step (ii) is an RNA molecule. In some embodiments, the nucleic acid molecule in step (ii) is on a viral vector, for example, a viral vector chosen from a lentivirus vector, an adenoviral vector, or a retrovirus vector. In some embodiments, the nucleic acid molecule in step (ii) is on a non-viral vector. In some embodiments, the nucleic acid molecule in step (ii) is on a plasmid. In some embodiments, the nucleic acid molecule in step (ii) is not on any vector. In some embodiments, step (ii) comprises transducing the population of cells (for example, T cells) with a viral vector comprising a nucleic acid molecule encoding the CAR. In some embodiments, step (ii) is performed together with step (i). In some embodiments, step (ii) is performed no later than 20 hours after the beginning of step (i). In some embodiments, step (ii) is performed no later than 12, 13, 14, 15, 16, 17, or 18 hours after the beginning of step (i). In some embodiments, step (ii) is performed no later than 18 hours after the beginning of step (i). In some embodiments, step (iii) is performed no later than 26 hours after the beginning of step (i). In some embodiments, step (iii) is performed no later than 22, 23, 24, or 25 hours after the beginning of step (i). In some embodiments, step (iii) is performed no later than 24 hours after the beginning of step (i). In some embodiments, step (iii) is performed no later than 30 hours after the beginning of step (ii). In some embodiments, step (iii) is performed no later than 22, 23, 24, 25, 26, 27, 28, 29, or 30 hours after the beginning of step (ii). In some embodiments, the nucleic acid molecule encoding the CAR is a nucleic acid molecule disclosed herein. In some embodiments, the nucleic acid molecule comprises a first nucleic acid sequence encoding a first CAR and a second nucleic acid sequence encoding a second CAR. In some embodiments, the first and second nucleic acid sequences are disposed on a single nucleic acid molecule, e.g., wherein the first nucleic acid sequence and the second nucleic acid sequence are separated by a third nucleic acid sequence encoding a self-cleavage site (e.g., a P2A site, a T2A site, an E2A site, or an F2A site). In some embodiments, the first and second nucleic acid sequences are disposed on separate nucleic acid molecules. In some embodiments, the nucleic acid molecule comprises a nucleic acid sequence encoding a CAR, wherein the CAR comprises a first VH (VH1), a first VL (VL1), a second VH (VH2), a second VL (VL2), a transmembrane domain, and an intracellular signaling domain, wherein the VH1 ad VL1 bind to a first antigen and the VH2 and VL2 bind to a second antigen, wherein the VH1, VL1, VH2, and VL2 are arranged in the following configuration from the N-terminus to the C-terminus: VH1-optionally linker 1 ("L1")-VH2-optionally linker 2 ("L2")-VL2-optionally linker 3 ("L3")-VL1, VH1-optionally L1-VL2-optionally L2-VH2-optionally L3-VL1, VL1-optionally L1-VH2-optionally L2-VL2-optionally L3-VH1, VL1-optionally L1-VL2-optionally L2-VH2-optionally L3-VH1, VH2-optionally L1-VH1-optionally L2-VL1-optionally L3-VL2, VH2-optionally L1-VL1-optionally L2-VH1-optionally L3-VL2, VL2-optionally L1-VH1-optionally L2-VL1-optionally L3-VH2; or VL2-optionally L1-VL1-optionally L2-VH1-optionally L3-VH2.

In some embodiments, the population of cells from step (iii) are not expanded. In some embodiments, the population of cells from step (iii) are expanded by no more than 5, 6, 7, 8, 9, 10, 11, 12, 13, 14, 15, 16, 17, 18, 19, 20, 25, 30, 35, or 40%, for example, as assessed by the number of living cells, compared to the population of cells at the beginning of step (i). In some embodiments, the population of cells from step (iii) are expanded by no more than 10%, for example, as assessed by the number of living cells, compared to the population of cells at the beginning of step (i).

In some embodiments, the nucleic acid molecule comprises a first nucleic acid sequence encoding a first CAR and a second nucleic acid sequence encoding a second CAR, wherein the first and second nucleic acid sequences are disposed on separate nucleic acid molecules.

In some embodiments, the first and second nucleic acid molecules are on separate viral vectors, and wherein step (ii) comprises transducing the population of cells (for example, T cells) with a first viral vector comprising the nucleic acid molecule encoding the first CAR and a second viral vector comprising the second nucleic acid molecule encoding the second CAR.

In some embodiments, the first CAR comprises an anti-BCMA binding domain (e.g., an anti-BCMA CAR) and the second CAR comprises an anti-CD19 binding domain (e.g., an anti-CD19 CAR).

In some embodiments, in step (ii), the population of cells is contacted with the first viral vector at a multiplicity of infection (MOI) that is higher than, equal to, or less than an MOI at which the population of cells is contacted with the second viral vector. In some embodiments, in step (ii), the population of cells is contacted with the first viral vector at a multiplicity of infection (MOI) that is higher than an MOI at which the population of cells is contacted with the second viral vector.

In some embodiments, in step (ii), the population of cells is contacted with the first viral vector at a first MOI and with the second viral vector at a second MOI, such that a resultant population of cells comprises a first population of cells that comprise the anti-BCMA CAR but not the anti-CD19 CAR, a second population of cells that comprise the anti-CD19 CAR but not the anti-BCMA CAR, and a third population of cells that comprise both the anti-BCMA CAR and the anti-CD19 CAR, wherein:

(a) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10;

(b) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined, e.g., as determined by a method described in Example 10;

(c) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the resultant population, e.g., as determined by a method described in Example 10;

(d) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10; or (e) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second population, e.g., as determined by a method described in Example 10. In some embodiments, in step (ii), the population of cells is contacted with the second viral vector at an MOI (e.g., an MOI that is sufficiently lower than an MOI at which the population of cells is contacted with the first viral vector, such that in a resultant population of cells:

(a) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10;

(b) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined, e.g., as determined by a method described in Example 10;

(c) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the resultant population, e.g., as determined by a method described in Example 10;

(d) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10; or (e) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second population, e.g., as determined by a method described in Example 10.

In some embodiments, in step (ii), the population of cells is contacted with the first viral vector at a first MOI, and the population of cells is contacted with the second viral vector at a second MOI, such that a resultant population of cells comprises:

(a) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10;

(b) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined, e.g., as determined by a method described in Example 10;

(c) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the resultant population, e.g., as determined by a method described in Example 10;

(d) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10; or (e) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second population, e.g., as determined by a method described in Example 10.

In some embodiments, in step (ii), the population of cells is contacted with:

(a) the first viral vector at an MOI of about 1 to about 10 (e.g., about 2 to about 9, about 3 to about 8, about 4 to about 7, about 5 to about 6, about 1 to about 8, about 1 to about 6, about 1 to about 4, about 8 to about 10, about 6 to about 10, about 4 to about 10, about 1 to about 3, about 2 to about 4, about 3 to about 5, about 4 to about 6, about 5 to about 7, about 6 to about 8, about 7 to about to about 9, about 8 to about 10, about 2.5 to about 5, about 1, about 2, about 3, about 4, about 5, about 6, about 7, about 8, about 9, or about 10);

(b) the second viral vector at an MOI of about 0.1 to about 5 (e.g., about 0.2 to about 4, about 0.3 to about 3, about 0.4 to about 2, about 0.5 to about 1, about 0.6 to about 0.9, about 0.7 to about 0.8, about 0.1 to about 4, about 0.1 to about 3, about 0.1 to about 2, about 0.1 to about 1, about 0.1 to about 0.5, about 4 to about 5, about 3 to about 5, about 2 to about 5, about 1 to about 5, about 0.5 to about 5, about 0.2 to about 5, about 0.1 to about 0.5, about 0.2 to about 1, about 0.5 to about 2, about 1 to about 3, about 2 to about 4, about 3 to about 5, about 0.5 to about 1, about 0.1, about 0.2, about 0.3, about 0.4, about 0.5, about 0.6, about 0.7, about 0.8, about 0.9, about 1, about 2, about 3, about 4, or about 5);

(c) the first viral vector at an MOI that is at least about 10% (e.g., at least about 20%, 30%, 40%, 50%, 60%, 70%, 80%, or 90%) or at least about 1 fold (e.g., at least about 2, 3, 4, 5, 6, 7, 8, 9, 10, 15, 20, 25, 30, 35, 40, 50, 60, 70, 80, 90, or 100 fold, e.g., about 2 to about 50 fold, about 3 to 20 fold, about 5 to about 15 fold, or about 8 to about 10 fold) higher than an MOI at which the population of cells is contacted with the second viral vector; and/or (d) the second viral vector at an MOI that is no more than 1/X, wherein X is 2, 3, 4, 5, 6, 7, 8, 9, 10, 12, 15, 20, 30, 40, 50, 60, 70. 80, 90, or 100, of an MOI at which the population of cells is contacted with the first viral vector.

In some embodiments, the population of cells is contacted with the first viral vector at an MOI of about 2.5 to about 5. In some embodiments, the population of cells is contacted with the second viral vector at an MOI of about 0.5 to about 1.0. In some embodiments, the first viral vector at an MOI that is about 8 to about 10 fold higher than an MOI at which the population of cells is contacted with the second viral vector. In some embodiments, the second viral vector at an MOI that is no more than 1/X, wherein X is 6, 8, 10, or 12, of an MOI at which the population of cells is contacted with the first viral vector.

In some embodiments, in step (ii), the population of cells is contacted with:

(a) the first viral vector at an MOI of between about 4 and about 5 (e.g., about 4.75); and/or (b) the second viral vector at an MOI between about 0.2 and about 1 (e.g., about 0.5).

In some embodiments, in step (ii), the population of cells comprises about $1\times10^8$ to about $5\times10^9$ (e.g., about $2\times10^8$ to about $2\times10^9$ or about $4\times10^8$ to about $1\times10^9$ total viable cells. In some embodiments, the cells are suspended in a culture at a concentration of about $1\times10^6$ to about $1\times10^7$ (e.g., about $2\times10^6$ to about $5\times10^6$ or about $3\times10^6$ to about $4\times10^6$) viable cells/mL.

In some embodiments, the agent that stimulates a CD3/TCR complex is an agent that stimulates CD3. In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a CD3/TCR complex does not comprise a bead. In some embodiments, the agent that stimulates a costimulatory molecule does not comprise a bead. In some embodiments, the agent that stimulates a CD3/TCR complex comprises an anti-CD3 antibody. In some embodiments, the agent that stimulates a costimulatory molecule comprises an anti-CD28 antibody. In some embodiments, the agent that stimulates a CD3/TCR complex comprises an anti-CD3 antibody covalently attached to a colloidal polymeric nanomatrix. In some embodiments, the agent that stimulates a costimulatory molecule comprises an anti-CD28 antibody covalently attached to a colloidal polymeric nanomatrix. In some embodiments, the agent that stimulates a CD3/TCR complex and the agent that stimulates a costimulatory molecule comprise T Cell TransAct™.

In some embodiments, the agent that stimulates a CD3/TCR complex does not comprise hydrogel. In some embodiments, the agent that stimulates a costimulatory molecule does not comprise hydrogel. In some embodiments, the agent that stimulates a CD3/TCR complex does not comprise alginate. In some embodiments, the agent that stimulates a costimulatory molecule does not comprise alginate.

In some embodiments, the agent that stimulates a CD3/TCR complex comprises hydrogel. In some embodiments, the agent that stimulates a costimulatory molecule comprises hydrogel. In some embodiments, the agent that stimulates a CD3/TCR complex comprises alginate. In some embodiments, the agent that stimulates a costimulatory molecule comprises alginate. In some embodiments, the agent that stimulates a CD3/TCR complex or the agent that stimulates a costimulatory molecule comprises MagCloudz™ from Quad Technologies.

In some embodiments, step (i) increases the percentage of CAR-expressing cells in the population of cells from step (iii), for example, the population of cells from step (iii) shows a higher percentage of CAR-expressing cells (for example, at least 10, 20, 30, 40, 50, or 60% higher), compared with cells made by an otherwise similar method without step (i).

In some embodiments, the percentage of naïve cells, for example, naïve T cells, for example, CD45RA+CD45RO− CCR7+ T cells, in the population of cells from step (iii) is the same as the percentage of naïve cells, for example, naïve T cells, for example, CD45RA+CD45RO− CCR7+ cells, in the population of cells at the beginning of step (i). In some embodiments, the percentage of naïve cells, for example, naïve T cells, for example, CD45RA+CD45RO− CCR7+ T cells, in the population of cells from step (iii) differs by no more than 3, 4, 5, 6, 7, 8, 9, 10, 11, or 12% from the percentage of naïve cells, for example, naïve T cells, for example, CD45RA+CD45RO− CCR7+ cells, in the population of cells at the beginning of step (i). In some embodiments, the percentage of naïve cells, for example, naïve T cells, for example, CD45RA+CD45RO− CCR7+ T cells, in the population of cells from step (iii) differs by no more than 5 or 10% from the percentage of naïve cells, for example, naïve T cells, for example, CD45RA+CD45RO− CCR7+ cells, in the population of cells at the beginning of step (i).

In some embodiments, the population of cells from step (iii) shows a higher percentage of naïve cells, for example, naïve T cells, for example, CD45RA+CD45RO− CCR7+ T cells (for example, at least 10, 11, 12, 13, 14, 15, 16, 17, 18, 19, 20, 25, 30, 35, or 40% higher), compared with cells made by an otherwise similar method in which step (iii) is performed more than 26 hours after the beginning of step (i), for example, more than 5, 6, 7, 8, 9, 10, 11, or 12 days after the beginning of step (i). In some embodiments, the population of cells from step (iii) shows a higher percentage of naïve cells, for example, naïve T cells, for example, CD45RA+ CD45RO− CCR7+ T cells (for example, at least 10, 11, 12, 13, 14, 15, 16, 17, 18, 19, 20, 25, 30, 35, or 40% higher), compared with cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the percentage of central memory cells, for example, central memory T cells, for example, CD95+ central memory T cells, in the population of cells from step (iii) is the same as the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (iii) differs by no more than 3, 4, 5, 6, 7, 8, 9, 10, 11, or 12% from the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (iii) differs by no more than 5 or 10% from the percentage of central memory cells, for example, central memory T cells, for example, CD95+ central memory T cells, in the population of cells at the beginning of step (i).

In some embodiments, the population of cells from step (iii) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method in which step (iii) is performed more than 26 hours after the beginning of step (i), for example, more than 5, 6, 7, 8, 9, 10, 11, or 12 days after the beginning of step (i). In some embodiments, the population of cells from step (iii) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the percentage of stem memory T cells, for example, CD45RA+CD95+IL-2 receptor β+CCR7+CD62L+ T cells, in the population of cells from step (iii) is increased, as compared to the percentage of stem memory T cells, for example, CD45RA+CD95+IL-2 receptor β+CCR7+CD62L+ T cells, in the population of cells at the beginning of step (i). In some embodiments, the percentage of CAR-expressing stem memory T cells, for example, CAR-expressing CD45RA+CD95+IL-2 receptor β+CCR7+CD62L+ T cells, in the population of cells from step (iii) is increased, as compared to the percentage of CAR-expressing stem memory T cells, for example, CAR-expressing CD45RA+CD95+IL-2 receptor β+CCR7+ CD62L+ T cells, in the population of cells at the beginning of step (i). In some embodiments, the percentage of stem memory T cells, for example, CD45RA+CD95+IL-2 receptor β+CCR7+CD62L+ T cells, in the population of cells from step (iii) is higher than the percentage of stem memory T cells, for example, CD45RA+CD95+IL-2 receptor β+CCR7+CD62L+ T cells, in cells made by an otherwise similar method in which step (iii) is performed more than 26 hours after the beginning of step (i), for example, more than 5, 6, 7, 8, 9, 10, 11, or 12 days after the beginning of step (i). In some embodiments, the percentage of CAR-expressing stem memory T cells, for example, CAR-expressing CD45RA+CD95+IL-2 receptor β+CCR7+CD62L+ T cells, in the population of cells from step (iii) is higher than the percentage of CAR-expressing stem memory T cells, for example, CAR-expressing CD45RA+CD95+IL-2 receptor β+CCR7+CD62L+ T cells, in cells made by an otherwise similar method in which step (iii) is performed more than 26 hours after the beginning of step (i), for example, more than 5, 6, 7, 8, 9, 10, 11, or 12 days after the beginning of step (i). In some embodiments, the percentage of stem memory T cells, for example, CD45RA+CD95+IL-2 receptor β+CCR7+CD62L+ T cells, in the population of cells from step (iii) is higher than the percentage of stem memory T cells, for example, CD45RA+CD95+IL-2 receptor β+CCR7+CD62L+ T cells, in cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the percentage of CAR-expressing stem memory T cells, for example, CAR-expressing CD45RA+CD95+IL-2 receptor β+CCR7+

CD62L+ T cells, in the population of cells from step (iii) is higher than the percentage of CAR-expressing stem memory T cells, for example, CAR-expressing CD45RA+CD95+ IL-2 receptor β+CCR7+CD62L+ T cells, in cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the median GeneSetScore (Up TEM vs. Down TSCM) of the population of cells from step (iii) is about the same as or differs by no more than (for example, increased by no more than) about 25, 50, 75, 100, or 125% from the median GeneSetScore (Up TEM vs. Down TSCM) of the population of cells at the beginning of step (i). In some embodiments, the median GeneSetScore (Up TEM vs. Down TSCM) of the population of cells from step (iii) is lower (for example, at least about 100, 150, 200, 250, or 300% lower) than the median GeneSetScore (Up TEM vs. Down TSCM) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up TEM vs. Down TSCM) of the population of cells from step (iii) is lower (for example, at least about 100, 150, 200, 250, or 300% lower) than the median GeneSetScore (Up TEM vs. Down TSCM) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Up Treg vs. Down Teff) of the population of cells from step (iii) is about the same as or differs by no more than (for example, increased by no more than) about 25, 50, 100, 150, or 200% from the median GeneSetScore (Up Treg vs. Down Teff) of the population of cells at the beginning of step (i). In some embodiments, the median GeneSetScore (Up Treg vs. Down Teff) of the population of cells from step (iii) is lower (for example, at least about 50, 100, 125, 150, or 175% lower) than the median GeneSetScore (Up Treg vs. Down Teff) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up Treg vs. Down Teff) of the population of cells from step (iii) is lower (for example, at least about 50, 100, 125, 150, or 175% lower) than the median GeneSetScore (Up Treg vs. Down Teff) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Down stemness) of the population of cells from step (iii) is about the same as or differs by no more than (for example, increased by no more than) about 25, 50, 100, 150, 200, or 250% from the median GeneSetScore (Down stemness) of the population of cells at the beginning of step (i). In some embodiments, the median GeneSetScore (Down stemness) of the population of cells from step (iii) is lower (for example, at least about 50, 100, or 125% lower) than the median GeneSetScore (Down stemness) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Down stemness) of the population of cells from step (iii) is lower (for example, at least about 50, 100, or 125% lower) than the median GeneSetScore (Down stemness) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Up hypoxia) of the population of cells from step (iii) is about the same as or differs by no more than (for example, increased by no more than) about 125, 150, 175, or 200% from the median GeneSetScore (Up hypoxia) of the population of cells at the beginning of step (i). In some embodiments, the median GeneSetScore (Up hypoxia) of the population of cells from step (iii) is lower (for example, at least about 40, 50, 60, 70, or 80% lower) than the median GeneSetScore (Up hypoxia) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up hypoxia) of the population of cells from step (iii) is lower (for example, at least about 40, 50, 60, 70, or 80% lower) than the median GeneSetScore (Up hypoxia) of cells made by an otherwise similar method which further comprises, after step (ii) and prior to step (iii), expanding the population of cells (for example, T cells) in vitro for more than 3 days, for example, for 5, 6, 7, 8 or 9 days. In some embodiments, the median GeneSetScore (Up autophagy) of the population of cells from step (iii) is about the same as or differs by no more than (for example, increased by no more than) about 180, 190, 200, or 210% from the median GeneSetScore (Up autophagy) of the population of cells at the beginning of step (i). In some embodiments, the median GeneSetScore (Up autophagy) of the population of cells from step (iii) is lower (for example, at least 20, 30, or 40% lower) than the median GeneSetScore (Up autophagy) of cells made by an otherwise similar method in which step (iii) is performed more than 26 hours after the beginning of step (i), for example, more than 5, 6, 7, 8, 9, 10, 11, or 12 days after the beginning of step (i). In some embodiments, the median GeneSetScore (Up autophagy) of the population of cells from step (iii) is lower (for example, at least 20, 30, or 40% lower) than the median GeneSetScore (Up autophagy) of cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii), after being incubated with a cell expressing an antigen recognized by the CAR, secretes IL-2 at a higher level (for example, at least 2, 4, 6, 8, 10, 12, or 14-fold higher) than cells made by an otherwise similar method in which step (iii) is performed more than 26 hours after the beginning of step (i), for example, more than 5, 6, 7, 8, 9, 10, 11, or 12 days after the beginning of step (i), or cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii), after being administered in vivo, persists longer or expands at a higher level (for example, at least 20, 25, 30, 35, 40, 45, 50, 55, 60, 65, 70, 75, 80, 85, or 90% higher), compared with cells made by an otherwise similar method in which step (iii) is performed more than 26 hours after the beginning of step (i), for example, more than 5, 6, 7, 8, 9, 10, 11, or 12 days after the beginning of step (i). In some embodiments, the population of cells from step (iii), after being administered in vivo, persists longer or expands at a higher level (for example, at least 20, 25, 30, 35, 40, 45, 50, 55, 60, 65, 70, 75, 80, 85, or 90% higher), compared with cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii), after being administered in vivo, shows a stronger anti-tumor activity (for example, a stronger anti-tumor activity at a low dose, for example, a dose no more than $0.15\times10^6$, $0.2\times10^6$, $0.25\times10^6$, or $0.3\times10^6$ viable CAR-expressing cells) than cells made by an otherwise similar method in which step (iii) is performed more than 26 hours after the beginning of step (i), for example, more than 5, 6, 7, 8, 9, 10, 11, or 12 days after the beginning of step (i), or cells made by an otherwise similar method which further comprises, after step (ii) and prior to step (iii), expanding the population of cells (for example, T cells) in vitro for more than 3 days, for example, for 5, 6, 7, 8 or 9 days.

In some embodiments, the population of cells from step (iii) are not expanded, for example, as assessed by the number of living cells, compared to the population of cells at the beginning of step (i). In some embodiments, the population of cells from step (iii) decreases from the number of living cells in the population of cells at the beginning of step (i), for example, as assessed by the number of living cells. In some embodiments, the population of cells from step (iii) are expanded by no more than 5, 6, 7, 8, 9, 10, 11, 12, 13, 14, 15, 16, 17, 18, 19, 20, 25, 30, 35, or 40%, for example, no more than 10%, for example, as assessed by the number of living cells, compared to the population of cells at the beginning of step (i). In some embodiments, the population of cells from step (iii) are not expanded, or expanded by less than 0.5, 1, 1.5, or 2 hours, for example, less than 1 or 1.5 hours, compared to the population of cells at the beginning of step (i).

In some embodiments, steps (i) and (ii) are performed in cell media (for example, serum-free media) comprising IL-2, IL-15 (for example, hetIL-15 (IL15/sIL-15Ra)), IL-6 (for example, IL-6/sIL-6Ra), a LSD1 inhibitor, or a MALT1 inhibitor. In some embodiments, steps (i) and (ii) are performed in cell media (for example, serum-free media) comprising IL-7, IL-21, or a combination thereof. In some embodiments, steps (i) and (ii) are performed in cell media (for example, serum-free media) comprising IL-2, IL-15 (for example, hetIL-15 (IL15/sIL-15Ra)), IL-21, IL-7, IL-6 (for example, IL-6/sIL-6Ra), a LSD1 inhibitor, a MALT1 inhibitor, or a combination thereof. In some embodiments, step (i) is performed in cell media (for example, serum-free media) comprising IL-2, IL-15 (for example, hetIL-15 (IL15/sIL-15Ra)), IL-6 (for example, IL-6/sIL-6Ra), a LSD1 inhibitor, or a MALT1 inhibitor. In some embodiments, step (ii) is performed in cell media (for example, serum-free media) comprising IL-2, IL-15 (for example, hetIL-15 (IL15/sIL-15Ra)), IL-6 (for example, IL-6/sIL-6Ra), a LSD1 inhibitor, or a MALT1 inhibitor. In some embodiments, step (i) is performed in cell media (for example, serum-free media) comprising IL-7, IL-21, or a combination thereof. In some embodiments, step (ii) is performed in cell media (for example, serum-free media) comprising IL-7, IL-21, or a combination thereof. In some embodiments, step (i) is performed in cell media (for example, serum-free media) comprising IL-2, IL-15 (for example, hetIL-15 (IL15/sIL-15Ra)), IL-21, IL-7, IL-6 (for example, IL-6/sIL-6Ra), a LSD1 inhibitor, a MALT1 inhibitor, or a combination thereof. In some embodiments, step (ii) is performed in cell media (for example, serum-free media) comprising IL-2, IL-15 (for example, hetIL-15 (IL15/sIL-15Ra)), IL-21, IL-7, IL-6 (for example, IL-6/sIL-6Ra), a LSD1 inhibitor, a MALT1 inhibitor, or a combination thereof. In some embodiments, the cell media is a serum-free media comprising a serum replacement. In some embodiments, the serum replacement is CTS™ Immune Cell Serum Replacement (ICSR).

In some embodiments, the aforementioned methods further comprise prior to step (i): (iv) receiving a fresh leukapheresis product (or an alternative source of hematopoietic tissue such as a fresh whole blood product, a fresh bone marrow product, or a fresh tumor or organ biopsy or removal (for example, a fresh product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a fresh leukapheresis product (or an alternative source of hematopoietic tissue such as a fresh whole blood product, a fresh bone marrow product, or a fresh tumor or organ biopsy or removal (for example, a fresh product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the aforementioned methods further comprise prior to step (i): receiving cryopreserved T cells isolated from a leukapheresis product (or an alternative source of hematopoietic tissue such as cryopreserved T cells isolated from whole blood, bone marrow, or tumor or organ biopsy or removal (for example, thymectomy)) from an entity, for example, a laboratory, hospital, or healthcare provider.

In some embodiments, the aforementioned methods further comprise prior to step (i): (iv) receiving a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the cells from step (iii) are cultured for about two to about four days, e.g., about three days (e.g., about 72 hours following harvesting) prior to measuring CAR expression level in the portion (for example, measuring the percentage of viable, CAR-expressing cells in the portion, for example, measuring the percentage of viable, anti-BCMA CAR-expressing cells in the portion). In some embodiments, the measuring of CAR expression occurs about 4 days (e.g., 96 hours) after step (ii). In some embodiments, the CAR expression level is measured by flow cytometry.

In some embodiments, this invention features a method of making a population of cells (for example, T cells) that express a chimeric antigen receptor (CAR), the method comprising: (1) contacting a population of cells (for example, T cells, for example, T cells isolated from a frozen leukapheresis product) with a cytokine chosen from IL-2, IL-7, IL-15, IL-21, IL-6, or a combination thereof, (2) contacting the population of cells (for example, T cells) with a nucleic acid molecule (for example, a DNA or RNA molecule) encoding the CAR, thereby providing a population of cells (for example, T cells) comprising the nucleic acid molecule, and (3) harvesting the population of cells (for example, T cells) for storage (for example, reformulating the population of cells in cryopreservation media) or administration, wherein: (a) step (2) is performed together with step (1) or no later than 5 hours after the beginning of step (1), for example, no later than 1, 2, 3, 4, or 5 hours after the beginning of step (1), and step (3) is performed no later than 26 hours after the beginning of step (1), for example, no later than 22, 23, 24, or 25 hours after the beginning of step (1), for example, no later than 24 hours after the beginning of step (1), or (b) the population of cells from step (3) are not expanded, or expanded by no more than 5, 10, 15, 20, 25, 30, 35, or 40%, for example, no more than 10%, for example, as assessed by the number of living cells, compared to the population of cells at the beginning of step (1). In some embodiments, the nucleic acid molecule in step (2) is a DNA molecule. In some embodiments, the nucleic acid molecule in step (2) is an RNA molecule. In some embodiments, the nucleic acid molecule in step (2) is on a viral vector, for example, a viral vector chosen from a lentivirus vector, an adenoviral vector, or a retrovirus vector. In some embodiments, the nucleic acid molecule in step (2) is on a non-viral vector. In some embodiments, the nucleic acid molecule in step (2) is on a plasmid. In some embodiments, the nucleic acid molecule in step (2) is not on any vector. In some embodiments, step (2) comprises transducing the population of cells (for example, T cells) with a viral vector comprising a nucleic acid molecule encoding the CAR. In some embodiments, the nucleic acid molecule encoding the CAR is a nucleic acid molecule disclosed herein. In some embodiments, the nucleic acid molecule comprises a first nucleic acid sequence encoding a first CAR and a second nucleic acid sequence encoding a second CAR. In some embodiments, the first and second nucleic acid sequences are disposed on a single nucleic acid molecule, e.g., wherein the first nucleic acid sequence and the second nucleic acid sequence are separated by a third nucleic acid sequence encoding a self-cleavage site (e.g., a P2A site, a T2A site, an E2A site, or an F2A site). In some embodiments, the first and second nucleic acid sequences are disposed on separate nucleic acid molecules. In some embodiments, the nucleic acid molecule comprises a nucleic acid sequence encoding a CAR, wherein the CAR comprises a first VH (VH1), a first VL (VL1), a second VH (VH2), a second VL (VL2), a transmembrane domain, and an intracellular signaling domain, wherein the VH1 ad VL1 bind to a first antigen and the VH2 and VL2 bind to a second antigen, wherein the VH1, VL1, VH2, and VL2 are arranged in the following configuration from the N-terminus to the C-terminus: VH1-optionally linker 1 ("L1")-VH2-optionally linker 2 ("L2")-VL2-optionally linker 3 ("L3")-VL1, VH1-optionally L1-VL2-optionally L2-VH2-optionally L3-VL1, VL1-optionally L1-VH2-optionally L2-VL2-optionally L3-VH1, VL1-optionally L1-VL2-optionally L2-VH2-optionally L3-VH1, VH2-optionally L1-VH1-optionally L2-VL1-optionally L3-VL2, VH2-optionally L1-VL1-optionally L2-VH1-optionally L3-VL2, VL2-optionally L1-VH1-optionally L2-VL1-optionally L3-VH2; or VL2-optionally L1-VL1-optionally L2-VH1-optionally L3-VH2.

In some embodiments, step (2) is performed together with step (1). In some embodiments, step (2) is performed no later than 5 hours after the beginning of step (1). In some embodiments, step (2) is performed no later than 1, 2, 3, 4, or 5 hours after the beginning of step (1). In some embodiments, step (3) is performed no later than 26 hours after the beginning of step (1). In some embodiments, step (3) is performed no later than 22, 23, 24, or 25 hours after the beginning of step (1). In some embodiments, step (3) is performed no later than 24 hours after the beginning of step (1).

In some embodiments, the population of cells from step (3) are not expanded, for example, as assessed by the number of living cells, compared to the population of cells at the beginning of step (1). In some embodiments, the population of cells from step (3) are expanded by no more than 5, 6, 7, 8, 9, 10, 11, 12, 13, 14, 15, 16, 17, 18, 19, 20, 25, 30, 35, or 40%, for example, as assessed by the number of living cells, compared to the population of cells at the beginning of step (1). In some embodiments, the population of cells from step (3) are expanded by no more than 10%, for example, as assessed by the number of living cells, compared to the population of cells at the beginning of step (1).

In some embodiments, step (1) comprises contacting the population of cells (for example, T cells) with IL-2. In some embodiments, step (1) comprises contacting the population of cells (for example, T cells) with IL-7. In some embodiments, step (1) comprises contacting the population of cells (for example, T cells) with IL-15 (for example, hetIL-15 (IL15/sIL-15Ra)). In some embodiments, step (1) comprises contacting the population of cells (for example, T cells) with IL-21. In some embodiments, step (1) comprises contacting the population of cells (for example, T cells) with IL-6 (for example, IL-6/sIL-6Ra). In some embodiments, step (1) comprises contacting the population of cells (for example, T cells) with IL-2 and IL-7. In some embodiments, step (1) comprises contacting the population of cells (for example, T cells) with IL-2 and IL-15 (for example, hetIL-15 (IL15/sIL-15Ra)). In some embodiments, step (1) comprises contacting the population of cells (for example, T cells) with IL-2 and IL-21. In some embodiments, step (1) comprises contacting the population of cells (for example, T cells) with IL-2 and IL-6 (for example, IL-6/sIL-6Ra). In some embodiments, step (1) comprises contacting the population of cells (for example, T cells) with IL-7 and IL-15 (for example, hetIL-15 (IL15/sIL-15Ra)). In some embodiments, step (1) comprises contacting the population of cells (for example, T cells) with IL-7 and IL-21. In some embodiments, step (1) comprises contacting the population of cells (for example, T cells) with IL-7 and IL-6 (for example, IL-6/sIL-6Ra). In some embodiments, step (1) comprises contacting the population of cells (for example, T cells) with IL-15 (for example, hetIL-15 (IL15/sIL-15Ra)) and IL-21. In some embodiments, step (1) comprises contacting the population of cells (for example, T cells) with IL-15 (for example, hetIL-15 (IL15/sIL-15Ra)) and IL-6 (for example, IL-6/sIL-6Ra). In some embodiments, step (1) comprises contacting the population of cells (for example, T cells) with IL-21 and IL-6 (for example, IL-6/sIL-6Ra). In some embodiments, step (1) comprises contacting the population of cells (for example, T cells) with IL-7, IL-15 (for example, hetIL-15 (IL15/sIL-15Ra)), and IL-21.

In some embodiments, the population of cells from step (3) shows a higher percentage of naïve cells among CAR-expressing cells (for example, at least 10, 11, 12, 13, 14, 15, 16, 17, 18, 19, 20, 25, 30, 35, or 40% higher), compared with cells made by an otherwise similar method which further comprises contacting the population of cells with, for example, an anti-CD3 antibody.

In some embodiments, the percentage of naïve cells, for example, naïve T cells, for example, CD45RA+CD45RO− CCR7+ T cells, in the population of cells from step (3) is the same as the percentage of naïve cells, for example, naïve T cells, for example, CD45RA+CD45RO− CCR7+ cells, in the population of cells at the beginning of step (1). In some embodiments, the percentage of naïve cells, for example, naïve T cells, for example, CD45RA+CD45RO− CCR7+ T cells, in the population of cells from step (3) differs by no more than 3, 4, 5, 6, 7, 8, 9, 10, 11, or 12% from the percentage of naïve cells, for example, naïve T cells, for example, CD45RA+CD45RO− CCR7+ cells, in the population of cells at the beginning of step (1). In some embodiments, the percentage of naïve cells, for example, naïve T cells, for example, CD45RA+CD45RO− CCR7+ T cells, in the population of cells from step (3) differs by no more than 5 or 10% from the percentage of naïve cells, for example, naïve T cells, for example, CD45RA+CD45RO− CCR7+ cells, in the population of cells at the beginning of step (1). In some embodiments, the percentage of naïve cells, for example, naïve T cells, for example, CD45RA+CD45RO− CCR7+ T cells, in the population of cells from step (3) is increased as compared to the percentage of naïve cells, for example, naïve T cells, for example, CD45RA+CD45RO− CCR7+ cells, in the population of cells at the beginning of step (1). In some embodiments, the percentage of naïve cells, for example, naïve T cells, for example, CD45RA+ CD45RO− CCR7+ T cells, in the population of cells from step (3) is increased by at least 10, 11, 12, 13, 14, 15, 16, 17, 18, 19, or 20%, as compared to the percentage of naïve cells, for example, naïve T cells, for example, CD45RA+ CD45RO− CCR7+ cells, in the population of cells at the beginning of step (1). In some embodiments, the percentage of naïve cells, for example, naïve T cells, for example, CD45RA+CD45RO− CCR7+ T cells, in the population of cells from step (3) is increased by at least 10 or 20%, as compared to the percentage of naïve cells, for example, naïve T cells, for example, CD45RA+CD45RO− CCR7+ cells, in the population of cells at the beginning of step (1).

In some embodiments, the population of cells from step (3) shows a higher percentage of naïve cells, for example, naïve T cells, for example, CD45RA+CD45RO− CCR7+ T cells (for example, at least 10, 11, 12, 13, 14, 15, 16, 17, 18, 19, 20, 25, 30, 35, or 40% higher), compared with cells made by an otherwise similar method in which step (3) is performed more than 26 hours after the beginning of step (1), for example, more than 5, 6, 7, 8, 9, 10, 11, or 12 days after the beginning of step (1). In some embodiments, the population of cells from step (3) shows a higher percentage of naïve cells, for example, naïve T cells, for example, CD45RA+CD45RO− CCR7+ T cells (for example, at least 10, 11, 12, 13, 14, 15, 16, 17, 18, 19, 20, 25, 30, 35, or 40% higher), compared with cells made by an otherwise similar method which further comprises, after step (2) and prior to step (3), expanding the population of cells (for example, T cells) in vitro for more than 3 days, for example, for 5, 6, 7, 8 or 9 days.

In some embodiments, the percentage of central memory cells, for example, central memory T cells, for example, CD95+ central memory T cells, in the population of cells from step (3) is the same as the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (3) differs by no more than 3, 4, 5, 6, 7, 8, 9, 10, 11, or 12% from the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (3) differs by no more than 5 or 10% from the percentage of central memory cells, for example, central memory T cells, for example, CD95+ central memory T cells, in the population of cells at the beginning of step (i). In some embodiments, the percentage of central memory cells, for example, central memory T cells, for example, CD95+ central memory T cells, in the population of cells from step (3) is decreased as compared to the percentage of central memory cells, for example, central memory T cells, for example, CD95+ central memory T cells, in the population of cells at the beginning of step (1). In some embodiments, the percentage of central memory cells, for example, central memory T cells, for example, CD95+ central memory T cells, in the population of cells from step (3) is decreased by at least 10 or 20%, as compared to the percentage of central memory cells, for example, central memory T cells, for example, CD95+ central memory T cells, in the population of cells at the beginning of step (1). In some embodiments, the percentage of central memory cells, for example, central memory T cells, for example, CD95+ central memory T cells, in the population of cells from step (3) is decreased by at least 10, 11, 12, 13, 14, 15, 16, 17, 18, 19, or 20%, as compared to the percentage of central memory cells, for example, central memory T cells, for example, CD95+ central memory T cells, in the population of cells at the beginning of step (1).

In some embodiments, the population of cells from step (3) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method in which step (3) is performed more than 26 hours after the beginning of step (1), for example, more than 5, 6, 7, 8, 9, 10, 11, or 12 days after the beginning of step (1). In some embodiments, the population of cells from step (3) shows a lower percentage of central memory cells, for example, central memory T cells, for example, CD95+ central memory T cells (for example, at least 10, 11, 12, 13, 14, 15, 16, 17, 18, 19, 20, 25, 30, 35, or 40% lower), compared with cells made by an otherwise similar method which further comprises, after step (2) and prior to step (3), expanding the population of cells (for example, T cells) in vitro for more than 3 days, for example, for 5, 6, 7, 8 or 9 days.

In some embodiments, the population of cells from step (3), after being administered in vivo, persists longer or expands at a higher level (for example, at least 20, 25, 30, 35, 40, 45, 50, 55, 60, 65, 70, 75, 80, 85, or 90% higher), compared with cells made by an otherwise similar method in which step (3) is performed more than 26 hours after the beginning of step (1), for example, more than 5, 6, 7, 8, 9, 10, 11, or 12 days after the beginning of step (1). In some embodiments, the population of cells from step (3), after being administered in vivo, persists longer or expands at a higher level (for example, at least 20, 25, 30, 35, 40, 45, 50, 55, 60, 65, 70, 75, 80, 85, or 90% higher), compared with cells made by an otherwise similar method which further comprises, after step (2) and prior to step (3), expanding the population of cells (for example, T cells) in vitro for more than 3 days, for example, for 5, 6, 7, 8 or 9 days.

In some embodiments, the population of cells from step (3) are not expanded, for example, as assessed by the number of living cells, compared to the population of cells at the beginning of step (1). In some embodiments, the population of cells from step (3) are expanded by no more than 5, 6, 7, 8, 9, 10, 11, 12, 13, 14, 15, 16, 17, 18, 19, 20, 25, 30, 35, or 40%, for example, as assessed by the number of living cells, compared to the population of cells at the beginning of step (1). In some embodiments, the population of cells from step (3) are expanded by no more than 10%, for example, as assessed by the number of living cells, compared to the population of cells at the beginning of step (1). In some embodiments, the number of living cells in the population of cells from step (3) decreases from the number of living cells in the population of cells at the beginning of step (1), for example, as assessed by the number of living cells.

In some embodiments, the population of cells from step (3) are not expanded compared to the population of cells at the beginning of step (1), for example, as assessed by the number of living cells. In some embodiments, the population of cells from step (3) are expanded by less than 0.5, 1, 1.5, or 2 hours, for example, less than 1 or 1.5 hours, compared to the population of cells at the beginning of step (1).

In some embodiments, the population of cells is not contacted in vitro with an agent that stimulates a CD3/TCR complex and/or an agent that stimulates a costimulatory molecule on the surface of the cells, or if contacted, the contacting step is less than 2 hours, for example, no more than 1 or 1.5 hours. In some embodiments, the agent that stimulates a CD3/TCR complex is an agent that stimulates CD3 (for example, an anti-CD3 antibody). In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex or the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand).

In some embodiments, steps (1) and/or (2) are performed in cell media comprising no more than 5, 4, 3, 2, 1, or 0% serum. In some embodiments, steps (1) and/or (2) are performed in cell media comprising no more than 2% serum. In some embodiments, steps (1) and/or (2) are performed in cell media comprising about 2% serum. In some embodiments, steps (1) and/or (2) are performed in cell media comprising a LSD1 inhibitor or a MALT1 inhibitor. In some embodiments, step (1) is performed in cell media comprising no more than 5, 4, 3, 2, 1, or 0% serum. In some embodiments, step (1) is performed in cell media comprising no more than 2% serum. In some embodiments, step (1) is performed in cell media comprising about 2% serum. In some embodiments, step (2) is performed in cell media comprising no more than 5, 4, 3, 2, 1, or 0% serum. In some embodiments, step (2) is performed in cell media comprising no more than 2% serum. In some embodiments, step (2) is performed in cell media comprising about 2% serum. In some embodiments, step (1) is performed in cell media comprising a LSD1 inhibitor or a MALT1 inhibitor. In some embodiments, step (2) is performed in cell media comprising a LSD1 inhibitor or a MALT1 inhibitor.

In some embodiments, the aforementioned methods further comprise prior to step (i): (iv) receiving a fresh leukapheresis product (or an alternative source of hematopoietic tissue such as a fresh whole blood product, a fresh bone marrow product, or a fresh tumor or organ biopsy or removal (for example, a fresh product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a fresh leukapheresis product (or an alternative source of hematopoietic tissue such as a fresh whole blood product, a fresh bone marrow product, or a fresh tumor or organ biopsy or removal (for example, a fresh product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the aforementioned methods further comprise prior to step (i): receiving cryopreserved T cells isolated from a leukapheresis product (or an alternative source of hematopoietic tissue such as cryopreserved T cells isolated from whole blood, bone marrow, or tumor or organ biopsy or removal (for example, thymectomy)) from an entity, for example, a laboratory, hospital, or healthcare provider.

In some embodiments, the aforementioned methods further comprise prior to step (i): (iv) receiving a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)) from an entity, for example, a laboratory, hospital, or healthcare provider.

In some embodiments, the aforementioned methods further comprise prior to step (i): (v) isolating the population of cells (for example, T cells, for example, CD8+ and/or CD4+ T cells) contacted in step (i) from a cryopreserved leukapheresis product (or an alternative source of hematopoietic tissue such as a cryopreserved whole blood product, a cryopreserved bone marrow product, or a cryopreserved tumor or organ biopsy or removal (for example, a cryopreserved product from thymectomy)). In some embodiments, step (iii) is performed no later than 35 hours after the beginning of step (v), for example, no later than 27, 28, 29, 30, 31, 32, 33, 34, or 35 hours after the beginning of step (v), for example, no later than 30 hours after the beginning of step (v). In some embodiments, the population of cells from step (iii) are not expanded, or expanded by no more than 5, 10, 15, 20, 25, 30, 35, or 40%, for example, no more than 10%, for example, as assessed by the number of living cells, compared to the population of cells at the end of step (v).

In some embodiments, the population of cells at the beginning of step (i) or step (1) has been enriched for IL6R-expressing cells (for example, cells that are positive for IL6Rα and/or IL6Rβ). In some embodiments, the population of cells at the beginning of step (i) or step (1) comprises no less than 40, 45, 50, 55, 60, 65, or 70% of IL6R-expressing cells (for example, cells that are positive for IL6Ra and/or IL6Rβ).

In some embodiments, steps (i) and (ii) or steps (1) and (2) are performed in cell media comprising IL-15 (for example, hetIL-15 (IL15/sIL-15Ra)). In some embodiments, IL-15 increases the ability of the population of cells to expand, for example, 10, 15, 20, or 25 days later. In some embodiments, IL-15 increases the percentage of IL6Rβ-expressing cells in the population of cells.

In some embodiments of the aforementioned methods, the methods are performed in a closed system. In some embodiments, T cell separation, activation, transduction, incubation, and washing are all performed in a closed system. In some embodiments of the aforementioned methods, the methods are performed in separate devices. In some embodiments, T cell separation, activation and transduction, incubation, and washing are performed in separate devices.

In some embodiments of the aforementioned methods, the methods further comprise adding an adjuvant or a transduction enhancement reagent in the cell culture medium to enhance transduction efficiency. In some embodiments, the adjuvant or transduction enhancement reagent comprises a cationic polymer. In some embodiments, the adjuvant or transduction enhancement reagent is chosen from: LentiBOOST™ (Sirion Biotech), vectofusin-1, F108, hexadimethrine bromide (Polybrene), PEA, Pluronic F68, Pluronic F127, Synperonic or LentiTrans™. In some embodiments, the adjuvant is LentiBOOST™ (Sirion Biotech).

In some embodiments of the aforementioned methods, the transducing the population of cells (for example, T cells) with a viral vector comprises subjecting the population of cells and viral vector to a centrifugal force under conditions such that transduction efficiency is enhanced. In an embodiment, the cells are transduced by spinoculation.

In some embodiments of the aforementioned methods, cells (e.g., T cells) are activated and transduced in a cell culture flask comprising a gas-permeable membrane at the base that supports large media volumes without substantially compromising gas exchange. In some embodiments, cell growth is achieved by providing access, e.g., substantially uninterrupted access, to nutrients through convection.

In some embodiments of the aforementioned methods, the CAR comprises an antigen binding domain, a transmembrane domain, and an intracellular signaling domain.

In some embodiments, the antigen binding domain binds to an antigen chosen from: CD19, CD20, CD22, BCMA, mesothelin, EGFRvIII, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (for example, ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In some embodiments, the antigen binding domain comprises a CDR, VH, VL, scFv or a CAR sequence disclosed herein. In some embodiments, the antigen binding domain comprises a VH and a VL, wherein the VH and VL are connected by a linker, optionally wherein the linker comprises the amino acid sequence of SEQ ID NO: 63 or 104.

In some embodiments, the transmembrane domain comprises a transmembrane domain of a protein chosen from the alpha, beta or zeta chain of T-cell receptor, CD28, CD3 epsilon, CD45, CD4, CD5, CD8, CD9, CD16, CD22, CD33, CD37, CD64, CD80, CD86, CD134, CD137 and CD154. In some embodiments, the transmembrane domain comprises a transmembrane domain of CD8. In some embodiments, the transmembrane domain comprises the amino acid sequence of SEQ ID NO: 6, or an amino acid sequence having at least about 85%, 90%, 95%, or 99% sequence identity thereof. In some embodiments, the nucleic acid molecule comprises a nucleic acid sequence encoding the transmembrane domain, wherein the nucleic acid sequence comprises the nucleic acid sequence of SEQ ID NO: 17, or a nucleic acid sequence having at least about 85%, 90%, 95%, or 99% sequence identity thereof.

In some embodiments, the antigen binding domain is connected to the transmembrane domain by a hinge region. In some embodiments, the hinge region comprises the amino acid sequence of SEQ ID NO: 2, 3, or 4, or an amino acid sequence having at least about 85%, 90%, 95%, or 99% sequence identity thereof. In some embodiments, the nucleic acid molecule comprises a nucleic acid sequence encoding the hinge region, wherein the nucleic acid sequence comprises the nucleic acid sequence of SEQ ID NO: 13, 14, or 15, or a nucleic acid sequence having at least about 85%, 90%, 95%, or 99% sequence identity thereof.

In some embodiments, the intracellular signaling domain comprises a primary signaling domain. In some embodiments, the primary signaling domain comprises a functional signaling domain derived from CD3 zeta, TCR zeta, FcR gamma, FcR beta, CD3 gamma, CD3 delta, CD3 epsilon, CDS, CD22, CD79a, CD79b, CD278 (ICOS), FcεRI, DAP10, DAP12, or CD66d. In some embodiments, the primary signaling domain comprises a functional signaling domain derived from CD3 zeta. In some embodiments, the primary signaling domain comprises the amino acid sequence of SEQ ID NO: 9 or 10, or an amino acid sequence having at least about 85%, 90%, 95%, or 99% sequence identity thereof. In some embodiments, the nucleic acid molecule comprises a nucleic acid sequence encoding the primary signaling domain, wherein the nucleic acid sequence comprises the nucleic acid sequence of SEQ ID NO: 20 or 21, or a nucleic acid sequence having at least about 85%, 90%, 95%, or 99% sequence identity thereof.

In some embodiments, the intracellular signaling domain comprises a costimulatory signaling domain. In some embodiments, the costimulatory signaling domain comprises a functional signaling domain derived from a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, or a ligand that specifically binds with CD83. In some embodiments, the costimulatory signaling domain comprises a functional signaling domain derived from 4-1BB. In some embodiments, the costimulatory signaling domain comprises the amino acid sequence of SEQ ID NO: 7, or an amino acid sequence having at least about 85%, 90%, 95%, or 99% sequence identity thereof. In some embodiments, the nucleic acid molecule comprises a nucleic acid sequence encoding the costimulatory signaling domain, wherein the nucleic acid sequence comprises the nucleic acid sequence of SEQ ID NO: 18, or a nucleic acid sequence having at least about 85%, 90%, 95%, or 99% sequence identity thereof.

In some embodiments, the intracellular signaling domain comprises a functional signaling domain derived from 4-1BB and a functional signaling domain derived from CD3 zeta. In some embodiments, the intracellular signaling domain comprises the amino acid sequence of SEQ ID NO: 7 (or an amino acid sequence having at least about 85%, 90%, 95%, or 99% sequence identity thereof) and the amino acid sequence of SEQ ID NO: 9 or 10 (or an amino acid sequence having at least about 85%, 90%, 95%, or 99% sequence identity thereof). In some embodiments, the intracellular signaling domain comprises the amino acid sequence of SEQ ID NO: 7 and the amino acid sequence of SEQ ID NO: 9 or 10.

In some embodiments, the CAR further comprises a leader sequence comprising the amino acid sequence of SEQ ID NO: 1.

In some embodiments, this invention features a population of CAR-expressing cells (for example, autologous or allogeneic CAR-expressing T cells or NK cells) made by any of the aforementioned methods or any other method disclosed herein. In some embodiments, disclosed herein is a pharmaceutical composition comprising a population of CAR-expressing cells disclosed herein and a pharmaceutically acceptable carrier.

In some embodiments, the population comprises:

(a) a first population of cells comprising an anti-BCMA CAR but not an anti-CD19 CAR;

(b) a second population of cells comprising an anti-CD19 CAR but not an anti-BCMA CAR; and (c) a third population of cells comprising both an anti-BCMA CAR and an anti-CD19 CAR.

In some embodiments:

(i) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined;

(ii) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined; and/or (iii) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the population.

In some embodiments, the population further comprises a fourth population of cells that do not comprise a CAR.

In some embodiments:

(i) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined;

(ii) the total number of viable cells in the second population is less than or equal to: about 45% to about 50% (e.g., about 47%); about 50 to about 55% (e.g., about 53%); about 60% to about 65% (e.g., about 63%); or about 80 to about 85% (e.g., about 82%) of the total number of viable cells in the first and third populations combined.

In some embodiments, in the final CAR cell product manufactured using the methods described herein, the total amount of beads (e.g., CD4 beads, CD8 beads, and/or TransACT beads) is no more than 0.04, 0.05, 0.06, 0.07, 0.08, 0.09, 0.1, 0.2, 0.3, 0.4, or 0.5% of the total amount of beads added during the manufacturing process.

In some embodiments, this invention features a population of CAR-expressing cells (for example, autologous or allogeneic CAR-expressing T cells or NK cells) comprising one or more of the following characteristics: (a) about the same percentage of naïve cells, for example, naïve T cells, for example, CD45RO− CCR7+ T cells, as compared to the percentage of naïve cells, for example, naïve T cells, for example, CD45RO− CCR7+ cells, in the same population of cells prior to being engineered to express the CAR; (b) a change within about 5% to about 10% of naïve cells, for example, naïve T cells, for example, CD45RO− CCR7+ T cells, for example, as compared to the percentage of naïve cells, for example, naïve T cells, for example, CD45RO− CCR7+ cells, in the same population of cells prior to being engineered to express the CAR; (c) an increased percentage of naïve cells, for example, naïve T cells, for example, CD45RO− CCR7+ T cells, for example, increased by at least 1.2, 1.4, 1.6, 1.8, 2.0, 2.2, 2.4, 2.6, 2.8, or 3-fold, as compared to the percentage of naïve cells, for example, naïve T cells, for example, CD45RO− CCR7+ cells, in the same population of cells prior to being engineered to express the CAR; (d) about the same percentage of central memory cells, for example, central memory T cells, for example, CCR7+CD45RO+ T cells, as compared to the percentage of central memory cells, for example, central memory T cells, for example, CCR7+CD45RO+ T cells, in the same population of cells prior to being engineered to express the CAR;

(e) a change within about 5% to about 10% of central memory cells, for example, central memory T cells, for example, CCR7+CD45RO+ T cells, as compared to the percentage of central memory cells, for example, central memory T cells, for example, CCR7+CD45RO+ T cells, in the same population of cells prior to being engineered to express the CAR; (f) a decreased percentage of central memory cells, for example, central memory T cells, for example, CCR7+CD45RO+ T cells, for example, decreased by at least 20, 25, 30, 35, 40, 45, or 50%, as compared to the percentage of central memory cells, for example, central memory T cells, for example, CCR7+CD45RO+ T cells, in the same population of cells prior to being engineered to express the CAR; (g) about the same percentage of stem memory T cells, for example, CD45RA+CD95+IL-2 receptor β+CCR7+CD62L+ T cells, as compared to the percentage of stem memory T cells, for example, CD45RA+CD95+IL-2 receptor β+CCR7+CD62L+ T cells, in the same population of cells prior to being engineered to express the CAR; (h) a change within about 5% to about 10% of stem memory T cells, for example, CD45RA+CD95+IL-2 receptor β+CCR7+CD62L+ T cells, as compared to the percentage of stem memory T cells, for example, CD45RA+CD95+IL-2 receptor β+CCR7+CD62L+ T cells, in the same population of cells prior to being engineered to express the CAR; or (i) an increased percentage of stem memory T cells, for example, CD45RA+CD95+IL-2 receptor β+CCR7+CD62L+ T cells, as compared to the percentage of stem memory T cells, for example, CD45RA+CD95+IL-2 receptor β+CCR7+CD62L+ T cells, in the same population of cells prior to being engineered to express the CAR.

In some embodiments, this invention features a population of CAR-expressing cells (for example, autologous or allogeneic CAR-expressing T cells or NK cells), wherein: (a) the median GeneSetScore (Up TEM vs. Down TSCM) of the population of cells is about the same as or differs by no more than (for example, increased by no more than) about 25, 50, 75, 100, or 125% from the median GeneSetScore (Up TEM vs. Down TSCM) of the same population of cells prior to being engineered to express the CAR; (b) the median GeneSetScore (Up Treg vs. Down Teff) of the population of cells is about the same as or differs by no more than (for example, increased by no more than) about 25, 50, 100, 150, or 200% from the median GeneSetScore (Up Treg vs. Down Teff) of the population of cells prior to being engineered to express the CAR; (c) the median GeneSetScore (Down stemness) of the population of cells is about the same as or differs by no more than (for example, increased by no more than) about 25, 50, 100, 150, 200, or 250% from the median GeneSetScore (Down stemness) of the population of cells prior to being engineered to express the CAR; (d) the median GeneSetScore (Up hypoxia) of the population of cells is about the same as or differs by no more than (for example, increased by no more than) about 125, 150, 175, or 200% from the median GeneSetScore (Up hypoxia) of the population of cells prior to being engineered to express the CAR; or (e) the median GeneSetScore (Up autophagy) of the population of cells is about the same as or differs by no more than (for example, increased by no more than) about 180, 190, 200, or 210% from the median GeneSetScore (Up autophagy) of the population of cells prior to being engineered to express the CAR.

In some embodiments, this invention features a method of increasing an immune response in a subject, comprising administering a population of CAR-expressing cells disclosed herein or a pharmaceutical composition disclosed herein to the subject, thereby increasing an immune response in the subject.

In some embodiments, disclosed herein is a method of treating a cancer in a subject, comprising administering a population of CAR-expressing cells disclosed herein or a pharmaceutical composition disclosed herein to the subject, thereby treating the cancer in the subject. In some embodiments, the cancer is a solid cancer, for example, chosen from: one or more of mesothelioma, malignant pleural mesothelioma, non-small cell lung cancer, small cell lung cancer, squamous cell lung cancer, large cell lung cancer, pancreatic cancer, pancreatic ductal adenocarcinoma, esophageal adenocarcinoma, breast cancer, glioblastoma, ovarian cancer, colorectal cancer, prostate cancer, cervical cancer, skin cancer, melanoma, renal cancer, liver cancer, brain cancer, thymoma, sarcoma, carcinoma, uterine cancer, kidney cancer, gastrointestinal cancer, urothelial cancer, pharynx cancer, head and neck cancer, rectal cancer, esophagus cancer, or bladder cancer, or a metastasis thereof. In some embodiments, the cancer is a liquid cancer, for example, chosen from: chronic lymphocytic leukemia (CLL), mantle cell lymphoma (MCL), multiple myeloma, acute lymphoid leukemia (ALL), Hodgkin lymphoma, B-cell acute lymphoid leukemia (BALL), T-cell acute lymphoid leukemia (TALL), small lymphocytic leukemia (SLL), B cell prolymphocytic leukemia, blastic plasmacytoid dendritic cell neoplasm, Burkitt's lymphoma, diffuse large B cell lymphoma (DLBCL), DLBCL associated with chronic inflammation, chronic myeloid leukemia, myeloproliferative neoplasms, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, myelodysplasia, myelodysplastic syndrome, non-Hodgkin lymphoma, plasmablastic lymphoma, plasmacytoid dendritic cell neoplasm, Waldenstrom macroglobulinemia, splenic marginal zone lymphoma, splenic lymphoma/leukemia, splenic diffuse red pulp small B-cell lymphoma, hairy cell leukemia-variant, lymphoplasmacytic lymphoma, a heavy chain disease, plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (thymic) large B-cell lymphoma, intravascular large B-cell lymphoma, ALK+ large B-cell lymphoma, large B-cell lymphoma arising in HHV8-associated multicentric Castleman disease, primary effusion lymphoma, B-cell lymphoma, acute myeloid leukemia (AML), or unclassifiable lymphoma.

In some embodiments, the method further comprises administering a second therapeutic agent to the subject. In some embodiments, the second therapeutic agent is an anti-cancer therapeutic agent, for example, a chemotherapy, a radiation therapy, or an immune-regulatory therapy. In some embodiments, the second therapeutic agent is IL-15 (for example, hetIL-15 (IL15/sIL-15Ra)).

In some embodiments, provided herein is an isolated cell or a population of cells made by a method as described herein comprising one or more cells comprising:

(a) a first nucleic acid molecule encoding a first CAR that comprises an anti-BCMA binding domain, a first transmembrane domain, and a first intracellular signaling domain, wherein the anti-BCMA binding domain comprises a heavy chain variable region (VH) comprising a heavy chain complementary determining region 1 (HC CDR1), a heavy chain complementary determining region 2 (HC CDR2), and a heavy chain complementary determining region 3 (HC CDR3), and a light chain variable region (VL) comprising a light chain complementary determining region 1 (LC CDR1), a light chain complementary determining region 2 (LC CDR2), and a light chain complementary determining region 3 (LC CDR3), wherein the HC CDR1, HC CDR2, HC CDR3, LC CDR1, LC CDR2, and LC CDR3 comprise the amino acid sequences of SEQ ID NOs: 86, 87, 88, 95, 96, and 97, respectively; and (b) a second nucleic acid molecule encoding a second CAR that comprises an anti-CD19 binding domain, a second transmembrane domain, and a second intracellular signaling domain, wherein the anti-CD19 binding domain comprises a VH comprising a HC CDR1, a HC CDR2, and a HC CDR3, and a VL comprising a LC CDR1, a LC CDR2, and a LC CDR3, wherein the HC CDR1, HC CDR2, HC CDR3, LC CDR1, LC CDR2, and LC CDR3 comprise the amino acid sequences of SEQ ID NOs: 295, 304, and 297-300, respectively.

In some embodiments, provided herein is an isolated cell comprising:

(a) a first nucleic acid molecule encoding a first CAR that comprises an anti-BCMA binding domain, a first transmembrane domain, and a first intracellular signaling domain, wherein the anti-BCMA binding domain comprises a heavy chain variable region (VH) comprising a heavy chain complementary determining region 1 (HC CDR1), a heavy chain complementary determining region 2 (HC CDR2), and a heavy chain complementary determining region 3 (HC CDR3), and a light chain variable region (VL) comprising a light chain complementary determining region 1 (LC CDR1), a light chain complementary determining region 2 (LC CDR2), and a light chain complementary determining region 3 (LC CDR3), wherein the HC CDR1, HC CDR2, HC CDR3, LC CDR1, LC CDR2, and LC CDR3 comprise the amino acid sequences of SEQ ID NOs: 86, 87, 88, 95, 96, and 97, respectively; and (b) a second nucleic acid molecule encoding a second CAR that comprises an anti-CD19 binding domain, a second transmembrane domain, and a second intracellular signaling domain, wherein the anti-CD19 binding domain comprises a VH comprising a HC CDR1, a HC CDR2, and a HC CDR3, and a VL comprising a LC CDR1, a LC CDR2, and a LC CDR3, wherein the HC CDR1, HC CDR2, HC CDR3, LC CDR1, LC CDR2, and LC CDR3 comprise the amino acid sequences of SEQ ID NOs: 295, 304, and 297-300, respectively.

In some embodiments, the VH and VL of the anti-BCMA binding domain comprise the amino acid sequences of SEQ ID NOs: 93 and 102, respectively. In some embodiments, the VH and VL of the anti-CD19 binding domain comprise the amino acid sequences of SEQ ID NOs: 250 and 251, respectively. In some embodiments, the VH and VL of the anti-BCMA binding domain comprise the amino acid sequences of SEQ ID NOs: 93 and 102, respectively, and the VH and VL of the anti-CD19 binding domain comprise the amino acid sequences of SEQ ID NOs: 250 and 251, respectively. In some embodiments, the anti-BCMA binding domain comprises the amino acid sequence of SEQ ID NO: 105. In some embodiments, the anti-CD19 binding domain comprises the amino acid sequence of SEQ ID NO: 293. In some embodiments, the anti-BCMA binding domain comprises the amino acid sequence of SEQ ID NO: 105 and the anti-CD19 binding domain comprises the amino acid sequence of SEQ ID NO: 293. In some embodiments, the first CAR comprises the amino acid sequence of SEQ ID NO: 107. In some embodiments, the second CAR comprise the amino acid sequence of SEQ ID NO: 225. In some embodiments, the first CAR comprises the amino acid sequence of SEQ ID NO: 107; and the second CAR comprise the amino acid sequence of SEQ ID NO: 225. In some embodiments, the first CAR is encoded by the nucleic acid sequence of SEQ ID NO: 259, 258, or 416. In some embodiments, the second CAR is encoded by the nucleic acid sequence of SEQ ID NO: 417, 355, 356, or 354. In some embodiments, the first CAR is encoded by the nucleic acid sequence of SEQ ID NO: 259, 258, or 416, and the second CAR is encoded by the nucleic acid sequence of SEQ ID NO: 417, 355, 356, or 354.

In some embodiments, provided herein is a pharmaceutical composition comprising the cell or population of cells, as described herein.

In some embodiments, provided herein is method of providing anti-tumor immunity in a subject or treating a subject having a disease associated with expression of BCMA comprising administering to the subject an effective amount of the cell or population of cells or the pharmaceutical composition, as described herein.

In some embodiments, the disease associated with BCMA expression is a hematologic cancer or a solid cancer, e.g., a hematologic cancer or a solid cancer described herein.

In some embodiments, the disease is chosen from: acute leukemia, B-cell acute lymphoid leukemia ("BALL"), T-cell acute lymphoid leukemia ("TALL"), acute lymphoid leukemia (ALL), chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell- or large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, prostate cancer (e.g., castrate-resistant or therapy-resistant prostate cancer, or metastatic prostate cancer), pancreatic cancer, lung cancer, a plasma cell proliferative disorder (e.g., asymptomatic myeloma (smoldering multiple myeloma or indolent myeloma), monoclonal gammapathy of undetermined significance (MGUS), Waldenstrom's macroglobulinemia, plasmacytoma (e.g., plasma cell dyscrasia, solitary myeloma, solitary plasmacytoma, extramedullary plasmacytoma, and multiple plasmacytoma), systemic amyloid light chain amyloidosis, or POEMS syndrome (also known as Crow-Fukase syndrome, Takatsuki disease, and PEP syndrome)), or a combination thereof.

In some embodiments, the disease is multiple myeloma.

Although methods and materials similar or equivalent to those described herein can be used in the practice or testing of the present invention, suitable methods and materials are described below. All publications, patent applications, patents, and other references (for example, sequence database reference numbers) mentioned herein are incorporated by reference in their entirety. For example, all GenBank, Unigene, and Entrez sequences referred to herein, for example, in any Table herein, are incorporated by reference. When one gene or protein references a plurality of sequence accession numbers, all of the sequence variants are encompassed.

In addition, the materials, methods, and examples are illustrative only and not intended to be limiting. Headings, sub-headings or numbered or lettered elements, for example, (a), (b), (i) etc., are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE FIGURES

FIGS. 1B and 1D are graphs showing expression level of BCMA CARs on JNL cells were detected by flow cytometry using a human recombinant (r)BCMA_Fc-AF647. 1× or 2× platform indicated 40,000 of H293 cells or 80,000 of H293 cells seeded for viral production.

FIG. 3A: CART cells were co-cultured with KMS11-luc target cells at the indicated E:T ratios. % cell killing was determined by the difference in luciferase signal between target cells without effector T cells (control) and with effector T cells (experimental), expressed as a percent of the control. UTD represents untransduced T cells. FIG. 3B: Background killing was observed for the BCMA-negative line NALM6. FIG. 3C: IFNγ was measured by MSD in the supernatants collected at 24 h from these co-culture systems with a E:T ratio of 2.5. All data is expressed as the average+/−standard deviation.

FIGS. 4A-4C: CAR expression in T cells transduced with a MOI=5 (viral titer defined by the first CAR expressed in SupT1 cells). FIG. 4A is a table summarizing % CAR19, % BCMA CAR, % Double Positive, % CAR19-only, and % BCMA-CAR-only of different constructs. FIG. 4B is a set of flow cytometry plots showing the staining of cells for surface BCMA CAR expression (x-axis) and surface CD19 CAR expression (y-axis). FIG. 4C is a pair of bar graphs showing BCMA CAR MFI (upper panel) and CD19 CAR MFI (lower panel).

FIGS. 5A-5C are a set of graphs showing % Killing against BCMA-positive KMS11 cells, CD19-positive Nalm6 cells, or BCMA/CD19-negative cells, respectively, at the indicated E:T ratios.

FIGS. 6A-6D: In vitro cytokine production using Day 8 CART cells. FIGS. 6A-6D are a set of bar graphs showing IFN gamma production of CART cells when co-cultured with BCMA-positive KMS11 cells or CD19-positive Nalm6 cells.

FIGS. 7A-7B are histograms showing the expression pattern of both anti-BCMA and anti-CD19 CARs at 24h or 72 h post-transduction of human primary T cells manufactured using the ARM process. The studies used a MOI of 1 based on the SupT1 titer determined by expression of the upstream CAR. In each of FIGS. 7A and 7B, the left part is a panel of histograms showing staining using rBCMA-Fc, and the right part is a panel of histograms showing staining using anti-idiotype antibody that binds to CD19 CAR. Constructs #244 ("c244") and #245 ("c245") are mono anti-CD19 CAR and mono anti-BCMA CAR, respectively. FIG. 7C is a panel of flow cytometry plots showing the anti-BCMA and anti-CD19 CAR expression pattern at 72 h post-transduction of human primary T cells using a MOI of 1 based on the upstream CAR titer.

FIG. 14A: NSG mice were injected with multiple myeloma cell line KMS11, which expressed a luciferase reporter gene. The tumor burden is expressed as total body luminescence (p/s), depicted as mean tumor burden+SEM. On day 8 post tumor inoculation, mice were treated with c236 and c238 at 9e4 BCMA-CD19 double CAR+ T cell dose (approximate number of viable CAR+ T cells). Vehicle (PBS) and non-transduced T cells (UTD) served as negative controls. FIG. 14B: The expansion of peripheral blood CAR+ T cells was analyzed by flow cytometry up to 4 weeks after infusion. Double anti-BCMA and CD19 CAR+ T cell expansion was observed in c236 and c238 CAR−T Rx groups.

FIG. 24D is a violin plot showing the distribution of gene set scores for a gene set comprised of genes that characterize a resting vs. activated T cell state for Day 1 cells, Day 9 cells, and input cells. In FIG. 24D, a higher gene set score (Up resting vs. Down activated) indicates an increasing resting T cell phenotype, whereas a lower gene set score (Up resting vs. Down activated) indicates an increasing activated T cell phenotype. Input cells were overall in more of a resting state compared to Day 9 and Day 1 cells. Day 1 cells show the greatest activation gene set score.

In FIG. 25A, a higher gene set score for the gene set "Up TEM vs. Down TSCM" indicates an increasing effector memory T cell (TEM) phenotype of the cells in that sample, whereas a lower gene set score indicates an increasing stem cell memory T cell (TSCM) phenotype. In FIG. 25B, a higher gene set score for the gene set "Up Treg vs. Down Teff" indicates an increasing regulatory T cell (Treg) phenotype, whereas a lower gene set score indicates an increasing effector T cell (Teff) phenotype. In FIG. 25C, a lower gene set score for the gene set "Down stemness" indicates an increasing stemness phenotype. In FIG. 25D, a higher gene set score for the gene set "Up hypoxia" indicates an increasing hypoxia phenotype. In FIG. 25E, a higher gene set score for the gene set "Up autophagy" indicates an increasing autophagy phenotype. Day 1 cells looked similar to the input cells in terms of memory, stem-like and differentiation signature. Day 9 cells, on the other hand, show a higher enrichment for metabolic stress.

FIGS. 26A-26C are violin plots showing the gene set scores from gene set analysis of the four clusters of the input cells. Each dot overlaying the violin plots in FIGS. 26A-26C represents a cell's gene set score. In FIG. 26A, a higher gene set score of the gene set "Up Treg vs. Down Teff" indicates an increasing Treg cell phenotype, whereas a lower gene set score of the gene set "Up Treg vs. Down Teff" indicates an increasing Teff cell phenotype. In FIG. 26B, a higher gene set score of the gene set "Progressively up in memory differentiation" indicates an increasing late memory T cell phenotype, whereas a lower gene set score of the gene set "Progressively up in memory differentiation" indicates an increasing early memory T cell phenotype. In FIG. 26C, a higher gene set score of the gene set "Up TEM vs. Down TN" indicates an increasing effector memory T cell phenotype, whereas a lower gene set score of the gene set "Up TEM vs. Down TN" indicates an increasing naïve T cell phenotype. The cells in Cluster 3 are shown to be in a later memory, further differentiated T cell state compared to the cells in Cluster 1 and Cluster 2 which are in an early memory, less differentiated T cell state. Cluster 0 appears to be in an intermediate T cell state. Taken together, this data shows that there is a considerable level of heterogeneity within input cells.

FIG. 28A: Flow cytometry plots showed mono anti-BCMA CAR, mono anti-CD19 CAR and double+ CAR expression on days 4 and 7 post-transduction under four different MOI conditions in addition to controls (UTD and single vector). FIG. 28B: Quantification of subsets of CAR+ populations including total anti-BCMA CAR+ T cells, total anti-CD19 CAR+ T cells as well as total CAR+ T cells (sum of the two mono CAR+ T cells and double+ CAR T cells) in each condition as described in FIG. 28A. Data shown are one representative from three donor T cells with consistent results. CAR+ cell percentages are gated on live CD3+ T cell population.

FIG. 31 is a bar graph showing % mono CD19 CAR+ cells, % mono BCMA CAR+ cells, and % double BCMA/CD19 CAR+ cells on day 4 post transduction (day 3 past harvest).

FIG. 32 is a graph showing % CD4+ T cells, CD8+ T cells, naïve T cells (Tn), central memory T cells (Tcm), effector memory T cells (Tem), and effector memory T cells re-expressing CD45RA (Temra), in the input material, post-enrichment material, and Day 1 Post-harvest material.

DETAILED DESCRIPTION

Definitions

Figure 1A:
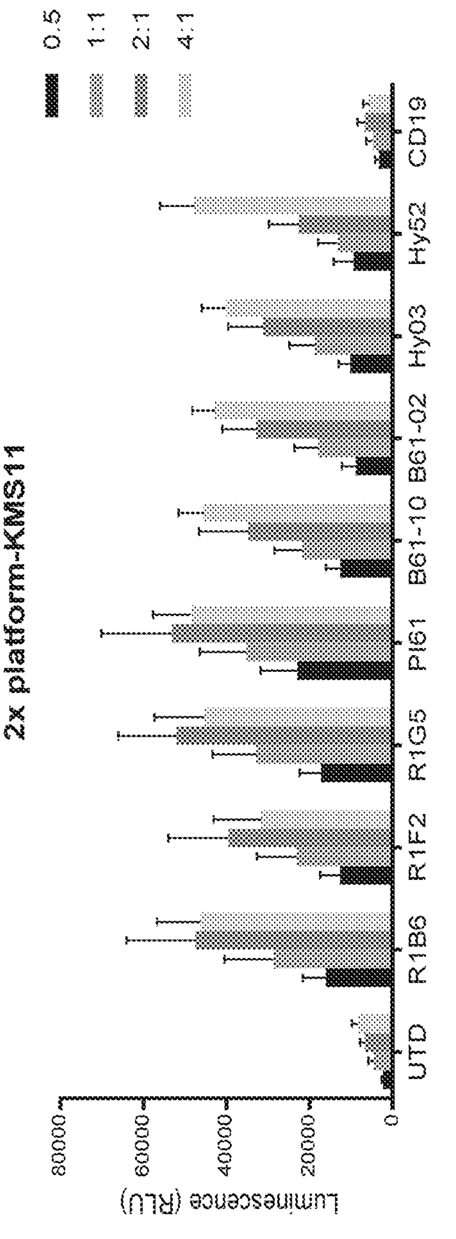
FIGS. 1A-1H: Jurkat NFAT Luciferase (JNL) reporter assay using an automated system was used to test the function of BCMA CARs. CAR clones were evaluated in the JNL reporter assay for antigen-dependent activity. JNL cells containing the indicated CAR clones or untransduced JNL cells (UTD) were co-cultured with media alone (FIGS. 1G and 1H) or with target cells lines (KMS11 as a BCMA-positive cell line (FIGS. 1A and 1C) and NALM6 as a BCMA-negative cell line (FIGS. 1E and 1F)) at different ratios and luciferase activity was measured as luminescence intensity. Clones were considered active when the luminescence intensity exceeded 2-fold the level of UTD cells in the presence of antigen-expressing cells. Luminescence readout is a direct measurement of CAR stimulation.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The compositions and methods of the present invention encompass polypeptides and nucleic acids having the sequences specified, or sequences substantially identical or similar thereto, for example, sequences at least 85%, 90%, or 95% identical or higher to the sequence specified. In the context of an amino acid sequence, the term "substantially identical" is used herein to refer to a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity, for example, amino acid sequences that contain a common structural domain having at least about 85%, 90%. 91%, 92%, 93%, 94%, 95%, 96%, 97%, 98% or 99% identity to a reference sequence, for example, a sequence provided herein.

In the context of a nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, for example, nucleotide sequences having at least about 75%, 80%, 85%, 90%, 91%, 92%, 93%, 94%, 95%, 96%, 97%, 98% or 99% identity to a reference sequence, for example, a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

The term cytokine (for example, IL-2, IL-7, IL-15, IL-21, or IL-6) includes full length, a fragment or a variant, for example, a functional variant, of a naturally-occurring cytokine (including fragments and functional variants thereof having at least 10%, 30%, 50%, or 80% of the activity, e.g., the immunomodulatory activity, of the naturally-occurring cytokine). In some embodiments, the cytokine has an amino acid sequence that is substantially identical (e.g., at least about 85%, 90%, 91%, 92%, 93%, 94%, 95%, 96%, 97%, 98% or 99% identity) to a naturally-occurring cytokine, or is encoded by a nucleotide sequence that is substantially identical (e.g., at least about 75%, 80%, 85%, 90%, 91%, 92%, 93%, 94%, 95%, 96%, 97%, 98% or 99% identity) to a naturally-occurring nucleotide sequence encoding a cytokine. In some embodiments, as understood in context, the cytokine further comprises a receptor domain, e.g., a cytokine receptor domain (e.g., an IL-15/IL-15R).

As used herein, the term "BCMA" refers to B-cell maturation antigen. BCMA (also known as TNFRSF17, BCM or CD269) is a member of the tumor necrosis receptor (TNFR) family and is predominantly expressed on terminally differentiated B cells, e.g., memory B cells, and plasma cells. Its ligand is called B-cell activator of the TNF family (BAFF) and a proliferation inducing ligand (APRIL). BCMA is involved in mediating the survival of plasma cells for maintaining long-term humoral immunity. The gene for BCMA is encoded on chromosome 16 producing a primary mRNA transcript of 994 nucleotides in length (NCBI accession NM_001192.2) that encodes a protein of 184 amino acids (NP_001183.2). A second antisense transcript derived from the BCMA locus has been described, which may play a role in regulating BCMA expression. (Laabi Y. et al., Nucleic Acids Res., 1994, 22:1147-1154). Additional transcript variants have been described with unknown significance (Smirnova A S et al. Mol Immunol., 2008, 45(4): 1179-1183. A second isoform, also known as TV4, has been identified (Uniprot identifier Q02223-2). As used herein, "BCMA" includes proteins comprising mutations, e.g., point mutations, fragments, insertions, deletions and splice variants of full length wild-type BCMA.

The phrase "disease associated with expression of BCMA" includes, but is not limited to, a disease associated with a cell which expresses BCMA (e.g., wild-type or mutant BCMA) or condition associated with a cell which expresses BCMA (e.g., wild-type or mutant BCMA) including, e.g., proliferative diseases such as a cancer or malignancy or a precancerous condition such as a myelodysplasia, a myelodysplastic syndrome or a preleukemia; or a noncancer related indication associated with a cell which expresses BCMA (e.g., wild-type or mutant BCMA). For the avoidance of doubt, a disease associated with expression of BCMA may include a condition associated with a cell which does not presently express BCMA, e.g., because BCMA expression has been downregulated, e.g., due to treatment with a molecule targeting BCMA, e.g., a BCMA inhibitor described herein, but which at one time expressed BCMA. In one aspect, a cancer associated with expression of BCMA (e.g., wild-type or mutant BCMA) is a hematological cancer. In one aspect, the hematological cancer is a leukemia or a lymphoma. In one aspect, a cancer associated with expression of BCMA (e.g., wild-type or mutant BCMA) is a malignancy of differentiated plasma B cells. In one aspect, a cancer associated with expression of BCMA (e.g., wild-type or mutant BCMA) includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of BMCA (e.g., wild-type or mutant BCMA) comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. In some embodiments, the cancer is multiple myeloma, Hodgkin's lymphoma, non-Hodgkin's lymphoma, or glioblastoma. In embodiments, a disease associated with expression of BCMA includes a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome). Further diseases associated with expression of BCMA (e.g., wild-type or mutant BCMA) expression include, but not limited to, e.g., atypical and/or non-classical cancers, malignancies, precancerous conditions or proliferative diseases associated with expression of BCMA (e.g., wild-type or mutant BCMA), e.g., a cancer described herein, e.g., a prostate cancer (e.g., castrate-resistant or therapy-resistant prostate cancer, or metastatic prostate cancer), pancreatic cancer, or lung cancer.

Non-cancer related conditions that are associated with BCMA (e.g., wild-type or mutant BCMA) include viral infections; e.g., HIV, fungal infections, e.g., *C. neoformans*; autoimmune disease; e.g. rheumatoid arthritis, system lupus erythematosus (SLE or lupus), pemphigus vulgaris, and Sjogren's syndrome; inflammatory bowel disease, ulcerative colitis; transplant-related allospecific immunity disorders related to mucosal immunity; and unwanted immune responses towards biologics (e.g., Factor VIII) where humoral immunity is important. In embodiments, a non-cancer related indication associated with expression of BCMA includes but is not limited to, e.g., autoimmune disease, (e.g., lupus), inflammatory disorders (allergy and asthma) and transplantation. In some embodiments, the tumor antigen-expressing cell expresses, or at any time expressed, mRNA encoding the tumor antigen. In an embodiment, the tumor antigen-expressing cell produces the tumor antigen protein (e.g., wild-type or mutant), and the tumor antigen protein may be present at normal levels or reduced levels. In an embodiment, the tumor antigen-expressing cell produced detectable levels of a tumor antigen protein at one point, and subsequently produced substantially no detectable tumor antigen protein.

The term "Chimeric Antigen Receptor" or alternatively a "CAR" or "CAR molecule" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, for example, comprise a chimeric fusion protein. In some embodiments, the domains in the CAR polypeptide construct are not contiguous with each other, for example, are in different polypeptide chains, for example, as provided in an RCAR as described herein.

In some embodiments, the cytoplasmic signaling domain comprises a primary signaling domain (for example, a primary signaling domain of CD3-zeta). In some embodiments, the cytoplasmic signaling domain further comprises one or more functional signaling domains derived from at least one costimulatory molecule as defined below. In some embodiments, the costimulatory molecule is chosen from 41BB (i.e., CD137), CD27, ICOS, and/or CD28. In some embodiments, the CAR comprises a chimeric fusion protein comprising an extracellular antigen recognition domain, a transmembrane domain and an intracellular signaling domain comprising a functional signaling domain derived from a stimulatory molecule. In some embodiments, the CAR comprises a chimeric fusion protein comprising an extracellular antigen recognition domain, a transmembrane domain and an intracellular signaling domain comprising a functional signaling domain derived from a costimulatory molecule and a functional signaling domain derived from a stimulatory molecule. In some embodiments, the CAR comprises a chimeric fusion protein comprising an extracellular antigen recognition domain, a transmembrane domain and an intracellular signaling domain comprising two functional signaling domains derived from one or more costimulatory molecule(s) and a functional signaling domain derived from a stimulatory molecule. In some embodiments, the CAR comprises a chimeric fusion protein comprising an extracellular antigen recognition domain, a transmembrane domain and an intracellular signaling domain comprising at least two functional signaling domains derived from one or more costimulatory molecule(s) and a functional signaling domain derived from a stimulatory molecule. In some embodiments the CAR comprises an optional leader sequence at the amino-terminus (N-terminus) of the CAR fusion protein. In some embodiments, the CAR further comprises a leader sequence at the N-terminus of the extracellular antigen recognition domain, wherein the leader sequence is optionally cleaved from the antigen recognition domain (for example, an scFv) during cellular processing and localization of the CAR to the cellular membrane.

A CAR that comprises an antigen binding domain (for example, an scFv, a single domain antibody, or TCR (for example, a TCR alpha binding domain or TCR beta binding domain)) that targets a specific tumor marker X, wherein X can be a tumor marker as described herein, is also referred to as XCAR. For example, a CAR that comprises an antigen binding domain that targets BCMA is referred to as BCMA CAR. The CAR can be expressed in any cell, for example, an immune effector cell as described herein (for example, a T cell or an NK cell).

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule, which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, for example, an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, for example, two, Fab fragments linked by a disulfide bridge at the hinge region, or two or more, for example, two isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, for example, Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, for example, with respect to the N-terminal and C-terminal ends of the polypeptide, the scFv may comprise VL-linker-VH or may comprise VH-linker-VL. In some embodiments, the scFv may comprise the structure of $NH_2$-$V_L$-linker-$V_H$-COOH or $NH_2$-$V_H$-linker-$V_L$-COOH.

The terms "complementarity determining region" or "CDR," as used herein, refer to the sequences of amino acids within antibody variable regions which confer antigen specificity and binding affinity. For example, in general, there are three CDRs in each heavy chain variable region (for example, HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof. In a combined Kabat and Chothia numbering scheme, in some embodiments, the CDRs correspond to the amino acid residues that are part of a Kabat CDR, a Chothia CDR, or both.

The portion of the CAR composition of the invention comprising an antibody or antibody fragment thereof may exist in a variety of forms, for example, where the antigen binding domain is expressed as part of a polypeptide chain including, for example, a single domain antibody fragment (sdAb), a single chain antibody (scFv), or for example, a human or humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In some embodiments, the antigen binding domain of a CAR composition of the invention comprises an antibody fragment. In some embodiments, the CAR comprises an antibody fragment that comprises an scFv.

As used herein, the term "binding domain" or "antibody molecule" (also referred to herein as "anti-target binding domain") refers to a protein, for example, an immunoglobulin chain or fragment thereof, comprising at least one immunoglobulin variable domain sequence. The term "binding domain" or "antibody molecule" encompasses antibodies and antibody fragments. In some embodiments, an antibody molecule is a multispecific antibody molecule, for example, it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope.

In some embodiments, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The terms "bispecific antibody" and "bispecific antibodies" refer to molecules that combine the antigen binding sites of two antibodies within a single molecule. Thus, a bispecific antibody is able to bind two different antigens simultaneously or sequentially. Methods for making bispecific antibodies are well known in the art. Various formats for combining two antibodies are also known in the art.

Forms of bispecific antibodies of the invention include, but are not limited to, a diabody, a single-chain diabody, Fab dimerization (Fab-Fab), Fab-scFv, and a tandem antibody, as known to those of skill in the art.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (K) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The terms "anti-tumor effect" and "anti-cancer effect" are used interchangeably and refer to a biological effect which can be manifested by various means, including but not limited to, for example, a decrease in tumor volume or cancer volume, a decrease in the number of tumor cells or cancer cells, a decrease in the number of metastases, an increase in life expectancy, a decrease in tumor cell proliferation or cancer cell proliferation, a decrease in tumor cell survival or cancer cell survival, or amelioration of various physiological symptoms associated with the cancerous condition. An "anti-tumor effect" or "anti-cancer effect" can also be manifested by the ability of the peptides, polynucleotides, cells and antibodies of the invention in prevention of the occurrence of tumor or cancer in the first place.

The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some embodiments, allogeneic material from individuals of the same species may be sufficiently unlike genetically to interact antigenically.

The term "xenogeneic" refers to a graft derived from an animal of a different species.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, for example, by retransfusion. Thus, in the context of "an apheresis sample" refers to a sample obtained using apheresis.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, cancers treated by the methods described herein include multiple myeloma, Hodgkin's lymphoma or non-Hodgkin's lymphoma.

The terms "tumor" and "cancer" are used interchangeably herein, for example, both terms encompass solid and liquid, for example, diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, for example, it does not mean that, to provide the intracellular signaling domain, one must start with a CD3zeta sequence and delete unwanted sequence, or impose mutations, to arrive at the intracellular signaling domain.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative substitutions are ones in which the amino acid residue is replaced with an amino acid residue having a similar side chain. Families of amino acid residues having similar side chains have been defined in the art. These families include amino acids with basic side chains (for example, lysine, arginine, histidine), acidic side chains (for example, aspartic acid, glutamic acid), uncharged polar side chains (for example, glycine, asparagine, glutamine, serine, threonine, tyrosine, cysteine, tryptophan), nonpolar side chains (for example, alanine, valine, leucine, isoleucine, proline, phenylalanine, methionine), beta-branched side chains (for example, threonine, valine, isoleucine) and aromatic side chains (for example, tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation" in the context of stimulation by a stimulatory and/or costimulatory molecule refers to a response, for example, a primary or secondary response, induced by binding of a stimulatory molecule (for example, a TCR/CD3 complex) and/or a costimulatory molecule (for example, CD28 or 4-1BB) with its cognate ligand thereby mediating a signal transduction event, such as, but not limited to, signal transduction via the TCR/CD3 complex. Stimulation can mediate altered expression of certain molecules and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In some embodiments, the ITAM-containing domain within the CAR recapitulates the signaling of the primary TCR independently of endogenous TCR complexes. In some embodiments, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI and CD66d, DAP10 and DAP12. In a specific CAR of the invention, the intracellular signaling domain in any one or more CARS of the invention comprises an intracellular signaling sequence, for example, a primary signaling sequence of CD3-zeta. The term "antigen presenting cell" or "APC" refers to an immune system cell such as an accessory cell (for example, a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular signaling domain generates a signal that promotes an immune effector function of the CAR containing cell, for example, a CART cell. Examples of immune effector function, for example, in a CART cell, include cytolytic activity and helper activity, including the secretion of cytokines.

In some embodiments, the intracellular signaling domain can comprise a primary intracellular signaling domain. Exemplary primary intracellular signaling domains include those derived from the molecules responsible for primary stimulation, or antigen dependent simulation. In some embodiments, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 (also known as "ICOS"), FcεRI, CD66d, DAP10 and DAP12.

The term "zeta" or alternatively "zeta chain", "CD3-zeta" or "TCR-zeta" refers to CD247. Swiss-Prot accession number P20963 provides exemplary human CD3 zeta amino acid sequences. A "zeta stimulatory domain" or alternatively a "CD3-zeta stimulatory domain" or a "TCR-zeta stimulatory domain" refers to a stimulatory domain of CD3-zeta or a variant thereof (for example, a molecule having mutations, for example, point mutations, fragments, insertions, or deletions). In some embodiments, the cytoplasmic domain of zeta comprises residues 52 through 164 of GenBank Acc. No. BAG36664.1 or a variant thereof (for example, a molecule having mutations, for example, point mutations, fragments, insertions, or deletions). In some embodiments, the "zeta stimulatory domain" or a "CD3-zeta stimulatory domain" is the sequence provided as SEQ ID NO: 9 or 10, or a variant thereof (for example, a molecule having mutations, for example, point mutations, fragments, insertions, or deletions).

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, TNF receptor proteins, Immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, and a ligand that specifically binds with CD83.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

The term "4-1BB" refers to CD137 or Tumor necrosis factor receptor superfamily member 9. Swiss-Prot accession number P20963 provides exemplary human 4-1BB amino acid sequences. A "4-1BB costimulatory domain" refers to a costimulatory domain of 4-1BB, or a variant thereof (for example, a molecule having mutations, for example, point mutations, fragments, insertions, or deletions). In some embodiments, the "4-1BB costimulatory domain" is the sequence provided as SEQ ID NO: 7 or a variant thereof (for example, a molecule having mutations, for example, point mutations, fragments, insertions, or deletions).

"Immune effector cell," as that term is used herein, refers to a cell that is involved in an immune response, for example, in the promotion of an immune effector response. Examples of immune effector cells include T cells, for example, alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, for example, of an immune effector cell, that enhances or promotes an immune attack of a target cell. For example, an immune effector function or response refers a property of a T or NK cell that promotes killing or the inhibition of growth or proliferation, of a target cell. In the case of a T cell, primary stimulation and costimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence. In some embodiments, expression comprises translation of an mRNA introduced into a cell.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (for example, naked or contained in liposomes) and viruses (for example, lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, for example, the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, for example, between two nucleic acid molecules, such as, two DNA molecules or two RNA molecules, or between two polypeptide molecules. When a subunit position in both of the two molecules is occupied by the same monomeric subunit; for example, if a position in each of two DNA molecules is occupied by adenine, then they are homologous or identical at that position. The homology between two sequences is a direct function of the number of matching or homologous positions; for example, if half (for example, five positions in a polymer ten subunits in length) of the positions in two sequences are homologous, the two sequences are 50% homologous; if 90% of the positions (for example, 9 of 10), are matched or homologous, the two sequences are 90% homologous.

"Humanized" forms of non-human (for example, murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, for example, where necessary to join two protein coding regions, are in the same reading frame.

The term "parenteral" administration of an immunogenic composition includes, for example, subcutaneous (s.c.), intravenous (i.v.), intramuscular (i.m.), or intrasternal injection, intratumoral, or infusion techniques.

The term "nucleic acid," "nucleic acid molecule," "polynucleotide," or "polynucleotide molecule" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. In some embodiments, a "nucleic acid," "nucleic acid molecule," "polynucleotide," or "polynucleotide molecule" comprise a nucleotide/nucleoside derivative or analog. Unless otherwise indicated, a particular nucleic acid sequence also implicitly encompasses conservatively modified variants thereof (for example, degenerate codon substitutions, for example, conservative substitutions), alleles, orthologs, SNPs, and complementary sequences as well as the sequence explicitly indicated. Specifically, degenerate codon substitutions, for example, conservative substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen," "tumor antigen," "hyperproliferative disorder antigen," and "antigen associated with a hyperproliferative disorder" interchangeably refer to antigens that are common to specific hyperproliferative disorders. In some embodiments, these terms refer to a molecule (typically a protein, carbohydrate or lipid) that is expressed on the surface of a cancer cell, either entirely or as a fragment (for example, MHC/peptide), and which is useful for the preferential targeting of a pharmacological agent to the cancer cell. In some embodiments, a tumor antigen is a marker expressed by both normal cells and cancer cells, for example, a lineage marker, for example, CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (for example, MHC/peptide), and not synthesized or expressed on the surface of a normal cell. In some embodiments, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer (for example, castrate-resistant or therapy-resistant prostate cancer, or metastatic prostate cancer), ovarian cancer, pancreatic cancer, and the like, or a plasma cell proliferative disorder, for example, asymptomatic myeloma (smoldering multiple myeloma or indolent myeloma), monoclonal gammopathy of undetermined significance (MGUS), Waldenstrom's macroglobulinemia, plasmacytomas (for example, plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome). In some embodiments, the CARs of the present invention include CARs comprising an antigen binding domain (for example, antibody or antibody fragment) that binds to a MHC presented peptide. Normally, peptides derived from endogenous proteins fill the pockets of Major histocompatibility complex (MHC) class I molecules and are recognized by T cell receptors (TCRs) on CD8+T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, for example, Sastry et al., J Virol. 2011 85(5):1935-1942; Sergeeva et al., Blood, 2011 117(16): 4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, for example, by promoting their growth or survival for example, resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of an scFv refers to a peptide linker that consists of amino acids such as glycine and/or serine residues used alone or in combination, to link variable heavy and variable light chain regions together. In some embodiments, the flexible polypeptide linker is a Gly/Ser linker and comprises the amino acid sequence (Gly-Gly-Gly-Ser)n, where n is a positive integer equal to or greater than 1 (SEQ ID NO: 41). For example, n=1, n=2, n=3. n=4, n=5 and n=6, n=7, n=8, n=9 and n=10 In some embodiments, the flexible polypeptide linkers include, but are not limited to, (Gly4 Ser)4 (SEQ ID NO: 27) or (Gly4 Ser)3 (SEQ ID NO: 28). In some embodiments, the linkers include multiple repeats of (Gly2Ser), (GlySer) or (Gly3Ser) (SEQ ID NO: 29). Also included within the scope of the invention are linkers described in WO2012/138475, incorporated herein by reference.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA that has been synthesized in vitro. In some embodiments the RNA is mRNA. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In some embodiments of a construct for transient expression, the poly(A) is between 50 and 5000 (SEQ ID NO: 30). In some embodiments the poly(A) is greater than 64. In some embodiments the poly(A) is greater than 100. In some embodiments the poly(A) is greater than 300. In some embodiments the poly(A) is greater than 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (for example, one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, for example, stabilization of a discernible symptom, physiologically by, for example, stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (for example, mammals, for example, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In some embodiments, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (for example, a stimulatory and/or costimulatory molecule present on a T cell) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with intracellular signal generation. In some embodiments, an RCAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, for example, are in different polypeptide chains. In some embodiments, the RCAR includes a dimerization switch that, upon the presence of a dimerization molecule, can couple the polypeptides to one another, for example, can couple an antigen binding domain to an intracellular signaling domain. In some embodiments, the RCAR is expressed in a cell (for example, an immune effector cell) as described herein, for example, an RCAR-expressing cell (also referred to herein as "RCARX cell"). In some embodiments the RCARX cell is a T cell and is referred to as a RCART cell. In some embodiments the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, for example, a myristoyl group, sufficient to anchor an extracellular or intracellular domain to the plasma membrane.

"Switch domain," as that term is used herein, for example, when referring to an RCAR, refers to an entity, typically a polypeptide-based entity, that, in the presence of a dimerization molecule, associates with another switch domain. The association results in a functional coupling of a first entity linked to, for example, fused to, a first switch domain, and a second entity linked to, for example, fused to, a second switch domain. A first and second switch domain are collectively referred to as a dimerization switch. In embodiments, the first and second switch domains are the same as one another, for example, they are polypeptides having the same primary amino acid sequence and are referred to collectively as a homodimerization switch. In embodiments, the first and second switch domains are different from one another, for example, they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, for example, FKBP or FRB-based, and the dimerization molecule is small molecule, for example, a rapalogue. In embodiments, the switch domain is a polypeptide-based entity, for example, an scFv that binds a myc peptide, and the dimerization molecule is a polypeptide, a fragment thereof, or a multimer of a polypeptide, for example, a myc ligand or multimers of a myc ligand that bind to one or more myc scFvs. In embodiments, the switch domain is a polypeptide-based entity, for example, myc receptor, and the dimerization molecule is an antibody or fragments thereof, for example, myc antibody.

"Dimerization molecule," as that term is used herein, for example, when referring to an RCAR, refers to a molecule that promotes the association of a first switch domain with a second switch domain. In embodiments, the dimerization molecule does not naturally occur in the subject or does not occur in concentrations that would result in significant dimerization. In embodiments, the dimerization molecule is a small molecule, for example, rapamycin or a rapalogue, for example, RAD001.

The term "low, immune enhancing, dose" when used in conjunction with an mTOR inhibitor, for example, an allosteric mTOR inhibitor, for example, RAD001 or rapamycin, or a catalytic mTOR inhibitor, refers to a dose of mTOR inhibitor that partially, but not fully, inhibits mTOR activity, for example, as measured by the inhibition of P70 S6 kinase activity. Methods for evaluating mTOR activity, for example, by inhibition of P70 S6 kinase, are discussed herein. The dose is insufficient to result in complete immune suppression but is sufficient to enhance the immune response. In some embodiments, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In some embodiments, the low, immune enhancing, dose of mTOR inhibitor results in an increase in the number of naive T cells. In some embodiments, the low, immune enhancing, dose of mTOR inhibitor results in one or more of the following:

- an increase in the expression of one or more of the following markers: CD62L$^{high}$ CD127$^{high}$ CD27$^{+}$, and BCL2, for example, on memory T cells, for example, memory T cell precursors;
- a decrease in the expression of KLRG1, for example, on memory T cells, for example, memory T cell precursors; and
- an increase in the number of memory T cell precursors, for example, cells with any one or combination of the following characteristics: increased CD62L$^{high}$ increased CD127$^{high}$, increased CD27+, decreased KLRG1, and increased BCL2;
- wherein any of the changes described above occurs, for example, at least transiently, for example, as compared to a non-treated subject.

"Refractory" as used herein refers to a disease, for example, cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or "relapse" as used herein refers to the return or reappearance of a disease (for example, cancer) or the signs and symptoms of a disease such as cancer after a period of improvement or responsiveness, for example, after prior treatment of a therapy, for example, cancer therapy. The initial period of responsiveness may involve the level of cancer cells falling below a certain threshold, for example, below 20%, 1%, 10%, 5%, 4%, 3%, 2%, or 1%. The reappearance may involve the level of cancer cells rising above a certain threshold, for example, above 20%, 1%, 10%, 5%, 4%, 3%, 2%, or 1%. For example, for example, in the context of B-ALL, the reappearance may involve, for example, a reappearance of blasts in the blood, bone marrow (>5%), or any extramedullary site, after a complete response. A complete response, in this context, may involve <5% BM blast. More generally, in some embodiments, a response (for example, complete response or partial response) can involve the absence of detectable MRD (minimal residual disease). In some embodiments, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

Ranges: throughout this disclosure, various embodiments of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

A "gene editing system" as the term is used herein, refers to a system, for example, one or more molecules, that direct and effect an alteration, for example, a deletion, of one or more nucleic acids at or near a site of genomic DNA targeted by said system. Gene editing systems are known in the art and are described more fully below.

Administered "in combination", as used herein, means that two (or more) different treatments are delivered to the subject during the course of the subject's affliction with the disorder, for example, the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, for example, an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The term "depletion" or "depleting", as used interchangeably herein, refers to the decrease or reduction of the level or amount of a cell, a protein, or macromolecule in a sample after a process, for example, a selection step, for example, a negative selection, is performed. The depletion can be a complete or partial depletion of the cell, protein, or macromolecule. In some embodiments, the depletion is at least a 1%, 2%, 5%, 10%, 15%, 20%, 25%, 30%, 35%, 40%, 45%, 50%, 55%, 60%, 65%, 70%, 75%, 80%, 85%, 90%, 95%, or 99% decrease or reduction of the level or amount of a cell, a protein, or macromolecule, as compared to the level or amount of the cell, protein or macromolecule in the sample before the process was performed.

As used herein, a "naïve T cell" refers to a T cell that is antigen-inexperienced. In some embodiments, an antigen-inexperienced T cell has encountered its cognate antigen in the thymus but not in the periphery. In some embodiments, naïve T cells are precursors of memory cells. In some embodiments, naïve T cells express both CD45RA and CCR7, but do not express CD45RO. In some embodiments, naïve T cells may be characterized by expression of CD62L, CD27, CCR7, CD45RA, CD28, and CD127, and the absence of CD95 or CD45RO isoform. In some embodiments, naïve T cells express CD62L, IL-7 receptor-α, IL-6 receptor, and CD132, but do not express CD25, CD44, CD69, or CD45RO. In some embodiments, naïve T cells express CD45RA, CCR7, and CD62L and do not express CD95 or IL-2 receptor β. In some embodiments, surface expression levels of markers are assessed using flow cytometry.

The term "central memory T cells" refers to a subset of T cells that in humans are CD45RO positive and express CCR7. In some embodiments, central memory T cells express CD95. In some embodiments, central memory T cells express IL-2R, IL-7R and/or IL-15R. In some embodiments, central memory T cells express CD45RO, CD95, IL-2 receptor β, CCR7, and CD62L. In some embodiments, surface expression levels of markers are assessed using flow cytometry.

The term "stem memory T cells," "stem cell memory T cells," "stem cell-like memory T cells," "memory stem T cells," "T memory stem cells," "T stem cell memory cells" or "TSCM cells" refers to a subset of memory T cells with stem cell-like ability, for example, the ability to self-renew and/or the multipotent capacity to reconstitute memory and/or effector T cell subsets. In some embodiments, stem memory T cells express CD45RA, CD95, IL-2 receptor R, CCR7, and CD62L. In some embodiments, surface expression levels of markers are assessed using flow cytometry. In some embodiments, exemplary stem memory T cells are disclosed in Gattinoni et al., Nat Med. 2017 Jan. 6; 23(1): 18-27, herein incorporated by reference in its entirety.

For clarity purposes, unless otherwise noted, classifying a cell or a population of cells as "not expressing," or having an "absence of" or being "negative for" a particular marker may not necessarily mean an absolute absence of the marker. The skilled artisan can readily compare the cell against a positive and/or a negative control, and/or set a predetermined threshold, and classify the cell or population of cells as not expressing or being negative for the marker when the cell has an expression level below the predetermined threshold or a population of cells has an overall expression level below the predetermined threshold using conventional detection methods, e.g., using flow cytometry, for example, as described in the Examples herein.

As used herein, the term "GeneSetScore (Up TEM vs. Down TSCM)" of a cell refers to a score that reflects the degree at which the cell shows an effector memory T cell (TEM) phenotype vs. a stem cell memory T cell (TSCM) phenotype. A higher GeneSetScore (Up TEM vs. Down TSCM) indicates an increasing TEM phenotype, whereas a lower GeneSetScore (Up TEM vs. Down TSCM) indicates an increasing TSCM phenotype. In some embodiments, the GeneSetScore (Up TEM vs. Down TSCM) is determined by measuring the expression of one or more genes that are up-regulated in TEM cells and/or down-regulated in TSCM cells, for example, one or more genes selected from the group consisting of MXRA7, CLIC1, NAT13, TBC1D2B, GLCCI1, DUSP10, APOBEC3D, CACNB3, ANXA2P2, TPRG1, EOMES, MATK, ARHGAP10, ADAM8, MAN1A1, SLFN12L, SH2D2A, EIF2C4, CD58, MYO1F, RAB27B, ERN1, NPC1, NBEAL2, APOBEC3G, SYTL2, SLC4A4, PIK3AP1, PTGDR, MAF, PLEKHA5, ADRB2, PLXND1, GNAO1, THBS1, PPP2R2B, CYTH3, KLRF1, FLJ16686, AUTS2, PTPRM, GNLY, and GFPT2. In some embodiments, the GeneSetScore (Up TEM vs. Down TSCM) is determined for each cell using RNA-seq, for example, single-cell RNA-seq (scRNA-seq), for example, as exemplified in Example 7 with respect to FIG. 25A. In some embodiments, the GeneSetScore (Up TEM vs. Down TSCM) is calculated by taking the mean log normalized gene expression value of all of the genes in the gene set.

As used herein, the term "GeneSetScore (Up Treg vs. Down Teff)" of a cell refers to a score that reflects the degree at which the cell shows a regulatory T cell (Treg) phenotype vs. an effector T cell (Teff) phenotype. A higher GeneSetScore (Up Treg vs. Down Teff) indicates an increasing Treg phenotype, whereas a lower GeneSetScore (Up Treg vs. Down Teff) indicates an increasing Teff phenotype. In some embodiments, the GeneSetScore (Up Treg vs. Down Teff) is determined by measuring the expression of one or more genes that are up-regulated in Treg cells and/or down-regulated in Teff cells, for example, one or more genes selected from the group consisting of C12orf75, SELPLG, SWAP70, RGS1, PRR11, SPATS2L, SPATS2L, TSHR, C14orf145, CASP8, SYT11, ACTN4, ANXA5, GLRX, HLA-DMB, PMCH, RAB1IFIP1, IL32, FAM160B1, SHMT2, FRMD4B, CCR3, TNFRSF13B, NTNG2, CLDND1, BARD1, FCER1G, TYMS, ATP1B1, GJB6, FGL2, TK1, SLC2A8, CDKN2A, SKAP2, GPR55, CDCA7, S100A4, GDPD5, PMAIP1, ACOT9, CEP55, SGMS1, ADPRH, AKAP2, HDAC9, IKZF4, CARD17, VAV3, OBFC2A, ITGB1, CIITA, SETD7, HLA-DMA, CCR10, KIAA0101, SLC14A1, PTTG3P, DUSP10, FAM164A, PYHINI, MYO1F, SLC1A4, MYBL2, PTTG1, RRM2, TP53INP1, CCR5, ST8SIA6, TOX, BFSP2, ITPRIPL1, NCAPH, HLA-DPB2, SYT4, NINJ2, FAM46C, CCR4, GBP5, C15orf53, LMCD1, MKI67, NUSAP1, PDE4A, E2F2, CD58, ARHGEF12, LOC100188949, FAS, HLA-DPB1, SELP, WEE1, HLA-DPA1, FCRL1, ICA1, CNTNAP1, OAS1, METTL7A, CCR6, HLA-DRB4, ANXA2P3, STAM, HLA-DQB2, LGALS1, ANXA2, P116, DUSP4, LAYN, ANXA2P2, PTPLA, ANXA2P1, ZNF365, LAIR2, LOC541471, RASGRP4, BCAS1, UTS2, MIAT, PRDM1, SEMA3G, FAM129A, HPGD, NCF4, LGALS3, CEACAM4, JAKMIP1, TIGIT, HLA-DRA, IKZF2, HLA-DRB1, FANK1, RTKN2, TRIB1, FCRL3, and FOXP3. In some embodiments, the GeneSetScore (Up Treg vs. Down Teff) is determined using RNA-seq, for example, single-cell RNA-seq (scRNA-seq), for example, as exemplified in Example 7 with respect to FIG. 25B. In some embodiments, the GeneSetScore (Up Treg vs. Down Teff) is calculated by taking the mean log normalized gene expression value of all of the genes in the gene set.

As used herein, the term "GeneSetScore (Down stemness)" of a cell refers to a score that reflects the degree at which the cell shows a stemness phenotype. A lower GeneSetScore (Down stemness) indicates an increasing stemness phenotype. In some embodiments, the GeneSetScore (Down sternness) is determined by measuring the expression of one or more genes that are upregulated in a differentiating stem cell vs downregulated in a hematopoietic stem cell, for example, one or more genes selected from the group consisting of ACE, BATF, CDK6, CHD2, ERCC2, HOXB4, MEOX1, SFRP1, SP7, SRF, TAL1, and XRCC5. In some embodiments, the GeneSetScore (Down stemness) is determined using RNA-seq, for example, single-cell RNA-seq (scRNA-seq), for example, as exemplified in Example 7 with respect to FIG. 25C. In some embodiments, the GeneSetScore (Down stemness) is calculated by taking the mean log normalized gene expression value of all of the genes in the gene set.

As used herein, the term "GeneSetScore (Up hypoxia)" of a cell refers to a score that reflects the degree at which the cell shows a hypoxia phenotype. A higher GeneSetScore (Up hypoxia) indicates an increasing hypoxia phenotype. In some embodiments, the GeneSetScore (Up hypoxia) is determined by measuring the expression of one or more genes that are up-regulated in cells undergoing hypoxia, for example, one or more genes selected from the group consisting of ABCB1, ACAT1, ADM, ADORA2B, AK2, AK3, ALDH1A1, ALDH1A3, ALDOA, ALDOC, ANGPT2, ANGPTL4, ANXA1, ANXA2, ANXA5, ARHGAP5, ARSE, ART1, BACE2, BATF3, BCL2L1, BCL2L2, BHLHE40, BHLHE41, BIK, BIRC2, BNIP3, BNIP3L, BPI, BTG1, C11orf2, C7orf68, CA12, CA9, CALD1, CCNG2, CCT6A, CD99, CDK1, CDKN1A, CDKN1B, CITED2, CLK1, CNOT7, COL4A5, COL5A1, COL5A2, COL5A3, CP, CTSD, CXCR4, D4S234E, DDIT3, DDIT4, 1-Dec, DKC1, DR1, EDN1, EDN2, EFNA1, EGF, EGR1, EIF4A3, ELF3, ELL2, ENG, ENO1, ENO3, ENPEP, EPO, ERRFI1, ETS1, F3, FABP5, FGF3, FKBP4, FLT1, FN1, FOS, FTL, GAPDH, GBE1, GLRX, GPI, GPRC5A, HAPI, HBP1, HDAC1, HDAC9, HERC3, HERPUD1, HGF, HIF1A, HK1, HK2, HLA-DQB1, HMOX1, HMOX2, HSPA5, HSPD1, HSPH1, HYOU1, ICAM1, ID2, IFI27, IGF2, IGFBP1, IGFBP2, IGFBP3, IGFBP5, IL6, IL8, INSIG1, IRF6, ITGA5, JUN, KDR, KRT14, KRT18, KRT19, LDHA, LDHB, LEP, LGALS1, LONP1, LOX, LRP1, MAP4, MET, MIF, MMP13, MMP2, MMP7, MPI, MT1L, MTL3P, MUC1, MXII, NDRG1, NFIL3, NFKB1, NFKB2, NOS1, NOS2, NOS2P1, NOS2P2, NOS3, NR3C1, NR4A1, NT5E, ODC1, P4HA1, P4HA2, PAICS, PDGFB, PDK3, PFKFB1, PFKFB3, PFKFB4, PFKL, PGAM1, PGF, PGK1, PGK2, PGM1, PIM1, PIM2, PKM2, PLAU, PLAUR, PLIN2, PLOD2, PNN, PNP, POLM, PPARA, PPAT, PROK1, PSMA3, PSMD9, PTGS1, PTGS2, QSOX1, RBPJ, RELA, RIOK3, RNASEL, RPL36A, RRP9, SAT1, SERPINB2, SERPINE1, SGSM2, SIAH2, SIN3A, SIRPA, SLC16A1, SLC16A2, SLC20A1, SLC2A1, SLC2A3, SLC3A2, SLC6A10P, SLC6A16, SLC6A6, SLC6A8, SORL1, SPP1, SRSF6, SSSCA1, STC2, STRA13, SYT7, TBPL1, TCEAL1, TEK, TF, TFF3, TFRC, TGFA, TGFB1, TGFB3, TGFBI, TGM2, TH, THBS1, THBS2, TIMM17A, TNFAIP3, TP53, TPBG, TPD52, TPI1, TXN, TXNIP, UMPS, VEGFA, VEGFB, VEGFC, VIM, VPS11, and XRCC6. In some embodiments, the GeneSetScore (Up hypoxia) is determined using RNA-seq, for example, single-cell RNA-seq (scRNA-seq), for example, as exemplified in Example 7 with respect to FIG. 25D. In some embodiments, the GeneSetScore (Up hypoxia) is calculated by taking the mean log normalized gene expression value of all of the genes in the gene set.

As used herein, the term "GeneSetScore (Up autophagy)" of a cell refers to a score that reflects the degree at which the cell shows an autophagy phenotype. A higher GeneSetScore (Up autophagy) indicates an increasing autophagy phenotype. In some embodiments, the GeneSetScore (Up autophagy) is determined by measuring the expression of one or more genes that are up-regulated in cells undergoing autophagy, for example, one or more genes selected from the group consisting of ABL1, ACBD5, ACIN1, ACTRT1, ADAMTS7, AKR1E2, ALKBH5, ALPK1, AMBRA1, ANXA5, ANXA7, ARSB, ASB2, ATG10, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATP13A2, ATP1B1, ATPAF1-AS1, ATPIF1, BECN1, BECN1P1, BLOC1S1, BMP2KL, BNIP1, BNIP3, BOC, C11orf2, C11orf41, Cl2orf44, C12orf5, Cl4orf133, C1orf210, C5, C6orf106, C7orf59, C7orf68, C8orf59, C9orf72, CA7, CALCB, CALCOCO2, CAPS, CCDC36, CD163L1, CD93, CDC37, CDKN2A, CHAF1B, CHMP2A, CHMP2B, CHMP3, CHMP4A, CHMP4B, CHMP4C, CHMP6, CHST3, CISD2, CLDN7, CLEC16A, CLN3, CLVS1, COX8A, CPA3, CRNKL1, CSPG5, CTSA, CTSB, CTSD, CXCR7, DAP, DKKL1, DNAAF2, DPF3, DRAM1, DRAM2, DYNLL1, DYNLL2, DZANK1, EI24, EIF2S1, EPG5, EPM2A, FABP1, FAM125A, FAM131B, FAM134B, FAM13B, FAM176A, FAM176B, FAM48A, FANCC, FANCF, FANCL, FBXO7, FCGR3B, FGF14, FGF7, FGFBP1, FIS1, FNBP1L, FOXO1, FUNDC1, FUNDC2, FXR2, GABARAP, GABARAPL1, GABARAPL2, GABARAPL3, GABRA5, GDF5, GMIP, HAP1, HAPLN1, HBXIP, HCAR1, HDAC6, HGS, HIST1H3A, HIST1H3B, HIST1H3C, HIST1H3D, HIST1H3E, HIST1H3F, HIST1H3G, HIST1H3H, HIST1H3I, HIST1H3J, HK2, HMGB1, HPR, HSF2BP, HSP90AA1, HSPA8, IFI16, IPPK, IRGM, IST1, ITGB4, ITPKC, KCNK3, KCNQ1, KIAA0226, KIAA1324, KRCC1, KRT15, KRT73, LAMPI, LAMP2, LAMTOR1, LAMTOR2, LAMTOR3, LARPIB, LENG9, LGALS8, LIX1, LIX1L, LMCD1, LRRK2, LRSAM1, LSM4, MAP1A, MAP1LC3A, MAP1LC3B, MAP1LC3B2, MAP1LC3C, MAP1S, MAP2K1, MAP3K12, MARK2, MBD5, MDH1, MEX3C, MFN1, MFN2, MLST8, MRPS10, MRPS2, MSTN, MTERFD1, MTMR14, MTMR3, MTOR, MTSS1, MYH11, MYLK, MYOM1, NBR1, NDUFB9, NEFM, NHLRC1, NME2, NPC1, NR2C2, NRBF2, NTHL1, NUP93, OBSCN, OPTN, P2RX5, PACS2, PARK2, PARK7, PDK1, PDK4, PEX13, PEX3, PFKP, PGK2, PHF23, PHYHIP, PI4K2A, PIK3C3, PIK3CA, PIK3CB, PIK3R4, PINK1, PLEKHM1, PLOD2, PNPO, PPARGC1A, PPY, PRKAA1, PRKAA2, PRKAB1, PRKAB2, PRKAG1, PRKAG2, PRKAG3, PRKD2, PRKG1, PSEN1, PTPN22, RAB12, RAB1A, RAB1B, RAB23, RAB24, RAB33B, RAB39, RAB7A, RB1CC1, RBM18, REEP2, REP15, RFWD3, RGS19, RHEB, RIMS3, RNF185, RNF41, RPS27A, RPTOR, RRAGA, RRAGB, RRAGC, RRAGD, S100A8, S100A9, SCN1A, SERPINB10, SESN2, SFRP4, SH3GLB1, SIRT2, SLC1A3, SLC1A4, SLC22A3, SLC25A19, SLC35B3, SLC35C1, SLC37A4, SLC6A1, SLCO1A2, SMURF1, SNAP29, SNAPIN, SNF8, SNRPB, SNRPB2, SNRPD1, SNRPF, SNTG1, SNX14, SPATA18, SQSTM1, SRPX, STAM, STAM2, STAT2, STBD1, STK11, STK32A, STOM, STX12, STX17, SUPT3H, TBC1D17, TBC1D25, TBC1D5, TCIRG1, TEAD4, TECPR1, TECPR2, TFEB, TM9SF1, TMBIM6, TMEM203, TMEM208, TMEM39A, TMEM39B, TMEM59, TMEM74, TMEM93, TNIK, TOLLIP, TOMM20, TOMM22, TOMM40, TOMM5, TOMM6, TOMM7, TOMM70A, TP53INP1, TP53INP2, TRAPPC8, TREM1, TRIM17, TRIMS, TSG101, TXLNA, UBA52, UBB, UBC, UBQLN1, UBQLN2, UBQLN4, ULK1, ULK2, ULK3, USP10, USP13, USP30, UVRAG, VAMP7, VAMP8, VDAC1, VMP1, VPS11, VPS16, VPS18, VPS25, VPS28, VPS33A, VPS33B, VPS36, VPS37A, VPS37B, VPS37C, VPS37D, VPS39, VPS41, VPS4A, VPS4B, VTA1, VTI1A, VTI1B, WDFY3, WDR45, WDR45L, WIPI1, WIPI2, XBP1, YIPF1, ZCCHC17, ZFYVE1, ZKSCAN3, ZNF189, ZNF593, and ZNF681. In some embodiments, the GeneSetScore (Up autophagy) is determined using RNA-seq, for example, single-cell RNA-seq (scRNA-seq), for example, as exemplified in Example 7 with respect to FIG. 25E. In some embodiments, the GeneSetScore (Up autophagy) is calculated by taking the mean log normalized gene expression value of all of the genes in the gene set.

As used herein, the term "GeneSetScore (Up resting vs. Down activated)" of a cell refers to a score that reflects the degree at which the cell shows a resting T cell phenotype vs. an activated T cell phenotype. A higher GeneSetScore (Up resting vs. Down activated) indicates an increasing resting T cell phenotype, whereas a lower GeneSetScore (Up resting vs. Down activated) indicates an increasing activated T cell phenotype. In some embodiments, the GeneSetScore (Up resting vs. Down activated) is determined by measuring the expression of one or more genes that are up-regulated in resting T cells and/or down-regulated in activated T cells, for example, one or more genes selected from the group consisting of ABCA7, ABCF3, ACAP2, AMT, ANKH, ATF7IP2, ATG14, ATP1A1, ATXN7, ATXN7L3B, BCL7A, BEX4, BSDC1, BTG1, BTG2, BTN3A1, C11orf21, C19orf22, C21orf2, CAMK2G, CARS2, CCNL2, CD248, CD5, CD55, CEP164, CHKB, CLK1, CLK4, CTSL1, DBP, DCUN1D2, DENND1C, DGKD, DLG1, DUSP1, EAPP, ECE1, ECHDC2, ERBB2IP, FAM117A, FAM134B, FAM134C, FAM169A, FAM190B, FAU, FLJ10038, FOXJ2, FOXJ3, FOXL1, FOXO1, FXYD5, FYB, HLA-E, HSPA1L, HYAL2, ICAM2, IFIT5, IFITM1, IKBKB, IQSEC1, IRS4, KIAA0664L3, KIAA0748, KLF3, KLF9, KRT18, LEF1, LINC00342, LIPA, LIPT1, LLGL2, LMBR1L, LPAR2, LTBP3, LYPD3, LZTFL1, MANBA, MAP2K6, MAP3K1, MARCH8, MAU2, MGEA5, MMP8, MPO, MSL1, MSL3, MYH3, MYLIP, NAGPA, NDST2, NISCH, NKTR, NLRP1, NOSIP, NPIP, NUMA1, PAIP2B, PAPD7, PBXIP1, PCIF1, PI4KA, PLCL2, PLEKHA1, PLEKHF2, PNISR, PPFIBP2, PRKCA, PRKCZ, PRKD3, PRMT2, PTP4A3, PXN, RASA2, RASA3, RASGRP2, RBM38, REPIN1, RNF38, RNF44, ROR1, RPL30, RPL32, RPLP1, RPS20, RPS24, RPS27, RPS6, RPS9, RXRA, RYK, SCAND2, SEMA4C, SETD1B, SETD6, SETX, SF3B1, SH2B1, SLC2A4RG, SLC35E2B, SLC46A3, SMAGP, SMARCE1, SMPD1, SNPH, SP140L, SPATA6, SPG7, SREK1IP1, SRSF5, STAT5B, SVIL, SYF2, SYNJ2BP, TAF1C, TBC1D4, TCF20, TECTA, TES, TMEM127, TMEM159, TMEM30B, TMEM66, TMEM8B, TP53TG1, TPCN1, TRIM22, TRIM44, TSC1, TSC22D1, TSC22D3, TSPYL2, TTC9, TTN, UBE2G2, USP33, USP34, VAMP1, VILL, VIPR1, VPS13C, ZBED5, ZBTB25, ZBTB40, ZC3H3, ZFPI61, ZFP36L1, ZFP36L2, ZHX2, ZMYM5, ZNF136, ZNF148, ZNF318, ZNF350, ZNF512B, ZNF609, ZNF652, ZNF83, ZNF862, and ZNF91. In some embodiments, the GeneSetScore (Up resting vs. Down activated) is determined using RNA-seq, for example, single-cell RNA-seq (scRNA-seq), for example, as exemplified in Example 7 with respect to FIG. 24D. In some embodiments, the GeneSetScore (Up resting vs. Down activated) is calculated by taking the mean log normalized gene expression value of all of the genes in the gene set.

As used herein, the term "GeneSetScore (Progressively up in memory differentiation)" of a cell refers to a score that reflects the stage of the cell in memory differentiation. A higher GeneSetScore (Progressively up in memory differentiation) indicates an increasing late memory T cell phenotype, whereas a lower GeneSetScore (Progressively up in memory differentiation) indicates an increasing early memory T cell phenotype. In some embodiments, the GeneSetScore (Up autophagy) is determined by measuring the expression of one or more genes that are up-regulated during memory differentiation, for example, one or more genes selected from the group consisting of MTCH2, RAB6C, KIAA0195, SETD2, C2orf24, NRD1, GNA13, COPA, SELT, TNIP1, CBFA2T2, LRP10, PRKCI, BRE, ANKS1A, PNPLA6, ARL6IP1, WDFY1, MAPK1, GPR153, SHKBP1, MAP1LC3B2, PIP4K2A, HCN3, GTPBP1, TLN1, C4orf34, KIF3B, TCIRG1, PPP3CA, ATG4D, TYMP, TRAF6, C17orf76, WIPF1, FAM108A1, MYL6, NRM, SPCS2, GGT3P, GALKI, CLIP4, ARL4C, YWHAQ, LPCAT4, ATG2A, IDS, TBC1D5, DMPK, ST6GALNAC6, REEP5, ABHD6, KIAA0247, EMB, TSEN54, SPIRE2, PIWIL4, ZSCAN22, ICAM1, CHD9, LPIN2, SETD8, ZC3H12A, ULBP3, IL15RA, HLA-DQB2, LCP1, CHP, RUNX3, TMEM43, REEP4, MEF2D, ABL1, TMEM39A, PCBP4, PLCD1, CHST12, RASGRP1, C1orf58, C11orf63, C6orf129, FHOD1, DKFZp434F142, PIK3CG, ITPR3, BTG3, C4orf50, CNNM3, IFI16, AK1, CDK2AP1, REL, BCL2L1, MVD, TTC39C, PLEKHA2, FKBP11, EML4, FANCA, CDCA4, FUCA2, MFSD10, TBCD, CAPN2, IQGAP1, CHST11, PIK3R1, MYOSA, KIR2DL3, DLG3, MXD4, RALGD5, S1PR5, WSB2, CCR3, TIPARP, SP140, CD151, SOX13, KRTAP5-2, NF1, PEA15, PARP8, RNF166, UEVLD, LIMK1, CACNB1, TMX4, SLC6A6, LBA1, SV2A, LLGL2, IRF1, PPP2R5C, CD99, RAPGEF1, PPP4R1, OSBPL7, FOXP4, SLA2, TBC1D2B, ST7, JAZF1, GGA2, PI4K2A, CD68, LPGAT1, STX11, ZAK, FAM160B1, RORA, C8orf80, APOBEC3F, TGFBI, DNAJC1, GPR114, LRP8, CD69, CMIP, NAT13, TGFB1, FLJ00049, ANTXR2, NR4A3, IL12RB1, NTNG2, RDX, MLLT4, GPRIN3, ADCY9, CD300A, SCD5, ABI3, PTPN22, LGALS1, SYTL3, BMPR1A, TBK1, PMAIP1, RASGEF1A, GCNT1, GABARAPL1, STOM, CALHM2, ABCA2, PPP1R16B, SYNE2, PAM, C12orf75, CLCF1, MXRA7, APOBEC3C, CLSTN3, ACOT9, HIP1, LAG3, TNFAIP3, DCBLD1, KLF6, CACNB3, RNF19A, RAB27A, FADS3, DLG5, APOBEC3D, TNFRSF1B, ACTN4, TBKBP1, ATXN1, ARAP2, ARHGEF12, FAM53B, MAN1A1, FAM38A, PLXNC1, GRLF1, SRGN, HLA-DRB5, B4GALT5, WIPI1, PTPRJ, SLFN11, DUSP2, ANXA5, AHNAK, NEO1, CLIC1, EIF2C4, MAP3K5, IL2RB, PLEKHG1, MYO6, GTDC1, EDARADD, GALM, TARP, ADAM8, MSC, HNRPLL, SYT11, ATP2B4, NHSL2, MATK, ARHGAP18, SLFN12L, SPATS2L, RAB27B, PIK3R3, TP53INP1, MBOAT1, GYG1, KATNAL1, FAM46C, ZC3HAV1L, ANXA2P2, CTNNA1, NPC1, C3AR1, CRIM1, SH2D2A, ERN1, YPEL1, TBX21, SLC1A4, FASLG, PHACTR2, GALNT3, ADRB2, PIK3AP1, TLR3, PLEKHA5, DUSP10, GNAO1, PTGDR, FRMD4B, ANXA2, EOMES, CADM1, MAF, TPRG1, NBEAL2, PPP2R2B, PELO, SLC4A4, KLRF1, FOSL2, RGS2, TGFBR3, PRF1, MYO1F, GAB3, C17orf66, MICAL2, CYTH3, TOX, HLA-DRA, SYNE1, WEE1, PYHINI, F2R, PLD1, THBS1, CD58, FAS, NETO2, CXCR6, ST6GALNAC2, DUSP4, AUTS2, C1orf2l, KLRG1, TNIP3, GZMA, PRR5L, PRDM1, ST8SIA6, PLXND1, PTPRM, GFPT2, MYBL1, SLAMF7, FLJ16686, GNLY, ZEB2, CST7, ILI8RAP, CCL5, KLRD1, and KLRB1. In some embodiments, the GeneSetScore (Progressively up in memory differentiation) is determined using RNA-seq, for example, single-cell RNA-seq (scRNA-seq), for example, as exemplified in Example 7 with respect to FIG. 26B. In some embodiments, the GeneSetScore (Progressively up in memory differentiation) is calculated by taking the mean log normalized gene expression value of all of the genes in the gene set.

As used herein, the term "GeneSetScore (Up TEM vs. Down TN)" of a cell refers to a score that reflects the degree at which the cell shows an effector memory T cell (TEM) phenotype vs. a naïve T cell (TN) phenotype. A higher GeneSetScore (Up TEM vs. Down TN) indicates an increasing TEM phenotype, whereas a lower GeneSetScore (Up TEM vs. Down TN) indicates an increasing TN phenotype. In some embodiments, the GeneSetScore (Up TEM vs. Down TN) is determined by measuring the expression of one or more genes that are up-regulated in TEM cells and/or down-regulated in TN cells, for example, one or more genes selected from the group consisting of MYOSA, MXD4, STK3, S1PR5, GLCCI1, CCR3, SOX13, KRTAP5-2, PEA15, PARP8, RNF166, UEVLD, LIMK1, SLC6A6, SV2A, KPNA2, OSBPL7, ST7, GGA2, PI4K2A, CD68, ZAK, RORA, TGFBI, DNAJC1, JOSD1, ZFYVE28, LRP8, OSBPL3, CMIP, NAT13, TGFB1, ANTXR2, NR4A3, RDX, ADCY9, CHN1, CD300A, SCD5, PTPN22, LGALS1, RASGEF1A, GCNT1, GLUL, ABCA2, CLDND1, PAM, CLCF1, MXRA7, CLSTN3, ACOT9, METRNL, BMPR1A, LRIG1, APOBEC3G, CACNB3, RNF19A, RAB27A, FADS3, ACTN4, TBKBP1, FAM53B, MAN1A1, FAM38A, GRLF1, B4GALT5, WIPI1, DUSP2, ANXA5, AHNAK, CLIC1, MAP3K5, ST8SIA1, TARP, ADAM8, MATK, SLFN12L, PIK3R3, FAM46C, ANXA2P2, CTNNA1, NPC1, SH2D2A, ERN1, YPEL1, TBX21, STOM, PHACTR2, GBP5, ADRB2, PIK3AP1, DUSP10, PTGDR, EOMES, MAF, TPRG1, NBEAL2, NCAPH, SLC4A4, FOSL2, RGS2, TGFBR3, MYO1F, C17orf66, CYTH3, WEE1, PYHINI, F2R, THBS1, CD58, AUTS2, FAM129A, TNIP3, GZMA, PRR5L, PRDM1, PLXND1, PTPRM, GFPT2, MYBL1, SLAMF7, ZEB2, CST7, CCL5, GZMK, and KLRB1. In some embodiments, the GeneSetScore (Up TEM vs. Down TN) is determined using RNA-seq, for example, single-cell RNA-seq (scRNA-seq), for example, as exemplified in Example 7 with respect to FIG. 26C. In some embodiments, the GeneSetScore (Up TEM vs. Down TN) is calculated by taking the mean log normalized gene expression value of all of the genes in the gene set.

Figure 25A:
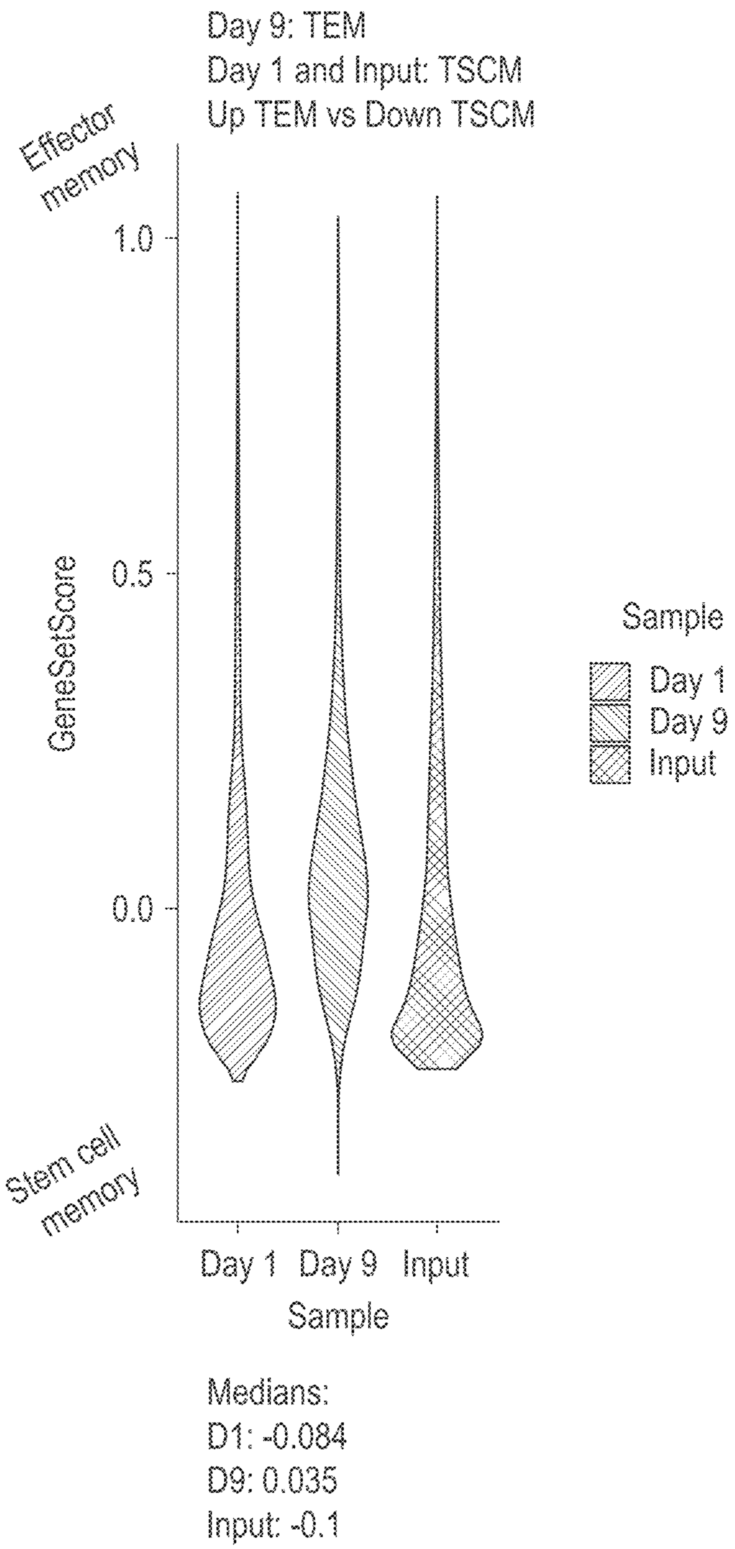
FIGS. 25A, 25B, 25C, 25D and 25E: Gene set analysis for input cells, Day 1 cells, and Day 9 cells.

In the context of GeneSetScore values (e.g., median GeneSetScore values), when a positive GeneSetScore is reduced by 100%, the value becomes 0. When a negative GeneSetScore is increased by 100%, the value becomes 0. For example, in FIG. 25A, the median GeneSetScore of the Day1 sample is −0.084; the median GeneSetScore of the Day9 sample is 0.035; and the median GeneSetScore of the input sample is −0.1. In FIG. 25A, increasing the median GeneSetScore of the input sample by 100% leads to a GeneSetScore value of 0; and increasing the median GeneSetScore of the input sample by 200% leads to a GeneSetScore value of 0.1. In FIG. 25A, decreasing the median GeneSetScore of the Day9 sample by 100% leads to a GeneSetScore value of 0; and decreasing the median GeneSetScore of the Day9 sample by 200% leads to a GeneSetScore value of −0.035.

As used herein, the term "bead" refers to a discrete particle with a solid surface, ranging in size from approximately 0.1 pm to several millimeters in diameter. Beads may be spherical (for example, microspheres) or have an irregular shape. Beads may comprise a variety of materials including, but not limited to, paramagnetic materials, ceramic, plastic, glass, polystyrene, methylstyrene, acrylic polymers, titanium, latex, Sepharose™, cellulose, nylon and the like. In some embodiments, the beads are relatively uniform, about 4.5 m in diameter, spherical, superparamagnetic polystyrene beads, for example, coated, for example, covalently coupled, with a mixture of antibodies against CD3 (for example, CD3 epsilon) and CD28. In some embodiments, the beads are Dynabeads®. In some embodiments, both anti-CD3 and anti-CD28 antibodies are coupled to the same bead, mimicking stimulation of T cells by antigen presenting cells. The property of Dynabeads® and the use of Dynabeads® for cell isolation and expansion are well known in the art, for example, see, Neurauter et al., *Cell isolation and expansion using Dynabeads*, Adv Biochem Eng Biotechnol. 2007; 106:41-73, herein incorporated by reference in its entirety.

As used herein, the term "nanomatrix" refers to a nanostructure comprising a matrix of mobile polymer chains. The nanomatrix is 1 to 500 nm, for example, 10 to 200 nm, in size. In some embodiments, the matrix of mobile polymer chains is attached to one or more agonists which provide activation signals to T cells, for example, agonist anti-CD3 and/or anti-CD28 antibodies. In some embodiments, the nanomatrix comprises a colloidal polymeric nanomatrix attached, for example, covalently attached, to an agonist of one or more stimulatory molecules and/or an agonist of one or more costimulatory molecules. In some embodiments, the agonist of one or more stimulatory molecules is a CD3 agonist (for example, an anti-CD3 agonistic antibody). In some embodiments, the agonist of one or more costimulatory molecules is a CD28 agonist (for example, an anti-CD28 agonistic antibody).

In some embodiments, the nanomatrix is characterized by the absence of a solid surface, for example, as the attachment point for the agonists, such as anti-CD3 and/or anti-CD28 antibodies. In some embodiments, the nanomatrix is the nanomatrix disclosed in WO2014/048920A1 or as given in the MACS® GMP T Cell TransAct™ kit from Miltenyi Biotec GmbH, herein incorporated by reference in their entirety. MACS® GMP T Cell TransAct™ consists of a colloidal polymeric nanomatrix covalently attached to humanized recombinant agonist antibodies against human CD3 and CD28.

Various embodiments of the compositions and methods herein are described in further detail below. Additional definitions are set out throughout the specification.

Description

Provided herein are compositions of matter and methods of use for the treatment of a disease such as cancer using cells expressing one or more chimeric antigen receptors (CARs). In some embodiments, the invention provides a cell (e.g., an immune effector cell, e.g., T cell or NK cell) engineered to express one or more CARs, wherein the CAR T cell ("CART") or CAR NK cell exhibits an antitumor property.

In some embodiments, the cell expresses at least two CARs. In some embodiments, the cell expresses a first CAR that binds to a first antigen and a second CAR that binds to a second antigen. In some embodiments, the first antigen and the second antigen are different. In some embodiments, the first antigen is BCMA. In some embodiments, the first CAR is an anti-BCMA CAR comprising a CDR, VH, VL, scFv, or CAR sequence disclosed herein, e.g., a sequence disclosed in Tables 3-15, 19, 20, 22, and 26, or an amino acid sequence having at least about 85%, 90%, 95%, or 99% sequence identity thereto, e.g., an anti-BCMA CAR disclosed herein. In some embodiments, the second antigen is CD19. In some embodiments, the second antigen is an anti-CD19 CAR comprising a CDR, VH, VL, scFv, or CAR sequence disclosed herein, e.g., a sequence disclosed in Tables 2, 19, and 22, or an amino acid sequence having at least about 85%, 90%, 95%, or 99% sequence identity thereto, e.g., an anti-CD19 CAR disclosed herein. In some embodiments, the first CAR and the second CAR are expressed by nucleic acid sequences disposed on a single nucleic acid molecule. In some embodiments, the nucleic acid sequence encoding the first CAR and the nucleic acid sequence encoding the second CAR are separated by a nucleic acid sequence encoding a self-cleavage site, e.g., a P2A site, a T2A site, an E2A site, or an F2A site. In some embodiments, the cell is a cell expressing dual CARs disclosed herein. In some embodiments, the first CAR and the second CAR are expressed by nucleic acid sequences disposed on separate nucleic acid molecules. In some embodiments, the cell is engineered using a co-transduction system disclosed herein.

In some embodiments, the cell expresses a CAR that binds to a first antigen and a second antigen. In some embodiments, the CAR is a diabody CAR disclosed herein. In some embodiments, the CAR comprises a binding domain that comprises a first VH (VH1), a first VL (VL1), a second VH (VH2), and a second VL (VL2). In some embodiments, the VH1 ad VL1 bind to a first antigen and the VH2 and VL2 bind to a second antigen. In some embodiments, the VH1, VL1, VH2, and VL2 are arranged in the following configuration from the N-terminus to the C-terminus: VH1-optionally linker 1 ("L1")-VH2-optionally linker 2 ("L2")-VL2-optionally linker 3 ("L3")-VL1, VH1-optionally L1-VL2-optionally L2-VH2-optionally L3-VL1, VL1-optionally L1-VH2-optionally L2-VL2-optionally L3-VH1, VL1-optionally L1-VL2-optionally L2-VH2-optionally L3-VH1, VH2-optionally L1-VH1-optionally L2-VL1-optionally L3-VL2, VH2-optionally L1-VL1-optionally L2-VH1-optionally L3-VL2, VL2-optionally L1-VH1-optionally L2-VL1-optionally L3-VH2; or VL2-optionally L1-VL1-optionally L2-VH1-optionally L3-VH2.

In some embodiments, the CARs of the invention combine an antigen binding domain with an intracellular signaling molecule. For example, in some embodiments, the intracellular signaling molecule includes, but is not limited to, CD3-zeta chain, 4-1BB and CD28 signaling modules and combinations thereof.

Furthermore, the present invention provides CAR compositions and their use in medicaments or methods for treating, among other diseases, cancer or any malignancy or autoimmune diseases.

Chimeric Antigen Receptor (CAR)

The present invention provides immune effector cells (for example, T cells or NK cells) that are engineered to contain one or more CARs that direct the immune effector cells to cancer. This is achieved through an antigen binding domain on the CAR that is specific for a cancer associated antigen. There are two classes of cancer associated antigens (tumor antigens) that can be targeted by the CARs described herein: (1) cancer associated antigens that are expressed on the surface of cancer cells; and (2) cancer associated antigens that themselves are intracellular, however, fragments (peptides) of such antigens are presented on the surface of the cancer cells by MHC (major histocompatibility complex).

Accordingly, an immune effector cell, for example, obtained by a method described herein, can be engineered to contain a CAR that targets one of the following cancer associated antigens (tumor antigens): CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, VEGFR2, LewisY, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, GPRC5D, CXORF61, CD97, CD179a, ALK, Plysialic acid, PLAC1, GloboH, NY-BR-1, UPK2, HAVCR1, ADRB3, PANX3, GPR20, LY6K, OR51E2, TARP, WTi, NY-ESO-1, LAGE-la, legumain, HPV E6, E7, MAGE-Al, MAGE Al, ETV6-

AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, and mut hsp70-2.

Sequences of non-limiting examples of various components that can be part of a CAR molecule described herein are listed in Table 1, where "aa" stands for amino acids, and "na" stands for nucleic acids that encode the corresponding peptide.

TABLE 1

Sequences of various components of CAR

| SEQ ID NO | Description | Sequence |
|---|---|---|
| SEQ ID NO: 11 | EF-1α promoter (na) | CGTGAGGCTCCGGTGCCCGTCAGTGGGCAGAGCGCACATCGCC<br>CACAGTCCCCGAGAAGTTGGGGGGAGGGGTCGGCAATTGAAC<br>CGGTGCCTAGAGAAGGTGGCGCGGGGTAAACTGGGAAAGTGA<br>TGTCGTGTACTGGCTCCGCCTTTTTCCCGAGGGTGGGGGAGAA<br>CCGTATATAAGTGCAGTAGTCGCCGTGAACGTTCTTTTTCGCA<br>ACGGGTTTGCCGCCAGAACACAGGTAAGTGCCGTGTGTGGTTC<br>CCGCGGGCCTGGCCTCTTTACGGGTTATGGCCCTTGCGTGCCTT<br>GAATTACTTCCACCTGGCTGCAGTACGTGATTCTTGATCCCGA<br>GCTTCGGGTTGGAAGTGGGTGGGAGAGTTCGAGGCCTTGCGCT<br>TAAGGAGCCCCTTCGCCTCGTGCTTGAGTTGAGGCCTGGCCTG<br>GGCGCTGGGGCCGCCGCGTGCGAATCTGGTGGCACCTTCGCGC<br>CTGTCTCGCTGCTTTCGATAAGTCTCTAGCCATTTAAAATTTTT<br>GATGACCTGCTGCGACGCTTTTTTTCTGGCAAGATAGTCTTGTA<br>AATGCGGGCCAAGATCTGCACACTGGTATTTCGGTTTTTGGGG<br>CCGCGGGCGGCGACGGGGCCCGTGCGTCCCAGCGCACATGTTC<br>GGCGAGGCGGGGCCTGCGAGCGCGGCCACCGAGAATCGGACG<br>GGGGTAGTCTCAAGCTGGCCGGCCTGCTCTGGTGCCTGGCCTC<br>GCGCCGCCGTGTATCGCCCCGCCCTGGGCGGCAAGGCTGGCCC<br>GGTCGGCACCAGTTGCGTGAGCGGAAAGATGGCCGCTTCCCG<br>GCCCTGCTGCAGGGAGCTCAAAATGGAGGACGCGGCGCTCGG<br>GAGAGCGGGCGGGTGAGTCACCCACACAAAGGAAAAGGGCCT<br>TTCCGTCCTCAGCCGTCGCTTCATGTGACTCCACGGAGTACCG<br>GGCGCCGTCCAGGCACCTCGATTAGTTCTCGAGCTTTTGGAGT<br>ACGTCGTCTTTAGGTTGGGGGGAGGGGTTTTATGCGATGGAGT<br>TTCCCCACACTGAGTGGGTGGAGACTGAAGTTAGGCCAGCTTG<br>GCACTTGATGTAATTCTCCTTGGAATTTGCCCTTTTTGAGTTTG<br>GATCTTGGTTCATTCTCAAGCCTCAGACAGTGGTTCAAAGTTTT<br>TTTCTTCCATTTCAGGTGTCGTGA |
| SEQ ID NO: 1 | Leader (aa) | MALPVTALLLPLALLLHAARP |
| SEQ ID NO: 12 | Leader (na) | ATGGCCCTGCCTGTGACAGCCCTGCTGCTGCCTCTGGCTCTGCT<br>GCTGCATGCCGCTAGACCC |
| SEQ ID NO: 199 | Leader (na) | ATGGCCCTCCCTGTCACCGCCCTGCTGCTTCCGCTGGCTCTTCT<br>GCTCCACGCCGCTCGGCCC |
| SEQ ID NO: 351 | Leader (aa) | MLLLVTSLLLCELPHPAFLLIP |
| SEQ ID NO: 352 | Leader (na) | ATGCTTCTCCTGGTGACAAGCCTTCTGCTCTGTGAGTTACCACA<br>CCCAGCATTCCTCCTGATCCCA |
| SEQ ID NO: 353 | Leader (na) | ATGCTGCTGCTGGTGACCAGCCTGCTGCTGTGCGAGCTGCCCC<br>ACCCCGCCTTTCTGCTGATCCCC |
| SEQ ID NO: 2 | CD 8 hinge (aa) | TTTPAPRPPTPAPTIASQPLSLRPEACRPAAGGAVHTRGLDFACD |
| SEQ ID NO: 13 | CD8 hinge (na) | ACCACGACGCCAGCGCCGCGACCACCAACACCGGCGCCCACC<br>ATCGCGTCGCAGCCCCTGTCCCTGCGCCCAGAGGCGTGCCGGC<br>CAGCGGCGGGGGGCGCAGTGCACACGAGGGGGCTGGACTTCG<br>CCTGTGAT |
| SEQ ID NO: 3 | Ig4 hinge (aa) | ESKYGPPCPPCPAPEFLGGPSVFLFPPKPKDTLMISRTPEVTCVVV<br>DVSQEDPEVQFNWYVDGVEVHNAKTKPREEQFNSTYRVVSVLT<br>VLHQDWLNGKEYKCKVSNKGLPSSIEKTISKAKGQPREPQVYTLP<br>PSQEEMTKNQVSLTCLVKGFYPSDIAVEWESNGQPENNYKTTPPV<br>LDSDGSFFLYSRLTVDKSRWQEGNVFSCSVMHEALHNHYTQKSL<br>SLSLGKM |

TABLE 1-continued

| Sequences of various components of CAR | | |
|---|---|---|
| SEQ ID NO | Description | Sequence |
| SEQ ID NO: 14 | Ig4 hinge (na) | GAGAGCAAGTACGGCCCTCCCTGCCCCCCTTGCCCTGCCCCCG AGTTCCTGGGCGGACCCAGCGTGTTCCTGTTCCCCCCCAAGCC CAAGGACACCCTGATGATCAGCCGGACCCCCGAGGTGACCTGT GTGGTGGTGGACGTGTCCCAGGAGGACCCCGAGGTCCAGTTCA ACTGGTACGTGGACGGCGTGGAGGTGCACAACGCCAAGACCA AGCCCCGGGAGGAGCAGTTCAATAGCACCTACCGGGTGGTGT CCGTGCTGACCGTGCTGCACCAGGACTGGCTGAACGGCAAGG AATACAAGTGTAAGGTGTCCAACAAGGGCCTGCCCAGCAGCA TCGAGAAAACCATCAGCAAGGCCAAGGGCCAGCCTCGGGAGC CCCAGGTGTACACCCTGCCCCCTAGCCAAGAGGAGATGACCA AGAACCAGGTGTCCCTGACCTGCCTGGTGAAGGGCTTCTACCC CAGCGACATCGCCGTGGAGTGGGAGAGCAACGGCCAGCCCGA GAACAACTACAAGACCACCCCCCCTGTGCTGGACAGCGACGG CAGCTTCTTCCTGTACAGCCGGCTGACCGTGGACAAGAGCCGG TGGCAGGAGGGCAACGTCTTTAGCTGCTCCGTGATGCACGAGG CCCTGCACAACCACTACACCCAGAAGAGCCTGAGCCTGTCCCT GGGCAAGATG |
| SEQ ID NO: 4 | IgD hinge (aa) | RWPESPKAQASSVPTAQPQAEGSLAKATTAPATTRNTGRGGEEK KKEKEKEEQEERETKTPECPSHTQPLGVYLLTPAVQDLWLRDKA TFTCFVVGSDLKDAHLTWEVAGKVPTGGVEEGLLERHSNGSQSQ HSRLTLPRSLWNAGTSVTCTLNHPSLPPQRLMALREPAAQAPVKL SLNLLASSDPPEAASWLLCEVSGFSPPNILLMWLEDQREVNTSGF APARPPPQPGSTTFWAWSVLRVPAPPSPQPATYTCVVSHEDSRTL LNASRSLEVSYVTDH |
| SEQ ID NO: 15 | IgD hinge (na) | AGGTGGCCCGAAAGTCCCAAGGCCCAGGCATCTAGTGTTCCTA CTGCACAGCCCCAGGCAGAAGGCAGCCTAGCCAAAGCTACTA CTGCACCTGCCACTACGCGCAATACTGGCCGTGGCGGGGAGG AGAAGAAAAAGGAGAAAGAGAAAGAAGAACAGGAAGAGAGG GAGACCAAGACCCCTGAATGTCCATCCCATACCCAGCCGCTGG GCGTCTATCTCTTGACTCCCGCAGTACAGGACTTGTGGCTTAG AGATAAGGCCACCTTTACATGTTTCGTCGTGGGCTCTGACCTG AAGGATGCCCATTTGACTTGGGAGGTTGCCGGAAAGGTACCCA CAGGGGGGGTTGAGGAAGGGTTGCTGGAGCGCCATTCCAATG GCTCTCAGAGCCAGCACTCAAGACTCACCCTTCCGAGATCCCT GTGGAACGCCGGGACCTCTGTCACATGTACTCTAAATCATCCT AGCCTGCCCCCACAGCGTCTGATGGCCCTTAGAGAGCCAGCCG CCCAGGCACCAGTTAAGCTTAGCCTGAATCTGCTCGCCAGTAG TGATCCCCCAGAGGCCGCCAGCTGGCTCTTATGCGAAGTGTCC GGCTTTAGCCCGCCCAACATCTTGCTCATGTGGCTGGAGGACC AGCGAGAAGTGAACACCAGCGGCTTCGCTCCAGCCCGGCCCC CACCCCAGCCGGGTTCTACCACATTCTGGGCCTGGAGTGTCTT AAGGGTCCCAGCACCACCTAGCCCCCAGCCAGCCACATACACC TGTGTTGTGTCCCATGAAGATAGCAGGACCCTGCTAAATGCTT CTAGGAGTCTGGAGGTTTCCTACGTGACTGACCATT |
| SEQ ID NO: 6 | CD8 Transmembrane (aa) | IYIWAPLAGTCGVLLLSLVITLYC |
| SEQ ID NO: 17 | CD8 Transmembrane (na) | ATCTACATCTGGGCGCCCTTGGCCGGGACTTGTGGGGTCCTTC TCCTGTCACTGGTTATCACCCTTTACTGC |
| SEQ ID NO: 7 | 4-1BB intracellular domain (aa) | KRGRKKLLYIFKQPFMRPVQTTQEEDGCSCRFPEEEEGGCEL |
| SEQ ID NO: 18 | 4-1BB intracellular domain (na) | AAACGGGGCAGAAAGAAACTCCTGTATATATTCAAACAACCA TTTATGAGACCAGTACAAACTACTCAAGAGGAAGATGGCTGTA GCTGCCGATTTCCAGAAGAAGAAGAAGGAGGATGTGAACTG |
| SEQ ID NO: 8 | CD27 (aa) | QRRKYRSNKGESPVEPAEPCRYSCPREEEGSTIPIQEDYRKPEPAC SP |
| SEQ ID NO: 19 | CD27 (na) | AGGAGTAAGAGGAGCAGGCTCCTGCACAGTGACTACATGAAC ATGACTCCCCGCCGCCCCGGGCCCACCCGCAAGCATTACCAGC CCTATGCCCCACCACGCGACTTCGCAGCCTATCGCTCC |
| SEQ ID NO: 9 | CD3-zeta (aa) (Q/K mutant) | RVKFSRSADAPAYKQGQNQLYNELNLGRREEYDVLDKRRGRDP EMGGKPRRKNPQEGLYNELQKDKMAEAYSEIGMKGERRRGKGH DGLYQGLSTATKDTYDALHMQALPPR |
| SEQ ID NO: 20 | CD3-zeta (na) (Q/K mutant) | AGAGTGAAGTTCAGCAGGAGCGCAGACGCCCCCGCGTACAAG CAGGGCCAGAACCAGCTCTATAACGAGCTCAATCTAGGACGA AGAGAGGAGTACGATGTTTTGGACAAGAGACGTGGCCGGGAC |

TABLE 1-continued

| Sequences of various components of CAR | | |
|---|---|---|
| SEQ ID NO | Description | Sequence |
| | | CCTGAGATGGGGGGAAAGCCGAGAAGGAAGAACCCTCAGGAA GGCCTGTACAATGAACTGCAGAAAGATAAGATGGCGGAGGCC TACAGTGAGATTGGGATGAAAGGCGAGCGCCGGAGGGGCAAG GGGCACGATGGCCTTTACCAGGGTCTCAGTACAGCCACCAAGG ACACCTACGACGCCCTTCACATGCAGGCCCTGCCCCCTCGC |
| SEQ ID NO: 10 | CD3-zeta (aa) (NCBI Reference Sequence NM_000734.3) | RVKFSRSADAPAYQQGQNQLYNELNLGRREEYDVLDKRRGRDP EMGGKPRRKNPQEGLYNELQKDKMAEAYSEIGMKGERRRGKGH DGLYQGLSTATKDTYDALHMQALPPR |
| SEQ ID NO: 21 | CD3-zeta (na) (NCBI Reference Sequence NM_000734.3) | AGAGTGAAGTTCAGCAGGAGCGCAGACGCCCCCGCGTACCAG CAGGGCCAGAACCAGCTCTATAACGAGCTCAATCTAGGACGA AGAGAGGAGTACGATGTTTTGGACAAGAGACGTGGCCGGGAC CCTGAGATGGGGGGAAAGCCGAGAAGGAAGAACCCTCAGGAA GGCCTGTACAATGAACTGCAGAAAGATAAGATGGCGGAGGCC TACAGTGAGATTGGGATGAAAGGCGAGCGCCGGAGGGGCAAG GGGCACGATGGCCTTTACCAGGGTCTCAGTACAGCCACCAAGG ACACCTACGACGCCCTTCACATGCAGGCCCTGCCCCCTCGC |
| SEQ ID NO: 36 | CD28 Intracellular domain (amino acid sequence) | RSKRSRLLHSDYMNMTPRRPGPTRKHYQPYAPPRDFAAYRS |
| SEQ ID NO: 37 | CD28 Intracellular domain (nucleotide sequence) | AGGAGTAAGAGGAGCAGGCTCCTGCACAGTGACTACATGAAC ATGACTCCCCGCCGCCCCGGGCCCACCCGCAAGCATTACCAGC CCTATGCCCCACCACGCGACTTCGCAGCCTATCGCTCC |
| SEQ ID NO: 38 | ICOS Intracellular domain (amino acid sequence) | T K K K Y S S S V H D P N G E Y M F M R A V N T A K K S R L T D V T L |
| SEQ ID NO: 39 | ICOS Intracellular domain (nucleotide sequence) | ACAAAAAAGAAGTATTCATCCAGTGTGCACGACCCTAACGGT GAATACATGTTCATGAGAGCAGTGAACACAGCCAAAAAATCC AGACTCACAGATGTGACCCTA |
| SEQ ID NO: 5 | GS hinge/linker (aa) | GGGGSGGGGS |
| SEQ ID NO: 16 | GS hinge/linker (na) | GGTGGCGGAGGTTCTGGAGGTGGAGGTTCC |
| SEQ ID NO: 40 | GS hinge/linker (na) | GGTGGCGGAGGTTCTGGAGGTGGGGGTTCC |
| SEQ ID NO: 25 | linker | GGGGS |
| SEQ ID NO: 26 | linker | (Gly-Gly-Gly-Gly-Ser)n, where n = 1-6, for example, GGGGSGGGGS GGGGSGGGGS GGGGSGGGGS |
| SEQ ID NO: 27 | linker | GGGGSGGGGSGGGGSGGGGS |
| SEQ ID NO: 28 | linker | GGGGSGGGGSGGGGS |
| SEQ ID NO: 29 | linker | GGGS |
| SEQ ID NO: 41 | linker | (Gly-Gly-Gly-Ser)n where n is a positive integer equal to or greater than 1 |
| SEQ ID NO: 42 | linker | (Gly-Gly-Gly-Ser)n, where n = 1-10, for example, GGGSGGGSGG GSGGGSGGGS GGGSGGGSGG GSGGGSGGGS |
| SEQ ID NO: 43 | linker | GSTSGSGKPGSGEGSTKG |
| SEQ ID NO: 30 | poly(A) | $(A)_{5000}$ This sequence may encompass 50-5000 adenines. |
| SEQ ID NO: 31 | polyT | $(T)_{100}$ |
| SEQ ID NO: | polyT | $(T)_{5000}$ |

TABLE 1-continued

| Sequences of various components of CAR | | |
|---|---|---|
| SEQ ID NO | Description | Sequence |
| 32 | | This sequence may encompass 50-5000 thymines. |
| SEQ ID NO: 33 | poly(A) | $(A)_{5000}$<br>This sequence may encompass 100-5000 adenines. |
| SEQ ID NO: 34 | poly(A) | $(A)_{400}$<br>This sequence may encompass 100-400 adenines. |
| SEQ ID NO: 35 | poly(A) | $(A)_{2000}$<br>This sequence may encompass 50-2000 adenines. |
| SEQ ID NO: 22 | PD1 CAR (aa) | pgwfldspdrpwnpptfspallvvtegdnatftcsfsntsesfvlnwyrmspsnqtdklaafpedrsq<br>pgqdcrfrvtqlpngrdfhmsvvrarrndsgtylcgaislapkaqikeslraelrvterraevptahpsp<br>sprpagqfqtlvtttpaprpptpaptiasqplslrpeacrpaaggavhtrgldfacdiyiwaplagtcgvl<br>llslvitlyckrgrkkllyifkqpfmrpvqttqeedgescrfpeeeeggcelrvkfsrsadapaykqgq<br>nqlynelnlgrreeydvldkrrgrdpemggkprrknpqeglynelqkdkmaeayseigmkgerrr<br>gkghdglyqglstatkdtydalhmqalppr |
| SEQ ID NO: 23 | PD-1 CAR (na)<br>(PD1 ECD<br>underlined) | atggccctccctgtcactgccctgcttctccccctcgcactcctgctccacgccgctagaccacccggat<br>ggtttctggactctccggatcgcccgtggaatcccccaaccttctcaccggcactcttggttgtgactgag<br>ggcgataatgcgaccttcacgtgctcgttctccaacacctccgaatcattcgtgctgaactggtaccgcat<br>gagcccgtcaaaccagaccgacaagctcgccgcgtttccggaagatcggtcgcaaccgggacaggat<br>tgtcggttccgcgtgactcaactgccgaatggcagagacttccacatgagcgtggtccgcgctaggcga<br>aacgactccgggacctacctgtgcggagccatctcgctggcgcctaaggcccaaatcaaagagagctt<br>gagggccgaactgagagtgaccgagcgcagagctgaggtgccaactgcacatccatccccatcgcct<br>cggcctgcggggcagtttcagaccctggtcacgaccactccggcgccgcgcccaccgactccggccc<br>caactatcgcgagccagcccctgtcgctgaggccggaagcatgccgccctgccgccggaggtgctgt<br>gcatacccggggattggacttcgcatgcgacatctacatttgggctcctctcgccggaacttgtggcgtg<br>ctccttctgtccctggtcatcaccctgtactgcaagcggggtcggaaaaagcttctgtacattttcaagca<br>gcccttcatgaggcccgtgcaaaccacccaggaggaggacggttgctcctgccggttccccgaagagg<br>aagaaggaggttgcgagctgcgcgtgaagttctcccggagcgccgacgcccccgcctataagcaggg<br>ccagaaccagctgtacaacgaactgaacctgggacggcgggaagagtacgatgtgctggacaagcg<br>gcgcggccgggaccccgaaatgggcgggaagcctagaagaaagaaccctcaggaaggcctgtataa<br>cgagctgcagaaggacaagatggccgaggcctactccgaaattgggatgaagggagagcggcgga<br>ggggaaaggggcacgacggcctgtaccaaggactgtccaccgccaccaaggacacatacgatgccc<br>tgcacatgcaggcccttccccctcgc |
| SEQ ID NO: 24 | PD-1 CAR (aa)<br>with signal<br>(PD1 ECD<br>underlined) | Malpvtalllplalllhaarppgwfldspdrpwnpptfspallvvtegdnatftcsfsntsesfvlnwyr<br>mspsnqtdklaafpedrsqpgqdcrfrvtqlpngrdfhmsvvrarrndsgtylcgaislapkaqikes<br>lraelrvterraevptahpspsprpagqfqtlvtttpaprpptpaptiasqplslrpeacrpaaggavhtr<br>gldfacdiyiwaplagtcgvlllslvitlyckrgrkkllyifkqpfmrpvqttqeedgcscrfpeeeegg<br>celrvkfsrsadapaykqgqnqlynelnlgrreeydvldkrrgrdpemggkprrknpqeglynelq<br>kdkmaeayseigmkgerrrgkghdglyqglstatkdtydalhmqalppr |

In some embodiments the antigen binding domain comprises the extracellular domain, or a counter-ligand binding fragment thereof, of molecule that binds a counterligand on the surface of a target cell.

The immune effector cells can comprise a recombinant DNA construct comprising sequences encoding a CAR, wherein the CAR comprises an antigen binding domain (for example, antibody or antibody fragment, TCR or TCR fragment) that binds specifically to a tumor antigen, for example, a tumor antigen described herein, and an intracellular signaling domain. The intracellular signaling domain can comprise a costimulatory signaling domain and/or a primary signaling domain, for example, a zeta chain. As described elsewhere, the methods described herein can include transducing a cell, for example, from the population of T regulatory-depleted cells, with a nucleic acid encoding a CAR, for example, a CAR described herein.

In some embodiments, a CAR comprises a scFv domain, wherein the scFv may be preceded by an optional leader sequence such as provided in SEQ ID NO: 1, and followed by an optional hinge sequence such as provided in SEQ ID NO:2 or SEQ ID NO:36 or SEQ ID NO:38, a transmembrane region such as provided in SEQ ID NO:6, an intracellular signaling domain that includes SEQ ID NO:7 or SEQ ID NO:16 and a CD3 zeta sequence that includes SEQ ID NO:9 or SEQ ID NO:10, for example, wherein the domains are contiguous with and in the same reading frame to form a single fusion protein.

In some embodiments, an exemplary CAR constructs comprise an optional leader sequence (for example, a leader sequence described herein), an extracellular antigen binding domain (for example, an antigen binding domain described herein), a hinge (for example, a hinge region described herein), a transmembrane domain (for example, a transmembrane domain described herein), and an intracellular stimulatory domain (for example, an intracellular stimulatory domain described herein). In some embodiments, an exemplary CAR construct comprises an optional leader sequence (for example, a leader sequence described herein), an extracellular antigen binding domain (for example, an antigen binding domain described herein), a hinge (for example, a hinge region described herein), a transmembrane domain (for example, a transmembrane domain described herein), an intracellular costimulatory signaling domain (for example, a costimulatory signaling domain described herein) and/or an intracellular primary signaling domain (for example, a primary signaling domain described herein).

An exemplary leader sequence is provided as SEQ ID NO: 1. Further exemplary leaders include those provided in SEQ ID NO: 351 or encoded by SEQ ID NOs: 352 or 353.

An exemplary hinge/spacer sequence is provided as SEQ ID NO: 2 or SEQ ID NO:36 or SEQ ID NO:38. An exemplary transmembrane domain sequence is provided as SEQ ID NO:6. An exemplary sequence of the intracellular signaling domain of the 4-1BB protein is provided as SEQ ID NO: 7. An exemplary sequence of the intracellular signaling domain of CD27 is provided as SEQ ID NO:16. An exemplary CD3zeta domain sequence is provided as SEQ ID NO: 9 or SEQ ID NO:10.

In some embodiments, the immune effector cell comprises a recombinant nucleic acid construct comprising a nucleic acid molecule encoding a CAR, wherein the nucleic acid molecule comprises a nucleic acid sequence encoding an antigen binding domain, wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, for example, CD3-zeta, CD28, CD27, 4-1BB, and the like. In some instances, the CAR can comprise any combination of CD3-zeta, CD28, 4-1BB, and the like.

The nucleic acid sequences coding for the desired molecules can be obtained using recombinant methods known in the art, such as, for example by screening libraries from cells expressing the nucleic acid molecule, by deriving the nucleic acid molecule from a vector known to include the same, or by isolating directly from cells and tissues containing the same, using standard techniques. Alternatively, the nucleic acid of interest can be produced synthetically, rather than cloned.

Nucleic acids encoding a CAR can be introduced into the immune effector cells using, for example, a retroviral or lentiviral vector construct.

Nucleic acids encoding a CAR can also be introduced into the immune effector cell using, for example, an RNA construct that can be directly transfected into a cell. A method for generating mRNA for use in transfection involves in vitro transcription (IVT) of a template with specially designed primers, followed by poly(A) addition, to produce a construct containing 3' and 5' untranslated sequence ("UTR") (for example, a 3' and/or 5' UTR described herein), a 5' cap (for example, a 5' cap described herein) and/or Internal Ribosome Entry Site (IRES) (for example, an IRES described herein), the nucleic acid to be expressed, and a poly(A) tail, typically 50-2000 bases in length (for example, described in the Examples, for example, SEQ ID NO:35). RNA so produced can efficiently transfect different kinds of cells. In some embodiments, the template includes sequences for the CAR. In some embodiments, an RNA CAR vector is transduced into a cell, for example, a T cell by electroporation.

Antigen Binding Domain

In some embodiments, a plurality of the immune effector cells, for example, the population of T regulatory-depleted cells, include a nucleic acid encoding a CAR that comprises a target-specific binding element otherwise referred to as an antigen binding domain. The choice of binding element depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in a CAR described herein include those associated with viral, bacterial and parasitic infections, autoimmune disease and cancer cells.

In some embodiments, the portion of the CAR comprising the antigen binding domain comprises an antigen binding domain that targets a tumor antigen, for example, a tumor antigen described herein.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, for example, single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

CD19 CAR

In some embodiments, the CAR-expressing cell described herein is a CD19 CAR-expressing cell (for example, a cell expressing a CAR that binds to human CD19).

In some embodiments, the antigen binding domain of the CD19 CAR has the same or a similar binding specificity as the FMC63 scFv fragment described in Nicholson et al. Mol. Immun. 34 (16-17): 1157-1165 (1997). In some embodiments, the antigen binding domain of the CD19 CAR includes the scFv fragment described in Nicholson et al. Mol. Immun. 34 (16-17): 1157-1165 (1997).

In some embodiments, the CD19 CAR includes an antigen binding domain (for example, a humanized antigen binding domain) according to Table 3 of WO2014/153270, incorporated herein by reference. WO2014/153270 also describes methods of assaying the binding and efficacy of various CAR constructs.

In some embodiments, the parental murine scFv sequence is the CAR19 construct provided in PCT publication WO2012/079000 (incorporated herein by reference). In some embodiments, the anti-CD19 binding domain is a scFv described in WO2012/079000.

In some embodiments, the CAR molecule comprises the fusion polypeptide sequence provided as SEQ ID NO: 12 in PCT publication WO2012/079000, which provides an scFv fragment of murine origin that specifically binds to human CD19.

In some embodiments, the CD19 CAR comprises an amino acid sequence provided as SEQ ID NO: 12 in PCT publication WO2012/079000.

In some embodiments, the amino acid sequence is: Diqmtqttsslsaslgdrvtiscrasqdisky-lnwyqqkpdgtvklliyhtsrlhsgvpsrfsgsgsgtdysltisnleqedi-atyfcqqgn tlpytfgggtkleitggggsggggsggggsevklgesgpglvap-sqslsvtctvsgvslpdygvswirqpprkglewlgviwgsettyynsalksr ltiikdnsksqvflkmnslqtddtaiyy-cakhyyyggsyamdywgqgtsvtvssttpaprpptpaptiasqplslrpeacr-paaggavhtrgldfa cdiyiwaplagtcgvlllslvitlyckrgrkklly-ifkqpfmrpvqttqeedgcscrfpeeeeggcelrvkfsrsadapaykqgqnqly-nelnlgrre eydvldkrrgrdpemggkprrknpgeglynelqkdkmaeaysei-gmkgerrrgkghdglyqglstatkdtydalhmqalppr (SEQ ID NO: 292), or a sequence substantially homologous thereto.

In some embodiments, the CD19 CAR has the USAN designation TISAGENLECLEUCEL-T. In embodiments, CTL019 is made by a gene modification of T cells is mediated by stable insertion via transduction with a self-inactivating, replication deficient Lentiviral (LV) vector containing the CTL019 transgene under the control of the EF-1 alpha promoter. CTL019 can be a mixture of transgene positive and negative T cells that are delivered to the subject on the basis of percent transgene positive T cells.

In other embodiments, the CD19 CAR comprises an antigen binding domain (for example, a humanized antigen binding domain) according to Table 3 of WO2014/153270, incorporated herein by reference.

Humanization of murine CD19 antibody is desired for the clinical setting, where the mouse-specific residues may induce a human-anti-mouse antigen (HAMA) response in patients who receive CART19 treatment, i.e., treatment with T cells transduced with the CAR19 construct. The production, characterization, and efficacy of humanized CD19 CAR sequences is described in International Application WO2014/153270 which is herein incorporated by reference in its entirety, including Examples 1-5 (p. 115-159).

In some embodiments, the CAR molecule is a humanized CD19 CAR comprising the amino acid sequence of:

(SEQ ID NO: 293)

EIVMTQSPATLSLSPGERATLSCRASQDISKYLNWYQQKPGQAPRLLIYHTSRLHSGIPARFSGS

GSGTDYTLTISSLQPEDFAVYFCQQGNTLPYTFGQGTKLEIKGGGGSGGGGSGGGGSQVQLQESG

PGLVKPSETLSLTCTVSGVSLPDYGVSWIRQPPGKGLEWIGVIWGSETTYYQSSLKSRVTISKDN

SKNQVSLKLSSVTAADTAVYYCAKHYYYGGSYAMDYWGQGTLVTVSS

In some embodiments, the CAR molecule is a humanized CD19 CAR comprising the amino acid sequence of:

(SEQ ID NO: 294)

EIVMTQSPATLSLSPGERATLSCRASQDISKYLNWYQQKPGQAPRLLIYHTSRLHSGIPARFSGS

GSGTDYTLTISSLQPEDFAVYFCQQGNTLPYTFGQGTKLEIKGGGGSGGGGSGGGGSQVQLQESG

PGLVKPSETLSLTCTVSGVSLPDYGVSWIRQPPGKGLEWIGVIWGSETTYYQSSLKSRVTISKDN

SKNQVSLKLSSVTAADTAVYYCAKHYYYGGSYAMDYWGQGTLVTVSSTTTPAPRPPTPAPTIASQ

PLSLRPEACRPAAGGAVHTRGLDFACDIYIWAPLAGTCGVLLLSLVITLYCKRGRKKLLYIFKQP

FMRPVQTTQEEDGCSCRFPEEEEGGCELRVKFSRSADAPAYKQGQNQLYNELNLGRREEYDVLDK

RRGRDPEMGGKPRRKNPQEGLYNELQKDKMAEAYSEIGMKGERRRGKGHDGLYQGLSTATKDTYD

ALHMQALPPR

In some embodiments, the CAR molecule is a humanized CD19 CAR comprising the amino acid sequence of:

(SEQ ID NO: 349)

MALPVTALLLPLALLLHAARPEIVMTQSPATLSLSPGERATLSCRASQDISKYLNWYQQKPGQAP

RLLIYHTSRLHSGIPARFSGSGSGTDYTLTISSLQPEDFAVYFCQQGNTLPYTFGQGTKLEIKGG

GGSGGGGSGGGGSQVQLQESGPGLVKPSETLSLTCTVSGVSLPDYGVSWIRQPPGKGLEWIGVIW

GSETTYYQSSLKSRVTISKDNSKNQVSLKLSSVTAADTAVYYCAKHYYYGGSYAMDYWGQGTLVT

VSSTTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELRVKFSRSADAPAYQQG

QNQLYNELNLGRREEYDVLDKRRGRDPEMGGKPRRKNPQEGLYNELQKDKMAEAYSEIGMKGERR

RGKGHDGLYQGLSTATKDTYDALHMQALPPR

In some embodiments, the CAR molecule is a humanized CD19 CAR comprising the amino acid sequence of:

(SEQ ID NO: 350)

EIVMTQSPATLSLSPGERATLSCRASQDISKYLNWYQQKPGQAPRLLIYHTSRLHSGIPARFSGS

GSGTDYTLTISSLQPEDFAVYFCQQGNTLPYTFGQGTKLEIKGGGGSGGGGSGGGGSQVQLQESG

PGLVKPSETLSLTCTVSGVSLPDYGVSWIRQPPGKGLEWIGVIWGSETTYYQSSLKSRVTISKDN

-continued

SKNQVSLKLSSVTAADTAVYYCAKHYYYGGSYAMDYWGQGTLVTVSSTTTPAPRPPTPAPTIASQ

PLSLRPEACRPAAGGAVHTRGLDFACDIYIWAPLAGTCGVLLLSLVITLYCKRGRKKLLYIFKQP

FMRPVQTTQEEDGCSCRFPEEEEGGCELRVKFSRSADAPAYQQGQNQLYNELNLGRREEYDVLDK

RRGRDPEMGGKPRRKNPQEGLYNELQKDKMAEAYSEIGMKGERRRGKGHDGLYQGLSTATKDTYD

ALHMQALPPR

Any known CD19 CAR, for example, the CD19 antigen binding domain of any known CD19 CAR, in the art can be used in accordance with the present disclosure. For example, LG-740; CD19 CAR described in the U.S. Pat. Nos. 8,399,645; 7,446,190; Xu et al., Leuk Lymphoma. 2013 54(2): 255-260(2012); Cruz et al., Blood 122(17):2965-2973 (2013); Brentjens et al., Blood, 118(18):4817-4828 (2011); Kochenderfer et al., Blood 116(20):4099-102 (2010); Kochenderfer et al., Blood 122 (25):4129-39(2013); and 16th Annu Meet Am Soc Gen Cell Ther (ASGCT) (May 15-18, Salt Lake City) 2013, Abst 10.

Exemplary CD19 CARs include CD19 CARs described herein or an anti-CD19 CAR described in Xu et al. Blood 123.24(2014):3750-9; Kochenderfer et al. Blood 122.25 (2013):4129-39, Cruz et al. Blood 122.17(2013):2965-73, NCT00586391, NCT01087294, NCT02456350, NCT00840853, NCT02659943, NCT02650999, NCT02640209, NCT01747486, NCT02546739, NCT02656147, NCT02772198, NCT00709033, NCT02081937, NCT00924326, NCT02735083, NCT02794246, NCT02746952, NCT01593696, NCT02134262, NCT01853631, NCT02443831, NCT02277522, NCT02348216, NCT02614066, NCT02030834, NCT02624258, NCT02625480, NCT02030847, NCT02644655, NCT02349698, NCT02813837, NCT02050347, NCT01683279, NCT02529813, NCT02537977, NCT02799550, NCT02672501, NCT02819583, NCT02028455, NCT01840566, NCT01318317, NCT01864889, NCT02706405, NCT01475058, NCT01430390, NCT02146924, NCT02051257, NCT02431988, NCT01815749, NCT02153580, NCT01865617, NCT02208362, NCT02685670, NCT02535364, NCT02631044, NCT02728882, NCT02735291, NCT01860937, NCT02822326, NCT02737085, NCT02465983, NCT02132624, NCT02782351, NCT01493453, NCT02652910, NCT02247609, NCT01029366, NCT01626495, NCT02721407, NCT01044069, NCT00422383, NCT01680991, NCT02794961, or NCT02456207, each of which is incorporated herein by reference in its entirety.

In some embodiments, CD19 CARs comprise a sequence, for example, a CDR, VH, VL, scFv, or full-CAR sequence, disclosed in Table 2, or a sequence having at least 80%, 85%, 90%, 95%, or 99% identity thereto.

TABLE 2

Amino acid sequences of exemplary anti-CD19 molecules

| SEQ ID NO | Region | Sequence |
|---|---|---|
| CTL019 | | |
| 295 | HCDR1 (Kabat) | DYGVS |
| 296 | HCDR2 (Kabat) | VIWGSETTYYNSALKS |
| 297 | HCDR3 (Kabat) | HYYYGGSYAMDY |
| 298 | LCDR1 (Kabat) | RASQDISKYLN |
| 299 | LCDR2 (Kabat) | HTSRLHS |
| 300 | LCDR3 (Kabat) | QQGNTLPYT |
| 301 | CTL019 Full amino acid sequence | MALPVTALLLPLALLLHAARPDIQMTQTTSSLSASLGDRVTISCRASQDIS<br>KYLNWYQQKPDGTVKLLIYHTSRLHSGVPSRFSGSGSGTDYSLTISNLEQ<br>EDIATYFCQQGNTLPYTFGGGTKLEITGGGGSGGGGSGGGGSEVKLQES<br>GPGLVAPSQSLSVTCTVSGVSLPDYGVSWIRQPPRKGLEWLGVIWGSET<br>TYYNSALKSRLTIIKDNSKSQVFLKMNSLQTDDTAIYYCAKHYYYGGSY<br>AMDYWGQGTSVTVSSTTTPAPRPPTPAPTIASQPLSLRPEACRPAAGGAV<br>HTRGLDFACDIYIWAPLAGTCGVLLLSLVITLYCKRGRKKLLYIFKQPFM<br>RPVQTTQEEDGCSCRFPEEEEGGCELRVKFSRSADAPAYKQGQNQLYNE<br>LNLGRREEYDVLDKRRGRDPEMGGKPRRKNPQEGLYNELQKDKMAEA<br>YSEIGMKGERRRGKGHDGLYQGLSTATKDTYDALHMQALPPR |

TABLE 2-continued

Amino acid sequences of exemplary anti-CD19 molecules

| SEQ ID NO | Region | Sequence |
|---|---|---|
| 302 | CTL019 Full nucleotide sequence | ATGGCCTTACCAGTGACCGCCTTGCTCCTGCCGCTGGCCTTGCTGCTC CACGCCGCCAGGCCGGACATCCAGATGACACAGACTACATCCTCCCT GTCTGCCTCTCTGGGAGACAGAGTCACCATCAGTTGCAGGGCAAGTC AGGACATTAGTAAATATTTAAATTGGTATCAGCAGAAACCAGATGGA ACTGTTAAACTCCTGATCTACCATACATCAAGATTACACTCAGGAGTC CCATCAAGGTTCAGTGGCAGTGGGTCTGGAACAGATTATTCTCTCACC ATTAGCAACCTGGAGCAAGAAGATATTGCCACTTACTTTTGCCAACA GGGTAATACGCTTCCGTACACGTTCGGAGGGGGGACCAAGCTGGAGA TCACAGGTGGCGGTGGCTCGGGCGGTGGTGGGTCGGGTGGCGGCGGA TCTGAGGTGAAACTGCAGGAGTCAGGACCTGGCCTGGTGGCGCCCTC ACAGAGCCTGTCCGTCACATGCACTGTCTCAGGGGTCTCATTACCCG ACTATGGTGTAAGCTGGATTCGCCAGCCTCCACGAAAGGGTCTGGAG TGGCTGGGAGTAATATGGGGTAGTGAAACCACATACTATAATTCAGC TCTCAAATCCAGACTGACCATCATCAAGGACAACTCCAAGAGCCAAG TTTTCTTAAAAATGAACAGTCTGCAAACTGATGACACAGCCATTTACT ACTGTGCCAAACATTATTACTACGGTGGTAGCTATGCTATGGACTACT GGGGCCAAGGAACCTCAGTCACCGTCTCCTCAACCACGACGCCAGCG CCGCGACCACCAACACCGGCGCCCACCATCGCGTCGCAGCCCCTGTC CCTGCGCCCAGAGGCGTGCCGGCCAGCGGCGGGGGGCGCAGTGCAC ACGAGGGGGCTGGACTTCGCCTGTGATATCTACATCTGGGCGCCCTT GGCCGGGACTTGTGGGGTCCTTCTCCTGTCACTGGTTATCACCCTTTA CTGCAAACGGGGCAGAAAGAAACTCCTGTATATATTCAAACAACCAT TTATGAGACCAGTACAAACTACTCAAGAGGAAGATGGCTGTAGCTGC CGATTTCCAGAAGAAGAAGAAGGAGGATGTGAACTGAGAGTGAAGT TCAGCAGGAGCGCAGACGCCCCCGCGTACAAGCAGGGCCAGAACCA GCTCTATAACGAGCTCAATCTAGGACGAAGAGAGGAGTACGATGTTT TGGACAAGAGACGTGGCCGGGACCCTGAGATGGGGGGAAAGCCGAG AAGGAAGAACCCTCAGGAAGGCCTGTACAATGAACTGCAGAAAGAT AAGATGGCGGAGGCCTACAGTGAGATTGGGATGAAAGGCGAGCGCC GGAGGGGCAAGGGGCACGATGGCCTTTACCAGGGTCTCAGTACAGCC ACCAAGGACACCTACGACGCCCTTCACATGCAGGCCCTGCCCCCTCGC |
| 303 | CTL019 scFv domain | DIQMTQTTSSLSASLGDRVTISCRASQDISKYLNWYQQKPDGTVKLLIYH TSRLHSGVPSRFSGSGSGTDYSLTISNLEQEDIATYFCQQGNTLPYTFGGG TKLEITGGGGSGGGGSGGGGSEVKLQESGPGLVAPSQSLSVTCTVSGVSL PDYGVSWIRQPPRKGLEWLGVIWGSETTYYNSALKSRLTIIKDNSKSQVF LKMNSLQTDDTAIYYCAKHYYYGGSYAMDYWGQGTSVTVSS |
| Humanized CAR2 | | |
| 295 | HCDR1 (Kabat) | DYGVS |
| 304 | HCDR2 (Kabat) | VIWGSETTYYQSSLKS |
| 297 | HCDR3 (Kabat) | HYYYGGSYAMDY |
| 298 | LCDR1 (Kabat) | RASQDISKYLN |
| 299 | LCDR2 (Kabat) | HTSRLHS |
| 300 | LCDR3 (Kabat) | QQGNTLPYT |
| 293 | CAR2 scFv domain - aa (Linker is underlined) | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQG TKLEIKGGGGSGGGGSGGGGSQVQLQESGPGLVKPSETLSLTCTVSGVS LPDYGVSWIRQPPGKGLEWIGVIWGSETTYYQSSLKSRVTISKDNSKNQ VSLKLSSVTAADTAVYYCAKHYYYGGSYAMDYWGQGTLVTVSS |
| 305 | CAR2 scFv domain - nt | GAAATTGTGATGACCCAGTCACCCGCCACTCTTAGCCTTTCACCCGGT GAGCGCGCAACCCTGTCTTGCAGAGCCTCCCAAGACATCTCAAAATA CCTTAATTGGTATCAACAGAAGCCCGGACAGGCTCCTCGCCTTCTGAT CTACCACACCAGCCGGCTCCATTCTGGAATCCCTGCCAGGTTCAGCG GTAGCGGATCTGGGACCGACTACACCCTCACTATCAGCTCACTGCAG CCAGAGGACTTCGCTGTCTATTTCTGTCAGCAAGGGAACACCCTGCC CTACACCTTTGGACAGGGCACCAAGCTCGAGATTAAAGGTGGAGGTG GCAGCGGAGGAGGTGGGTCCGGCGGTGGAGGAAGCCAGGTCCAACT CCAAGAAAGCGGACCGGGTCTTGTGAAGCCATCAGAAACTCTTTCAC TGACTTGTACTGTGAGCGGAGTGTCTCTCCCCGATTACGGGGTGTCTT GGATCAGACAGCCACCGGGGAAGGGTCTGGAATGGATTGGAGTGATT |

TABLE 2-continued

| Amino acid sequences of exemplary anti-CD19 molecules | | |
|---|---|---|
| SEQ ID NO | Region | Sequence |
| | | TGGGGCTCTGAGACTACTTACTACCAATCATCCCTCAAGTCACGCGTC<br>ACCATCTCAAAGGACAACTCTAAGAATCAGGTGTCACTGAAACTGTC<br>ATCTGTGACCGCAGCCGACACCGCCGTGTACTATTGCGCTAAGCATT<br>ACTATTATGGCGGGAGCTACGCAATGGATTACTGGGGACAGGGTACT<br>CTGGTCACCGTGTCCAGC |
| 306 | CAR 2 -<br>Full - aa | MALPVTALLLPLALLLHAARPEIVMTQSPATLSLSPGERATLSCRASQDIS<br>KYLNWYQQKPGQAPRLLIYHTSRLHSGIPARFSGSGSGTDYTLTISSLQPE<br>DFAVYFCQQGNTLPYTFGQGTKLEIKGGGGSGGGGSGGGGSQVQLQES<br>GPGLVKPSETLSLTCTVSGVSLPDYGVSWIRQPPGKGLEWIGVIWGSETT<br>YYQSSLKSRVTISKDNSKNQVSLKLSSVTAADTAVYYCAKHYYYGGSY<br>AMDYWGQGTLVTVSSTTTPAPRPPTPAPTIASQPLSLRPEACRPAAGGAV<br>HTRGLDFACDIYIWAPLAGTCGVLLLSLVITLYCKRGRKKLLYIFKQPFM<br>RPVQTTQEEDGCSCRFPEEEEGGCELRVKFSRSADAPAYKQGQNQLYNE<br>LNLGRREEYDVLDKRRGRDPEMGGKPRRKNPQEGLYNELQKDKMAEA<br>YSEIGMKGERRRGKGHDGLYQGLSTATKDTYDALHMQALPPR |
| 307 | CAR 2 -<br>Full - nt | atggccctccctgtcaccgccctgctgcttccgctggctcttctgctccacgccgctcggcccgaaattgtgatgacc<br>cagtcacccgccactcttagcctttcacccggtgagcgcgcaaccctgtcttgcagagcctcccaagacatctcaaa<br>ataccttaattggtatcaacagaagcccggacaggctcctcgccttctgatctaccacaccagccggctccattctgg<br>aatccctgccaggttcagcggtagcggatctgggaccgactacaccctcactatcagctcactgcagccagagga<br>cttcgctgtctatttctgtcagcaagggaacaccctgccctacacctttggacagggcaccaagctcgagattaaag<br>gtggaggtggcagcggaggaggtgggtccggcggtggaggaagccaggtccaactccaagaaagcggaccg<br>ggtcttgtgaagccatcagaaactctttcactgacttgtactgtgagcggagtgtctctccccgattacggggtgtctt<br>ggatcagacagccaccggggaagggtctggaatggattggagtgatttggggctctgagactacttactaccaatc<br>atccctcaagtcacgcgtcaccatctcaaaggacaactctaagaatcaggtgtcactgaaactgtcatctgtgaccg<br>cagccgacaccgccgtgtactattgcgctaagcattactattatggcgggagctacgcaatggattactggggaca<br>gggtactctggtcaccgtgtccagcaccactaccccagcaccgaggccacccaccccggctcctaccatcgcctc<br>ccagcctctgtccctgcgtccggaggcatgtagacccgcagctggtggggccgtgcatacccggggtcttgacttc<br>gcctgcgatatctacatttgggcccctctggctggtacttgcggggtcctgctgctttcactcgtgatcactctttact<br>gtaagcgcggtcggaagaagctgctgtacatctttaagcaacccttcatgaggcctgtgcagactactcaagaggagg<br>acggctgttcatgccggttcccagaggaggaggaaggggctgcgaactgcgcgtgaaattcagccgcagcgca<br>gatgctccagcctacaagcaggggcagaaccagctctacaacgaactcaatcttggtcggagagaggagtacga<br>cgtgctggacaagcggagaggacgggacccagaaatgggggggaagccgcgcagaaagaatccccaagagg<br>gcctgtacaacgagctccaaaaggataagatggcagaagcctatagcgagattggtatgaaaggggaacgcaga<br>agaggcaaaggccacgacggactgtaccagggactcagcaccgccaccaaggacacctatgacgctcttcacat<br>gcaggccctgccgcctcgg |
| 349 | CAR 2A-<br>Full amino<br>acid<br>sequence;<br>signal<br>peptide<br>underlined | MALPVTALLLPLALLLHAARPEIVMTQSPATLSLSPGERATLSCRASQDIS<br>KYLNWYQQKPGQAPRLLIYHTSRLHSGIPARFSGSGSGTDYTLTISSLQPE<br>DFAVYFCQQGNTLPYTFGQGTKLEIKGGGGSGGGGSGGGGSQVQLQES<br>GPGLVKPSETLSLTCTVSGVSLPDYGVSWIRQPPGKGLEWIGVIWGSETT<br>YYQSSLKSRVTISKDNSKNQVSLKLSSVTAADTAVYYCAKHYYYGGSY<br>AMDYWGQGTLVTVSSTTTPAPRPPTPAPTIASQPLSLRPEACRPAAGGAV<br>HTRGLDFACDIYIWAPLAGTCGVLLLSLVITLYCKRGRKKLLYIFKQPFM<br>RPVQTTQEEDGCSCRFPEEEEGGCELRVKFSRSADAPAYQQGQNQLYNE<br>LNLGRREEYDVLDKRRGRDPEMGGKPRRKNPQEGLYNELQKDKMAEA<br>YSEIGMKGERRRGKGHDGLYQGLSTATKDTYDALHMQALPPR |
| 225 | CAR 2A -<br>amino acid<br>sequence;<br>no signal<br>peptide | EIVMTQSPATLSLSPGERATLSCRASQDISKYLNWYQQKPGQAPRLLIYH<br>TSRLHSGIPARFSGSGSGTDYTLTISSLQPEDFAVYFCQQGNTLPYTFGQG<br>TKLEIKGGGGSGGGGSGGGGSQVQLQESGPGLVKPSETLSLTCTVSGVS<br>LPDYGVSWIRQPPGKGLEWIGVIWGSETTYYQSSLKSRVTISKDNSKNQ<br>VSLKLSSVTAADTAVYYCAKHYYYGGSYAMDYWGQGTLVTVSSTTTP<br>APRPPTPAPTIASQPLSLRPEACRPAAGGAVHTRGLDFACDIYIWAPLAG<br>TCGVLLLSLVITLYCKRGRKKLLYIFKQPFMRPVQTTQEEDGCSCRFPEE<br>EEGGCELRVKFSRSADAPAYQQGQNQLYNELNLGRREEYDVLDKRRGR<br>DPEMGGKPRRKNPQEGLYNELQKDKMAEAYSEIGMKGERRRGKGHDG<br>LYQGLSTATKDTYDALHMQALPPR |
| 354 | CAR 2A<br>full nucleic<br>acid<br>sequence;<br>signal<br>peptide and<br>stop codon<br>underlined | atggccctccctgtcaccgccctgctgcttccgctggctcttctgctccacgccgctcggcccgaaattgtgatgacc<br>cagtcacccgccactcttagcctttcacccggtgagcgcgcaaccctgtcttgcagagcctcccaagacatctcaaa<br>ataccttaattggtatcaacagaagcccggacaggctcctcgccttctgatctaccacaccagccggctccattctgg<br>aatccctgccaggttcagcggtagcggatctgggaccgactacaccctcactatcagctcactgcagccagagga<br>cttcgctgtctatttctgtcagcaagggaacaccctgccctacacctttggacagggcaccaagctcgagattaaag<br>gtggaggtggcagcggaggaggtgggtccggcggtggaggaagccaggtccaactccaagaaagcggaccg<br>ggtcttgtgaagccatcagaaactctttcactgacttgtactgtgagcggagtgtctctccccgattacggggtgtctt<br>ggatcagacagccaccggggaagggtctggaatggattggagtgatttggggctctgagactacttactaccaatc<br>atccctcaagtcacgcgtcaccatctcaaaggacaactctaagaatcaggtgtcactgaaactgtcatctgtgaccg<br>cagccgacaccgccgtgtactattgcgctaagcattactattatggcgggagctacgcaatggattactggggaca<br>gggtactctggtcaccgtgtccagcaccactaccccagcaccgaggccacccaccccggctcctaccatcgcctc<br>ccagcctctgtccctgcgtccggaggcatgtagacccgcagctggtggggccgtgcatacccggggtcttgacttc<br>gcctgcgatatctacatttgggcccctctggctggtacttgcggggtcctgctgctttcactcgtgatcactctttact<br>gtaagcgcggtcggaagaagctgctgtacatctttaagcaacccttcatgaggcctgtgcagactactcaagaggagg<br>acggctgttcatgccggttcccagaggaggaggaaggggctgcgaactgcgcgtgaaattcagccgcagcgca<br>gatgctccagcctaccagcaggggcagaaccagctctacaacgaactcaatcttggtcggagagaggagtacga |

TABLE 2-continued

| Amino acid sequences of exemplary anti-CD19 molecules | | |
|---|---|---|
| SEQ ID NO | Region | Sequence |
| | | cgtgctggacaagcggagaggacgggacccagaaatggggggaagccgcgcagaaagaatccccaagagg<br>gcctgtacaacgagctccaaaaggataagatggcagaagcctatagcgagattggtatgaaaggggaacgcaga<br>agaggcaaaggccacgacggactgtaccagggactcagcaccgccaccaaggacacctatgacgctcttcacat<br>gcaggccctgccgcctcggtaa |
| 355 | CAR 2A nucleic acid sequence; signal peptide underlined; no stop codon | atggccctccctgtcaccgccctgctgcttccgctggctcttctgctccacgccgctcggcccgaaattgtgatgacc<br>cagtcacccgccactcttagcctttcacccggtgagcgcgcaaccctgtcttgcagagcctcccaagacatctcaaa<br>ataccttaattggtatcaacagaagcccggacaggctcctcgccttctgatctaccacaccagccggctccattctgg<br>aatccctgccaggttcagcggtagcggatctgggaccgactacaccctcactatcagctcactgcagccagagga<br>cttcgctgtctatttctgtcagcaagggaacaccctgccctacacctttggacagggcaccaagctcgagattaaag<br>gtggaggtggcagcggaggaggtgggtccggcggtggaggaagccaggtccaactccaagaaagcggaccg<br>ggtcttgtgaagccatcagaaactctttcactgacttgtactgtgagcggagtgtctctccccgattacggggtgtctt<br>ggatcagacagccaccggggaagggtctggaatggattggagtgatttggggctctgagactacttactaccaatc<br>atccctcaagtcacgcgtcaccatctcaaaggacaactctaagaatcaggtgtcactgaaactgtcatctgtgaccg<br>cagccgacaccgccgtgtactattgcgctaagcattactattatggcgggagctacgcaatggattactggggaca<br>gggtactctggtcaccgtgtccagcaccactaccccagcaccgaggccacccaccccggctcctaccatcgcctc<br>ccagcctctgtccctgcgtccggaggcatgtagacccgcagctggtggggccgtgcatacccggggtcttgacttc<br>gcctgcgatatctacatttgggcccctctggctggtacttgcggggtcctgctgctttcactcgtgatcactctttact<br>gtaagcgcggtcggaagaagctgctgtacatctttaagcaacccttcatgaggcctgtgcagactactcaagaggagg<br>acggctgttcatgccggttcccagaggaggaggaaggggctgcgaactgcgcgtgaaattcagccgcagcgca<br>gatgctccagcctaccagcaggggcagaaccagctctacaacgaactcaatcttggtcggagagaggagtacga<br>cgtgctggacaagcggagaggacgggacccagaaatgggcgggaagccgcgcagaaagaatccccaagagg<br>gcctgtacaacgagctccaaaaggataagatggcagaagcctatagcgagattggtatgaaaggggaacgcaga<br>agaggcaaaggccacgacggactgtaccagggactcagcaccgccaccaaggacacctatgacgctcttcacat<br>gcaggccctgccgcctcgg |
| 356 | CAR 2A nucleic acid sequence; no signal peptide; stop codon underlined | gaaattgtgatgacccagtcacccgccactcttagcctttcacccggtgagcgcgcaaccctgtcttgcagagcctc<br>ccaagacatctcaaaataccttaattggtatcaacagaagcccggacaggctcctcgccttctgatctaccacacca<br>gccggctccattctggaatccctgccaggttcagcggtagcggatctgggaccgactacaccctcactatcagctc<br>actgcagccagaggacttcgctgtctatttctgtcagcaagggaacaccctgccctacacctttggacagggcacca<br>agctcgagattaaaggtggaggtggcagcggaggaggtgggtccggcggtggaggaagccaggtccaactcca<br>agaaagcggaccgggtcttgtgaagccatcagaaactctttcactgacttgtactgtgagcggagtgtctctccccg<br>attacggggtgtcttggatcagacagccaccggggaagggtctggaatggattggagtgatttggggctctgagac<br>tacttactaccaatcatccctcaagtcacgcgtcaccatctcaaaggacaactctaagaatcaggtgtcactgaaact<br>gtcatctgtgaccgcagccgacaccgccgtgtactattgcgctaagcattactattatggcgggagctacgcaatgg<br>attactggggacagggtactctggtcaccgtgtccagcaccactaccccagcaccgaggccacccaccccggctc<br>ctaccatcgcctcccagcctctgtccctgcgtccggaggcatgtagacccgcagctggtggggccgtgcataccc<br>ggggtcttgacttcgcctgcgatatctacatttgggcccctctggctggtacttgcggggtcctgctgctttcactcgt<br>gatcactctttactgtaagcgcggtcggaagaagctgctgtacatctttaagcaacccttcatgaggcctgtgcagact<br>actcaagaggaggacggctgttcatgccggttcccagaggaggaggaaggggctgcgaactgcgcgtgaaatt<br>cagccgcagcgcagatgctccagcctaccagcaggggcagaaccagctctacaacgaactcaatcttggtcgga<br>gagaggagtacgacgtgctggacaagcggagaggacgggacccagaaatgggcgggaagccgcgcagaaa<br>gaatccccaagagggcctgtacaacgagctccaaaaggataagatggcagaagcctatagcgagattggtatgaa<br>aggggaacgcagaagaggcaaaggccacgacggactgtaccagggactcagcaccgccaccaaggacaccta<br>tgacgctcttcacatgcaggccctgccgcctcggtaa |
| SEQ ID NO: 417 | CAR 2A nucleic acid sequence; no signal peptide; no stop codon | gaaattgtgatgacccagtcacccgccactcttagcctttcacccggtgagcgcgcaaccctgtcttgca<br>gagcctcccaagacatctcaaaataccttaattggtatcaacagaagcccggacaggctcctcgccttct<br>gatctaccacaccagccggctccattctggaatccctgccaggttcagcggtagcggatctgggaccga<br>ctacaccctcactatcagctcactgcagccagaggacttcgctgtctatttctgtcagcaagggaacaccc<br>tgccctacacctttggacagggcaccaagctcgagattaaaggtggaggtggcagcggaggaggtgg<br>gtccggcggtggaggaagccaggtccaactccaagaaagcggaccgggtcttgtgaagccatcagaa<br>actctttcactgacttgtactgtgagcggagtgtctctccccgattacggggtgtcttggatcagacagcca<br>ccggggaagggtctggaatggattggagtgatttggggctctgagactacttactaccaatcatccctca<br>agtcacgcgtcaccatctcaaaggacaactctaagaatcaggtgtcactgaaactgtcatctgtgaccgc<br>agccgacaccgccgtgtactattgcgctaagcattactattatggcgggagctacgcaatggattactgg<br>ggacagggtactctggtcaccgtgtccagcaccactaccccagcaccgaggccacccaccccggctc<br>ctaccatcgcctcccagcctctgtccctgcgtccggaggcatgtagacccgcagctggtggggccgtg<br>catacccggggtcttgacttcgcctgcgatatctacatttgggcccctctggctggtacttgcggggtcct<br>gctgctttcactcgtgatcactctttactgtaagcgcggtcggaagaagctgctgtacatctttaagcaacc<br>cttcatgaggcctgtgcagactactcaagaggaggacggctgttcatgccggttcccagaggaggagg<br>aaggcggctgcgaactgcgcgtgaaattcagccgcagcgcagatgctccagcctaccagcaggggc<br>agaaccagctctacaacgaactcaatcttggtcggagagaggagtacgacgtgctggacaagcggag<br>aggacgggacccagaaatgggcgggaagccgcgcagaaagaatccccaagagggcctgtacaacg<br>agctccaaaaggataagatggcagaagcctatagcgagattggtatgaaaggggaacgcagaagagg<br>caaaggccacgacggactgtaccagggactcagcaccgccaccaaggacacctatgacgctcttcac<br>atgcaggccctgccgcctcgg |
| 357 | VH | CAGGTCCAGCTGCAGGAATCAGGACCAGGGCTGGTGAAACCTAGCG<br>AAACTCTGAGTCTGACTTGTACCGTCTCCGGGGTGTCTCTGCCAGACT<br>ACGGCGTGAGCTGGATCAGACAGCCCCCTGGCAAGTGCCTGGAGTGG<br>ATCGGCGTGATCTGGGGCTCCGAGACCACATACTATCAGAGCTCCCT<br>GAAGTCTCGGGTGACCATCTCCAAGGACAACTCTAAGAATCAGGTGA<br>GCCTGAAGCTGTCTAGCGTGACCGCCGCCGATACAGCCGTGTACTAT<br>TGTGCCAAGCACTACTATTACGGCGGCTCCTATGCCATGGATTACTGG<br>GGCCAGGGCACCCTGGTGACAGTGTCCTCT |

TABLE 2-continued

| Amino acid sequences of exemplary anti-CD19 molecules | | |
|---|---|---|
| SEQ ID NO | Region | Sequence |
| 358 | VH | CAGGTCCAGCTGCAGGAATCCGGCCCAGGACTGGTGAAGCCTAGCGA<br>GACCCTGTCCCTGACCTGCACAGTGAGCGGCGTGTCCCTGCCCGATT<br>ACGGCGTGAGCTGGATCAGACAGCCCCCTGGCAAGTGTCTGGAGTGG<br>ATCGGCGTGATCTGGGGCTCTGAGACCACATACTATCAGTCCTCTCTG<br>AAGAGCAGGGTGACCATCTCTAAGGACAACAGCAAGAATCAGGTGT<br>CCCTGAAGCTGAGCTCCGTGACCGCAGCAGATACAGCCGTGTACTAT<br>TGCGCCAAGCACTACTATTACGGCGGCTCCTATGCTATGGATTATTGG<br>GGGCAGGGCACTCTGGTCACTGTCTCATCA |
| 359 | VH | CAGGTGCAGCTGCAGGAATCTGGACCCGGACTGGTGAAACCTAGTGA<br>AACTCTGTCTCTGACTTGTACCGTCTCAGGGGTCTCACTGCCAGACTA<br>CGGCGTGTCCTGGATCAGACAGCCCCCTGGCAAGTGCCTGGAGTGGA<br>TCGGCGTGATCTGGGGCTCTGAGACCACATACTATCAGAGCTCCCTG<br>AAGAGCCGGGTGACCATCTCCAAGGACAACTCTAAGAATCAGGTGTC<br>CCTGAAGCTGTCTAGCGTGACCGCCGCCGATACAGCCGTGTACTATT<br>GTGCCAAGCACTACTATTACGGCGGCAGCTATGCCATGGATTACTGG<br>GGCCAGGGCACCCTGGTGACAGTGTCCTCT |
| 360 | VH | CAGGTCCAGCTGCAGGAAAGCGGCCCAGGACTGGTGAAGCCTAGCG<br>AGACCCTGTCCCTGACCTGCACAGTGAGCGGCGTGTCCCTGCCTGATT<br>ACGGCGTGTCCTGGATCAGACAGCCCCCTGGCAAGTGTCTGGAGTGG<br>ATCGGCGTGATCTGGGGCTCCGAGACCACATACTATCAGTCCTCTCTG<br>AAGTCTAGGGTGACAATCTCTAAGGACAACAGCAAGAATCAGGTGA<br>GCCTGAAGCTGAGCTCCGTGACCGCAGCAGATACAGCCGTGTACTAT<br>TGTGCCAAGCACTACTATTACGGCGGCTCTTATGCTATGGATTATTGG<br>GGGCAGGGCACTCTGGTCACTGTCTCAAGC |
| 361 | VH | CAGGTGCAGCTGCAGGAGAGCGGCCCAGGACTGGTGAAGCCTTCCG<br>AGACACTGTCTCTGACCTGTACAGTGAGCGGCGTGTCCCTGCCCGAC<br>TACGGCGTGTCCTGGATCAGACAGCCACCTGGCAAGGGACTGGAGTG<br>GATCGGCGTGATCTGGGGCAGCGAGACCACATACTATCAGAGCTCCC<br>TGAAGTCCAGGGTGACCATCAGCAAGGACAACTCCAAGAATCAGGT<br>GAGCCTGAAGCTGTCTAGCGTGACCGCCGCCGATACAGCCGTGTACT<br>ATTGCGCCAAGCACTACTATTACGGCGGCTCCTATGCCATGGATTACT<br>GGGGCCAGGGCACCCTGGTCACAGTGTCCTCT |
| 362 | VH | CAGGTGCAGCTGCAGGAGTCTGGCCCAGGACTGGTGAAGCCTTCTGA<br>GACCCTGAGCCTGACCTGCACAGTGTCCGGCGTGTCTCTGCCCGATTA<br>CGGCGTGTCCTGGATCAGACAGCCACCTGGCAAGGGACTGGAGTGGA<br>TCGGCGTGATCTGGGGCTCTGAGACCACATACTATCAGTCTAGCCTG<br>AAGAGCCGGGTGACAATCTCCAAGGACAACTCTAAGAATCAGGTGTC<br>CCTGAAGCTGTCCTCTGTGACCGCCGCCGATACAGCCGTGTACTATTG<br>TGCCAAGCACTACTATTACGGCGGCAGCTATGCCATGGACTACTGGG<br>GCCAGGGCACCCTGGTGACAGTGAGCTCC |
| 363 | VH | CAGGTGCAGCTGCAGGAGTCTGGCCCAGGACTGGTGAAGCCTTCTGA<br>GACCCTGAGCCTGACCTGCACAGTGAGCGGCGTGTCCCTGCCCGATT<br>ACGGCGTGTCCTGGATCAGACAGCCACCTGGCAAGGGACTGGAGTGG<br>ATCGGCGTGATCTGGGGCAGCGAGACCACATACTATCAGTCCTCTCT<br>GAAGTCCAGGGTGACAATCTCCAAGGACAACTCTAAGAATCAGGTGA<br>GCCTGAAGCTGAGCTCCGTGACCGCAGCAGATACAGCCGTGTACTAT<br>TGCGCCAAGCACTACTATTACGGCGGCTCCTATGCCATGGACTACTG<br>GGGCCAGGGCACCCTGGTCACAGTGTCTAGC |
| 364 | VH | CAGGTGCAGCTGCAGGAGTCCGGCCCAGGACTGGTGAAGCCTTCCGA<br>GACACTGTCTCTGACCTGTACAGTGTCCGGCGTGTCTCTGCCCGACTA<br>CGGCGTGAGCTGGATCAGACAGCCACCTGGCAAGGGACTGGAGTGG<br>ATCGGCGTGATCTGGGGCTCTGAGACCACATACTATCAGTCCTCTCTG<br>AAGAGCCGGGTGACCATCAGCAAGGACAACTCCAAGAATCAGGTGT<br>CCCTGAAGCTGAGCTCCGTGACCGCAGCAGATACAGCCGTGTACTAT<br>TGCGCCAAGCACTACTATTACGGCGGCAGCTATGCCATGGATTACTG<br>GGGCCAGGGCACCCTGGTGACAGTGTCTAGC |
| 365 | VL | GAGATCGTGATGACCCAGAGCCCAGCCACACTGAGCCTGTCCCCAGG<br>AGAGAGGGCCACACTGTCTTGTAGAGCCAGCCAGGATATCTCCAAGT<br>ATCTGAACTGGTACCAGCAGAAGCCTGGACAGGCACCAAGGCTGCTG<br>ATCTACCACACCTCTAGACTGCACAGCGGCATCCCTGCCAGGTTTTCT<br>GGCAGCGGCTCCGGCACAGACTATACCCTGACAATCTCTAGCCTGCA<br>GCCAGAGGATTTCGCCGTGTACTTTTGTCAGCAGGGCAATACTCTGCC<br>ATACACCTTTGGATGCGGAACTAAACTGGAAATCAAG |
| 366 | VL | GAAATTGTGATGACCCAGTCCCCCGCTACTCTGTCTCTGTCCCCCGGA<br>GAACGGGCTACTCTGTCTTGTCGCGCTTCCCAGGATATTAGCAAGTAC<br>CTGAACTGGTATCAGCAGAAGCCAGGACAGGCACCAAGGCTGCTGAT<br>CTACCACACCTCTCGCCTGCACAGCGGCATCCCTGCACGGTTCTCTGG |

TABLE 2-continued

| Amino acid sequences of exemplary anti-CD19 molecules | | |
|---|---|---|
| SEQ ID NO | Region | Sequence |
| | | CAGCGGCTCCGGCACAGACTACACCCTGACAATCAGCTCCCTGCAGC CTGAGGATTTCGCCGTGTACTTTTGCCAGCAGGGCAATACCCTGCCAT ATACATTTGGCTGTGGCACCAAGCTGGAGATCAAG |
| 367 | VL | GAGATCGTGATGACCCAGTCCCCAGCCACACTGAGCCTGTCCCCAGG AGAGAGGGCCACCCTGTCTTGTAGAGCCAGCCAGGATATCTCCAAGT ATCTGAACTGGTACCAGCAGAAGCCTGGACAGGCACCAAGGCTGCTG ATCTACCACACCTCTAGACTGCACAGCGGCATCCCTGCCAGGTTTTCT GGCAGCGGCTCCGGCACAGACTATACCCTGACAATCTCTAGCCTGCA GCCAGAGGATTTCGCCGTGTACTTTTGTCAGCAGGGAAATACTCTGCC ATACACCTTTGGATGCGGAACTAAACTGGAAATCAAG |
| 368 | VL | GAGATTGTGATGACCCAGTCCCCCGCCACCCTGAGTCTGAGCCCCGG AGAACGAGCTACCCTGAGTTGCCGAGCTTCCCAGGACATTTCCAAGT ACCTGAACTGGTATCAGCAGAAGCCAGGACAGGCACCAAGGCTGCT GATCTACCACACCTCTCGCCTGCACAGCGGCATCCCAGCACGGTTCTC TGGCAGCGGCTCCGGCACAGACTACACCCTGACAATCAGCTCCCTGC AGCCTGAGGATTTCGCCGTGTACTTTTGCCAGCAGGGCAATACCCTG CCATATACATTTGGCTGTGGCACCAAGCTGGAGATCAAG |
| 369 | VL | GAGATCGTGATGACCCAGTCTCCAGCCACACTGTCTCTGAGCCCAGG AGAGAGGGCCACCCTGTCTTGCCGCGCCAGCCAGGATATCTCCAAGT ATCTGAACTGGTACCAGCAGAAGCCAGGACAGGCACCAAGGCTGCT GATCTACCACACCTCTCGCCTGCACAGCGGCATCCCAGCACGGTTCTC CGGCTCTGGCAGCGGCACAGACTACACCCTGACAATCTCCTCTCTGC AGCCCGAGGATTTCGCCGTGTATTTTTGCCAGCAGGGCAATACCCTG CCTTACACATTTGGCCAGGGCACCAAGCTGGAGATCAAG |
| 370 | VL | GAGATCGTGATGACCCAGAGCCCAGCCACACTGAGCCTGTCCCCAGG AGAGAGGGCCACCCTGAGCTGCAGAGCCTCCCAGGATATCTCTAAGT ATCTGAACTGGTACCAGCAGAAGCCTGGACAGGCACCAAGGCTGCTG ATCTACCACACCAGCAGACTGCACTCCGGCATCCCTGCAAGGTTCTCT GGCAGCGGCTCCGGCACAGACTACACCCTGACAATCTCTAGCCTGCA GCCTGAGGATTTCGCCGTGTATTTTTGTCAGCAGGGCAATACCCTGCC ATACACATTTGGCCAGGGCACCAAGCTGGAGATCAAG |
| 371 | VL | GAGATCGTGATGACCCAGAGCCCAGCCACACTGTCTCTGAGCCCAGG AGAGAGGGCCACCCTGAGCTGTCGCGCCTCCCAGGATATCTCTAAGT ATCTGAACTGGTACCAGCAGAAGCCAGGACAGGCACCAAGGCTGCT GATCTACCACACCAGCCGCCTGCACTCCGGCATCCCAGCACGGTTCT CCGGCTCTGGCAGCGGCACAGACTACACCCTGACAATCTCCTCTCTG CAGCCCGAGGATTTCGCCGTGTATTTTTGCCAGCAGGGCAATACCCT GCCTTACACATTTGGCCAGGGCACCAAGCTGGAGATCAAG |
| 372 | VL | GAGATCGTGATGACCCAGTCTCCAGCCACACTGAGCCTGTCCCCAGG AGAGAGGGCCACCCTGTCTTGCAGAGCCAGCCAGGATATCTCCAAGT ATCTGAACTGGTACCAGCAGAAGCCTGGACAGGCACCAAGGCTGCTG ATCTACCACACCTCTAGACTGCACAGCGGCATCCCAGCAAGGTTCTC TGGCAGCGGCTCCGGCACAGACTACACCCTGACAATCTCTAGCCTGC AGCCTGAGGATTTCGCCGTGTATTTTTGCCAGCAGGGCAATACCCTGC CATACACATTTGGCCAGGGCACCAAGCTGGAGATCAAG |
| SEQ ID NO: 250 | Anti-CD19 VH | QVQLQESGPGLVKPSETLSLTCTVSGVSLPDYGVSWIRQPPGKGLEWIGV IWGSETTYYQSSLKSRVTISKDNSKNQVSLKLSSVTAADTAVYYCAKHY YYGGSYAMDYWGQGTLVTVSS |
| SEQ ID NO: 251 | Anti-CD19 VL | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGQG TKLEIK |
| SEQ ID NO: 331 | VH | QVQLQESGPGLVKPSETLSLTCTVSGVSLPDYGVSWIRQPPGKCLEWIGV IWGSETTYYQSSLKSRVTISKDNSKNQVSLKLSSVTAADTAVYYCAKHY YYGGSYAMDYWGQGTLVTVSS |
| SEQ ID NO: 332 | VL | EIVMTQSPATLSLSPGERATLSCRASQDISKYLNWYQQKPGQAPRLLIYH TSRLHSGIPARFSGSGSGTDYTLTISSLQPEDFAVYFCQQGNTLPYTFGCG TKLEIK |
| 373 | CAR 1 scFv | EIVMTQSPATLSLSPGERATLSCRASQDISKYLNWYQQKPGQAPRLLIYHTSRL HSGIPARFSGSGSGTDYTLTISSLQPEDFAVYFCQQGNTLPYTFGQGTKLEIKG GGGSGGGGSGGGGSQVQLQESGPGLVKPSETLSLTCTVSGVSLPDYGVSWIRQP PGKGLEWIGVIWGSETTYYSSSLKSRVTISKDNSKNQVSLKLSSVTAADTAVYY CAKHYYYGGSYAMDYWGQGTLVTVSS |
| 374 | CAR 3 scFv | qvqlqesgpglvkpsetlsltctvsgvslpdygvswirqppgkglewigviwgs ettyyssslksrvtiskdnsknqvslklssvtaadtavyycakhyyyggsyamd |

TABLE 2-continued

Amino acid sequences of exemplary anti-CD19 molecules

| SEQ ID NO | Region | Sequence |
|---|---|---|
| | | ywgqgtlvtvssggggsggggsggggseivmtqspatlslspgeratlscrasq<br>diskylnwyqqkpgqaprlliyhtsrlhsgiparfsgsgsgtdytltisslqpe<br>dfavyfcqqgntlpytfgqgtkleik |
| 375 | CAR 4<br>scFv | qvqlqesgpglvkpsetlsltctvsgvslpdygvswirqppgkglewigviwgs<br>ettyyqsslksrvtiskdnsknqvslklssvtaadtavyycakhyyyggsyamd<br>ywgqgtlvtvssggggsggggggggseivmtqspatlslspgeratlscrasq<br>diskylnwyqqkpgqaprlliyhtsrlhsgiparfsgsgsgtdytltisslqpe<br>dfavyfcqqgntlpytfgqgtkleik |
| 376 | CAR 5<br>scFv | eivmtqspatlslspgeratlscrasqdiskylnwyqqkpgqaprlliyhtsrl<br>hsgiparfsgsgsgtdytltisslqpedfavyfcqqgntlpytfgqgtkleikg<br>gggsggggsggggsggggsqvqlqesgpglvkpsetlsltctvsgvslpdygvs<br>wirqppgkglewigviwgsettyyssslksrvtiskdnsknqvslklssvtaad<br>tavyycakhyyyggsyamdywgqgtlvtvss |
| 377 | CAR 6<br>scFv | eivmtqspatlslspgeratlscrasqdiskylnwyqqkpgqaprlliyhtsrl<br>hsgiparfsgsgsgtdytltisslqpedfavyfcqqgntlpytfgqgtkleikg<br>gggsggggggggsggggsqvqlqesgpglvkpsetlsltctvsgvslpdygvs<br>wirqppgkglewigviwgsettyyqsslksrvtiskdnsknqvslklssvtaad<br>tavyycakhyyyggsyamdywgqgtlvtvss |
| 378 | CAR 7<br>scFv | qvqlqesgpglvkpsetlsltctvsgvslpdygvswirqppgkglewigviwgs<br>ettyyssslksrvtiskdnsknqvslklssvtaadtavyycakhyyyggsyamd<br>ywgqgtlvtvssggggsggggggggsggggseivmtqspatlslspgeratls<br>crasqdiskylnwyqqkpgqaprlliyhtsrlhsgiparfsgsgsgtdytltis<br>slqpedfavyfcqqgntlpytfgqgtkleik |
| 379 | CAR 8<br>scFv | qvqlqesgpglvkpsetlsltctvsgvslpdygvswirqppgkglewigviwgs<br>ettyyqsslksrvtiskdnsknqvslklssvtaadtavyycakhyyyggsyamd<br>ywgqgtlvtvssggggsggggsggggsggggseivmtqspatlslspgeratls<br>crasqdiskylnwyqqkpgqaprlliyhtsrlhsgiparfsgsgsgtdytltis<br>slqpedfavyfcqqgntlpytfgqgtkleik |
| 380 | CAR 9<br>scFv | eivmtqspatlslspgeratlscrasqdiskylnwyqqkpgqaprlliyhtsrl<br>hsgiparfsgsgsgtdytltisslqpedfavyfcqqgntlpytfgqgtkleikg<br>gggsggggsggggsggggsqvqlqesgpglvkpsetlsltctvsgvslpdygvs<br>wirqppgkglewigviwgsettyynsslksrvtiskdnsknqvslklssvtaad<br>tavyycakhyyyggsyamdywgqgtlvtvss |
| 381 | CAR 10<br>scFv | qvqlqesgpglvkpsetlsltctvsgvslpdygvswirqppgkglewigviwgs<br>ettyynsslksrvtiskdnsknqvslklssvtaadtavyycakhyyyggsyamd<br>ywgqgtlvtvssggggggggsggggsggggseivmtqspatlslspgeratls<br>crasqdiskylnwyqqkpgqaprlliyhtsrlhsgiparfsgsgsgtdytltis<br>slqpedfavyfcqqgntlpytfgqgtkleik |
| 382 | CAR 11<br>scFv | eivmtqspatlslspgeratlscrasqdiskylnwyqqkpgqaprlliyhtsrl<br>hsgiparfsgsgsgtdytltisslqpedfavyfcqqgntlpytfgqgtkleikg<br>gggsggggsggggsqvqlqesgpglvkpsetlsltctvsgvslpdygvswirqp<br>pgkglewigviwgsettyynsslksrvtiskdnsknqvslklssvtaadtavyy<br>cakhyyyggsyamdywgqgtlvtvss |
| 383 | CAR 12<br>scFv | qvqlqesgpglvkpsetlsltctvsgvslpdygvswirqppgkglewigviwgs<br>ettyynsslksrvtiskdnsknqvslklssvtaadtavyycakhyyyggsyamd<br>ywgqgtlvtvssggggsggggsggggseivmtqspatlslspgeratlscrasq<br>diskylnwyqqkpgqaprlliyhtsrlhsgiparfsgsgsgtdytltisslqpe<br>dfavyfcqqgntlpytfgqgtkleik |
| 384 | CAR A full<br>nucleotide<br>sequence;<br>with leader | atgcttctcctggtgacaagccttctgctctgtgagttaccacacccagcattc<br>ctcctgatcccagacatccagatgacacagactacatcctccctgtctgcctct<br>ctgggagacagagtcaccatcagttgcagggcaagtcaggacattagtaaatat<br>ttaaattggtatcagcagaaaccagatggaactgttaaactcctgatctaccat<br>acatcaagattacactcaggagtcccatcaaggttcagtggcagtgggtctgga<br>acagattattctctcaccattagcaacctggagcaagaagatattgccacttac<br>ttttgccaacagggtaatacgcttccgtacacgttcggaggggggactaagttg<br>gaaataacaggctccacctctggatccggcaagcccggatctggcgagggatcc<br>accaagggcgaggtgaaactgcaggagtcaggacctggcctggtggcgccctca<br>cagagcctgtccgtcacatgcactgtctcaggggtctcattacccgactatggt<br>gtaagctggattcgccagcctccacgaaagggtctggagtggctgggagtaata<br>tggggtagtgaaaccacatactataattcagctctcaaatccagactgaccatc<br>atcaaggacaactccaagagccaagttttcttaaaaatgaacagtctgcaaact<br>gatgacacagccatttactactgtgccaaacattattactacggtggtagctat<br>gctatggactactggggtcaaggaacctcagtcaccgtctcctcagcggccgca<br>attgaagttatgtatcctcctccttacctagacaatgagaagagcaatggaacc<br>attatccatgtgaaagggaaacacctttgtccaagtcccctatttcccggacct<br>tctaagcccttttgggtgctggtggtggttgggggagtcctggcttgctatagc |

TABLE 2-continued

Amino acid sequences of exemplary anti-CD19 molecules

| SEQ ID NO | Region | Sequence |
|---|---|---|
| | | ttgctagtaacagtggcctttattattttctgggtgaggagtaagaggagcagg<br>ctcctgcacagtgactacatgaacatgactccccgccgccccgggcccacccgc<br>aagcattaccagccctatgccccaccacgcgacttcgcagcctatcgctccaga<br>gtgaagttcagcaggagcgcagacgcccccgcgtaccagcagggccagaaccag<br>ctctataacgagctcaatctaggacgaagagaggagtacgatgttttggacaag<br>agacgtggccgggaccctgagatggggggaaagccgagaaggaagaaccctcag<br>gaaggcctgtacaatgaactgcagaaagataagatggcggaggcctacagtgag<br>attgggatgaaaggcgagcgccggaggggcaaggggcacgatggcctttaccag<br>ggtctcagtacagccaccaaggacacctacgacgcccttcacatgcaggccctg<br>ccccctcgc |
| 385 | CAR A-<br>full amino<br>acid<br>transgene<br>sequence;<br>with leader | MLLLVTSLLLCELPHPAFLLIPDIQMTQTTSSLSASLGDRVTISCRASQDISKY<br>LNWYQQKPDGTVKLLIYHTSRLHSGVPSRFSGSGSGTDYSLTISNLEQEDIATY<br>FCQQGNTLPYTFGGGTKLEITGSTSGSGKPGSGEGSTKGEVKLQESGPGLVAPS<br>QSLSVTCTVSGVSLPDYGVSWIRQPPRKGLEWLGVIWGSETTYYNSALKSRLTI<br>IKDNSKSQVFLKMNSLQTDDTAIYYCAKHYYYGGSYAMDYWGQGTSVTVSSAAA<br>IEVMYPPPYLDNEKSNGTIIHVKGKHLCPSPLFPGPSKPFWVLVVVGGVLACYS<br>LLVTVAFIIFWVRSKRSRLLHSDYMNMTPRRPGPTRKHYQPYAPPRDFAAYRSR<br>VKFSRSADAPAYQQGQNQLYNELNLGRREEYDVLDKRRGRDPEMGGKPRRKNPQ<br>EGLYNELQKDKMAEAYSEIGMKGERRRGKGHDGLYQGLSTATKDTYDALHMQAL<br>PPR |
| 386 | CAR A-<br>CD19 scFv<br>nucleotide<br>sequence<br>with leader | atgcttctcctggtgacaagccttctgctctgtgagttaccacacccagcattc<br>ctcctgatcccagacatccagatgacacagactacatcctccctgtctgcctct<br>ctgggagacagagtcaccatcagttgcagggcaagtcaggacattagtaaatat<br>ttaaattggtatcagcagaaaccagatggaactgttaaactcctgatctaccat<br>acatcaagattacactcaggagtcccatcaaggttcagtggcagtgggtctgga<br>acagattattctctcaccattagcaacctggagcaagaagatattgccacttac<br>ttttgccaacagggtaatacgcttccgtacacgttcggaggggggactaagttg<br>gaaataacaggctccacctctggatccggcaagcccggatctggcgagggatcc<br>accaagggcgaggtgaaactgcaggagtcaggacctggcctggtggcgccctca<br>cagagcctgtccgtcacatgcactgtctcaggggtctcattacccgactatggt<br>gtaagctggattcgccagcctccacgaaagggtctggagtggctgggagtaata<br>tggggtagtgaaaccacatactataattcagctctcaaatccagactgaccatc<br>atcaaggacaactccaagagccaagttttcttaaaaatgaacagtctgcaaact<br>gatgacacagccatttactactgtgccaaacattattactacggtggtagctat<br>gctatggactactggggtcaaggaacctcagtcaccgtctcctca |
| 387 | CAR A-<br>CD19 scFv<br>amino acid<br>sequence;<br>with leader | MLLLVTSLLLCELPHPAFLLIPDIQMTQTTSSLSASLGDRVTISCRASQDISKY<br>LNWYQQKPDGTVKLLIYHTSRLHSGVPSRFSGSGSGTDYSLTISNLEQEDIATY<br>FCQQGNTLPYTFGGGTKLEITGSTSGSGKPGSGEGSTKGEVKLQESGPGLVAPS<br>QSLSVTCTVSGVSLPDYGVSWIRQPPRKGLEWLGVIWGSETTYYNSALKSRLTI<br>IKDNSKSQVFLKMNSLQTDDTAIYYCAKHYYYGGSYAMDYWGQGTSVTVS |
| 388 | CAR A-<br>full<br>nucleotide<br>sequence;<br>no leader | gacatccagatgacacagactacatcctccctgtctgcctctctgggagacaga<br>gtcaccatcagttgcagggcaagtcaggacattagtaaatatttaaattggtat<br>cagcagaaaccagatggaactgttaaactcctgatctaccatacatcaagatta<br>cactcaggagtcccatcaaggttcagtggcagtgggtctggaacagattattct<br>ctcaccattagcaacctggagcaagaagatattgccacttacttttgccaacag<br>ggtaatacgcttccgtacacgttcggaggggggactaagttggaaataacaggc<br>tccacctctggatccggcaagcccggatctggcgagggatccaccaagggcgag<br>gtgaaactgcaggagtcaggacctggcctggtggcgccctcacagagcctgtcc<br>gtcacatgcactgtctcaggggtctcattacccgactatggtgtaagctggatt<br>cgccagcctccacgaaagggtctggagtggctgggagtaatatggggtagtgaa<br>accacatactataattcagctctcaaatccagactgaccatcatcaaggacaac<br>tccaagagccaagttttcttaaaaatgaacagtctgcaaactgatgacacagcc<br>atttactactgtgccaaacattattactacggtggtagctatgctatggactac<br>tggggtcaaggaacctcagtcaccgtctcctcagcggccgcaattgaagttatg<br>tatcctcctccttacctagacaatgagaagagcaatggaaccattatccatgtg<br>aaagggaaacacctttgtccaagtcccctatttcccggaccttctaagcccttt<br>tgggtgctggtggtggttgggggagtcctggcttgctatagcttgctagtaaca<br>gtggcctttattattttctgggtgaggagtaagaggagcaggctcctgcacagt<br>gactacatgaacatgactccccgccgccccgggcccacccgcaagcattaccag<br>ccctatgccccaccacgcgacttcgcagcctatcgctccagagtgaagttcagc<br>aggagcgcagacgcccccgcgtaccagcagggccagaaccagctctataacgag<br>ctcaatctaggacgaagagaggagtacgatgttttggacaagagacgtggccgg<br>gaccctgagatggggggaaagccgagaaggaagaaccctcaggaaggcctgtac<br>aatgaactgcagaaagataagatggcggaggcctacagtgagattgggatgaaa<br>ggcgagcgccggaggggcaaggggcacgatggcctttaccagggtctcagtaca<br>gccaccaaggacacctacgacgcccttcacatgcaggccctgccccctcgc |
| 389 | CAR A-<br>full amino<br>acid<br>transgene<br>sequence; | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEITG<br>STSGSGKPGSGEGSTKGEVKLQESGPGLVAPSQSLSVTCTVSGVSLPDYGVSWI<br>RQPPRKGLEWLGVIWGSETTYYNSALKSRLTIIKDNSKSQVFLKMNSLQTDDTA<br>IYYCAKHYYYGGSYAMDYWGQGTSVTVSSAAAIEVMYPPPYLDNEKSNGTIIHV |

TABLE 2-continued

| Amino acid sequences of exemplary anti-CD19 molecules | | |
|---|---|---|
| SEQ ID NO | Region | Sequence |
| | no leader | KGKHLCPSPLFPGPSKPFWVLVVVGGVLACYSLLVTVAFIIFWVRSKRSRLLHS<br>DYMNMTPRRPGPTRKHYQPYAPPRDFAAYRSRVKFSRSADAPAYQQGQNQLYNE<br>LNLGRREEYDVLDKRRGRDPEMGGKPRRKNPQEGLYNELQKDKMAEAYSEIGMK<br>GERRRGKGHDGLYQGLSTATKDTYDALHMQALPPR |
| 390 | CAR A-<br>CD19 scFv<br>nucleotide;<br>no leader | gacatccagatgacacagactacatcctccctgtctgcctctctgggagacaga<br>gtcaccatcagttgcagggcaagtcaggacattagtaaatatttaaattggtat<br>cagcagaaaccagatggaactgttaaactcctgatctaccatacatcaagatta<br>cactcaggagtcccatcaaggttcagtggcagtgggtctggaacagattattct<br>ctcaccattagcaacctggagcaagaagatattgccacttacttttgccaacag<br>ggtaatacgcttccgtacacgttcggaggggggactaagttggaaataacaggc<br>tccacctctggatccggcaagcccggatctggcgagggatccaccaagggcgag<br>gtgaaactgcaggagtcaggacctggcctggtggcgccctcacagagcctgtcc<br>gtcacatgcactgtctcaggggtctcattacccgactatggtgtaagctggatt<br>cgccagcctccacgaaagggtctggagtggctgggagtaatatggggtagtgaa<br>accacatactataattcagctctcaaatccagactgaccatcatcaaggacaac<br>tccaagagccaagttttcttaaaaatgaacagtctgcaaactgatgacacagcc<br>atttactactgtgccaaacattattactacggtggtagctatgctatggactac<br>tggggtcaaggaacctcagtcaccgtctcctca |
| 391 | CAR A-<br>CD19 scFv<br>amino acid<br>sequence;<br>no leader | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEITG<br>STSGSGKPGSGEGSTKGEVKLQESGPGLVAPSQSLSVTCTVSGVSLPDYGVSWI<br>RQPPRKGLEWLGVIWGSETTYYNSALKSRLTIIKDNSKSQVFLKMNSLQTDDTA<br>IYYCAKHYYYGGSYAMDYWGQGTSVTVSS |
| 392 | CAR B-<br>full<br>nucleotide<br>sequence;<br>with leader | ATGCTGCTGCTGGTGACCAGCCTGCTGCTGTGCGAGCTGCCCCACCCCGCCTTT<br>CTGCTGATCCCCGACATCCAGATGACCCAGACCACCTCCAGCCTGAGCGCCAGC<br>CTGGGCGACCGGGTGACCATCAGCTGCCGGGCCAGCCAGGACATCAGCAAGTAC<br>CTGAACTGGTATCAGCAGAAGCCCGACGGCACCGTCAAGCTGCTGATCTACCAC<br>ACCAGCCGGCTGCACAGCGGCGTGCCCAGCCGGTTTAGCGGCAGCGGCTCCGGC<br>ACCGACTACAGCCTGACCATCTCCAACCTGGAACAGGAAGATATCGCCACCTAC<br>TTTTGCCAGCAGGGCAACACACTGCCCTACACCTTTGGCGGCGGAACAAAGCTG<br>GAAATCACCGGCAGCACCTCCGGCAGCGGCAAGCCTGGCAGCGGCGAGGGCAGC<br>ACCAAGGGCGAGGTGAAGCTGCAGGAAAGCGGCCCTGGCCTGGTGGCCCCCAGC<br>CAGAGCCTGAGCGTGACCTGCACCGTGAGCGGCGTGAGCCTGCCCGACTACGGC<br>GTGAGCTGGATCCGGCAGCCCCCCAGGAAGGGCCTGGAATGGCTGGGCGTGATC<br>TGGGGCAGCGAGACCACCTACTACAACAGCGCCCTGAAGAGCCGGCTGACCATC<br>ATCAAGGACAACAGCAAGAGCCAGGTGTTCCTGAAGATGAACAGCCTGCAGACC<br>GACGACACCGCCATCTACTACTGCGCCAAGCACTACTACTACGGCGGCAGCTAC<br>GCCATGGACTACTGGGGCCAGGGCACCAGCGTGACCGTGAGCAGCGAATCTAAG<br>TACGGACCGCCCTGCCCCCCTTGCCCTATGTTCTGGGTGCTGGTGGTGGTCGGA<br>GGCGTGCTGGCCTGCTACAGCCTGCTGGTCACCGTGGCCTTCATCATCTTTTGG<br>GTGAAACGGGGCAGAAAGAAACTCCTGTATATATTCAAACAACCATTTATGAGA<br>CCAGTACAAACTACTCAAGAGGAAGATGGCTGTAGCTGCCGATTTCCAGAAGAA<br>GAAGAAGGAGGATGTGAACTGCGGGTGAAGTTCAGCAGAAGCGCCGACGCCCCT<br>GCCTACCAGCAGGGCCAGAATCAGCTGTACAACGAGCTGAACCTGGGCAGAAGG<br>GAAGAGTACGACGTCCTGGATAAGCGGAGAGGCCGGGACCCTGAGATGGGCGGC<br>AAGCCTCGGCGGAAGAACCCCCAGGAAGGCCTGTATAACGAACTGCAGAAAGAC<br>AAGATGGCCGAGGCCTACAGCGAGATCGGCATGAAGGGCGAGCGGAGGCGGGGC<br>AAGGGCCACGACGGCCTGTATCAGGGCCTGTCCACCGCCACCAAGGATACCTAC<br>GACGCCCTGCACATGCAGGCCCTGCCCCCAAGG |
| 393 | CAR B-<br>full<br>transgene<br>amino acid<br>sequence;<br>with leader | MLLLVTSLLLCELPHPAFLLIPDIQMTQTTSSLSASLGDRVTISCRASQDISKY<br>LNWYQQKPDGTVKLLIYHTSRLHSGVPSRFSGSGSGTDYSLTISNLEQEDIATY<br>FCQQGNTLPYTFGGGTKLEITGSTSGSGKPGSGEGSTKGEVKLQESGPGLVAPS<br>QSLSVTCTVSGVSLPDYGVSWIRQPPRKGLEWLGVIWGSETTYYNSALKSRLTI<br>IKDNSKSQVFLKMNSLQTDDTAIYYCAKHYYYGGSYAMDYWGQGTSVTVSSESK<br>YGPPCPPCPMFWVLVVVGGVLACYSLLVTVAFIIFWVKRGRKKLLYIFKQPFMR<br>PVQTTQEEDGCSCRFPEEEEGGCELRVKFSRSADAPAYQQGQNQLYNELNLGRR<br>EEYDVLDKRRGRDPEMGGKPRRKNPQEGLYNELQKDKMAEAYSEIGMKGERRRG<br>KGHDGLYQGLSTATKDTYDALHMQALPPR |
| 394 | CAR B-<br>CD19 scFv<br>nucleotide<br>sequence;<br>with leader | ATGCTGCTGCTGGTGACCAGCCTGCTGCTGTGCGAGCTGCCCCACCCCGCCTTT<br>CTGCTGATCCCCGACATCCAGATGACCCAGACCACCTCCAGCCTGAGCGCCAGC<br>CTGGGCGACCGGGTGACCATCAGCTGCCGGGCCAGCCAGGACATCAGCAAGTAC<br>CTGAACTGGTATCAGCAGAAGCCCGACGGCACCGTCAAGCTGCTGATCTACCAC<br>ACCAGCCGGCTGCACAGCGGCGTGCCCAGCCGGTTTAGCGGCAGCGGCTCCGGC<br>ACCGACTACAGCCTGACCATCTCCAACCTGGAACAGGAAGATATCGCCACCTAC<br>TTTTGCCAGCAGGGCAACACACTGCCCTACACCTTTGGCGGCGGAACAAAGCTG<br>GAAATCACCGGCAGCACCTCCGGCAGCGGCAAGCCTGGCAGCGGCGAGGGCAGC<br>ACCAAGGGCGAGGTGAAGCTGCAGGAAAGCGGCCCTGGCCTGGTGGCCCCCAGC<br>CAGAGCCTGAGCGTGACCTGCACCGTGAGCGGCGTGAGCCTGCCCGACTACGGC<br>GTGAGCTGGATCCGGCAGCCCCCCAGGAAGGGCCTGGAATGGCTGGGCGTGATC<br>TGGGGCAGCGAGACCACCTACTACAACAGCGCCCTGAAGAGCCGGCTGACCATC<br>ATCAAGGACAACAGCAAGAGCCAGGTGTTCCTGAAGATGAACAGCCTGCAGACC |

TABLE 2-continued

Amino acid sequences of exemplary anti-CD19 molecules

| SEQ ID NO | Region | Sequence |
|---|---|---|
| | | GACGACACCGCCATCTACTACTGCGCCAAGCACTACTACTACGGCGGCAGCTAC<br>GCCATGGACTACTGGGGCCAGGGCACCAGCGTGACCGTGAGCAGC |
| 395 | CAR B-<br>CD19 scFv<br>amino acid<br>sequence;<br>with leader | MLLLVTSLLLCELPHPAFLLIPDIQMTQTTSSLSASLGDRVTISCRASQDISKY<br>LNWYQQKPDGTVKLLIYHTSRLHSGVPSRFSGSGSGTDYSLTISNLEQEDIATY<br>FCQQGNTLPYTFGGGTKLEITGSTSGSGKPGSGEGSTKGEVKLQESGPGLVAPS<br>QSLSVTCTVSGVSLPDYGVSWIRQPPRKGLEWLGVIWGSETTYYNSALKSRLTI<br>IKDNSKSQVFLKMNSLQTDDTAIYYCAKHYYYGGSYAMDYWGQGTSVTVSS |
| 396 | CAR B-<br>full<br>nucleotide<br>sequence;<br>no leader | GACATCCAGATGACCCAGACCACCTCCAGCCTGAGCGCCAGCCTGGGCGACCGG<br>GTGACCATCAGCTGCCGGGCCAGCCAGGACATCAGCAAGTACCTGAACTGGTAT<br>CAGCAGAAGCCCGACGGCACCGTCAAGCTGCTGATCTACCACACCAGCCGGCTG<br>CACAGCGGCGTGCCCAGCCGGTTTAGCGGCAGCGGCTCCGGCACCGACTACAGC<br>CTGACCATCTCCAACCTGGAACAGGAAGATATCGCCACCTACTTTTGCCAGCAG<br>GGCAACACACTGCCCTACACCTTTGGCGGCGGAACAAAGCTGGAAATCACCGGC<br>AGCACCTCCGGCAGCGGCAAGCCTGGCAGCGGCGAGGGCAGCACCAAGGGCGAG<br>GTGAAGCTGCAGGAAAGCGGCCCTGGCCTGGTGGCCCCCAGCCAGAGCCTGAGC<br>GTGACCTGCACCGTGAGCGGCGTGAGCCTGCCCGACTACGGCGTGAGCTGGATC<br>CGGCAGCCCCCCAGGAAGGGCCTGGAATGGCTGGGCGTGATCTGGGGCAGCGAG<br>ACCACCTACTACAACAGCGCCCTGAAGAGCCGGCTGACCATCATCAAGGACAAC<br>AGCAAGAGCCAGGTGTTCCTGAAGATGAACAGCCTGCAGACCGACGACACCGCC<br>ATCTACTACTGCGCCAAGCACTACTACTACGGCGGCAGCTACGCCATGGACTAC<br>TGGGGCCAGGGCACCAGCGTGACCGTGAGCAGCGAATCTAAGTACGGACCGCCC<br>TGCCCCCCTTGCCCTATGTTCTGGGTGCTGGTGGTGGTCGGAGGCGTGCTGGCC<br>TGCTACAGCCTGCTGGTCACCGTGGCCTTCATCATCTTTTGGGTGAAACGGGGC<br>AGAAAGAAACTCCTGTATATATTCAAACAACCATTTATGAGACCAGTACAAACT<br>ACTCAAGAGGAAGATGGCTGTAGCTGCCGATTTCCAGAAGAAGAAGAAGGAGGA<br>TGTGAACTGCGGGTGAAGTTCAGCAGAAGCGCCGACGCCCCTGCCTACCAGCAG<br>GGCCAGAATCAGCTGTACAACGAGCTGAACCTGGGCAGAAGGGAAGAGTACGAC<br>GTCCTGGATAAGCGGAGAGGCCGGGACCCTGAGATGGGCGGCAAGCCTCGGCGG<br>AAGAACCCCCAGGAAGGCCTGTATAACGAACTGCAGAAAGACAAGATGGCCGAG<br>GCCTACAGCGAGATCGGCATGAAGGGCGAGCGGAGGCGGGGCAAGGGCCACGAC<br>GGCCTGTATCAGGGCCTGTCCACCGCCACCAAGGATACCTACGACGCCCTGCAC<br>ATGCAGGCCCTGCCCCCAAGG |
| 397 | CAR B-<br>full amino<br>acid<br>transgene<br>sequence;<br>no leader | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEITG<br>STSGSGKPGSGEGSTKGEVKLQESGPGLVAPSQSLSVTCTVSGVSLPDYGVSWI<br>RQPPRKGLEWLGVIWGSETTYYNSALKSRLTIIKDNSKSQVFLKMNSLQTDDTA<br>IYYCAKHYYYGGSYAMDYWGQGTSVTVSSESKYGPPCPPCPMFWVLVVVGGVLA<br>CYSLLVTVAFIIFWVKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRR<br>KNPQEGLYNELQKDKMAEAYSEIGMKGERRRGKGHDGLYQGLSTATKDTYDALH<br>MQALPPR |
| 398 | CAR B-<br>CD19 scFv<br>sequence;<br>no leader | GACATCCAGATGACCCAGACCACCTCCAGCCTGAGCGCCAGCCTGGGCGACCGG<br>GTGACCATCAGCTGCCGGGCCAGCCAGGACATCAGCAAGTACCTGAACTGGTAT<br>CAGCAGAAGCCCGACGGCACCGTCAAGCTGCTGATCTACCACACCAGCCGGCTG<br>CACAGCGGCGTGCCCAGCCGGTTTAGCGGCAGCGGCTCCGGCACCGACTACAGC<br>CTGACCATCTCCAACCTGGAACAGGAAGATATCGCCACCTACTTTTGCCAGCAG<br>GGCAACACACTGCCCTACACCTTTGGCGGCGGAACAAAGCTGGAAATCACCGGC<br>AGCACCTCCGGCAGCGGCAAGCCTGGCAGCGGCGAGGGCAGCACCAAGGGCGAG<br>GTGAAGCTGCAGGAAAGCGGCCCTGGCCTGGTGGCCCCCAGCCAGAGCCTGAGC<br>GTGACCTGCACCGTGAGCGGCGTGAGCCTGCCCGACTACGGCGTGAGCTGGATC<br>CGGCAGCCCCCCAGGAAGGGCCTGGAATGGCTGGGCGTGATCTGGGGCAGCGAG<br>ACCACCTACTACAACAGCGCCCTGAAGAGCCGGCTGACCATCATCAAGGACAAC<br>AGCAAGAGCCAGGTGTTCCTGAAGATGAACAGCCTGCAGACCGACGACACCGCC<br>ATCTACTACTGCGCCAAGCACTACTACTACGGCGGCAGCTACGCCATGGACTAC<br>TGGGGCCAGGGCACCAGCGTGACCGTGAGCAGC |
| 399 | CAR B-<br>CD19 scFv<br>sequence;<br>no leader | DIQMTQTTSSLSASLGDRVTISCRASQDISKYLNWYQQKPDGTVKLLIYHTSRL<br>HSGVPSRFSGSGSGTDYSLTISNLEQEDIATYFCQQGNTLPYTFGGGTKLEITG<br>STSGSGKPGSGEGSTKGEVKLQESGPGLVAPSQSLSVTCTVSGVSLPDYGVSWI<br>RQPPRKGLEWLGVIWGSETTYYNSALKSRLTIIKDNSKSQVFLKMNSLQTDDTA<br>IYYCAKHYYYGGSYAMDYWGQGTSVTVSS |

BCMA CAR

In some embodiments, the CAR-expressing cell described herein is a BCMA CAR-expressing cell (for example, a cell expressing a CAR that binds to human BCMA). Exemplary BCMA CARs can include sequences disclosed in Table 1 or 16 of WO2016/014565, incorporated herein by reference. The BCMA CAR construct can include an optional leader sequence; an optional hinge domain, for example, a CD8 hinge domain; a transmembrane domain, for example, a CD8 transmembrane domain; an intracellular domain, for example, a 4-1BB intracellular domain; and a functional signaling domain, for example, a CD3 zeta domain. In certain embodiments, the domains are contiguous and in the same reading frame to form a single fusion protein. In other embodiments, the domains are in separate polypeptides, for example, as in an RCAR molecule as described herein.

In some embodiments, the BCMA CAR molecule includes one or more CDRs, VH, VL, scFv, or full-length sequences of BCMA-1, BCMA-2, BCMA-3, BCMA-4, BCMA-5, BCMA-6, BCMA-7, BCMA-8, BCMA-9, BCMA-10, BCMA-11, BCMA-12, BCMA-13, BCMA-14, BCMA-15, 149362, 149363, 149364, 149365, 149366, 149367, 149368, 149369, BCMA_EBB-C1978-A4, BCMA_EBB-C1978-G1, BCMA_EBB-C1979-C1, BCMA_EBB-C1978-C7, BCMA_EBB-C1978-D10, BCMA_EBB-C1979-C12, BCMA_EBB-C1980-G4, BCMA_EBB-C1980-D2, BCMA_EBB-C1978-A10, BCMA_EBB-C1978-D4, BCMA_EBB-C1980-A2, BCMA_EBB-C1981-C3, BCMA_EBB-C1978-G4, A7D12.2, C11D5.3, C12A3.2, or C13F12.1 disclosed in WO2016/014565, or a sequence substantially (for example, 95-99%) identical thereto.

Additional exemplary BCMA-targeting sequences that can be used in the anti-BCMA CAR constructs are disclosed in WO 2017/021450, WO 2017/011804, WO 2017/025038, WO 2016/090327, WO 2016/130598, WO 2016/210293, WO 2016/090320, WO 2016/014789, WO 2016/094304, WO 2016/154055, WO 2015/166073, WO 2015/188119, WO 2015/158671, U.S. Pat. Nos. 9,243,058, 8,920,776, 9,273,141, 7,083,785, 9,034,324, US 2007/0049735, US 2015/0284467, US 2015/0051266, US 2015/0344844, US 2016/0131655, US 2016/0297884, US 2016/0297885, US 2017/0051308, US 2017/0051252, US 2017/0051252, WO 2016/020332, WO 2016/087531, WO 2016/079177, WO 2015/172800, WO 2017/008169, U.S. Pat. No. 9,340,621, US 2013/0273055, US 2016/0176973, US 2015/0368351, US 2017/0051068, US 2016/0368988, and US 2015/0232557, herein incorporated by reference in their entirety. In some embodiments, additional exemplary BCMA CAR constructs are generated using the VH and VL sequences from PCT Publication WO2012/0163805 (the contents of which are hereby incorporated by reference in its entirety).

In some embodiments, BCMA CARs comprise a sequence, for example, a CDR, VH, VL, scFv, or full-CAR sequence, disclosed in Tables 3-15, or a sequence having at least 80%, 85%, 90%, 95%, or 99% identity thereto. In some embodiments, the antigen binding domain comprises a human antibody or a human antibody fragment. In some embodiments, the human anti-BCMA binding domain comprises one or more (for example, all three) LC CDR1, LC CDR2, and LC CDR3 of a human anti-BCMA binding domain described herein (for example, in Tables 3-15), and/or one or more (for example, all three) HC CDR1, HC CDR2, and HC CDR3 of a human anti-BCMA binding domain described herein (for example, in Tables 3-15). In some embodiments, the human anti-BCMA binding domain comprises a human VL described herein (for example, in Tables 3, 7, 11, 11a, and 12) and/or a human VH described herein (for example, in Tables 3, 7, 11, 11a, and 12). In some embodiments, the anti-BCMA binding domain is a scFv comprising a VL and a VH of an amino acid sequence of Tables 3, 7, 11, 11a, and 12. In some embodiments, the anti-BCMA binding domain (for example, an scFv) comprises: a VL comprising an amino acid sequence having at least one, two or three modifications (for example, substitutions, for example, conservative substitutions) but not more than 30, 20 or 10 modifications (for example, substitutions, for example, conservative substitutions) of an amino acid sequence provided in Tables 3, 7, 11, 11a, and 12, or a sequence with 95-99% identity with an amino acid sequence of Tables 3, 7, 11, 11a, and 12, and/or a VH comprising an amino acid sequence having at least one, two or three modifications (for example, substitutions, for example, conservative substitutions) but not more than 30, 20 or 10 modifications (for example, substitutions, for example, conservative substitutions) of an amino acid sequence provided in Tables 3, 7, 11, 11a, and 12, or a sequence with 95-99% identity to an amino acid sequence of Tables 3, 7, 11, 11a, and 12.

TABLE 3

Amino acid and nucleic acid sequences of exemplary PALLAS-derived anti-BCMA mlecules

| SEQ ID NO | Name/ Description | Sequence |
|---|---|---|
| R1B6 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 46 | HCDR3 (Kabat) | REWVPYDVSWYFDY |
| SEQ ID NO: 47 | HCDR1 (Chothia) | GFTFSSY |
| SEQ ID NO: 48 | HCDR2 (Chothia) | SGSGGS |
| SEQ ID NO: 46 | HCDR3 (Chothia) | REWVPYDVSWYFDY |
| SEQ ID NO: 49 | HCDR1 (IMGT) | GFTFSSYA |
| SEQ ID NO: 50 | HCDR2 (IMGT) | ISGSGGST |

TABLE 3-continued

Amino acid and nucleic acid sequences of exemplary PALLAS-derived anti-BCMA mlecules

| SEQ ID NO | Name/ Description | Sequence |
|---|---|---|
| SEQ ID NO: 51 | HCDR3 (IMGT) | ARREWVPYDVSWYFDY |
| SEQ ID NO: 52 | VH | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWVPYDVSWYFDYWGQGTLVTVSS |
| SEQ ID NO: 53 | DNA VH | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGGTGCCCTACGATGTCAGCTGGTACTTCGACTA CTGGGGACAGGGCACTCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKLLIYAA SSLQSGVPSRFSGSGSGTDFTLTISSLQPEDFATYYCQQSYSTPLTFGQGTK VEIK |
| SEQ ID NO: 62 | DNA VL | GACATTCAAATGACTCAGTCCCCGTCCTCCCTCTCCGCCTCCGTGGGA GATCGCGTCACGATCACGTGCAGGGCCAGCCAGAGCATCTCCAGCTAC CTGAACTGGTACCAGCAGAAGCCAGGGAAGGCACCGAAGCTCCTGAT CTACGCCGCTAGCTCGCTGCAGTCCGGCGTCCCTTCACGGTTCTCGGG ATCGGGCTCAGGCACCGACTTCACCCTGACCATTAGCAGCCTGCAGCC GGAGGACTTCGCGACATACTACTGTCAGCAGTCATACTCCACCCCTCT GACCTTCGGCCAAGGGACCAAAGTGGAGATCAAG |
| SEQ ID NO: 63 | Linker | GGGGSGGGGSGGGGSGGGGS |
| SEQ ID NO: 64 | scFv (VH-linker-VL) | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWVPYDVSWYFDYWGQGTLVTVSSGGGGSGGGGSGGGGSGGGGSDIQ MTQSPSSLSASVGDRVTITCRASQSISSYLNWYQQKPGKAPKLLIYAASSL QSGVPSRFSGSGSGTDFTLTISSLQPEDFATYYCQQSYSTPLTFGQGTKVEI K |
| SEQ ID NO: 65 | DNA scFv | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGGTGCCCTACGATGTCAGCTGGTACTTCGACTA CTGGGGACAGGGCACTCTCGTGACTGTGTCCTCCGGTGGTGGTGGATC GGGGGGTGGTGGTTCGGGCGGAGGAGGATCTGGAGGAGGAGGGTCGG |

TABLE 3-continued

Amino acid and nucleic acid sequences of exemplary PALLAS-derived anti-BCMA mlecules

| SEQ ID NO | Name/ Description | Sequence |
|---|---|---|
| | | ACATTCAAATGACTCAGTCCCCGTCCTCCCTCTCCGCCTCCGTGGGAG ATCGCGTCACGATCACGTGCAGGGCCAGCCAGAGCATCTCCAGCTACC TGAACTGGTACCAGCAGAAGCCAGGGAAGGCACCGAAGCTCCTGATC TACGCCGCTAGCTCGCTGCAGTCCGGCGTCCCTTCACGGTTCTCGGGA TCGGGCTCAGGCACCGACTTCACCCTGACCATTAGCAGCCTGCAGCCG GAGGACTTCGCGACATACTACTGTCAGCAGTCATACTCCACCCCTCTG ACCTTCGGCCAAGGGACCAAAGTGGAGATCAAG |
| SEQ ID NO: 66 | Full CAR amino acid sequence | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWVPYDVSWYFDYWGQGTLVTVSSGGGGSGGGGSGGGGSGGGGSDIQ MTQSPSSLSASVGDRVTITCRASQSISSYLNWYQQKPGKAPKLLIYAASSL QSGVPSRFSGSGSGTDFTLTISSLQPEDFATYYCQQSYSTPLTFGQGTKVEI KTTTPAPRPPTPAPTIASQPLSLRPEACRPAAGGAVHTRGLDFACDIYIWAP LAGTCGVLLLSLVITLYCKRGRKKLLYIFKQPFMRPVQTTQEEDGCSCRFP EEEEGGCELRVKFSRSADAPAYQQGQNQLYNELNLGRREEYDVLDKRRG RDPEMGGKPRRKNPQEGLYNELQKDKMAEAYSEIGMKGERRRGKGHDG LYQGLSTATKDTYDALHMQALPPR GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGGTGCCCTACGATGTCAGCTGGTACTTCGACTA CTGGGGACAGGGCACTCTCGTGACTGTGTCCTCCGGTGGTGGTGGATC GGGGGGTGGTGGTTCGGGCGGAGGAGGATCTGGAGGAGGAGGGTCGG |
| SEQ ID NO: 67 | Full CAR DNA sequence | ACATTCAAATGACTCAGTCCCCGTCCTCCCTCTCCGCCTCCGTGGGAG ATCGCGTCACGATCACGTGCAGGGCCAGCCAGAGCATCTCCAGCTACC TGAACTGGTACCAGCAGAAGCCAGGGAAGGCACCGAAGCTCCTGATC TACGCCGCTAGCTCGCTGCAGTCCGGCGTCCCTTCACGGTTCTCGGGA TCGGGCTCAGGCACCGACTTCACCCTGACCATTAGCAGCCTGCAGCCG GAGGACTTCGCGACATACTACTGTCAGCAGTCATACTCCACCCCTCTG ACCTTCGGCCAAGGGACCAAAGTGGAGATCAAGACCACTACCCCAGC ACCGAGGCCACCCACCCCGGCTCCTACCATCGCCTCCCAGCCTCTGTC CCTGCGTCCGGAGGCATGTAGACCCGCAGCTGGTGGGGCCGTGCATAC CCGGGGTCTTGACTTCGCCTGCGATATCTACATTTGGGCCCCTCTGGCT GGTACTTGCGGGGTCCTGCTGCTTTCACTCGTGATCACTCTTTACTGTA AGCGCGGTCGGAAGAAGCTGCTGTACATCTTTAAGCAACCCTTCATGA GGCCTGTGCAGACTACTCAAGAGGAGGACGGCTGTTCATGCCGGTTCC CAGAGGAGGAGGAAGGCGGCTGCGAACTGCGCGTGAAATTCAGCCGC AGCGCAGATGCTCCAGCCTACCAGCAGGGGCAGAACCAGCTCTACAA CGAACTCAATCTTGGTCGGAGAGAGGAGTACGACGTGCTGGACAAGC GGAGAGGACGGGACCCAGAAATGGGCGGGAAGCCGCGCAGAAAGAA TCCCCAAGAGGGCCTGTACAACGAGCTCCAAAAGGATAAGATGGCAG AAGCCTATAGCGAGATTGGTATGAAAGGGGAACGCAGAAGAGGCAAA GGCCACGACGGACTGTACCAGGGACTCAGCACCGCCACCAAGGACAC CTATGACGCTCTTCACATGCAGGCCCTGCCGCCTCGG |
| R1F2 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 68 | HCDR3 (Kabat) | REWWYDDWYLDY |
| SEQ ID NO: 47 | HCDR1 (Chothia) | GFTFSSY |
| SEQ ID NO: 48 | HCDR2 (Chothia) | SGSGGS |
| SEQ ID NO: 68 | HCDR3 (Chothia) | REWWYDDWYLDY |
| SEQ ID NO: 49 | HCDR1 (IMGT) | GFTFSSYA |

TABLE 3-continued

Amino acid and nucleic acid sequences of exemplary PALLAS-derived anti-BCMA mlecules

| SEQ ID NO | Name/ Description | Sequence |
|---|---|---|
| SEQ ID NO: 50 | HCDR2 (IMGT) | ISGSGGST |
| SEQ ID NO: 69 | HCDR3 (IMGT) | ARREWWYDDWYLDY |
| SEQ ID NO: 70 | VH | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWWYDDWYLDYWGQGTLVTVSS |
| SEQ ID NO: 71 | DNA VH | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGTGGTACGACGATTGGTACCTGGACTACTGGG GACAGGGCACTCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKLLIYAA SSLQSGVPSRFSGSGSGTDFTLTISSLQPEDFATYYCQQSYSTPLTFGQGTK VEIK |
| SEQ ID NO: 62 | DNA VL | GACATTCAAATGACTCAGTCCCCGTCCTCCCTCTCCGCCTCCGTGGGA GATCGCGTCACGATCACGTGCAGGGCCAGCCAGAGCATCTCCAGCTAC CTGAACTGGTACCAGCAGAAGCCAGGGAAGGCACCGAAGCTCCTGAT CTACGCCGCTAGCTCGCTGCAGTCCGGCGTCCCTTCACGGTTCTCGGG ATCGGGCTCAGGCACCGACTTCACCCTGACCATTAGCAGCCTGCAGCC GGAGGACTTCGCGACATACTACTGTCAGCAGTCATACTCCACCCCTCT GACCTTCGGCCAAGGGACCAAAGTGGAGATCAAG |
| SEQ ID NO: 63 | Linker | GGGGSGGGGSGGGGSGGGGS |
| SEQ ID NO: 72 | scFv (VH-linker-VL) | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWWYDDWYLDYWGQGTLVTVSSGGGGSGGGGSGGGGSGGGGSDIQMT QSPSSLSASVGDRVTITCRASQSISSYLNWYQQKPGKAPKLLIYAASSLQS GVPSRFSGSGSGTDFTLTISSLQPEDFATYYCQQSYSTPLTFGQGTKVEIK |
| SEQ ID NO: 73 | DNA scFv | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGTGGTACGACGATTGGTACCTGGACTACTGGG |

TABLE 3-continued

Amino acid and nucleic acid sequences of exemplary PALLAS-derived anti-BCMA mlecules

| SEQ ID NO | Name/ Description | Sequence |
|---|---|---|
| | | GACAGGGCACTCTCGTGACTGTGTCCTCCGGTGGTGGTGGATCGGGGG GTGGTGGTTCGGGCGGAGGAGGATCTGGAGGAGGAGGGTCGGACATT CAAATGACTCAGTCCCCGTCCTCCCTCTCCGCCTCCGTGGGAGATCGC GTCACGATCACGTGCAGGGCCAGCCAGAGCATCTCCAGCTACCTGAAC TGGTACCAGCAGAAGCCAGGGAAGGCACCGAAGCTCCTGATCTACGC CGCTAGCTCGCTGCAGTCCGGCGTCCCTTCACGGTTCTCGGGATCGGG CTCAGGCACCGACTTCACCCTGACCATTAGCAGCCTGCAGCCGGAGGA CTTCGCGACATACTACTGTCAGCAGTCATACTCCACCCCTCTGACCTTC GGCCAAGGGACCAAAGTGGAGATCAAG |
| SEQ ID NO: 74 | Full CAR amino acid sequence | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWWYDDWYLDYWGQGTLVTVSSGGGGSGGGGSGGGGSGGGGSDIQMT QSPSSLSASVGDRVTITCRASQSISSYLNWYQQKPGKAPKLLIYAASSLQS GVPSRFSGSGSGTDFTLTISSLQPEDFATYYCQQSYSTPLTFGQGTKVEIKT TTPAPRPPTPAPTIASQPLSLRPEACRPAAGGAVHTRGLDFACDIYIWAPLA GTCGVLLLSLVITLYCKRGRKKLLYIFKQPFMRPVQTTQEEDGCSCRFPEE EEGGCELRVKFSRSADAPAYQQGQNQLYNELNLGRREEYDVLDKRRGR DPEMGGKPRRKNPQEGLYNELQKDKMAEAYSEIGMKGERRRGKGHDGL YQGLSTATKDTYDALHMQALPPR |
| SEQ ID NO: 75 | Full CAR DNA sequence | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGTGGTACGACGATTGGTACCTGGACTACTGGG GACAGGGCACTCTCGTGACTGTGTCCTCCGGTGGTGGTGGATCGGGGG GTGGTGGTTCGGGCGGAGGAGGATCTGGAGGAGGAGGGTCGGACATT CAAATGACTCAGTCCCCGTCCTCCCTCTCCGCCTCCGTGGGAGATCGC GTCACGATCACGTGCAGGGCCAGCCAGAGCATCTCCAGCTACCTGAAC TGGTACCAGCAGAAGCCAGGGAAGGCACCGAAGCTCCTGATCTACGC CGCTAGCTCGCTGCAGTCCGGCGTCCCTTCACGGTTCTCGGGATCGGG CTCAGGCACCGACTTCACCCTGACCATTAGCAGCCTGCAGCCGGAGGA CTTCGCGACATACTACTGTCAGCAGTCATACTCCACCCCTCTGACCTTC GGCCAAGGGACCAAAGTGGAGATCAAGACCACTACCCCAGCACCGAG GCCACCCACCCCGGCTCCTACCATCGCCTCCCAGCCTCTGTCCCTGCGT CCGGAGGCATGTAGACCCGCAGCTGGTGGGGCCGTGCATACCCGGGG TCTTGACTTCGCCTGCGATATCTACATTTGGGCCCCTCTGGCTGGTACT TGCGGGGTCCTGCTGCTTTCACTCGTGATCACTCTTTACTGTAAGCGCG GTCGGAAGAAGCTGCTGTACATCTTTAAGCAACCCTTCATGAGGCCTG TGCAGACTACTCAAGAGGAGGACGGCTGTTCATGCCGGTTCCCAGAGG AGGAGGAAGGCGGCTGCGAACTGCGCGTGAAATTCAGCCGCAGCGCA GATGCTCCAGCCTACCAGCAGGGGCAGAACCAGCTCTACAACGAACT CAATCTTGGTCGGAGAGAGGAGTACGACGTGCTGGACAAGCGGAGAG GACGGGACCCAGAAATGGGCGGGAAGCCGCGCAGAAAGAATCCCCAA GAGGGCCTGTACAACGAGCTCCAAAAGGATAAGATGGCAGAAGCCTA TAGCGAGATTGGTATGAAAGGGGAACGCAGAAGAGGCAAAGGCCACG ACGGACTGTACCAGGGACTCAGCACCGCCACCAAGGACACCTATGAC GCTCTTCACATGCAGGCCCTGCCGCCTCGG |
| R1G5 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 76 | HCDR3 (Kabat) | REWWGESWLFDY |
| SEQ ID NO: 47 | HCDR1 (Chothia) | GFTFSSY |
| SEQ ID NO: 48 | HCDR2 (Chothia) | SGSGGS |
| SEQ ID NO: 76 | HCDR3 (Chothia) | REWWGESWLFDY |
| SEQ ID NO: 49 | HCDR1 (IMGT) | GFTFSSYA |

TABLE 3-continued

| Amino acid and nucleic acid sequences of exemplary PALLAS-derived anti-BCMA mlecules | | |
|---|---|---|
| SEQ ID NO | Name/ Description | Sequence |
| SEQ ID NO: 50 | HCDR2 (IMGT) | ISGSGGST |
| SEQ ID NO: 77 | HCDR3 (IMGT) | ARREWWGESWLFDY |
| SEQ ID NO: 78 | VH | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWWGESWLFDYWGQGTLVTVSS |
| SEQ ID NO: 79 | DNA VH | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGTGGGGAGAAAGCTGGCTGTTCGACTACTGGG GACAGGGCACTCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKLLIYAA SSLQSGVPSRFSGSGSGTDFTLTISSLQPEDFATYYCQQSYSTPLTFGQGTK VEIK |
| SEQ ID NO: 62 | DNA VL | GACATTCAAATGACTCAGTCCCCGTCCTCCCTCTCCGCCTCCGTGGGA GATCGCGTCACGATCACGTGCAGGGCCAGCCAGAGCATCTCCAGCTAC CTGAACTGGTACCAGCAGAAGCCAGGGAAGGCACCGAAGCTCCTGAT CTACGCCGCTAGCTCGCTGCAGTCCGGCGTCCCTTCACGGTTCTCGGG ATCGGGCTCAGGCACCGACTTCACCCTGACCATTAGCAGCCTGCAGCC GGAGGACTTCGCGACATACTACTGTCAGCAGTCATACTCCACCCCTCT GACCTTCGGCCAAGGGACCAAAGTGGAGATCAAG |
| SEQ ID NO: 63 | Linker | GGGGSGGGGSGGGGSGGGGS |
| SEQ ID NO: 80 | scFv (VH-linker-VL) | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWWGESWLFDYWGQGTLVTVSSGGGGSGGGGSGGGGSGGGGSDIQMT QSPSSLSASVGDRVTITCRASQSISSYLNWYQQKPGKAPKLLIYAASSLQS GVPSRFSGSGSGTDFTLTISSLQPEDFATYYCQQSYSTPLTFGQGTKVEIK |
| SEQ ID NO: 81 | DNA scFv | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG |

TABLE 3-continued

| Amino acid and nucleic acid sequences of exemplary PALLAS-derived anti-BCMA mlecules | | |
|---|---|---|
| SEQ ID NO | Name/ Description | Sequence |
| | | CGCTAGACGGGAGTGGTGGGGAGAAAGCTGGCTGTTCGACTACTGGG<br>GACAGGGCACTCTCGTGACTGTGTCCTCCGGTGGTGGTGGATCGGGGG<br>GTGGTGGTTCGGGCGGAGGAGGATCTGGAGGAGGAGGGTCGGACATT<br>CAAATGACTCAGTCCCCGTCCTCCCTCTCCGCCTCCGTGGGAGATCGC<br>GTCACGATCACGTGCAGGGCCAGCCAGAGCATCTCCAGCTACCTGAAC<br>TGGTACCAGCAGAAGCCAGGGAAGGCACCGAAGCTCCTGATCTACGC<br>CGCTAGCTCGCTGCAGTCCGGCGTCCCTTCACGGTTCTCGGGATCGGG<br>CTCAGGCACCGACTTCACCCTGACCATTAGCAGCCTGCAGCCGGAGGA<br>CTTCGCGACATACTACTGTCAGCAGTCATACTCCACCCCTCTGACCTTC<br>GGCCAAGGGACCAAAGTGGAGATCAAG |
| SEQ ID NO: 82 | Full CAR amino acid sequence | EVQLLESGGGLVQPGGSLRLSCAASGFTFSSYAMSWVRQAPGKGLEWVS<br>AISGSGGSTYYADSVKGRFTISRDNSKNTLYLQMNSLRAEDTAVYYCARR<br>EWWGESWLFDYWGQGTLVTVSSGGGGSGGGGSGGGGSGGGGSDIQMT<br>QSPSSLSASVGDRVTITCRASQSISSYLNWYQQKPGKAPKLLIYAASSLQS<br>GVPSRFSGSGSGTDFTLTISSLQPEDFATYYCQQSYSTPLTFGQGTKVEIKT<br>TTPAPRPPTPAPTIASQPLSLRPEACRPAAGGAVHTRGLDFACDIYIWAPLA<br>GTCGVLLLSLVITLYCKRGRKKLLYIFKQPFMRPVQTTQEEDGCSCRFPEE<br>EEGGCELRVKFSRSADAPAYQQGQNQLYNELNLGRREEYDVLDKRRGR<br>DPEMGGKPRRKNPQEGLYNELQKDKMAEAYSEIGMKGERRRGKGHDGL<br>YQGLSTATKDTYDALHMQALPPR |
| SEQ ID NO: 83 | Full CAR DNA sequence | GAAGTGCAGTTGCTGGAGTCAGGCGGAGGACTGGTGCAGCCCGGAGG<br>ATCGCTTCGCTTGAGCTGCGCAGCCTCAGGCTTTACCTTCTCCTCCTAC<br>GCCATGTCCTGGGTCAGACAGGCTCCCGGGAAGGGACTGGAATGGGT<br>GTCCGCCATTAGCGGTTCCGGCGGAAGCACTTACTATGCCGACTCTGT<br>GAAGGGCCGCTTCACTATCTCCCGGGACAACTCCAAGAACACCCTGTA<br>TCTCCAAATGAATTCCCTGAGGGCCGAAGATACCGCGGTGTACTACTG<br>CGCTAGACGGGAGTGGTGGGGAGAAAGCTGGCTGTTCGACTACTGGG<br>GACAGGGCACTCTCGTGACTGTGTCCTCCGGTGGTGGTGGATCGGGGG<br>GTGGTGGTTCGGGCGGAGGAGGATCTGGAGGAGGAGGGTCGGACATT<br>CAAATGACTCAGTCCCCGTCCTCCCTCTCCGCCTCCGTGGGAGATCGC<br>GTCACGATCACGTGCAGGGCCAGCCAGAGCATCTCCAGCTACCTGAAC<br>TGGTACCAGCAGAAGCCAGGGAAGGCACCGAAGCTCCTGATCTACGC<br>CGCTAGCTCGCTGCAGTCCGGCGTCCCTTCACGGTTCTCGGGATCGGG<br>CTCAGGCACCGACTTCACCCTGACCATTAGCAGCCTGCAGCCGGAGGA<br>CTTCGCGACATACTACTGTCAGCAGTCATACTCCACCCCTCTGACCTTC<br>GGCCAAGGGACCAAAGTGGAGATCAAGACCACTACCCCAGCACCGAG<br>GCCACCCACCCCGGCTCCTACCATCGCCTCCCAGCCTCTGTCCCTGCGT<br>CCGGAGGCATGTAGACCCGCAGCTGGTGGGGCCGTGCATACCCGGGG<br>TCTTGACTTCGCCTGCGATATCTACATTTGGGCCCCTCTGGCTGGTACT<br>TGCGGGGTCCTGCTGCTTTCACTCGTGATCACTCTTTACTGTAAGCGCG<br>GTCGGAAGAAGCTGCTGTACATCTTTAAGCAACCCTTCATGAGGCCTG<br>TGCAGACTACTCAAGAGGAGGACGGCTGTTCATGCCGGTTCCCAGAGG<br>AGGAGGAAGGCGGCTGCGAACTGCGCGTGAAATTCAGCCGCAGCGCA<br>GATGCTCCAGCCTACCAGCAGGGGCAGAACCAGCTCTACAACGAACT<br>CAATCTTGGTCGGAGAGAGGAGTACGACGTGCTGGACAAGCGGAGAG<br>GACGGGACCCAGAAATGGGCGGGAAGCCGCGCAGAAAGAATCCCCAA<br>GAGGGCCTGTACAACGAGCTCCAAAAGGATAAGATGGCAGAAGCCTA<br>TAGCGAGATTGGTATGAAAGGGGAACGCAGAAGAGGCAAAGGCCACG<br>ACGGACTGTACCAGGGACTCAGCACCGCCACCAAGGACACCTATGAC<br>GCTCTTCACATGCAGGCCCTGCCGCCTCGG |

TABLE 4

| Kabat CDRs of exemplary PALLAS-derived anti-BCMA molecules | | | | | | |
|---|---|---|---|---|---|---|
| Kabat | HCDR1 | HCDR2 | HCDR3 | LCDR1 | LCDR2 | LCDR3 |
| R1B6 | SYAMS (SEQ ID NO: 44) | AISGSGGSTY YADSVKG (SEQ ID NO: 45) | REWVPYDVS WYFDY (SEQ ID NO: 46) | RASQSISS YLN (SEQ ID NO: 54) | AASSL QS (SEQ ID NO: 55) | QQSYSTP LT (SEQ ID NO: 56) |
| R1F2 | SYAMS (SEQ ID NO: 44) | AISGSGGSTY YADSVKG (SEQ ID NO: 45) | REWWYDD WYLDY (SEQ ID NO: 68) | RASQSISS YLN (SEQ ID NO: 54) | AASSL QS (SEQ ID NO: 55) | QQSYSTP LT (SEQ ID NO: 56) |

TABLE 4-continued

Kabat CDRs of exemplary PALLAS-derived anti-BCMA molecules

| Kabat | HCDR1 | HCDR2 | HCDR3 | LCDR1 | LCDR2 | LCDR3 |
|---|---|---|---|---|---|---|
| R1G5 | SYAMS (SEQ ID NO: 44) | AISGSGGSTYYADSVKG (SEQ ID NO: 45) | REWWGESWLFDY (SEQ ID NO: 76) | RASQSISSYLN (SEQ ID NO: 54) | AASSLQS (SEQ ID NO: 55) | QQSYSTPLT (SEQ ID NO: 56) |
| Consensus | SYAMS (SEQ ID NO: 44) | AISGSGGSTYYADSVKG (SEQ ID NO: 45) | REWX1X2X3X4X5X6WX7X8DY, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is For L (SEQ ID NO: 84) | RASQSISSYLN (SEQ ID NO: 54) | AASSLQS (SEQ ID NO: 55) | QQSYSTPLT (SEQ ID NO: 56) |

TABLE 5

Chothia CDRs of exemplary PALLAS-derived anti-BCMA molecules

| Chothia | HCDR1 | HCDR2 | HCDR3 | LCDR1 | LCDR2 | LCDR3 |
|---|---|---|---|---|---|---|
| R1B6 | GFTFSSY (SEQ ID NO: 47) | SGSGGS (SEQ ID NO: 48) | REWVPYDVSWYFDY (SEQ ID NO: 46) | SQSISSY (SEQ ID NO: 57) | AAS (SEQ ID NO: 58) | SYSTPL (SEQ ID NO: 59) |
| R1F2 | GFTFSSY (SEQ ID NO: 47) | SGSGGS (SEQ ID NO: 48) | REWWYDDWYLDY (SEQ ID NO: 68) | SQSISSY (SEQ ID NO: 57) | AAS (SEQ ID NO: 58) | SYSTPL (SEQ ID NO: 59) |
| R1G5 | GFTFSSY (SEQ ID NO: 47) | SGSGGS (SEQ ID NO: 48) | REWWGESWLFDY (SEQ ID NO: 76) | SQSISSY (SEQ ID NO: 57) | AAS (SEQ ID NO: 58) | SYSTPL (SEQ ID NO: 59) |
| Consensus | GFTFSSY (SEQ ID NO: 47) | SGSGGS (SEQ ID NO: 48) | REW$X_1X_2X_3X_4X_5X_6$W$X_7X_8$DY, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is For L (SEQ ID NO: 84) | SQSISSY (SEQ ID NO: 57) | AAS (SEQ ID NO: 58) | SYSTPL (SEQ ID NO: 59) |

TABLE 6

IMGT CDRs of exemplary PALLAS-derived anti-BCMA molecules

| IMGT | HCDR1 | HCDR2 | HCDR3 | LCDR1 | LCDR2 | LCDR3 |
|---|---|---|---|---|---|---|
| R1B6 | GFTFSSYA (SEQ ID NO: 49) | ISGSGGST (SEQ ID NO: 50) | ARREWVPYDVSWYFDY (SEQ ID NO: 51) | QSISSY (SEQ ID NO: 60) | AAS (SEQ ID NO: 58) | QQSYSTPLT (SEQ ID NO: 56) |
| R1F2 | GFTFSSYA (SEQ ID NO: 49) | ISGSGGST (SEQ ID NO: 50) | ARREWWYDDWYLDY (SEQ ID NO: 69) | QSISSY (SEQ ID NO: 60) | AAS (SEQ ID NO: 58) | QQSYSTPLT (SEQ ID NO: 56) |

TABLE 6-continued

| IMGT CDRs of exemplary PALLAS-derived anti-BCMA molecules | | | | | | |
|---|---|---|---|---|---|---|
| IMGT | HCDR1 | HCDR2 | HCDR3 | LCDR1 | LCDR2 | LCDR3 |
| R1G5 | GFTFSSYA (SEQ ID NO: 49) | ISGSGGST (SEQ ID NO: 50) | ARREWWGE SWLFDY (SEQ ID NO: 77) | QSISSY (SEQ ID NO: 60) | AAS (SEQ ID NO: 58) | QQSYSTP LT (SEQ ID NO: 56) |
| Consensus | GFTFSSYA (SEQ ID NO: 49) | ISGSGGST (SEQ ID NO: 50) | ARREW$X_1X_2$ $X_3X_4X_5X_6$W$X_7$ $X_8$DY, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is For L (SEQ ID NO: 85) | QSISSY (SEQ ID NO: 60) | AAS (SEQ ID NO: 58) | QQSYSTP LT (SEQ ID NO: 56) |

TABLE 7

| Amino acid and nucleic acid sequences of exemplary B cell-derived anti-BCMA molecules | | |
|---|---|---|
| SEQ ID NO | Name/ Description | Sequence |
| PI61 | | |
| SEQ ID NO: 86 | HCDR1 (Kabat) | SYGMH |
| SEQ ID NO: 87 | HCDR2 (Kabat) | VISYDGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 89 | HCDR2 (Chothia) | SYDGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 91 | HCDR2 (IMGT) | ISYDGSNK |
| SEQ ID NO: 92 | HCDR3 (IMGT) | GGSGYALHDDYYGLDV |
| SEQ ID NO: 93 | VH | QVQLQESGGGVVQPGRSLRLSCAASGFTFSSYGMHWVRQAPGKGLEWVA VISYDGSNKYYADSVKGRFTISRDNSKNTLYLQMNSLRAEDTAVYYCGGS GYALHDDYYGLDVWGQGTLVTVSS |
| SEQ ID NO: 94 | DNA VH | CAAGTGCAGCTGCAGGAATCCGGTGGCGGAGTCGTGCAGCCTGGAAGG AGCCTGAGACTCTCATGCGCCGCGTCAGGGTTCACCTTTTCCTCCTACG GGATGCATTGGGTCAGACAGGCCCCCGGAAAGGGACTCGAATGGGTGG CTGTGATCAGCTACGACGGCTCCAACAAGTACTACGCCGACTCCGTGA AAGGCCGGTTCACTATCTCCCGGGACAACTCCAAGAACACGCTGTATCT GCAAATGAATTCACTGCGCGCGGAGGATACCGCTGTGTACTACTGCGG TGGCTCCGGTTACGCCCTGCACGATGACTATTACGGCCTTGACGTCTGG GGCCAGGGAACCCTCGTGACTGTGTCCAGC |
| SEQ ID NO: 95 | LCDR1 (Kabat) | TGTSSDVGGYNYVS |
| SEQ ID NO: 96 | LCDR2 (Kabat) | DVSNRPS |

TABLE 7-continued

Amino acid and nucleic acid sequences of exemplary B cell-derived anti-BCMA molecules

| SEQ ID NO | Name/ Description | Sequence |
|---|---|---|
| SEQ ID NO: 97 | LCDR3 (Kabat) | SSYTSSSTLYV |
| SEQ ID NO: 98 | LCDR1 (Chothia) | TSSDVGGYNY |
| SEQ ID NO: 99 | LCDR2 (Chothia) | DVS |
| SEQ ID NO: 100 | LCDR3 (Chothia) | YTSSSTLY |
| SEQ ID NO: 101 | LCDR1 (IMGT) | SSDVGGYNY |
| SEQ ID NO: 99 | LCDR2 (IMGT) | DVS |
| SEQ ID NO: 97 | LCDR3 (IMGT) | SSYTSSSTLYV |
| SEQ ID NO: 102 | VL | QSALTQPASVSGSPGQSITISCTGTSSDVGGYNYVSWYQQHPGKAPKLMIY DVSNRPSGVSNRFSGSKSGNTASLTISGLQAEDEADYYCSSYTSSSTLYVFG SGTKVTVL |
| SEQ ID NO: 103 | DNA VL | CAGAGCGCACTGACTCAGCCGGCATCCGTGTCCGGTAGCCCCGGACAG TCGATTACCATCTCCTGTACCGGCACCTCCTCCGACGTGGGAGGGTACA ACTACGTGTCGTGGTACCAGCAGCACCCAGGAAAGGCCCCTAAGTTGA TGATCTACGATGTGTCAAACCGCCCGTCTGGAGTCTCCAACCGGTTCTC CGGCTCCAAGTCCGGCAACACCGCCAGCCTGACCATTAGCGGGCTGCA AGCCGAGGATGAGGCCGACTACTACTGCTCGAGCTACACATCCTCGAG CACCCTCTACGTGTTCGGCTCGGGGACTAAGGTCACCGTGCTG |
| SEQ ID NO: 104 | Linker | GGGGSGGGGSGGGGS |
| SEQ ID NO: 105 | scFv (VH-linker-VL) | QVQLQESGGGVVQPGRSLRLSCAASGFTFSSYGMHWVRQAPGKGLEWVA VISYDGSNKYYADSVKGRFTISRDNSKNTLYLQMNSLRAEDTAVYYCGGS GYALHDDYYGLDVWGQGTLVTVSSGGGGSGGGGSGGGGSQSALTQPAS VSGSPGQSITISCTGTSSDVGGYNYVSWYQQHPGKAPKLMIYDVSNRPSGV SNRFSGSKSGNTASLTISGLQAEDEADYYCSSYTSSSTLYVFGSGTKVTVL |
| SEQ ID NO: 106 | DNA scFv | CAAGTGCAGCTGCAGGAATCCGGTGGCGGAGTCGTGCAGCCTGGAAGG AGCCTGAGACTCTCATGCGCCGCGTCAGGGTTCACCTTTTCCTCCTACG GGATGCATTGGGTCAGACAGGCCCCCGGAAAGGGACTCGAATGGGTGG CTGTGATCAGCTACGACGGCTCCAACAAGTACTACGCCGACTCCGTGA AAGGCCGGTTCACTATCTCCCGGGACAACTCCAAGAACACGCTGTATCT GCAAATGAATTCACTGCGCGCGGAGGATACCGCTGTGTACTACTGCGG TGGCTCCGGTTACGCCCTGCACGATGACTATTACGGCCTTGACGTCTGG GGCCAGGGAACCCTCGTGACTGTGTCCAGCGGTGGAGGAGGTTCGGGC GGAGGAGGATCAGGAGGGGGTGGATCGCAGAGCGCACTGACTCAGCC GGCATCCGTGTCCGGTAGCCCCGGACAGTCGATTACCATCTCCTGTACC GGCACCTCCTCCGACGTGGGAGGGTACAACTACGTGTCGTGGTACCAG CAGCACCCAGGAAAGGCCCCTAAGTTGATGATCTACGATGTGTCAAAC CGCCCGTCTGGAGTCTCCAACCGGTTCTCCGGCTCCAAGTCCGGCAACA CCGCCAGCCTGACCATTAGCGGGCTGCAAGCCGAGGATGAGGCCGACT ACTACTGCTCGAGCTACACATCCTCGAGCACCCTCTACGTGTTCGGCTC GGGGACTAAGGTCACCGTGCTG |
| SEQ ID NO: 107 | Full CAR amino acid sequence | QVQLQESGGGVVQPGRSLRLSCAASGFTFSSYGMHWVRQAPGKGLEWVA VISYDGSNKYYADSVKGRFTISRDNSKNTLYLQMNSLRAEDTAVYYCGGS GYALHDDYYGLDVWGQGTLVTVSSGGGGSGGGGSGGGGSQSALTQPAS VSGSPGQSITISCTGTSSDVGGYNYVSWYQQHPGKAPKLMIYDVSNRPSGV SNRFSGSKSGNTASLTISGLQAEDEADYYCSSYTSSSTLYVFGSGTKVTVLT TTPAPRPPTPAPTIASQPLSLRPEACRPAAGGAVHTRGLDFACDIYIWAPLA GTCGVLLLSLVITLYCKRGRKKLLYIFKQPFMRPVQTTQEEDGCSCRFPEEE EGGCELRVKFSRSADAPAYQQGQNQLYNELNLGRREEYDVLDKRRGRDP EMGGKPRRKNPQEGLYNELQKDKMAEAYSEIGMKGERRRGKGHDGLYQ GLSTATKDTYDALHMQALPPR |

TABLE 7-continued

| Amino acid and nucleic acid sequences of exemplary B cell-derived anti-BCMA molecules | | |
|---|---|---|
| SEQ ID NO | Name/ Description | Sequence |
| SEQ ID NO: 108 | Full CAR DNA sequence | CAAGTGCAGCTGCAGGAATCCGGTGGCGGAGTCGTGCAGCCTGGAAGG AGCCTGAGACTCTCATGCGCCGCGTCAGGGTTCACCTTTTCCTCCTACG GGATGCATTGGGTCAGACAGGCCCCCGGAAAGGGACTCGAATGGGTGG CTGTGATCAGCTACGACGGCTCCAACAAGTACTACGCCGACTCCGTGA AAGGCCGGTTCACTATCTCCCGGGACAACTCCAAGAACACGCTGTATCT GCAAATGAATTCACTGCGCGCGGAGGATACCGCTGTGTACTACTGCGG TGGCTCCGGTTACGCCCTGCACGATGACTATTACGGCCTTGACGTCTGG GGCCAGGGAACCCTCGTGACTGTGTCCAGCGGTGGAGGAGGTTCGGGC GGAGGAGGATCAGGAGGGGGTGGATCGCAGAGCGCACTGACTCAGCC GGCATCCGTGTCCGGTAGCCCCGGACAGTCGATTACCATCTCCTGTACC GGCACCTCCTCCGACGTGGGAGGGTACAACTACGTGTCGTGGTACCAG CAGCACCCAGGAAAGGCCCCTAAGTTGATGATCTACGATGTGTCAAAC CGCCCGTCTGGAGTCTCCAACCGGTTCTCCGGCTCCAAGTCCGGCAACA CCGCCAGCCTGACCATTAGCGGGCTGCAAGCCGAGGATGAGGCCGACT ACTACTGCTCGAGCTACACATCCTCGAGCACCCTCTACGTGTTCGGCTC GGGGACTAAGGTCACCGTGCTGACCACTACCCCAGCACCGAGGCCACC CACCCCGGCTCCTACCATCGCCTCCCAGCCTCTGTCCCTGCGTCCGGAG GCATGTAGACCCGCAGCTGGTGGGGCCGTGCATACCCGGGGTCTTGAC TTCGCCTGCGATATCTACATTTGGGCCCCTCTGGCTGGTACTTGCGGGG TCCTGCTGCTTTCACTCGTGATCACTCTTTACTGTAAGCGCGGTCGGAA GAAGCTGCTGTACATCTTTAAGCAACCCTTCATGAGGCCTGTGCAGACT ACTCAAGAGGAGGACGGCTGTTCATGCCGGTTCCCAGAGGAGGAGGAA GGCGGCTGCGAACTGCGCGTGAAATTCAGCCGCAGCGCAGATGCTCCA GCCTACCAGCAGGGGCAGAACCAGCTCTACAACGAACTCAATCTTGGT CGGAGAGAGGAGTACGACGTGCTGGACAAGCGGAGAGGACGGGACCC AGAAATGGGCGGGAAGCCGCGCAGAAAGAATCCCCAAGAGGGCCTGT ACAACGAGCTCCAAAAGGATAAGATGGCAGAAGCCTATAGCGAGATTG GTATGAAAGGGGAACGCAGAAGAGGCAAAGGCCACGACGGACTGTAC CAGGGACTCAGCACCGCCACCAAGGACACCTATGACGCTCTTCACATG CAGGCCCTGCCGCCTCGG |
| B61-02 | | |
| SEQ ID NO: 86 | HCDR1 (Kabat) | SYGMH |
| SEQ ID NO: 109 | HCDR2 (Kabat) | VISYKGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 110 | HCDR2 (Chothia) | SYKGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 111 | HCDR2 (IMGT) | ISYKGSNK |
| SEQ ID NO: 92 | HCDR3 (IMGT) | GGSGYALHDDYYGLDV |
| SEQ ID NO: 112 | VH | QVQLVESGGGVVQPGRSLRLSCAASGFTFSSYGMHWVRQAPGKGLEWVA VISYKGSNKYYADSVKGRFTISRDNSKNTLYLQMNSLRAEDTAVYYCGGS GYALHDDYYGLDVWGQGTLVTVSS |
| SEQ ID NO: 113 | DNA VH | CAAGTGCAGCTTGTCGAATCGGGAGGCGGAGTGGTGCAGCCTGGACGA TCGCTCCGGCTCTCATGTGCCGCGAGCGGATTCACCTTCTCGAGCTACG GCATGCACTGGGTCAGACAAGCCCCAGGAAAGGGCCTGGAATGGGTGG CTGTCATCTCGTACAAGGGCTCAAACAAGTACTACGCCGACTCCGTGAA GGGCCGGTTCACCATCTCCCGCGATAACTCCAAGAATACCCTCTATCTG CAAATGAACAGCCTGAGGGCCGAGGATACTGCAGTGTACTACTGCGGG GGTTCAGGCTACGCGCTGCACGACGACTACTACGGATTGGACGTCTGG GGCCAAGGAACTCTTGTGACCGTGTCCTCT |

TABLE 7-continued

Amino acid and nucleic acid sequences of exemplary B cell-derived anti-BCMA molecules

| SEQ ID NO | Name/ Description | Sequence |
|---|---|---|
| SEQ ID NO: 95 | LCDR1 (Kabat) | TGTSSDVGGYNYVS |
| SEQ ID NO: 114 | LCDR2 (Kabat) | EVSNRLR |
| SEQ ID NO: 115 | LCDR3 (Kabat) | SSYTSSSALYV |
| SEQ ID NO: 98 | LCDR1 (Chothia) | TSSDVGGYNY |
| SEQ ID NO: 116 | LCDR2 (Chothia) | EVS |
| SEQ ID NO: 117 | LCDR3 (Chothia) | YTSSSALY |
| SEQ ID NO: 101 | LCDR1 (IMGT) | SSDVGGYNY |
| SEQ ID NO: 116 | LCDR2 (IMGT) | EVS |
| SEQ ID NO: 115 | LCDR3 (IMGT) | SSYTSSSALYV |
| SEQ ID NO: 118 | VL | QSALTQPASVSGSPGQSITISCTGTSSDVGGYNYVSWYQQHPGKAPKLMIY EVSNRLRGVSNRFSGSKSGNTASLTISGLQAEDEADYYCSSYTSSSALYVF GSGTKVTVL |
| SEQ ID NO: 119 | DNA VL | CAGAGCGCGCTGACTCAGCCTGCCTCCGTGAGCGGTTCGCCGGGACAG TCCATTACCATTTCGTGCACCGGGACCTCCTCCGACGTGGGAGGCTACA ACTACGTGTCCTGGTACCAGCAGCATCCCGGAAAGGCCCCGAAGCTGA TGATCTACGAAGTGTCGAACAGACTGCGGGGAGTCTCCAACCGCTTTTC CGGGTCCAAGTCCGGCAACACCGCCAGCCTGACCATCAGCGGGCTCCA GGCAGAAGATGAGGCTGACTATTACTGCTCCTCCTACACGTCAAGCTCC GCCCTCTACGTGTTCGGGTCCGGGACCAAAGTCACTGTGCTG |
| SEQ ID NO: 63 | Linker | GGGGSGGGGSGGGGSGGGGS |
| SEQ ID NO: 120 | scFv (VH-linker-VL) | QVQLVESGGGVVQPGRSLRLSCAASGFTFSSYGMHWVRQAPGKGLEWVA VISYKGSNKYYADSVKGRFTISRDNSKNTLYLQMNSLRAEDTAVYYCGGS GYALHDDYYGLDVWGQGTLVTVSSGGGGSGGGGSGGGGSGGGGSQSAL TQPASVSGSPGQSITISCTGTSSDVGGYNYVSWYQQHPGKAPKLMIYEVSN RLRGVSNRFSGSKSGNTASLTISGLQAEDEADYYCSSYTSSSALYVFGSGT KVTVL |
| SEQ ID NO: 121 | DNA scFv | CAAGTGCAGCTTGTCGAATCGGGAGGCGGAGTGGTGCAGCCTGGACGA TCGCTCCGGCTCTCATGTGCCGCGAGCGGATTCACCTTCTCGAGCTACG GCATGCACTGGGTCAGACAAGCCCCAGGAAAGGGCCTGGAATGGGTGG CTGTCATCTCGTACAAGGGCTCAAACAAGTACTACGCCGACTCCGTGAA GGGCCGGTTCACCATCTCCCGCGATAACTCCAAGAATACCCTCTATCTG CAAATGAACAGCCTGAGGGCCGAGGATACTGCAGTGTACTACTGCGGG GGTTCAGGCTACGCGCTGCACGACGACTACTACGGATTGGACGTCTGG GGCCAAGGAACTCTTGTGACCGTGTCCTCTGGTGGAGGCGGATCAGGG GGTGGCGGATCTGGGGGTGGTGGTTCCGGGGGAGGAGGATCGCAGAGC GCGCTGACTCAGCCTGCCTCCGTGAGCGGTTCGCCGGGACAGTCCATTA CCATTTCGTGCACCGGGACCTCCTCCGACGTGGGAGGCTACAACTACGT GTCCTGGTACCAGCAGCATCCCGGAAAGGCCCCGAAGCTGATGATCTA CGAAGTGTCGAACAGACTGCGGGGAGTCTCCAACCGCTTTTCCGGGTCC AAGTCCGGCAACACCGCCAGCCTGACCATCAGCGGGCTCCAGGCAGAA GATGAGGCTGACTATTACTGCTCCTCCTACACGTCAAGCTCCGCCCTCT ACGTGTTCGGGTCCGGGACCAAAGTCACTGTGCTG |
| SEQ ID NO: 122 | Full CAR amino acid sequence | QVQLVESGGGVVQPGRSLRLSCAASGFTFSSYGMHWVRQAPGKGLEWVA VISYKGSNKYYADSVKGRFTISRDNSKNTLYLQMNSLRAEDTAVYYCGGS GYALHDDYYGLDVWGQGTLVTVSSGGGGSGGGGSGGGGSGGGGSQSAL TQPASVSGSPGQSITISCTGTSSDVGGYNYVSWYQQHPGKAPKLMIYEVSN RLRGVSNRFSGSKSGNTASLTISGLQAEDEADYYCSSYTSSSALYVFGSGT KVTVLTTTPAPRPPTPAPTIASQPLSLRPEACRPAAGGAVHTRGLDFACDIYI WAPLAGTCGVLLLSLVITLYCKRGRKKLLYIFKQPFMRPVQTTQEEDGCSC RFPEEEEGGCELRVKFSRSADAPAYQQGQNQLYNELNLGRREEYDVLDKR |

TABLE 7-continued

Amino acid and nucleic acid sequences of exemplary B cell-derived anti-BCMA molecules

| SEQ ID NO | Name/ Description | Sequence |
|---|---|---|
| | | RGRDPEMGGKPRRKNPQEGLYNELQKDKMAEAYSEIGMKGERRRGKGH DGLYQGLSTATKDTYDALHMQALPPR |
| SEQ ID NO: 123 | Full CAR DNA sequence | CAAGTGCAGCTTGTCGAATCGGGAGGCGGAGTGGTGCAGCCTGGACGA TCGCTCCGGCTCTCATGTGCCGCGAGCGGATTCACCTTCTCGAGCTACG GCATGCACTGGGTCAGACAAGCCCCAGGAAAGGGCCTGGAATGGGTGG CTGTCATCTCGTACAAGGGCTCAAACAAGTACTACGCCGACTCCGTGAA GGGCCGGTTCACCATCTCCCGCGATAACTCCAAGAATACCCTCTATCTG CAAATGAACAGCCTGAGGGCCGAGGATACTGCAGTGTACTACTGCGGG GGTTCAGGCTACGCGCTGCACGACGACTACTACGGATTGGACGTCTGG GGCCAAGGAACTCTTGTGACCGTGTCCTCTGGTGGAGGCGGATCAGGG GGTGGCGGATCTGGGGGTGGTGGTTCCGGGGGAGGAGGATCGCAGAGC GCGCTGACTCAGCCTGCCTCCGTGAGCGGTTCGCCGGGACAGTCCATTA CCATTTCGTGCACCGGGACCTCCTCCGACGTGGGAGGCTACAACTACGT GTCCTGGTACCAGCAGCATCCCGGAAAGGCCCCGAAGCTGATGATCTA CGAAGTGTCGAACAGACTGCGGGGAGTCTCCAACCGCTTTTCCGGGTCC AAGTCCGGCAACACCGCCAGCCTGACCATCAGCGGGCTCCAGGCAGAA GATGAGGCTGACTATTACTGCTCCTCCTACACGTCAAGCTCCGCCCTCT ACGTGTTCGGGTCCGGGACCAAAGTCACTGTGCTGACCACTACCCCAGC ACCGAGGCCACCCACCCCGGCTCCTACCATCGCCTCCCAGCCTCTGTCC CTGCGTCCGGAGGCATGTAGACCCGCAGCTGGTGGGGCCGTGCATACC CGGGGTCTTGACTTCGCCTGCGATATCTACATTTGGGCCCCTCTGGCTG GTACTTGCGGGGTCCTGCTGCTTTCACTCGTGATCACTCTTTACTGTAAG CGCGGTCGGAAGAAGCTGCTGTACATCTTTAAGCAACCCTTCATGAGGC CTGTGCAGACTACTCAAGAGGAGGACGGCTGTTCATGCCGGTTCCCAG AGGAGGAGGAAGGCGGCTGCGAACTGCGCGTGAAATTCAGCCGCAGC GCAGATGCTCCAGCCTACCAGCAGGGGCAGAACCAGCTCTACAACGAA CTCAATCTTGGTCGGAGAGAGGAGTACGACGTGCTGGACAAGCGGAGA GGACGGGACCCAGAAATGGGCGGGAAGCCGCGCAGAAAGAATCCCCA AGAGGGCCTGTACAACGAGCTCCAAAAGGATAAGATGGCAGAAGCCTA TAGCGAGATTGGTATGAAAGGGGAACGCAGAAGAGGCAAAGGCCACG ACGGACTGTACCAGGGACTCAGCACCGCCACCAAGGACACCTATGACG CTCTTCACATGCAGGCCCTGCCGCCTCGG |
| B61-10 | | |
| SEQ ID NO: 86 | HCDR1 (Kabat) | SYGMH |
| SEQ ID NO: 109 | HCDR2 (Kabat) | VISYKGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 110 | HCDR2 (Chothia) | SYKGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 111 | HCDR2 (IMGT) | ISYKGSNK |
| SEQ ID NO: 92 | HCDR3 (IMGT) | GGSGYALHDDYYGLDV |
| SEQ ID NO: 112 | VH | QVQLVESGGGVVQPGRSLRLSCAASGFTFSSYGMHWVRQAPGKGLEWVA VISYKGSNKYYADSVKGRFTISRDNSKNTLYLQMNSLRAEDTAVYYCGGS GYALHDDYYGLDVWGQGTLVTVSS |
| SEQ ID NO: 113 | DNA VH | CAAGTGCAGCTTGTCGAATCGGGAGGCGGAGTGGTGCAGCCTGGACGA TCGCTCCGGCTCTCATGTGCCGCGAGCGGATTCACCTTCTCGAGCTACG GCATGCACTGGGTCAGACAAGCCCCAGGAAAGGGCCTGGAATGGGTGG CTGTCATCTCGTACAAGGGCTCAAACAAGTACTACGCCGACTCCGTGAA GGGCCGGTTCACCATCTCCCGCGATAACTCCAAGAATACCCTCTATCTG |

TABLE 7-continued

| Amino acid and nucleic acid sequences of exemplary B cell-derived anti-BCMA molecules | | |
|---|---|---|
| SEQ ID NO | Name/ Description | Sequence |
| | | CAAATGAACAGCCTGAGGGCCGAGGATACTGCAGTGTACTACTGCGGG GGTTCAGGCTACGCGCTGCACGACGACTACTACGGATTGGACGTCTGG GGCCAAGGAACTCTTGTGACCGTGTCCTCT |
| SEQ ID NO: 95 | LCDR1 (Kabat) | TGTSSDVGGYNYVS |
| SEQ ID NO: 114 | LCDR2 (Kabat) | EVSNRLR |
| SEQ ID NO: 97 | LCDR3 (Kabat) | SSYTSSSTLYV |
| SEQ ID NO: 98 | LCDR1 (Chothia) | TSSDVGGYNY |
| SEQ ID NO: 116 | LCDR2 (Chothia) | EVS |
| SEQ ID NO: 100 | LCDR3 (Chothia) | YTSSSTLY |
| SEQ ID NO: 101 | LCDR1 (IMGT) | SSDVGGYNY |
| SEQ ID NO: 116 | LCDR2 (IMGT) | EVS |
| SEQ ID NO: 97 | LCDR3 (IMGT) | SSYTSSSTLYV |
| SEQ ID NO: 124 | VL | QSALTQPASVSGSPGQSITISCTGTSSDVGGYNYVSWYQQHPGKAPKLMIY EVSNRLRGVSNRFSGSKSGNTASLTISGLQAEDEADYYCSSYTSSSTLYVFG SGTKVTVL |
| SEQ ID NO: 125 | DNA VL | CAGAGCGCGCTGACTCAGCCTGCCTCCGTGAGCGGTTCGCCGGGACAG TCCATTACCATTTCGTGCACCGGGACCTCCTCCGACGTGGGAGGCTACA ACTACGTGTCCTGGTACCAGCAGCATCCCGGAAAGGCCCCGAAGCTGA TGATCTACGAAGTGTCGAACAGACTGCGGGGAGTCTCCAACCGCTTTTC CGGGTCCAAGTCCGGCAACACCGCCAGCCTGACCATCAGCGGGCTCCA GGCAGAAGATGAGGCTGACTATTACTGCTCCTCCTACACGTCAAGCTCC ACCCTCTACGTGTTCGGGTCCGGGACCAAAGTCACTGTGCTG |
| SEQ ID NO: 63 | Linker | GGGGSGGGGSGGGGSGGGGS |
| SEQ ID NO: 126 | scFv (VH-linker-VL) | QVQLVESGGGVVQPGRSLRLSCAASGFTFSSYGMHWVRQAPGKGLEWVA VISYKGSNKYYADSVKGRFTISRDNSKNTLYLQMNSLRAEDTAVYYCGGS GYALHDDYYGLDVWGQGTLVTVSSGGGGSGGGGSGGGGSGGGGSQSAL TQPASVSGSPGQSITISCTGTSSDVGGYNYVSWYQQHPGKAPKLMIYEVSN RLRGVSNRFSGSKSGNTASLTISGLQAEDEADYYCSSYTSSSTLYVFGSGTK VTVL |
| SEQ ID NO: 127 | DNA scFv | CAAGTGCAGCTTGTCGAATCGGGAGGCGGAGTGGTGCAGCCTGGACGA TCGCTCCGGCTCTCATGTGCCGCGAGCGGATTCACCTTCTCGAGCTACG GCATGCACTGGGTCAGACAAGCCCCAGGAAAGGGCCTGGAATGGGTGG CTGTCATCTCGTACAAGGGCTCAAACAAGTACTACGCCGACTCCGTGAA GGGCCGGTTCACCATCTCCCGCGATAACTCCAAGAATACCCTCTATCTG CAAATGAACAGCCTGAGGGCCGAGGATACTGCAGTGTACTACTGCGGG GGTTCAGGCTACGCGCTGCACGACGACTACTACGGATTGGACGTCTGG GGCCAAGGAACTCTTGTGACCGTGTCCTCTGGTGGAGGCGGATCAGGG GGTGGCGGATCTGGGGGTGGTGGTTCCGGGGGAGGAGGATCGCAGAGC GCGCTGACTCAGCCTGCCTCCGTGAGCGGTTCGCCGGGACAGTCCATTA CCATTTCGTGCACCGGGACCTCCTCCGACGTGGGAGGCTACAACTACGT GTCCTGGTACCAGCAGCATCCCGGAAAGGCCCCGAAGCTGATGATCTA CGAAGTGTCGAACAGACTGCGGGGAGTCTCCAACCGCTTTTCCGGGTCC AAGTCCGGCAACACCGCCAGCCTGACCATCAGCGGGCTCCAGGCAGAA GATGAGGCTGACTATTACTGCTCCTCCTACACGTCAAGCTCCACCCTCT ACGTGTTCGGGTCCGGGACCAAAGTCACTGTGCTG |
| SEQ ID NO: 128 | Full CAR amino acid sequence | QVQLVESGGGVVQPGRSLRLSCAASGFTFSSYGMHWVRQAPGKGLEWVA VISYKGSNKYYADSVKGRFTISRDNSKNTLYLQMNSLRAEDTAVYYCGGS GYALHDDYYGLDVWGQGTLVTVSSGGGGSGGGGSGGGGSGGGGSQSAL TQPASVSGSPGQSITISCTGTSSDVGGYNYVSWYQQHPGKAPKLMIYEVSN |

TABLE 7-continued

| Amino acid and nucleic acid sequences of exemplary B cell-derived anti-BCMA molecules | | |
|---|---|---|
| SEQ ID NO | Name/ Description | Sequence |
| | | RLRGVSNRFSGSKSGNTASLTISGLQAEDEADYYCSSYTSSSTLYVFGSGTK<br>VTVLTTTPAPRPPTPAPTIASQPLSLRPEACRPAAGGAVHTRGLDFACDIYI<br>WAPLAGTCGVLLLSLVITLYCKRGRKKLLYIFKQPFMRPVQTTQEEDGCSC<br>RFPEEEEGGCELRVKFSRSADAPAYQQGQNQLYNELNLGRREEYDVLDKR<br>RGRDPEMGGKPRRKNPQEGLYNELQKDKMAEAYSEIGMKGERRRGKGH<br>DGLYQGLSTATKDTYDALHMQALPPR |
| SEQ ID NO: 129 | Full CAR DNA sequence | CAAGTGCAGCTTGTCGAATCGGGAGGCGGAGTGGTGCAGCCTGGACGA<br>TCGCTCCGGCTCTCATGTGCCGCGAGCGGATTCACCTTCTCGAGCTACG<br>GCATGCACTGGGTCAGACAAGCCCCAGGAAAGGGCCTGGAATGGGTGG<br>CTGTCATCTCGTACAAGGGCTCAAACAAGTACTACGCCGACTCCGTGAA<br>GGGCCGGTTCACCATCTCCCGCGATAACTCCAAGAATACCCTCTATCTG<br>CAAATGAACAGCCTGAGGGCCGAGGATACTGCAGTGTACTACTGCGGG<br>GGTTCAGGCTACGCGCTGCACGACGACTACTACGGATTGGACGTCTGG<br>GGCCAAGGAACTCTTGTGACCGTGTCCTCTGGTGGAGGCGGATCAGGG<br>GGTGGCGGATCTGGGGGTGGTGGTTCCGGGGGAGGAGGATCGCAGAGC<br>GCGCTGACTCAGCCTGCCTCCGTGAGCGGTTCGCCGGGACAGTCCATTA<br>CCATTTCGTGCACCGGGACCTCCTCCGACGTGGGAGGCTACAACTACGT<br>GTCCTGGTACCAGCAGCATCCCGGAAAGGCCCCGAAGCTGATGATCTA<br>CGAAGTGTCGAACAGACTGCGGGGAGTCTCCAACCGCTTTTCCGGGTCC<br>AAGTCCGGCAACACCGCCAGCCTGACCATCAGCGGGCTCCAGGCAGAA<br>GATGAGGCTGACTATTACTGCTCCTCCTACACGTCAAGCTCCACCCTCT<br>ACGTGTTCGGGTCCGGGACCAAAGTCACTGTGCTGACCACTACCCCAGC<br>ACCGAGGCCACCCACCCCGGCTCCTACCATCGCCTCCCAGCCTCTGTCC<br>CTGCGTCCGGAGGCATGTAGACCCGCAGCTGGTGGGGCCGTGCATACC<br>CGGGGTCTTGACTTCGCCTGCGATATCTACATTTGGGCCCCTCTGGCTG<br>GTACTTGCGGGGTCCTGCTGCTTTCACTCGTGATCACTCTTTACTGTAAG<br>CGCGGTCGGAAGAAGCTGCTGTACATCTTTAAGCAACCCTTCATGAGGC<br>CTGTGCAGACTACTCAAGAGGAGGACGGCTGTTCATGCCGGTTCCCAG<br>AGGAGGAGGAAGGCGGCTGCGAACTGCGCGTGAAATTCAGCCGCAGC<br>GCAGATGCTCCAGCCTACCAGCAGGGGCAGAACCAGCTCTACAACGAA<br>CTCAATCTTGGTCGGAGAGAGGAGTACGACGTGCTGGACAAGCGGAGA<br>GGACGGGACCCAGAAATGGGCGGGAAGCCGCGCAGAAAGAATCCCCA<br>AGAGGGCCTGTACAACGAGCTCCAAAAGGATAAGATGGCAGAAGCCTA<br>TAGCGAGATTGGTATGAAAGGGGAACGCAGAAGAGGCAAAGGCCACG<br>ACGGACTGTACCAGGGACTCAGCACCGCCACCAAGGACACCTATGACG<br>CTCTTCACATGCAGGCCCTGCCGCCTCGG |

TABLE 8

| Kabat CDRs of exemplary B cell-derived anti-BCMA molecules | | | | | | |
|---|---|---|---|---|---|---|
| Kabat | HCDR1 | HCDR2 | HCDR3 | LCDR1 | LCDR2 | LCDR3 |
| PI61 | SYGMH (SEQ ID NO: 86) | VISYDGSN KYYADSV KG (SEQ ID NO: 87) | SGYALHDD YYGLDV (SEQ ID NO: 88) | TGTSSDV GGYNYV S (SEQ ID NO: 95) | DVSNRPS (SEQ ID NO: 96) | SSYTSSS TLYV (SEQ ID NO: 97) |
| B61-02 | SYGMH (SEQ ID NO: 86) | VISYKGSN KYYADSV KG (SEQ ID NO: 109) | SGYALHDD YYGLDV (SEQ ID NO: 88) | TGTSSDV GGYNYV S (SEQ ID NO: 95) | EVSNRLR (SEQ ID NO: 114) | SSYTSSS ALYV (SEQ ID NO: 115) |
| B61-10 | SYGMH (SEQ ID NO: 86) | VISYKGSN KYYADSV KG (SEQ ID NO: 109) | SGYALHDD YYGLDV (SEQ ID NO: 88) | TGTSSDV GGYNYV S (SEQ ID NO: 95) | EVSNRLR (SEQ ID NO: 114) | SSYTSSS TLYV (SEQ ID NO: 97) |
| Consensus | SYGMH (SEQ ID NO: 86) | VISYXGSN KYYADSV KG, wherein X is D or K (SEQ ID NO: 130) | SGYALHDD YYGLDV (SEQ ID NO: 88) | TGTSSDV GGYNYV S (SEQ ID NO: 95) | $X_1VSNRX_2X_3$, wherein $X_1$ is D or E; $X_2$ is P or L; and $X_3$ is S or R (SEQ ID NO: 131) | SSYTSSS XLYV, wherein X is T or A (SEQ ID NO: 132) |

TABLE 9

Chothia CDRs of exemplary B cell-derived anti-BCMA molecules

| Chothia | HCDR1 | HCDR2 | HCDR3 | LCDR1 | LCDR2 | LCDR3 |
|---|---|---|---|---|---|---|
| PI61 | GFTFSSY (SEQ ID NO: 47) | SYDGSN (SEQ ID NO: 89) | SGYALHDDY YGLDV (SEQ ID NO: 88) | TSSDVGG YNY (SEQ ID NO: 98) | DVS (SEQ ID NO: 99) | YTSSSTLY (SEQ ID NO: 100) |
| B61-02 | GFTFSSY (SEQ ID NO: 47) | SYKGSN (SEQ ID NO: 110) | SGYALHDDY YGLDV (SEQ ID NO: 88) | TSSDVGG YNY (SEQ ID NO: 98) | EVS (SEQ ID NO: 116) | YTSSSAL Y (SEQ ID NO: 117) |
| B61-10 | GFTFSSY (SEQ ID NO: 47) | SYKGSN (SEQ ID NO: 110) | SGYALHDDY YGLDV (SEQ ID NO: 88) | TSSDVGG YNY (SEQ ID NO: 98) | EVS (SEQ ID NO: 116) | YTSSSTLY (SEQ ID NO: 100) |
| Consensus | GFTFSSY (SEQ ID NO: 47) | SYXGSN, wherein X is D or K (SEQ ID NO: 133) | SGYALHDDY YGLDV (SEQ ID NO: 88) | TSSDVGG YNY (SEQ ID NO: 98) | XVS, wherein X is D or E (SEQ ID NO: 134) | YTSSSXL Y, wherein X is T or A (SEQ ID NO: 135) |

TABLE 10

IMGT CDRs of exemplary B cell-derived anti-BCMA molecules

| IMGT | HCDR1 | HCDR2 | HCDR3 | LCDR1 | LCDR2 | LCDR3 |
|---|---|---|---|---|---|---|
| PI61 | GFTFSSYG (SEQ ID NO: 90) | ISYDGSN K (SEQ ID NO: 91) | GGSGYALHDD YYGLDV (SEQ ID NO: 92) | SSDVGGY NY (SEQ ID NO: 101) | DVS (SEQ ID NO: 99) | SSYTSSSTL YV (SEQ ID NO: 97) |
| B61-02 | GFTFSSYG (SEQ ID NO: 90) | ISYKGSN K (SEQ ID NO: 111) | GGSGYALHDD YYGLDV (SEQ ID NO: 92) | SSDVGGY NY (SEQ ID NO: 101) | EVS (SEQ ID NO: 116) | SSYTSSSA LYV (SEQ ID NO: 115) |
| B61-10 | GFTFSSYG (SEQ ID NO: 90) | ISYKGSN K (SEQ ID NO: 111) | GGSGYALHDD YYGLDV (SEQ ID NO: 92) | SSDVGGY NY (SEQ ID NO: 101) | EVS (SEQ ID NO: 116) | SSYTSSSTL YV (SEQ ID NO: 97) |
| Consensus | GFTFSSYG (SEQ ID NO: 90) | ISYXGSN K, wherein X is D or K (SEQ ID NO: 136) | GGSGYALHDD YYGLDV (SEQ ID NO: 92) | SSDVGGY NY (SEQ ID NO: 101) | XVS, wherein X is D or E (SEQ ID NO: 134) | SSYTSSSX LYV, wherein X is T or A (SEQ ID NO: 132) |

TABLE 11

Amino acid and nucleic acid sequences of exemplary anti-BCMA molecules based on PI61

| Identification | Protein sequence | DNA sequence (5'-3') |
|---|---|---|
| Signal peptide | MALPVTALLLPLALLLHAARP (SEQ ID NO: 1) | Atggccctccctgtcaccgctctgttgctgccgcttgctctgctgctcc acgcagcgcgaccg (SEQ ID NO: 252) |
| PI61 VH | QVQLQESGGGVVQPGRSLRLS CAASGFTFSSYGMHWVRQAP GKGLEWVAVISYDGSNKYYA DSVKGRFTISRDNSKNTLYLQ MNSLRAEDTAVYYCGGSGYA LHDDYYGLDVWGQGTLVTVS S (SEQ ID NO: 93) | CAGGTACAATTGCAGGAGTCTGGAGGCGG TGTGGTGCAACCCGGTCGCAGCTTGCGCCT GAGTTGTGCTGCGTCTGGATTTACATTTTC ATCTTACGGAATGCATTGGGTACGCCAGG CACCGGGGAAAGGCCTTGAATGGGTGGCT GTAATTTCATACGATGGTTCCAACAAATAC TATGCTGACTCAGTCAAGGGTCGATTTACA ATTAGTCGGGACAACTCCAAGAACACCCT TTATCTTCAAATGAATTCCCTTAGAGCAGA GGATACGGCGGTCTATTACTGTGGTGGCA GTGGTTATGCACTTCATGATGATTACTATG GCTTGGATGTCTGGGGGCAAGGGACGCTT GTAACTGTATCCTCT (SEQ ID NO: 260) |
| PI61 VL | QSALTQPASVSGSPGQSITISCT GTSSDVGGYNYVSWYQQHPG KAPKLMIYDVSNRPSGVSNRFS | CAATCTGCTCTGACTCAACCAGCAAGCGT ATCAGGGTCACCGGGACAGAGTATTACCA TAAGTTGCACGGGGACCTCTAGCGATGTA |

TABLE 11-continued

Amino acid and nucleic acid sequences of exemplary anti-BCMA molecules based on PI61

| Identification | Protein sequence | DNA sequence (5'-3') |
|---|---|---|
| | GSKSGNTASLTISGLQAEDEAD YYCSSYTSSSTLYVFGSGTKVT VL (SEQ ID NO: 102) | GGGGGGTATAATTATGTATCTTGGTATCAA CAACACCCCGGGAAAGCCCCTAAATTGAT GATCTACGACGTGAGCAATCGACCTAGTG GCGTATCAAATCGCTTCTCTGGTAGCAAGA GTGGGAATACGGCGTCCCTTACTATTAGCG GATTGCAAGCAGAAGATGAGGCCGATTAC TACTGCAGCTCCTATACTAGCTCTTCTACA TTGTACGTCTTTGGGAGCGGAACAAAAGT AACAGTACTC (SEQ ID NO: 261) |
| Linker | GGGGSGGGGSGGGGS (SEQ ID NO: 104) | |
| ScFv PI61 | QVQLQESGGGVVQPGRSLRLS CAASGFTFSSYGMHWVRQAP GKGLEWVAVISYDGSNKYYA DSVKGRFTISRDNSKNTLYLQ MNSLRAEDTAVYYCGGSGYA LHDDYYGLDVWGQGTLVTVS SGGGGSGGGGSGGGGSQSALT QPASVSGSPGQSITISCTGTSSD VGGYNYVSWYQQHPGKAPKL MIYDVSNRPSGVSNRFSGSKSG NTASLTISGLQAEDEADYYCSS YTSSSTLYVFGSGTKVTVL (SEQ ID NO: 105) | CaggtacaattgcaggagtctggaggcggtgtgGtgcaacccggtc gcagcttgcgcctgagttgtGctgcgtctggatttacattttcatcttac ggaAtgcattgggtacgccaggcaccggggaaaggcCttgaatgg gtggctgtaatttcatacgatggtTccaacaaatactatgctgactcag tcaagggtCgatttacaattagtcgggacaactccaagaacAcccttt atcttcaaatgaattcccttagagcaGaggatacggcggtctattactg tggtggcagtGgttatgcacttcatgatgattactatggcttgGatgtct gggggcaagggacgcttgtaactgtaTcctctggtggtggtggtagt ggtgggggaggcTccggcggtggcggctctcaatctgctctgactC aaccagcaagcgtatcagggtcaccgggacagAgtattaccataag ttgcacggggacctctagcGatgtagggggtataattatgtatcttg gtatCaacaacaccccgggaaagcccctaaattgatgAtctacgac gtgagcaatcgacctagtggcgtaTcaaatcgcttctctggtagcaag agtgggaatAcggcgtcccttactattagcggattgcaagcaGaag atgaggccgattactactgcagctcctatActagctcttctacattgtac gtctttgggagcggaacaaaagtaacagtactc (SEQ ID NO: 253) |
| Transmembrane domain and hinge | TTTPAPRPPTPAPTIASQPLSLR PEACRPAAGGAVHTRGLDFAC DIYIWAPLAGTCGVLLLSLVIT LYC (SEQ ID NO: 202) | AcaacaacacctgccccgagaccgcctacaccaGccccgactatt gccagccagcctctgagcctcAggcctgaggcctgtaggcccgca gcgggcggcGcagttcatacacggggcttggatttcgcttgtGatatt tatatttgggctcctttggcggggacaTgtggcgtgctgcttctgtcac ttgttattacactgtactgt (SEQ ID NO: 254) |
| 4-1BB | KRGRKKLLYIFKQPFMRPVQT TQEEDGCSCRFPEEEEGGCEL (SEQ ID NO: 7) | AaacgcgggcgaaaaaaattgctgtatatttttAagcagccatttatg aggcccgttcagacgacgCaggaggaggacggttgctcttgcaggt tcccagaagaggaagaagggggctgtgaattg (SEQ ID NO: 255) |
| CD3zeta | RVKFSRSADAPAYQQGQNQLY NELNLGRREEYDVLDKRRGRD PEMGGKPRRKNPQEGLYNELQ KDKMAEAYSEIGMKGERRRG KGHDGLYQGLSTATKDTYDA LHMQALPPR (SEQ ID NO: 10) | CgggttaaattttcaagatccgcagacgctccaGcataccaacaggg acaaaaccaactctataacGagctgaatcttggaagaagggaggaat atgatGtgctggataaacggcgcggtagagatccggagAtgggcg gaaaaccaaggcgaaaaaaccctcagGagggactctacaacgaac tgcagaaagacaaaAtggcggaggcttattccgaaataggcatgaa gGcgagcggaggcgagggaaagggcacgacggaCtgtatcaa ggcctctcaaccgcgactaaggatAcgtacgacgccctgcacatgc aggccctgcctccgaga (SEQ ID NO: 256) |
| PI61 full CAR construct | MALPVTALLLPLALLLHAARP QVQLQESGGGVVQPGRSLRLS CAASGFTFSSYGMHWVRQAP GKGLEWVAVISYDGSNKYYA DSVKGRFTISRDNSKNTLYLQ MNSLRAEDTAVYYCGGSGYA LHDDYYGLDVWGQGTLVTVS SGGGGSGGGGSGGGGSQSALT QPASVSGSPGQSITISCTGTSSD VGGYNYVSWYQQHPGKAPKL MIYDVSNRPSGVSNRFSGSKSG NTASLTISGLQAEDEADYYCSS YTSSSTLYVFGSGTKVTVLTTT PAPRPPTPAPTIASQPLSLRPEA CRPAAGGAVHTRGLDFACDIY IWAPLAGTCGVLLLSLVITLYC KRGRKKLLYIFKQPFMRPVQT TQEEDGCSCRFPEEEEGGCELR VKFSRSADAPAYQQGQNQLY NELNLGRREEYDVLDKRRGRD PEMGGKPRRKNPQEGLYNELQ KDKMAEAYSEIGMKGERRRG KGHDGLYQGLSTATKDTYDA LHMQALPPR (SEQ ID NO: 257) | ATGGCCCTCCCTGTCACCGCTCTGTTGCTG CCGCTTGCTCTGCTGCTCCACGCAGCGCGA CCGCAGGTACAATTGCAGGAGTCTGGAGG CGGTGTGGTGCAACCCGGTCGCAGCTTGC GCCTGAGTTGTGCTGCGTCTGGATTTACAT TTTCATCTTACGGAATGCATTGGGTACGCC AGGCACCGGGGAAAGGCCTTGAATGGGTG GCTGTAATTTCATACGATGGTTCCAACAAA TACTATGCTGACTCAGTCAAGGGTCGATTT ACAATTAGTCGGGACAACTCCAAGAACAC CCTTTATCTTCAAATGAATTCCCTTAGAGC AGAGGATACGGCGGTCTATTACTGTGGTG GCAGTGGTTATGCACTTCATGATGATTACT ATGGCTTGGATGTCTGGGGGCAAGGGACG CTTGTAACTGTATCCTCTGGTGGTGGTGGT AGTGGTGGGGGAGGCTCCGGCGGTGGCGG CTCTCAATCTGCTCTGACTCAACCAGCAAG CGTATCAGGGTCACCGGGACAGAGTATTA CCATAAGTTGCACGGGGACCTCTAGCGAT GTAGGGGGGTATAATTATGTATCTTGGTAT CAACAACACCCCGGGAAAGCCCCTAAATT GATGATCTACGACGTGAGCAATCGACCTA GTGGCGTATCAAATCGCTTCTCTGGTAGCA AGAGTGGGAATACGGCGTCCCTTACTATT AGCGGATTGCAAGCAGAAGATGAGGCCGA |

TABLE 11-continued

Amino acid and nucleic acid sequences of exemplary anti-BCMA molecules based on PI61

| Identification | Protein sequence | DNA sequence (5'-3') |
|---|---|---|
| | | TTACTACTGCAGCTCCTATACTAGCTCTTC TACATTGTACGTCTTTGGGAGCGGAACAA AAGTAACAGTACTCACAACAACACCTGCC CCGAGACCGCCTACACCAGCCCCGACTAT TGCCAGCCAGCCTCTGAGCCTCAGGCCTG AGGCCTGTAGGCCCGCAGCGGGCGGCGCA GTTCATACACGGGGCTTGGATTTCGCTTGT GATATTTATATTTGGGCTCCTTTGGCGGGG ACATGTGGCGTGCTGCTTCTGTCACTTGTT ATTACACTGTACTGTAAACGCGGGCGAAA AAAATTGCTGTATATTTTTAAGCAGCCATT TATGAGGCCCGTTCAGACGACGCAGGAGG AGGACGGTTGCTCTTGCAGGTTCCCAGAA GAGGAAGAAGGGGGCTGTGAATTGCGGGT TAAATTTTCAAGATCCGCAGACGCTCCAGC ATACCAACAGGGACAAAACCAACTCTATA ACGAGCTGAATCTTGGAAGAAGGGAGGAA TATGATGTGCTGGATAAACGGCGCGGTAG AGATCCGGAGATGGGCGGAAAACCAAGGC GAAAAAACCCTCAGGAGGGACTCTACAAC GAACTGCAGAAAGACAAAATGGCGGAGG CTTATTCCGAAATAGGCATGAAGGGCGAG CGGAGGCGAGGGAAAGGGCACGACGGAC TGTATCAAGGCCTCTCAACCGCGACTAAG GATACGTACGACGCCCTGCACATGCAGGC CCTGCCTCCGAGA (SEQ ID NO: 258) |
| PI61 full CAR construct (Nucleic acid with signal peptide and stop codons) | | ATGGCCCTCCCTGTCACCGCTCTGTTGCTGCCGC TTGCTCTGCTGCTCCACGCAGCGCGACCGCAGGT ACAATTGCAGGAGTCTGGAGGCGGTGTGGTGCAA CCCGGTCGCAGCTTGCGCCTGAGTTGTGCTGCGT CTGGATTTACATTTTCATCTTACGGAATGCATTG GGTACGCCAGGCACCGGGGAAAGGCCTTGAATGG GTGGCTGTAATTTCATACGATGGTTCCAACAAAT ACTATGCTGACTCAGTCAAGGGTCGATTTACAAT TAGTCGGGACAACTCCAAGAACACCCTTTATCTT CAAATGAATTCCCTTAGAGCAGAGGATACGGCGG TCTATTACTGTGGTGGCAGTGGTTATGCACTTCA TGATGATTACTATGGCTTGGATGTCTGGGGGCAA GGGACGCTTGTAACTGTATCCTCTGGTGGTGGTG GTAGTGGTGGGGGAGGCTCCGGCGGTGGCGGCTC TCAATCTGCTCTGACTCAACCAGCAAGCGTATCA GGGTCACCGGGACAGAGTATTACCATAAGTTGCA CGGGGACCTCTAGCGATGTAGGGGGGTATAATTA TGTATCTTGGTATCAACAACACCCCGGGAAAGCC CCTAAATTGATGATCTACGACGTGAGCAATCGAC CTAGTGGCGTATCAAATCGCTTCTCTGGTAGCAA GAGTGGGAATACGGCGTCCCTTACTATTAGCGGA TTGCAAGCAGAAGATGAGGCCGATTACTACTGCA GCTCCTATACTAGCTCTTCTACATTGTACGTCTT TGGGAGCGGAACAAAAGTAACAGTACTCACAACA ACACCTGCCCCGAGACCGCCTACACCAGCCCCGA CTATTGCCAGCCAGCCTCTGAGCCTCAGGCCTGA GGCCTGTAGGCCCGCAGCGGGCGGCGCAGTTCAT ACACGGGGCTTGGATTTCGCTTGTGATATTTATA TTTGGGCTCCTTTGGCGGGGACATGTGGCGTGCT GCTTCTGTCACTTGTTATTACACTGTACTGTAAA CGCGGGCGAAAAAAATTGCTGTATATTTTTAAGC AGCCATTTATGAGGCCCGTTCAGACGACGCAGGA GGAGGACGGTTGCTCTTGCAGGTTCCCAGAAGAG GAAGAAGGGGGCTGTGAATTGCGGGTTAAATTTT CAAGATCCGCAGACGCTCCAGCATACCAACAGGG ACAAAACCAACTCTATAACGAGCTGAATCTTGGA AGAAGGGAGGAATATGATGTGCTGGATAAACGGC GCGGTAGAGATCCGGAGATGGGCGGAAAACCAAG GCGAAAAAACCCTCAGGAGGGACTCTACAACGAA CTGCAGAAAGACAAAATGGCGGAGGCTTATTCCG AAATAGGCATGAAGGGCGAGCGGAGGCGAGGGAA AGGGCACGACGGACTGTATCAAGGCCTCTCAACC GCGACTAAGGATACGTACGACGCCCTGCACATGC AGGCCCTGCCTCCGAGATGATAA (SEQ ID NO: 416) |
| PI61 mature CAR protein | QVQLQESGGGVVQPGRSLRLS CAASGFTFSSYGMHWVRQAP GKGLEWVAVISYDGSNKYYA | caggtacaattgcaggagtctggaggcggtgtggtgcaacccggtc gcagcttgcgcctgagttgtgctgcgtctggatttacattttcatcttacg gaatgcattgggtacgccaggcaccggggaaaggccttgaatgggt |

TABLE 11-continued

Amino acid and nucleic acid sequences of exemplary anti-BCMA molecules based on PI61

| Identification | Protein sequence | DNA sequence (5'-3') |
|---|---|---|
| | DSVKGRFTISRDNSKNTLYLQ<br>MNSLRAEDTAVYYCGGSGYA<br>LHDDYYGLDVWGQGTLVTVS<br>SGGGGSGGGGSGGGGSQSALT<br>QPASVSGSPGQSITISCTGTSSD<br>VGGYNYVSWYQQHPGKAPKL<br>MIYDVSNRPSGVSNRFSGSKSG<br>NTASLTISGLQAEDEADYYCSS<br>YTSSSTLYVFGSGTKVTVLTTT<br>PAPRPPTPAPTIASQPLSLRPEA<br>CRPAAGGAVHTRGLDFACDIY<br>IWAPLAGTCGVLLLSLVITLYC<br>KRGRKKLLYIFKQPFMRPVQT<br>TQEEDGCSCRFPEEEEGGCELR<br>VKFSRSADAPAYQQGQNQLY<br>NELNLGRREEYDVLDKRRGRD<br>PEMGGKPRRKNPQEGLYNELQ<br>KDKMAEAYSEIGMKGERRRG<br>KGHDGLYQGLSTATKDTYDA<br>LHMQALPPR (SEQ ID NO: 107) | ggctgtaatttcatacgatggttccaacaaatactatgctgactcagtca<br>agggtcgatttacaattagtcgggacaactccaagaacaccctttatctt<br>caaatgaattcccttagagcagaggatacggcggtctattactgtggtg<br>gcagtggttatgcacttcatgatgattactatggcttggatgtctggggg<br>caagggacgcttgtaactgtatcctctggtggtggtggtagtggtggg<br>ggaggctccggcggtggcggctctcaatctgctctgactcaaccagc<br>aagcgtatcagggtcaccgggacagagtattaccataagttgcacgg<br>ggacctctagcgatgtagggggtataattatgtatcttggtatcaaca<br>acaccccgggaaagcccctaaattgatgatctacgacgtgagcaatc<br>gacctagtggcgtatcaaatcgcttctctggtagcaagagtgggaata<br>cggcgtcccttactattagcggattgcaagcagaagatgaggccgatt<br>actactgcagctcctatactagctcttctacattgtacgtctttgggagcg<br>gaacaaaagtaacagtactcacaacaacacctgccccgagaccgect<br>acaccagccccgactattgccagccagcctctgagcctcaggcctga<br>ggcctgtaggcccgcagcgggcggcgcagttcatacacggggcttg<br>gatttcgcttgtgatatttatatttgggctcctttggcggggacatgtggc<br>gtgctgcttctgtcacttgttattacactgtactgtaaacgcgggcgaaa<br>aaaattgctgtatattttaagcagccatttatgaggcccgttcagacga<br>cgcaggaggaggacggttgctcttgcaggttcccagaagaggaaga<br>agggggctgtgaattgcgggttaaattttcaagatccgcagacgctcc<br>agcataccaacagggacaaaaccaactctataacgagctgaatcttg<br>gaagaagggaggaatatgatgtgctggataaacggcgcggtagaga<br>tccggagatgggcggaaaaccaaggcgaaaaaaccctcaggaggg<br>actctacaacgaactgcagaaagacaaaatggcggaggcttattccg<br>aaataggcatgaagggcgagcggaggcgagggaaagggcacgac<br>ggactgtatcaaggcctctcaaccgcgactaaggatacgtacgacgc<br>cctgcacatgcaggccctgcctccgaga (SEQ ID NO: 259) |

TABLE 11A

Additional exemplary anti-BCMA binder sequences based on PI161

| SEQ ID NO | Region | Sequence |
|---|---|---|
| 400 | VH | CAGGTGCAGCTGCAGGAGTCCGGCGGCGGCGTGGTGCAGCCAGGCC<br>GGTCCCTGAGACTGTCTTGTGCCGCCAGCGGCTTCACCTTTTCCTCTT<br>ATGGCATGCACTGGGTGAGACAGGCACCTGGCAAGGGACTGGAGTG<br>GGTGGCCGTGATCTCCTACGACGGCTCTAACAAGTATTACGCCGATA<br>GCGTGAAGGGCAGGTTCACCATCAGCCGCGACAACTCCAAGAATACA<br>CTGTATCTGCAGATGAATAGCCTGCGGGCCGAGGATACCGCCGTGTA<br>TTACTGCGGAGGCTCCGGCTACGCACTGCACGACGATTATTACGGAC<br>TGGACGTGTGGGGACAGGGCACCCTGGTCACAGTGAGCTCC |
| 401 | VH | CAGGTGCAGCTGCAGGAGTCTGGCGGAGGAGTGGTGCAGCCAGGCC<br>GGTCCCTGAGACTGTCTTGCGCCGCCAGCGGCTTCACATTTTCTAGCT<br>ACGGAATGCACTGGGTGCGCCAGGCACCTGGCAAGGGACTGGAGTG<br>GGTGGCCGTGATCTCCTATGACGGCTCTAACAAGTACTATGCCGATTC<br>CGTGAAGGGCAGGTTCACCATCAGCCGCGACAACTCCAAGAATACAC<br>TGTACCTGCAGATGAATTCCCTGCGGGCCGAGGATACCGCCGTGTAC<br>TATTGTGGCGGCTCTGGCTATGCCCTGCACGACGATTACTATGGACTG<br>GACGTGTGGGGACAGGGCACCCTGGTGACAGTGTCCTCT |
| 402 | VH | CAGGTGCAGCTGCAGGAGTCTGGCGGAGGAGTGGTGCAGCCAGGCC<br>GGAGCCTGAGACTGTCCTGCGCCGCCTCTGGCTTCACCTTTAGCTCCT<br>ATGGCATGCACTGGGTGAGACAGGCACCTGGCAAGGGACTGGAGTG<br>GGTGGCCGTGATCAGCTACGACGGCTCCAACAAGTATTACGCCGATA<br>GCGTGAAGGGCAGGTTCACCATCTCTCGCGACAACAGCAAGAATACA<br>CTGTATCTGCAGATGAATTCCCTGCGGGCCGAGGATACAGCCGTGTA<br>TTACTGCGGAGGCAGCGGCTACGCACTGCACGACGATTATTACGGAC<br>TGGACGTGTGGGGACAGGGCACCCTGGTCACAGTGTCTAGC |
| 403 | VH | CAGGTGCAGCTGCAGGAGAGCGGCGGCGGCGTGGTGCAGCCCGGCC<br>GGTCTCTGAGACTGAGCTGTGCCGCCTCCGGCTTCACCTTTAGCTCCT<br>ACGGAATGCACTGGGTGCGCCAGGCACCTGGCAAGGGACTGGAGTG<br>GGTGGCCGTGATCTCTTATGACGGCAGCAACAAGTACTATGCCGATA<br>GCGTGAAGGGCAGGTTCACCATCTCCCGCGACAACTCTAAGAATACA<br>CTGTACCTGCAGATGAATAGCCTGCGGGCCGAGGATACCGCCGTGTA<br>CTATTGCGGAGGCTCCGGCTATGCACTGCACGACGATTACTATGGAC<br>TGGACGTGTGGGGACAGGGCACCCTGGTGACAGTGTCTAGC |
| 404 | VH | CAGGTCCAGCTGCAGGAGAGTGGGGGGGGGGTCGTCCAGCCCGGAA<br>GAAGCCTGAGACTGTCATGTGCCGCATCTGGGTTTACTTTTAGCTCCT |

TABLE 11A-continued

Additional exemplary anti-BCMA binder sequences based on PI161

| SEQ ID NO | Region | Sequence |
|---|---|---|
| | | ATGGAATGCACTGGGTGCGCCAGGCACCTGGCAAGTGCCTGGAGTGG GTGGCCGTGATCTCCTACGACGGCTCTAACAAGTACTATGCCGATAG CGTGAAGGGCCGGTTCACCATCAGCAGAGACAACTCCAAGAATACAC TGTATCTGCAGATGAATTCTCTGCGGGCCGAGGATACCGCCGTGTACT ATTGTGGAGGCTCCGGCTACGCACTGCACGACGATTACTATGGACTG GACGTGTGGGGACAGGGCACCCTGGTGACAGTGTCTAGC |
| 405 | VH | CAGGTCCAGCTGCAGGAATCCGGCGGAGGAGTGGTGCAGCCAGGCC GGTCTCTGAGACTGAGCTGCGCCGCCTCCGGCTTCACATTTTCCTCTT ATGGCATGCACTGGGTGAGACAGGCCCCTGGCAAGTGTCTGGAGTGG GTGGCCGTGATCTCTTACGACGGCAGCAACAAGTATTACGCCGATAG CGTGAAGGGCAGGTTCACCATCTCCCGCGACAACTCTAAGAATACAC TGTATCTGCAGATGAATTCCCTGCGGGCCGAGGATACCGCCGTGTATT ACTGCGGCGGCTCTGGCTACGCCCTGCACGACGACTACTATGGACTG GATGTCTGGGGGCAGGGCACACTGGTCACTGTCTCTTCA |
| 406 | VH | CAGGTCCAGCTGCAGGAATCAGGGGGGGGGGTCGTCCAGCCCGGAA GAAGTCTGAGACTGTCATGTGCCGCATCAGGGTTTACCTTTAGCTCCT ATGGAATGCACTGGGTGCGCCAGGCACCTGGCAAGTGCCTGGAGTGG GTGGCCGTGATCTCCTACGACGGCTCTAACAAGTACTATGCCGATAG CGTGAAGGGCCGGTTCACCATCAGCAGAGACAACTCCAAGAATACAC TGTATCTGCAGATGAATTCTCTGCGGGCCGAGGATACCGCCGTGTACT ATTGTGGAGGCTCCGGCTACGCACTGCACGACGATTACTATGGACTG GACGTGTGGGGACAGGGCACCCTGGTGACAGTGTCTAGC |
| 407 | VH | CAGGTCCAGCTGCAGGAATCCGGCGGAGGAGTGGTGCAGCCAGGCC GGTCTCTGAGACTGAGCTGCGCCGCCTCCGGCTTCACCTTTTCCTCTT ATGGCATGCACTGGGTGAGACAGGCCCCTGGCAAGTGTCTGGAGTGG GTGGCCGTGATCTCTTACGACGGCAGCAACAAGTATTACGCCGATAG CGTGAAGGGCAGGTTCACCATCTCCCGCGACAACTCTAAGAATACAC TGTATCTGCAGATGAATTCCCTGCGGGCCGAGGATACAGCCGTGTAT TACTGTGGCGGCTCTGGCTACGCCCTGCATGATGATTATTATGGACTG GATGTCTGGGGGCAGGGCACACTGGTCACTGTCTCTTCC |
| 408 | VL | CAGTCTGCCCTGACCCAGCCAGCAAGCGTGTCCGGCTCTCCTGGCCA GAGCATCACAATCTCCTGCACCGGCACAAGCTCCGACGTGGGAGGCT ATAACTACGTGAGCTGGTATCAGCAGCACCCAGGCAAGGCCCCCAAG CTGATGATCTACGACGTGAGCAACAGGCCTTCTGGCGTGAGCAATCG CTTCAGCGGCTCCAAGTCTGGCAATACCGCCTCTCTGACAATCAGCG GCCTGCAGGCAGAGGACGAGGCAGATTATTACTGCTCTAGCTATACC TCCTCTAGCACACTGTACGTGTTTGGCAGCGGCACCAAGGTGACAGT GCTG |
| 409 | VL | CAGAGCGCCCTGACCCAGCCAGCATCCGTGTCTGGCAGCCCAGGCCA GTCTATCACAATCAGCTGCACCGGCACAAGCTCCGACGTGGGAGGCT ACAACTATGTGAGCTGGTACCAGCAGCACCCTGGCAAGGCCCCAAAG CTGATGATCTATGACGTGAGCAACCGGCCATCCGGCGTGTCTAATAG ATTCTCCGGCTCTAAGAGCGGCAATACCGCCTCCCTGACAATCTCTGG CCTGCAGGCAGAGGACGAGGCAGATTACTATTGTTCTAGCTACACCT CCTCTAGCACACTGTACGTGTTCGGCAGCGGCACCAAGGTGACAGTG CTG |
| 410 | VL | CAGTCTGCCCTGACCCAGCCAGCAAGCGTGTCCGGCTCTCCTGGCCA GTCCATCACAATCTCTTGTACCGGCACATCCTCTGACGTGGGCGGCTA TAACTACGTGTCCTGGTATCAGCAGCACCCAGGCAAGGCCCCCAAGC TGATGATCTACGATGTGAGCAACAGGCCTTCTGGCGTGAGCAATCGC TTCAGCGGCTCCAAGTCTGGCAATACCGCCAGCCTGACAATCTCCGG CCTGCAGGCAGAGGACGAGGCAGATTATTACTGCAGCTCCTATACCT CTAGCTCCACACTGTACGTGTTTGGCAGCGGCACCAAGGTGACAGTG CTG |
| 411 | VL | CAGAGCGCCCTGACCCAGCCAGCATCCGTGTCTGGCAGCCCAGGCCA GTCCATCACAATCTCTTGCACCGGCACATCTAGCGACGTGGGCGGCT ACAACTACGTGAGCTGGTACCAGCAGCACCCTGGCAAGGCCCCAAAG CTGATGATCTATGATGTGAGCAACCGGCCCTCCGGCGTGTCTAATAG ATTCTCCGGCTCTAAGAGCGGCAATACCGCCAGCCTGACAATCTCCG GCCTGCAGGCAGAGGACGAGGCAGATTACTATTGCTCCTCTTACACC AGCTCCTCTACACTGTACGTGTTCGGCTCCGGCACCAAGGTGACAGT GCTG |
| 412 | VL | CAGTCTGCCCTGACCCAGCCTGCAAGCGTGTCCGGCTCTCCAGGCCA GTCTATCACAATCAGCTGTACCGGCACAAGCTCCGACGTGGGCGGCT ATAACTACGTGAGCTGGTATCAGCAGCACCCTGGCAAGGCCCCAAAG CTGATGATCTACGACGTGAGCAACCGGCCCTCTGGCGTGAGCAATCG GTTCAGCGGCAGCAAGTCTGGCAATACCGCCTCCCTGACAATCTCTG |

TABLE 11A-continued

Additional exemplary anti-BCMA binder sequences based on PI161

| SEQ ID NO | Region | Sequence |
|---|---|---|
| | | GCCTGCAGGCAGAGGACGAGGCAGATTATTACTGTAGCAGTTATACT<br>TCAAGCTCAACCCTGTACGTGTTTGGATGCGGCACTAAGGTCACCGT<br>CCTG |
| 413 | VL | CAGTCTGCTCTGACCCAGCCCGCTTCCGTCTCAGGGTCTCCAGGACAG<br>TCAATTACCATTAGTTGCACAGGCACCTCATCCGATGTGGGCGGCTAT<br>AACTACGTGTCCTGGTATCAGCAGCACCCAGGCAAGGCCCCCAAGCT<br>GATGATCTACGACGTGAGCAACAGGCCATCTGGCGTGAGCAATCGCT<br>TCAGCGGCTCCAAGTCTGGCAATACCGCCAGCCTGACAATCTCCGGC<br>CTGCAGGCAGAGGACGAGGCAGATTACTATTGCAGCTCCTATACCTC<br>TAGCTCCACACTGTACGTGTTTGGCTGTGGCACCAAGGTGACAGTGCT<br>G |
| 414 | VL | CAGTCTGCCCTGACCCAGCCTGCAAGCGTGTCCGGCTCTCCAGGCCA<br>GTCTATCACAATCAGCTGTACCGGCACAAGCTCCGACGTGGGCGGCT<br>ATAACTACGTGAGCTGGTATCAGCAGCACCCTGGCAAGGCCCCAAAG<br>CTGATGATCTACGACGTGAGCAACCGGCCCTCTGGCGTGAGCAATCG<br>GTTCAGCGGCAGCAAGTCTGGCAATACCGCCTCCCTGACAATCTCTG<br>GCCTGCAGGCAGAGGACGAGGCAGATTATTACTGTAGCTCCTACACT<br>TCTTCAAGCACACTGTATGTCTTTGGATGCGGAACTAAGGTCACTGTC<br>CTG |
| 415 | VL | CAGTCTGCTCTGACCCAGCCCGCTTCCGTCTCAGGATCTCCAGGACAG<br>TCTATTACAATTAGTTGCACAGGAACCTCTTCCGATGTGGGCGGCTAT<br>AACTACGTGTCCTGGTATCAGCAGCACCCAGGCAAGGCCCCCAAGCT<br>GATGATCTACGACGTGAGCAACAGGCCTTCTGGCGTGAGCAATCGCT<br>TCAGCGGCTCCAAGTCTGGCAATACCGCCAGCCTGACAATCTCCGGC<br>CTGCAGGCAGAGGACGAGGCAGATTACTATTGCAGCTCCTATACCTC<br>TAGCTCCACACTGTACGTGTTTGGCTGTGGCACCAAGGTGACAGTGCT<br>G |
| SEQ ID NO: 93 | Ant-BCMA VH (PI61) | QVQLQESGGGVVQPGRSLRLSCAASGFTFSSYGMHWVRQAPGKGLEW<br>VAVISYDGSNKYYADSVKGRFTISRDNSKNTLYLQMNSLRAEDTAVYY<br>CGGSGYALHDDYYGLDVWGQGTLVTVSS |
| SEQ ID NO: 102 | Anti-BCMA VL (PI61) | QSALTQPASVSGSPGQSITISCTGTSSDVGGYNYVSWYQQHPGKAPKLMI<br>YDVSNRPSGVSNRFSGSKSGNTASLTISGLQAEDEADYYCSSYTSSSTLY<br>VFGSGTKVTVL |
| SEQ ID NO: 333 | Anti-BCMA VH (PI61) variant | QVQLQESGGGVVQPGRSLRLSCAASGFTFSSYGMHWVRQAPGKCLEW<br>VAVISYDGSNKYYADSVKGRFTISRDNSKNTLYLQMNSLRAEDTAVYY<br>CGGSGYALHDDYYGLDVWGQGTLVTVSS |
| SEQ ID NO: 334 | Anti-BCMA VL (PI61) variant | QSALTQPASVSGSPGQSITISCTGTSSDVGGYNYVSWYQQHPGKAPKLMI<br>YDVSNRPSGVSNRFSGSKSGNTASLTISGLQAEDEADYYCSSYTSSSTLY<br>VFGCGTKVTVL |

TABLE 12

Amino acid and nucleic acid sequences of exemplary hybridoma-derived anti-BCMA molecules

| SEQ ID NO | Name/Description | Sequence |
|---|---|---|
| Hy03 | | |
| SEQ ID NO: 137 | HCDR1 (Kabat) | GFWMS |
| SEQ ID NO: 138 | HCDR2 (Kabat) | NIKQDGSEKYYVDSVRG |
| SEQ ID NO: 139 | HCDR3 (Kabat) | ALDYYGMDV |
| SEQ ID NO: 140 | HCDR1 (Chothia) | GFTFSGF |

TABLE 12-continued

Amino acid and nucleic acid sequences of exemplary hybridoma-derived anti-BCMA molecules

| SEQ ID NO | Name/ Description | Sequence |
|---|---|---|
| SEQ ID NO: 141 | HCDR2 (Chothia) | KQDGSE |
| SEQ ID NO: 139 | HCDR3 (Chothia) | ALDYYGMDV |
| SEQ ID NO: 142 | HCDR1 (IMGT) | GFTFSGFW |
| SEQ ID NO: 143 | HCDR2 (IMGT) | IKQDGSEK |
| SEQ ID NO: 144 | HCDR3 (IMGT) | ARALDYYGMDV |
| SEQ ID NO: 145 | VH | EVQLVESGGGLVQPGGSLRLSCAASGFTFSGFWMSWVRQAPGKGLEWV ANIKQDGSEKYYVDSVRGRFTISRDNAKNSLYLQMNSLRAEDTAVYYCA RALDYYGMDVWGQGTTVTVSS |
| SEQ ID NO: 146 | DNA VH | GAAGTGCAACTGGTGGAGAGCGGTGGAGGGCTTGTCCAGCCCGGAGG ATCGCTGCGGCTGTCCTGTGCTGCGTCCGGGTTCACCTTCTCCGGCTTC TGGATGTCCTGGGTCAGACAGGCACCGGGAAAGGGCCTCGAATGGGT GGCCAACATCAAGCAGGATGGCTCCGAGAAGTACTACGTCGACTCCGT GAGAGGCCGCTTCACCATCTCCCGGGACAACGCCAAGAACTCGCTGTA CCTCCAAATGAATAGCCTCAGGGCGGAAGATACTGCTGTGTATTACTG CGCACGCGCCCTTGACTACTACGGCATGGACGTCTGGGGCCAAGGGAC CACTGTGACCGTGTCTAGC |
| SEQ ID NO: 147 | LCDR1 (Kabat) | RSSQSLLDSDDGNTYLD |
| SEQ ID NO: 148 | LCDR2 (Kabat) | TLSYRAS |
| SEQ ID NO: 149 | LCDR3 (Kabat) | TQRLEFPSIT |
| SEQ ID NO: 150 | LCDR1 (Chothia) | SQSLLDSDDGNTY |
| SEQ ID NO: 151 | LCDR2 (Chothia) | TLS |
| SEQ ID NO: 152 | LCDR3 (Chothia) | RLEFPSI |
| SEQ ID NO: 153 | LCDR1 (IMGT) | QSLLDSDDGNTY |
| SEQ ID NO: 151 | LCDR2 (IMGT) | TLS |
| SEQ ID NO: 149 | LCDR3 (IMGT) | TQRLEFPSIT |
| SEQ ID NO: 154 | VL | DIVMTQTPLSLPVTPGEPASISCRSSQSLLDSDDGNTYLDWYLQKPGQSPR LLIYTLSYRASGVPDRFSGSGSGTDFTLKISRVEAEDVGLYYCTQRLEFPSI TFGQGTRLEIK |
| SEQ ID NO: 155 | DNA VL | GATATCGTGATGACCCAGACTCCCCTGTCCCTGCCTGTGACTCCCGGA GAACCAGCCTCCATTTCCTGCCGGTCCTCCCAGTCCCTGCTGGACAGC GACGACGGCAACACTTACCTGGACTGGTACTTGCAGAAGCCGGGCCA ATCGCCTCGCCTGCTGATCTATACCCTGTCATACCGGGCCTCAGGAGT GCCTGACCGCTTCTCGGGATCAGGGAGCGGGACCGATTTCACCCTGAA AATTTCCCGAGTGGAAGCCGAGGACGTCGGACTGTACTACTGCACCCA GCGCCTCGAATTCCCGTCGATTACGTTTGGACAGGGTACCCGGCTTGA GATCAAG |
| SEQ ID NO: 63 | Linker | GGGGSGGGGSGGGGSGGGGS |
| SEQ ID NO: 156 | scFv (VH-linker-VL) | EVQLVESGGGLVQPGGSLRLSCAASGFTFSGFWMSWVRQAPGKGLEWV ANIKQDGSEKYYVDSVRGRFTISRDNAKNSLYLQMNSLRAEDTAVYYCA RALDYYGMDVWGQGTTVTVSSGGGGSGGGGSGGGGSGGGGSDIVMTQ |

TABLE 12-continued

Amino acid and nucleic acid sequences of exemplary hybridoma-derived anti-BCMA molecules

| SEQ ID NO | Name/ Description | Sequence |
|---|---|---|
| | | TPLSLPVTPGEPASISCRSSQSLLDSDDGNTYLDWYLQKPGQSPRLLIYTLS YRASGVPDRFSGSGSGTDFTLKISRVEAEDVGLYYCTQRLEFPSITFGQGT RLEIK |
| SEQ ID NO: 157 | DNA scFv | GAAGTGCAACTGGTGGAGAGCGGTGGAGGGCTTGTCCAGCCCGGAGG ATCGCTGCGGCTGTCCTGTGCTGCGTCCGGGTTCACCTTCTCCGGCTTC TGGATGTCCTGGGTCAGACAGGCACCGGGAAAGGGCCTCGAATGGGT GGCCAACATCAAGCAGGATGGCTCCGAGAAGTACTACGTCGACTCCGT GAGAGGCCGCTTCACCATCTCCCGGGACAACGCCAAGAACTCGCTGTA CCTCCAAATGAATAGCCTCAGGGCGGAAGATACTGCTGTGTATTACTG CGCACGCGCCCTTGACTACTACGGCATGGACGTCTGGGGCCAAGGGAC CACTGTGACCGTGTCTAGCGGAGGCGGAGGTTCAGGGGGCGGTGGAT CAGGCGGAGGAGGATCGGGGGGTGGTGGATCGGATATCGTGATGACC CAGACTCCCCTGTCCCTGCCTGTGACTCCCGGAGAACCAGCCTCCATTT CCTGCCGGTCCTCCCAGTCCCTGCTGGACAGCGACGACGGCAACACTT ACCTGGACTGGTACTTGCAGAAGCCGGGCCAATCGCCTCGCCTGCTGA TCTATACCCTGTCATACCGGGCCTCAGGAGTGCCTGACCGCTTCTCGG GATCAGGGAGCGGGACCGATTTCACCCTGAAAATTTCCCGAGTGGAA GCCGAGGACGTCGGACTGTACTACTGCACCCAGCGCCTCGAATTCCCG TCGATTACGTTTGGACAGGGTACCCGGCTTGAGATCAAG |
| SEQ ID NO: 158 | Full CAR amino acid sequence | EVQLVESGGGLVQPGGSLRLSCAASGFTFSGFWMSWVRQAPGKGLEWV ANIKQDGSEKYYVDSVRGRFTISRDNAKNSLYLQMNSLRAEDTAVYYCA RALDYYGMDVWGQGTTVTVSSGGGGSGGGGSGGGGSGGGGSDIVMTQ TPLSLPVTPGEPASISCRSSQSLLDSDDGNTYLDWYLQKPGQSPRLLIYTLS YRASGVPDRFSGSGSGTDFTLKISRVEAEDVGLYYCTQRLEFPSITFGQGT RLEIKTTTPAPRPPTPAPTIASQPLSLRPEACRPAAGGAVHTRGLDFACDIYI WAPLAGTCGVLLLSLVITLYCKRGRKKLLYIFKQPFMRPVQTTQEEDGCS CRFPEEEEGGCELRVKFSRSADAPAYQQGQNQLYNELNLGRREEYDVLD KRRGRDPEMGGKPRRKNPQEGLYNELQKDKMAEAYSEIGMKGERRRGK GHDGLYQGLSTATKDTYDALHMQALPPR |
| SEQ ID NO: 159 | Full CAR DNA sequence | GAAGTGCAACTGGTGGAGAGCGGTGGAGGGCTTGTCCAGCCCGGAGG ATCGCTGCGGCTGTCCTGTGCTGCGTCCGGGTTCACCTTCTCCGGCTTC TGGATGTCCTGGGTCAGACAGGCACCGGGAAAGGGCCTCGAATGGGT GGCCAACATCAAGCAGGATGGCTCCGAGAAGTACTACGTCGACTCCGT GAGAGGCCGCTTCACCATCTCCCGGGACAACGCCAAGAACTCGCTGTA CCTCCAAATGAATAGCCTCAGGGCGGAAGATACTGCTGTGTATTACTG CGCACGCGCCCTTGACTACTACGGCATGGACGTCTGGGGCCAAGGGAC CACTGTGACCGTGTCTAGCGGAGGCGGAGGTTCAGGGGGCGGTGGAT CAGGCGGAGGAGGATCGGGGGGTGGTGGATCGGATATCGTGATGACC CAGACTCCCCTGTCCCTGCCTGTGACTCCCGGAGAACCAGCCTCCATTT CCTGCCGGTCCTCCCAGTCCCTGCTGGACAGCGACGACGGCAACACTT ACCTGGACTGGTACTTGCAGAAGCCGGGCCAATCGCCTCGCCTGCTGA TCTATACCCTGTCATACCGGGCCTCAGGAGTGCCTGACCGCTTCTCGG GATCAGGGAGCGGGACCGATTTCACCCTGAAAATTTCCCGAGTGGAA GCCGAGGACGTCGGACTGTACTACTGCACCCAGCGCCTCGAATTCCCG TCGATTACGTTTGGACAGGGTACCCGGCTTGAGATCAAGACCACTACC CCAGCACCGAGGCCACCCACCCCGGCTCCTACCATCGCCTCCCAGCCT CTGTCCCTGCGTCCGGAGGCATGTAGACCCGCAGCTGGTGGGGCCGTG CATACCCGGGGTCTTGACTTCGCCTGCGATATCTACATTTGGGCCCCTC TGGCTGGTACTTGCGGGGTCCTGCTGCTTTCACTCGTGATCACTCTTTA CTGTAAGCGCGGTCGGAAGAAGCTGCTGTACATCTTTAAGCAACCCTT CATGAGGCCTGTGCAGACTACTCAAGAGGAGGACGGCTGTTCATGCCG GTTCCCAGAGGAGGAGGAAGGCGGCTGCGAACTGCGCGTGAAATTCA GCCGCAGCGCAGATGCTCCAGCCTACCAGCAGGGGCAGAACCAGCTC TACAACGAACTCAATCTTGGTCGGAGAGAGGAGTACGACGTGCTGGA CAAGCGGAGAGGACGGGACCCAGAAATGGGCGGGAAGCCGCGCAGA AAGAATCCCCAAGAGGGCCTGTACAACGAGCTCCAAAAGGATAAGAT GGCAGAAGCCTATAGCGAGATTGGTATGAAAGGGGAACGCAGAAGAG GCAAAGGCCACGACGGACTGTACCAGGGACTCAGCACCGCCACCAAG GACACCTATGACGCTCTTCACATGCAGGCCCTGCCGCCTCGG |
| Hy52 | | |
| SEQ ID NO: 160 | HCDR1 (Kabat) | SFRMN |
| SEQ ID NO: 161 | HCDR2 (Kabat) | SISSSSSYIYYADSVKG |
| SEQ ID NO: 162 | HCDR3 (Kabat) | WLSYYGMDV |

TABLE 12-continued

Amino acid and nucleic acid sequences of exemplary hybridoma-derived anti-BCMA molecules

| SEQ ID NO | Name/ Description | Sequence |
|---|---|---|
| SEQ ID NO: 163 | HCDR1 (Chothia) | GFTFSSF |
| SEQ ID NO: 164 | HCDR2 (Chothia) | SSSSSY |
| SEQ ID NO: 162 | HCDR3 (Chothia) | WLSYYGMDV |
| SEQ ID NO: 165 | HCDR1 (IMGT) | GFTFSSFR |
| SEQ ID NO: 166 | HCDR2 (IMGT) | ISSSSSYI |
| SEQ ID NO: 167 | HCDR3 (IMGT) | ARWLSYYGMDV |
| SEQ ID NO: 168 | VH | EVQLVESGGGLVKPGGSLRLSCAASGFTFSSFRMNWVRQAPGKGLEWVS SISSSSSYIYYADSVKGRFTISRDNAKNSLYLQMNSLRAEDTAVYYCARW LSYYGMDVWGQGTTVTVSS |
| SEQ ID NO: 169 | DNA VH | GAAGTGCAACTGGTGGAGAGCGGTGGAGGGCTTGTCAAGCCCGGAGG ATCGCTGCGGCTGTCCTGTGCTGCGTCCGGGTTCACCTTCTCCTCGTTC CGCATGAACTGGGTCAGACAGGCACCGGGAAAGGGCCTCGAATGGGT GTCCTCAATCTCATCGTCCTCGTCCTACATCTACTACGCCGACTCCGTG AAAGGCCGCTTCACCATCTCCCGGGACAACGCCAAGAACTCGCTGTAC CTCCAAATGAATAGCCTCAGGGCGGAAGATACTGCTGTGTATTACTGC GCACGCTGGCTTTCCTACTACGGCATGGACGTCTGGGGCCAAGGGACC ACTGTGACCGTGTCTAGC |
| SEQ ID NO: 147 | LCDR1 (Kabat) | RSSQSLLDSDDGNTYLD |
| SEQ ID NO: 170 | LCDR2 (Kabat) | TLSFRAS |
| SEQ ID NO: 171 | LCDR3 (Kabat) | MQRIGFPIT |
| SEQ ID NO: 150 | LCDR1 (Chothia) | SQSLLDSDDGNTY |
| SEQ ID NO: 151 | LCDR2 (Chothia) | TLS |
| SEQ ID NO: 172 | LCDR3 (Chothia) | RIGFPI |
| SEQ ID NO: 153 | LCDR1 (IMGT) | QSLLDSDDGNTY |
| SEQ ID NO: 151 | LCDR2 (IMGT) | TLS |
| SEQ ID NO: 171 | LCDR3 (IMGT) | MQRIGFPIT |
| SEQ ID NO: 173 | VL | DIVMTQTPLSLPVTPGEPASISCRSSQSLLDSDDGNTYLDWYLQKPGQSPQ LLIYTLSFRASGVPDRFSGSGSGTDFTLKIRRVEAEDVGVYYCMQRIGFPIT FGQGTRLEIK |
| SEQ ID NO: 174 | DNA VL | GATATCGTGATGACCCAGACTCCCCTGTCCCTGCCTGTGACTCCCGGA GAACCAGCCTCCATTTCCTGCCGGTCCTCCCAGTCCCTGCTGGACAGC GACGACGGCAACACTTACCTGGACTGGTACTTGCAGAAGCCGGGCCA ATCGCCTCAGCTGCTGATCTATACCCTGTCATTCCGGGCCTCAGGAGT GCCTGACCGCTTCTCGGGATCAGGGAGCGGGACCGATTTCACCCTGAA AATTAGGCGAGTGGAAGCCGAGGACGTCGGAGTGTACTACTGCATGC AGCGCATCGGCTTCCCGATTACGTTTGGACAGGGTACCCGGCTTGAGA TCAAG |
| SEQ ID NO: 63 | Linker | GGGGSGGGGSGGGGSGGGGS |

TABLE 12-continued

Amino acid and nucleic acid sequences of exemplary hybridoma-derived anti-BCMA molecules

| SEQ ID NO | Name/ Description | Sequence |
|---|---|---|
| SEQ ID NO: 175 | scFv (VH-linker-VL) | EVQLVESGGGLVKPGGSLRLSCAASGFTFSSFRMNWVRQAPGKGLEWVS SISSSSSYIYYADSVKGRFTISRDNAKNSLYLQMNSLRAEDTAVYYCARW LSYYGMDVWGQGTTVTVSSGGGGSGGGGSGGGGSGGGGSDIVMTQTPL SLPVTPGEPASISCRSSQSLLDSDDGNTYLDWYLQKPGQSPQLLIYTLSFRA SGVPDRFSGSGSGTDFTLKIRRVEAEDVGVYYCMQRIGFPITFGQGTRLEI K |
| SEQ ID NO: 176 | DNA scFv | GAAGTGCAACTGGTGGAGAGCGGTGGAGGGCTTGTCAAGCCCGGAGG ATCGCTGCGGCTGTCCTGTGCTGCGTCCGGGTTCACCTTCTCCTCGTTC CGCATGAACTGGGTCAGACAGGCACCGGGAAAGGGCCTCGAATGGGT GTCCTCAATCTCATCGTCCTCGTCCTACATCTACTACGCCGACTCCGTG AAAGGCCGCTTCACCATCTCCCGGGACAACGCCAAGAACTCGCTGTAC CTCCAAATGAATAGCCTCAGGGCGGAAGATACTGCTGTGTATTACTGC GCACGCTGGCTTTCCTACTACGGCATGGACGTCTGGGGCCAAGGGACC ACTGTGACCGTGTCTAGCGGAGGCGGAGGTTCAGGGGGCGGTGGATC AGGCGGAGGAGGATCGGGGGGTGGTGGATCGGATATCGTGATGACCC AGACTCCCCTGTCCCTGCCTGTGACTCCCGGAGAACCAGCCTCCATTTC CTGCCGGTCCTCCCAGTCCCTGCTGGACAGCGACGACGGCAACACTTA CCTGGACTGGTACTTGCAGAAGCCGGGCCAATCGCCTCAGCTGCTGAT CTATACCCTGTCATTCCGGGCCTCAGGAGTGCCTGACCGCTTCTCGGG ATCAGGGAGCGGGACCGATTTCACCCTGAAAATTAGGCGAGTGGAAG CCGAGGACGTCGGAGTGTACTACTGCATGCAGCGCATCGGCTTCCCGA TTACGTTTGGACAGGGTACCCGGCTTGAGATCAAG |
| SEQ ID NO: 177 | Full CAR amino acid sequence | EVQLVESGGGLVKPGGSLRLSCAASGFTFSSFRMNWVRQAPGKGLEWVS SISSSSSYIYYADSVKGRFTISRDNAKNSLYLQMNSLRAEDTAVYYCARW LSYYGMDVWGQGTTVTVSSGGGGSGGGGSGGGGSGGGGSDIVMTQTPL SLPVTPGEPASISCRSSQSLLDSDDGNTYLDWYLQKPGQSPQLLIYTLSFRA SGVPDRFSGSGSGTDFTLKIRRVEAEDVGVYYCMQRIGFPITFGQGTRLEI KTTTPAPRPPTPAPTIASQPLSLRPEACRPAAGGAVHTRGLDFACDIYIWAP LAGTCGVLLLSLVITLYCKRGRKKLLYIFKQPFMRPVQTTQEEDGCSCRFP EEEEGGCELRVKFSRSADAPAYQQGQNQLYNELNLGRREEYDVLDKRRG RDPEMGGKPRRKNPQEGLYNELQKDKMAEAYSEIGMKGERRRGKGHDG LYQGLSTATKDTYDALHMQALPPR |
| SEQ ID NO: 178 | Full CAR DNA sequence | GAAGTGCAACTGGTGGAGAGCGGTGGAGGGCTTGTCAAGCCCGGAGG ATCGCTGCGGCTGTCCTGTGCTGCGTCCGGGTTCACCTTCTCCTCGTTC CGCATGAACTGGGTCAGACAGGCACCGGGAAAGGGCCTCGAATGGGT GTCCTCAATCTCATCGTCCTCGTCCTACATCTACTACGCCGACTCCGTG AAAGGCCGCTTCACCATCTCCCGGGACAACGCCAAGAACTCGCTGTAC CTCCAAATGAATAGCCTCAGGGCGGAAGATACTGCTGTGTATTACTGC GCACGCTGGCTTTCCTACTACGGCATGGACGTCTGGGGCCAAGGGACC ACTGTGACCGTGTCTAGCGGAGGCGGAGGTTCAGGGGGCGGTGGATC AGGCGGAGGAGGATCGGGGGGTGGTGGATCGGATATCGTGATGACCC AGACTCCCCTGTCCCTGCCTGTGACTCCCGGAGAACCAGCCTCCATTTC CTGCCGGTCCTCCCAGTCCCTGCTGGACAGCGACGACGGCAACACTTA CCTGGACTGGTACTTGCAGAAGCCGGGCCAATCGCCTCAGCTGCTGAT CTATACCCTGTCATTCCGGGCCTCAGGAGTGCCTGACCGCTTCTCGGG ATCAGGGAGCGGGACCGATTTCACCCTGAAAATTAGGCGAGTGGAAG CCGAGGACGTCGGAGTGTACTACTGCATGCAGCGCATCGGCTTCCCGA TTACGTTTGGACAGGGTACCCGGCTTGAGATCAAGACCACTACCCCAG CACCGAGGCCACCCACCCCGGCTCCTACCATCGCCTCCCAGCCTCTGT CCCTGCGTCCGGAGGCATGTAGACCCGCAGCTGGTGGGGCCGTGCATA CCCGGGGTCTTGACTTCGCCTGCGATATCTACATTTGGGCCCCTCTGGC TGGTACTTGCGGGGTCCTGCTGCTTTCACTCGTGATCACTCTTTACTGT AAGCGCGGTCGGAAGAAGCTGCTGTACATCTTTAAGCAACCCTTCATG AGGCCTGTGCAGACTACTCAAGAGGAGGACGGCTGTTCATGCCGGTTC CCAGAGGAGGAGGAAGGCGGCTGCGAACTGCGCGTGAAATTCAGCCG CAGCGCAGATGCTCCAGCCTACCAGCAGGGGCAGAACCAGCTCTACA ACGAACTCAATCTTGGTCGGAGAGAGGAGTACGACGTGCTGGACAAG CGGAGAGGACGGGACCCAGAAATGGGCGGGAAGCCGCGCAGAAAGA ATCCCCAAGAGGGCCTGTACAACGAGCTCCAAAAGGATAAGATGGCA GAAGCCTATAGCGAGATTGGTATGAAAGGGGAACGCAGAAGAGGCAA AGGCCACGACGGACTGTACCAGGGACTCAGCACCGCCACCAAGGACA CCTATGACGCTCTTCACATGCAGGCCCTGCCGCCTCGG |

TABLE 13

Kabat CDRs of exemplary hybridoma-derived anti-BCMA molecules

| Kabat | HCDR1 | HCDR2 | HCDR3 | LCDR1 | LCDR2 | LCDR3 |
|---|---|---|---|---|---|---|
| Hy03 | GFWMS (SEQ ID NO: 137) | NIKQDGSEK YYVDSVRG (SEQ ID NO: 138) | ALDYYGMD V (SEQ ID NO: 139) | RSSQSLLDS DDGNTYLD (SEQ ID NO: 147) | TLSYRA S (SEQ ID NO: 148) | TQRLEFP SIT (SEQ ID NO: 149) |
| Hy52 | SFRMN (SEQ ID NO: 160) | SISSSSSYIYY ADSVKG (SEQ ID NO: 161) | WLSYYGMD V (SEQ ID NO: 162) | RSSQSLLDS DDGNTYLD (SEQ ID NO: 147) | TLSFRAS (SEQ ID NO: 170) | MQRIGFP IT (SEQ ID NO: 171) |
| Consensus | $X_1FX_2MX_3$, wherein $X_1$ is G or S; $X_2$ is W or R; and $X_3$ is S or N (SEQ ID NO: 179) | $X_1IX_2X_3X_4X_5S$ $X_6X_7YYX_8DS$ $VX_9G$, wherein $X_1$ is N or S; $X_2$ is K or S; $X_3$ is Q or S; $X_4$ is D or S; $X_5$ is G or S; $X_6$ is E or Y; $X_7$ is K or I; $X_8$ is V or A; and $X_9$ is R or K (SEQ ID NO: 180) | $X_1LX_2YYGM$ DV, wherein $X_1$ is A or W; and $X_2$ is D or S (SEQ ID NO: 181) | RSSQSLLDS DDGNTYLD (SEQ ID NO: 147) | TLSXRA S, wherein X is Y or F (SEQ ID NO: 182) | $X_1QRX_2X_3$ $FPX_4IT$, wherein $X_1$ is T or M; $X_2$ is L or I; $X_3$ is E or G; and $X_4$ is S or absent (SEQ ID NO: 183) |

TABLE 14

Chothia CDRs of exemplary hybridoma-derived anti-BCMA molecules

| Chothia | HCDR1 | HCDR2 | HCDR3 | LCDR1 | LCDR2 | LCDR3 |
|---|---|---|---|---|---|---|
| Hy03 | GFTFSGF (SEQ ID NO: 140) | KQDGSE (SEQ ID NO: 141) | ALDYYGMD V (SEQ ID NO: 139) | SQSLLDSD DGNTY (SEQ ID NO: 150) | TLS (SEQ ID NO: 151) | RLEFPSI (SEQ ID NO: 152) |
| Hy52 | GFTFSSF (SEQ ID NO: 163) | SSSSSY (SEQ ID NO: 164) | WLSYYGMD V (SEQ ID NO: 162) | SQSLLDSD DGNTY (SEQ ID NO: 150) | TLS (SEQ ID NO: 151) | RIGFPI (SEQ ID NO: 172) |
| Consensus | GFTFSXF, wherein X is G or S (SEQ ID NO: 184) | $X_1X_2X_3X_4SX_5$, wherein $X_1$ is K or S; $X_2$ is Q or S; $X_3$ is D or S; $X_4$ is G or S; and $X_5$ is E or Y (SEQ ID NO: 185) | $X_1LX_2YYGM$ DV, wherein $X_1$ is A or W; and $X_2$ is D or S (SEQ ID NO: 181) | SQSLLDSD DGNTY (SEQ ID NO: 150) | TLS (SEQ ID NO: 151) | RX1X2FP $X_3I$, wherein $X_1$ is L or I; $X_2$ is E or G; and $X_3$ is S or absent (SEQ ID NO: 186) |

TABLE 15

IMGT CDRs of exemplary hybridoma-derived anti-BCMA molecules

| IMGT | HCDR1 | HCDR2 | HCDR3 | LCDR1 | LCDR2 | LCDR3 |
|---|---|---|---|---|---|---|
| Hy03 | GFTFSGF W (SEQ ID NO: 142) | IKQDGSEK (SEQ ID NO: 143) | ARALDYYG MDV (SEQ ID NO: 144) | QSLLDSDD GNTY (SEQ ID NO: 153) | TLS (SEQ ID NO: 151) | TQRLEFPS IT (SEQ ID NO: 149) |
| Hy52 | GFTFSSFR (SEQ ID NO: 165) | ISSSSSYI (SEQ ID NO: 166) | ARWLSYYG MDV (SEQ ID NO: 167) | QSLLDSDD GNTY (SEQ ID NO: 153) | TLS (SEQ ID NO: 151) | MQRIGFPI T (SEQ ID NO: 171) |

TABLE 15-continued

| IMGT CDRs of exemplary hybridoma-derived anti-BCMA molecules | | | | | | |
|---|---|---|---|---|---|---|
| IMGT | HCDR1 | HCDR2 | HCDR3 | LCDR1 | LCDR2 | LCDR3 |
| Consensus | GFTFS$X_1$F$X_2$, wherein $X_1$ is G or S; and $X_2$ is W or R (SEQ ID NO: 187) | I$X_1$$X_2$$X_3$$X_4$S$X_5$$X_6$, wherein $X_1$ is K or S; $X_2$ is Q or S; $X_3$ is D or S; $X_4$ is G or S; $X_5$ is E or Y; and $X_6$ is K or I (SEQ ID NO: 188) | AR$X_1$L$X_2$YYGMDV, wherein $X_1$ is A or W; and $X_2$ is D or S (SEQ ID NO: 189) | QSLLDSDDGNTY (SEQ ID NO: 153) | TLS (SEQ ID NO: 151) | $X_1$QR$X_2$$X_3$FP$X_4$IT, wherein $X_1$ is T or M; $X_2$ is L or I; $X_3$ is E or G; and $X_4$ is S or absent (SEQ ID NO: 183) |

TABLE 20

| Amino acid and nucleic acid sequences of exemplary anti-BCMA molecules | | |
|---|---|---|
| SEQ ID NO | Name/ Description | Sequence |
| duBCMA.4 | | |
| SEQ ID NO: 231 | HCDR1 (Kabat) | NHGMS |
| SEQ ID NO: 232 | HCDR2 (Kabat) | GIVYSGSTYYAASVKG |
| SEQ ID NO: 233 | HCDR3 (Kabat) | HGGESDV |
| SEQ ID NO: 234 | HCDR1 (Chothia) | GFALSNH |
| SEQ ID NO: 235 | HCDR2 (Chothia) | VYSGS |
| SEQ ID NO: 233 | HCDR3 (Chothia) | HGGESDV |
| SEQ ID NO: 236 | HCDR1 (IMGT) | GFALSNHG |
| SEQ ID NO: 237 | HCDR2 (IMGT) | IVYSGST |
| SEQ ID NO: 238 | HCDR3 (IMGT) | SAHGGESDV |
| SEQ ID NO: 239 | VH | EVQLVESGGGLVQPGGSLRLSCAVSGFALSNHGMSWVRRAPGKGLEWVS GIVYSGSTYYAASVKGRFTISRDNSRNTLYLQMNSLRPEDTAIYYCSAHGG ESDVWGQGTTVTVSS |
| SEQ ID NO: 262 | DNA VH | GAAGTGCAATTGGTGGAATCAGGGGGAGGACTTGTGCAGCCTGGAGGA TCGCTGAGACTGTCATGTGCCGTGTCCGGCTTTGCCCTGTCCAACCACG GGATGTCCTGGGTCCGCCGCGCGCCTGGAAAGGGCCTCGAATGGGTGT CGGGTATTGTGTACAGCGGTAGCACCTACTATGCCGCATCCGTGAAGGG GAGATTCACCATCAGCCGGGACAACTCCAGGAACACTCTGTACCTCCAA ATGAATTCGCTGAGGCCAGAGGACACTGCCATCTACTACTGCTCCGCGC ATGGCGGAGAGTCCGACGTCTGGGGACAGGGGACCACCGTGACCGTGT CTAGC |
| SEQ ID NO: 54 | LCDR1 (Kabat) | RASQSISSYLN |
| SEQ ID NO: 55 | LCDR2 (Kabat) | AASSLQS |
| SEQ ID NO: 240 | LCDR3 (Kabat) | QQSYSTPYT |
| SEQ ID NO: 57 | LCDR1 (Chothia) | SQSISSY |

TABLE 20-continued

Amino acid and nucleic acid sequences of exemplary anti-BCMA molecules

| SEQ ID NO | Name/ Description | Sequence |
|---|---|---|
| SEQ ID NO: 58 | LCDR2 (Chothia) | AAS |
| SEQ ID NO: 241 | LCDR3 (Chothia) | SYSTPY |
| SEQ ID NO: 60 | LCDR1 (IMGT) | QSISSY |
| SEQ ID NO: 58 | LCDR2 (IMGT) | AAS |
| SEQ ID NO: 240 | LCDR3 (IMGT) | QQSYSTPYT |
| SEQ ID NO: 242 | VL | DIQLTQSPSSLSASVGDRVTITCRASQSISSYLNWYQQKPGKAPKLLIYAASS<br>LQSGVPSRFSGSGSGTDFTLTISSLQPEDFATYYCQQSYSTPYTFGQGTKVEI<br>K |
| SEQ ID NO: 263 | DNA VL | GACATCCAGCTCACCCAGTCCCCGAGCTCGCTGTCCGCCTCCGTGGGAG<br>ATCGGGTCACCATCACGTGCCGCGCCAGCCAGTCGATTTCCTCCTACCT<br>GAACTGGTACCAACAGAAGCCCGGAAAAGCCCCGAAGCTTCTCATCTA<br>CGCCGCCTCGAGCCTGCAGTCAGGAGTGCCCTCACGGTTCTCCGGCTCC<br>GGTTCCGGTACTGATTTCACCCTGACCATTTCCTCCCTGCAACCGGAGG<br>ACTTCGCTACTTACTACTGCCAGCAGTCGTACTCCACCCCCTACACTTTC<br>GGACAAGGCACCAAGGTCGAAATCAAG |
| SEQ ID NO: 243 | Linker | ASGGGGSGGGGSGGGGS |
| SEQ ID NO: 200 | scFv (VH-linker-VL) | EVQLVESGGGLVQPGGSLRLSCAVSGFALSNHGMSWVRRAPGKGLEWVS<br>GIVYSGSTYYAASVKGRFTISRDNSRNTLYLQMNSLRPEDTAIYYCSAHGG<br>ESDVWGQGTTVTVSSASGGGGSGGGGSGGGGSDIQLTQSPSSLSASVGDR<br>VTITCRASQSISSYLNWYQQKPGKAPKLLIYAASSLQSGVPSRFSGSGSGTD<br>FTLTISSLQPEDFATYYCQQSYSTPYTFGQGTKVEIK |
| SEQ ID NO: 201 | DNA scFv | GAAGTGCAATTGGTGGAATCAGGGGGAGGACTTGTGCAGCCTGGAGGA<br>TCGCTGAGACTGTCATGTGCCGTGTCCGGCTTTGCCCTGTCCAACCACG<br>GGATGTCCTGGGTCCGCCGCGCGCCTGGAAAGGGCCTCGAATGGGTGT<br>CGGGTATTGTGTACAGCGGTAGCACCTACTATGCCGCATCCGTGAAGGG<br>GAGATTCACCATCAGCCGGGACAACTCCAGGAACACTCTGTACCTCCAA<br>ATGAATTCGCTGAGGCCAGAGGACACTGCCATCTACTACTGCTCCGCGC<br>ATGGCGGAGAGTCCGACGTCTGGGGACAGGGGACCACCGTGACCGTGT<br>CTAGCGCGTCCGGCGGAGGCGGCAGCGGGGGTGGTGGTTCAGGGGGCG<br>GCGGATCGGACATCCAGCTCACCCAGTCCCCGAGCTCGCTGTCCGCCTC<br>CGTGGGAGATCGGGTCACCATCACGTGCCGCGCCAGCCAGTCGATTTCC<br>TCCTACCTGAACTGGTACCAACAGAAGCCCGGAAAAGCCCCGAAGCTT<br>CTCATCTACGCCGCCTCGAGCCTGCAGTCAGGAGTGCCCTCACGGTTCT<br>CCGGCTCCGGTTCCGGTACTGATTTCACCCTGACCATTTCCTCCCTGCAA<br>CCGGAGGACTTCGCTACTTACTACTGCCAGCAGTCGTACTCCACCCCCT<br>ACACTTTCGGACAAGGCACCAAGGTCGAAATCAAG |
| SEQ ID NO: 230 | Full CAR amino acid sequence | EVQLVESGGGLVQPGGSLRLSCAVSGFALSNHGMSWVRRAPGKGLEWVS<br>GIVYSGSTYYAASVKGRFTISRDNSRNTLYLQMNSLRPEDTAIYYCSAHGG<br>ESDVWGQGTTVTVSSASGGGGSGGGGSGGGGSDIQLTQSPSSLSASVGDR<br>VTITCRASQSISSYLNWYQQKPGKAPKLLIYAASSLQSGVPSRFSGSGSGTD<br>FTLTISSLQPEDFATYYCQQSYSTPYTFGQGTKVEIKTTTPAPRPPTPAPTIAS<br>QPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSA<br>DAPAYQQGQNQLYNELNLGRREEYDVLDKRRGRDPEMGGKPRRKNPQEG<br>LYNELQKDKMAEAYSEIGMKGERRRGKGHDGLYQGLSTATKDTYDALH<br>MQALPPR |

TABLE 26

CDRs of exemplary anti-BCMA molecules

| duBCMA.4 | HCDR1 | HCDR2 | HCDR3 | LCDR1 | LCDR2 | LCDR3 |
|---|---|---|---|---|---|---|
| Kabat | SEQ ID NO: 231 | SEQ ID NO: 232 | SEQ ID NO: 233 | SEQ ID NO: 54 | SEQ ID NO: 55 | SEQ ID NO: 240 |

TABLE 26-continued

| CDRs of exemplary anti-BCMA molecules | | | | | | |
|---|---|---|---|---|---|---|
| duBCMA.4 | HCDR1 | HCDR2 | HCDR3 | LCDR1 | LCDR2 | LCDR3 |
| Chothia | SEQ ID NO: 234 | SEQ ID NO: 235 | SEQ ID NO: 233 | SEQ ID NO: 57 | SEQ ID NO: 58 | SEQ ID NO: 241 |
| IMGT | SEQ ID NO: 236 | SEQ ID NO: 237 | SEQ ID NO: 238 | SEQ ID NO: 60 | SEQ ID NO: 58 | SEQ ID NO: 240 |

In some embodiments, the human anti-BCMA binding domain comprises a HC CDR1, HC CDR2, HC CDR3, LC CDR1, LC CDR2, and LC CDR3.

In certain embodiments, the CAR molecule described herein or the anti-BCMA binding domain described herein includes:

(1) one, two, or three light chain (LC) CDRs chosen from:
  (i) a LC CDR1 of SEQ ID NO: 54, LC CDR2 of SEQ ID NO: 55 and LC CDR3 of SEQ ID NO: 56; and/or
(2) one, two, or three heavy chain (HC) CDRs from one of the following:
  (i) a HC CDR1 of SEQ ID NO: 44, HC CDR2 of SEQ ID NO: 45 and HC CDR3 of SEQ ID NO: 84; (ii) a HC CDR1 of SEQ ID NO: 44, HC CDR2 of SEQ ID NO: 45 and HC CDR3 of SEQ ID NO: 46; (iii) a HC CDR1 of SEQ ID NO: 44, HC CDR2 of SEQ ID NO: 45 and HC CDR3 of SEQ ID NO: 68; or (iv) a HC CDR1 of SEQ ID NO: 44, HC CDR2 of SEQ ID NO: 45 and HC CDR3 of SEQ ID NO: 76.

In certain embodiments, the CAR molecule described herein or the anti-BCMA binding domain described herein includes:

(1) one, two, or three light chain (LC) CDRs from one of the following:
  (i) a LC CDR1 of SEQ ID NO: 95, LC CDR2 of SEQ ID NO: 131 and LC CDR3 of SEQ ID NO: 132; (ii) a LC CDR1 of SEQ ID NO: 95, LC CDR2 of SEQ ID NO: 96 and LC CDR3 of SEQ ID NO: 97; (iii) a LC CDR1 of SEQ ID NO: 95, LC CDR2 of SEQ ID NO: 114 and LC CDR3 of SEQ ID NO: 115; or (iv) a LC CDR1 of SEQ ID NO: 95, LC CDR2 of SEQ ID NO: 114 and LC CDR3 of SEQ ID NO: 97; and/or
(2) one, two, or three heavy chain (HC) CDRs from one of the following:
  (i) a HC CDR1 of SEQ ID NO: 86, HC CDR2 of SEQ ID NO: 130 and HC CDR3 of SEQ ID NO: 88; (ii) a HC CDR1 of SEQ ID NO: 86, HC CDR2 of SEQ ID NO: 87 and HC CDR3 of SEQ ID NO: 88; or (iii) a HC CDR1 of SEQ ID NO: 86, HC CDR2 of SEQ ID NO: 109 and HC CDR3 of SEQ ID NO: 88.

In certain embodiments, the CAR molecule described herein or the anti-BCMA binding domain described herein includes:

(1) one, two, or three light chain (LC) CDRs from one of the following:
  (i) a LC CDR1 of SEQ ID NO: 147, LC CDR2 of SEQ ID NO: 182 and LC CDR3 of SEQ ID NO: 183; (ii) a LC CDR1 of SEQ ID NO: 147, LC CDR2 of SEQ ID NO: 148 and LC CDR3 of SEQ ID NO: 149; or (iii) a LC CDR1 of SEQ ID NO: 147, LC CDR2 of SEQ ID NO: 170 and LC CDR3 of SEQ ID NO: 171; and/or
(2) one, two, or three heavy chain (HC) CDRs from one of the following:
  (i) a HC CDR1 of SEQ ID NO: 179, HC CDR2 of SEQ ID NO: 180 and HC CDR3 of SEQ ID NO: 181; (ii) a HC CDR1 of SEQ ID NO: 137, HC CDR2 of SEQ ID NO: 138 and HC CDR3 of SEQ ID NO: 139; or (iii) a HC CDR1 of SEQ ID NO: 160, HC CDR2 of SEQ ID NO: 161 and HC CDR3 of SEQ ID NO: 162.

In some embodiments, the HC CDR1, HC CDR2, HC CDR3, LC CDR1, LC CDR2, and LC CDR3 comprise the amino acid sequences of SEQ ID NOs: 44, 45, 84, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 46, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 68, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 76, 54, 55, and 56, respectively.

In some embodiments, the HC CDR1, HC CDR2, HC CDR3, LC CDR1, LC CDR2, and LC CDR3 comprise the amino acid sequences of SEQ ID NOs: 47, 48, 84, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 46, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 68, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 76, 57, 58, and 59, respectively.

In some embodiments, the HC CDR1, HC CDR2, HC CDR3, LC CDR1, LC CDR2, and LC CDR3 comprise the amino acid sequences of SEQ ID NOs: 49, 50, 85, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 51, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 69, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 77, 60, 58, and 56, respectively.

In some embodiments, the human anti-BCMA binding domain comprises a scFv comprising a VH (for example, a VH described herein) and VL (for example, a VL described herein). In some embodiments, the VH is attached to the VL via a linker, for example, a linker described herein, for example, a linker described in Table 1. In some embodiments, the human anti-BCMA binding domain comprises a ($Gly_4$-Ser)n linker, wherein n is 1, 2, 3, 4, 5, or 6, preferably 3 or 4 (SEQ ID NO: 26). The light chain variable region and heavy chain variable region of a scFv can be, for example, in any of the following orientations: light chain variable region-linker-heavy chain variable region or heavy chain variable region-linker-light chain variable region.

In some embodiments, the anti-BCMA binding domain is a fragment, for example, a single chain variable fragment (scFv). In some embodiments, the anti-BCMA binding domain is a Fv, a Fab, a (Fab')2, or a bi-functional (for example bi-specific) hybrid antibody (for example, Lanzavecchia et al., Eur. J. Immunol. 17, 105 (1987)). In some embodiments, the antibodies and fragments thereof of the invention binds a BCMA protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (for example, a Ser-Gly linker) with an optimized length and/or amino acid composition. The linker length can greatly affect how the variable regions of a scFv fold and interact. In fact, if a short polypeptide linker is employed (for example, between 5-10 amino acids) intrachain folding is prevented. Interchain folding is also required to bring the two variable regions together to form a functional epitope binding site. For examples of linker orientation and size see, for example, Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In some embodiments, the linker sequence comprises sets of glycine and serine repeats such as ($Gly_4$Ser)n, where n is a positive integer equal to or greater than 1 (SEQ ID NO: 25). In some embodiments, the linker can be $(Gly_4Ser)_4$ (SEQ ID NO: 27) or $(Gly_4Ser)_3$ (SEQ ID NO: 28). Variation in the linker length may retain or enhance activity, giving rise to superior efficacy in activity studies.

CD20 CAR

In some embodiments, the CAR-expressing cell described herein is a CD20 CAR-expressing cell (for example, a cell expressing a CAR that binds to human CD20). In some embodiments, the CD20 CAR-expressing cell includes an antigen binding domain according to WO2016164731 and WO2018067992, incorporated herein by reference. Exemplary CD20-binding sequences or CD20 CAR sequences are disclosed in, for example, Tables 1-5 of WO2018067992. In some embodiments, the CD20 CAR comprises a CDR, variable region, scFv, or full-length sequence of a CD20 CAR disclosed in WO2018067992 or WO2016164731.

CD22 CAR

In some embodiments, the CAR-expressing cell described herein is a CD22 CAR-expressing cell (for example, a cell expressing a CAR that binds to human CD22). In some embodiments, the CD22 CAR-expressing cell includes an antigen binding domain according to WO2016164731 and WO2018067992, incorporated herein by reference. Exemplary CD22-binding sequences or CD22 CAR sequences are disclosed in, for example, Tables 6A, 6B, 7A, 7B, 7C, 8A, 8B, 9A, 9B, 10A, and 10B of WO2016164731 and Tables 6-10 of WO2018067992. In some embodiments, the CD22 CAR sequences comprise a CDR, variable region, scFv or full-length sequence of a CD22 CAR disclosed in WO2018067992 or WO2016164731.

In embodiments, the CAR molecule comprises an antigen binding domain that binds to CD22 (CD22 CAR). In some embodiments, the antigen binding domain targets human CD22. In some embodiments, the antigen binding domain includes a single chain Fv sequence as described herein.

The sequences of human CD22 CAR are provided below. In some embodiments, a human CD22 CAR is CAR22-65.

Human CD22 CAR scFv Sequence (SEQ ID NO: 285)
EVQLQQSGPGLVKPSQTLSLTCAISGDSMLSNSDTWNWIRQSPSRGLEW

LGRTYHRSTWYDDYASSVRGRVSINVDTSKNQYSLQLNAVTPEDTGVYY

CARVRLQDGNSWSDAFDVWGQGTMVTVSSGGGGSGGGGSGGGGSQSALT

QPASASGSPGQSVTISCTGTSSDVGGYNYVSWYQQHPGKAPKLMIYDVS

NRPSGVSNRFSGSKSGNTASLTISGLQAEDEADYYCSSYTSSSTLYVFG

TGTQLTVL

Human CD22 CAR Heavy Chain Variable Region

EVQLQQSGPGLVKPSQTLSLTCAISGDSMLSNSDTWNWIRQSPSRGLEWLGRTYHRSTWYDDYASSVRGRVSINVDTSKNQYSLQLNAVTPEDTGVYYCARVRLQDGNSWSDAFDVWGQGTMVT VSS (SEQ ID NO 286)

Human CD22 CAR Light Chain Variable Region

QSALTQPASASGSPGQSVTISCTGTSSDVGGYNYVSWYQQHPGKAPKLMIYDVSNRPSGVSNRFSGSKSGNTASLTISGLQAEDEADYYCSSYTSSSTLYVFGTGTQLTVL (SEQ ID NO 287)

TABLE 16

Heavy Chain Variable Domain CDRs of CD22 CAR (CAR22-65)

| Candidate | HCDR1 | SEQ ID NO: | HCDR2 | SEQ ID NO: | HCDR3 | SEQ ID NO: |
|---|---|---|---|---|---|---|
| CAR22-65 Combined | GDSML SNSDT WN | 288 | RTYHRSTWYDDYA SSVRG | 290 | VRLQDGNSWSD AFDV | 291 |
| CAR22-65 Kabat | SNSDT WN | 289 | RTYHRSTWYDDYA SSVRG | 290 | VRLQDGNSWSD AFDV | 291 |

TABLE 17

Light Chain Variable Domain CDRs of CD22 CAR (CAR22-65). The LC CDR sequences in this table have the same sequence under the Kabat or combined definitions.

| Candidate | LCDR1 | SEQ ID NO: | LCDR2 | SEQ ID NO: | LCDR3 | SEQ ID NO: |
|---|---|---|---|---|---|---|
| CAR22-65 Combined | TGTSSDVGGYNYVS | 95 | DVSNRPS | 96 | SSYTSSSTLYV | 97 |

In some embodiments, the antigen binding domain comprises a HC CDR1, a HC CDR2, and a HC CDR3 of any heavy chain binding domain amino acid sequences listed in Table 16. In embodiments, the antigen binding domain further comprises a LC CDR1, a LC CDR2, and a LC CDR3. In embodiments, the antigen binding domain comprises a LC CDR1, a LC CDR2, and a LC CDR3 amino acid sequences listed in Table 17.

In some embodiments, the antigen binding domain comprises one, two or all of LC CDR1, LC CDR2, and LC CDR3 of any light chain binding domain amino acid sequences listed in Table 17, and one, two or all of HC CDR1, HC CDR2, and HC CDR3 of any heavy chain binding domain amino acid sequences listed in Table 16.

In some embodiments, the CDRs are defined according to the Kabat numbering scheme, the Chothia numbering scheme, or a combination thereof.

The order in which the VL and VH domains appear in the scFv can be varied (i.e., VL-VH, or VH-VL orientation), and where any of one, two, three or four copies of the "G4S" subunit (SEQ ID NO: 25), in which each subunit comprises the sequence GGGGS (SEQ ID NO: 25) (for example, $(G4S)_3$ (SEQ ID NO: 28) or $(G4S)_4$ (SEQ ID NO: 27)), can connect the variable domains to create the entirety of the scFv domain. Alternatively, the CAR construct can include, for example, a linker including the sequence GSTSGSGKPGSGEGSTKG (SEQ ID NO: 43). Alternatively, the CAR construct can include, for example, a linker including the sequence LAEAAAK (SEQ ID NO: 308). In some embodiments, the CAR construct does not include a linker between the VL and VH domains.

These clones all contained a Q/K residue change in the signal domain of the co-stimulatory domain derived from CD3zeta chain.

EGFR CAR

In some embodiments, the CAR-expressing cell described herein is an EGFR CAR-expressing cell (for example, a cell expressing a CAR that binds to human EGFR). In some embodiments, the CAR-expressing cell described herein is an EGFRvIII CAR-expressing cell (for example, a cell expressing a CAR that binds to human EGFRvIII). Exemplary EGFRvIII CARs can include sequences disclosed in WO2014/130657, for example, Table 2 of WO2014/130657, incorporated herein by reference.

Exemplary EGFRvIII-binding sequences or EGFR CAR sequences may comprise a CDR, a variable region, an scFv, or a full-length CAR sequence of a EGFR CAR disclosed in WO2014/130657.

Mesothelin CAR

In some embodiments, the CAR-expressing cell described herein is a mesothelin CAR-expressing cell (for example, a cell expressing a CAR that binds to human mesothelin). Exemplary mesothelin CARs can include sequences disclosed in WO2015090230 and WO2017112741, for example, Tables 2, 3, 4, and 5 of WO2017112741, incorporated herein by reference.

Other Exemplary CARs

In other embodiments, the CAR-expressing cells can specifically bind to CD123, for example, can include a CAR molecule (for example, any of the CAR1 to CAR8), or an antigen binding domain according to Tables 1-2 of WO 2014/130635, incorporated herein by reference. The amino acid and nucleotide sequences encoding the CD123 CAR molecules and antigen binding domains (for example, including one, two, three VH CDRs; and one, two, three VL CDRs according to Kabat or Chothia), are specified in WO 2014/130635. In other embodiments, the CAR-expressing cells can specifically bind to CD123, for example, can include a CAR molecule (for example, any of the CAR123-1 to CAR123-4 and hzCAR123-1 to hzCAR123-32), or an antigen binding domain according to Tables 2, 6, and 9 of WO2016/028896, incorporated herein by reference. The amino acid and nucleotide sequences encoding the CD123 CAR molecules and antigen binding domains (for example, including one, two, three VH CDRs; and one, two, three VL CDRs according to Kabat or Chothia), are specified in WO2016/028896.

In some embodiments, the CAR molecule comprises a CLL1 CAR described herein, for example, a CLL1 CAR described in US2016/0051651A1, incorporated herein by reference. In embodiments, the CLL1 CAR comprises an amino acid, or has a nucleotide sequence shown in US2016/0051651A1, incorporated herein by reference. In other embodiments, the CAR-expressing cells can specifically bind to CLL-1, for example, can include a CAR molecule, or an antigen binding domain according to Table 2 of WO2016/014535, incorporated herein by reference. The amino acid and nucleotide sequences encoding the CLL-1 CAR molecules and antigen binding domains (for example, including one, two, three VH CDRs; and one, two, three VL CDRs according to Kabat or Chothia), are specified in WO2016/014535.

In some embodiments, the CAR molecule comprises a CD33 CAR described herein, e.ga CD33 CAR described in US2016/0096892A1, incorporated herein by reference. In embodiments, the CD33 CAR comprises an amino acid, or has a nucleotide sequence shown in US2016/0096892A1, incorporated herein by reference. In other embodiments, the CAR-expressing cells can specifically bind to CD33, for example, can include a CAR molecule (for example, any of CAR33-1 to CAR-33-9), or an antigen binding domain according to Table 2 or 9 of WO2016/014576, incorporated herein by reference. The amino acid and nucleotide sequences encoding the CD33 CAR molecules and antigen binding domains (for example, including one, two, three VH CDRs; and one, two, three VL CDRs according to Kabat or Chothia), are specified in WO2016/014576.

In some embodiments, the antigen binding domain comprises one, two three (for example, all three) heavy chain CDRs, HC CDR1, HC CDR2 and HC CDR3, from an antibody described herein (for example, an antibody described in WO2015/142675, US-2015-0283178-A1, US-2016-0046724-A1, US2014/0322212A1, US2016/0068601A1, US2016/0051651A1, US2016/0096892A1, US2014/0322275A1, or WO2015/090230, incorporated herein by reference), and/or one, two, three (for example, all three) light chain CDRs, LC CDR1, LC CDR2 and LC CDR3, from an antibody described herein (for example, an antibody described in WO2015/142675, US-2015-0283178-A1, US-2016-0046724-A1, US2014/0322212A1, US2016/0068601A1, US2016/0051651A1, US2016/0096892A1, US2014/0322275A1, or WO2015/090230, incorporated herein by reference). In some embodiments, the antigen binding domain comprises a heavy chain variable region and/or a variable light chain region of an antibody listed above.

In embodiments, the antigen binding domain is an antigen binding domain described in WO2015/142675, US-2015-0283178-A1, US-2016-0046724-A1, US2014/0322212A1, US2016/0068601A1, US2016/0051651A1, US2016/0096892A1, US2014/0322275A1, or WO2015/090230, incorporated herein by reference.

In embodiments, the antigen binding domain targets BCMA and is described in US-2016-0046724-A1. In embodiments, the antigen binding domain targets CD19 and is described in US-2015-0283178-A1. In embodiments, the antigen binding domain targets CD123 and is described in US2014/0322212A1, US2016/0068601A1. In embodiments, the antigen binding domain targets CLL1 and is described in US2016/0051651A1. In embodiments, the antigen binding domain targets CD33 and is described in US2016/0096892A1.

Exemplary target antigens that can be targeted using the CAR-expressing cells, include, but are not limited to, CD19, CD123, EGFRvIII, CD33, mesothelin, BCMA, and GFR ALPHA-4, among others, as described in, for example, WO2014/153270, WO 2014/130635, WO2016/028896, WO 2014/130657, WO2016/014576, WO 2015/090230, WO2016/014565, WO2016/014535, and WO2016/025880, each of which is herein incorporated by reference in its entirety.

In other embodiments, the CAR-expressing cells can specifically bind to GFR ALPHA-4, for example, can include a CAR molecule, or an antigen binding domain according to Table 2 of WO2016/025880, incorporated herein by reference. The amino acid and nucleotide sequences encoding the GFR ALPHA-4 CAR molecules and antigen binding domains (for example, including one, two, three VH CDRs; and one, two, three VL CDRs according to Kabat or Chothia), are specified in WO2016/025880.

In some embodiments, the antigen binding domain of any of the CAR molecules described herein (for example, any of CD19, CD123, EGFRvIII, CD33, mesothelin, BCMA, and GFR ALPHA-4) comprises one, two three (for example, all three) heavy chain CDRs, HC CDR1, HC CDR2 and HC CDR3, from an antibody listed above, and/or one, two, three (for example, all three) light chain CDRs, LC CDR1, LC CDR2 and LC CDR3, from an antigen binding domain listed above. In some embodiments, the antigen binding domain comprises a heavy chain variable region and/or a variable light chain region of an antibody listed or described above.

In some embodiments, the antigen binding domain comprises one, two three (for example, all three) heavy chain CDRs, HC CDR1, HC CDR2 and HC CDR3, from an antibody listed above, and/or one, two, three (for example, all three) light chain CDRs, LC CDR1, LC CDR2 and LC CDR3, from an antibody listed above. In some embodiments, the antigen binding domain comprises a heavy chain variable region and/or a variable light chain region of an antibody listed or described above.

In some embodiments, the tumor antigen is a tumor antigen described in International Application WO2015/142675, filed Mar. 13, 2015, which is herein incorporated by reference in its entirety. In some embodiments, the tumor antigen is chosen from one or more of: CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma-associated antigen 1 (MAGE-A1); ETS translocation-variant gene 6, located on chromosome 12p (ETV6-AML); sperm protein 17 (SPA17); X Antigen Family, Member 1A (XAGE1);

angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the antigen binding domain comprises one, two three (for example, all three) heavy chain CDRs, HC CDR1, HC CDR2 and HC CDR3, from an antibody listed above, and/or one, two, three (for example, all three) light chain CDRs, LC CDR1, LC CDR2 and LC CDR3, from an antibody listed above. In some embodiments, the antigen binding domain comprises a heavy chain variable region and/or a variable light chain region of an antibody listed or described above.

In some embodiments, the anti-tumor antigen binding domain is a fragment, for example, a single chain variable fragment (scFv). In some embodiments, the anti-a cancer associate antigen as described herein binding domain is a Fv, a Fab, a (Fab')2, or a bi-functional (for example bi-specific) hybrid antibody (for example, Lanzavecchia et al., Eur. J. Immunol. 17, 105 (1987)). In some embodiments, the antibodies and fragments thereof of the invention binds a cancer associate antigen as described herein protein with wild-type or enhanced affinity.

In some instances, scFvs can be prepared according to a method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (for example, a Ser-Gly linker) with an optimized length and/or amino acid composition. The linker length can greatly affect how the variable regions of a scFv fold and interact. In fact, if a short polypeptide linker is employed (for example, between 5-10 amino acids) intrachain folding is prevented. Interchain folding is also required to bring the two variable regions together to form a functional epitope binding site. For examples of linker orientation and size see, for example, Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, which are incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In some embodiments, the linker sequence comprises sets of glycine and serine repeats such as $(Gly_4Ser)n$, where n is a positive integer equal to or greater than 1 (SEQ ID NO: 25). In some embodiments, the linker can be $(Gly_4Ser)_4$ (SEQ ID NO: 27) or $(Gly_4Ser)_3$ (SEQ ID NO: 28). Variation in the linker length may retain or enhance activity, giving rise to superior efficacy in activity studies.

In some embodiments, the antigen binding domain is a T cell receptor ("TCR"), or a fragment thereof, for example, a single chain TCR (scTCR). Methods to make such TCRs are known in the art.

See, for example, Willemsen R A et al, Gene Therapy 7: 1369-1377 (2000); Zhang T et al, Cancer Gene Ther 11: 487-496 (2004); Aggen et al, Gene Ther. 19(4):365-74 (2012) (references are incorporated herein by its entirety). For example, scTCR can be engineered that contains the Vα and Vβ genes from a T cell clone linked by a linker (for example, a flexible peptide). This approach is very useful to cancer associated target that itself is intracellular, however, a fragment of such antigen (peptide) is presented on the surface of the cancer cells by MHC.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, for example, one or more amino acid associated with the extracellular region of the protein from which the transmembrane was derived (for example, 1, 2, 3, 4, 5, 6, 7, 8, 9, 10 up to 15 amino acids of the extracellular region) and/or one or more additional amino acids associated with the intracellular region of the protein from which the transmembrane protein is derived (for example, 1, 2, 3, 4, 5, 6, 7, 8, 9, 10 up to 15 amino acids of the intracellular region). In some embodiments, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, for example, to minimize interactions with other members of the receptor complex. In some embodiments, the transmembrane domain is capable of homodimerization with another CAR on the CAR-expressing cell, for example, CART cell, surface. In some embodiments the amino acid sequence of the transmembrane domain may be modified or substituted so as to minimize interactions with the binding domains of the native binding partner present in the same CAR-expressing cell, for example, CART.

The transmembrane domain may be derived either from a natural or from a recombinant source. Where the source is natural, the domain may be derived from any membrane-bound or transmembrane protein. In some embodiments the transmembrane domain is capable of signaling to the intracellular domain(s) whenever the CAR has bound to a target. A transmembrane domain of particular use in this invention may include at least the transmembrane region(s) of, for example, the alpha, beta or zeta chain of T-cell receptor, CD28, CD3 epsilon, CD45, CD4, CD5, CD8 (for example, CD8 alpha, CD8 beta), CD9, CD16, CD22, CD33, CD37, CD64, CD80, CD86, CD134, CD137, CD154. In some embodiments, a transmembrane domain may include at least the transmembrane region(s) of a costimulatory molecule, for example, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In some instances, the transmembrane domain can be attached to the extracellular region of the CAR, for example, the antigen binding domain of the CAR, via a hinge, for example, a hinge from a human protein. For example, in some embodiments, the hinge can be a human Ig (immunoglobulin) hinge, for example, an IgG4 hinge, or a CD8a hinge. In some embodiments, the hinge or spacer comprises (for example, consists of) the amino acid sequence of SEQ ID NO: 2. In some embodiments, the transmembrane domain comprises (for example, consists of) a transmembrane domain of SEQ ID NO: 6.

In some embodiments, the hinge or spacer comprises an IgG4 hinge. For example, in some embodiments, the hinge or spacer comprises a hinge of SEQ ID NO: 3. In some embodiments, the hinge or spacer comprises a hinge encoded by the nucleotide sequence of SEQ ID NO: 14.

In some embodiments, the hinge or spacer comprises an IgD hinge. For example, in some embodiments, the hinge or spacer comprises a hinge of the amino acid sequence of SEQ ID NO: 4. In some embodiments, the hinge or spacer comprises a hinge encoded by the nucleotide sequence of SEQ ID NO:15.

In some embodiments, the transmembrane domain may be recombinant, in which case it will comprise predominantly hydrophobic residues such as leucine and valine. In some embodiments, a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in some embodiments, the linker comprises the amino acid sequence of SEQ ID NO: 5. In some embodiments, the linker is encoded by a nucleotide sequence of SEQ ID NO: 16.

In some embodiments, the hinge or spacer comprises a KIR2DS2 hinge.

Cytoplasmic Domain

The cytoplasmic domain or region of a CAR of the present invention includes an intracellular signaling domain. An intracellular signaling domain is generally responsible for activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, for example, a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In some embodiments, a CAR of the invention comprises an intracellular signaling domain, for example, a primary signaling domain of CD3-zeta.

In some embodiments, a primary signaling domain comprises a modified ITAM domain, for example, a mutated ITAM domain which has altered (for example, increased or decreased) activity as compared to the native ITAM domain. In some embodiments, a primary signaling domain comprises a modified ITAM-containing primary intracellular signaling domain, for example, an optimized and/or truncated ITAM-containing primary intracellular signaling domain. In some embodiments, a primary signaling domain comprises one, two, three, four or more ITAM motifs.

Further examples of molecules containing a primary intracellular signaling domain that are of particular use in the invention include those of DAP10, DAP12, and CD32.

The intracellular signaling domain of the CAR can comprise the primary signaling domain, for example, CD3-zeta signaling domain, by itself or it can be combined with any other desired intracellular signaling domain(s) useful in the context of a CAR of the invention. For example, the intracellular signaling domain of the CAR can comprise a primary signaling domain, for example, CD3 zeta chain portion, and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen.

Examples of such molecules include MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). The intracellular signaling sequences within the cytoplasmic portion of the CAR of the invention may be linked to each other in a random or specified order. Optionally, a short oligo- or polypeptide linker, for example, between 2 and 10 amino acids (for example, 2, 3, 4, 5, 6, 7, 8, 9, or 10 amino acids) in length may form the linkage between intracellular signaling sequence. In some embodiments, a glycine-serine doublet can be used as a suitable linker. In some embodiments, a single amino acid, for example, an alanine, a glycine, can be used as a suitable linker.

In some embodiments, the intracellular signaling domain is designed to comprise two or more, for example, 2, 3, 4, 5, or more, costimulatory signaling domains. In some embodiments, the two or more, for example, 2, 3, 4, 5, or more, costimulatory signaling domains, are separated by a linker molecule, for example, a linker molecule described herein. In some embodiments, the intracellular signaling domain comprises two costimulatory signaling domains. In some embodiments, the linker molecule is a glycine residue. In some embodiments, the linker is an alanine residue.

In some embodiments, the intracellular signaling domain is designed to comprise the signaling domain of CD3-zeta and the signaling domain of CD28. In some embodiments, the intracellular signaling domain is designed to comprise the signaling domain of CD3-zeta and the signaling domain of 4-1BB. In some embodiments, the signaling domain of 4-1BB is a signaling domain of SEQ ID NO: 7. In some embodiments, the signaling domain of CD3-zeta is a signaling domain of SEQ ID NO: 9 (mutant CD3zeta) or SEQ ID NO: 10 (wild type human CD3zeta).

In some embodiments, the intracellular signaling domain is designed to comprise the signaling domain of CD3-zeta and the signaling domain of CD27. In some embodiments, the signaling domain of CD27 comprises the amino acid sequence of SEQ ID NO: 8. In some embodiments, the signaling domain of CD27 is encoded by the nucleic acid sequence of SEQ ID NO: 19.

In some embodiments, the intracellular is designed to comprise the signaling domain of CD3-zeta and the signaling domain of CD28. In some embodiments, the signaling domain of CD28 comprises the amino acid sequence of SEQ ID NO: 36. In some embodiments, the signaling domain of CD28 is encoded by the nucleic acid sequence of SEQ ID NO: 37.

In some embodiments, the intracellular is designed to comprise the signaling domain of CD3-zeta and the signaling domain of ICOS. In some embodiments, the signaling domain of ICOS comprises the amino acid sequence of SEQ ID NO: 38. In some embodiments, the signaling domain of ICOS is encoded by the nucleic acid sequence of SEQ ID NO: 39.

CAR Configurations

Dual CARs

In an embodiment, an immune cell (e.g., a T cell or NK cell) expresses two CARs, e.g., a first CAR that binds to a first antigen and a second CAR that binds to a second antigen. In an embodiment, the first antigen and the second antigen are different. In an embodiment, the first or second antigen is chosen from an antigen expressed on B cells, an antigen expressed on acute myeloid leukemia cells, or an antigen on solid tumor cells. In an embodiment, the first or second antigen is chosen from CD10, CD19, CD20, CD22, CD34, CD123, BCMA, FLT-3, ROR1, CD79b, CD179b, CD79a, CD34, CLL-1, folate receptor beta, FLT3, EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC.

In an embodiment, the first antigen is CD19. In an embodiment, the second antigen is not CD19. In an embodiment, the second antigen is an antigen disclosed herein that is not CD19.

In an embodiment, the first antigen is BCMA. In an embodiment, the second antigen is not BCMA. In an embodiment, the second antigen is an antigen disclosed herein that is not BCMA. In an embodiment, the second antigen is chosen from an antigen expressed on B cells, an antigen expressed on acute myeloid leukemia cells, or an antigen on solid tumor cells. In an embodiment, the second antigen is chosen from CD10, CD19, CD20, CD22, CD34, CD123, FLT-3, ROR1, CD79b, CD179b, CD79a, CD34, CLL-1, folate receptor beta, FLT3, EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC. In an embodiment, the first antigen is BCMA and the second antigen is CD19.

In an embodiment, the first CAR is encoded by a first nucleic acid sequence. In an embodiment, the second CAR is encoded by a second nucleic acid sequence. In an embodiment, the first and second nucleic acid sequences are disposed on a single nucleic acid molecule. In an embodiment, the first and second nucleic acid sequences are disposed on separate nucleic acid molecules. In an embodiment, the nucleic acid molecule or nucleic acid molecules are DNA or RNA molecules. In embodiments, the first and second nucleic acid sequences are situated in the same orientation, e.g., transcription of the first and second nucleic acid sequences proceeds in the same direction. In embodiments, the first and second nucleic acid sequences are situated in different orientations. In embodiments, a single promoter controls expression of the first and second nucleic acid sequences. In embodiments, a nucleic acid encoding a protease cleavage site (such as a T2A, P2A, E2A, or F2A cleavage site) is situated between the first and second nucleic acid sequences. In embodiments, the protease cleavage site is placed such that a cell can express a fusion protein comprising the first CAR and the second CAR and the fusion protein is subsequently processed into two peptides by proteolytic cleavage. In some embodiments, the first nucleic acid sequence is upstream of the second nucleic acid sequence, or the second nucleic acid sequence is upstream of the first nucleic acid sequence. In embodiments, a first promoter controls expression of the first nucleic acid sequence and a second promoter controls expression of the second nucleic acid sequence. In embodiments, the nucleic acid molecule is a plasmid. In embodiments, the nucleic acid molecule comprises a viral packaging element. In embodiments, the immune cell may comprise a protease (e.g., endogenous or exogenous protease) that cleaves a T2A, P2A, E2A, or F2A cleavage site.

In an embodiment, the first CAR comprises a first antigen-binding domain and the second CAR comprises a second antigen-binding domain. In an embodiment, the first or second antigen binding domain comprises a CDR, a VH, a VL, or a scFv disclosed herein, or an amino acid sequence having at least about 85%, 90%, 95%, or 99% sequence identity thereto. In an embodiment, the first or second antigen binding domain comprises a CDR, a VH, a VL, or a scFv of an anti-BCMA antigen binding domain disclosed herein (e.g., an amino acid sequence disclosed in Tables 3-15, 19, 20, 22, and 26, or an amino acid sequence having at least about 85%, 90%, 95%, or 99% sequence identity thereto). In an embodiment, the first or second antigen binding domain comprises a CDR, a VH, a VL, or a scFv of an anti-CD19 antigen binding domain disclosed herein (e.g., an amino acid sequence disclosed in Tables 2, 19, and 22, or an amino acid sequence having at least about 85%, 90%, 95%, or 99% sequence identity thereto).

In an embodiment, the first antigen is BCMA and the second antigen is CD19. In an embodiment, an immune cell (e.g., a T cell or NK cell) expresses an anti-BCMA CAR, e.g., an anti-BCMA CAR described herein and an anti-CD19 CAR, e.g., an anti-CD19 CAR described herein. In an embodiment, the immune cell (e.g., a T cell or NK cell) comprises a first nucleic acid sequence encoding an anti-BCMA CAR, e.g., an anti-BCMA CAR described herein and a second nucleic acid sequence encoding an anti-CD19 CAR, e.g., an anti-CD19 CAR described herein. Table 19 shows exemplary amino acid and nucleic acid sequences of dual CAR constructs.

TABLE 19

Exemplary BCMA/CD19 dual CAR constructs and components thereof
Dual BCMA/CD19 constructs

| Identification | Protein sequence | DNA sequence (5'-3') |
|---|---|---|
| Signal peptide (in the anti-BCMA CAR arm) | MALPVTALLLPLALLLHAARP (SEQ ID NO: 1) | Atggccctccctgtcaccgccctgctgcttccgctggctcttctgctccacgccgctcggccc (SEQ ID NO: 199) |
| ScFv R1G5 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWGESWLFDYWGQGTLVTVSSGGGGSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK (SEQ ID NO: 80) | Gaagtgcagttgctggagtcaggcggaggactggtgcagcccggaggatcgcttcgcttgagctgcgcagcctcaggctttaccttctcctcctacgccatgtcctgggtcagacaggctcccgggaagggactggaatgggtgtccgccattagcggttccggcggaagcacttactatgccgactctgtgaagggccgcttcactatctcccgggacaactccaagaacaccctgtatctccaaatgaattccctgagggccgaagataccgcggtgtactactgcgctagacgggagtggtggggagaaagctggctgttcgactactggggacagggcactctcgtgactgtgtcctccggtggtggtggatcgggggtggtggttcgggcggaggaggatctggaggaggagggtcggacattcaaatgactcagtccccgtcctccctctccgcctccgtgggagatcgcgtcacgatcacgtgcagggccagccagagcatctccagctacctgaactggtaccagcagaagccagggaaggcaccgaagctcctgatctacgccgctagctcgctgcagtccggcgtcccttcacggttctcgggatcgggctcaggcaccgacttcaccctgaccattagcagcctgcagccggaggacttcgcgacatactactgtcagcagtcatactccacccctctgaccttcggccaagggaccaaagtggagatcaag (SEQ ID NO: 81) |
| ScFv PI61 | QVQLQESGGGVVQPGRSLRLSCAASGFTFSSYGMHWVRQAPGKGLEWVAVIS | Caagtgcagctgcaggaatccggtggcggagtcgtgcagcctggaaggagcctgagactctcatgcgccg |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | YDGSNKYYADSVKGRFTISRDNSKNTLYLQMNSLRAEDTAVYYCGGSGYALHDDYYGLDVWGQGTLVTVSSGGGGSGGGGSGGGGSQSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTLYVFGSGTKVTVL (SEQ ID NO: 105) | cgtcagggttcaccttttcctcctacgggatgcattgggtcagacaggcccccggaaagggactcgaatgggtggctgtgatcagctacgacggctccaacaagtactacgccgactccgtgaaaggccggttcactatctcccgggacaactccaagaacacgctgtatctgcaaatgaattcactgcgcgcggaggataccgctgtgtactactgcggtggctccggttacgccctgcacgatgactattacggccttgacgtctggggccagggaaccctcgtgactgtgtccagcggtggaggaggttcggcggaggaggatcaggagggggtggatcgcagagcgcactgactcagccggcatccgtgtccggtagccccggacagtcgattaccatctcctgtaccggcacctcctccgacgtgggagggtacaactacgtgtcgtggtaccagcagcacccaggaaaggcccctaagttgatgatctacgatgtgtcaaaccgcccgtctggagtctccaaccggttctccggctccaagtccggcaacaccgccagcctgaccattagcgggctgcaagccgaggatgaggccgactactactgctcgagctacacatcctcgagcaccctctacgtgttcggctcggggactaaggtcaccgtgctg (SEQ ID NO: 106) |
| ScFv R1B6 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWVPYDVSWYFDYWGQGTLVTVSSGGGGSGGGGSGGGGSGGGGSDIQMTQSPSSLSASVGDRVTITCRASQSISSYLNWYQQKPGKAPKLLIYAASSLQSGVPSRFSGSGSGTDFTLTISSLOPEDFATYYCQQSYSTPLTFGQGTKVEIK (SEQ ID NO: 64) | Gaagtgcagttgctggagtcaggcggaggactggtgcagcccggaggatcgcttcgcttgagctgcgcagcctcaggctttaccttctcctcctacgccatgtcctgggtcagacaggctcccgggaagggactggaatgggtgtccgccattagcggttccggcggaagcacttactatgccgactctgtgaagggccgcttcactatctcccgggacaactccaagaacaccctgtatctccaaatgaattccctgagggccgaagataccgcggtgtactactgcgctagacgggagtgggtgccctacgatgtcagctggtacttcgactactggggacagggcactctcgtgactgtgtcctccggtggtggtggatcggggggtggtggttcgggcggaggaggatctggaggaggagggtcggacattcaaatgactcagtccccgtcctccctctccgcctccgtgggagatcgcgtcacgatcacgtgcagggccagccagagcatctccagctacctgaactggtaccagcagaagccagggaaggcaccgaagctcctgatctacgccgctagctcgctgcagtccggcgtcccttcacggttctcgggatcgggctcaggcaccgacttcaccctgaccattagcagcctgcagccggaggacttcgcgacatactactgtcagcagtcatactccacccctctgaccttcggccaagggaccaaagtggagatcaag (SEQ ID NO: 65) |
| ScFv duBCMA.4 | EVQLVESGGGLVQPGGSLRLSCAVSGFALSNHGMSWVRRAPGKGLEWVSGIVYSGSTYYAASVKGRFTISRDNSRNTLYLQMNSLRPEDTAIYYCSAHGGESDVWGQGTTVTVSSASGGGGGGGGSGGGGSDIQLTQSPSSLSASVGDRVTITCRASQSISSYLNWYQQKPGKAPKLLIYAASSLQSGVPSRFSGSGSGTDFTLTISSLQPEDFATYYCQQSYSTPYTFGQGTKVEIK (SEQ ID NO: 200) | Gaagtgcaattggtggaatcaggggggaggacttgtgcagcctggaggatcgctgagactgtcatgtgccgtgtccggctttgccctgtccaaccacgggatgtcctgggtccgccgcgcgcctggaaagggcctcgaatgggtgtcgggtattgtgtacagcggtagcacctactatgccgcatccgtgaaggggagattcaccatcagccgggacaactccaggaacactctgtacctccaaatgaattcgctgaggccagaggacactgccatctactactgctccgcgcatggcggagagtccgacgtctggggacaggggaccaccgtgaccgtgtctagcgcgtccggcggaggcggcagcgggggtggtggttcaggggcggcggatcggacatccagctcacccagtccccgagctcgctgtccgcctccgtgggagatcgggtcaccatcacgtgccgcgccagccagtcgatttcctcctacctgaactggtaccaacagaagcccggaaaagccccgaagcttctcatctacgccgcctcgagcctgcagtcaggagtgccctcacggttctccggctccggttccggtactgatttcaccctgaccatttcctccctgcaaccggaggacttcgctacttactactgccagcagtcgtactccacccccctacactttcggacaaggcaccaaggtcgaaatcaag (SEQ ID NO: 201) |
| Hinge and transmembrane domain (in the anti-BCMA CAR arm) | TTTPAPRPPTPAPTIASQPLSLRPEACRPAAGGAVHTRGLDFACDIYIWAPLAGTCGVLLLSLVITLYC (SEQ ID NO: 202) | Accactaccccagcaccgaggccacccaccccggctcctaccatcgcctcccagcctctgtccctgcgtccggaggcatgtagacccgcagctggtggggccgtgcatacccggggtcttgacttcgcctgcgatatctacatttgggcccctctggctggtacttgcggggtcctgctgctttcactcgtgatcactctttactgt (SEQ ID NO: 203) |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| Hinge (in the anti-BCMA CAR arm) | TTTPAPRPPTPAPTIASQPLSLRPEACRPAAGGAVHTRGLDFACD (SEQ ID NO: 2) | Accactaccccagcaccgaggccacccaccccggctcctaccatcgcctcccagcctctgtccctgcgtccggaggcatgtagacccgcagctggtggggccgtgcatacccggggtcttgacttcgcctgcgat (SEQ ID NO: 337) |
| Transmembrane domain (in the anti-BCMA CAR arm) | IYIWAPLAGTCGVLLLSLVITLYC (SEQ ID NO: 6) | Atctacatttgggcccctctggctggtacttgcggggtcctgctgctttcactcgtgatcactctttactgt (SEQ ID NO: 338) |
| 4-1BB (in the anti-BCMA CAR arm) | KRGRKKLLYIFKQPFMRPVQTTQEEDGCSCRFPEEEEGGCEL (SEQ ID NO: 7) | Aagcgcggtcggaagaagctgctgtacatctttaagcaacccttcatgaggcctgtgcagactactcaagaggaggacggctgttcatgccggttcccagaggaggaggaaggcggctgcgaactg (SEQ ID NO: 204) |
| CD3zeta (in the anti-BCMA CAR arm) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 10) | Cgcgtgaaattcagccgcagcgcagatgctccagcctaccagcaggggcagaaccagctctacaacgaactcaatcttggtcggagagaggagtacgacgtgctggacaagcggagaggacgggacccagaaatgggcgggaagccgcgcagaaagaatccccaagagggcctgtacaacgagctccaaaaggataagatggcagaagcctatagcgagattggtatgaaaggggaacgcagaagaggcaaaggccacgacggactgtaccagggactcagcaccgccaccaaggacacctatgacgctcttcacatgcaggccctgccgcctcgg (SEQ ID NO: 205) |
| Linker | GSG (SEQ ID NO: 206) | Ggaagcgga (SEQ ID NO: 207) |
| P2A sequence | ATNFSLLKQAGDVEENPGP (SEQ ID NO: 208) | Gctactaacttcagcctgctgaagcaggctggagacgtggaggagaaccctggacct (SEQ ID NO: 209) |
| Signal peptide (in the anti-CD19 CAR arm) | MALPVTALLLPLALLLHAARP (SEQ ID NO: 1) | Atggccttaccagtgaccgccttgctcctgccgctggccttgctgctccacgccgccaggccg (SEQ ID NO: 210) |
| ScFv duCD19.1 | EIVMTQSPATLSLSPGERATLSCRASQDISKYLNWYQQKPGQAPRLLIYHTSRLHSGIPARFSGSGSGTDYTLTISSLQPEDFAVYFCQQGNTLPYTFGQGTKLEIKGGGGSGGGGSGGGGSQVQLQESGPGLVKPSETLSLTCTVSGVSLPDYGVSWIRQPPGKGLEWIGVIWGSETTYYQSSLKSRVTISKDNSKNQVSLKLSSVTAADTAVYYCAKHYYYGGSYAMDYWGQGTLVTVSS (SEQ ID NO: 211) | Gaaattgtgatgacccagtcacccgccactcttagcctttcacccggtgagcgcgcaaccctgtcttgcagagcctcccaagacatctcaaaatacttaattggtatcaacagaagcccggacaggctcctcgccttctgatctaccacaccagccggctccattctggaatccctgccaggttcagcggtagcggatctgggaccgactacaccctcactatcagctcactgcagccagaggacttcgctgtctatttctgtcagcaagggaacaccctgccctacacctttggacagggcaccaagctcgagattaaaggtggaggtggcagcggaggaggtgggtccggcggtggaggaagccaggtccaactccaagaaagcggaccgggtcttgtgaagccatcagaaactctttcactgacttgtactgtgagcggagtgtctctcccccgattacggggtgtcttggatcagacagccaccggggaagggtctggaatggattggagtgatttggggctctgagactacttactaccaatcatccctcaagtcacgcgtcaccatctcaaaggacaactctaagaatcaggtgtcactgaaactgtcatctgtgaccgcagccgacaccgccgtgtactattgcgctaagcattactattatggcgggagctacgcaatggattactggggacagggtactctggtcaccgtgtccagc (SEQ ID NO: 212) |
| Hinge and transmembrane domain (in the anti-CD19 CAR arm) | TTTPAPRPPTPAPTIASQPLSLRPEACRPAAGGAVHTRGLDFACDIYIWAPLAGTCGVLLLSLVITLYC (SEQ ID NO: 202) | Accacgacgccagcgccgcgaccaccaacaccggcgcccaccatcgcgtcgcagcccctgtccctgcgcccagaggcgtgccggccagcggcggggggcgcagtgcacacgagggggctggacttcgcctgtgatatctacatctgggcgcccttggccgggacttgtggggtccttctcctgtcactggttatcaccctttactgc (SEQ ID NO: 213) |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| Hinge (in the anti-CD19 CAR arm) | TTTPAPRPPTPAPTIASQPLSLRPEACRPAAGGAVHTRGLDFACD (SEQ ID NO: 2) | Accacgacgccagcgccgcgaccaccaacaccggcgcccaccatcgcgtcgcagcccctgtccctgcgcccagaggcgtgccggccagcggcggggggcgcagtgcacacgagggggctggacttcgcctgtgat (SEQ ID NO: 13) |
| Transmembrane domain (in the anti-CD19 CAR arm) | IYIWAPLAGTCGVLLLSLVITLYC (SEQ ID NO: 6) | Atctacatctgggcgcccttggccgggacttgtggggtccttctcctgtcactggttatcaccctttactgc (SEQ ID NO: 17) |
| 4-1BB (in the anti-CD19 CAR arm) | KRGRKKLLYIFKQPFMRPVQTTQEEDGCSCRFPEEEEGGCEL (SEQ ID NO: 7) | Aaacggggcagaaagaaactcctgtatatattcaaacaaccatttatgagaccagtacaaactactcaagaggaagatggctgtagctgccgatttccagaagaagaagaaggaggatgtgaactg (SEQ ID NO: 18) |
| CD3zeta (in the anti-CD19 CAR arm) | RVKFSRSADAPAYQQGONOLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 10) | Agagtgaagttcagcaggagcgcagacgcccccgcgtaccagcagggccagaaccagctctataacgagctcaatctaggacgaagagaggagtacgatgttttggacaagagacgtggccgggaccctgagatggggggaaagccgagaaggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgacgcccttcacatgcaggccctgccccctcgc (SEQ ID NO: 21) |
| R1G5-P2A-duCD19.1 | MALPVTALLLPLALLLHAARPEVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWWGESWLEDYWGQGTLVTVSSGGGGSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPRGSGATNFSLLKQAGDVEENPGPMALPVTALLLPLALLLHAARPEIVMTQSPATLSLSPGERATLSCRASQDISKYLNWYQQKPGQAPRLLIYHTSRLHSGIPARFSGSGSGTDYTLTISSLQPEDFAVYFCQQGNTLPYTFGQGTKLEIKGGGGSGGGGSGGGGSQVQLQESGPGLVKPSETLSLTCTVSGVSLPDYGVSWIRQPPGKGLEWIGVIWGSETTYYQSSLKSRVTISKDNSKNQVSLKLSSVTAADTAVYYCAKHYYYGGSYAMDYWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 214) | atggccctccctgtcaccgccctgctgcttccgctggctcttctgctccacgccgctcggcccgaagtgcagttgctggagtcaggcggaggactggtgcagcccggaggatcgcttcgcttgagctgcgcagcctcaggctttaccttctcctcctacgccatgtcctgggtcagacaggctcccgggaagggactggaatgggtgtccgccattagcggttccggcggaagcacttactatgccgactctgtgaagggccgcttcactatctcccgggacaactccaagaacaccctgtatctccaaatgaattccctgagggccgaagataccgcggtgtactactgcgctagacgggagtggtggggagaaagctggctgttcgactactggggacagggcactctcgtgactgtgtcctccggtggtggtggatcgggggggtggtggttcgggcggaggaggatctggaggaggagggtcggacattcaaatgactcagtccccgtcctccctctccgcctccgtgggagatcgcgtcacgatcacgtgcagggccagccagagcatctccagctacctgaactggtaccagcagaagccagggaaggcaccgaagctcctgatctacgccgctagctcgctgcagtccggcgtcccttcacggttctcgggatcgggctcaggcaccgacttcaccctgaccattagcagcctgcagccggaggacttcgcgacatactactgtcagcagtcatactccacccctctgaccttcggccaagggaccaaagtggagatcaagaccactaccccagcaccgaggccacccaccccggctcctaccatcgcctcccagcctctgtccctgcgtccggaggcatgtagacccgcagctggtggggccgtgcatacccggggtcttgacttcgcctgcgatatctacatttgggcccctctggctggtacttgcggggtcctgctgctttcactcgtgatcactctttactgtaagcgcggtcggaagaagctgctgtacatctttaagcaacccttcatgaggcctgtgcagactactcaagaggaggacggctgttcatgccggttcccagaggaggaggaaggcggctgcgaactgcgcgtgaaattcagccgcagcgcagatgctccagcctaccagcaggggcagaaccagctctacaacgaactcaatcttggtcggagagaggagtacgacgtgctggacaagcggagaggacgggacccagaaatgggcgggaagccgcgcagaaagaatccccaagagggcctgtacaacgagctccaaaaggataagatggcagaagcctatagcgagattggtatgaaaggggaacgcagaagaggcaaaggccacgacggactgtaccagggactcagcaccgccaccaaggacacctatgacgctcttcacatgcaggccctgccgcctcggggaagcggagctactaacttcagcctgctgaagcaggctggagacgtggaggagaaccctggacctatggccttaccagtgaccgccttgctcctgccg |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | | ctggccttgctgctccacgccgccaggccggaaat |
| | | tgtgatgacccagtcacccgccactcttagccttt |
| | | cacccggtgagcgcgcaaccctgtcttgcagagcc |
| | | tcccaagacatctcaaaataccttaattggtatca |
| | | acagaagcccggacaggctcctcgccttctgatct |
| | | accacaccagccggctccattctggaatccctgcc |
| | | aggttcagcggtagcggatctgggaccgactacac |
| | | cctcactatcagctcactgcagccagaggacttcg |
| | | ctgtctatttctgtcagcaagggaacaccctgccc |
| | | tacacctttggacagggcaccaagctcgagattaa |
| | | aggtggaggtggcagcggaggaggtgggtccggcg |
| | | gtggaggaagccaggtccaactccaagaaagcgga |
| | | ccgggtcttgtgaagccatcagaaactctttcact |
| | | gacttgtactgtgagcggagtgtctctccccgatt |
| | | acggggtgtcttggatcagacagccaccggggaag |
| | | ggtctggaatggattggagtgatttggggctctga |
| | | gactacttactaccaatcatccctcaagtcacgcg |
| | | tcaccatctcaaaggacaactctaagaatcaggtg |
| | | tcactgaaactgtcatctgtgaccgcagccgacac |
| | | cgccgtgtactattgcgctaagcattactattatg |
| | | gcgggagctacgcaatggattactggggacagggt |
| | | actctggtcaccgtgtccagcaccacgacgccagc |
| | | gccgcgaccaccaacaccggcgcccaccatcgcgt |
| | | cgcagcccctgtccctgcgcccagaggcgtgccgg |
| | | ccagcggcggggggcgcagtgcacacgagggggct |
| | | ggacttcgcctgtgatatctacatctgggcgccct |
| | | tggccgggacttgtggggtccttctcctgtcactg |
| | | gttatcaccctttactgcaaacggggcagaaagaa |
| | | actcctgtatatattcaaacaaccatttatgagac |
| | | cagtacaaactactcaagaggaagatggctgtagc |
| | | tgccgatttccagaagaagaagaaggaggatgtga |
| | | actgagagtgaagttcagcaggagcgcagacgccc |
| | | ccgcgtaccagcagggccagaaccagctctataac |
| | | gagctcaatctaggacgaagagaggagtacgatgt |
| | | tttggacaagagacgtggccgggaccctgagatgg |
| | | ggggaaagccgagaaggaagaaccctcaggaaggc |
| | | ctgtacaatgaactgcagaaagataagatggcgga |
| | | ggcctacagtgagattgggatgaaaggcgagcgcc |
| | | ggaggggcaaggggcacgatggcctttaccagggt |
| | | ctcagtacagccaccaaggacacctacgacgccct |
| | | tcacatgcaggccctgccccctcgc (SEQ ID |
| | | NO: 215) |
| PI61-P2A- | MALPVTALLLPLALLLHAARPQVQLQ | atggccctccctgtcaccgccctgctgcttccgct |
| duCD19.1 | ESGGGVVQPGRSLRLSCAASGFTFSS | ggctcttctgctccacgccgctcggccccaagtgc |
| | YGMHWVRQAPGKGLEWVAVISYDGSN | agctgcaggaatccggtggcggagtcgtgcagcct |
| | KYYADSVKGRFTISRDNSKNTLYLQM | ggaaggagcctgagactctcatgcgccgcgtcagg |
| | NSLRAEDTAVYYCGGSGYALHDDYYG | gttcacctttcctcctacgggatgcattgggtca |
| | LDVWGQGTLVTVSSGGGGSGGGGSGG | gacaggcccccggaaagggactcgaatgggggct |
| | GGSQSALTQPASVSGSPGQSITISCT | gtgatcagctacgacggctccaacaagtactacgc |
| | GTSSDVGGYNYVSWYQQHPGKAPKLM | cgactccgtgaaaggccggttcactatctcccggg |
| | IYDVSNRPSGVSNRFSGSKSGNTASL | acaactccaagaacacgctgtatctgcaaatgaat |
| | TISGLQAEDEADYYCSSYTSSSTLYV | tcactgcgcgcggaggataccgctgtgtactactg |
| | FGSGTKVTVLITTPAPRPPTPAPTIA | cggtggctccggttacgccctgcacgatgactatt |
| | SQPLSLRPEACRPAAGGAVHTRGLDF | acggccttgacgtctggggccagggaaccctcgtg |
| | ACDIYIWAPLAGTCGVLLLSLVITLY | actgtgtccagcggtggaggaggttcgggcggagg |
| | CKRGRKKLLYIFKQPFMRPVQTTQEE | aggatcaggaggggggtggatcgcagagcgcactga |
| | DGCSCRFPEEEEGGCELRVKFSRSAD | ctcagccggcatccgtgtccggtagccccggacag |
| | APAYQQGQNQLYNELNLGRREEYDVL | tcgattaccatctcctgtaccggcacctcctccga |
| | DKRRGRDPEMGGKPRRKNPQEGLYNE | cgtgggagggtacaactacgtgtcgtggtaccagc |
| | LQKDKMAEAYSEIGMKGERRRGKGHD | agcacccaggaaaggcccctaagttgatgatctac |
| | GLYQGLSTATKDTYDALHMQALPPRG | gatgtgtcaaaccgcccgtctggagtctccaaccg |
| | SGATNFSLLKQAGDVEENPGPMALPV | gttctccggctccaagtccggcaacaccgccagcc |
| | TALLLPLALLLHAARPEIVMTQSPAT | tgaccattagcgggctgcaagccgaggatgaggcc |
| | LSLSPGERATLSCRASQDISKYLNWY | gactactactgctcgagctacacatcctcgagcac |
| | QQKPGQAPRLLIYHTSRLHSGIPARF | cctctacgtgttcggctcggggactaaggtcaccg |
| | SGSGSGTDYTLTISSLQPEDFAVYFC | tgctgaccactaccccagcaccgaggccacccacc |
| | QQGNTLPYTFGQGTKLEIKGGGGSGG | ccggctcctaccatcgcctcccagcctctgtccct |
| | GGSGGGGSQVQLQESGPGLVKPSETL | gcgtccggaggcatgtagacccgcagctggtgggg |
| | SLTCTVSGVSLPDYGVSWIRQPPGKG | ccgtgcatacccggggtcttgacttcgcctgcgat |
| | LEWIGVIWGSETTYYQSSLKSRVTIS | atctacatttgggcccctctggctggtacttgcgg |
| | KDNSKNQVSLKLSSVTAADTAVYYCA | ggtcctgctgctttcactcgtgatcactctttact |
| | KHYYYGGSYAMDYWGQGTLVTVSSTT | gtaagcgcggtcggaagaagctgctgtacatcttt |
| | TPAPRPPTPAPTIASQPLSLRPEACR | aagcaacccttcatgaggcctgtgcagactactca |
| | PAAGGAVHTRGLDFACDIYIWAPLAG | agaggaggacggctgttcatgccggttcccagagg |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | TCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 216) | aggaggaaggcggctgcgaactgcgcgtgaaattcagccgcagcgcagatgctccagcctaccagcagggagcagaaccagctctacaacgaactcaatcttggtcggagagaggagtacgacgtgctggacaagcggagaggacgggacccagaaatgggcgggaagccgcgcagaaagaatccccaagagggcctgtacaacgagctccaaaaggataagatggcagaagcctatagcgagattggtatgaaaggggaacgcagaagaggcaaaggccacgacggactgtaccagggactcagcaccgccaccaaggacacctatgacgctcttcacatgcaggccctgccgcctcggggaagcggagctactaacttcagcctgctgaagcaggctggagacgtggaggagaaccctggacctatggccttaccagtgaccgccttgctcctgccgctggccttgctgctccacgccgccaggccggaaattgtgatgacccagtcacccgccactcttagcctttcacccggtgagcgcgcaaccctgtcttgcagagcctcccaagacatctcaaaataccttaattggtatcaacagaagcccggacaggctcctcgccttctgatctaccacaccagccggctccattctggaatccctgccaggttcagcggtagcggatctgggaccgactacaccctcactatcagctcactgcagccagaggacttcgctgtctatttctgtcagcaagggaacaccctgccctacacctttggacagggcaccaagctcgagattaaaggtggaggtggcagcggaggaggtgggtccggcggtggaggaagccaggtccaactccaagaaagcggaccgggtcttgtgaagccatcagaaactctttcactgacttgtactgtgagcggagtgtctctccccgattacggggtgtcttggatcagacagccaccggggaagggtctggaatggattggagtgatttggggctctgagactacttactaccaatcatccctcaagtcacgcgtcaccatctcaaaggacaactctaagaatcaggtgtcactgaaactgtcatctgtgaccgcagccgacaccgccgtgtactattgcgctaagcattactattatggcgggagctacgcaatggattactggggacagggtactctggtcaccgtgtccagcaccacgacgccagcgccgcgaccaccaacaccggcgcccaccatcgcgtcgcagcccctgtccctgcgcccagaggcgtgccggccagcggcggggggcgcagtgcacacgagggggctggacttcgcctgtgatatctacatctgggcgcccttggccgggacttgtggggtccttctcctgtcactggttatcaccctttactgcaaacggggcagaaagaaactcctgtatatattcaaacaaccatttatgagaccagtacaaactactcaagaggaagatggctgtagctgccgatttccagaagaagaagaaggaggatgtgaactgagagtgaagttcagcaggagcgcagacgcccccgcgtaccagcagggccagaaccagctctataacgagctcaatctaggacgaagagaggagtacgatgttttggacaagagacgtggccgggaccctgagatggggggaaagccgagaaggaagaaccctcaggaaggcctgtacaatgaactgcagaaagataagatggcggaggcctacagtgagattgggatgaaaggcgagcgccggaggggcaaggggcacgatggcctttaccagggtctcagtacagccaccaaggacacctacgacgcccttcacatgcaggccctgccccctcgc (SEQ ID NO: 217) |
| R1B6-P2A-duCD19.1 | MALPVTALLLPLALLLHAARPEVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARREWVPYDVSWYFDYWGQGTLVTVSSGGGGSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIKTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | atggccctccctgtcaccgccctgctgcttccgctggctcttctgctccacgccgctcggcccgaagtgcagttgctggagtcaggcggaggactggtgcagcccggaggatcgcttcgcttgagctgcgcagcctcaggctttaccttctcctcctacgccatgtcctgggtcagacaggctcccgggaagggactggaatgggtgtccgccattagcggttccggcggaagcacttactatgccgactctgtgaagggccgcttcactatctcccgggacaactccaagaacaccctgtatctccaaatgaattccctgagggccgaagataccgcggtgtactactgcgctagacgggagtgggtgccctacgatgtcagctggtacttcgactactggggacagggcactctcgtgactgtgtcctccggtggtggtggatcgggggtggtggttcgggcggaggaggatctggaggaggagggtcggacattcaaatgactcagtccccgtcctccctctccgcctccgtgggagatcgcgtcacgatcacgtgcagggccagccagagcatctccagctacctgaactggtaccagcagaagccagggaaggcaccgaagctcctgatctacgccgctagctcgctgcagtccggcgt |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | GSGATNFSLLKQAGDVEENPGPMALP<br>VTALLLPLALLLHAARPEIVMTQSPA<br>TLSLSPGERATLSCRASQDISKYLNW<br>YQQKPGQAPRLLIYHTSRLHSGIPAR<br>FSGSGSGTDYTLTISSLQPEDFAVYF<br>CQQGNTLPYTFGQGTKLEIKGGGGSG<br>GGGSGGGGSQVQLQESGPGLVKPSET<br>LSLTCTVSGVSLPDYGVSWIRQPPGK<br>GLEWIGVIWGSETTYYQSSLKSRVTI<br>SKDNSKNQVSLKLSSVTAADTAVYYC<br>AKHYYYGGSYAMDYWGQGTLVTVSST<br>TTPAPRPPTPAPTIASQPLSLRPEAC<br>RPAAGGAVHTRGLDFACDIYIWAPLA<br>GTCGVLLLSLVITLYCKRGRKKLLYI<br>FKQPFMRPVQTTQEEDGCSCRFPEEE<br>EGGCELRVKFSRSADAPAYQQGQNQL<br>YNELNLGRREEYDVLDKRRGRDPEMG<br>GKPRRKNPQEGLYNELQKDKMAEAYS<br>EIGMKGERRRGKGHDGLYQGLSTATK<br>DTYDALHMQALPPR (SEQ ID NO:<br>218) | cccttcacggttctcgggatcgggctcaggcaccg<br>acttcaccctgaccattagcagcctgcagccggag<br>gacttcgcgacatactactgtcagcagtcatactc<br>cacccctctgaccttcggccaagggaccaaagtgg<br>agatcaagaccactaccccagcaccgaggccaccc<br>accccggctcctaccatcgcctcccagcctctgtc<br>cctgcgtccggaggcatgtagacccgcagctggtg<br>gggccgtgcatacccggggtcttgacttcgcctgc<br>gatatctacatttgggcccctctggctggtacttg<br>cggggtcctgctgctttcactcgtgatcactcttt<br>actgtaagcgcggtcggaagaagctgctgtacatc<br>tttaagcaacccttcatgaggcctgtgcagactac<br>tcaagaggaggacggctgttcatgccggttcccag<br>aggaggaggaaggcggctgcgaactgcgcgtgaaa<br>ttcagccgcagcgcagatgctccagcctaccagca<br>ggggcagaaccagctctacaacgaactcaatcttg<br>gtcggagagaggagtacgacgtgctggacaagcgg<br>agaggacgggacccagaaatgggggaagccgcg<br>cagaaagaatccccaagagggcctgtacaacgagc<br>tccaaaaggataagatggcagaagcctatagcgag<br>attggtatgaaaggggaacgcagaagaggcaaagg<br>ccacgacggactgtaccagggactcagcaccgcca<br>ccaaggacacctatgacgctcttcacatgcaggcc<br>ctgccgcctcggggaagcggagctactaacttcag<br>cctgctgaagcaggctggagacgtggaggagaacc<br>ctggacctatggccttaccagtgaccgccttgctc<br>ctgccgctggccttgctgctccacgccgccaggcc<br>ggaaattgtgatgacccagtcacccgccactctta<br>gcctttcacccggtgagcgcgcaaccctgtcttgc<br>agagcctcccaagacatctcaaaataccttaattg<br>gtatcaacagaagcccggacaggctcctcgccttc<br>tgatctaccacaccagccggctccattctggaatc<br>cctgccaggttcagcggtagcggatctgggaccga<br>ctacaccctcactatcagctcactgcagccagagg<br>acttcgctgtctatttctgtcagcaagggaacacc<br>ctgccctacacctttggacagggcaccaagctcga<br>gattaaaggtggaggtggcagcggaggaggtgggt<br>ccggcggtggaggaagccaggtccaactccaagaa<br>agcggaccgggtcttgtgaagccatcagaaactct<br>ttcactgacttgtactgtgagcggagtgtctctcc<br>ccgattacggggtgtcttggatcagacagccaccg<br>gggaagggtctggaatggattggagtgatttgggg<br>ctctgagactacttactaccaatcatccctcaagt<br>cacgcgtcaccatctcaaaggacaactctaagaat<br>caggtgtcactgaaactgtcatctgtgaccgcagc<br>cgacaccgccgtgtactattgcgctaagcattact<br>attatggcgggagctacgcaatggattactgggga<br>cagggtactctggtcaccgtgtccagcaccacgac<br>gccagcgccgcgaccaccaacaccggcgcccacca<br>tcgcgtcgcagcccctgtccctgcgcccagaggcg<br>tgccggccagcggcgggggggcgcagtgcacacgag<br>ggggctggacttcgcctgtgatatctacatctggg<br>cgcccttggccgggacttgtggggtccttctcctg<br>tcactggttatcaccctttactgcaaacggggcag<br>aaagaaactcctgtatatattcaaacaaccattta<br>tgagaccagtacaaactactcaagaggaagatggc<br>tgtagctgccgatttccagaagaagaagaaggagg<br>atgtgaactgagagtgaagttcagcaggagcgcag<br>acgcccccgcgtaccagcagggccagaaccagctc<br>tataacgagctcaatctaggacgaagagaggagta<br>cgatgttttggacaagagacgtggccgggaccctg<br>agatgggggaaagccgagaaggaagaaccctcag<br>gaaggcctgtacaatgaactgcagaaagataagat<br>ggcggaggcctacagtgagattgggatgaaaggcg<br>agcgccggaggggcaaggggcacgatggcctttac<br>cagggtctcagtacagccaccaaggacacctacga<br>cgcccttcacatgcaggccctgccccctcgc<br>(SEQ ID NO: 219) |
| duBCMA.4-<br>P2A-<br>duCD19.1 | MALPVTALLLPLALLLHAARPEVQLV<br>ESGGGLVQPGGSLRLSCAVSGFALSN<br>HGMSWVRRAPGKGLEWVSGIVYSGST<br>YYAASVKGRFTISRDNSRNTLYLQMN<br>SLRPEDTAIYYCSAHGGESDVWGQGT<br>TVTVSSASGGGGSGGGGSGGGGSDIQ | atggccctccctgtcaccgccctgctgcttccgct<br>ggctcttctgctccacgccgctcggcccgaagtgc<br>ggaggatcgctgagactgtcatgtgccgtgtccgg<br>aattggtggaatcaggggggaggacttgtgcagcct<br>ctttgccctgtccaaccacgggatgtcctgggtcc<br>gccgcgcgcctggaaagggcctcgaatgggtgtcg |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | LTQSPSSLSASVGDRVTITCRASQSI | ggtattgtgtacagcggtagcacctactatgccgc |
| | SSYLNWYQQKPGKAPKLLIYAASSLQ | atccgtgaaggggagattcaccatcagccgggaca |
| | SGVPSRFSGSGSGTDFTLTISSLQPE | actccaggaacactctgtacctccaaatgaattcg |
| | DFATYYCQQSYSTPYTFGQGTKVEIK | ctgaggccagaggacactgccatctactactgctc |
| | TTTPAPRPPTPAPTIASQPLSLRPEA | cgcgcatggcggagagtccgacgtctggggacagg |
| | CRPAAGGAVHTRGLDFACDIYIWAPL | ggaccaccgtgaccgtgtctagcgcgtccggcgga |
| | AGTCGVLLLSLVITLYCKRGRKKLLY | ggcggcagcgggggtggtggttcaggggggcggcgg |
| | IFKQPFMRPVQTTQEEDGCSCRFPEE | atcggacatccagctcacccagtccccgagctcgc |
| | EEGGCELRVKFSRSADAPAYQQGQNQ | tgtccgcctccgtgggagatcgggtcaccatcacg |
| | LYNELNLGRREEYDVLDKRRGRDPEM | tgccgcgccagccagtcgatttcctcctacctgaa |
| | GGKPRRKNPQEGLYNELQKDKMAEAY | ctggtaccaacagaagcccggaaaagccccgaagc |
| | SEIGMKGERRRGKGHDGLYQGLSTAT | ttctcatctacgccgcctcgagcctgcagtcagga |
| | KDTYDALHMQALPPRGSGATNFSLLK | gtgccctcacggttctccggctccggttccggtac |
| | QAGDVEENPGPMALPVTALLLPLALL | tgatttcaccctgaccatttcctccctgcaaccgg |
| | LHAARPEIVMTQSPATLSLSPGERAT | aggacttcgctacttactactgccagcagtcgtac |
| | LSCRASQDISKYLNWYQQKPGQAPRL | tccacccccctacactttcggacaaggcaccaaggt |
| | LIYHTSRLHSGIPARFSGSGSGTDYT | cgaaatcaagaccactaccccagcaccgaggccac |
| | LTISSLQPEDFAVYFCQQGNTLPYTF | ccaccccggctcctaccatcgcctcccagcctctg |
| | GQGTKLEIKGGGGSGGGGSGGGGSQV | tccctgcgtccggaggcatgtagacccgcagctgg |
| | QLQESGPGLVKPSETLSLTCTVSGVS | tggggccgtgcatacccggggtcttgacttcgcct |
| | LPDYGVSWIRQPPGKGLEWIGVIWGS | gcgatatctacatttgggcccctctggctggtact |
| | ETTYYQSSLKSRVTISKDNSKNQVSL | tgcggggtcctgctgctttcactcgtgatcactct |
| | KLSSVTAADTAVYYCAKHYYYGGSYA | ttactgtaagcgcggtcggaagaagctgctgtaca |
| | MDYWGQGTLVTVSSTTTPAPRPPTPA | tctttaagcaacccttcatgaggcctgtgcagact |
| | PTIASQPLSLRPEACRPAAGGAVHTR | actcaagaggaggacggctgttcatgccggttccc |
| | GLDFACDIYIWAPLAGTCGVLLLSLV | agaggaggaggaaggcggctgcgaactgcgcgtga |
| | ITLYCKRGRKKLLYIFKQPFMRPVQT | aattcagccgcagcgcagatgctccagcctaccag |
| | TQEEDGCSCRFPEEEEGGCELRVKFS | caggggcagaaccagctctacaacgaactcaatct |
| | RSADAPAYQQGQNQLYNELNLGRREE | tggtcggagagaggagtacgacgtgctggacaagc |
| | YDVLDKRRGRDPEMGGKPRRKNPQEG | ggagaggacgggacccagaaatgggcgggaagccg |
| | LYNELQKDKMAEAYSEIGMKGERRRG | cgcagaaagaatccccaagagggcctgtacaacga |
| | KGHDGLYQGLSTATKDTYDALHMQAL | gctccaaaaggataagatggcagaagcctatagcg |
| | PPR (SEQ ID NO: 220) | agattggtatgaaaggggaacgcagaagaggcaaa |
| | | ggccacgacggactgtaccagggactcagcaccgc |
| | | caccaaggacacctatgacgctcttcacatgcagg |
| | | ccctgccgcctcggggaagcggagctactaacttc |
| | | agcctgctgaagcaggctggagacgtggaggagaa |
| | | ccctggacctatggccttaccagtgaccgccttgc |
| | | tcctgccgctggccttgctgctccacgccgccagg |
| | | ccggaaattgtgatgacccagtcacccgccactct |
| | | tagcctttcacccggtgagcgcgcaaccctgtctt |
| | | gcagagcctcccaagacatctcaaaataccttaat |
| | | tggtatcaacagaagcccggacaggctcctcgcct |
| | | tctgatctaccacaccagccggctccattctggaa |
| | | tccctgccaggttcagcggtagcggatctgggacc |
| | | gactacaccctcactatcagctcactgcagccaga |
| | | ggacttcgctgtctatttctgtcagcaagggaaca |
| | | ccctgccctacacctttggacagggcaccaagctc |
| | | gagattaaaggtggaggtggcagcggaggaggtgg |
| | | gtccggcggtggaggaagccaggtccaactccaag |
| | | aaagcggaccgggtcttgtgaagccatcagaaact |
| | | ctttcactgacttgtactgtgagcggagtgtctct |
| | | ccccgattacggggtgtcttggatcagacagccac |
| | | cggggaagggtctggaatggattggagtgatttgg |
| | | ggctctgagactacttactaccaatcatccctcaa |
| | | gtcacgcgtcaccatctcaaaggacaactctaaga |
| | | atcaggtgtcactgaaactgtcatctgtgaccgca |
| | | gccgacaccgccgtgtactattgcgctaagcatta |
| | | ctattatggcgggagctacgcaatggattactggg |
| | | gacagggtactctggtcaccgtgtccagcaccacg |
| | | acgccagcgccgcgaccaccaacaccggcgcccac |
| | | catcgcgtcgcagcccctgtccctgcgcccagagg |
| | | cgtgccggccagcggcgggggggcgcagtgcacacg |
| | | agggggctggacttcgcctgtgatatctacatctg |
| | | ggcgcccttggccgggacttgtggggtccttctcc |
| | | tgtcactggttatcaccctttactgcaaacggggc |
| | | agaaagaaactcctgtatatattcaaacaaccatt |
| | | tatgagaccagtacaaactactcaagaggaagatg |
| | | gctgtagctgccgatttccagaagaagaagaagga |
| | | ggatgtgaactgagagtgaagttcagcaggagcgc |
| | | agacgcccccgcgtaccagcagggccagaaccagc |
| | | tctataacgagctcaatctaggacgaagagaggag |
| | | tacgatgttttggacaagagacgtggccgggaccc |
| | | tgagatgggggaaagccgagaaggaagaaccctc |
| | | aggaaggcctgtacaatgaactgcagaaagataag |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | | atggcggaggcctacagtgagattgggatgaaagg |
| | | cgagcgccggaggggcaaggggcacgatggccttt |
| | | accagggtctcagtacagccaccaaggacacctac |
| | | gacgcccttcacatgcaggccctgccccctcgc |
| | | (SEQ ID NO: 221) |
| duCD19.1- | MALPVTALLLPLALLLHAARPEIVMT | atggccttaccagtgaccgccttgctcctgccgct |
| P2A- | QSPATLSLSPGERATLSCRASQDISK | ggccttgctgctccacgccgccaggccggaaattg |
| duBCMA.4 | YLNWYQQKPGQAPRLLIYHTSRLHSG | tgatgacccagtcacccgccactcttagcctttca |
| | IPARFSGSGSGTDYTLTISSLQPEDF | cccggtgagcgcgcaaccctgtcttgcagagcctc |
| | AVYFCQQGNTLPYTFGQGTKLEIKGG | ccaagacatctcaaaatacctta attggtatcaac |
| | GGSGGGGSGGGGSQVQLQESGPGLVK | agaagcccggacaggctcctcgccttctgatctac |
| | PSETLSLTCTVSGVSLPDYGVSWIRQ | cacaccagccggctccattctggaatccctgccag |
| | PPGKGLEWIGVIWGSETTYYQSSLKS | gttcagcggtagcggatctgggaccgactacaccc |
| | RVTISKDNSKNQVSLKLSSVTAADTA | tcactatcagctcactgcagccagaggacttcgct |
| | VYYCAKHYYYGGSYAMDYWGQGTLVT | gtctatttctgtcagcaagggaacaccctgcccta |
| | VSSTTTPAPRPPTPAPTIASQPLSLR | cacctttggacagggcaccaagctcgagattaaag |
| | PEACRPAAGGAVHTRGLDFACDIYIW | gtggaggtggcagcggaggaggtgggtccggcggt |
| | APLAGTCGVLLLSLVITLYCKRGRKK | ggaggaagccaggtccaactccaagaaagcggacc |
| | LLYIFKQPFMRPVQTTQEEDGCSCRF | gggtcttgtgaagccatcagaaactctttcactga |
| | PEEEEGGCELRVKFSRSADAPAYQQG | cttgtactgtgagcggagtgtctctccccgattac |
| | QNQLYNELNLGRREEYDVLDKRRGRD | ggggtgtcttggatcagacagccaccggggaaggg |
| | PEMGGKPRRKNPQEGLYNELQKDKMA | tctggaatggattggagtgatttggggctctgaga |
| | EAYSEIGMKGERRRGKGHDGLYQGLS | ctacttactaccaatcatccctcaagtcacgcgtc |
| | TATKDTYDALHMQALPPRGSGATNFS | accatctcaaaggacaactctaagaatcaggtgtc |
| | LLKQAGDVEENPGPMALPVTALLLPL | actgaaactgtcatctgtgaccgcagccgacaccg |
| | ALLLHAARPEVQLVESGGGLVQPGGS | ccgtgtactattgcgctaagcattactattatggc |
| | LRLSCAVSGFALSNHGMSWVRRAPGK | gggagctacgcaatggattactggggacagggtac |
| | GLEWVSGIVYSGSTYYAASVKGRFTI | tctggtcaccgtgtccagcaccacgacgccagcgc |
| | SRDNSRNTLYLQMNSLRPEDTAIYYC | cgcgaccaccaacaccggcgcccaccatcgcgtcg |
| | SAHGGESDVWGQGTTVTVSSASGGGG | cagcccctgtccctgcgcccagaggcgtgccggcc |
| | SGGGGSGGGGSDIQLTQSPSSLSASV | agcggcggggggcgcagtgcacacgagggggctgg |
| | GDRVTITCRASQSISSYLNWYQQKPG | acttcgcctgtgatatctacatctgggcgcccttg |
| | KAPKLLIYAASSLQSGVPSRFSGSGS | gccgggacttgtggggtccttctcctgtcactggt |
| | GTDFTLTISSLQPEDFATYYCQQSYS | tatcaccctttactgcaaacggggcagaaagaaac |
| | TPYTFGQGTKVEIKTTTPAPRPPTPA | tcctgtatatattcaaacaaccatttatgagacca |
| | PTIASQPLSLRPEACRPAAGGAVHTR | gtacaaactactcaagaggaagatggctgtagctg |
| | GLDFACDIYIWAPLAGTCGVLLLSLV | ccgatttccagaagaagaagaaggaggatgtgaac |
| | ITLYCKRGRKKLLYIFKQPFMRPVQT | tgagagtgaagttcagcaggagcgcagacgccccc |
| | TQEEDGCSCRFPEEEEGGCELRVKFS | gcgtaccagcagggccagaaccagctctataacga |
| | RSADAPAYQQGQNQLYNELNLGRREE | gctcaatctaggacgaagagaggagtacgatgttt |
| | YDVLDKRRGRDPEMGGKPRRKNPQEG | tggacaagagacgtggccgggaccctgagatgggg |
| | LYNELQKDKMAEAYSEIGMKGERRRG | ggaaagccgagaaggaagaaccctcaggaaggcct |
| | KGHDGLYQGLSTATKDTYDALHMQAL | gtacaatgaactgcagaaagataagatggcggagg |
| | PPR | cctacagtgagattgggatgaaaggcgagcgccgg |
| | (SEQ ID NO: 222) | aggggcaaggggcacgatggcctttaccagggtct |
| | | cagtacagccaccaaggacacctacgacgcccttc |
| | | acatgcaggccctgccccctcgcggaagcggagct |
| | | actaacttcagcctgctgaagcaggctggagacgt |
| | | ggaggagaaccctggacctatggccctccctgtca |
| | | ccgccctgctgcttccgctggctcttctgctccac |
| | | gccgctcggcccgaagtgcaattggtggaatcagg |
| | | gggaggacttgtgcagcctggaggatcgctgagac |
| | | tgtcatgtgccgtgtccggctttgccctgtccaac |
| | | cacgggatgtcctgggtccgccgcgcgcctggaaa |
| | | gggcctcgaatgggtgtcgggtattgtgtacagcg |
| | | gtagcacctactatgccgcatccgtgaaggggaga |
| | | ttcaccatcagccgggacaactccaggaacactct |
| | | gtacctccaaatgaattcgctgaggccagaggaca |
| | | ctgccatctactactgctccgcgcatggcggagag |
| | | tccgacgtctggggacaggggaccaccgtgaccgt |
| | | gtctagcgcgtccggcggaggcggcagcgggggtg |
| | | gtggttcaggggggcggcggatcggacatccagctc |
| | | acccagtccccgagctcgctgtccgcctccgtggg |
| | | agatcgggtcaccatcacgtgccgcgccagccagt |
| | | cgatttcctcctacctgaactggtaccaacagaag |
| | | cccggaaaagccccgaagcttctcatctacgccgc |
| | | ctcgagcctgcagtcaggagtgccctcacggttct |
| | | ccggctccggttccggtactgatttcaccctgacc |
| | | atttcctccctgcaaccggaggacttcgctactta |
| | | ctactgccagcagtcgtactccaccccctacactt |
| | | tcggacaaggcaccaaggtcgaaatcaagaccact |
| | | accccagcaccgaggccacccaccccggctcctac |
| | | catcgcctcccagcctctgtccctgcgtccggagg |
| | | catgtagacccgcagctggtggggccgtgcatacc |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | | cggggtcttgacttcgcctgcgatatctacatttg ggcccctctggctggtacttgcggggtcctgctgc tttcactcgtgatcactctttactgtaagcgcggt cggaagaagctgctgtacatctttaagcaaccctt catgaggcctgtgcagactactcaagaggaggacg gctgttcatgccggttcccagaggaggaggaaggc ggctgcgaactgcgcgtgaaattcagccgcagcgc agatgctccagcctaccagcaggggcagaaccagc tctacaacgaactcaatcttggtcggagagaggag tacgacgtgctggacaagcggagaggacgggaccc agaaatgggcgggaagccgcgcagaaagaatcccc aagagggcctgtacaacgagctccaaaaggataag atggcagaagcctatagcgagattggtatgaaagg ggaacgcagaagaggcaaaggccacgacggactgt accagggactcagcaccgccaccaaggacacctat gacgctcttcacatgcaggccctgccgcctcgg (SEQ ID NO: 223) |
| Predicted resultant proteins from R1G5-P2A-duCD19.1 | Anti-BCMA CAR arm: EVQLLESGGGLVQPGGSLRLSCAASG FTFSSYAMSWVRQAPGKGLEWVSAIS GSGGSTYYADSVKGRFTISRDNSKNT LYLQMNSLRAEDTAVYYCARREWWGE SWLFDYWGQGTLVTVSSGGGGSGGGG SGGGGSGGGGSDIQMTQSPSSLSASV GDRVTITCRASQSISSYLNWYQQKPG KAPKLLIYAASSLQSGVPSRFSGSGS GTDFTLTISSLQPEDFATYYCQQSYS TPLTFGQGTKVEIKTTTPAPRPPTPA PTIASQPLSLRPEACRPAAGGAVHTR GLDFACDIYIWAPLAGTCGVLLLSLV ITLYCKRGRKKLLYIFKQPFMRPVQT TQEEDGCSCRFPEEEEGGCELRVKFS RSADAPAYQQGQNQLYNELNLGRREE YDVLDKRRGRDPEMGGKPRRKNPQEG LYNELQKDKMAEAYSEIGMKGERRRG KGHDGLYQGLSTATKDTYDALHMQAL PPRGSGATNFSLLKQAGDVEENPG (SEQ ID NO: 224) Anti-CD19 CAR arm: EIVMTQSPATLSLSPGERATLSCRAS QDISKYLNWYQQKPGQAPRLLIYHTS RLHSGIPARFSGSGSGTDYTLTISSL QPEDFAVYFCQQGNTLPYTFGQGTKL EIKGGGGSGGGGSGGGGSQVQLQESG PGLVKPSETLSLTCTVSGVSLPDYGV SWIRQPPGKGLEWIGVIWGSETTYYQ SSLKSRVTISKDNSKNQVSLKLSSVT AADTAVYYCAKHYYYGGSYAMDYWGQ GTLVTVSSTTTPAPRPPTPAPTIASQ PLSLRPEACRPAAGGAVHTRGLDFAC DIYIWAPLAGTCGVLLLSLVITLYCK RGRKKLLYIFKQPFMRPVQTTQEEDG CSCRFPEEEEGGCELRVKFSRSADAP AYQQGQNQLYNELNLGRREEYDVLDK RRGRDPEMGGKPRRKNPQEGLYNELQ KDKMAEAYSEIGMKGERRRGKGHDGL YQGLSTATKDTYDALHMQALPPR (SEQ ID NO: 225) | |
| Predicted resultant proteins from PI61-P2A-duCD19.1 | Anti-BCMA CAR arm: QVQLQESGGGVVQPGRSLRLSCAASG FTFSSYGMHWVRQAPGKGLEWVAVIS YDGSNKYYADSVKGRFTISRDNSKNT LYLQMNSLRAEDTAVYYCGGSGYALH DDYYGLDVWGQGTLVTVSSGGGGSGG GGSGGGGSQSALTQPASVSGSPGQSI TISCTGTSSDVGGYNYVSWYQQHPGK APKLMIYDVSNRPSGVSNRFSGSKSG NTASLTISGLQAEDEADYYCSSYTSS STLYVFGSGTKVTVLTTTPAPRPPTP APTIASQPLSLRPEACRPAAGGAVHT RGLDFACDIYIWAPLAGTCGVLLLSL VITLYCKRGRKKLLYIFKQPFMRPVQ TTQEEDGCSCRFPEEEEGGCELRVKF | |

TABLE 19-continued

| Exemplary BCMA/CD19 dual CAR constructs and components thereof<br>Dual BCMA/CD19 constructs | | |
|---|---|---|
| Identification | Protein sequence | DNA sequence (5'-3') |
| | SRSADAPAYQQGQNQLYNELNLGRRE EYDVLDKRRGRDPEMGGKPRRKNPQE GLYNELQKDKMAEAYSEIGMKGERRR GKGHDGLYQGLSTATKDTYDALHMQA LPPRGSGATNFSLLKQAGDVEENPG (SEQ ID NO: 226)<br>Anti-CD19 CAR arm:<br>EIVMTQSPATLSLSPGERATLSCRAS QDISKYLNWYQQKPGQAPRLLIYHTS RLHSGIPARFSGSGSGTDYTLTISSL QPEDFAVYFCQQGNTLPYTFGQGTKL EIKGGGGSGGGGSGGGGSQVQLQESG PGLVKPSETLSLTCTVSGVSLPDYGV SWIRQPPGKGLEWIGVIWGSETTYYQ SSLKSRVTISKDNSKNQVSLKLSSVT AADTAVYYCAKHYYYGGSYAMDYWGQ GTLVTVSSTTTPAPRPPTPAPTIASQ PLSLRPEACRPAAGGAVHTRGLDFAC DIYIWAPLAGTCGVLLLSLVITLYCK RGRKKLLYIFKQPFMRPVQTTQEEDG CSCRFPEEEEGGCELRVKFSRSADAP AYQQGQNQLYNELNLGRREEYDVLDK RRGRDPEMGGKPRRKNPQEGLYNELQ KDKMAEAYSEIGMKGERRRGKGHDGL YQGLSTATKDTYDALHMQALPPR (SEQ ID NO: 225) | |
| Predicted resultant proteins from R1B6-P2A-duCD19.1 | Anti-BCMA CAR arm:<br>EVQLLESGGGLVQPGGSLRLSCAASG FTFSSYAMSWVRQAPGKGLEWVSAIS GSGGSTYYADSVKGRFTISRDNSKNT LYLQMNSLRAEDTAVYYCARREWVPY DVSWYFDYWGQGTLVTVSSGGGGSGG GGSGGGGSGGGGSDIQMTQSPSSLSA SVGDRVTITCRASQSISSYLNWYQQK PGKAPKLLIYAASSLQSGVPSRFSGS GSGTDFTLTISSLQPEDFATYYCQQS YSTPLTFGQGTKVEIKTTTPAPRPPT PAPTIASQPLSLRPEACRPAAGGAVH TRGLDFACDIYIWAPLAGTCGVLLLS LVITLYCKRGRKKLLYIFKQPFMRPV QTTQEEDGCSCRFPEEEEGGCELRVK FSRSADAPAYQQGQNQLYNELNLGRR EEYDVLDKRRGRDPEMGGKPRRKNPQ EGLYNELQKDKMAEAYSEIGMKGERR RGKGHDGLYQGLSTATKDTYDALHMQ ALPPRGSGATNFSLLKQAGDVEENPG (SEQ ID NO: 227)<br>Anti-CD19 CAR arm:<br>EIVMTQSPATLSLSPGERATLSCRAS QDISKYLNWYQQKPGQAPRLLIYHTS RLHSGIPARFSGSGSGTDYTLTISSL QPEDFAVYFCQQGNTLPYTFGQGTKL EIKGGGGGGGGSGGGGSQVQLQESG PGLVKPSETLSLTCTVSGVSLPDYGV SWIRQPPGKGLEWIGVIWGSETTYYQ SSLKSRVTISKDNSKNQVSLKLSSVT AADTAVYYCAKHYYYGGSYAMDYWGQ GTLVTVSSTTTPAPRPPTPAPTIASQ PLSLRPEACRPAAGGAVHTRGLDFAC DIYIWAPLAGTCGVLLLSLVITLYCK RGRKKLLYIFKQPFMRPVQTTQEEDG CSCRFPEEEEGGCELRVKFSRSADAP AYQQGQNQLYNELNLGRREEYDVLDK RRGRDPEMGGKPRRKNPQEGLYNELQ KDKMAEAYSEIGMKGERRRGKGHDGL YQGLSTATKDTYDALHMQALPPR (SEQ ID NO: 225) | |
| Predicted resultant proteins from duBCMA.4-P2A-duCD19.1 | Anti-BCMA CAR arm:<br>EVQLVESGGGLVQPGGSLRLSCAVSG FALSNHGMSWVRRAPGKGLEWVSGIV YSGSTYYAASVKGRFTISRDNSRNTL YLQMNSLRPEDTAIYYCSAHGGESDV WGQGTTVTVSSASGGGGSGGGGSGGG | |

TABLE 19-continued

Exemplary BCMA/CD19 dual CAR constructs and components thereof
Dual BCMA/CD19 constructs

| Identification | Protein sequence | DNA sequence (5'-3') |
|---|---|---|
| | GSDIQLTQSPSSLSASVGDRVTITCR ASQSISSYLNWYQQKPGKAPKLLIYA ASSLQSGVPSRFSGSGSGTDFTLTIS SLQPEDFATYYCQQSYSTPYTFGQGT KVEIKTTTPAPRPPTPAPTIASQPLS LRPEACRPAAGGAVHTRGLDFACDIY IWAPLAGTCGVLLLSLVITLYCKRGR KKLLYIFKQPFMRPVQTTQEEDGCSC RFPEEEEGGCELRVKFSRSADAPAYQ QGQNQLYNELNLGRREEYDVLDKRRG RDPEMGGKPRRKNPQEGLYNELQKDK MAEAYSEIGMKGERRRGKGHDGLYQG LSTATKDTYDALHMQALPPRGSGAIN FSLLKQAGDVEENPG (SEQ ID NO: 228)<br>Anti-CD19 CAR arm:<br>EIVMTQSPATLSLSPGERATLSCRAS QDISKYLNWYQQKPGQAPRLLIYHTS RLHSGIPARFSGSGSGTDYTLTISSL QPEDFAVYFCQQGNTLPYTFGQGTKL EIKGGGGSGGGGSGGGGSQVQLQESG PGLVKPSETLSLTCTVSGVSLPDYGV SWIRQPPGKGLEWIGVIWGSETTYYQ SSLKSRVTISKDNSKNQVSLKLSSVT AADTAVYYCAKHYYYGGSYAMDYWGQ GTLVTVSSTTTPAPRPPTPAPTIASQ PLSLRPEACRPAAGGAVHTRGLDFAC DIYIWAPLAGTCGVLLLSLVITLYCK RGRKKLLYIFKQPFMRPVQTTQEEDG CSCRFPEEEEGGCELRVKFSRSADAP AYQQGQNQLYNELNLGRREEYDVLDK RRGRDPEMGGKPRRKNPQEGLYNELQ KDKMAEAYSEIGMKGERRRGKGHDGL YQGLSTATKDTYDALHMQALPPR (SEQ ID NO: 225) | |
| Predicted resultant proteins from duCD19.1-P2A-duBCMA.4 | Anti-CD19 CAR arm:<br>EIVMTQSPATLSLSPGERATLSCRAS QDI SKY-LNWYQQKPGQAPRLLIYHTS RLHSGIPARFSGSGSGTDYTLTISSL QPEDFAVYFCQQGNTLPYTFGQGTKL EIKGGGGSGGGGSGGGGSQVQLQESG PGLVKPSETLSLTCTVSGVSLPDYGV SWIRQPPGKGLEWIGVIWGSETTYYQ SSLKSRVTISKDNSKNQVSLKLSSVT AADTAVYYCAKHYYYGGSYAMDYWGQ GTLVTVSSTTTPAPRPPTPAPTIASQ PLSLRPEACRPAAGGAVHTRGLDFAC DIYIWAPLAGTCGVLLLSLVITLYCK RGRKKLLYIFKQPFMRPVQTTQEEDG CSCRFPEEEEGGCELRVKFSRSADAP AYQQGQNQLYNELNLGRREEYDVLDK RRGRDPEMGGKPRRKNPQEGLYNELQ KDKMAEAYSEIGMKGERRRGKGHDGL YQGLSTATKDTYDALHMQALPPRGSG ATNFSLLKQAGDVEENPG (SEQ ID NO: 229)<br>Anti-BCMA CAR arm:<br>EVQLVESGGGLVQPGGSLRLSCAVSG FALSNHGMSWVRRAPGKGLEWVSGIV YSGSTYYAASVKGRFTISRDNSRNTL YLQMNSLRPEDTAIYYCSAHGGESDV WGQGTTVTVSSASGGGGSGGGGSGGG GSDIQLTQSPSSLSASVGDRVTITCR ASQSISSYLNWYQQKPGKAPKLLIYA ASSLQSGVPSRFSGSGSGTDFTLTIS SLQPEDFATYYCQQSYSTPYTFGQGT KVEIKTTTPAPRPPTPAPTIASQPLS LRPEACRPAAGGAVHTRGLDFACDIY IWAPLAGTCGVLLLSLVITLYCKRGR KKLLYIFKQPFMRPVQTTQEEDGCSC RFPEEEEGGCELRVKFSRSADAPAYQ QGQNQLYNELNLGRREEYDVLDKRRG RDPEMGGKPRRKNPQEGLYNELQKDK | |

TABLE 19-continued

| Exemplary BCMA/CD19 dual CAR constructs and components thereof<br>Dual BCMA/CD19 constructs | | |
|---|---|---|
| Identification | Protein sequence | DNA sequence (5'-3') |
| | MAEAYSEIGMKGERRRGKGHDGLYQG LSTATKDTYDALHMQALPPR (SEQ ID NO: 230) | |

TABLE 22

Amino acid sequences of exemplary components of dual CARs

| SEQ ID NO | Name/ Description | Sequence |
|---|---|---|
| PI61 | | |
| SEQ ID NO: 86 | HCDR1 (Kabat) | SYGMH |
| SEQ ID NO: 87 | HCDR2 (Kabat) | VISYDGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 89 | HCDR2 (Chothia) | SYDGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 91 | HCDR2 (IMGT) | ISYDGSNK |
| SEQ ID NO: 92 | HCDR3 (IMGT) | GGSGYALHDDYYGLDV |
| SEQ ID NO: 93 | VH | QVQLQESGGGVVQPGRSLRLSCAASGFTFSSYGMHWVRQAPGKGLEWV AVISYDGSNKYYADSVKGRFTISRDNSKNTLYLQMNSLRAEDTAVYYCG GSGYALHDDYYGLDVWGQGTLVTVSS |
| SEQ ID NO: 94 | DNA VH | CAAGTGCAGCTGCAGGAATCCGGTGGCGGAGTCGTGCAGCCTGGAAG GAGCCTGAGACTCTCATGCGCCGCGTCAGGGTTCACCTTTTCCTCCTAC GGGATGCATTGGGTCAGACAGGCCCCCGGAAAGGGACTCGAATGGGT GGCTGTGATCAGCTACGACGGCTCCAACAAGTACTACGCCGACTCCGT GAAAGGCCGGTTCACTATCTCCCGGGACAACTCCAAGAACACGCTGTA TCTGCAAATGAATTCACTGCGCGCGGAGGATACCGCTGTGTACTACTG CGGTGGCTCCGGTTACGCCCTGCACGATGACTATTACGGCCTTGACGT CTGGGGCCAGGGAACCCTCGTGACTGTGTCCAGC |
| SEQ ID NO: 95 | LCDR1 (Kabat) | TGTSSDVGGYNYVS |
| SEQ ID NO: 96 | LCDR2 (Kabat) | DVSNRPS |
| SEQ ID NO: 97 | LCDR3 (Kabat) | SSYTSSSTLYV |
| SEQ ID NO: 98 | LCDR1 (Chothia) | TSSDVGGYNY |
| SEQ ID NO: 99 | LCDR2 (Chothia) | DVS |

TABLE 22-continued

Amino acid sequences of exemplary components of dual CARs

| SEQ ID NO | Name/ Description | Sequence |
|---|---|---|
| SEQ ID NO: 100 | LCDR3 (Chothia) | YTSSSTLY |
| SEQ ID NO: 101 | LCDR1 (IMGT) | SSDVGGYNY |
| SEQ ID NO: 99 | LCDR2 (IMGT) | DVS |
| SEQ ID NO: 97 | LCDR3 (IMGT) | SSYTSSSTLYV |
| SEQ ID NO: 102 | VL | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTLYV FGSGTKVTVL |
| SEQ ID NO: 103 | DNA VL | CAGAGCGCACTGACTCAGCCGGCATCCGTGTCCGGTAGCCCCGGACAG TCGATTACCATCTCCTGTACCGGCACCTCCTCCGACGTGGGAGGGTAC AACTACGTGTCGTGGTACCAGCAGCACCCAGGAAAGGCCCCTAAGTTG ATGATCTACGATGTGTCAAACCGCCCGTCTGGAGTCTCCAACCGGTTC TCCGGCTCCAAGTCCGGCAACACCGCCAGCCTGACCATTAGCGGGCTG CAAGCCGAGGATGAGGCCGACTACTACTGCTCGAGCTACACATCCTCG AGCACCCTCTACGTGTTCGGCTCGGGGACTAAGGTCACCGTGCTG |
| SEQ ID NO: 104 | Linker | GGGGSGGGGSGGGGS |
| SEQ ID NO: 105 | scFv (VH-linker-VL) | QVQLQESGGGVVQPGRSLRLSCAASGFTFSSYGMHWVRQAPGKGLEWV AVISYDGSNKYYADSVKGRFTISRDNSKNTLYLQMNSLRAEDTAVYYCG GSGYALHDDYYGLDVWGQGTLVTVSSGGGGSGGGGSGGGGSQSALTQP ASVSGSPGQSITISCTGTSSDVGGYNYVSWYQQHPGKAPKLMIYDVSNRP SGVSNRFSGSKSGNTASLTISGLQAEDEADYYCSSYTSSSTLYVFGSGTKV TVL |
| SEQ ID NO: 106 | DNA scFv | CAAGTGCAGCTGCAGGAATCCGGTGGCGGAGTCGTGCAGCCTGGAAG GAGCCTGAGACTCTCATGCGCCGCGTCAGGGTTCACCTTTTCCTCCTAC GGGATGCATTGGGTCAGACAGGCCCCCGGAAAGGGACTCGAATGGGT GGCTGTGATCAGCTACGACGGCTCCAACAAGTACTACGCCGACTCCGT GAAAGGCCGGTTCACTATCTCCCGGGACAACTCCAAGAACACGCTGTA TCTGCAAATGAATTCACTGCGCGCGGAGGATACCGCTGTGTACTACTG CGGTGGCTCCGGTTACGCCCTGCACGATGACTATTACGGCCTTGACGT CTGGGGCCAGGGAACCCTCGTGACTGTGTCCAGCGGTGGAGGAGGTTC GGGCGGAGGAGGATCAGGAGGGGGTGGATCGCAGAGCGCACTGACTC AGCCGGCATCCGTGTCCGGTAGCCCCGGACAGTCGATTACCATCTCCT GTACCGGCACCTCCTCCGACGTGGGAGGGTACAACTACGTGTCGTGGT ACCAGCAGCACCCAGGAAAGGCCCCTAAGTTGATGATCTACGATGTGT CAAACCGCCCGTCTGGAGTCTCCAACCGGTTCTCCGGCTCCAAGTCCG GCAACACCGCCAGCCTGACCATTAGCGGGCTGCAAGCCGAGGATGAG GCCGACTACTACTGCTCGAGCTACACATCCTCGAGCACCCTCTACGTG TTCGGCTCGGGGACTAAGGTCACCGTGCTG |
| R1B6 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 46 | HCDR3 (Kabat) | REWVPYDVSWYFDY |
| SEQ ID NO: 47 | HCDR1 (Chothia) | GFTFSSY |
| SEQ ID NO: 48 | HCDR2 (Chothia) | SGSGGS |
| SEQ ID NO: 46 | HCDR3 (Chothia) | REWVPYDVSWYFDY |
| SEQ ID NO: 49 | HCDR1 (IMGT) | GFTFSSYA |

TABLE 22-continued

Amino acid sequences of exemplary components of dual CARs

| SEQ ID NO | Name/ Description | Sequence |
|---|---|---|
| SEQ ID NO: 50 | HCDR2 (IMGT) | ISGSGGST |
| SEQ ID NO: 51 | HCDR3 (IMGT) | ARREWVPYDVSWYFDY |
| SEQ ID NO: 52 | VH | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWVPYDVSWYFDYWGQGTLVTVSS |
| SEQ ID NO: 53 | DNA VH | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGGTGCCCTACGATGTCAGCTGGTACTTCGACTA CTGGGGACAGGGCACTCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKLLIYAA SSLQSGVPSRFSGSGSGTDFTLTISSLQPEDFATYYCQQSYS- TPLTFGQGTK VEIK |
| SEQ ID NO: 62 | DNA VL | GACATTCAAATGACTCAGTCCCCGTCCTCCCTCTCCGCCTCCGTGGGA GATCGCGTCACGATCACGTGCAGGGCCAGCCAGAGCATCTCCAGCTAC CTGAACTGGTACCAGCAGAAGCCAGGGAAGGCACCGAAGCTCCTGAT CTACGCCGCTAGCTCGCTGCAGTCCGGCGTCCCTTCACGGTTCTCGGG ATCGGGCTCAGGCACCGACTTCACCCTGACCATTAGCAGCCTGCAGCC GGAGGACTTCGCGACATACTACTGTCAGCAGTCATACTCCACCCCTCT GACCTTCGGCCAAGGGACCAAAGTGGAGATCAAG |
| SEQ ID NO: 63 | Linker | GGGGSGGGGSGGGGSGGGGS |
| SEQ ID NO: 64 | scFv (VH-linker-VL) | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWVPYDVSWYFDYWGQGTLVTVSSGGGGSGGGGSGGGGSGGGGSDIQ MTQSPSSLSASVGDRVTITCRASQSISSYLNWYQQKPGKAPKLLIYAASSL QSGVPSRFSGSGSGTDFTLTISSLQPEDFATYYCQQSYS- TPLTFGQGTKVEI K |
| SEQ ID NO: 65 | DNA scFv | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA |

TABLE 22-continued

Amino acid sequences of exemplary components of dual CARs

| SEQ ID NO | Name/Description | Sequence |
|---|---|---|
| | | TCTCCAAATGAATTCCCTGAGGGCCGAAGATACCGCGGTGTACTACTG<br>CGCTAGACGGGAGTGGGTGCCCTACGATGTCAGCTGGTACTTCGACTA<br>CTGGGGACAGGGCACTCTCGTGACTGTGTCCTCCGGTGGTGGTGGATC<br>GGGGGGTGGTGGTTCGGGCGGAGGAGGATCTGGAGGAGGAGGGTCGG<br>ACATTCAAATGACTCAGTCCCCGTCCTCCCTCTCCGCCTCCGTGGGAG<br>ATCGCGTCACGATCACGTGCAGGGCCAGCCAGAGCATCTCCAGCTACC<br>TGAACTGGTACCAGCAGAAGCCAGGGAAGGCACCGAAGCTCCTGATC<br>TACGCCGCTAGCTCGCTGCAGTCCGGCGTCCCTTCACGGTTCTCGGGA<br>TCGGGCTCAGGCACCGACTTCACCCTGACCATTAGCAGCCTGCAGCCG<br>GAGGACTTCGCGACATACTACTGTCAGCAGTCATACTCCACCCCTCTG<br>ACCTTCGGCCAAGGGACCAAAGTGGAGATCAAG |

R1G5

| SEQ ID NO | Name/Description | Sequence |
|---|---|---|
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 76 | HCDR3 (Kabat) | REWWGESWLFDY |
| SEQ ID NO: 47 | HCDR1 (Chothia) | GFTFSSY |
| SEQ ID NO: 48 | HCDR2 (Chothia) | SGSGGS |
| SEQ ID NO: 76 | HCDR3 (Chothia) | REWWGESWLFDY |
| SEQ ID NO: 49 | HCDR1 (IMGT) | GFTFSSYA |
| SEQ ID NO: 50 | HCDR2 (IMGT) | ISGSGGST |
| SEQ ID NO: 77 | HCDR3 (IMGT) | ARREWWGESWLFDY |
| SEQ ID NO: 78 | VH | EVQLLESGGGLVQPGGSLRLSCAASGFTFSSYAMSWVRQAPGKGLEWVS<br>AISGSGGSTYYADSVKGRFTISRDNSKNTLYLQMNSLRAEDTAVYYCARR<br>EWWGESWLFDYWGQGTLVTVSS |
| SEQ ID NO: 79 | DNA VH | GAAGTGCAGTTGCTGGAGTCAGGCGGAGGACTGGTGCAGCCCGGAGG<br>ATCGCTTCGCTTGAGCTGCGCAGCCTCAGGCTTTACCTTCTCCTCCTAC<br>GCCATGTCCTGGGTCAGACAGGCTCCCGGGAAGGGACTGGAATGGGT<br>GTCCGCCATTAGCGGTTCCGGCGGAAGCACTTACTATGCCGACTCTGT<br>GAAGGGCCGCTTCACTATCTCCCGGGACAACTCCAAGAACACCCTGTA<br>TCTCCAAATGAATTCCCTGAGGGCCGAAGATACCGCGGTGTACTACTG<br>CGCTAGACGGGAGTGGTGGGGAGAAAGCTGGCTGTTCGACTACTGGG<br>GACAGGGCACTCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |

TABLE 22-continued

Amino acid sequences of exemplary components of dual CARs

| SEQ ID NO | Name/ Description | Sequence |
|---|---|---|
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKLLIYAA SSLQSGVPSRFSGSGSGTDFTLTISSLQPEDFATYYCQQSYS-TPLTFGQGTK VEIK |
| SEQ ID NO: 62 | DNA VL | GACATTCAAATGACTCAGTCCCCGTCCTCCCTCTCCGCCTCCGTGGGA GATCGCGTCACGATCACGTGCAGGGCCAGCCAGAGCATCTCCAGCTAC CTGAACTGGTACCAGCAGAAGCCAGGGAAGGCACCGAAGCTCCTGAT CTACGCCGCTAGCTCGCTGCAGTCCGGCGTCCCTTCACGGTTCTCGGG ATCGGGCTCAGGCACCGACTTCACCCTGACCATTAGCAGCCTGCAGCC GGAGGACTTCGCGACATACTACTGTCAGCAGTCATACTCCACCCCTCT GACCTTCGGCCAAGGGACCAAAGTGGAGATCAAG |
| SEQ ID NO: 63 | Linker | GGGGSGGGGSGGGGSGGGGS |
| SEQ ID NO: 80 | scFv (VH-linker-VL) | EVQLLESGGGLVQPGGSLRLSCAASGFTFSSYAMSWVRQAPGKGLEWVS AISGSGGSTYYADSVKGRFTISRDNSKNTLYLQMNSLRAEDTAVYYCARR EWWGESWLFDYWGQGTLVTVSSGGGGSGGGGSGGGGSGGGGSDIQMT QSPSSLSASVGDRVTITCRASQSISSYLNWYQQKPGKAPKLLIYAASSLQS GVPSRFSGSGSGTDFTLTISSLQPEDFATYYCQQSYSTPLTFGQGTKVEIK |
| SEQ ID NO: 81 | DNA scFv | GAAGTGCAGTTGCTGGAGTCAGGCGGAGGACTGGTGCAGCCCGGAGG ATCGCTTCGCTTGAGCTGCGCAGCCTCAGGCTTTACCTTCTCCTCCTAC GCCATGTCCTGGGTCAGACAGGCTCCCGGGAAGGGACTGGAATGGGT GTCCGCCATTAGCGGTTCCGGCGGAAGCACTTACTATGCCGACTCTGT GAAGGGCCGCTTCACTATCTCCCGGGACAACTCCAAGAACACCCTGTA TCTCCAAATGAATTCCCTGAGGGCCGAAGATACCGCGGTGTACTACTG CGCTAGACGGGAGTGGTGGGGAGAAAGCTGGCTGTTCGACTACTGGG GACAGGGCACTCTCGTGACTGTGTCCTCCGGTGGTGGTGGATCGGGGG GTGGTGGTTCGGGCGGAGGAGGATCTGGAGGAGGAGGGTCGGACATT CAAATGACTCAGTCCCCGTCCTCCCTCTCCGCCTCCGTGGGAGATCGC GTCACGATCACGTGCAGGGCCAGCCAGAGCATCTCCAGCTACCTGAAC TGGTACCAGCAGAAGCCAGGGAAGGCACCGAAGCTCCTGATCTACGC CGCTAGCTCGCTGCAGTCCGGCGTCCCTTCACGGTTCTCGGGATCGGG CTCAGGCACCGACTTCACCCTGACCATTAGCAGCCTGCAGCCGGAGGA CTTCGCGACATACTACTGTCAGCAGTCATACTCCACCCCTCTGACCTTC GGCCAAGGGACCAAAGTGGAGATCAAG |
| duBCM A.4 | | |
| SEQ ID NO: 231 | HCDR1 (Kabat) | NHGMS |
| SEQ ID NO: 232 | HCDR2 (Kabat) | GIVYSGSTYYAASVKG |
| SEQ ID NO: 233 | HCDR3 (Kabat) | HGGESDV |
| SEQ ID NO: 234 | HCDR1 (Chothia) | GFALSNH |
| SEQ ID NO: 235 | HCDR2 (Chothia) | VYSGS |
| SEQ ID NO: 233 | HCDR3 (Chothia) | HGGESDV |
| SEQ ID NO: 236 | HCDR1 (IMGT) | GFALSNHG |
| SEQ ID NO: 237 | HCDR2 (IMGT) | IVYSGST |
| SEQ ID NO: 238 | HCDR3 (IMGT) | SAHGGESDV |

TABLE 22-continued

| SEQ ID NO | Name/ Description | Sequence |
|---|---|---|
| Amino acid sequences of exemplary components of dual CARs | | |
| SEQ ID NO: 239 | VH | EVQLVESGGGLVQPGGSLRLSCAVSGFALSNHGMSWVRRAPGKGLEWV SGIVYSGSTYYAASVKGRFTISRDNSRNTLYLQMNSLRPEDTAIYYCSAHG GESDVWGQGTTVTVSS |
| SEQ ID NO: 262 | DNA VH | GAAGTGCAATTGGTGGAATCAGGGGGAGGACTTGTGCAGCCTGGAGG ATCGCTGAGACTGTCATGTGCCGTGTCCGGCTTTGCCCTGTCCAACCAC GGGATGTCCTGGGTCCGCCGCGCGCCTGGAAAGGGCCTCGAATGGGT GTCGGGTATTGTGTACAGCGGTAGCACCTACTATGCCGCATCCGTGAA GGGGAGATTCACCATCAGCCGGGACAACTCCAGGAACACTCTGTACCT CCAAATGAATTCGCTGAGGCCAGAGGACACTGCCATCTACTACTGCTC CGCGCATGGCGGAGAGTCCGACGTCTGGGGACAGGGGACCACCGTGA CCGTGTCTAGC |
| SEQ ID NO: 54 | LCDR1 (Kabat) | RASQSISSYLN |
| SEQ ID NO: 55 | LCDR2 (Kabat) | AASSLQS |
| SEQ ID NO: 240 | LCDR3 (Kabat) | QQSYSTPYT |
| SEQ ID NO: 57 | LCDR1 (Chothia) | SQSISSY |
| SEQ ID NO: 58 | LCDR2 (Chothia) | AAS |
| SEQ ID NO: 241 | LCDR3 (Chothia) | SYSTPY |
| SEQ ID NO: 60 | LCDR1 (IMGT) | QSISSY |
| SEQ ID NO: 58 | LCDR2 (IMGT) | AAS |
| SEQ ID NO: 240 | LCDR3 (IMGT) | QQSYSTPYT |
| SEQ ID NO: 242 | VL | DIQLTQSPSSLSASVGDRVTITCRASQSISSYLNWYQQKPGKAPKLLI- YAAS SLQSGVPSRFSGSGSGTDFTLTISSLQPEDFATYYCQQSYSTPYTFGQGTK VEIK |
| SEQ ID NO: 263 | DNA VL | GACATCCAGCTCACCCAGTCCCCGAGCTCGCTGTCCGCCTCCGTGGGA GATCGGGTCACCATCACGTGCCGCGCCAGCCAGTCGATTTCCTCCTAC CTGAACTGGTACCAACAGAAGCCCGGAAAAGCCCCGAAGCTTCTCATC TACGCCGCCTCGAGCCTGCAGTCAGGAGTGCCCTCACGGTTCTCCGGC TCCGGTTCCGGTACTGATTTCACCCTGACCATTTCCTCCCTGCAACCGG AGGACTTCGCTACTTACTACTGCCAGCAGTCGTACTCCACCCCCTACA CTTTCGGACAAGGCACCAAGGTCGAAATCAAG |
| SEQ ID NO: 243 | Linker | ASGGGGSGGGGSGGGGS |
| SEQ ID NO: 200 | scFv (VH- linker-VL) | EVQLVESGGGLVQPGGSLRLSCAVSGFALSNHGMSWVRRAPGKGLEWV SGIVYSGSTYYAASVKGRFTISRDNSRNTLYLQMNSLRPEDTAIYYCSAHG GESDVWGQGTTVTVSSASGGGGSGGGGSGGGGSDIQLTQSPSSLSASVGD RVTITCRASQSISSYLNWYQQKPGKAPKLLIYAASSLQSGVPSRFSGSGSG TDFTLTISSLQPEDFATYYCQQSYSTPYTFGQGTKVEIK |
| SEQ ID NO: 201 | DNA scFv | GAAGTGCAATTGGTGGAATCAGGGGGAGGACTTGTGCAGCCTGGAGG ATCGCTGAGACTGTCATGTGCCGTGTCCGGCTTTGCCCTGTCCAACCAC GGGATGTCCTGGGTCCGCCGCGCGCCTGGAAAGGGCCTCGAATGGGT GTCGGGTATTGTGTACAGCGGTAGCACCTACTATGCCGCATCCGTGAA GGGGAGATTCACCATCAGCCGGGACAACTCCAGGAACACTCTGTACCT CCAAATGAATTCGCTGAGGCCAGAGGACACTGCCATCTACTACTGCTC CGCGCATGGCGGAGAGTCCGACGTCTGGGGACAGGGGACCACCGTGA CCGTGTCTAGCGCGTCCGGCGGAGGCGGCAGCGGGGGTGGTGGTTCA GGGGGCGGCGGATCGGACATCCAGCTCACCCAGTCCCCGAGCTCGCTG |

TABLE 22-continued

Amino acid sequences of exemplary components of dual CARs

| SEQ ID NO | Name/ Description | Sequence |
|---|---|---|
| | | TCCGCCTCCGTGGGAGATCGGGTCACCATCACGTGCCGCGCCAGCCAG TCGATTTCCTCCTACCTGAACTGGTACCAACAGAAGCCCGGAAAAGCC CCGAAGCTTCTCATCTACGCCGCCTCGAGCCTGCAGTCAGGAGTGCCC TCACGGTTCTCCGGCTCCGGTTCCGGTACTGATTTCACCCTGACCATTT CCTCCCTGCAACCGGAGGACTTCGCTACTTACTACTGCCAGCAGTCGT ACTCCACCCCCTACACTTTCGGACAAGGCACCAAGGTCGAAATCAAG |
| duCD19.1 | | |
| SEQ ID NO: 244 | HCDR1 | GVSLPDYGVS |
| SEQ ID NO: 245 | HCDR2 | VIWGSETTYYQSSLKS |
| SEQ ID NO: 246 | HCDR3 | HYYYGGSYAMDY |
| SEQ ID NO: 295 | HCDR1 (Kabat) | DYGVS |
| SEQ ID NO: 245 | HCDR2 (Kabat) | VIWGSETTYYQSSLKS |
| SEQ ID NO: 246 | HCDR3 (Kabat) | HYYYGGSYAMDY |
| SEQ ID NO: 310 | HCDR1 (Chothia) | GVSLPDY |
| SEQ ID NO: 311 | HCDR2 (Chothia) | WGSET |
| SEQ ID NO: 246 | HCDR3 (Chothia) | HYYYGGSYAMDY |
| SEQ ID NO: 312 | HCDR1 (IMGT) | GVSLPDYG |
| SEQ ID NO: 313 | HCDR2 (IMGT) | IWGSETT |
| SEQ ID NO: 314 | HCDR3 (IMGT) | AKHYYYGGSYAMDY |
| SEQ ID NO: 250 | VH | QVQLQESGPGLVKPSETLSLTCTVSGVSLPDYGVSWIRQPPGKGLEWIGVI WGSETTYYQSSLKSRVTISKDNSKNQVSLKLSSVTAADTAVYYCAKHYY YGGSYAMDYWGQGTLVTVSS |
| SEQ ID NO: 315 | DNA VH | CAGGTCCAACTCCAAGAAAGCGGACCGGGTCTTGTGAAGCCATCAGA AACTCTTTCACTGACTTGTACTGTGAGCGGAGTGTCTCTCCCCGATTAC GGGGTGTCTTGGATCAGACAGCCACCGGGGAAGGGTCTGGAATGGAT TGGAGTGATTTGGGGCTCTGAGACTACTTACTACCAATCATCCCTCAA GTCACGCGTCACCATCTCAAAGGACAACTCTAAGAATCAGGTGTCACT GAAACTGTCATCTGTGACCGCAGCCGACACCGCCGTGTACTATTGCGC TAAGCATTACTATTATGGCGGGAGCTACGCAATGGATTACTGGGGACA GGGTACTCTGGTCACCGTGTCCAGC |
| SEQ ID NO: 247 | LCDR1 | RASQDISKYLN |
| SEQ ID NO: 248 | LCDR2 | HTSRLHS |
| SEQ ID NO: 249 | LCDR3 | QQGNTLPYT |
| SEQ ID NO: 247 | LCDR1 (Kabat) | RASQDISKYLN |
| SEQ ID NO: 248 | LCDR2 (Kabat) | HTSRLHS |
| SEQ ID NO: 249 | LCDR3 (Kabat) | QQGNTLPYT |

TABLE 22-continued

| Amino acid sequences of exemplary components of dual CARs | | |
|---|---|---|
| SEQ ID NO | Name/ Description | Sequence |
| SEQ ID NO: 316 | LCDR1 (Chothia) | SQDISKY |
| SEQ ID NO: 317 | LCDR2 (Chothia) | HTS |
| SEQ ID NO: 318 | LCDR3 (Chothia) | GNTLPY |
| SEQ ID NO: 319 | LCDR1 (IMGT) | QDISKY |
| SEQ ID NO: 317 | LCDR2 (IMGT) | HTS |
| SEQ ID NO: 300 | LCDR3 (IMGT) | QQGNTLPYT |
| SEQ ID NO: 251 | VL | EIVMTQSPATLSLSPGERATLSCRASQDISKYLNWYQQKPGQAPRLLIYHT SRLHSGIPARFSGSGSGTDYTLTISSLQPEDFAVYFCQQGNTLPYTFGQGT KLEIK |
| SEQ ID NO: 320 | DNA VL | GAAATTGTGATGACCCAGTCACCCGCCACTCTTAGCCTTTCACCCGGT GAGCGCGCAACCCTGTCTTGCAGAGCCTCCCAAGACATCTCAAAATAC CTTAATTGGTATCAACAGAAGCCCGGACAGGCTCCTCGCCTTCTGATC TACCACACCAGCCGGCTCCATTCTGGAATCCCTGCCAGGTTCAGCGGT AGCGGATCTGGGACCGACTACACCCTCACTATCAGCTCACTGCAGCCA GAGGACTTCGCTGTCTATTTCTGTCAGCAAGGGAACACCCTGCCCTAC ACCTTTGGACAGGGCACCAAGCTCGAGATTAAA |
| SEQ ID NO: 104 | Linker | GGGGSGGGGSGGGGS |
| SEQ ID NO: 211 | CAR2 scFv domain - aa (Linker is underlined) | EIVMTQSPATLSLSPGERATLSCRASQDISKYLNWYQQKPGQAPRLLIYHT SRLHSGIPARFSGSGSGTDYTLTISSLQPEDFAVYFCQQGNTLPYTFGQGT KLEIKGGGGSGGGGSGGGGSQVQLQESGPGLVKPSETLSLTCTVSGVSLP DYGVSWIRQPPGKGLEWIGVIWGSETTYYQSSLKSRVTISKDNSKNQVSL KLSSVTAADTAVYYCAKHYYYGGSYAMDYWGQGTLVTVSS |
| SEQ ID NO: 305 | CAR2 scFv domain - nt | GAAATTGTGATGACCCAGTCACCCGCCACTCTTAGCCTTTCACCCGGT GAGCGCGCAACCCTGTCTTGCAGAGCCTCCCAAGACATCTCAAAATAC CTTAATTGGTATCAACAGAAGCCCGGACAGGCTCCTCGCCTTCTGATC TACCACACCAGCCGGCTCCATTCTGGAATCCCTGCCAGGTTCAGCGGT AGCGGATCTGGGACCGACTACACCCTCACTATCAGCTCACTGCAGCCA GAGGACTTCGCTGTCTATTTCTGTCAGCAAGGGAACACCCTGCCCTAC ACCTTTGGACAGGGCACCAAGCTCGAGATTAAAGGTGGAGGTGGCAG CGGAGGAGGTGGGTCCGGCGGTGGAGGAAGCCAGGTCCAACTCCAAG AAAGCGGACCGGGTCTTGTGAAGCCATCAGAAACTCTTTCACTGACTT GTACTGTGAGCGGAGTGTCTCTCCCCGATTACGGGGTGTCTTGGATCA GACAGCCACCGGGGAAGGGTCTGGAATGGATTGGAGTGATTTGGGGC TCTGAGACTACTTACTACCAATCATCCCTCAAGTCACGCGTCACCATCT CAAAGGACAACTCTAAGAATCAGGTGTCACTGAAACTGTCATCTGTGA CCGCAGCCGACACCGCCGTGTACTATTGCGCTAAGCATTACTATTATG GCGGGAGCTACGCAATGGATTACTGGGGACAGGGTACTCTGGTCACC GTGTCCAGC |
| SEQ ID NO: 225 | Full CAR | EIVMTQSPATLSLSPGERATLSCRASQDISKYLNWYQQKPGQAPRLLIYHT SRLHSGIPARFSGSGSGTDYTLTISSLQPEDFAVYFCQQGNTLPYTFGQGT KLEIKGGGGSGGGGSGGGGSQVQLQESGPGLVKPSETLSLTCTVSGVSLP DYGVSWIRQPPGKGLEWIGVIWGSETTYYQSSLKSRVTISKDNSKNQVSL KLSSVTAADTAVYYCAKHYYYGGSYAMDYWGQGTLVTVSSTTTPAPRP PTPAPTIASQPLSLRPEACRPAAGGAVHTRGLDFACDIYIWAPLAGTCGVL LLSLVITLYCKRGRKKLLYIFKQPFMRPVQTTQEEDGCSCRFPEEEEGGCE LRVKFSRSADAPAYQQGQNQLYNELNLGRREEYDVLDKRRGRDPEMGG KPRRKNPQEGLYNELQKDKMAEAYSEIGMKGERRRGKGHDGLYQGLST ATKDTYDALHMQALPPR |

In some embodiments, disclosed herein is an isolated nucleic acid molecule comprising a first nucleic acid sequence encoding a first CAR polypeptide and a second nucleic acid sequence encoding a second CAR polypeptide, wherein the first CAR polypeptide comprises a first antigen-binding domain which is an anti-BCMA binding domain (e.g., human anti-BCMA binding domain), a first transmembrane domain, and a first intracellular signaling domain, and wherein the second CAR polypeptide comprises a second antigen-binding domain which is an anti-CD 19 binding domain, a second transmembrane domain, and a second intracellular signaling domain. In some embodiments, the first CAR polypeptide comprises a VH comprising a HC CDR1, HC CDR2, and HC CDR3 of an anti-BCMA sequence listed in Table 20 or 26 and a VL comprising a LC CDR1, LC CDR2, and LC CDR3 of an anti-BCMA sequence listed in Table 20 or 26, wherein the VH and VL are connected by a linker comprising the amino acid sequence of SEQ ID NO: 243. In some embodiment, the first CAR polypeptide comprises a VH and VL comprising the amino acid sequences of SEQ ID NOs: 239 and 242, respectively, wherein the VH and VL are connected by a linker comprising the amino acid sequence of SEQ ID NO: 243. In some embodiment, the first CAR polypeptide comprises an scFv comprising the amino acid sequence of SEQ ID NO: 200. In some embodiment, the first CAR polypeptide comprises the amino acid sequence of SEQ ID NO: 230 or 228. In some embodiments, the second CAR polypeptide comprises a HC CDR1, HC CDR2, HC CDR3, LC CDR1, LC CDR2, and/or LC CDR3 of an anti-CD19 sequence listed in Table 19 or Table 22 (e.g., a HC CDR1, HC CDR2, HC CDR3, LC CDR1, LC CDR2, and LC CDR3 comprising the amino acid sequences of SEQ ID NOs: 295 and 245-249, respectively). In some embodiments, the second CAR polypeptide comprises a VH and/or VL of an anti-CD19 sequence listed in Table 19 or Table 22 (e.g., a VH and VL comprising the amino acid sequences of SEQ ID NOs: 250 and 251, respectively), or an amino acid sequence having at least about 85%, 90%, 95%, or 99% sequence identity thereto. In some embodiments, the second CAR polypeptide comprises a scFv of an anti-CD19 sequence listed in Table 19 or Table 22 (e.g., a scFv comprising the amino acid sequence of SEQ ID NO: 211), or an amino acid sequence having at least about 85%, 90%, 95%, or 99% sequence identity thereto. In some embodiments, the second CAR polypeptide comprises a CAR polypeptide of an anti-CD19 sequence listed in Table 19 or Table 22 (e.g., a CAR polypeptide comprising the amino acid sequence of SEQ ID NO: 225 or 229), or an amino acid sequence having at least about 85%, 90%, 95%, or 99% sequence identity thereto. In some embodiments, the nucleic acid molecule comprises the nucleic acid sequence of SEQ ID NO: 221 or 223. In some embodiments, the nucleic acid molecule encodes the amino acid sequence of SEQ ID NO: 220 or 222, with or without the signal peptide of SEQ ID NO: 1.

Multi-Specific CARs

In an embodiment, a CAR of the invention is a multi-specific CAR. In one embodiment, the multi-specific CAR is a bispecific CAR. In one embodiment, the bispecific CAR comprises an antigen binding domain which is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In some embodiments, a CAR of the invention comprises an antigen binding domain that is a multi-specific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CHI region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620.

Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$.

In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 26). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different.

Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for BCMA, e.g., comprises a scFv as described herein, or comprises the light chain CDRs and/or heavy chain CDRs from a BCMA scFv described herein, and a second immunoglobulin variable domain sequence that has binding specificity for a second epitope on a different antigen. In one aspect, the second immunoglobulin variable domain sequence has binding specificity for an antigen expressed on AML cells, e.g., an antigen other than BCMA. For example, the second immunoglobulin variable domain sequence has binding specificity for CD123. As another example, the second immunoglobulin variable domain sequence has binding specificity for CLL-1. As another example, the second immunoglobulin variable domain sequence has binding specificity for CD34. As another example, the second immunoglobulin variable domain sequence has binding specificity for FLT3. For example, the second immunoglobulin variable domain sequence has binding specificity for folate receptor beta. In some aspects, the second immunoglobulin variable domain sequence has binding specificity for an antigen expressed on B-cells, for example, CD10, CD19, CD20, CD22, CD34, CD123, FLT-3, ROR1, CD79b, CD179b, or CD79a.

Diabody CAR

In some embodiments, a CAR of the invention is a bispecific CAR. In some embodiments, a CAR of the invention is a diabody CAR. In some embodiments, the diabody CAR comprises an antigen binding domain that binds to a first antigen and a second antigen. In some embodiments, the antigen binding domain comprises a VH1, a VL1, a VH2, and a VL2, wherein the VH1 and VL1 bind to the first antigen and the VH2 and VL2 bind to the second antigen. In some embodiments, the antigen binding domain has the arrangement VH1-optionally linker 1 ("L1")-VH2-optionally linker 2 ("L2")-VL2-optionally linker 3 ("L3")-VL1 from the N-terminus to the C-terminus. In some embodiments, the antigen binding domain has the arrangement VH1-optionally L1-VL2-optionally L2-VH2-optionally L3-VL1 from the N-terminus to the C-terminus. In some embodiments, the antigen binding domain has the arrangement VL1-optionally L1-VH2-optionally L2-VL2-optionally L3-VH1 from the N-terminus to the C-terminus. In some embodiments, the antigen binding domain has the arrangement VL1-optionally L1-VL2-optionally L2-VH2-optionally L3-VH1 from the N-terminus to the C-terminus. In some embodiments, the antigen binding domain has the arrangement VH2-optionally L1-VH1-optionally L2-VL1-optionally L3-VL2 from the N-terminus to the C-terminus. In some embodiments, the antigen binding domain has the arrangement VH2-optionally L1-VL1-optionally L2-VH1-optionally L3-VL2 from the N-terminus to the C-terminus. In some embodiments, the antigen binding domain has the arrangement VL2-optionally L1-VH1-optionally L2-VL1-optionally L3-VH2 from the N-terminus to the C-terminus. In some embodiments, the antigen binding domain has the arrangement VL2-optionally L1-VL1-optionally L2-VH1-optionally L3-VH2 from the N-terminus to the C-terminus.

In some embodiments, the antigen binding domain has the arrangement VH1-linker 1 ("L1")-VH2-linker 2 ("L2")-VL2-linker 3 ("L3")-VL1 from the N-terminus to the C-terminus. In some embodiments, the antigen binding domain has the arrangement VH1-L1-VL2-L2-VH2-L3-VL1 from the N-terminus to the C-terminus. In some embodiments, the antigen binding domain has the arrangement VL1-L1-VH2-L2-VL2-L3-VH1 from the N-terminus to the C-terminus. In some embodiments, the antigen binding domain has the arrangement VL1-L1-VL2-L2-VH2-L3-VH1 from the N-terminus to the C-terminus. In some embodiments, the antigen binding domain has the arrangement VH2-L1-VH1-L2-VL1-L3-VL2 from the N-terminus to the C-terminus. In some embodiments, the antigen binding domain has the arrangement VH2-L1-VL1-L2-VH1-L3-VL2 from the N-terminus to the C-terminus. In some embodiments, the antigen binding domain has the arrangement VL2-L1-VH1-L2-VL1-L3-VH2 from the N-terminus to the C-terminus. In some embodiments, the antigen binding domain has the arrangement VL2-L1-VL1-L2-VH1-L3-VH2 from the N-terminus to the C-terminus. In some embodiments, the variable regions are fused by a linker comprising the amino acid sequence of GGGGSGGGGS (SEQ ID NO: 5). In some embodiments, the variable regions are fused by a linker comprising the amino acid sequence of GGGGSGGGGSGGGGSGGGGS (SEQ ID NO: 63). In some embodiments, L1 comprises the amino acid sequence of SEQ ID NO: 5. In some embodiments, L2 comprises the amino acid sequence of SEQ ID NO: 63. In some embodiments, L3 comprises the amino acid sequence of SEQ ID NO: 5. In some embodiments, the VH1, VL1, VH2, or VL2 comprises a CDR, a VH, or a VL sequence disclosed herein, or an amino acid sequence having at least about 85%, 90%, 95%, or 99% sequence identity thereto. In some embodiments, a diabody disclosed herein comprises an engineered disulfide bridge, e.g., to stabilize the diabody and/or to facilitate correct pairing of the VH and VL. In some embodiments, the engineered disulfide bridge is between the variable region that is most proximal to the hinge region (e.g., the VH or VL region that is most proximal to the hinge region) and its corresponding pairing partner (e.g., the corresponding VL or the corresponding VH).

In some embodiments, the first antigen and the second antigen are different. In some embodiments, the first or second antigen is chosen from an antigen expressed on B cells, an antigen expressed on acute myeloid leukemia cells, or an antigen on solid tumor cells. In some embodiments, the first or second antigen is chosen from CD10, CD19, CD20, CD22, CD34, CD123, BCMA, FLT-3, ROR1, CD79b, CD179b, CD79a, CD34, CLL-1, folate receptor beta, FLT3, EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu, MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRα4, or a peptide of any of these antigens presented on MHC.

In some embodiments, the first antigen is BCMA and the second antigen is CD19. In some embodiments, the CAR comprises an antigen binding domain that binds to BCMA and CD19. In some embodiments, the antigen binding domain comprises a $VH_1$ and a $VL_1$ that bind to BCMA ("BCMA VH" and "BCMA VL") and a $VH_2$ and a $VL_2$ that bind to CD19 ("CD19 VH" and "CD19 VL"). In some embodiments, the antigen binding domain has the arrangement BCMA VH-optionally linker 1 ("L1")-CD19 VH-optionally linker 2 ("L2")-CD19 VL-optionally linker 3 ("L3")-BCMA VL from the N-terminus to the C-terminus. In some embodiments, the antigen binding domain has the arrangement BCMA VH-optionally L1-CD19 VL-optionally L2-CD19 VH-optionally L3-BCMA VL from the N-terminus to the C-terminus. In some embodiments, the antigen binding domain has the arrangement BCMA VL-optionally L1-CD19 VH-optionally L2-CD19 VL-optionally L3-BCMA VH from the N-terminus to the C-terminus. In some embodiments, the antigen binding domain has the arrangement BCMA VL-optionally L1-CD19 VL-optionally L2-CD19 VH-optionally L3-BCMA VH from the N-terminus to the C-terminus. In some embodiments, the antigen binding domain has the arrangement CD19 VH-optionally L1-BCMA VH-optionally L2-BCMA VL-optionally L3-CD19 VL from the N-terminus to the C-terminus. In some embodiments, the antigen binding domain has the arrangement CD19 VH-optionally L1-BCMA VL-optionally L2-BCMA VH-optionally L3-CD19 VL from the N-terminus to the C-terminus. In some embodiments, the antigen binding domain has the arrangement CD19 VL-optionally L1-BCMA VH-optionally L2-BCMA VL-optionally L3-CD19 VH from the N-terminus to the C-terminus. In some embodiments, the antigen binding domain has the arrangement CD19 VL-optionally L1-BCMA VL-optionally L2-BCMA VH-optionally L3-CD19 VH from the N-terminus to the C-terminus. In some embodiments, the antigen binding domain has the arrangement BCMA VH-linker 1 ("L1")-CD19 VH-linker 2 ("L2")-CD19 VL-linker 3 ("L3")-BCMA VL from the N-terminus to the C-terminus. In some embodiments, the antigen binding domain has the arrangement BCMA VH-L1-CD19 VL-L2-CD19 VH-L3-BCMA VL from the N-terminus to the C-terminus. In some embodiments, the antigen binding domain has the arrangement BCMA VL-L1-CD19 VH-L2-CD19 VL-L3-BCMA VH from the N-terminus to the C-terminus. In some embodiments, the antigen binding domain has the arrangement BCMA VL-L1-CD19 VL-L2-CD19 VH-L3-BCMA VH from the N-terminus to the C-terminus. In some embodiments, the antigen binding domain has the arrangement CD19 VH-L1-BCMA VH-L2-BCMA VL-L3-CD19 VL from the N-terminus to the C-terminus. In some embodiments, the antigen binding domain has the arrangement CD19 VH-L1-BCMA VL-L2-BCMA VH-L3-CD19 VL from the N-terminus to the C-terminus. In some embodiments, the antigen binding domain has the arrangement CD19 VL-L1-BCMA VH-L2-BCMA VL-L3-CD19 VH from the N-terminus to the C-terminus. In some embodiments, the antigen binding domain has the arrangement CD19 VL-L1-BCMA VL-L2-BCMA VH-L3-CD19 VH from the N-terminus to the C-terminus. In some embodiments, the variable regions are fused by a linker comprising the amino acid sequence of SEQ ID NO: 5 or 63, or an amino acid sequence having at least 80, 85, 90, 95, or 99% identity thereto. In some embodiments, L1 comprises the amino acid sequence of SEQ ID NO: 5. In some embodiments, L2 comprises the amino acid sequence of SEQ ID NO: 63. In some embodiments, L3 comprises the amino acid sequence of SEQ ID NO: 5.

In some embodiments, the BCMA VH comprises CDR or VH sequences disclosed herein, e.g., CDR or VH sequences disclosed in Tables 3-15, 19, 20, 22, 26, and 31, or an amino acid sequence having at least 80, 85, 90, 95, or 99% identity thereto. In some embodiments, the BCMA VL comprises CDR or VL sequences disclosed herein, e.g., CDR or VL sequences disclosed in Tables 3-15, 19, 20, 22, 26, and 31, or an amino acid sequence having at least 80, 85, 90, 95, or 99% identity thereto. In some embodiments, the CD19 VH comprises CDR or VH sequences disclosed herein, e.g., CDR or VH sequences disclosed in Tables 2, 19, 22, and 31, or an amino acid sequence having at least 80, 85, 90, 95, or 99% identity thereto. In some embodiments, the CD19 VL comprises CDR or VL sequences disclosed herein, e.g., CDR or VL sequences disclosed in Tables 2, 19, 22, and 31, or an amino acid sequence having at least 80, 85, 90, 95, or 99% identity thereto.

In some embodiments, the CAR, e.g., a diabody CAR, further comprises a hinge region, a transmembrane domain, and/or an intracellular signaling domain. In some embodiments, the hinge region comprises a CD8 hinge region. In some embodiments, the hinge region comprises a hinge region sequence disclosed herein, e.g., the amino acid sequence of SEQ ID NO: 2, or an amino acid sequence having at least 80, 85, 90, 95, or 99% identity thereto. In some embodiments, the transmembrane domain comprises a CD8 transmembrane domain. In some embodiments, the transmembrane domain comprises a transmembrane domain sequence disclosed herein, e.g., the amino acid sequence of SEQ ID NO: 6, or an amino acid sequence having at least 80, 85, 90, 95, or 99% identity thereto. In some embodiments, the intracellular signaling domain comprises a 4-1BB intracellular domain. In some embodiments, the intracellular signaling domain comprises a costimulatory signaling domain sequence disclosed herein, e.g., the amino acid sequence of SEQ ID NO: 7, or an amino acid sequence having at least 80, 85, 90, 95, or 99% identity thereto. In some embodiments, the intracellular signaling domain comprises a CD3 intracellular domain. In some embodiments, the intracellular signaling domain comprises a primary signaling domain sequence disclosed herein, e.g., the amino acid sequence of SEQ ID NO: 9 or 10, or an amino acid sequence having at least 80, 85, 90, 95, or 99% identity thereto.

Exemplary diabody sequences are disclosed in Table 31. In some embodiments, the CAR comprises an antigen binding domain comprising an amino acid sequence selected from the group consisting of SEQ ID NOs: 321-330, or an amino acid sequence having at least 80, 85, 90, 95, or 99% identity thereto. In some embodiments, the CAR comprises an amino acid sequence selected from the group consisting of SEQ ID NOs: 339-348, or an amino acid sequence having at least 80, 85, 90, 95, or 99% identity thereto.

TABLE 31

Exemplary components of diabody CARs.

| SEQ ID NO | Description | Amino acid sequence* |
|---|---|---|
| SEQ ID NO: 321 | JL1 antigen binding domain | *QVQLQESGPGLVKPSETLSLTCTVSGVSLPDYGVSWIRQPPGKCLEWIGVIWGS*<br>*ETTYYQSSLKSRVTISKDNSKNQVSLKLSSVTAADTAVYYCAKHYYYGGSYAMDY*<br>*WGQGTLVTVSS*GGGGSQSALTQPASVSGSPGQSITISCTGTSSDVGGYNYVS<br>WYQQHPGKAPKLMIYDVSNRPSGVSNRESGSKSGNTASLTISGLQAEDEAD<br>YYCSSYTSSSTLYVFGSGTKVTVLGGGGSGGGGSGGGGSGGGGSQVQLQE<br>SGGGVVQPGRSLRLSCAASGFTFSSYGMHWVRQAPGKGLEWVAVISYDGS<br>NKYYADSVKGRFTISRDNSKNTLYLQMNSLRAEDTAVYYCGGSGYALHD<br>DYYGLDVWGQGTLVTVSSGGGGS*EIVMTQSPATLSLSPGERATLSCRASQDIS*<br>*KYLNWYQQKPGQAPRLLIYHTSRLHSGIPARFSGSGSGTDYTLTISSLQPEDFAV*<br>*YFCQQGNTLPYTFGCGTKLEIK* |
| SEQ ID NO: 339 | JL1 full length diabody CAR | QVQLQESGPGLVKPSETLSLTCTVSGVSLPDYGVSWIRQPPGKCLEWIGVI<br>WGSETTYYQSSLKSRVTISKDNSKNQVSLKLSSVTAADTAVYYCAKHYYY<br>GGSYAMDYWGQGTLVTVSSGGGGSQSALTQPASVSGSPGQSITISCTGTSS<br>DVGGYNYVSWYQQHPGKAPKLMIYDVSNRPSGVSNRFSGSKSGNTASLTI<br>SGLQAEDEADYYCSSYTSSSTLYVFGSGTKVTVLGGGGSGGGGSGGGGSG<br>GGGSQVQLQESGGGVVQPGRSLRLSCAASGFTFSSYGMHWVRQAPGKGL<br>EWVAVISYDGSNKYYADSVKGRFTISRDNSKNTLYLQMNSLRAEDTAVYY<br>CGGSGYALHDDYYGLDVWGQGTLVTVSSGGGGSEIVMTQSPATLSLSPGE<br>RATLSCRASQDISKYLNWYQQKPGQAPRLLIYHTSRLHSGIPARFSGSGSGT<br>DYTLTISSLQPEDFAVYFCQQGNTLPYTFGCGTKLEIKTTTPAPRPPTPAPTI<br>ASQPLSLRPEACRPAAGGAVHTRGLDFACDIYIWAPLAGTCGVLLLSLVITL<br>YCKRGRKKLLYIFKQPFMRPVQTTQEEDGCSCRFPEEEEGGCELRVKESRS<br>ADAPAYKQGQNQLYNELNLGRREEYDVLDKRRGRDPEMGGKPRRKNPQE<br>GLYNELQKDKMAEAYSEIGMKGERRRGKGHDGLYQGLSTATKDTYDALH<br>MQALPPR |
| SEQ ID NO: 322 | JL2 antigen binding domain | *EIVMTQSPATLSLSPGERATLSCRASQDISKYLNWYQQKPGQAPRLLIYHTSRLHS*<br>*GIPARFSGSGSGTDYTLTISSLQPEDFAVYFCQQGNTLPYTFGCGTKLEIK*GGGG<br>SQVQLQESGGGVVQPGRSLRLSCAASGFTFSSYGMHWVRQAPGKGLEWV<br>AVISYDGSNKYYADSVKGRFTISRDNSKNTLYLQMNSLRAEDTAVYYCGG<br>SGYALHDDYYGLDVWGQGTLVTVSSGGGGSGGGGSGGGGSGGGGSQSA<br>LTQPASVSGSPGQSITISCTGTSSDVGGYNYVSWYQQHPGKAPKLMIYDVS<br>NRPSGVSNRFSGSKSGNTASLTISGLQAEDEADYYCSSYTSSSTLYVFGSGT<br>KVTVLGGGGS*QVQLQESGPGLVKPSETLSLTCTVSGVSLPDYGVSWIRQPPGK*<br>*CLEWIGVIWGSETTYYQSSLKSRVTISKDNSKNQVSLKLSSVTAADTAVYYCAKHY*<br>*YYGGSYAMDYWGQGTLVTVSS* |
| SEQ ID | JL2 full | EIVMTQSPATLSLSPGERATLSCRASQDISKYLNWYQQKPGQAPRLLIYHTS |

TABLE 31-continued

Exemplary components of diabody CARs.

| SEQ ID NO | Description | Amino acid sequence* |
|---|---|---|
| SEQ ID NO: 340 | length diabody CAR | RLHSGIPARFSGSGSGTDYTLTISSLQPEDFAVYFCQQGNTLPYTFGCGTKL<br>EIKGGGGSQVQLQESGGGVVQPGRSLRLSCAASGFTFSSYGMHWVRQAPG<br>KGLEWVAVISYDGSNKYYADSVKGRFTISRDNSKNTLYLQMNSLRAEDTA<br>VYYCGGSGYALHDDYYGLDVWGQGTLVTVSSGGGGSGGGGSGGGGSGG<br>GGSQSALTQPASVSGSPGQSITISCTGTSSDVGGYNYVSWYQQHPGKAPKL<br>MIYDVSNRPSGVSNRFSGSKSGNTASLTISGLQAEDEADYYCSSYTSSSTLY<br>VFGSGTKVTVLGGGGSQVQLQESGPGLVKPSETLSLTCTVSGVSLPDYGVS<br>WIRQPPGKCLEWIGVIWGSETTYYQSSLKSRVTISKDNSKNQVSLKLSSVTA<br>ADTAVYYCAKHYYYGGSYAMDYWGQGTLVTVSSTTTPAPRPPTPAPTIAS<br>QPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSA<br>DAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALH<br>MQALPPR |
| SEQ ID NO: 323 | JL3 antigen binding domain | *QVQLQESGPGLVKPSETLSLTCTVSGVSLPDYGVSWIRQPPGKCLEWIGVIWGS<br>ETTYYQSSLKSRVTISKDNSKNQVSLKLSSVTAADTAVYYCAKHYYYGGSYAMDY<br>WGQGTLVTVSS*GGGGSQVQLQESGGGVVQPGRSLRLSCAASGFTFSSYGMH<br>WVRQAPGKGLEWVAVISYDGSNKYYADSVKGRFTISRDNSKNTLYLQMN<br>SLRAEDTAVYYCGGSGYALHDDYYGLDVWGQGTLVTVSSGGGGSGGGG<br>SGGGGSGGGGS*QSALTQPASVSGSPGQSITISCTGTSSDVGGYNYVSWYQQ<br>HPGKAPKLMIYDVSNRPSGVSNRFSGSKSGNTASLTISGLQAEDEADYYCS<br>SYTSSSTLYVFGSGTKVTVL*GGGGS*EIVMTQSPATLSLSPGERATLSCRASQDI<br>SKYLNWYQQKPGQAPRLLIYHTSRLHSGIPARFSGSGSGTDYTLTISSLQPEDFAV<br>YFCQQGNTLPYTFGCGTKLEIK* |
| SEQ ID NO: 341 | JL3 full length diabody CAR | QVQLQESGPGLVKPSETLSLTCTVSGVSLPDYGVSWIRQPPGKCLEWIGVI<br>WGSETTYYQSSLKSRVTISKDNSKNQVSLKLSSVTAADTAVYYCAKHYYY<br>GGSYAMDYWGQGTLVTVSSGGGGSQVQLQESGGGVVQPGRSLRLSCAAS<br>GFTFSSYGMHWVRQAPGKGLEWVAVISYDGSNKYYADSVKGRFTISRDNS<br>KNTLYLQMNSLRAEDTAVYYCGGSGYALHDDYYGLDVWGQGTLVTVSS<br>GGGGSGGGGSGGGGSGGGGSQSALTQPASVSGSPGQSITISCTGTSSDVGG<br>YNYVSWYQQHPGKAPKLMIYDVSNRPSGVSNRFSGSKSGNTASLTISGLQ<br>AEDEADYYCSSYTSSSTLYVFGSGTKVTVLGGGGSEIVMTQSPATLSLSPGE<br>RATLSCRASQDISKYLNWYQQKPGQAPRLLIYHTSRLHSGIPARFSGSGSGT<br>DYTLTISSLQPEDFAVYFCQQGNTLPYTFGCGTKLEIKTTTPAPRPPTPAPTI<br>ASQPLSLRPEACRPAAGGAVHTRGLDFACDIYIWAPLAGTCGVLLLSLVITL<br>YCKRGRKKLLYIFKQPFMRPVQTTQEEDGCSCRFPEEEEGGCELRVKFSRS<br>ADAPAYKQGQNQLYNELNLGRREEYDVLDKRRGRDPEMGGKPRRKNPQE<br>GLYNELQKDKMAEAYSEIGMKGERRRGKGHDGLYQGLSTATKDTYDALH<br>MQALPPR |
| SEQ ID NO: 324 | JL4 antigen binding domain | *EIVMTQSPATLSLSPGERATLSCRASQDISKYLNWYQQKPGQAPRLLIYHTSRLHS<br>GIPARFSGSGSGTDYTLTISSLQPEDFAVYFCQQGNTLPYTFGCGTKLEIK*GGGG<br>SQSALTQPASVSGSPGQSITISCTGTSSDVGGYNYVSWYQQHPGKAPKLMI<br>YDVSNRPSGVSNRESGSKSGNTASLTISGLQAEDEADYYCSSYTSSSTLYVF<br>GSGTKVTVLGGGGSGGGGSGGGGSGGGGSQVQLQESGGGVVQPGRSLRL<br>SCAASGFTESSYGMHWVRQAPGKGLEWVAVISYDGSNKYYADSVKGRFTI<br>SRDNSKNTLYLQMNSLRAEDTAVYYCGGSGYALHDDYYGLDVWGQGTL<br>VTVSSGGGGS*QVQLQESGPGLVKPSETLSLTCTVSGVSLPDYGVSWIRQPPGK<br>CLEWIGVIWGSETTYYQSSLKSRVTISKDNSKNQVSLKLSSVTAADTAVYYCAKHY<br>YYGGSYAMDYWGQGTLVTVSS* |
| SEQ ID NO: 342 | JL4 full length diabody CAR | EIVMTQSPATLSLSPGERATLSCRASQDISKYLNWYQQKPGQAPRLLIYHTS<br>RLHSGIPARFSGSGSGTDYTLTISSLQPEDFAVYFCQQGNTLPYTFGCGTKL<br>EIKGGGGSQSALTQPASVSGSPGQSITISCTGTSSDVGGYNYVSWYQQHPG<br>KAPKLMIYDVSNRPSGVSNRFSGSKSGNTASLTISGLQAEDEADYYCSSYTS<br>SSTLYVFGSGTKVTVLGGGGSGGGGSGGGGSGGGGSQVQLQESGGGVVQ<br>PGRSLRLSCAASGFTFSSYGMHWVRQAPGKGLEWVAVISYDGSNKYYADS<br>VKGRFTISRDNSKNTLYLQMNSLRAEDTAVYYCGGSGYALHDDYYGLDV<br>WGQGTLVTVSSGGGGSQVQLQESGPGLVKPSETLSLTCTVSGVSLPDYGVS<br>WIRQPPGKCLEWIGVIWGSETTYYQSSLKSRVTISKDNSKNQVSLKLSSVTA<br>ADTAVYYCAKHYYYGGSYAMDYWGQGTLVTVSSTTTPAPRPPTPAPTIAS<br>QPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSA<br>DAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALH<br>MQALPPR |
| SEQ ID NO: 325 | JL5 antigen binding domain | QVQLQESGGGVVQPGRSLRLSCAASGFTFSSYGMHWVRQAPGKCLEWVA<br>VISYDGSNKYYADSVKGRFTISRDNSKNTLYLQMNSLRAEDTAVYYCGGS<br>GYALHDDYYGLDVWGQGTLVTVSSGGGGS*EIVMTQSPATLSLSPGERATLS<br>CRASQDISKYLNWYQQKPGQAPRLLIYHTSRLHSGIPARFSGSGSGTDYTLTISSL<br>QPEDFAVYFCQQGNTLPYTFGQGTKLEIK*GGGGSGGGGSGGGGSGGGGS*QV<br>QLQESGPGLVKPSETLSLTCTVSGVSLPDYGVSWIRQPPGKGLEWIGVIWGSETT* |

TABLE 31-continued

Exemplary components of diabody CARs.

| SEQ ID NO | Description | Amino acid sequence* |
|---|---|---|
| | | YYQSSLKSRVTISKDNSKNQVSLKLSSVTAADTAVYYCAKHYYYGGSYAMDYWGQ<br>GTLVTVSSGGGGSQSALTQPASVSGSPGQSITISCTGTSSDVGGYNYVSWYQ<br>QHPGKAPKLMIYDVSNRPSGVSNRESGSKSGNTASLTISGLQAEDEADYYC<br>SSYTSSSTLYVFGCGTKVTVL |
| SEQ ID NO: 343 | JL5 full length diabody CAR | QVQLQESGGGVVQPGRSLRLSCAASGFTFSSYGMHWVRQAPGKCLEWVA<br>VISYDGSNKYYADSVKGRFTISRDNSKNTLYLQMNSLRAEDTAVYYCGGS<br>GYALHDDYYGLDVWGQGTLVTVSSGGGGSEIVMTQSPATLSLSPGERATL<br>SCRASQDISKYLNWYQQKPGQAPRLLIYHTSRLHSGIPARFSGSGSGTDYTL<br>TISSLQPEDFAVYFCQQGNTLPYTFGQGTKLEIKGGGGSGGGGSGGGGSGG<br>GGSQVQLQESGPGLVKPSETLSLTCTVSGVSLPDYGVSWIRQPPGKGLEWI<br>GVIWGSETTYYQSSLKSRVTISKDNSKNQVSLKLSSVTAADTAVYYCAKH<br>YYYGGSYAMDYWGQGTLVTVSSGGGGSQSALTQPASVSGSPGQSITISCT<br>GTSSDVGGYNYVSWYQQHPGKAPKLMIYDVSNRPSGVSNRFSGSKSGNTA<br>SLTISGLQAEDEADYYCSSYTSSSTLYVFGCGTKVTVLTTTPAPRPPTPAPTI<br>ASQPLSLRPEACRPAAGGAVHTRGLDFACDIYIWAPLAGTCGVLLLSLVITL<br>YCKRGRKKLLYIFKQPFMRPVQTTQEEDGCSCRFPEEEEGGCELRVKFSRS<br>ADAPAYKQGQNQLYNELNLGRREEYDVLDKRRGRDPEMGGKPRRKNPQE<br>GLYNELQKDKMAEAYSEIGMKGERRRGKGHDGLYQGLSTATKDTYDALH<br>MQALPPR |
| SEQ ID NO: 326 | JL6 antigen binding domain | QSALTQPASVSGSPGQSITISCTGTSSDVGGYNYVSWYQQHPGKAPKLMIY<br>DVSNRPSGVSNRESGSKSGNTASLTISGLQAEDEADYYCSSYTSSSTLYVFG<br>CGTKVTVLGGGGSQVQLQESGPGLVKPSETLSLTCTVSGVSLPDYGVSWIRQP<br>PGKGLEWIGVIWGSETTYYQSSLKSRVTISKDNSKNQVSLKLSSVTAADTAVYYCA<br>KHYYYGGSYAMDYWGQGTLVTVSSGGGGSGGGGSGGGGSGGGGSEIVMTQS<br>PATLSLSPGERATLSCRASQDISKYLNWYQQKPGQAPRLLIYHTSRLHSGIPARFS<br>GSGSGTDYTLTISSLQPEDFAVYFCQQGNTLPYTFGQGTKLEIKGGGGSQVQL<br>QESGGGVVQPGRSLRLSCAASGFTFSSYGMHWVRQAPGKCLEWVAVISYD<br>GSNKYYADSVKGRFTISRDNSKNTLYLQMNSLRAEDTAVYYCGGSGYAL<br>HDDYYGLDVWGQGTLVTVSS |
| SEQ ID NO: 344 | JL6 full length diabody CAR | QSALTQPASVSGSPGQSITISCTGTSSDVGGYNYVSWYQQHPGKAPKLMIY<br>DVSNRPSGVSNRFSGSKSGNTASLTISGLQAEDEADYYCSSYTSSSTLYVFG<br>CGTKVTVLGGGGSQVQLQESGPGLVKPSETLSLTCTVSGVSLPDYGVSWIR<br>QPPGKGLEWIGVIWGSETTYYQSSLKSRVTISKDNSKNQVSLKLSSVTAAD<br>TAVYYCAKHYYYGGSYAMDYWGQGTLVTVSSGGGGSGGGGSGGGGSGG<br>GGSEIVMTQSPATLSLSPGERATLSCRASQDISKYLNWYQQKPGQAPRLLIY<br>HTSRLHSGIPARFSGSGSGTDYTLTISSLQPEDFAVYFCQQGNTLPYTFGQG<br>TKLEIKGGGGSQVQLQESGGGVVQPGRSLRLSCAASGFTFSSYGMHWVRQ<br>APGKCLEWVAVISYDGSNKYYADSVKGRFTISRDNSKNTLYLQMNSLRAE<br>DTAVYYCGGSGYALHDDYYGLDVWGQGTLVTVSSTTTPAPRPPTPAPTIA<br>SQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSA<br>DAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALH<br>MQALPPR |
| SEQ ID NO: 327 | JL7 antigen binding domain | QVQLQESGGGVVQPGRSLRLSCAASGFTFSSYGMHWVRQAPGKCLEWVA<br>VISYDGSNKYYADSVKGRFTISRDNSKNTLYLQMNSLRAEDTAVYYCGGS<br>GYALHDDYYGLDVWGQGTLVTVSSGGGGSQVQLQESGPGLVKPSETLSLTC<br>TVSGVSLPDYGVSWIRQPPGKGLEWIGVIWGSETTYYQSSLKSRVTISKDNSKNQ<br>VSLKLSSVTAADTAVYYCAKHYYYGGSYAMDYWGQGTLVTVSSGGGGSGGGGS<br>GGGGSGGGGSEIVMTQSPATLSLSPGERATLSCRASQDISKYLNWYQQKPGQA<br>PRLLIYHTSRLHSGIPARFSGSGSGTDYTLTISSLQPEDFAVYFCQQGNTLPYTFG<br>QGTKLEIKGGGGSQSALTQPASVSGSPGQSITISCTGTSSDVGGYNYVSWYQ<br>QHPGKAPKLMIYDVSNRPSGVSNRESGSKSGNTASLTISGLQAEDEADYYC<br>SSYTSSSTLYVFGCGTKVTVL |
| SEQ ID NO: 345 | JL7 full length diabody CAR | QVQLQESGGGVVQPGRSLRLSCAASGFTFSSYGMHWVRQAPGKCLEWVA<br>VISYDGSNKYYADSVKGRFTISRDNSKNTLYLQMNSLRAEDTAVYYCGGS<br>GYALHDDYYGLDVWGQGTLVTVSSGGGGSQVQLQESGPGLVKPSETLSLT<br>CTVSGVSLPDYGVSWIRQPPGKGLEWIGVIWGSETTYYQSSLKSRVTISKD<br>NSKNQVSLKLSSVTAADTAVYYCAKHYYYGGSYAMDYWGQGTLVTVSS<br>GGGGSGGGGSGGGGSGGGGSEIVMTQSPATLSLSPGERATLSCRASQDISK<br>YLNWYQQKPGQAPRLLIYHTSRLHSGIPARFSGSGSGTDYTLTISSLQPEDF<br>AVYFCQQGNTLPYTFGQGTKLEIKGGGGSQSALTQPASVSGSPGQSITISCT<br>GTSSDVGGYNYVSWYQQHPGKAPKLMIYDVSNRPSGVSNRFSGSKSGNTA<br>SLTISGLQAEDEADYYCSSYTSSSTLYVFGCGTKVTVLTTTPAPRPPTPAPTI<br>ASQPLSLRPEACRPAAGGAVHTRGLDFACDIYIWAPLAGTCGVLLLSLVITL<br>YCKRGRKKLLYIFKQPFMRPVQTTQEEDGCSCRFPEEEEGGCELRVKFSRS<br>ADAPAYKQGQNQLYNELNLGRREEYDVLDKRRGRDPEMGGKPRRKNPQE<br>GLYNELQKDKMAEAYSEIGMKGERRRGKGHDGLYQGLSTATKDTYDALH<br>MQALPPR |

TABLE 31-continued

Exemplary components of diabody CARs.

| SEQ ID NO | Description | Amino acid sequence* |
|---|---|---|
| SEQ ID NO: 328 | JL8 antigen binding domain | QSALTQPASVSGSPGQSITISCTGTSSDVGGYNYVSWYQQHPGKAPKLMIY<br>DVSNRPSGVSNRFSGSKSGNTASLTISGLQAEDEADYYCSSYTSSSTLYVFG<br>CGTKVTVLGGGGS*EIVMTQSPATLSLSPGERATLSCRASQDISKYLNWYQQKP*<br>*GQAPRLLIYHTSRLHSGIPARFSGSGSGTDYTLTISSLQPEDFAVYFCQQGNTLPY*<br>*TFGQGTKLEIK*GGGGSGGGGSGGGGSGGGGS*QVQLQESGPGLVKPSETLSLT*<br>*CTVSGVSLPDYGVSWIRQPPGKGLEWIGVIWGSETTYYQSSLKSRVTISKDNSKN*<br>*QVSLKLSSVTAADTAVYYCAKHYYYGGSYAMDYWGQGTLVTVSS*GGGGSQVQL<br>QESGGGVVQPGRSLRLSCAASGFTFSSYGMHWVRQAPGKCLEWVAVISYD<br>GSNKYYADSVKGRFTISRDNSKNTLYLQMNSLRAEDTAVYYCGGSGYAL<br>HDDYYGLDVWGQGTLVTVSS |
| SEQ ID NO: 346 | JL8 full length diabody CAR | QSALTQPASVSGSPGQSITISCTGTSSDVGGYNYVSWYQQHPGKAPKLMIY<br>DVSNRPSGVSNRFSGSKSGNTASLTISGLQAEDEADYYCSSYTSSSTLYVFG<br>CGTKVTVLGGGGSEIVMTQSPATLSLSPGERATLSCRASQDISKYLNWYQQ<br>KPGQAPRLLIYHTSRLHSGIPARFSGSGSGTDYTLTISSLQPEDFAVYFCQQG<br>NTLPYTFGQGTKLEIKGGGGSGGGGSGGGGSGGGGSQVQLQESGPGLVKP<br>SETLSLTCTVSGVSLPDYGVSWIRQPPGKGLEWIGVIWGSETTYYQSSLKSR<br>VTISKDNSKNQVSLKLSSVTAADTAVYYCAKHYYYGGSYAMDYWGQGTL<br>VTVSSGGGGSQVQLQESGGGVVQPGRSLRLSCAASGFTFSSYGMHWVRQ<br>APGKCLEWVAVISYDGSNKYYADSVKGRFTISRDNSKNTLYLQMNSLRAE<br>DTAVYYCGGSGYALHDDYYGLDVWGQGTLVTVSSTTTPAPRPPTPAPTIA<br>SQPLSLRPEACRPAAGGAVHTRGLDFACDIYIWAPLAGTCGVLLLSLVITLY<br>CKRGRKKLLYIFKQPFMRPVQTTQEEDGCSCRFPEEEEGGCELRVKFSRSA<br>DAPAYKQGQNQLYNELNLGRREEYDVLDKRRGRDPEMGGKPRRKNPQEG<br>LYNELQKDKMAEAYSEIGMKGERRRGKGHDGLYQGLSTATKDTYDALH<br>MQALPPR |
| SEQ ID NO: 329 | JL9 antigen binding domain | *QVQLQESGPGLVKPSETLSLTCTVSGVSLPDYGVSWIRQPPGKCLEWIGVIWGS*<br>*ETTYYQSSLKSRVTISKDNSKNQVSLKLSSVTAADTAVYYCAKHYYYGGSYAMDY*<br>*WGQGTLVTVSS*GGGGSDIQMTQSPSSLSASVGDRVTITCRASQSISSYLNWY<br>QQKPGKAPKLLIYAASSLQSGVPSRFSGSGSGTDFTLTISSLQPEDFATYYC<br>QQSYSTPLTFGQGTKVEIKGGGGSGGGGSGGGGSGGGGSEVQLLESGGGL<br>VQPGGSLRLSCAASGFTFSSYAMSWVRQAPGKGLEWVSAISGSGGSTYYA<br>DSVKGRFTISRDNSKNTLYLQMNSLRAEDTAVYYCARREWWGESWLFDY<br>WGQGTLVTVSSGGGGS*EIVMTQSPATLSLSPGERATLSCRASQDISKYLNWYQ*<br>*QKPGQAPRLLIYHTSRLHSGIPARFSGSGSGTDYTLTISSLQPEDFAVYFCQQGN*<br>*TLPYTFGCGTKLEIK* |
| SEQ ID NO: 347 | JL9 full length diabody CAR | QVQLQESGPGLVKPSETLSLTCTVSGVSLPDYGVSWIRQPPGKCLEWIGVI<br>WGSETTYYQSSLKSRVTISKDNSKNQVSLKLSSVTAADTAVYYCAKHYYY<br>GGSYAMDYWGQGTLVTVSSGGGGSDIQMTQSPSSLSASVGDRVTITCRAS<br>QSISSYLNWYQQKPGKAPKLLIYAASSLQSGVPSRFSGSGSGTDFTLTISSLQ<br>PEDFATYYCQQSYSTPLTFGQGTKVEIKGGGGSGGGGSGGGGSGGGGSEV<br>QLLESGGGLVQPGGSLRLSCAASGFTFSSYAMSWVRQAPGKGLEWVSAIS<br>GSGGSTYYADSVKGRFTISRDNSKNTLYLQMNSLRAEDTAVYYCARREW<br>WGESWLFDYWGQGTLVTVSSGGGGSEIVMTQSPATLSLSPGERATLSCRA<br>SQDISKYLNWYQQKPGQAPRLLIYHTSRLHSGIPARFSGSGSGTDYTLTISSL<br>QPEDFAVYFCQQGNTLPYTFGCGTKLEIKTTTPAPRPPTPAPTIASQPLSLRP<br>EACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYKQ<br>GQNQLYNELNLGRREEYDVLDKRRGRDPEMGGKPRRKNPQEGLYNELQK<br>DKMAEAYSEIGMKGERRRGKGHDGLYQGLSTATKDTYDALHMQALPPR |
| SEQ ID NO: 330 | JL10 antigen binding domain | EVQLLESGGGLVQPGGSLRLSCAASGFTFSSYAMSWVRQAPGKCLEWVSA<br>ISGSGGSTYYADSVKGRFTISRDNSKNTLYLQMNSLRAEDTAVYYCARRE<br>WWGESWLFDYWGQGTLVTVSSGGGGS*EIVMTQSPATLSLSPGERATLSCRAS*<br>*QDISKYLNWYQQKPGQAPRLLIYHTSRLHSGIPARFSGSGSGTDYTLTISSLQPED*<br>*FAVYFCQQGNTLPYTFGQGTKLEIK*GGGGSGGGGSGGGGSGGGGS*QVQLQE*<br>*SGPGLVKPSETLSLTCTVSGVSLPDYGVSWIRQPPGKGLEWIGVIWGSETTYYQS*<br>*SLKSRVTISKDNSKNQVSLKLSSVTAADTAVYYCAKHYYYGGSYAMDYWGQGTL*<br>*VTVSS*GGGGSDIQMTQSPSSLSASVGDRVTITCRASQSISSYLNWYQQKPGK<br>APKLLIYAASSLQSGVPSRFSGSGSGTDFTLTISSLQPEDFATYYCQQSYSTP<br>LTFGCGTKVEIK |
| SEQ ID NO: 348 | JL10 full length diabody CAR | EVQLLESGGGLVQPGGSLRLSCAASGFTFSSYAMSWVRQAPGKCLEWVSA<br>ISGSGGSTYYADSVKGRFTISRDNSKNTLYLQMNSLRAEDTAVYYCARRE<br>WWGESWLFDYWGQGTLVTVSSGGGGSEIVMTQSPATLSLSPGERATLSCR<br>ASQDISKYLNWYQQKPGQAPRLLIYHTSRLHSGIPARFSGSGSGTDYTLTIS<br>SLQPEDFAVYFCQQGNTLPYTFGQGTKLEIKGGGGSGGGGSGGGGSGGGG<br>SQVQLQESGPGLVKPSETLSLTCTVSGVSLPDYGVSWIRQPPGKGLEWIGVI<br>WGSETTYYQSSLKSRVTISKDNSKNQVSLKLSSVTAADTAVYYCAKHYYY<br>GGSYAMDYWGQGTLVTVSSGGGGSDIQMTQSPSSLSASVGDRVTITCRAS<br>QSISSYLNWYQQKPGKAPKLLIYAASSLQSGVPSRFSGSGSGTDFTLTISSLQ<br>PEDFATYYCQQSYSTPLTFGCGTKVEIKTTTPAPRPPTPAPTIASQPLSLRPE<br>ACRPAAGGAVHTRGLDFACDIYIWAPLAGTCGVLLLSLVITLYCKRGRKKL |

TABLE 31-continued

Exemplary components of diabody CARs.

| SEQ ID NO | Description | Amino acid sequence* |
|---|---|---|
| | | LYIFKQPFMRPVQTTQEEDGCSCRFPEEEEGGCELRVKFSRSADAPAYKQG QNQLYNELNLGRREEYDVLDKRRGRDPEMGGKPRRKNPQEGLYNELQKD KMAEAYSEIGMKGERRRGKGHDGLYQGLSTATKDTYDALHMQALPPR |
| SEQ ID NO: 250 | Anti-CD19 VH (CTL119) | QVQLQESGPGLVKPSETLSLTCTVSGVSLPDYGVSWIRQPPGKGLEWIGVI WGSETTYYQSSLKSRVTISKDNSKNQVSLKLSSVTAADTAVYYCAKHYYY GGSYAMDYWGQGTLVTVSS |
| SEQ ID NO: 251 | Anti-CD19 VL (CTL119) | EIVMTQSPATLSLSPGERATLSCRASQDISKYLNWYQQKPGQAPRLLIYHTS RLHSGIPARFSGSGSGTDYTLTISSLQPEDFAVYFCQQGNTLPYTFGQGTKL EIK |
| SEQ ID NO: 331 | Anti-CD19 VH (CTL119) variant | QVQLQESGPGLVKPSETLSLTCTVSGVSLPDYGVSWIRQPPGKCLEWIGVI WGSETTYYQSSLKSRVTISKDNSKNQVSLKLSSVTAADTAVYYCAKHYYY GGSYAMDYWGQGTLVTVSS |
| SEQ ID NO: 332 | Anti-CD19 VL (CTL119) variant | EIVMTQSPATLSLSPGERATLSCRASQDISKYLNWYQQKPGQAPRLLIYHTS RLHSGIPARFSGSGSGTDYTLTISSLQPEDFAVYFCQQGNTLPYTFGCGTKL EIK |
| SEQ ID NO: 93 | Anti-BCMA VH (PI61) | QVQLQESGGGVVQPGRSLRLSCAASGFTFSSYGMHWVRQAPGKGLEWVA VISYDGSNKYYADSVKGRFTISRDNSKNTLYLQMNSLRAEDTAVYYCGGS GYALHDDYYGLDVWGQGTLVTVSS |
| SEQ ID NO: 102 | Anti-BCMA VL (PI61) | QSALTQPASVSGSPGQSITISCTGTSSDVGGYNYVSWYQQHPGKAPKLMIY DVSNRPSGVSNRFSGSKSGNTASLTISGLQAEDEADYYCSSYTSSSTLYVFG SGTKVTVL |
| SEQ ID NO: 333 | Anti-BCMA VH (PI61) variant | QVQLQESGGGVVQPGRSLRLSCAASGFTFSSYGMHWVRQAPGKCLEWVA VISYDGSNKYYADSVKGRFTISRDNSKNTLYLQMNSLRAEDTAVYYCGGS GYALHDDYYGLDVWGQGTLVTVSS |
| SEQ ID NO: 334 | Anti-BCMA VL (PI61) variant | QSALTQPASVSGSPGQSITISCTGTSSDVGGYNYVSWYQQHPGKAPKLMIY DVSNRPSGVSNRFSGSKSGNTASLTISGLQAEDEADYYCSSYTSSSTLYVFG CGTKVTVL |
| SEQ ID NO: 78 | Anti-BCMA VH (R1G5) | EVQLLESGGGLVQPGGSLRLSCAASGFTFSSYAMSWVRQAPGKGLEWVSA ISGSGGSTYYADSVKGRFTISRDNSKNTLYLQMNSLRAEDTAVYYCARRE WWGESWLFDYWGQGTLVTVSS |
| SEQ ID NO: 61 | Anti-BCMA VL (R1G5) | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPLTFGQGTKVE IK |
| SEQ ID NO: 335 | Anti-BCMA VH (R1G5) variant | EVQLLESGGGLVQPGGSLRLSCAASGFTFSSYAMSWVRQAPGKCLEWVSA ISGSGGSTYYADSVKGRFTISRDNSKNTLYLQMNSLRAEDTAVYYCARRE WWGESWLFDYWGQGTLVTVSS |
| SEQ ID NO: 336 | Anti-BCMA VL (R1G5) variant | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPLTFGCGTKVE IK |
| SEQ ID NO: 5 | Linker | GGGGSGGGGS |
| SEQ ID NO: 63 | Linker | GGGGSGGGGGGGGSGGGGS |

*VH sequences are underlined and VL sequences are double-underlined. CD19-binding sequences (VH and VL) are shown in italic.

Chimeric TCR

In one aspect, the antibodies and antibody fragments of the present invention can be grafted to one or more constant domain of a T cell receptor ("TCR") chain, for example, a TCR alpha or TCR beta chain, to create a chimeric TCR. Without being bound by theory, it is believed that chimeric TCRs will signal through the TCR complex upon antigen binding. For example, a scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, an antibody fragment, for example a VL domain as described herein, can be grafted to the constant domain of a TCR alpha chain, and an antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of an antibody or antibody fragment, e.g., the CDRs of an antibody or antibody fragment as described herein may be grafted into a TCR alpha and/or beta chain to create a chimeric TCR. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4):365-74).

Additional Embodiments

In one aspect, the CAR-expressing cell described herein can further comprise a second CAR, e.g., a second CAR that includes a different antigen binding domain, e.g., to the same target (BCMA) or a different target (e.g., CD19, CD20, or CS-1, or other multiple myeloma targets, e.g., kappa light chain, CD138, Lewis Y antigen, or CD38 (Garfall et al., Discovery Medicine, 2014, 17(91):37-46)). In one embodiment, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27 ICOS, or OX-40, onto the first CAR, and the primary signaling domain, e.g., CD3 zeta, on the second CAR can limit the CAR activity to cells where both targets are expressed. In one embodiment, the CAR expressing cell comprises a first BCMA CAR that includes a BCMA binding domain, a transmembrane domain and a costimulatory domain and a second CAR that targets an antigen other than BCMA (e.g., an antigen expressed on leukemia or lymphoma cells, e.g., CD19, CD20, CS-1, kappa light chain, CD139, Lewis Y antigen, or CD38) and includes an antigen binding domain, a transmembrane domain and a primary signaling domain. In another embodiment, the CAR expressing cell comprises a first BCMA CAR that includes a BCMA binding domain, a transmembrane domain and a primary signaling domain and a second CAR that targets an antigen other than BCMA (e.g., an antigen expressed on leukemia or lymphoma cells, e.g., CD19, CD20, CS-1, kappa light chain, CD139, Lewis Y antigen, or CD38) and includes an antigen binding domain to the antigen, a transmembrane domain and a costimulatory signaling domain. In one embodiment, the CAR-expressing cell comprises a BCMA CAR described herein and a CAR that targets CD19 (CD19 CAR).

In one embodiment, the CAR-expressing cell comprises a BCMA CAR described herein and an inhibitory CAR. In one embodiment, the inhibitory CAR comprises an antigen binding domain that binds an antigen found on normal cells but not cancer cells. In one embodiment, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In one embodiment, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies.

SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of said first CAR said second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, in one embodiment, the agent can be an agent which inhibits an inhibitory molecule, e.g., an agent described herein. Inhibitory molecules, e.g., PD1, can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 ICOS, or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). In embodiments, the CAR-expressing cell described herein comprises a switch costimulatory receptor, e.g., as described in WO 2013/019615, which is incorporated herein by reference in its entirety. PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In one embodiment, the PD1 CAR, when used in combinations with a BCMA CAR described herein, improves the persistence of the CAR-expressing cell, e.g., T cell or NK cell. In one embodiment, the CAR is a PD1 CAR comprising the extracellular domain of PD1 indicated as underlined in SEQ ID NO: 24. In one embodiment, the PD1 CAR comprises the amino acid sequence of SEQ ID NO: 24.

In one embodiment, the PD1 CAR comprises the amino acid sequence provided below (SEQ ID NO: 22).

In one embodiment, the agent comprises a nucleic acid sequence encoding the PD1 CAR, e.g., the PD1 CAR described herein. In one embodiment, the nucleic acid sequence for the PD1 CAR is provided as SEQ ID NO: 23, with the PD1 ECD underlined.

In another aspect, the present invention provides a population of CAR-expressing cells, e.g., CART cells or CAR-expressing NK cells. In some embodiments, the population of CAR-expressing cells comprises a mixture of cells expressing different CARs. For example, in one embodiment, the population of CAR-expressing cells (e.g., CART cells or CAR-expressing NK cells) can include a first cell expressing a CAR having an anti-BCMA binding domain described herein, and a second cell expressing a CAR having a different anti-BCMA binding domain, e.g., an anti-BCMA binding domain described herein that differs from the anti-BCMA binding domain in the CAR expressed by the first cell. As another example, the population of CAR-expressing cells can include a first cell expressing a CAR that includes an anti-BCMA binding domain, e.g., as described herein, and a second cell expressing a CAR that includes an antigen binding domain to a target other than BCMA (e.g., CD19, CD20, CS-1, kappa light chain, CD139, Lewis Y antigen, or CD38). In one embodiment, the population of CAR-expressing cells includes a first cell expressing a CAR comprising an anti-BCMA binding domain, e.g., as described herein, and a second cell expressing a CAR comprising an antigen binding domain that targets CD19 (CD19 CAR). In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-BCMA domain described herein, and a second cell expressing another agent, e.g., an agent which enhances the activity of a CAR-expressing cell. For example, in one embodiment, the agent can be an agent which inhibits an inhibitory molecule.

Inhibitory molecules, e.g., can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27, ICOS, or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells (e.g., CART cells or CAR-expressing NK cells), e.g., a mixture of cells expressing different CARs, in combination with another agent, e.g., a kinase inhibitor, such as a kinase inhibitor described herein. In another aspect, the present invention provides methods comprising administering a population of cells wherein at least one cell in the population expresses a CAR having an anti-cancer associated antigen binding domain as described herein, and a second cell expressing another agent, e.g., an agent which enhances the activity of a CAR-expressing cell, in combination with another agent, e.g., a kinase inhibitor, such as a kinase inhibitor described herein.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Non-Antibody Scaffolds

In embodiments, the antigen binding domain comprises a non-antibody scaffold, for example, a fibronectin, ankyrin, domain antibody, lipocalin, small modular immuno-pharmaceutical, maxybody, Protein A, or affilin. The non-antibody scaffold has the ability to bind to target antigen on a cell. In embodiments, the antigen binding domain is a polypeptide or fragment thereof of a naturally occurring protein expressed on a cell. In some embodiments, the antigen binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, MA), ankyrin (Molecular Partners AG, Zurich, Switzerland), domain antibodies (Domantis, Ltd., Cambridge, MA, and Ablynx nv, Zwijnaarde, Belgium), lipocalin (Pieris Proteolab AG, Freising, Germany), small modular immuno-pharmaceuticals (Trubion Pharmaceuticals Inc., Seattle, WA), maxybodies (Avidia, Inc., Mountain View, CA), Protein A (Affibody AG, Sweden), and affilin (gamma-crystallin or ubiquitin) (Scil Proteins GmbH, Halle, Germany).

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI¾β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/lgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CAR-expressing cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8)853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH®, a monoclonal anti-CD52 antibody that selectively binds and targets mature lymphocytes, e.g., CAR-expressing cells, for destruction, e.g., by inducing ADCC. In other embodiments, CAR-expressing cells can be selectively targeted using a CAR ligand, e.g., an anti-idiotypic antibody. In some embodiments, the anti-idiotypic antibody can cause effector cell activity, e.g., ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In some embodiments, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. Additional description and exemplary configurations of such regulatable CARs are provided herein and in International Publication No. WO 2015/090229, hereby incorporated by reference in its entirety.

In an embodiment, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets a tumor antigen described herein, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 4-1BB, CD28, CD27, ICOS, and OX40, and in embodiments, no primary intracellular signaling domain. In an embodiment, the antigen binding member comprises the following costimulatory signaling domains, from the extracellular to intracellular direction: 4-1BB- CD27; 4-1BB-CD27; CD27-4-1BB; 4-1BB-CD28; CD28-4-1BB; OX40-CD28; CD28-OX40; CD28-4-1BB; or 4-1BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 4-1BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization switches Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

An exemplary amino acid sequence of FKBP is as follows:

DVPDYASLGGPSSPKKKRKVSRGVQVETISP-
GDGRTFPKRGQT
CVVHYTGMLEDGKKFDSSRDRNKPFKFMLGKQE-

VIRGWEEGVAQM SVGQRAKLTISPDYAYGATGHPGIIPPHATLVFDVELLKLETSY (SEQ ID NO: 275)

In embodiments, an FKBP switch domain can comprise a fragment of FKBP having the ability to bind with FRB, or a fragment or analog thereof, in the presence of rapamycin or a rapalog. In one embodiment, the FKBP switch domain comprises the amino acid sequence of:

VQVETISPGDGRTFPKRGQTCVVHYTGMLEDGKKFDSSRDRN KPFKFMLGKQEVIRGWEEGVAQMSVGQRAKLTISPDYAYGATGHP GIIPPHATLVFDVELLKLETS (SEQ ID NO: 276)

The amino acid sequence of FRB is as follows:

ILWHEMWHEG LEEASRLYFG ERNVKGMFEV LEPLHAMMER GPQTLKETSF NQAYGRDLME AQEWCRKYMK SGNVKDLTQA WDLYYHVFRR ISK (SEQ ID NO: 277)

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 275 or 276; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 277. In an embodiment, a RCAR described herein comprises one switch domain comprises amino acid residues disclosed in SEQ ID NO: 275 (or SEQ ID NO: 276), and one switch domain comprises amino acid residues disclosed in SEQ ID NO: 277.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E20321), e.g., SEQ ID NO: 278, or leucine (E2032L), e.g., SEQ ID NO: 279. In an embodiment, a mutant FRB comprises a mutation at T2098, where T2098 is mutated to phenylalanine (T2098F) or leucine (T2098L), e.g., SEQ ID NO: 280. In an embodiment, a mutant FRB comprises a mutation at E2032 and at T2098, where E2032 is mutated to any amino acid, and where T2098 is mutated to any amino acid, e.g., SEQ ID NO: 281. In an embodiment, a mutant FRB comprises an E20321 and a T2098L mutation, e.g., SEQ ID NO: 282. In an embodiment, a mutant FRB comprises an E2032L and a T2098L mutation, e.g., SEQ ID NO: 283.

TABLE 18

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKE TSFNQAYGRDLMEAQEWCRKYMKSGNVKDLTQAWDLYYHVERRISKTS | 278 |
| E2032L mutant | ILWHEMWHEGLLEASRLYFGERNVKGMFEVLEPLHAMMERGPQTLKE TSFNQAYGRDLMEAQEWCRKYMKSGNVKDLIQAWDLYYHVERRISKTS | 279 |
| T2098L mutant | ILWHEMWHEGLEEASRLYFGERNVKGMFEVLEPLHAMMERGPQTLKE TSFNQAYGRDLMEAQEWCRKYMKSGNVKDLLQAWDLYYHVERRISKTS | 280 |
| E2032, T2098 mutant | ILWHEMWHEGLXEASRLYFGERNVKGMFEVLEPLHAMMERGPQTLKE TSFNQAYGRDLMEAQEWCRKYMKSGNVKDLXQAWDLYYHVERRISKTS wherein X is any amino acid residue | 281 |
| E2032I, T2098L mutant | ILWHEMWHEGLIEASRLYFGERNVKGMFEVLEPLHAMMERGPQTLKE TSFNQAYGRDLMEAQEWCRKYMKSGNVKDLLQAWDLYYHVERRISKTS | 282 |
| E2032L, T2098L mutant | ILWHEMWHEGLLEASRLYFGERNVKGMFEVLEPLHAMMERGPQTLKE TSFNQAYGRDLMEAQEWCRKYMKSGNVKDLLQAWDLYYHVFRRISKTS | 283 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001

(everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Combination with a Low, Immune Enhancing, Dose of an mTOR inhibitor".

Split CAR

In some embodiments, the CAR-expressing cell uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes BCMA, e.g., comprises an antigen binding domain described herein, and the second antigen binding domain recognizes an antigen expressed on acute myeloid leukemia cells, e.g., CD123, CLL-1, CD34, FLT3, or folate receptor beta. In embodiments the first antigen binding domain recognizes BCMA, e.g., comprises an antigen binding domain described herein, and the second antigen binding domain recognizes an antigen expressed on B-cells, e.g., CD10, CD19, CD20, CD22, CD34, CD123, FLT-3, ROR1, CD79b, CD179b, or CD79a.

Co-Expression of CAR with Other Molecules or Agents

Co-Expression of a Second CAR

In some embodiments, the CAR-expressing cell described herein can further comprise a second CAR, for example, a second CAR that includes a different antigen binding domain, for example, to the same target (for example, CD19) or a different target (for example, a target other than CD19, for example, a target described herein). In some embodiments, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. Placement of a costimulatory signaling domain, for example, 4-1BB, CD28, CD27, OX-40 or ICOS, onto the first CAR, and the primary signaling domain, for example, CD3 zeta, on the second CAR can limit the CAR activity to cells where both targets are expressed. In some embodiments, the CAR expressing cell comprises a first CAR that includes an antigen binding domain, a transmembrane domain and a costimulatory domain and a second CAR that targets another antigen and includes an antigen binding domain, a transmembrane domain and a primary signaling domain. In some embodiments, the CAR expressing cell comprises a first CAR that includes an antigen binding domain, a transmembrane domain and a primary signaling domain and a second CAR that targets another antigen and includes an antigen binding domain to the antigen, a transmembrane domain and a costimulatory signaling domain.

In some embodiments, the CAR-expressing cell comprises an XCAR described herein and an inhibitory CAR. In some embodiments, the inhibitory CAR comprises an antigen binding domain that binds an antigen found on normal cells but not cancer cells, for example, normal cells that also express X. In some embodiments, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (CEACAM-1, CEACAM-3, and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF (for example, TGF beta).

In some embodiments, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, for example, as a fragment, for example, an scFv, that does not form an association with the antigen binding domain of the second CAR, for example, the antigen binding domain of the second CAR is a VHH.

In some embodiments, the antigen binding domain comprises a single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In some embodiments, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

In some embodiments, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (for example, selected by phage display).

It has also been discovered, that cells having a plurality of chimeric membrane embedded receptors comprising an antigen binding domain that interactions between the antigen binding domain of the receptors can be undesirable, for example, because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising an antigen binding domains that minimize such interactions, as well as methods of making and using such cells and nucleic acids. In some embodiments the antigen binding domain of one of the first and the second non-naturally occurring chimeric membrane embedded receptor, comprises an scFv, and the other comprises a single VH domain, for example, a camelid, shark, or lamprey single VH domain, or a single VH domain derived from a human or mouse sequence.

In some embodiments, a composition herein comprises a first and second CAR, wherein the antigen binding domain of one of the first and the second CAR does not comprise a variable light domain and a variable heavy domain. In some embodiments, the antigen binding domain of one of the first and the second CAR is an scFv, and the other is not an scFv. In some embodiments, the antigen binding domain of one of the first and the second CAR comprises a single VH domain, for example, a camelid, shark, or lamprey single VH domain, or a single VH domain derived from a human or mouse sequence. In some embodiments, the antigen binding domain of one of the first and the second CAR comprises a nanobody. In some embodiments, the antigen binding domain of one of the first and the second CAR comprises a camelid VHH domain.

In some embodiments, the antigen binding domain of one of the first and the second CAR comprises an scFv, and the other comprises a single VH domain, for example, a camelid, shark, or lamprey single VH domain, or a single VH domain derived from a human or mouse sequence. In some embodiments, the antigen binding domain of one of the first and the second CAR comprises an scFv, and the other comprises a nanobody. In some embodiments, the antigen binding domain of one of the first and the second CAR comprises an scFv, and the other comprises a camelid VHH domain.

In some embodiments, when present on the surface of a cell, binding of the antigen binding domain of the first CAR to its cognate antigen is not substantially reduced by the presence of the second CAR. In some embodiments, binding of the antigen binding domain of the first CAR to its cognate antigen in the presence of the second CAR is at least 85%, 90%, 95%, 96%, 97%, 98% or 99%, for example, 85%, 90%, 95%, 96%, 97%, 98% or 99% of binding of the antigen binding domain of the first CAR to its cognate antigen in the absence of the second CAR.

In some embodiments, when present on the surface of a cell, the antigen binding domains of the first and the second CAR, associate with one another less than if both were scFv antigen binding domains. In some embodiments, the antigen binding domains of the first and the second CAR, associate with one another at least 85%, 90%, 95%, 96%, 97%, 98% or 99% less than, for example, 85%, 90%, 95%, 96%, 97%, 98% or 99% less than if both were scFv antigen binding domains.

Co-Expression of an Agent that Enhances CAR Activity

In some embodiments, the CAR-expressing cell described herein can further express another agent, for example, an agent that enhances the activity or fitness of a CAR-expressing cell.

For example, in some embodiments, the agent can be an agent which inhibits a molecule that modulates or regulates, for example, inhibits, T cell function. In some embodiments, the molecule that modulates or regulates T cell function is an inhibitory molecule. Inhibitory molecules, for example, PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGF beta.

In embodiments, an agent, for example, an inhibitory nucleic acid, for example, a dsRNA, for example, an siRNA or shRNA; or for example, an inhibitory protein or system, for example, a clustered regularly interspaced short palindromic repeats (CRISPR), a transcription-activator like effector nuclease (TALEN), or a zinc finger endonuclease (ZFN), for example, as described herein, can be used to inhibit expression of a molecule that modulates or regulates, for example, inhibits, T-cell function in the CAR-expressing cell. In some embodiments the agent is an shRNA, for example, an shRNA described herein. In some embodiments, the agent that modulates or regulates, for example, inhibits, T-cell function is inhibited within a CAR-expressing cell. For example, a dsRNA molecule that inhibits expression of a molecule that modulates or regulates, for example, inhibits, T-cell function is linked to the nucleic acid that encodes a component, for example, all of the components, of the CAR.

In some embodiments, the agent which inhibits an inhibitory molecule comprises a first polypeptide, for example, an inhibitory molecule, associated with a second polypeptide that provides a positive signal to the cell, for example, an intracellular signaling domain described herein. In some embodiments, the agent comprises a first polypeptide, for example, of an inhibitory molecule such as PD1, PD-L1, CTLA4, TIM3, LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, or TGF beta, or a fragment of any of these (for example, at least a portion of an extracellular domain of any of these), and a second polypeptide which is an intracellular signaling domain described herein (for example, comprising a costimulatory domain (for example, 41BB, CD27 or CD28, for example, as described herein) and/or a primary signaling domain (for example, a CD3 zeta signaling domain described herein). In some embodiments, the agent comprises a first polypeptide of PD1 or a fragment thereof (for example, at least a portion of an extracellular domain of PD1), and a second polypeptide of an intracellular signaling domain described herein (for example, a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In some embodiments, the agent comprises the extracellular domain (ECD) of an inhibitory molecule, for example, Programmed Death 1 (PD1), can be fused to a transmembrane domain and intracellular signaling domains such as 41BB and CD3 zeta (also referred to herein as a PD1 CAR). In some embodiments, the PD1 CAR, when used in combinations with an XCAR described herein, improves the persistence of the T cell. In some embodiments, the CAR is a PD1 CAR comprising the extracellular domain of PD1 indicated as underlined in SEQ ID NO: 24. In some embodiments, the PD1 CAR comprises the amino acid sequence of SEQ ID NO: 24.

In some embodiments, the PD1 CAR comprises the amino acid sequence of SEQ ID NO: 22.

In some embodiments, the agent comprises a nucleic acid sequence encoding the PD1 CAR, for example, the PD1 CAR described herein. In some embodiments, the nucleic acid sequence for the PD1 CAR is provided as SEQ ID NO: 23, with the PD1 ECD underlined.

In another example, in some embodiments, the agent which enhances the activity of a CAR-expressing cell can be a costimulatory molecule or costimulatory molecule ligand. Examples of costimulatory molecules include MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83., for example, as described herein. Examples of costimulatory molecule ligands include CD80, CD86, CD40L, ICOSL, CD70, OX40L, 4-1BBL, GITRL, and LIGHT. In embodiments, the costimulatory molecule ligand is a ligand for a costimulatory molecule different from the costimulatory molecule domain of the CAR. In embodiments, the costimulatory molecule ligand is a ligand for a costimulatory molecule that is the same as the costimulatory molecule domain of the CAR. In some embodiments, the costimulatory molecule ligand is 4-1BBL. In some embodiments, the costimulatory ligand is CD80 or CD86. In some embodiments, the costimulatory molecule ligand is CD70. In embodiments, a CAR-expressing immune effector cell described herein can be further engineered to express one or more additional costimulatory molecules or costimulatory molecule ligands.

Co-expression of CAR with a Chemokine Receptor In embodiments, the CAR-expressing cell described herein, for example, CD19 CAR-expressing cell, further comprises a chemokine receptor molecule. Transgenic expression of chemokine receptors CCR2b or CXCR2 in T cells enhances trafficking to CCL2- or CXCL1-secreting solid tumors including melanoma and neuroblastoma (Craddock et al., J Immunother. 2010 October; 33(8):780-8 and Kershaw et al., Hum Gene Ther. 2002 Nov. 1; 13(16):1971-80). Thus, without wishing to be bound by theory, it is believed that chemokine receptors expressed in CAR-expressing cells that recognize chemokines secreted by tumors, for example, solid tumors, can improve homing of the CAR-expressing cell to the tumor, facilitate the infiltration of the CAR-expressing cell to the tumor, and enhances antitumor efficacy of the CAR-expressing cell. The chemokine receptor molecule can comprise a naturally occurring or recombinant chemokine receptor or a chemokine-binding fragment thereof. A chemokine receptor molecule suitable for expression in a CAR-expressing cell (for example, CAR–Tx) described herein include a CXC chemokine receptor (for example, CXCR1, CXCR2, CXCR3, CXCR4, CXCR5, CXCR6, or CXCR7), a CC chemokine receptor (for example, CCR1, CCR2, CCR3, CCR4, CCR5, CCR6, CCR7, CCR8, CCR9, CCR10, or CCR11), a CX3C chemokine receptor (for example, CX3CR1), a XC chemokine receptor (for example, XCR1), or a chemokine-binding fragment thereof. In some embodiments, the chemokine receptor molecule to be expressed with a CAR described herein is selected based on the chemokine(s) secreted by the tumor. In some embodiments, the CAR-expressing cell described herein further comprises, for example, expresses, a CCR2b receptor or a CXCR2 receptor. In some embodiments, the CAR described herein and the chemokine receptor molecule are on the same vector or are on two different vectors. In embodiments where the CAR described herein and the chemokine receptor molecule are on the same vector, the CAR and the chemokine receptor molecule are each under control of two different promoters or are under the control of the same promoter.

Nucleic Acid Constructs Encoding a CAR

The present invention also provides an immune effector cell, for example, made by a method described herein, that includes a nucleic acid molecule encoding one or more CAR constructs described herein. In some embodiments, the nucleic acid molecule is provided as a messenger RNA transcript. In some embodiments, the nucleic acid molecule is provided as a DNA construct.

The nucleic acid molecules described herein can be a DNA molecule, an RNA molecule, or a combination thereof. In some embodiments, the nucleic acid molecule is an mRNA encoding a CAR polypeptide as described herein. In other embodiments, the nucleic acid molecule is a vector that includes any of the aforesaid nucleic acid molecules.

In some embodiments, the antigen binding domain of a CAR of the invention (for example, a scFv) is encoded by a nucleic acid molecule whose sequence has been codon optimized for expression in a mammalian cell. In some embodiments, entire CAR construct of the invention is encoded by a nucleic acid molecule whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, for example, methods disclosed in at least U.S. Pat. Nos. 5,786,464 and 6,114,148.

Accordingly, in some embodiments, an immune effector cell, for example, made by a method described herein, includes a nucleic acid molecule encoding a chimeric antigen receptor (CAR), wherein the CAR comprises an antigen binding domain that binds to a tumor antigen described herein, a transmembrane domain (for example, a transmembrane domain described herein), and an intracellular signaling domain (for example, an intracellular signaling domain described herein) comprising a stimulatory domain, for example, a costimulatory signaling domain (for example, a costimulatory signaling domain described herein) and/or a primary signaling domain (for example, a primary signaling domain described herein, for example, a zeta chain described herein).

The present invention also provides vectors in which a nucleic acid molecule encoding a CAR, for example, a nucleic acid molecule described herein, is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, for example, a gammaretroviral vector. A gammaretroviral vector may include, for example, a promoter, a packaging signal (ψ), a primer binding site (PBS), one or more (for example, two) long terminal repeats (LTR), and a transgene of interest, for example, a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, for example, in Tobias Maetzig et al., "Gammaretroviral Vectors: Biology, Technology and Application" Viruses. 2011 June; 3(6): 677-713.

In some embodiments, the vector comprising the nucleic acid encoding the desired CAR is an adenoviral vector (A5/35). In some embodiments, the expression of nucleic acids encoding CARs can be accomplished using of transposons such as sleeping beauty, crisper, CAS9, and zinc finger nucleases. See below June et al. 2009Nature Reviews Immunology 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (for example, WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used.

A number of adenovirus vectors are known in the art. In some embodiments, lentivirus vectors are used. Additional promoter elements, for example, enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription. Exemplary promoters include the CMV IE gene, EF-1α, ubiquitin C, or phosphoglycerokinase (PGK) promoters.

An example of a promoter that is capable of expressing a CAR encoding nucleic acid molecule in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from nucleic acid molecules cloned into a lentiviral vector. See, for example, Milone et al., Mol. Ther. 17(8): 1453-1464 (2009). In some embodiments, the EF1a promoter comprises the sequence provided in the Examples.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (for example, a PGK promoter with one or more, for example, 1, 2, 5, 10, 100, 200, 300, or 400, nucleotide deletions when compared to the wild-type PGK promoter sequence) may be desired.

The nucleotide sequences of exemplary PGK promoters are provided below.

WT PGK Promoter:

(SEQ ID NO: 190)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

GGCGACGAGAGCCGCGCGGGACGACTCGTCGGCGATAACCGGTGTCGGG

TAGCGCCAGCCGCGCGACGGTAACGAGGGACCGCGACAGGCAGACGCTC

CCATGATCACTCTGCACGCCGAAGGCAAATAGTGCAGGCCGTGCGGCGC

TTGGCGTTCCTTGGAAGGGCTGAATCCCCGCCTCGTCCTTCGCAGCGGC

CCCCCGGGTGTTCCCATCGCCGCTTCTAGGCCCACTGCGACGCTTGCCT

GCACTTCTTACACGCTCTGGGTCCCAGCCGCGGCGACGCAAAGGGCCTT

GGTGCGGGTCTCGTCGGCGCAGGGACGCGTTTGGGTCCCGACGGAACCT

TTTCCGCGTTGGGGTTGGGGCACCATAAGCT

Exemplary truncated PGK Promoters:

PGK100:

ACCCCTCTCTCCAGC-CACTAAGCCAGTTGCTCCCTCGGCTGACGGCT-GCACGCGAG GCCTCCGAACGTCT-TACGCCTTGTGGCGCGCCCGTCCTTGTCCCGGG-TGTGATGGCGGGGT G (SEQ ID NO: 198)

PGK200:

ACCCCTCTCTCCAGC-CACTAAGCCAGTTGCTCCCTCGGCTGACGGC-TGCACGCGAG GCCTCCGAACGTCT-TACGCCTTGTGGCGCGCCCGTCCTTGTCCCGGGT-GTGATGGCGGGGT GTGGGGCG-GAGGGCGTGGCGGG-GAAGGGCCGGCGACGAGAGCCGCGCGGGACG-ACTCGT CGGCGA-TAACCGGTGTCGGGTAGCGCCAGCCGCGCGACG-GTAACG (SEQ ID NO: 191)

PGK300:

(SEQ ID NO: 192)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

GGCGACGAGAGCCGCGCGGGACGACTCGTCGGCGATAACCGGTGTCGGG

TAGCGCCAGCCGCGCGACGGTAACGAGGGACCGCGACAGGCAGACGCTC

CCATGATCACTCTGCACGCCGAAGGCAAATAGTGCAGGCCGTGCGGCGC

TTGGCGTTCCTTGGAAGGGCTGAATCCCCG

PGK400:

(SEQ ID NO: 193)
ACCCCTCTCTCCAGCCACTAAGCCAGTTGCTCCCTCGGCTGACGGCTGC

ACGCGAGGCCTCCGAACGTCTTACGCCTTGTGGCGCGCCCGTCCTTGTC

CCGGGTGTGATGGCGGGGTGTGGGGCGGAGGGCGTGGCGGGGAAGGGCC

-continued

GGCGACGAGAGCCGCGCGGGACGACTCGTCGGCGATAACCGGTGTCGGG

TAGCGCCAGCCGCGCGACGGTAACGAGGGACCGCGACAGGCAGACGCTC

CCATGATCACTCTGCACGCCGAAGGCAAATAGTGCAGGCCGTGCGGCGC

TTGGCGTTCCTTGGAAGGGCTGAATCCCCGCCTCGTCCTTCGCAGCGGC

CCCCCGGGTGTTCCCATCGCCGCTTCTAGGCCCACTGCGACGCTTGCCT

GCACTTCTTACACGCTCTGGGTCCCAGCCG

A vector may also include, for example, a signal sequence to facilitate secretion, a polyadenylation signal and transcription terminator (for example, from Bovine Growth Hormone (BGH) gene), an element allowing episomal replication and replication in prokaryotes (for example SV40 origin and ColE1 or others known in the art) and/or elements to allow selection (for example, ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, for example, enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (for example, Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In embodiments, the vector may comprise two or more nucleic acid sequences encoding a CAR, for example, a CAR described herein, for example, a CD19 CAR, and a second CAR, for example, an inhibitory CAR or a CAR that specifically binds to an antigen other than CD19. In such embodiments, the two or more nucleic acid sequences encoding the CAR are encoded by a single nucleic molecule in the same frame and as a single polypeptide chain. In some embodiments, the two or more CARs, can, for example, be separated by one or more peptide cleavage sites. (for example, an auto-cleavage site or a substrate for an intracellular protease). Examples of peptide cleavage sites include T2A, P2A, E2A, or F2A sites.

Methods of introducing and expressing genes into a cell are known in the art. In the context of an expression vector, the vector can be readily introduced into a host cell, for example, mammalian, bacterial, yeast, or insect cell by any method, for example, one known in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A suitable method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, for example, human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (for example, an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In some embodiments, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid.

Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant nucleic acid sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, for example, by immunological means (ELISAs and Western blots) or by assays described herein to identify agents falling within the scope of the invention.

RNA Transfection

Disclosed herein are methods for producing an in vitro transcribed RNA CAR. RNA CAR and methods of using the same are described, for example, in paragraphs 553-570 of in International Application WO2015/142675, filed Mar. 13, 2015, which is herein incorporated by reference in its entirety.

An immune effector cell can include a CAR encoded by a messenger RNA (mRNA). In some embodiments, the mRNA encoding a CAR described herein is introduced into an immune effector cell, for example, made by a method described herein, for production of a CAR-expressing cell.

In some embodiments, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR described herein. For example, the template for the RNA CAR comprises an extracellular region comprising a single chain variable domain of an antibody to a tumor associated antigen described herein; a hinge region (for example, a hinge region described herein), a transmembrane domain (for example, a transmembrane domain described herein such as a transmembrane domain of CD8a); and a cytoplasmic region that includes an intracellular signaling domain, for example, an intracellular signaling domain described herein, for example, comprising the signaling domain of CD3-zeta and the signaling domain of 4-1BB.

In some embodiments, the DNA to be used for PCR contains an open reading frame. The DNA can be from a naturally occurring DNA sequence from the genome of an organism. In some embodiments, the nucleic acid can include some or all of the 5' and/or 3' untranslated regions (UTRs). The nucleic acid can include exons and introns. In some embodiments, the DNA to be used for PCR is a human nucleic acid sequence. In some embodiments, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In some embodiments, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA in embodiments has 5' and 3' UTRs. In some embodiments, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In some embodiments, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In some embodiments, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In some embodiments, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of poly(A)/T stretches into a DNA template is molecular cloning. However, poly(A)/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with poly(A)/T 3' stretch without cloning highly desirable.

The poly(A)/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In some embodiments, the poly(A) tail is between 100 and 5000 adenosines (for example, SEQ ID NO: 33).

Poly(A) tails of RNAs can be further extended following in vitro transcription with the use of a poly(A) polymerase, such as *E. coli* poly(A) polymerase (E-PAP). In some embodiments, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. 5' caps on also provide stability to RNA molecules. In some embodiments, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some embodiments, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac™ (PB) transposon system. See, for example, Aronovich et al. Hum. Mol. Genet. 20.R1(2011): R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013):166; Williams. Molecular Therapy 16.9 (2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, for example, Aronovich et al. supra.

Exemplary transposons include a pT2-based transposon. See, for example, Grabundzija et al. Nucleic Acids Res. 41.3(2013):1829-47; and Singh et al. Cancer Res. 68.8 (2008): 2961-2971, all of which are incorporated herein by reference. Exemplary transposases include a Tc1/mariner-type transposase, for example, the SB10 transposase or the SB11 transposase (a hyperactive transposase which can be expressed, for example, from a cytomegalovirus promoter). See, for example, Aronovich et al.; Kebriaei et al.; and Grabundzija et al., all of which are incorporated herein by reference.

Use of the SBTS permits efficient integration and expression of a transgene, for example, a nucleic acid encoding a CAR described herein. Provided herein are methods of generating a cell, for example, T cell or NK cell, that stably expresses a CAR described herein, for example, using a transposon system such as SBTS.

In accordance with methods described herein, in some embodiments, one or more nucleic acids, for example, plasmids, containing the SBTS components are delivered to a cell (for example, T or NK cell). For example, the nucleic acid(s) are delivered by standard methods of nucleic acid (for example, plasmid DNA) delivery, for example, methods described herein, for example, electroporation, transfection, or lipofection. In some embodiments, the nucleic acid contains a transposon comprising a transgene, for example, a nucleic acid encoding a CAR described herein. In some embodiments, the nucleic acid contains a transposon comprising a transgene (for example, a nucleic acid encoding a CAR described herein) as well as a nucleic acid sequence encoding a transposase enzyme. In other embodiments, a system with two nucleic acids is provided, for example, a dual-plasmid system, for example, where a first plasmid contains a transposon comprising a transgene, and a second plasmid contains a nucleic acid sequence encoding a transposase enzyme. For example, the first and the second nucleic acids are co-delivered into a host cell.

In some embodiments, cells, for example, T or NK cells, are generated that express a CAR described herein by using a combination of gene insertion using the SBTS and genetic editing using a nuclease (for example, Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, for example, T or NK cells, and direct infusion of the cells into a subject. Advantages of non-viral vectors include but are not limited to the ease and relatively low cost of producing sufficient amounts required to meet a patient population, stability during storage, and lack of immunogenicity.

Methods of Manufacture/Production

The present invention also provides methods of making a cell disclosed herein, e.g., methods of engineering a T cell or NK cell to express a nucleic acid molecule encoding one or more CAR constructs described herein. In some embodiments, the manufacturing methods disclosed herein are used to manufacture a cell comprising a nucleic acid molecule encoding two CARs disclosed herein (e.g., an anti-BCMA CAR and an anti-CD19 CAR disclosed herein). In some embodiments, the manufacturing methods disclosed herein are used to manufacture a cell comprising a nucleic acid molecule encoding a diabody CAR disclosed herein, e.g., an anti-BCMA/anti-CD19 diabody CAR disclosed herein. In some embodiments, the manufacturing methods disclosed herein are used to manufacture a cell comprising two nucleic acid molecules, each of which encodes a CAR disclosed herein (e.g., one nucleic acid molecule encoding an anti-BCMA CAR and one nucleic acid molecule encoding an anti-CD19 CAR). In some embodiments, provided herein is a population of cells (for example, immune effector cells, for example, T cells or NK cells) made by any of the manufacturing processes described herein.

Activation Process

In some embodiments, the methods disclosed herein may manufacture immune effector cells engineered to express one or more CARs in less than 24 hours. Without wishing to be bound by theory, the methods provided herein preserve the undifferentiated phenotype of T cells, such as naïve T cells, during the manufacturing process. These CAR-expressing cells with an undifferentiated phenotype may persist longer and/or expand better in vivo after infusion. In some embodiments, CART cells produced by the manufacturing methods provided herein comprise a higher percentage of stem cell memory T cells, compared to CART cells produced by the traditional manufacturing process, e.g., as measured using scRNA-seq (e.g., as measured using methods described in Example 7 with respect to FIG. 25A). In some embodiments, CART cells produced by the manufacturing methods provided herein comprise a higher percentage of effector T cells, compared to CART cells produced by the traditional manufacturing process, e.g., as measured using scRNA-seq (e.g., as measured using methods described in Example 7 with respect to FIG. 25B). In some embodiments, CART cells produced by the manufacturing methods provided herein better preserve the stemness of T cells, compared to CART cells produced by the traditional manufacturing process, e.g., as measured using scRNA-seq (e.g., as measured using methods described in Example 7 with respect to FIG. 25C). In some embodiments, CART cells produced by the manufacturing methods provided herein show a lower level of hypoxia, compared to CART cells produced by the traditional manufacturing process, e.g., as measured using scRNA-seq (e.g., as measured using methods described in Example 7 with respect to FIG. 25D). In some embodiments, CART cells produced by the manufacturing methods provided herein show a lower level of autophagy, compared to CART cells produced by the traditional manufacturing process, e.g., as measured using scRNA-seq (e.g., as measured using methods described in Example 7 with respect to FIG. 25E). In some embodiments, the immune effector cells are engineered to comprise a nucleic acid molecule encoding two CARs disclosed herein (e.g., an anti-BCMA CAR and an anti-CD19 CAR disclosed herein). In some embodiments, the immune effector cells are engineered to comprise a nucleic acid molecule encoding a diabody CAR disclosed herein, e.g., an anti-BCMA/anti-CD19 diabody CAR disclosed herein. In some embodiments, the immune effector cells are engineered to comprise two nucleic acid molecules, each of which encodes a CAR disclosed herein (e.g., one nucleic acid molecule encoding an anti-BCMA CAR and one nucleic acid molecule encoding an anti-CD19 CAR).

In some embodiments, the methods disclosed herein do not involve using a bead, such as Dynabeads® (for example, CD3/CD28 Dynabeads®), and do not involve a de-beading step. In some embodiments, the CART cells manufactured by the methods disclosed herein may be administered to a subject with minimal ex vivo expansion, for example, less than 1 day, less than 12 hours, less than 8 hours, less than 6 hours, less than 4 hours, less than 3 hours, less than 2 hours, less than 1 hour, or no ex vivo expansion. Accordingly, the methods described herein provide a fast manufacturing process of making improved CAR-expressing cell products for use in treating a disease in a subject.

In some embodiments, the present disclosure provides methods of making a population of cells (for example, T cells) that express a chimeric antigen receptor (CAR) (e.g., one or more CARs, e.g., two CARs) comprising: (i) contacting a population of cells (for example, T cells, for example, T cells isolated from a frozen or fresh leukapheresis product) with an agent that stimulates a CD3/TCR complex and/or an agent that stimulates a costimulatory molecule on the surface of the cells; (ii) contacting the population of cells (for example, T cells) with a nucleic acid molecule(s) (for example, a DNA or RNA molecule) encoding the CAR(s), thereby providing a population of cells (for example, T cells) comprising the nucleic acid molecule, and (iii) harvesting the population of cells (for example, T cells) for storage (for example, reformulating the population of cells in cryopreservation media) or administration, wherein: (a) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 26 hours after the beginning of step (i), for example, no later than 22, 23, or 24 hours after the beginning of step (i), for example, no later than 24 hours after the beginning of step (i); (b) step (ii) is performed together with step (i) or no later than 20 hours after the beginning of step (i), for example, no later than 12, 13, 14, 15, 16, 17, or 18 hours after the beginning of step (i), for example, no later than 18 hours after the beginning of step (i), and step (iii) is performed no later than 30 hours after the beginning of step (ii), for example, no later than 22, 23, 24, 25, 26, 27, 28, 29, or 30 hours after the beginning of step (ii); or (c) the population of cells from step (iii) are not expanded, or expanded by no more than 5, 10, 15, 20, 25, 30, 35, or 40%, for example, no more than 10%, for example, as assessed by the number of living cells, compared to the population of cells at the beginning of step (i). In some embodiments, the nucleic acid molecule in step (ii) is a DNA molecule. In some embodiments, the nucleic acid molecule in step (ii) is an RNA molecule. In some embodiments, the nucleic acid molecule in step (ii) is on a viral vector, for example, a viral vector chosen from a lentivirus vector, an adenoviral vector, or a retrovirus vector. In some embodiments, the nucleic acid molecule in step (ii) is on a non-viral vector. In some embodiments, the nucleic acid molecule in step (ii) is on a plasmid. In some embodiments, the nucleic acid molecule in step (ii) is not on any vector. In some embodiments, step (ii)

comprises transducing the population of cells (for example, T cells) a viral vector(s) comprising a nucleic acid molecule encoding the CAR(s).

In some embodiments, the population of cells (for example, T cells) is collected from an apheresis sample (for example, a leukapheresis sample) from a subject.

In some embodiments, the apheresis sample (for example, a leukapheresis sample) is collected from the subject and shipped as a frozen sample (for example, a cryopreserved sample) to a cell manufacturing facility. Then the frozen apheresis sample is thawed, and T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the activation process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject and shipped as a fresh product (for example, a product that is not frozen) to a cell manufacturing facility. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the activation process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then shipped as a frozen sample (for example, a cryopreserved sample) to a cell manufacturing facility. The selected T cells (for example, CD4+ T cells and/or CD8+ T cells) are later thawed and seeded for CART manufacturing using the activation process described herein.

In some embodiments, cells (for example, T cells) are contacted with anti-CD3 and anti-CD28 antibodies for, for example, 12 hours, followed by transduction with a vector (for example, a lentiviral vector) (e.g. one or more vectors) encoding a CAR (e.g. one or more CARs). 24 hours after culture initiation, the cells are washed and formulated for storage or administration.

Without wishing to be bound by theory, brief CD3 and CD28 stimulation may promote efficient transduction of self-renewing T cells. Compared to traditional CART manufacturing approaches, the activation process provided herein does not involve prolonged ex vivo expansion. Similar to the cytokine process, the activation process provided herein also preserves undifferentiated T cells during CART manufacturing.

In some embodiments, the population of cells is contacted with an agent that stimulates a CD3/TCR complex and/or an agent that stimulates a costimulatory molecule on the surface of the cells.

In some embodiments, the agent that stimulates a CD3/TCR complex is an agent that stimulates CD3. In some embodiments, the agent that stimulates a costimulatory molecule is an agent that stimulates CD28, ICOS, CD27, HVEM, LIGHT, CD40, 4-1BB, OX40, DR3, GITR, CD30, TIM1, CD2, CD226, or any combination thereof. In some embodiments, the agent that stimulates a costimulatory molecule is an agent that stimulates CD28. In some embodiments, the agent that stimulates a CD3/TCR complex is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a CD3/TCR complex is an antibody. In some embodiments, the agent that stimulates a CD3/TCR complex is an anti-CD3 antibody. In some embodiments, the agent that stimulates a costimulatory molecule is chosen from an antibody (for example, a single-domain antibody (for example, a heavy chain variable domain antibody), a peptibody, a Fab fragment, or a scFv), a small molecule, or a ligand (for example, a naturally-existing, recombinant, or chimeric ligand). In some embodiments, the agent that stimulates a costimulatory molecule is an antibody. In some embodiments, the agent that stimulates a costimulatory molecule is an anti-CD28 antibody. In some embodiments, the agent that stimulates a CD3/TCR complex or the agent that stimulates a costimulatory molecule does not comprise a bead. In some embodiments, the agent that stimulates a CD3/TCR complex comprises an anti-CD3 antibody covalently attached to a colloidal polymeric nanomatrix. In some embodiments, the agent that stimulates a costimulatory molecule comprises an anti-CD28 antibody covalently attached to a colloidal polymeric nanomatrix. In some embodiments, the agent that stimulates a CD3/TCR complex and the agent that stimulates a costimulatory molecule comprise T Cell TransAct™.

In some embodiments, the matrix comprises or consists of a polymeric, for example, biodegradable or biocompatible inert material, for example, which is non-toxic to cells. In some embodiments, the matrix is composed of hydrophilic polymer chains, which obtain maximal mobility in aqueous solution due to hydration of the chains. In some embodiments, the mobile matrix may be of collagen, purified proteins, purified peptides, polysaccharides, glycosaminoglycans, or extracellular matrix compositions. A polysaccharide may include for example, cellulose ethers, starch, gum arabic, agarose, dextran, chitosan, hyaluronic acid, pectins, xanthan, guar gum or alginate. Other polymers may include polyesters, polyethers, polyacrylates, polyacrylamides, polyamines, polyethylene imines, polyquaternium polymers, polyphosphazenes, polyvinylalcohols, polyvinylacetates, polyvinylpyrrolidones, block copolymers, or polyurethanes. In some embodiments, the mobile matrix is a polymer of dextran.

In some embodiments, the population of cells is contacted with a nucleic acid molecule (e.g. one or more nucleic acid molecules) encoding a CAR (e.g. one or more CARs). In some embodiments, the population of cells is transduced with a DNA molecule (e.g. one or more DNA molecules) encoding a CAR (e.g. one or more CARs).

In some embodiments, in the case of a co-transduction of two nucleic acid molecules (e.g., lentiviral vectors), each of which encodes a CAR disclosed herein (e.g., one nucleic acid molecule encoding an anti-BCMA CAR and one nucleic acid molecule encoding an anti-CD19 CAR, as disclosed herein), each of the vectors containing nucleic acid molecules encoding the CAR can be added to the reaction mixture (e.g., containing a cell population) at a different multiplicity of infection (MOI).

Without wishing to be bound by theory, it is believed that, in some embodiments, using different MOIs for the vectors containing nucleic acid molecules which encode distinct CAR molecules may affect the final composition of the cellular population. For example, in the case of a co-transduction of a lentiviral vector encoding an anti-BCMA CAR and a lentiviral vector encoding an anti-CD19 CAR, different MOIs can be used to maximize the percent of mono BCMA CART cells and BCMA/CD19 dual CART cells, while resulting in fewer mono CD19 CART cells and untransduced cells.

In some embodiments, in the case of a co-transduction of a lentiviral vector encoding an anti-BCMA CAR and a lentiviral vector encoding an anti-CD19 CAR, a population of cells is contacted with the first viral vector at a multiplicity of infection (MOI) that is higher than, equal to, or less than an MOI at which the population of cells is contacted with the second viral vector. In some embodiments, the population of cells is contacted with the first viral vector at a multiplicity of infection (MOI) that is higher than an MOI at which the population of cells is contacted with the second viral vector.

In some embodiments, the population of cells is contacted with the first viral vector at a first MOI and with the second viral vector at a second MOI, such that a resultant population of cells comprises a first population of cells that comprise the anti-BCMA CAR but not the anti-CD19 CAR, a second population of cells that comprise the anti-CD19 CAR but not the anti-BCMA CAR, and a third population of cells that comprise both the anti-BCMA CAR and the anti-CD19 CAR, wherein:

(a) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10;

(b) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined, e.g., as determined by a method described in Example 10;

(c) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the resultant population, e.g., as determined by a method described in Example 10;

(d) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10; or (e) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second population, e.g., as determined by a method described in Example 10.

In some embodiments, the population of cells is contacted with the second viral vector at an MOI (e.g., an MOI that is sufficiently lower than an MOI at which the population of cells is contacted with the first viral vector, such that in a resultant population of cells:

(a) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10;

(b) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined, e.g., as determined by a method described in Example 10;

(c) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the resultant population, e.g., as determined by a method described in Example 10;

(d) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10; or (e) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second population, e.g., as determined by a method described in Example 10.

In some embodiments, the population of cells is contacted with the first viral vector at a first MOI, and the population of cells is contacted with the second viral vector at a second MOI, such that a resultant population of cells comprises:

(a) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10;

(b) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined, e.g., as determined by a method described in Example 10;

(c) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the resultant population, e.g., as determined by a method described in Example 10;

(d) the total number of viable cells in the second population is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined, e.g., as determined by a method described in Example 10; or (e) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second population, e.g., as determined by a method described in Example 10.

In some embodiments, the population of cells is contacted with:

(a) the first viral vector at an MOI of about 1 to about 10 (e.g., about 2 to about 9, about 3 to about 8, about 4 to about 7, about 5 to about 6, about 1 to about 8, about 1 to about 6, about 1 to about 4, about 8 to about 10, about 6 to about 10, about 4 to about 10, about 1 to about 3, about 2 to about 4, about 3 to about 5, about 4 to about 6, about 5 to about 7, about 6 to about 8, about 7 to about to about 9, about 8 to about 10, about 2.5 to about 5, about 1, about 2, about 3, about 4, about 5, about 6, about 7, about 8, about 9, or about 10);

(b) the second viral vector at an MOI of about 0.1 to about 5 (e.g., about 0.2 to about 4, about 0.3 to about 3, about 0.4 to about 2, about 0.5 to about 1, about 0.6 to about 0.9, about 0.7 to about 0.8, about 0.1 to about 4, about 0.1 to about 3, about 0.1 to about 2, about 0.1 to about 1, about 0.1 to about 0.5, about 4 to about 5, about 3 to about 5, about 2 to about 5, about 1 to about 5, about 0.5 to about 5, about 0.2 to about 5, about 0.1 to about 0.5, about 0.2 to about 1, about 0.5 to about 2, about 1 to about 3, about 2 to about 4, about 3 to about 5, about 0.5 to about 1, about 0.1, about 0.2, about 0.3, about 0.4, about 0.5, about 0.6, about 0.7, about 0.8, about 0.9, about 1, about 2, about 3, about 4, or about 5);

(c) the first viral vector at an MOI that is at least about 10% (e.g., at least about 20%, 30%, 40%, 50%, 60%, 70%, 80%, or 90%) or at least about 1 fold (e.g., at least about 2, 3, 4, 5, 6, 7, 8, 9, 10, 15, 20, 25, 30, 35, 40, 50, 60, 70, 80, 90, or 100 fold, e.g., about 2 to about 50 fold, about 3 to 20 fold, about 5 to about 15 fold, or about 8 to about 10 fold) higher than an MOI at which the population of cells is contacted with the second viral vector; and/or (d) the second viral vector at an MOI that is no more than 1/X, wherein X is 2, 3, 4, 5, 6, 7, 8, 9, 10, 12, 15, 20, 30, 40, 50, 60, 70. 80, 90, or 100, of an MOI at which the population of cells is contacted with the first viral vector.

In some embodiments, the population of cells is contacted with the first viral vector at an MOI of about 2.5 to about 5. In some embodiments, the population of cells is contacted with the second viral vector at an MOI of about 0.5 to about 1.0. In some embodiments, the first viral vector at an MOI that is about 8 to about 10 fold higher than an MOI at which the population of cells is contacted with the second viral vector. In some embodiments, the second viral vector at an MOI that is no more than 1/X, wherein X is 6, 8, 10, or 12, of an MOI at which the population of cells is contacted with the first viral vector.

In some embodiments, in step (ii), the population of cells is contacted with:

(a) the first viral vector at an MOI of between about 4 and about 5 (e.g., about 4.75); and/or (b) the second viral vector at an MOI between about 0.2 and about 1 (e.g., about 0.5).

In some embodiments, in step (ii), the population of cells comprises about $1\times10^8$ to about $5\times10^9$ (e.g., about $2\times10^8$ to about $2\times10^9$ or about $4\times10^8$ to about $1\times10^9$ total viable cells. In some embodiments, the cells are suspended in a culture at a concentration of about $1\times10^6$ to about $1\times10^7$ (e.g., about $2\times10^6$ to about $5\times10^6$ or about $3\times10^6$ to about $4\times10^6$) viable cells/mL.

The precise MOI used for each vector can be adjusted or determined based on a number of factors, including, but not limited to, properties of the batch of viral vector, characteristics of the cells to be transduced, and transduction efficiency. In some embodiments, contacting the population of cells with the nucleic acid molecule(s) encoding the CAR(s) occurs simultaneously with contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 20 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 19 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 18 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 17 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 16 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 15 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 14 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 14 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 13 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 12 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 11 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 10 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 9 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 8 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 7 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 6 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 5 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 4 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 3 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule encoding the CAR(s) occurs no later than 2 hours after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 1 hour after the beginning of contacting the population of cells with the agent that stimulates a CD3/TCR complex and/or the agent that stimulates a costimulatory molecule on the surface of the cells described above. In some embodiments, contacting the population of cells with the nucleic acid molecule(s) encoding the CAR(s) occurs no later than 30 minutes after the beginning of contacting the population of cells with the agent that stimulates a CD3/TCR complex and/or the agent that stimulates a costimulatory molecule on the surface of the cells described above.

In some embodiments, the population of cells is harvested for storage or administration.

In some embodiments, the population of cells is harvested for storage or administration no later than 72, 60, 48, 36, 32, 31, 30, 29, 28, 27, 26, 25, 24, 23, 22, 21, 20, 19, or 18 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 26 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 25 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 24 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 23 hours after the beginning of contacting the population of cells with the agent that stimulates a CD3/TCR complex and/or the agent that stimulates a costimulatory molecule on the surface of the cells described above. In some embodiments, the population of cells is harvested for storage or administration no later than 22 hours after the beginning of contacting the population of cells with the agent that stimulates a CD3/TCR complex and/or the agent that stimulates a costimulatory molecule on the surface of the cells described above.

In some embodiments, the population of cells is not expanded ex vivo.

In some embodiments, the population of cells is expanded by no more than 5, 6, 7, 8, 9, 10, 11, 12, 13, 14, 15, 16, 17, 18, 19, 20, 25, 30, 35, 40, 45, 50, 55, or 60%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 5%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 10%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 15%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 20%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 25%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 30%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 35%, for example, as assessed by the number of living cells, compared to the population of cells before it is contacted with the agent that stimulates a CD3/TCR complex and/or the agent that stimulates a costimulatory molecule on the surface of the cells described above. In some embodiments, the population of cells is expanded by no more than 40%, for example, as assessed by the number of living cells, compared to the population of cells before it is contacted with the agent that stimulates a CD3/TCR complex and/or the agent that stimulates a costimulatory molecule on the surface of the cells described above.

In some embodiments, the population of cells is expanded by no more than 1, 1.5, 2, 2.5, 3, 3.5, 4, 4.5, 5, 6, 7, 8, 9, 10, 11, 12, 16, 20, 24, 36, or 48 hours, for example, as assessed by the number of living cells, compared to the population of cells before it is contacted with the one or more cytokines described above.

In some embodiments, the activation process is conducted in serum free cell media. In some embodiments, the activation process is conducted in cell media comprising one or more cytokines chosen from: IL-2, IL-15 (for example, hetIL-15 (IL15/sIL-15Ra)), or IL-6 (for example, IL-6/sIL-6Ra). In some embodiments, hetIL-15 comprises the amino acid sequence of NWVNVISDLKKIEDLIQSM-HIDATLYTESDVHPSCKVTAMKCFLLELQVISLESG-DASIHDTVEN LIILANNSLSSNGNVTESGCKE-CEELEEKNIKEFLQSFVHIVQMFINTSITCPPPMSVE-HADIWVK SYSLYSRERYICNSGFKRKAGTSSLTECVLNKATN-VAHWTTPSLKCIRDPALVHQRPAPPSTVT TAGVTPQPESLSPSGKEPAASSPSSNNTAAT-TAAIVPGSQLMPSKSPSTGTTEISSHESSHGTPSQT TAKNWELTASASHQPPGVYPQG (SEQ ID NO: 309). In some embodiments, hetIL-15 comprises an amino acid sequence having at least about 70, 75, 80, 85, 90, 95, or 99% identity to SEQ ID NO: 309. In some embodiments, the activation process is conducted in cell media comprising a LSD1 inhibitor. In some embodiments, the activation process is conducted in cell media comprising a MALT1 inhibitor. In some embodiments, the serum free cell media comprises a serum replacement. In some embodiments, the serum replacement is CTS™ Immune Cell Serum Replacement (ICSR). In some embodiments, the level of ICSR can be, for example, up to 5%, for example, about 1%, 2%, 3%, 4%, or 5%. Without wishing to be bound by theory, using cell media, for example, Rapid Media shown in Table 21 or Table 25, comprising ICSR, for example, 2% ICSR, may improve cell viability during a manufacture process described herein.

In some embodiments, the present disclosure provides methods of making a population of cells (for example, T cells) that express a chimeric antigen receptor (CAR) comprising: (a) providing an apheresis sample (for example, a fresh or cryopreserved leukapheresis sample) collected from a subject; (b) selecting T cells from the apheresis sample (for example, using negative selection, positive selection, or selection without beads); (c) seeding isolated T cells at, for example, $1\times10^6$ to $1\times10^7$ cells/mL; (d) contacting T cells with an agent that stimulates T cells, for example, an agent that stimulates a CD3/TCR complex and/or an agent that stimulates a costimulatory molecule on the surface of the cells (for example, contacting T cells with anti-CD3 and/or anti-CD28 antibody, for example, contacting T cells with TransAct); (e) contacting T cells with a nucleic acid molecule(s) (for example, a DNA or RNA molecule) encoding the CAR(s) (for example, contacting T cells with a virus comprising a nucleic acid molecule(s) encoding the CAR(s)) for, for example, 6-48 hours, for example, 20-28 hours; and (f) washing and harvesting T cells for storage (for example, reformulating T cells in cryopreservation media) or administration. In some embodiments, step (f) is performed no later than 30 hours after the beginning of step (d) or (e), for example, no later than 22, 23, 24, 25, 26, 27, 28, 29, or 30 hours after the beginning of step (d) or (e).

In some embodiments, provided herein is a population of cells (for example, immune effector cells, for example, T cells or NK cells) made by any of the manufacturing processes described herein (e.g., the Activation Process described herein).

In some embodiments, the percentage of naïve cells, for example, naïve T cells, for example, CD45RA+CD45RO− CCR7+ T cells, in the population of cells at the end of the manufacturing process (for example, at the end of the cytokine process or the activation process described herein) (1) is the same as, (2) differs, for example, by no more than 4, 5, 6, 7, 8, 9, 10, 11, 12, 13, 14, or 15%, from, or (3) is increased, for example, by at least 5, 6, 7, 8, 9, 10, 11, 12, 13, 14, 15, 16, 17, 18, 19, 20, 21, 22, 23, 24, or 25%, as compared to, the percentage of naïve cells, for example, naïve T cells, for example, CD45RA+CD45RO− CCR7+ cells, in the population of cells at the beginning of the manufacturing process (for example, at the beginning of the cytokine process or the activation process described herein). In some embodiments, the population of cells at the end of the manufacturing process (for example, at the end of the cytokine process or the activation process described herein) shows a higher percentage of naïve cells, for example, naïve T cells, for example, CD45RA+CD45RO− CCR7+ T cells (for example, at least 5, 6, 7, 8, 9, 10, 11, 12, 13, 14, 15, 16, 17, 18, 19, 20, 25, 30, 35, 40, 45, or 50% higher), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the percentage of naïve cells, for example, naïve T cells, for example, CD45RA+CD45RO− CCR7+ T cells, in the population of cells at the end of the manufacturing process (for example, at the end of the cytokine process or the activation process described herein) is not less than 20, 25, 30, 35, 40, 45, 50, 55, or 60%.

In some embodiments, the percentage of central memory cells, for example, central memory T cells, for example, CD95+ central memory T cells, in the population of cells at the end of the manufacturing process (for example, at the end of the cytokine process or the activation process described herein) (1) is the same as, (2) differs, for example, by no more than 4, 5, 6, 7, 8, 9, 10, 11, 12, 13, 14, or 15% from, or (3) is decreased, for example, by at least 5, 6, 7, 8, 9, 10, 11, 12, 13, 14, 15, 16, 17, 18, 19, 20, 21, 22, 23, 24, or 25%, as compared to, the percentage of central memory cells, for example, central memory T cells, for example, CD95+ central memory T cells, in the population of cells at the beginning of the manufacturing process (for example, at the beginning of the cytokine process or the activation process described herein). In some embodiments, the population of cells at the end of the manufacturing process (for example, at the end of the cytokine process or the activation process described herein) shows a lower percentage of central memory cells, for example, central memory T cells, for example, CD95+ central memory T cells (for example, at least 5, 6, 7, 8, 9, 10, 11, 12, 13, 14, 15, 16, 17, 18, 19, 20, 25, 30, 35, 40, 45, or 50% lower), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the percentage of central memory cells, for example, central memory T cells, for example, CD95+ central memory T cells, in the population of cells at the end of the manufacturing process (for example, at the end of the cytokine process or the activation process described herein) is no more than 40, 45, 50, 55, 60, 65, 70, 75, or 80%.

In some embodiments, the population of cells at the end of the manufacturing process (for example, at the end of the cytokine process or the activation process described herein) after being administered in vivo, persists longer or expands at a higher level (for example, at least 20, 25, 30, 35, 40, 45, 50, 55, 60, 65, 70, 75, 80, 85, or 90% higher), compared with cells made by an otherwise similar method which lasts, for example, more than 26 hours (for example, which lasts more than 5, 6, 7, 8, 9, 10, 11, or 12 days) or which involves expanding the population of cells in vitro for, for example, more than 3 days (for example, expanding the population of cells in vitro for 3, 4, 5, 6, 7, 8, 9, 10, 11, 12, 13, 14, or 15 days).

In some embodiments, the population of cells has been enriched for IL6R-expressing cells (for example, cells that are positive for IL6Rα and/or IL6Rβ) prior to the beginning of the manufacturing process (for example, prior to the beginning of the cytokine process or the activation process described herein). In some embodiments, the population of cells comprises, for example, no less than 30, 35, 40, 45, 50, 55, 60, 65, 70, 75, or 80% of IL6R-expressing cells (for example, cells that are positive for IL6Rα and/or IL6Rβ) at the beginning of the manufacturing process (for example, at the beginning of the cytokine process or the activation process described herein).

Cytokine Process

In some embodiments, the present disclosure provides methods of making a population of cells (for example, T cells) that express a chimeric antigen receptor (CAR) (e.g., one or more CARs, e.g., two CARs) comprising: (1) contacting a population of cells with a cytokine chosen from IL-2, IL-7, IL-15, IL-21, IL-6, or a combination thereof, (2) contacting the population of cells (for example, T cells) with a nucleic acid molecule(s) (for example, a DNA or RNA molecule) encoding the CAR(s), thereby providing a population of cells (for example, T cells) comprising the nucleic acid molecule, and (3) harvesting the population of cells (for example, T cells) for storage (for example, reformulating the population of cells in cryopreservation media) or administration, wherein: (a) step (2) is performed together with step (1) or no later than 5 hours after the beginning of step (1), for example, no later than 1, 2, 3, 4, or 5 hours after the beginning of step (1), and step (3) is performed no later than 26 hours after the beginning of step (1), for example, no later than 22, 23, or 24 hours after the beginning of step (1), for example, no later than 24 hours after the beginning of step (1), or (b) the population of cells from step (3) are not expanded, or expanded by no more than 5, 10, 15, 20, 25, 30, 35, or 40%, for example, no more than 10%, for example, as assessed by the number of living cells, compared to the population of cells at the beginning of step (1). In some embodiments, the nucleic acid molecule in step (2) is a DNA molecule. In some embodiments, the nucleic acid molecule in step (2) is an RNA molecule. In some embodiments, the nucleic acid molecule in step (2) is on a viral vector, for example, a viral vector chosen from a lentivirus vector, an adenoviral vector, or a retrovirus vector. In some embodiments, the nucleic acid molecule in step (2) is on a non-viral vector. In some embodiments, the nucleic acid molecule in step (2) is on a plasmid. In some embodiments, the nucleic acid molecule in step (2) is not on any vector. In some embodiments, step (2) comprises transducing the population of cells (for example, T cells) with a viral vector comprising a nucleic acid molecule(s) encoding the CAR(s). In some embodiments, the cells are engineered to comprise a nucleic acid molecule encoding two CARs disclosed herein (e.g., an anti-BCMA CAR and an anti-CD19 CAR disclosed herein). In some embodiments, the cells are engineered to comprise a nucleic acid molecule encoding a diabody CAR disclosed herein, e.g., an anti-BCMA/anti-CD19 diabody CAR disclosed herein. In some embodiments, the cells are engineered to comprise two nucleic acid molecules, each of which encodes a CAR disclosed herein (e.g., one nucleic acid molecule encoding an anti-BCMA CAR and one nucleic acid molecule encoding an anti-CD19 CAR).

In some embodiments, the population of cells (for example, T cells) is collected from an apheresis sample (for example, a leukapheresis sample) from a subject.

In some embodiments, the apheresis sample (for example, a leukapheresis sample) is collected from the subject and shipped as a frozen sample (for example, a cryopreserved sample) to a cell manufacturing facility. The frozen apheresis sample is then thawed, and T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the cytokine process described herein. In some embodiments, at the end of the cytokine process, the CAR T cells are cryopreserved and later thawed and administered to the subject. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject and shipped as a fresh product (for example, a product that is not frozen) to a cell manufacturing facility. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then seeded for CART manufacturing using the cytokine process described herein. In some embodiments, the selected T cells (for example, CD4+ T cells and/or CD8+ T cells) undergo one or more rounds of freeze-thaw before being seeded for CART manufacturing.

In some embodiments, the apheresis sample (for example, a leukapheresis sample) is collected from the subject. T cells (for example, CD4+ T cells and/or CD8+ T cells) are selected from the apheresis sample, for example, using a cell sorting machine (for example, a CliniMACS® Prodigy® device). The selected T cells (for example, CD4+ T cells and/or CD8+ T cells) are then shipped as a frozen sample (for example, a cryopreserved sample) to a cell manufacturing facility. The selected T cells (for example, CD4+ T cells and/or CD8+ T cells) are later thawed and seeded for CART manufacturing using the cytokine process described herein.

In some embodiments, after cells (for example, T cells) are seeded, one or more cytokines (for example, one or more cytokines chosen from IL-2, IL-7, IL-15 (for example, hetIL-15 (IL15/sIL-15Ra)), IL-21, or IL-6 (for example, IL-6/sIL-6R)) as well as a vector (for example, a lentiviral vector) (e.g. one or more vectors) encoding a CAR (e.g., one or more CARs) are added to the cells. After incubation for 20-24 hours, the cells are washed and formulated for storage or administration.

Different from traditional CART manufacturing approaches, the cytokine process provided herein does not involve CD3 and/or CD28 stimulation, or ex vivo T cell expansion. T cells that are contacted with anti-CD3 and anti-CD28 antibodies and expanded extensively ex vivo tend to show differentiation towards a central memory phenotype. Without wishing to be bound by theory, the cytokine process provided herein preserves or increases the undifferentiated phenotype of T cells during CART manufacturing, generating a CART product that may persist longer after being infused into a subject.

In some embodiments, the population of cells is contacted with one or more cytokines (for example, one or more cytokines chosen from IL-2, IL-7, IL-15 (for example, hetIL-15 (IL15/sIL-15Ra)), IL-21, or IL-6 (for example, IL-6/sIL-6Ra).

In some embodiments, the population of cells is contacted with IL-2. In some embodiments, the population of cells is contacted with IL-7. In some embodiments, the population of cells is contacted with IL-15 (for example, hetIL-15 (IL15/sIL-15Ra)). In some embodiments, the population of cells is contacted with IL-21. In some embodiments, the population of cells is contacted with IL-6 (for example, IL-6/sIL-6Ra). In some embodiments, the population of cells is contacted with IL-2 and IL-7. In some embodiments, the population of cells is contacted with IL-2 and IL-15 (for example, hetIL-15 (IL15/sIL-15Ra)). In some embodiments, the population of cells is contacted with IL-2 and IL-21. In some embodiments, the population of cells is contacted with IL-2 and IL-6 (for example, IL-6/sIL-6Ra). In some embodiments, the population of cells is contacted with IL-7 and IL-15 (for example, hetIL-15 (IL15/sIL-15Ra)). In some embodiments, the population of cells is contacted with IL-7 and IL-21. In some embodiments, the population of cells is contacted with IL-7 and IL-6 (for example, IL-6/sIL-6Ra). In some embodiments, the population of cells is contacted with IL-15 (for example, hetIL-15 (IL15/sIL-15Ra)) and IL-21. In some embodiments, the population of cells is contacted with IL-15 (for example, hetIL-15 (IL15/sIL-15Ra)) and IL-6 (for example, IL-6/sIL-6Ra). In some embodiments, the population of cells is contacted with IL-21 and IL-6 (for example, IL-6/sIL-6Ra). In some embodiments, the population of cells is contacted with IL-7, IL-15 (for example, hetIL-15 (IL15/sIL-15Ra)), and IL-21. In some embodiments, the population of cells is further contacted with a LSD1 inhibitor. In some embodiments, the population of cells is further contacted with a MALT1 inhibitor.

In some embodiments, the population of cells is contacted with 20, 30, 40, 50, 60, 70, 80, 90, 100, 110, 120, 130, 140, 150, 160, 170, 180, 190, 200, 210, 220, 230, 240, 250, 260, 270, 280, 290, or 300 U/ml of IL-2. In some embodiments, the population of cells is contacted with 1, 2, 3, 4, 5, 6, 7, 8, 9, 10, 11, 12, 13, 14, 15, 16, 17, 18, 19, or 20 ng/ml of IL-7. In some embodiments, the population of cells is contacted with 1, 2, 3, 4, 5, 6, 7, 8, 9, 10, 11, 12, 13, 14, 15, 16, 17, 18, 19, or 20 ng/ml of IL-15.

In some embodiments, the population of cells is contacted with a nucleic acid molecule (e.g. one or more nucleic acid molecules) encoding a CAR (e.g., one or more CARs). In some embodiments, the population of cells is transduced with a DNA molecule (e.g. one or more DNA molecules) encoding a CAR (e.g. one or more CARs).

In some embodiments, contacting the population of cells with the nucleic acid molecule encoding the CAR(s) occurs simultaneously with contacting the population of cells with the one or more cytokines described above. In some embodiments, contacting the population of cells with the nucleic acid molecule encoding the CAR(s) occurs no later than 1, 1.5, 2, 2.5, 3, 3.5, 4, 4.5, 5, 5.5, 6, 6.5, 7, 7.5, 8, 8.5, 9, 9.5 or 10 hours after the beginning of contacting the population of cells with the one or more cytokines described above. In some embodiments, contacting the population of cells with the nucleic acid molecule encoding the CAR(s) occurs no later than 5 hours after the beginning of contacting the population of cells with the one or more cytokines described above. In some embodiments, contacting the population of cells with the nucleic acid molecule encoding the CAR(s) occurs no later than 4 hours after the beginning of contacting the population of cells with the one or more cytokines described above. In some embodiments, contacting the population of cells with the nucleic acid molecule encoding the CAR(s) occurs no later than 3 hours after the beginning of contacting the population of cells with the one or more cytokines described above. In some embodiments, contacting the population of cells with the nucleic acid molecule encoding the CAR(s) occurs no later than 2 hours after the beginning of contacting the population of cells with the one or more cytokines described above. In some embodiments, contacting the population of cells with the nucleic acid molecule encoding the CAR(s) occurs no later than 1 hour after the beginning of contacting the population of cells with the one or more cytokines described above.

In some embodiments, the population of cells is harvested for storage or administration.

In some embodiments, the population of cells is harvested for storage or administration no later than 72, 60, 48, 36, 32, 31, 30, 29, 28, 27, 26, 25, 24, 23, 22, 21, 20, 19, or 18 hours after the beginning of contacting the population of cells with the one or more cytokines described above. In some embodiments, the population of cells is harvested for storage or administration no later than 26 hours after the beginning of contacting the population of cells with the one or more cytokines described above. In some embodiments, the population of cells is harvested for storage or administration no later than 25 hours after the beginning of contacting the population of cells with the one or more cytokines described above. In some embodiments, the population of cells is harvested for storage or administration no later than 24 hours after the beginning of contacting the population of cells with the one or more cytokines described above. In some embodiments, the population of cells is harvested for storage or administration no later than 23 hours after the beginning of contacting the population of cells with the one or more cytokines described above. In some embodiments, the population of cells is harvested for storage or administration no later than 22 hours after the beginning of contacting the population of cells with the one or more cytokines described above.

In some embodiments, the population of cells is not expanded ex vivo.

In some embodiments, the population of cells is expanded by no more than 5, 6, 7, 8, 9, 10, 11, 12, 13, 14, 15, 16, 17, 18, 19, 20, 25, 30, 35, 40, 45, 50, 55, or 60%, for example, as assessed by the number of living cells, compared to the population of cells before it is contacted with the one or more cytokines described above. In some embodiments, the population of cells is expanded by no more than 5%, for example, as assessed by the number of living cells, compared to the population of cells before it is contacted with the one or more cytokines described above. In some embodiments, the population of cells is expanded by no more than 10%, for example, as assessed by the number of living cells, compared to the population of cells before it is contacted with the one or more cytokines described above. In some embodiments, the population of cells is expanded by no more than 15%, for example, as assessed by the number of living cells, compared to the population of cells before it is contacted with the one or more cytokines described above. In some embodiments, the population of cells is expanded by no more than 20%, for example, as assessed by the number of living cells, compared to the population of cells before it is contacted with the one or more cytokines described above. In some embodiments, the population of cells is expanded by no more than 25%, for example, as assessed by the number of living cells, compared to the population of cells before it is contacted with the one or more cytokines described above. In some embodiments, the population of cells is expanded by no more than 30%, for example, as assessed by the number of living cells, compared to the population of cells before it is contacted with the one or more cytokines described above. In some embodiments, the population of cells is expanded by no more than 35%, for example, as assessed by the number of living cells, compared to the population of cells before it is contacted with the one or more cytokines described above. In some embodiments, the population of cells is expanded by no more than 40%, for example, as assessed by the number of living cells, compared to the population of cells before it is contacted with the one or more cytokines described above.

In some embodiments, the population of cells is expanded by no more than 1, 1.5, 2, 2.5, 3, 3.5, 4, 4.5, 5, 6, 7, 8, 9, 10, 11, 12, 16, 20, 24, 36, or 48 hours, for example, as assessed by the number of living cells, compared to the population of cells before it is contacted with the one or more cytokines described above.

In some embodiments, the population of cells is not contacted in vitro with an agent that stimulates a CD3/TCR complex (for example, an anti-CD3 antibody) and/or an agent that stimulates a costimulatory molecule on the surface of the cells (for example, an anti-CD28 antibody), or if contacted, the contacting step is less than 1, 1.5, 2, 2.5, 3, 3.5, 4, 4.5, or 5 hours.

In some embodiments, the population of cells is contacted in vitro with an agent that stimulates a CD3/TCR complex (for example, an anti-CD3 antibody) and/or an agent that stimulates a costimulatory molecule on the surface of the cells (for example, an anti-CD28 antibody) for 20, 21, 22, 23, 24, 25, 26, 27, or 28 hours.

In some embodiments, the population of cells manufactured using the cytokine process provided herein shows a higher percentage of naïve cells among CAR-expressing cells (for example, at least 5, 6, 7, 8, 9, 10, 11, 12, 13, 14, 15, 16, 17, 18, 19, 20, 25, 30, 35, 40, 45, 50, 55, or 60% higher), compared with cells made by an otherwise similar method which further comprises contacting the population of cells with, for example, an agent that binds a CD3/TCR complex (for example, an anti-CD3 antibody) and/or an agent that binds a costimulatory molecule on the surface of the cells (for example, an anti-CD28 antibody).

In some embodiments, the cytokine process provided herein is conducted in cell media comprising no more than 0, 0.5, 1, 1.5, 2, 2.5, 3, 3.5, 4, 4.5, 5, 5.5, 6, 6.5, 7, 7.5, or 8% serum. In some embodiments, the cytokine process provided herein is conducted in cell media comprising a LSD1 inhibitor, a MALT1 inhibitor, or a combination thereof.

Additional Exemplary Manufacturing Methods

In some embodiments, cells, e.g., T cells or NK cells are activated, e.g., using anti-CD3/anti-CD28 antibody coated Dynabeads®, contacted with one or more nucleic acid molecules encoding a CAR (e.g. one or more CARs) and then expanded in vitro for, for example, 7, 8, 9, 10, or 11 days. In some embodiments, the cells, e.g., T cells or NK cells are selected from a fresh or cryopreserved leukapheresis sample, e.g., using positive or negative selection. In some embodiments, the cells are contacted with a nucleic acid molecule (e.g. one or more nucleic acid molecules) encoding a CAR (e.g. one or more CARs). In some embodiments, the cells are contacted with a nucleic acid molecule encoding two CARs disclosed herein (e.g., an anti-BCMA CAR and an anti-CD19 CAR). In some embodiments, the cells are contacted with two nucleic acid molecules, one expressing a first CAR (e.g., an anti-BCMA CAR) and the other expressing a second CAR (e.g., an anti-CD19 CAR). In some embodiments, the cells are contacted with a nucleic acid molecule encoding a diabody CAR (e.g., an anti-BCMA/anti-CD19 diabody CAR disclosed herein).

Elutriation

In some embodiments, the methods described herein feature an elutriation method that removes unwanted cells, for example, monocytes and blasts, thereby resulting in an improved enrichment of desired immune effector cells suitable for CAR expression. In some embodiments, the elutriation method described herein is optimized for the enrichment of desired immune effector cells suitable for CAR expression from a previously frozen sample, for example, a thawed sample. In some embodiments, the elutriation method described herein provides a preparation of cells with improved purity as compared to a preparation of cells collected from the elutriation protocols known in the art. In some embodiments, the elutriation method described herein includes using an optimized viscosity of the starting sample, for example, cell sample, for example, thawed cell sample, by dilution with certain isotonic solutions (for example, PBS), and using an optimized combination of flow rates and collection volume for each fraction collected by an elutriation device. Exemplary elutriation methods that could be applied in the present invention are described on pages 48-51 of WO 2017/117112, herein incorporated by reference in its entirety.

Density Gradient Centrifugation

Manufacturing of adoptive cell therapeutic product requires processing the desired cells, for example, immune effector cells, away from a complex mixture of blood cells and blood elements present in peripheral blood apheresis starting materials. Peripheral blood-derived lymphocyte samples have been successfully isolated using density gradient centrifugation through Ficoll solution. However, Ficoll is not a preferred reagent for isolating cells for therapeutic use, as Ficoll is not qualified for clinical use. In addition, Ficoll contains glycol, which has toxic potential to the cells. Furthermore, Ficoll density gradient centrifugation of thawed apheresis products after cryopreservation yields a suboptimal T cell product, for example, as described in the Examples herein. For example, a loss of T cells in the final product, with a relative gain of non-T cells, especially undesirable B cells, blast cells and monocytes was observed in cell preparations isolated by density gradient centrifugation through Ficoll solution.

Without wishing to be bound by theory, it is believed that immune effector cells, for example, T cells, dehydrate during cryopreservation to become denser than fresh cells. Without wishing to be bound by theory, it is also believed that immune effector cells, for example, T cells, remain denser longer than the other blood cells, and thus are more readily lost during Ficoll density gradient separation as compared to other cells. Accordingly, without wishing to be bound by theory, a medium with a density greater than Ficoll is believed to provide improved isolation of desired immune effector cells in comparison to Ficoll or other mediums with the same density as Ficoll, for example, 1.077 g/mL.

In some embodiments, the density gradient centrifugation method described herein includes the use of a density gradient medium comprising iodixanol. In some embodiments, the density gradient medium comprises about 60% iodixanol in water.

In some embodiments, the density gradient centrifugation method described herein includes the use of a density gradient medium having a density greater than Ficoll. In some embodiments, the density gradient centrifugation method described herein includes the use of a density gradient medium having a density greater than 1.077 g/mL, for example, greater than 1.077 g/mL, greater than 1.1 g/mL, greater than 1.15 g/mL, greater than 1.2 g/mL, greater than 1.25 g/mL, greater than 1.3 g/mL, greater than 1.31 g/mL. In some embodiments, the density gradient medium has a density of about 1.32 g/mL.

Additional embodiments of density gradient centrifugation are described on pages 51-53 of WO 2017/117112, herein incorporated by reference in its entirety.

Enrichment by Selection

Provided herein are methods for selection of specific cells to improve the enrichment of the desired immune effector cells suitable for CAR expression. In some embodiments, the selection comprises a positive selection, for example, selection for the desired immune effector cells. In some embodiments, the selection comprises a negative selection, for example, selection for unwanted cells, for example, removal of unwanted cells. In embodiments, the positive or negative selection methods described herein are performed under flow conditions, for example, by using a flow-through device, for example, a flow-through device described herein. Exemplary positive and negative selections are described on pages 53-57 of WO 2017/117112, herein incorporated by reference in its entirety. Selection methods can be performed under flow conditions, for example, by using a flow-through device, also referred to as a cell processing system, to further enrich a preparation of cells for desired immune effector cells, for example, T cells, suitable for CAR expression. Exemplary flow-through devices are described on pages 57-70 of WO 2017/117112, herein incorporated by reference in its entirety. Exemplary cell separation and debeading methods are described on pages 70-78 of WO 2017/117112, herein incorporated by reference in its entirety.

Selection procedures are not limited to ones described on pages 57-70 of WO 2017/117112. Negative T cell selection via removal of unwanted cells with CD19, CD14 and CD26 Miltenyi beads in combination with column technology (CliniMACS® Plus or CliniMACS® Prodigy®) or positive T cell selection with a combination of CD4 and CD8 Miltenyi beads and column technology (CliniMACS® Plus or CliniMACS® Prodigy®) can be used. Alternatively, column-free technology with releasable CD3 beads (GE Healthcare) can be used.

In addition, bead-free technologies such as ThermoGenesis X-series devices can be utilized as well.

Clinical Applications

All of the processes herein may be conducted according to clinical good manufacturing practice (cGMP) standards.

The processes may be used for cell purification, enrichment, harvesting, washing, concentration or for cell media exchange, particularly during the collection of raw, starting materials (particularly cells) at the start of the manufacturing process, as well as during the manufacturing process for the selection or expansion of cells for cell therapy.

The cells may include any plurality of cells. The cells may be of the same cell type, or mixed cell types. In addition, the cells may be from one donor, such as an autologous donor or a single allogenic donor for cell therapy. The cells may be obtained from patients by, for example, leukapheresis or apheresis. The cells may include T cells, for example may include a population that has greater than 50% T cells, greater than 60% T cells, greater than 70% T cells, greater than 80% T cells, or 90% T cells.

Selection processes may be particularly useful in selecting cells prior to culture and expansion. For instance, paramagnetic particles coated with anti-CD3 and/or anti CD28 may be used to select T cells for expansion or for introduction of a nucleic acid encoding a chimeric antigen receptor (CAR) or other protein. Such a process is used to produce CTL019 T cells for treatment of acute lymphoblastic leukemia (ALL).

The debeading processes and modules disclosed herein may be particularly useful in the manufacture of cells for cell therapy, for example in purifying cells prior to, or after, culture and expansion. For instance, paramagnetic particles coated with anti-CD3 and/or anti CD28 antibodies may be used to selectively expand T cells, for example T cells that are, or will be, modified by introduction of a nucleic acid encoding a chimeric antigen receptor (CAR) or other protein, such that the CAR is expressed by the T cells. During the manufacture of such T cells, the debeading processes or modules may be used to separate T cells from the paramagnetic particles. Such a debeading process or module is used to produce, for example, CTL019 T cells for treatment of acute lymphoblastic leukemia (ALL).

In one such process, illustrated here by way of example, cells, for example, T cells, are collected from a donor (for example, a patient to be treated with an autologous chimeric antigen receptor T cell product) via apheresis (for example, leukapheresis). Collected cells may then be optionally purified, for example, by an elutriation step, or via positive or negative selection of target cells (for example, T cells). Paramagnetic particles, for example, anti-CD3/anti-CD28-coated paramagnetic particles, may then be added to the cell population, to expand the T cells. The process may also include a transduction step, wherein nucleic acid encoding one or more desired proteins, for example, a CAR, for example a CAR targeting CD19, is introduced into the cell. The nucleic acid may be introduced in a lentiviral vector. The cells, for example, the lentivirally transduced cells, may then be expanded for a period of days, for example, 1, 2, 3, 4, 5, 6, 7, 8, 9, 10, or more days, for example in the presence of a suitable medium. After expansion, the debeading processes/modules disclosed herein may be used to separate the desired T cells from the paramagnetic particles. The process may include one or more debeading steps according to the processes of the present disclosure. The debeaded cells may then be formulated for administration to the patient. Examples of CAR T cells and their manufacture are further described, for example, in WO2012/079000, which is incorporated herein by reference in its entirety. The systems and methods of the present disclosure may be used for any cell separation/purification/debeading processes described in or associated with WO2012/079000. Additional CAR T manufacturing processes are described in, for example, WO2016109410 and WO2017117112, herein incorporated by reference in their entireties.

The systems and methods herein may similarly benefit other cell therapy products by wasting fewer desirable cells, causing less cell trauma, and more reliably removing magnetic and any non-paramagnetic particles from cells with less or no exposure to chemical agents, as compared to conventional systems and methods.

Although only exemplary embodiments of the disclosure are specifically described above, it will be appreciated that modifications and variations of these examples are possible without departing from the spirit and intended scope of the disclosure. For example, the magnetic modules and systems containing them may be arranged and used in a variety of configurations in addition to those described. Besides, non-magnetic modules can be utilized as well. In addition, the systems and methods may include additional components and steps not specifically described herein. For instance, methods may include priming, where a fluid is first introduced into a component to remove bubbles and reduce resistance to cell suspension or buffer movement. Furthermore, embodiments may include only a portion of the systems described herein for use with the methods described herein. For example, embodiments may relate to disposable modules, hoses, etc. usable within non-disposable equipment to form a complete system able to separate or debead cells to produce a cell product.

Additional manufacturing methods and processes that can be combined with the present invention have been described in the art. For example, pages 86-91 of WO 2017/117112 describe improved wash steps and improved manufacturing process.

Sources of Immune Effector Cells

This section provides additional methods or steps for obtaining an input sample comprising desired immune effector cells, isolating and processing desired immune effector cells, for example, T cells, and removing unwanted materials, for example, unwanted cells. The additional methods or steps described in this section can be used in combination with any of the elutriation, density gradient centrifugation, selection under flow conditions, or improved wash step described in the preceding sections.

A source of cells, for example, T cells or natural killer (NK) cells, can be obtained from a subject. Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In some embodiments of the present disclosure, immune effector cells, for example, T cells, can be obtained from a unit of blood collected from a subject using any number of techniques known to the skilled artisan, and any of the methods disclosed herein, in any combination of steps thereof. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and, optionally, to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. In some embodiments, the cells are washed using the improved wash step described herein.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate™, or the Haemonetics Cell Saver 5), Haemonetics Cell Saver Elite (GE Healthcare Sepax or Sefia), or a device utilizing the spinning membrane filtration technology (Fresenius Kabi LOVO), according to the manufacturer's instructions. After washing, the cells may be resuspended in a variety of biocompatible buffers, such as, for example, Ca-free, Mg-free PBS, PlasmaLyte A, PBS-EDTA supplemented with human serum albumin (HSA), or other saline solution with or without buffer. Alternatively, the undesirable components of the apheresis sample may be removed and the cells directly resuspended in culture media.

In some embodiments, desired immune effector cells, for example, T cells, are isolated from peripheral blood lymphocytes by lysing the red blood cells and depleting the monocytes, for example, by centrifugation through a PERCOLL™ gradient or by counterflow centrifugal elutriation.

The methods described herein can include, for example, selection of a specific subpopulation of immune effector cells, for example, T cells, that are a T regulatory cell-depleted population, for example, CD25+ depleted cells or $CD25^{high}$ depleted cells, using, for example, a negative selection technique, for example, described herein. In some embodiments, the population of T regulatory-depleted cells contains less than 30%, 25%, 20%, 15%, 10%, 5%, 4%, 3%, 2%, 1% of CD25+ cells or $CD25^{high}$ cells.

In some embodiments, T regulatory cells, for example, CD25+ T cells or $CD25^{high}$ T cells, are removed from the population using an anti-CD25 antibody, or fragment thereof, or a CD25-binding ligand, for example IL-2. In some embodiments, the anti-CD25 antibody, or fragment thereof, or CD25-binding ligand is conjugated to a substrate, for example, a bead, or is otherwise coated on a substrate, for example, a bead. In some embodiments, the anti-CD25 antibody, or fragment thereof, is conjugated to a substrate as described herein.

In some embodiments, the T regulatory cells, for example, CD25+ T cells or $CD25^{high}$ T cells, are removed from the population using CD25 depleting reagent from Miltenyi™. In some embodiments, the ratio of cells to CD25 depletion reagent is 1e7 cells to 20 μL, or 1e7 cells to 15 μL, or 1e7 cells to 10 μL, or 1e7 cells to 5 μL, or 1e7 cells to 2.5 μL, or 1e7 cells to 1.25 μL. In some embodiments, for example, for T regulatory cells, greater than 500 million cells/ml is used. In some embodiments, a concentration of cells of 600, 700, 800, or 900 million cells/ml is used.

In some embodiments, the population of immune effector cells to be depleted includes about $6 \times 10^9$ CD25+ T cells. In some embodiments, the population of immune effector cells to be depleted include about $1\times10^9$ to $1\times10^{10}$ CD25+ T cell, and any integer value in between. In some embodiments, the resulting population T regulatory-depleted cells has $2\times10^9$ T regulatory cells, for example, CD25+ cells or $CD25^{high}$ cells, or less (for example, $1\times10^9$, $5\times10^8$, $1\times10^8$, $5\times10^7$, $1\times10^7$, or less T regulatory cells).

In some embodiments, the T regulatory cells, for example, CD25+ cells or $CD25^{high}$ cells, are removed from the population using the CliniMAC system with a depletion tubing set, such as, for example, tubing 162-01. In some embodiments, the CliniMAC system is run on a depletion setting such as, for example, DEPLETION2.1.

Without wishing to be bound by a particular theory, decreasing the level of negative regulators of immune cells (for example, decreasing the number of unwanted immune cells, for example, Treg cells), in a subject prior to apheresis or during manufacturing of a CAR-expressing cell product significantly reduces the risk of subject relapse. For example, methods of depleting Treg cells are known in the art. Methods of decreasing Treg cells include, but are not limited to, cyclophosphamide, anti-GITR antibody (an anti-GITR antibody described herein), CD25-depletion, and combinations thereof.

In some embodiments, the manufacturing methods comprise reducing the number of (for example, depleting) Treg cells prior to manufacturing of the CAR-expressing cell. For example, manufacturing methods comprise contacting the sample, for example, the apheresis sample, with an anti-GITR antibody and/or an anti-CD25 antibody (or fragment thereof, or a CD25-binding ligand), for example, to deplete Treg cells prior to manufacturing of the CAR-expressing cell (for example, T cell, NK cell) product.

Without wishing to be bound by a particular theory, decreasing the level of negative regulators of immune cells (for example, decreasing the number of unwanted immune cells, for example, Treg cells), in a subject prior to apheresis or during manufacturing of a CAR-expressing cell product can reduce the risk of a subject's relapse. In some embodiments, a subject is pre-treated with one or more therapies that reduce Treg cells prior to collection of cells for CAR-expressing cell product manufacturing, thereby reducing the risk of subject relapse to CAR-expressing cell treatment. In some embodiments, methods of decreasing Treg cells include, but are not limited to, administration to the subject of one or more of cyclophosphamide, anti-GITR antibody, CD25-depletion, or a combination thereof. In some embodiments, methods of decreasing Treg cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product. Administration of one or more of cyclophosphamide, anti-GITR antibody, CD25-depletion, or a combination thereof, can occur before, during or after an infusion of the CAR-expressing cell product.

In some embodiments, the manufacturing methods comprise reducing the number of (for example, depleting) Treg cells prior to manufacturing of the CAR-expressing cell. For example, manufacturing methods comprise contacting the sample, for example, the apheresis sample, with an anti-GITR antibody and/or an anti-CD25 antibody (or fragment thereof, or a CD25-binding ligand), for example, to deplete Treg cells prior to manufacturing of the CAR-expressing cell (for example, T cell, NK cell) product.

In some embodiments, a subject is pre-treated with cyclophosphamide prior to collection of cells for CAR-expressing cell product manufacturing, thereby reducing the risk of subject relapse to CAR-expressing cell treatment (for example, CTL019 treatment). In some embodiments, a subject is pre-treated with an anti-GITR antibody prior to collection of cells for CAR-expressing cell (for example, T cell or NK cell) product manufacturing, thereby reducing the risk of subject relapse to CAR-expressing cell treatment.

In some embodiments, the CAR-expressing cell (for example, T cell, NK cell) manufacturing process is modified to deplete Treg cells prior to manufacturing of the CAR-expressing cell (for example, T cell, NK cell) product (for example, a CTL019 product). In some embodiments, CD25-depletion is used to deplete Treg cells prior to manufacturing of the CAR-expressing cell (for example, T cell, NK cell) product (for example, a CTL019 product).

In some embodiments, the population of cells to be removed are neither the regulatory T cells or tumor cells, but cells that otherwise negatively affect the expansion and/or function of CART cells, for example cells expressing CD14, CD11b, CD33, CD15, or other markers expressed by potentially immune suppressive cells. In some embodiments, such cells are envisioned to be removed concurrently with regulatory T cells and/or tumor cells, or following said depletion, or in another order.

The methods described herein can include more than one selection step, for example, more than one depletion step. Enrichment of a T cell population by negative selection can be accomplished, for example, with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, for example, a tumor antigen that does not comprise CD25, for example, CD19, CD30, CD38, CD123, CD20, CD14 or CD11b, to thereby provide a population of T regulatory-depleted, for example, CD25+ depleted or $CD25^{high}$ depleted, and tumor antigen depleted cells that are suitable for expression of a CAR, for example, a CAR described herein. In some embodiments, tumor antigen expressing cells are removed simultaneously with the T regulatory, for example, CD25+ cells or $CD25^{high}$ cells. For example, an anti-CD25 antibody, or fragment thereof, and an anti-tumor antigen antibody, or fragment thereof, can be attached to the same substrate, for example, bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, for example, CD25+ cells or $CD25^{high}$ cells, and the removal of the tumor antigen expressing cells is sequential, and can occur, for example, in either order.

Also provided are methods that include removing cells from the population which express a check point inhibitor, for example, a check point inhibitor described herein, for example, one or more of PD1+ cells, LAG3+ cells, and TIM3+ cells, to thereby provide a population of T regulatory-depleted, for example, CD25+ depleted cells, and check point inhibitor depleted cells, for example, PD1+, LAG3+ and/or TIM3+ depleted cells. Exemplary check point inhibitors include PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF (for example, TGF beta), for example, as described herein. In some embodiments, check point inhibitor expressing cells are removed simultaneously with the T regulatory, for example, CD25+ cells or $CD25^{high}$ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, for example, CD25+ cells or $CD25^{high}$ cells, and the removal of the check point inhibitor expressing cells is sequential, and can occur, for example, in either order.

Methods described herein can include a positive selection step. For example, T cells can isolated by incubation with anti-CD3/anti-CD28 (for example, 3×28)-conjugated beads, such as Dynabeads® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least 1, 2, 3, 4, 5, or 6 hours. In some embodiments, the time period is 10 to 24 hours, for example, 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points.

In some embodiments, a T cell population can be selected that expresses one or more of IFN-γ, TNFα, IL-17A, IL-2, IL-3, IL-4, GM-CSF, IL-10, IL-13, granzyme B, and perforin, or other appropriate molecules, for example, other cytokines. Methods for screening for cell expression can be determined, for example, by the methods described in PCT Publication No.: WO 2013/126712.

For isolation of a desired population of cells by positive or negative selection, the concentration of cells and surface (for example, particles such as beads) can be varied. In some embodiments, it may be desirable to significantly decrease the volume in which beads and cells are mixed together (for example, increase the concentration of cells), to ensure maximum contact of cells and beads. For example, in some embodiments, a concentration of 10 billion cells/ml, 9 billion/ml, 8 billion/ml, 7 billion/ml, 6 billion/ml, or 5 billion/ml is used. In some embodiments, a concentration of 1 billion cells/ml is used. In some embodiments, a concentration of cells from 75, 80, 85, 90, 95, or 100 million cells/ml is used. In some embodiments, concentrations of 125 or 150 million cells/ml can be used.

Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (for example, leukemic blood, tumor tissue, etc.). Such populations of cells may have therapeutic value and would be desirable to obtain. For example, using high concentration of cells allows more efficient selection of CD8+ T cells that normally have weaker CD28 expression.

In some embodiments, it may be desirable to use lower concentrations of cells. By significantly diluting the mixture of T cells and surface (for example, particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In some embodiments, the concentration used can be from about $1\times10^5$/ml to $1\times10^6$/ml, and any integer value in between.

In some embodiments, the cells may be incubated on a rotator for varying lengths of time at varying speeds at either 2-10° C. or at room temperature.

In some embodiments, a plurality of the immune effector cells of the population do not express diaglycerol kinase (DGK), for example, is DGK-deficient. In some embodiments, a plurality of the immune effector cells of the population do not express Ikaros, for example, is Ikaros-deficient. In some embodiments, a plurality of the immune effector cells of the population do not express DGK and Ikaros, for example, is both DGK and Ikaros-deficient.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in immune effector cell therapy for any number of diseases or conditions that would benefit from immune effector cell therapy, such as those described herein. In some embodiments a blood sample or an apheresis is taken from a generally healthy subject. In some embodiments, a blood sample or an apheresis is taken from a generally healthy subject who is at risk of developing a disease, but who has not yet developed a disease, and the cells of interest are isolated and frozen for later use. In some embodiments, the T cells may be expanded, frozen, and used at a later time. In some embodiments, samples are collected from a patient shortly after diagnosis of a particular disease as described herein but prior to any treatments. In some embodiments, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In some embodiments of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In some embodiments, the immune effector cells expressing a CAR molecule, for example, a CAR molecule described herein, are obtained from a subject that has received a low, immune enhancing dose of an mTOR inhibitor. In some embodiments, the population of immune effector cells, for example, T cells, to be engineered to express a CAR, are harvested after a sufficient time, or after sufficient dosing of the low, immune enhancing, dose of an mTOR inhibitor, such that the level of PD1 negative immune effector cells, for example, T cells, or the ratio of PD1 negative immune effector cells, for example, T cells/PD1 positive immune effector cells, for example, T cells, in the subject or harvested from the subject has been, at least transiently, increased.

In other embodiments, population of immune effector cells, for example, T cells, which have, or will be engineered to express a CAR, can be treated ex vivo by contact with an amount of an mTOR inhibitor that increases the number of PD1 negative immune effector cells, for example, T cells or increases the ratio of PD1 negative immune effector cells, for example, T cells/PD1 positive immune effector cells, for example, T cells.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS™ Immune Cell Serum Replacement" Clinical & Translational Immunology (2015) 4, e31; doi:10.1038/cti.2014.31.

In some embodiments, the methods of the application can utilize media conditions comprising at least about 0.1%, 0.5%, 1.0%, 1.5%, 2%, 2.5%, 3%, 3.5%, 4%, 4.5%, 5%, 6%, 7%, 8%, 9% or 10% serum. In some embodiments, the media comprises about 0.5%-5%, about 0.5%-4.5%, about 0.5%-4%, about 0.5%-3.5%, about 0.5%-3%, about 0.5%-2.5%, about 0.5%-2%, about 0.5%-1.5%, about 0.5%-1.0%, about 1.0%-5%, about 1.5%-5%, about 2%-5%, about 2.5%-5%, about 3%-5%, about 3.5%-5%, about 4%-5%, or about 4.5%-5% serum. In some embodiments, the media comprises about 0.5% serum. In some embodiments, the media comprises about 0.5% serum. In some embodiments, the media comprises about 1% serum. In some embodiments, the media comprises about 1.5% serum. In some embodiments, the media comprises about 2% serum. In some embodiments, the media comprises about 2.5% serum. In some embodiments, the media comprises about 3% serum. In some embodiments, the media comprises about 3.5% serum. In some embodiments, the media comprises about 4% serum. In some embodiments, the media comprises about 4.5% serum. In some embodiments, the media comprises about 5% serum. In some embodiments, the serum comprises human serum, e.g., human AB serum. In some embodiments, the serum is human serum that has been allowed to naturally coagulate after collection, e.g., off-the-clot (OTC) serum. In some embodiments, the serum is plasma-derived serum human serum. Plasma-derived serum can be produced by defibrinating pooled human plasma collected in the presence of an anticoagulant, e.g., sodium citrate.

In some embodiments, the methods of the application can utilize culture media conditions comprising serum-free medium. In some embodiments, the serum free medium is OpTmizer™ CTS™ (LifeTech), Immunocult™ XF (Stemcell technologies), CellGro™ (CellGenix), TexMacs™ (Miltenyi), Stemline™ (Sigma), Xvivo15™ (Lonza), PrimeXV® (Irvine Scientific), or StemXVivo® (RandD systems). The serum-free medium can be supplemented with a serum substitute such as ICSR (immune cell serum replacement) from LifeTech. The level of serum substitute (for example, ICSR) can be, for example, up to 5%, for example, about 1%, 2%, 3%, 4%, or 5%. In some embodiments, the serum-free medium can be supplemented with serum, e.g., human serum, e.g., human AB serum. In some embodiments, the serum is human serum that has been allowed to naturally coagulate after collection, e.g., off-the-clot (OTC) serum. In some embodiments, the serum is plasma-derived human serum. Plasma-derived serum can be produced by defibrinating pooled human plasma collected in the presence of an anticoagulant, e.g., sodium citrate.

In some embodiments, a T cell population is diaglycerol kinase (DGK)-deficient. DGK-deficient cells include cells that do not express DGK RNA or protein, or have reduced or inhibited DGK activity. DGK-deficient cells can be generated by genetic approaches, for example, administering RNA-interfering agents, for example, siRNA, shRNA, miRNA, to reduce or prevent DGK expression. Alternatively, DGK-deficient cells can be generated by treatment with DGK inhibitors described herein.

In some embodiments, a T cell population is Ikaros-deficient. Ikaros-deficient cells include cells that do not express Ikaros RNA or protein, or have reduced or inhibited Ikaros activity, Ikaros-deficient cells can be generated by genetic approaches, for example, administering RNA-interfering agents, for example, siRNA, shRNA, miRNA, to reduce or prevent Ikaros expression. Alternatively, Ikaros-deficient cells can be generated by treatment with Ikaros inhibitors, for example, lenalidomide.

In embodiments, a T cell population is DGK-deficient and Ikaros-deficient, for example, does not express DGK and Ikaros, or has reduced or inhibited DGK and Ikaros activity. Such DGK and Ikaros-deficient cells can be generated by any of the methods described herein.

In some embodiments, the NK cells are obtained from the subject. In some embodiments, the NK cells are an NK cell line, for example, NK-92 cell line (Conkwest).

Allogeneic CAR-Expressing Cells

In embodiments described herein, the immune effector cell can be an allogeneic immune effector cell, for example, T cell or NK cell. For example, the cell can be an allogeneic T cell, for example, an allogeneic T cell lacking expression of a functional T cell receptor (TCR) and/or human leukocyte antigen (HLA), for example, HLA class I and/or HLA class II.

A T cell lacking a functional TCR can be, for example, engineered such that it does not express any functional TCR on its surface, engineered such that it does not express one or more subunits that comprise a functional TCR (for example, engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, for example, by expression of mutated or truncated forms of one or more of the subunits of the TCR. The term "substantially impaired TCR" means that this TCR will not elicit an adverse immune reaction in a host.

A T cell described herein can be, for example, engineered such that it does not express a functional HLA on its surface. For example, a T cell described herein, can be engineered such that cell surface expression HLA, for example, HLA class 1 and/or HLA class II, is downregulated. In some embodiments, downregulation of HLA may be accomplished by reducing or eliminating expression of beta-2 microglobulin (B2M).

In some embodiments, the T cell can lack a functional TCR and a functional HLA, for example, HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not express or expresses at low levels an inhibitory molecule, for example by any method described herein. For example, the cell can be a cell that does not express or expresses at low levels an inhibitory molecule, for example, that can decrease the ability of a CAR-expressing cell to mount an immune effector response. Examples of inhibitory molecules include PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF (for example, TGF beta). Inhibition of an inhibitory molecule, for example, by inhibition at the DNA, RNA or protein level, can optimize a CAR-expressing cell performance. In embodiments, an inhibitory nucleic acid, for example, an inhibitory nucleic acid, for example, a dsRNA, for example, an siRNA or shRNA, a clustered regularly interspaced short palindromic repeats (CRISPR), a transcription-activator like effector nuclease (TALEN), or a zinc finger endonuclease (ZFN), for example, as described herein, can be used.

siRNA and shRNA to Inhibit TCR or HLA

In some embodiments, TCR expression and/or HLA expression can be inhibited using siRNA or shRNA that targets a nucleic acid encoding a TCR and/or HLA, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

Expression systems for siRNA and shRNAs, and exemplary shRNAs, are described, for example, in paragraphs 649 and 650 of International Application WO2015/142675, filed Mar. 13, 2015, which is incorporated by reference in its entirety.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

The CRISPR/Cas system, and uses thereof, are described, for example, in paragraphs 651-658 of International Application WO2015/142675, filed Mar. 13, 2015, which is incorporated by reference in its entirety.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA and/or TCR gene, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

TALENs, and uses thereof, are described, for example, in paragraphs 659-665 of International Application WO2015/142675, filed Mar. 13, 2015, which is incorporated by reference in its entirety.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA and/or TCR gene, and/or an inhibitory molecule described herein (for example, PD1, PD-L1, PD-L2, CTLA4, TIM3, CEACAM (for example, CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGF beta), in a cell, for example, T cell.

ZFNs, and uses thereof, are described, for example, in paragraphs 666-671 of International Application WO2015/142675, filed Mar. 13, 2015, which is incorporated by reference in its entirety.

Telomerase Expression

Telomeres play a crucial role in somatic cell persistence, and their length is maintained by telomerase (TERT). Telomere length in CLL cells may be very short (Roth et al., "Significantly shorter telomeres in T-cells of patients with ZAP-70+/CD38 chronic lymphocytic leukaemia" British Journal of Haematology, 143, 383-386., Aug. 28 2008), and may be even shorter in manufactured CAR-expressing cells, for example, CART19 cells, limiting their potential to expand after adoptive transfer to a patient. Telomerase expression can rescue CAR-expressing cells from replicative exhaustion.

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in some embodiments, an immune effector cell, for example, a T cell, ectopically expresses a telomerase subunit, for example, the catalytic subunit of telomerase, for example, TERT, for example, hTERT. In some embodiments, this disclosure provides a method of producing a CAR-expressing cell, comprising contacting a cell with a nucleic acid encoding a telomerase subunit, for example, the catalytic subunit of telomerase, for example, TERT, for example, hTERT. The cell may be contacted with the nucleic acid before, simultaneous with, or after being contacted with a construct encoding a CAR.

Telomerase expression may be stable (for example, the nucleic acid may integrate into the cell's genome) or transient (for example, the nucleic acid does not integrate, and expression declines after a period of time, for example, several days). Stable expression may be accomplished by transfecting or transducing the cell with DNA encoding the telomerase subunit and a selectable marker, and selecting for stable integrants. Alternatively, or in combination, stable expression may be accomplished by site-specific recombination, for example, using the Cre/Lox or FLP/FRT system.

Transient expression may involve transfection or transduction with a nucleic acid, for example, DNA or RNA such as mRNA. In some embodiments, transient mRNA transfection avoids the genetic instability sometimes associated with stable transfection with TERT. Transient expression of exogenous telomerase activity is described, for example, in International Application WO2014/130909, which is incorporated by reference herein in its entirety. In embodiments, mRNA-based transfection of a telomerase subunit is performed according to the messenger RNA Therapeutics™ platform commercialized by Moderna Therapeutics. For instance, the method may be a method described in U.S. Pat. Nos. 8,710,200, 8,822,663, 8,680,069, 8,754,062, 8,664,194, or 8680069.

In some embodiments, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795):

```
                                       (SEQ ID NO: 284)
MPRAPRCRAVRSLLRSHYREVLPLATFVRRLGPQGWRLVQRGDPAAFRA

LVAQCLVCVPWDARPPPAAPSFRQVSCLKELVARVLQRLCERGAKNVLA

FGFALLDGARGGPPEAFTTSVRSYLPNTVTDALRGSGAWGLLLRRVGDD

VLVHLLARCALFVLVAPSCAYQVCGPPLYQLGAATQARPPPHASGPRRR

LGCERAWNHSVREAGVPLGLPAPGARRRGGSASRSLPLPKRPRRGAAPE

PERTPVGQGSWAHPGRTRGPSDRGFCVVSPARPAEEATSLEGALSGTRH
```

-continued

SHPSVGRQHHAGPPSTSRPPRPWDTPCPPVYAETKHFLYSSGDKEQLRP

SFLLSSLRPSLTGARRLVETIFLGSRPWMPGTPRRLPRLPQRYWQMRPL

FLELLGNHAQCPYGVLLKTHCPLRAAVTPAAGVCAREKPQGSVAAPEEE

DTDPRRLVQLLRQHSSPWQVYGFVRACLRRLVPPGLWGSRHNERRFLRN

TKKFISLGKHAKLSLQELTWKMSVRGCAWLRRSPGVGCVPAAEHRLREE

ILAKFLHWLMSVYVVELLRSFFYVTETTFQKNRLFFYRKSVWSKLQSIG

IRQHLKRVQLRELSEAEVRQHREARPALLTSRLRFIPKPDGLRPIVNMD

YVVGARTFRREKRAERLTSRVKALFSVLNYERARRPGLLGASVLGLDDI

HRAWRTFVLRVRAQDPPPELYFVKVDVTGAYDTIPQDRLTEVIASIIKP

QNTYCVRRYAVVQKAAHGHVRKAFKSHVSTLTDLQPYMRQFVAHLQETS

PLRDAVVIEQSSSLNEASSGLFDVFLRFMCHHAVRIRGKSYVQCQGIPQ

GSILSTLLCSLCYGDMENKLFAGIRRDGLLLRLVDDFLLVTPHLTHAKT

FLRTLVRGVPEYGCVVNLRKTVVNFPVEDEALGGTAFVQMPAHGLFPWC

GLLLDTRTLEVQSDYSSYARTSIRASLTFNRGFKAGRNMRRKLFGVLRL

KCHSLFLDLQVNSLQTVCTNIYKILLLQAYRFHACVLQLPFHQQVWKNP

TFFLRVISDTASLCYSILKAKNAGMSLGAKGAAGPLPSEAVQWLCHQAF

LLKLTRHRVTYVPLLGSLRTAQTQLSRKLPGTTLTALEAAANPALPSDF

KTILD

In some embodiments, the hTERT has a sequence at least 80%, 85%, 90%, 95%, 96%, 97%, 98%, or 99% identical to the sequence of SEQ ID NO: 284. In some embodiments, the hTERT has a sequence of SEQ ID NO: 284. In some embodiments, the hTERT comprises a deletion (for example, of no more than 5, 10, 15, 20, or 30 amino acids) at the N-terminus, the C-terminus, or both. In some embodiments, the hTERT comprises a transgenic amino acid sequence (for example, of no more than 5, 10, 15, 20, or 30 amino acids) at the N-terminus, the C-terminus, or both.

In some embodiments, the hTERT is encoded by the nucleic acid sequence of GenBank Accession No. AF018167 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795).

Activation and Expansion of Immune Effector Cells (for Example, T Cells)

Immune effector cells such as T cells generated or enriched by the methods described herein may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, a population of immune effector cells may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (for example, bryostatin) in conjunction with a calcium ionophore. For costimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In some embodiments, the agent providing the costimulatory signal is bound to a cell surface and the agent providing the primary activation signal is in solution or coupled to a surface. In some embodiments, both agents can be in solution. In some embodiments, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In some embodiments, a 1:1 ratio of each antibody bound to the beads for CD4+ T cell expansion and T cell growth is used. In some embodiments of the present invention, a ratio of anti CD3:CD28 antibodies bound to the beads is used such that an increase in T cell expansion is observed as compared to the expansion observed using a ratio of 1:1. In some embodiments an increase of from about 1 to about 3 fold is observed as compared to the expansion observed using a ratio of 1:1. In some embodiments, the ratio of CD3:CD28 antibody bound to the beads ranges from 100:1 to 1:100 and all integer values there between. In some embodiments, more anti-CD28 antibody is bound to the particles than anti-CD3 antibody, i.e., the ratio of CD3:CD28 is less than one. In some embodiments, the ratio of anti CD28 antibody to anti CD3 antibody bound to the beads is greater than 2:1. In some embodiments, a 1:100 CD3:CD28 ratio of antibody bound to beads is used. In some embodiments, a 1:75 CD3:CD28 ratio of antibody bound to beads is used. In some embodiments, a 1:50 CD3:CD28 ratio of antibody bound to beads is used. In some embodiments, a 1:30 CD3:CD28 ratio of antibody bound to beads is used. In some embodiments, a 1:10 CD3:CD28 ratio of antibody bound to beads is used. In some embodiments, a 1:3 CD3:CD28 ratio of antibody bound to the beads is used. In some embodiments, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In some embodiments the ratio of cells to particles ranges from 1:100 to 100:1 and any integer values in-between and in some embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain suitable values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one suitable ratio being at least 1:1 particles per T cell. In some embodiments, a ratio of particles to cells of 1:1 or less is used. In some embodiments, a suitable particle: cell ratio is 1:5. In some embodiments, the ratio of particles to cells can be varied depending on the day of stimulation. For example, in some embodiments, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In some embodiments, the ratio of particles to cells is 1:1 on the first day of stimulation and adjusted to 1:5 on the third and fifth days of stimulation. In some embodiments, particles are added on a daily or every other day basis to a final ratio of 1:1 on the first day, and 1:5 on the third and fifth days of stimulation. In some embodiments, the ratio of particles to cells is 2:1 on the first day of stimulation and adjusted to 1:10 on the third and fifth days of stimulation. In some embodiments, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In some embodiments, the most typical ratios for use are in the neighborhood of 1:1, 2:1 and 3:1 on the first day.

In some embodiments, the cells, such as T cells, are combined with agent-coated beads, the beads and the cells are subsequently separated, and then the cells are cultured. In some embodiments, prior to culture, the agent-coated beads and cells are not separated but are cultured together. In some embodiments, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In some embodiments the cells (for example, $10^4$ to 10' T cells) and beads (for example, Dynabeads® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In some embodiments, it may be desirable to significantly decrease the volume in which particles and cells are mixed together (i.e., increase the concentration of cells), to ensure maximum contact of cells and particles. For example, in some embodiments, a concentration of about 10 billion cells/ml, 9 billion/ml, 8 billion/ml, 7 billion/ml, 6 billion/ml, 5 billion/ml, or 2 billion cells/ml is used. In some embodiments, greater than 100 million cells/ml is used. In some embodiments, a concentration of cells of 10, 15, 20, 25, 30, 35, 40, 45, or 50 million cells/ml is used. In some embodiments, a concentration of cells from 75, 80, 85, 90, 95, or 100 million cells/ml is used. In some embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in some embodiments. For example, using high concentration of cells allows more efficient selection of CD8+ T cells that normally have weaker CD28 expression.

In some embodiments, cells transduced with a nucleic acid encoding a CAR, for example, a CAR described herein, for example, a CD19 CAR described herein, are expanded, for example, by a method described herein. In some embodiments, the cells are expanded in culture for a period of several hours (for example, about 2, 3, 4, 5, 6, 7, 8, 9, 10, 15, 18, 21 hours) to about 14 days (for example, 1, 2, 3, 4, 5, 6, 7, 8, 9, 10, 11, 12, 13 or 14 days). In some embodiments, the cells are expanded for a period of 4 to 9 days. In some embodiments, the cells are expanded for a period of 8 days or less, for example, 7, 6 or 5 days. In some embodiments, the cells are expanded in culture for 5 days, and the resulting cells are more potent than the same cells expanded in culture for 9 days under the same culture conditions. Potency can be defined, for example, by various T cell functions, for example proliferation, target cell killing, cytokine production, activation, migration, surface CAR expression, CAR quantitative PCR, or combinations thereof. In some embodiments, the cells, for example, a CD19 CAR cell described herein, expanded for 5 days show at least a one, two, three or four-fold increase in cells doublings upon antigen stimulation as compared to the same cells expanded in culture for 9 days under the same culture conditions. In some embodiments, the cells, for example, the cells expressing a CD19 CAR described herein, are expanded in culture for 5 days, and the resulting cells exhibit higher proinflammatory cytokine production, for example, IFN-γ and/or GM-CSF levels, as compared to the same cells expanded in culture for 9 days under the same culture conditions. In some embodiments, the cells, for example, a CD19 CAR cell described herein, expanded for 5 days show at least a one, two, three, four, five, ten-fold or more increase in pg/ml of proinflammatory cytokine production, for example, IFN-γ and/or GM-CSF levels, as compared to the same cells expanded in culture for 9 days under the same culture conditions.

Several cycles of stimulation may also be desired such that culture time of T cells can be 60 days or more. Conditions appropriate for T cell culture include an appropriate media (for example, Minimal Essential Media, a-MEM, RPMI Media 1640, AIM-V, DMEM, F-12, or X-vivo 15 (Lonza), X-Vivo 20, OpTmizer, and IMDM) that may contain factors necessary for proliferation and viability, including serum (for example, fetal bovine or human serum), interleukin-2 (IL-2), insulin, IFNγ, IL-4, IL-7, GM-CSF, IL-10, IL-12, IL-15, TGFβ, and TNFα or any other additives for the growth of cells known to the skilled artisan. Other additives for the growth of cells include, but are not limited to, surfactant, plasmanate, and reducing agents such as N-acetyl-cysteine and 2-mercaptoethanol. Media can include, but is not limited to RPMI 1640, AIM-V, DMEM, MEM, a-MEM, F-12, X-Vivo 15, X-Vivo 20, OpTmizer, and IMDM with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, for example, penicillin and streptomycin, are included only in experimental cultures, not in cultures of cells that are to be infused into a subject. The target cells are maintained under conditions necessary to support growth, for example, an appropriate temperature (for example, 37° C.) and atmosphere (for example, air plus 5% $CO_2$).

In some embodiments, the cells are expanded in an appropriate media (for example, media described herein) that includes one or more interleukin that result in at least a 200-fold (for example, 200-fold, 250-fold, 300-fold, 350-fold) increase in cells over a 14-day expansion period, for example, as measured by a method described herein such as flow cytometry. In some embodiments, the cells are expanded in the presence IL-15 and/or IL-7 (for example, IL-15 and IL-7).

In embodiments, methods described herein, for example, CAR-expressing cell manufacturing methods, comprise removing T regulatory cells, for example, CD25+ T cells or $CD25^{high}$ T cells, from a cell population, for example, using an anti-CD25 antibody, or fragment thereof, or a CD25-binding ligand, IL-2. Methods of removing T regulatory cells, for example, CD25+ T cells or $CD25^{high}$ T cells, from a cell population are described herein. In embodiments, the methods, for example, manufacturing methods, further comprise contacting a cell population (for example, a cell population in which T regulatory cells, such as CD25+ T cells or $CD25^{high}$ T cells, have been depleted; or a cell population that has previously contacted an anti-CD25 antibody, fragment thereof, or CD25-binding ligand) with IL-15 and/or IL-7. For example, the cell population (for example, that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide for example, hetIL-15, during the manufacturing of the CAR-expressing cell, for example, ex vivo. In embodiments, a CAR-expressing cell described herein is contacted with a composition comprising an IL-15 polypeptide during the manufacturing of the CAR-expressing cell, for example, ex vivo. In embodiments, a CAR-expressing cell described herein is contacted with a composition comprising a combination of both an IL-15 polypeptide and a IL-15 Ra polypeptide during the manufacturing of the CAR-expressing cell, for example, ex vivo. In embodiments, a CAR-expressing cell described herein is contacted with a composition comprising hetIL-15 during the manufacturing of the CAR-expressing cell, for example, ex vivo.

In some embodiments the CAR-expressing cell described herein is contacted with a composition comprising hetIL-15 during ex vivo expansion. In some embodiments, the CAR-expressing cell described herein is contacted with a composition comprising an IL-15 polypeptide during ex vivo expansion. In some embodiments, the CAR-expressing cell described herein is contacted with a composition comprising both an IL-15 polypeptide and an IL-15Ra polypeptide during ex vivo expansion. In some embodiments the contacting results in the survival and proliferation of a lymphocyte subpopulation, for example, CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a CAR described herein is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a CAR of the present invention are described in further detail below Western blot analysis of CAR expression in primary T cells can be used to detect the presence of monomers and dimers, for example, as described in paragraph 695 of International Application WO2015/142675, filed Mar. 13, 2015, which is herein incorporated by reference in its entirety.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, for example, Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2A ribosomal skipping sequence. Cultures are re-stimulated with either a cancer associated antigen as described herein$^+$ K562 cells (K562-expressing a cancer associated antigen as described herein), wild-type K562 cells (K562 wild type) or K562 cells expressing hCD32 and 4-1BBL in the presence of antiCD3 and anti-CD28 antibody (K562-BBL-3/28). Exogenous IL-2 is added to the cultures every other day at 100 IU/ml. $GFP^+$ T cells are enumerated by flow cytometry using bead-based counting. See, for example, Milone et al., Molecular Therapy 17(8): 1453-1464 (2009).

Sustained $CAR^+$ T cell expansion in the absence of re-stimulation can also be measured. See, for example, Milone et al., Molecular Therapy 17(8): 1453-1464 (2009). Briefly, mean T cell volume (fl) is measured on day 8 of culture using a Coulter Multisizer III particle counter or a higher version, a Nexcelom Cellometer Vision, Millipore Scepter or other cell counters, following stimulation with αCD3/αCD28 coated magnetic beads on day 0, and transduction with the indicated CAR on day 1.

Animal models can also be used to measure a CAR-expressing cell activity, for example, as described in paragraph 698 of International Application WO2015/142675, filed Mar. 13, 2015, which is herein incorporated by reference in its entirety.

Dose dependent CAR treatment response can be evaluated, for example, as described in paragraph 699 of International Application WO2015/142675, filed Mar. 13, 2015, which is herein incorporated by reference in its entirety.

Assessment of cell proliferation and cytokine production has been previously described, as described in paragraph 700 of International Application WO2015/142675, filed Mar. 13, 2015, which is herein incorporated by reference in its entirety.

Cytotoxicity can be assessed by a standard 51Cr-release assay, for example, as described in paragraph 701 of International Application WO2015/142675, filed Mar. 13, 2015, which is herein incorporated by reference in its entirety. Alternative non-radioactive methods can be utilized as well.

Cytotoxicity can also be assessed by measuring changes in adherent cell's electrical impedance, for example, using an xCELLigence real time cell analyzer (RTCA). In some embodiments, cytotoxicity is measured at multiple time points.

Imaging technologies can be used to evaluate specific trafficking and proliferation of CARs in tumor-bearing animal models, for example, as described in paragraph 702 of International Application WO2015/142675, filed Mar. 13, 2015, which is herein incorporated by reference in its entirety.

Other assays, including those described in the Example section herein as well as those that are known in the art can also be used to evaluate the CARs described herein.

Alternatively, or in combination to the methods disclosed herein, methods and compositions for one or more of: detection and/or quantification of CAR-expressing cells (for example, in vitro or in vivo (for example, clinical monitoring)); immune cell expansion and/or activation; and/or CAR-specific selection, that involve the use of a CAR ligand, are disclosed. In some embodiments, the CAR ligand is an antibody that binds to the CAR molecule, for example, binds to the extracellular antigen binding domain of CAR (for example, an antibody that binds to the antigen binding domain, for example, an anti-idiotypic antibody; or an antibody that binds to a constant region of the extracellular binding domain). In other embodiments, the CAR ligand is a CAR antigen molecule (for example, a CAR antigen molecule as described herein).

In some embodiments, a method for detecting and/or quantifying CAR-expressing cells is disclosed. For example, the CAR ligand can be used to detect and/or quantify CAR-expressing cells in vitro or in vivo (for example, clinical monitoring of CAR-expressing cells in a patient, or dosing a patient). The method includes:

- providing the CAR ligand (optionally, a labelled CAR ligand, for example, a CAR ligand that includes a tag, a bead, a radioactive or fluorescent label);
- acquiring the CAR-expressing cell (for example, acquiring a sample containing CAR-expressing cells, such as a manufacturing sample or a clinical sample);
- contacting the CAR-expressing cell with the CAR ligand under conditions where binding occurs, thereby detecting the level (for example, amount) of the CAR-expressing cells present. Binding of the CAR-expressing cell with the CAR ligand can be detected using standard techniques such as FACS, ELISA and the like.

In some embodiments, a method of expanding and/or activating cells (for example, immune effector cells) is disclosed. The method includes:

- providing a CAR-expressing cell (for example, a first CAR-expressing cell or a transiently expressing CAR cell);
- contacting said CAR-expressing cell with a CAR ligand, for example, a CAR ligand as described herein), under conditions where immune cell expansion and/or proliferation occurs, thereby producing the activated and/or expanded cell population.

In certain embodiments, the CAR ligand is present on a substrate (for example, is immobilized or attached to a substrate, for example, a non-naturally occurring substrate). In some embodiments, the substrate is a non-cellular substrate. The non-cellular substrate can be a solid support chosen from, for example, a plate (for example, a microtiter plate), a membrane (for example, a nitrocellulose membrane), a matrix, a chip or a bead. In embodiments, the CAR ligand is present in the substrate (for example, on the substrate surface). The CAR ligand can be immobilized, attached, or associated covalently or non-covalently (for example, cross-linked) to the substrate. In some embodiments, the CAR ligand is attached (for example, covalently attached) to a bead. In the aforesaid embodiments, the immune cell population can be expanded in vitro or ex vivo. The method can further include culturing the population of immune cells in the presence of the ligand of the CAR molecule, for example, using any of the methods described herein.

In other embodiments, the method of expanding and/or activating the cells further comprises addition of a second stimulatory molecule, for example, CD28. For example, the CAR ligand and the second stimulatory molecule can be immobilized to a substrate, for example, one or more beads, thereby providing increased cell expansion and/or activation.

In some embodiments, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In some embodiments, the CAR ligand is coupled to a toxic agent (for example, a toxin or a cell ablative drug). In some embodiments, the anti-idiotypic antibody can cause effector cell activity, for example, ADCC or ADC activities.

Exemplary anti-CAR antibodies that can be used in the methods disclosed herein are described, for example, in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference.

In some embodiments, the compositions and methods herein are optimized for a specific subset of T cells, for example, as described in US Serial No. PCT/US2015/043219 filed Jul. 31, 2015, the contents of which are incorporated herein by reference in their entirety. In some embodiments, the optimized subsets of T cells display an enhanced persistence compared to a control T cell, for example, a T cell of a different type (for example, CD8+ or CD4+) expressing the same construct.

In some embodiments, a CD4+ T cell comprises a CAR described herein, which CAR comprises an intracellular signaling domain suitable for (for example, optimized for, for example, leading to enhanced persistence in) a CD4+ T cell, for example, an ICOS domain. In some embodiments, a CD8+ T cell comprises a CAR described herein, which CAR comprises an intracellular signaling domain suitable for (for example, optimized for, for example, leading to enhanced persistence of) a CD8+ T cell, for example, a 4-1BB domain, a CD28 domain, or another costimulatory domain other than an ICOS domain. In some embodiments, the CAR described herein comprises an antigen binding domain described herein, for example, a CAR comprising an antigen binding domain.

In some embodiments, described herein is a method of treating a subject, for example, a subject having cancer. The method includes administering to said subject, an effective amount of:

1) a CD4+ T cell comprising a CAR (the CARCD4+) comprising:
  - an antigen binding domain, for example, an antigen binding domain described herein;
  - a transmembrane domain; and
  - an intracellular signaling domain, for example, a first costimulatory domain, for example, an ICOS domain; and
2) a CD8+ T cell comprising a CAR (the CARCD8+) comprising:
  - an antigen binding domain, for example, an antigen binding domain described herein;
  - a transmembrane domain; and
  - an intracellular signaling domain, for example, a second costimulatory domain, for example, a 4-1BB domain, a CD28 domain, or another costimulatory domain other than an ICOS domain;
  - wherein the CARCD4+ and the CARCD8+ differ from one another.

Optionally, the method further includes administering:

3) a second CD8+ T cell comprising a CAR (the second CARCD8+) comprising:
  - an antigen binding domain, for example, an antigen binding domain described herein;
  - a transmembrane domain; and
  - an intracellular signaling domain, wherein the second CARCD8+ comprises an intracellular signaling domain, for example, a costimulatory signaling domain, not present on the CARCD8+, and, optionally, does not comprise an ICOS signaling domain.

Biopolymer Delivery Methods

In some embodiments, one or more CAR-expressing cells as disclosed herein can be administered or delivered to the subject via a biopolymer scaffold, for example, a biopolymer implant. Biopolymer scaffolds can support or enhance the delivery, expansion, and/or dispersion of the CAR-expressing cells described herein. A biopolymer scaffold comprises a biocompatible (for example, does not substantially induce an inflammatory or immune response) and/or a biodegradable polymer that can be naturally occurring or synthetic. Exemplary biopolymers are described, for example, in paragraphs 1004-1006 of International Application WO2015/142675, filed Mar. 13, 2015, which is herein incorporated by reference in its entirety.

Pharmaceutical Compositions and Treatments

In some embodiments, the disclosure provides a method of treating a patient, comprising administering CAR-expressing cells produced as described herein, optionally in combination with one or more other therapies. In some embodiments, the disclosure provides a method of treating a patient, comprising administering a reaction mixture comprising CAR-expressing cells as described herein, optionally in combination with one or more other therapies. In some embodiments, the disclosure provides a method of shipping or receiving a reaction mixture comprising CAR-expressing cells as described herein. In some embodiments, the disclosure provides a method of treating a patient, comprising receiving a CAR-expressing cell that was produced as described herein, and further comprising administering the CAR-expressing cell to the patient, optionally in combination with one or more other therapies. In some embodiments, the disclosure provides a method of treating a patient, comprising producing a CAR-expressing cell as described herein, and further comprising administering the CAR-expressing cell to the patient, optionally in combination with one or more other therapies. The other therapy may be, for example, a cancer therapy such as chemotherapy.

In some embodiments, cells expressing a CAR described herein are administered to a subject in combination with a molecule that decreases the Treg cell population. Methods that decrease the number of (for example, deplete) Treg cells are known in the art and include, for example, CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (for example, Tregs) in the tumor microenvironment and reduces the subject's risk of relapse.

In some embodiments, a therapy described herein, for example, a CAR-expressing cell, is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In some embodiments, the GITR binding molecules and/or molecules modulating GITR functions (for example, GITR agonist and/or Treg depleting GITR antibodies) are administered prior to the CAR-expressing cell. For example, in some embodiments, a GITR agonist can be administered prior to apheresis of the cells. In embodiments, cyclophosphamide is administered to the subject prior to administration (for example, infusion or re-infusion) of the CAR-expressing cell or prior to apheresis of the cells. In embodiments, cyclophosphamide and an anti-GITR antibody are administered to the subject prior to administration (for example, infusion or re-infusion) of the CAR-expressing cell or prior to apheresis of the cells. In some embodiments, the subject has cancer (for example, a solid cancer or a hematological cancer such as ALL or CLL). In some embodiments, the subject has CLL. In embodiments, the subject has ALL. In embodiments, the subject has a solid cancer, for example, a solid cancer described herein. Exemplary GITR agonists include, for example, GITR fusion proteins and anti-GITR antibodies (for example, bivalent anti-GITR antibodies) such as, for example, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, for example, in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In some embodiments, a CAR expressing cell described herein is administered to a subject in combination with a GITR agonist, for example, a GITR agonist described herein. In some embodiments, the GITR agonist is administered prior to the CAR-expressing cell. For example, in some embodiments, the GITR agonist can be administered prior to apheresis of the cells. In some embodiments, the subject has CLL.

The methods described herein can further include formulating a CAR-expressing cell in a pharmaceutical composition. Pharmaceutical compositions may comprise a CAR-expressing cell, for example, a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (for example, aluminum hydroxide); and preservatives. Compositions can be formulated, for example, for intravenous administration.

In some embodiments, the pharmaceutical composition is substantially free of, for example, there are no detectable levels of a contaminant, for example, selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In some embodiments, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anticancer effective amount," "a cancer-inhibiting effective amount," or "therapeutic amount" is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the immune effector cells (for example, T cells, NK cells) described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, for example, Rosenberg et al., New Eng. J. of Med. 319:1676, 1988).

Exemplary BCMA/CDJ9 CART Pharmaceutical Compositions

In some embodiments a BCMA/CD19 dual CART cell composition is produced by co-transduction with two unique vectors. Accordingly, in some embodiments, the cell composition comprises a heterogeneous population of cells. In some embodiments, the heterogeneous cell composition includes untransduced T cells, mono BCMA-specific CART cells, mono CD19-specific CART cells, and dual CART cells expressing both BCMA-specific CAR molecules and CD19-specific CAR molecules. These distinct cell populations may exhibit different activities in the context of treating a disease in a subject.

Without wishing to be bound by theory, in the context of treating multiple myeloma, for example, activation of BCMA-specific CART cells can be a main factor in the anti-tumor response in patients, while CD19-specific activity can play a role in eliminating less-prevalent CD19-positive tumor cells.

In some embodiments, the cell composition can be evaluated to assess the relative percentages of the four distinct cell populations, e.g., to select a cell composition that contains a greater percentage of BCMA-specific CAR cells (e.g., mono BCMA-specific CAR cells and BCMA/CD19 dual CAR cells) than mono CD19-specific CAR cells.

In some embodiments, the cell composition comprises:
(a) a first population of cells comprising an anti-BCMA CAR but not an anti-CD19 CAR;
(b) a second population of cells comprising an anti-CD19 CAR but not an anti-BCMA CAR; and
(c) a third population of cells comprising both an anti-BCMA CAR and an anti-CD19 CAR.

In some embodiments:
(i) the total number of viable cells in the second and third populations combined is less than or equal to about 110% (e.g., less than or equal to about 105%, 100%, 90%, 80%, 70%, 60%, 50%, 40%, 30%, 20%, 10%, 5%, 1%, or less) of the total number of viable cells in the first and third populations combined;
(ii) the total number of viable cells in the first and third populations combined is greater than or equal to about 90% (e.g., greater than or equal to about 100%, 125%, 150%, 175%, 200%, 250%, 300%, 400%, 500%, 750%, 1000%, 2000%, 5000, 10000% or more) of the total number of viable cells in the second and third populations combined; and/or
(iii) the total number of viable cells in the first and third populations combined is greater than or equal to about 5% (e.g., greater than or equal to about 10%, 20%, 30%, 40%, 50%, 60%, 70%, 80%, or 90%) of the total number of viable cells in the population.

In some embodiments, the cell composition further comprises a fourth population of cells that do not comprise a CAR. In some embodiments, the cell composition comprises a population of mono CD19-specific CAR cells that are less than or equal to 110% (e.g., less than or equal to about 105%, 100%, 90%, 80%, 70%, 60%, 50%, 40%, 30%, 20%, 10%, 5%, 1%, or less) of the number of BCMA-specific CAR cells (e.g., the total number of mono BCMA-specific CAR cells and BCMA/CD19 dual CAR cells). In some embodiments, the cell composition comprises a population of mono CD19 CAR+ cells that comprise about 45% to about 50% (e.g., about 47%) of the number of BCMA-specific CART cells. In some embodiments, the cell composition comprises a population of mono CD19 CAR+ cells that comprise about 60% to about 65% (e.g., about 63%) of the number of BCMA-specific CART cells. In some embodiments, the cell composition comprises a population of mono CD19 CAR+ cells that comprise about 50% to about 55% (e.g., about 53%) of the number of BCMA-specific CART cells. In some embodiments, the cell composition comprises a population of mono CD19 CAR+ cells that comprise about 82% of the number of BCMA-specific CART cells.

In some embodiments, the cell composition can be evaluated to assess the percentage of CAR-positive viable cells to allow for sufficient dosing. Accordingly, in some embodiments, the cell composition comprises a population of BCMA-specific CAR cells (e.g., the total number of mono BCMA-specific CAR cells and BCMA/CD19 dual CAR cells) that are greater than or equal to about 5% (e.g., greater than or equal to about 10%, 20%, 30%, 40%, 50%, 60%, 70%, 80%, 90%, 95%, 99%, or 100%) of the total number of viable cells in the cell composition.

In some embodiments, the BCMA-specific CAR cells are BCMA-specific CART cells. In some embodiments, the mono BCMA-specific CAR cells are mono BCMA-specific CART cells. In some embodiments, the CD19-specific CAR cells are CD19-specific CART cells. In some embodiments, the mono CD19-specific CAR cells are mono CD19-specific CART cells. In some embodiments, the BCMA/CD19 dual CAR cells are BCMA/CD19 dual CART cells.

Dosing

In some embodiments, a dose of CAR cells (for example, CD19 CAR cells) comprises about $1\times10^6$, $1.1\times10^6$,$2\times10^6$, $3.6\times10^6$,$5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (for example, CD19 CAR cells) comprises at least about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (for example, CD19 CAR cells) comprises up to about $1\times10^6$, $1.1\times10^6$, $2\times10^6$, $3.6\times10^6$, $5\times10^6$, $1\times10^7$, $1.8\times10^7$, $2\times10^7$, $5\times10^7$, $1\times10^8$, $2\times10^8$, or $5\times10^8$ cells/kg. In some embodiments, a dose of CAR cells (for example, CD19 CAR cells) comprises about $1.1\times10^6$-$1.8\times10^7$ cells/kg. In some embodiments, a dose of CAR cells (for example, CD19 CAR cells) comprises about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (for example, CD19 CAR cells) comprises at least about $1\times10^7$, $2\times10^7$, $5\times10^7$, $1\times10^8$, $2\times10^8$, $5\times10^8$, $1\times10^9$, $2\times10^9$, or $5\times10^9$ cells. In some embodiments, a dose of CAR cells (for example, CD19 CAR cells) comprises up to about $1\times10^7$, $2\times10^7$, $5\times10^7$, $1\times10^8$, $2\times10^8$, $5\times10^8$, $1\times10^9$, $2\times10^9$, or $5\times10^9$ cells.

In some embodiments, it may be desired to administer activated immune effector cells (for example, T cells, NK cells) to a subject and then subsequently redraw blood (or have an apheresis performed), activate immune effector cells (for example, T cells, NK cells) therefrom, and reinfuse the patient with these activated and expanded immune effector cells (for example, T cells, NK cells). This process can be carried out multiple times every few weeks. In some embodiments, immune effector cells (for example, T cells, NK cells) can be activated from blood draws of from 10cc to 400cc. In some embodiments, immune effector cells (for example, T cells, NK cells) are activated from blood draws of 20cc, 30cc, 40cc, 50cc, 60cc, 70cc, 80cc, 90cc, or 100cc.

The administration of the subject compositions may be carried out in any convenient manner. The compositions described herein may be administered to a patient trans arterially, subcutaneously, intradermally, intratumorally, intranodally, intramedullary, intramuscularly, by intravenous (i.v.) injection, or intraperitoneally, for example, by intradermal or subcutaneous injection. The compositions of immune effector cells (for example, T cells, NK cells) may be injected directly into a tumor, lymph node, or site of infection.

T Cell Depletion

In some embodiments, the methods disclosed herein further include administering a T cell depleting agent after treatment with the cell (for example, an immune effector cell as described herein), thereby reducing (for example, depleting) the CAR-expressing cells (for example, the CD19CAR-expressing cells). Such T cell depleting agents can be used to effectively deplete CAR-expressing cells (for example, CD19CAR-expressing cells) to mitigate toxicity. In some embodiments, the CAR-expressing cells were manufactured according to a method herein, for example, assayed (for example, before or after transfection or transduction) according to a method herein.

In some embodiments, the T cell depleting agent is administered one, two, three, four, or five weeks after administration of the cell, for example, the population of immune effector cells, described herein.

In some embodiments, the T cell depleting agent is an agent that depletes CAR-expressing cells, for example, by inducing antibody dependent cell-mediated cytotoxicity (ADCC) and/or complement-induced cell death. For example, CAR-expressing cells described herein may also express an antigen (for example, a target antigen) that is recognized by molecules capable of inducing cell death, for example, ADCC or complement-induced cell death. For example, CAR expressing cells described herein may also express a target protein (for example, a receptor) capable of being targeted by an antibody or antibody fragment. Examples of such target proteins include, but are not limited to, EpCAM, VEGFR, integrins (for example, integrins αvβ3, α4, αI¾β3, α4β7, α5β1, αvβ3, αv), members of the TNF receptor superfamily (for example, TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/lgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (for example, versions preserving one or more extracellular epitopes but lacking one or more regions within the cytoplasmic domain).

In some embodiments, the CAR expressing cell co-expresses the CAR and the target protein, for example, naturally expresses the target protein or is engineered to express the target protein. For example, the cell, for example, the population of immune effector cells, can include a nucleic acid (for example, vector) comprising the CAR nucleic acid (for example, a CAR nucleic acid as described herein) and a nucleic acid encoding the target protein.

In some embodiments, the T cell depleting agent is a CD52 inhibitor, for example, an anti-CD52 antibody molecule, for example, alemtuzumab.

In other embodiments, the cell, for example, the population of immune effector cells, expresses a CAR molecule as described herein (for example, CD19CAR) and the target protein recognized by the T cell depleting agent. In some embodiments, the target protein is CD20. In embodiments where the target protein is CD20, the T cell depleting agent is an anti-CD20 antibody, for example, rituximab.

In further embodiments of any of the aforesaid methods, the methods further include transplanting a cell, for example, a hematopoietic stem cell, or a bone marrow, into the mammal.

In some embodiments, the invention features a method of conditioning a mammal prior to cell transplantation. The method includes administering to the mammal an effective amount of the cell comprising a CAR nucleic acid or polypeptide, for example, a CD19 CAR nucleic acid or polypeptide.

In some embodiments, the cell transplantation is a stem cell transplantation, for example, a hematopoietic stem cell transplantation, or a bone marrow transplantation. In other embodiments, conditioning a subject prior to cell transplantation includes reducing the number of target-expressing cells in a subject, for example, CD19-expressing normal cells or CD19-expressing cancer cells.

Dosage Regimen

In some embodiments, a dose of viable CAR-expressing cells (for example, viable CD19, BCMA, CD20, or CD22 CAR-expressing cells) or a pharmaceutical composition comprising said cells comprises about $1\times10^6$ to about $1\times10^8$ (e.g., about $2\times10^6$ to about $5\times10^7$, about $5\times10^6$ to about $2\times10^7$, about $1\times10^6$ to about $1\times10^7$, about $1\times10^7$ to about $1\times10^8$, about $1\times10^6$ to about $3\times10^6$, about $2\times10^6$ to about $4\times10^6$, about $3\times10^6$ to about $5\times10^6$, about $4\times10^6$ to about $6\times10^6$, about $5\times10^6$ to about $7\times10^6$, about $6\times10^6$ to about $8\times10^6$, about $7\times10^6$ to about $9\times10^6$, about $8\times10^6$ to about $1\times10^7$, about $9\times10^6$ to about $2\times10^7$, about $1\times10^7$ to about $3\times10^7$, about $2\times10^7$ to about $4\times10^7$, about $3\times10^7$ to about $5\times10^7$, about $4\times10^7$ to about $6\times10^7$, about $5\times10^7$ to about $7\times10^7$, about $6\times10^7$ to about $8\times10^7$, about $7\times10^7$ to about $9\times10^7$, about $8\times10^7$ to about $1\times10^8$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$) CAR-positive viable cells (e.g., BCMA CAR+ T cells). In some embodiments, a dose of viable CAR-expressing cells (for example, viable CD19, BCMA, CD20, or CD22 CAR-expressing cells) comprises about $0.5\times10^6$ viable CAR-expressing cells to about $1.25\times10^9$ viable CAR-expressing cells (for example, $0.5\times10^6$ viable CAR-expressing cells to $1.25\times10^9$ viable CAR-expressing cells). In some embodiments, a dose of viable CAR-expressing cells (for example, viable CD19, BCMA, CD20, or CD22 CAR-expressing cells) comprises about $1\times10^6$, about $2.5\times10^6$, about $5\times10^6$, about $1.25\times10^7$, about $2.5\times10^7$, about $5\times10^7$, about $5.75\times10^7$, or about $8\times10^7$ viable CAR-expressing cells.

In some embodiments, the dose calculation is based on the number of BCMA-CAR+ viable T-cells (e.g., single-positive BCMA CAR cells plus double-positive BCMA+/CD19+ CAR cells), measured by flow cytometry on day 4 (96h) post-transduction (day 3 (72h) post-harvest), as described herein. In some embodiments, a dose of viable CAR-expressing cells (for example a BCMA/CD19 dual CART cellular product) comprises about $5\times10^6$ to about $2\times10^7$ CAR-positive viable cells (e.g., BCMA CAR+ T cells).

In some embodiments, a dose of viable CAR-expressing cells (for example, viable CD19, BCMA, CD20, or CD22 CAR-expressing cells) or a pharmaceutical composition comprising said cells is administered to the subject in one or more (e.g., 2, 3, 4, or more) doses. In some embodiments, the cells or pharmaceutical composition is administered to the subject in two doses. In some embodiments, the one or more doses comprises a first dose and a second dose, wherein the number of CAR-positive viable cells (e.g., BCMA CAR+ T cells) in the first dose is greater than, equal to, or less than the number of CAR-positive viable cells (e.g., BCMA CAR+ T cells) in the second dose.

In some embodiments, the one or more doses comprise a first dose and a second dose, wherein:

(a) the first dose comprises about $1\times10^6$ to about $1\times10^7$ (e.g., about $2\times10^6$ to about $8\times10^6$, about $4\times10^6$ to about $6\times10^6$, about $1\times10^6$ to about $5\times10^6$, about $5\times10^6$ to about $1\times10^7$, about $1\times10^6$ to about $3\times10^6$, about $2\times10^6$ to about $4\times10^6$, about $3\times10^6$ to about $5\times10^6$, about $4\times10^6$ to about $6\times10^6$, about $5\times10^6$ to about $7\times10^6$, about $6\times10^6$ to about $8\times10^6$, about $7\times10^6$ to about $9\times10^6$, about $8\times10^6$ to about $1\times10^7$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$) viable CAR-positive cells (e.g., BCMA CAR+ T cells);

(b) the second dose comprises about $1\times10^7$ to about $1\times10^8$ (e.g., about $2\times10^7$ to about $8\times10^7$, about $4\times10^7$ to about $6\times10^7$, about $1\times10^7$ to about $5\times10^7$, about $5\times10^7$ to about $1\times10^8$, about $1\times10^7$ to about $3\times10^7$, about $2\times10^7$ to about $4\times10^7$, about $3\times10^7$ to about $5\times10^7$, about $4\times10^7$ to about $6\times10^7$, about $5\times10^7$ to about $7\times10^7$, about $6\times10^7$ to about $8\times10^7$, about $7\times10^7$ to about $9\times10^7$, about $8\times10^7$ to about $1\times10^8$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, or about $1\times10^8$) CAR-positive viable cells (e.g., BCMA CAR+ T cells);

(c) the number of CAR-positive viable cells (e.g., BCMA CAR+ T cells) in the first dose is no more than 1/X, wherein X is 1, 2, 3, 4, 5, 6, 7, 8, 9, 10, 20, 30, 40, 50, 60, 70, 80, 90, or 100, of the number of CAR-positive viable cells (e.g., BCMA CAR+ T cells) in the second dose; and/or (d) the number of CAR-positive viable cells (e.g., BCMA CAR+ T cells) in the first dose is between about 1% and 100% (e.g., between about 10% and about 90%, between about 20% and about 80%, between about 30% and about 70%, between about 40% and about 60%, between about 10% and about 50%, between about 50% and about 90%, between about 10% and about 30%, between about 20% and about 40%, between about 30% and about 50%, between about 50% and about 70%, between about 60% and about 80%, or between about 70% and about 90%) of the number of CAR-positive viable cells (e.g., BCMA CAR+ T cells) in the second dose.

In some embodiments, the first dose comprises about $5\times10^6$ viable CAR-positive cells (e.g., BCMA CAR+ T cells). In some embodiments, the second dose comprises about $1\times10^7$ or about $2\times10^7$ viable CAR-positive cells (e.g., BCMA CAR+ T cells).

In some embodiments, the dose of CAR-positive cells may be increased from the starting dose at a subsequent administration. For example, patient may receive a starting dose of about $1\times10^6$ to about $1\times10^7$ (e.g., about $5\times10^6$) viable CAR-positive cells and may receive a second dose of about $1\times10^7$ to about $1\times10^8$ (e.g., about $1\times10^7$ or about $2\times10^7$) CAR-positive viable cells (e.g., BCMA CAR+ T cells).

Patient Selection

In some embodiments of any of the methods of treating a subject, or composition for use disclosed herein, the subject has a cancer, for example, a hematological cancer. In some embodiments, the cancer is chosen from lymphocytic leukemia (CLL), mantle cell lymphoma (MCL), multiple myeloma, acute lymphoid leukemia (ALL), Hodgkin lymphoma, B-cell acute lymphoid leukemia (BALL), T-cell acute lymphoid leukemia (TALL), small lymphocytic leukemia (SLL), B cell prolymphocytic leukemia, blastic plasmacytoid dendritic cell neoplasm, Burkitt's lymphoma, diffuse large B cell lymphoma (DLBCL), DLBCL associated with chronic inflammation, chronic myeloid leukemia, myeloproliferative neoplasms, follicular lymphoma, pediatric follicular lymphoma, hairy cell leukemia, small cell- or a large cell-follicular lymphoma, malignant lymphoproliferative conditions, MALT lymphoma (extranodal marginal zone lymphoma of mucosa-associated lymphoid tissue), Marginal zone lymphoma, myelodysplasia, myelodysplastic syndrome, non-Hodgkin lymphoma, plasmablastic lymphoma, plasmacytoid dendritic cell neoplasm, Waldenstrom macroglobulinemia, splenic marginal zone lymphoma, splenic lymphoma/leukemia, splenic diffuse red pulp small B-cell lymphoma, hairy cell leukemia-variant, lymphoplasmacytic lymphoma, a heavy chain disease, plasma cell myeloma, solitary plasmocytoma of bone, extraosseous plasmocytoma, nodal marginal zone lymphoma, pediatric nodal marginal zone lymphoma, primary cutaneous follicle center lymphoma, lymphomatoid granulomatosis, primary mediastinal (thymic) large B-cell lymphoma, intravascular large B-cell lymphoma, ALK+ large B-cell lymphoma, large B-cell lymphoma arising in HHV8-associated multicentric Castleman disease, primary effusion lymphoma, B-cell lymphoma, acute myeloid leukemia (AML), or unclassifiable lymphoma. In some embodiments, the cancer is a relapsed and/or refractory cancer.

In some embodiments of any of the methods of treating a subject, or composition for use disclosed herein, the subject has CLL or SLL. In some embodiments, the subject having CLL or SLL has previously been administered a BTK inhibitor therapy, for example, ibrutinib, for least 1-12 months, for example, 6 months. In some embodiments, the BTK inhibitor therapy, for example, ibrutinib therapy, is a second line therapy. In some embodiments, the subject had a partial response, or had stable disease in response to the BTK inhibitor therapy. In some embodiments, the subject did not response to the BTK inhibitor therapy. In some embodiments, the subject developed resistance, for example, developed ibrutinib resistance mutations. In some embodiments, the ibrutinib resistance mutations comprise a mutation in the gene encoding BTK and/or the gene encoding PLCg2. In some embodiments, the subject is an adult, for example, at least 18 years of age.

In some embodiments of any of the methods of treating a subject, or composition for use disclosed herein, the subject has DLBCL, for example, relapsed and/or refractory DLBCL. In some embodiments, the subject having DLBCL, for example, relapsed and/or refractory DLBCL, has previously been administered at least 2 lines of chemotherapy, for example, an anti-CD20 therapy and/or an anthracycline-based chemotherapy. In some embodiments, the subject has previously received stem cell therapy, for example, autologous stem cell therapy, and has not responded to said stem cell therapy. In some embodiments, the subject is not eligible for stem cell therapy, for example, autologous stem cell therapy. In some embodiments, the subject is an adult, for example, at least 18 years of age.

Therapeutic Application

BCMA Associated Diseases and/or Disorders

In one aspect, the invention provides methods for treating a disease associated with BCMA expression. In one aspect, the invention provides methods for treating a disease wherein part of the tumor is negative for BCMA and part of the tumor is positive for BCMA For example, the CAR of the invention is useful for treating subjects that have undergone treatment for a disease associated with elevated expression of BCMA, wherein the subject that has undergone treatment for elevated levels of BCMA exhibits a disease associated with elevated levels of BCMA. In embodiments, the CAR of the invention is useful for treating subjects that have undergone treatment for a disease associated with expression of BCMA, wherein the subject that has undergone treatment related to expression of BCMA exhibits a disease associated with expression of BCMA.

In one embodiment, the invention provides methods for treating a disease wherein BCMA is expressed on both normal cells and cancers cells, but is expressed at lower levels on normal cells. In one embodiment, the method further comprises selecting a CAR that binds of the invention with an affinity that allows the BCMA CAR to bind and kill the cancer cells expressing BCMA but less than 30%, 25%, 20%, 15%, 10%, 5% or less of the normal cells expressing BCMA are killed, e.g., as determined by an assay described herein. For example, a killing assay such as flow cytometry based on Cr51 CTL can be used. In one embodiment, the BCMA CAR has an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In one embodiment, the BCMA antigen binding domain has a binding affinity that is at least five-fold, 10-fold, 20-fold, 30-fold, 50-fold, 100-fold or 1,000-fold less than a reference antibody, e.g., an antibody described herein.

In one aspect, the invention pertains to a vector comprising BCMA CAR operably linked to promoter for expression in mammalian immune effector cells, e.g., T cells or NK cells. In one aspect, the invention provides a recombinant immune effector cell, e.g., T cell or NK cell, expressing the BCMA CAR for use in treating BCMA-expressing tumors, wherein the recombinant immune effector cell (e.g., T cell or NK cell) expressing the BCMA CAR is termed a BCMA CAR-expressing cell (e.g., BCMA CART or BCMA CAR-expressing NK cell). In one aspect, the BCMA CAR-expressing cell (e.g., BCMA CART or BCMA CAR-expressing NK cell) of the invention is capable of contacting a tumor cell with at least one BCMA CAR of the invention expressed on its surface such that the BCMA CAR-expressing cell (e.g., BCMA CART or BCMA CAR-expressing NK cell) targets the tumor cell and growth of the tumor is inhibited.

In one aspect, the invention pertains to a method of inhibiting growth of a BCMA-expressing tumor cell, comprising contacting the tumor cell with a BCMA CAR-expressing cell (e.g., BCMA CART or BCMA CAR-expressing NK cell) of the present invention such that the BCMA CAR-expressing cell (e.g., BCMA CART or BCMA CAR-expressing NK cell) is activated in response to the antigen and targets the cancer cell, wherein the growth of the tumor is inhibited.

In one aspect, the invention pertains to a method of treating cancer in a subject. The method comprises administering to the subject a BCMA CAR-expressing cell (e.g., BCMA CART or BCMA CAR-expressing NK cell) of the present invention such that the cancer is treated in the subject. An example of a cancer that is treatable by the BCMA CAR-expressing cell (e.g., BCMA CART or BCMA CAR-expressing NK cell) of the invention is a cancer associated with expression of BCMA.

The invention includes a type of cellular therapy where immune effector cells (e.g., T cells or NK cells) are genetically modified to express a chimeric antigen receptor (CAR) and the BCMA CAR-expressing cell (e.g., BCMA CART or BCMA CAR-expressing NK cell) is infused to a recipient in need thereof. The infused cell is able to kill tumor cells in the recipient. Unlike antibody therapies, CAR-modified cells, e.g., T cells or NK cells, are able to replicate in vivo resulting in long-term persistence that can lead to sustained tumor control. In various aspects, the cells (e.g., T cells or NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the cell (e.g., T cell or NK cell) to the patient.

The invention also includes a type of cellular therapy where immune effector cells (e.g., T cells or NK cells) are modified, e.g., by in vitro transcribed RNA, to transiently express a chimeric antigen receptor (CAR) and the immune effector cell (e.g., T cell or NK cell) is infused to a recipient in need thereof. The infused cell is able to kill tumor cells in the recipient. Thus, in various aspects, the immune effector cells (e.g., T cells or NK cells) administered to the patient, is present for less than one month, e.g., three weeks, two weeks, one week, after administration of the immune effector cell (e.g., T cell or NK cell) to the patient.

Without wishing to be bound by theory, the anti-tumor immunity response elicited by the CAR-modified immune effector cells (e.g., T cells or NK cells) may be an active or a passive immune response, or alternatively may be due to a direct vs indirect immune response. In one aspect, the CAR transduced immune effector cells (e.g., T cells or NK cells) exhibit specific proinflammatory cytokine secretion and potent cytolytic activity in response to human cancer cells expressing the BCMA, resist soluble BCMA inhibition, mediate bystander killing and mediate regression of an established human tumor. For example, antigen-less tumor cells within a heterogeneous field of BCMA-expressing tumor may be susceptible to indirect destruction by BCMA-redirected immune effector cells (e.g., T cells or NK cells) that has previously reacted against adjacent antigen-positive cancer cells.

In one aspect, the fully-human CAR-modified immune effector cells (e.g., T cells or NK cells) of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. For example, the CAR-modified immune effector cells (e.g., T cells or NK cells) of the invention are used in the treatment of diseases, disorders and conditions associated with expression of BCMA. In some aspects, the cells of the invention are used in the treatment of patients at risk for developing diseases, disorders and conditions associated with expression of BCMA. Thus, the present invention provides methods for the treatment or prevention of diseases, disorders and conditions associated with expression of BCMA comprising administering to a subject in need thereof, a therapeutically effective amount of the CAR-modified immune effector cells (e.g., T cells or NK cells) of the invention.

In one aspect the CAR-expressing cells (e.g., CART cells or CAR-expressing NK cells) of the inventions may be used to treat a proliferative disease such as a cancer or malignancy or is a precancerous condition such as a myelodysplasia, a myelodysplastic syndrome or a preleukemia. In one aspect, the cancer is a hematological cancer. Hematological cancer conditions are the types of cancer such as leukemia and malignant lymphoproliferative conditions that affect blood, bone marrow and the lymphatic system. In one aspect, the hematological cancer is a leukemia or a hematological. An example of a disease or disorder associated with BCMA is multiple myeloma (also known as MM) (See Claudio et al., Blood. 2002, 100(6):2175-86; and Novak et al., Blood. 2004, 103(2):689-94). Multiple myeloma, also known as plasma cell myeloma or Kahler's disease, is a cancer characterized by an accumulation of abnormal or malignant plasma B-cells in the bone marrow. Frequently, the cancer cells invade adjacent bone, destroying skeletal structures and resulting in bone pain and fractures. Most cases of myeloma also features the production of a paraprotein (also known as M proteins or myeloma proteins), which is an abnormal immunoglobulin produced in excess by the clonal proliferation of the malignant plasma cells. Blood serum paraprotein levels of more than 30 g/L is diagnostic of multiple myeloma, according to the diagnostic criteria of the International Myeloma Working Group (IMWG) (See Kyle et al. (2009), Leukemia. 23:3-9). Other symptoms or signs of multiple myeloma include reduced kidney function or renal failure, bone lesions, anemia, hypercalcemia, and neurological symptoms.

Criteria for distinguishing multiple myeloma from other plasma cell proliferative disorders have been established by the International Myeloma Working Group (See Kyle et al. (2009), Leukemia. 23:3-9). All three of the following criteria must be met:

Clonal bone marrow plasma cells ≥10%

Present of serum and/or urinary monoclonal protein (except in patients with true non-secretory multiple myeloma)

Evidence of end-organ damage attributable to the underlying plasma cell proliferative disorder, specifically:

Hypercalcemia: serum calcium >11.5 mg/100 ml

Renal insufficiency: serum creatinine >1.73 mmol/l

Anemia: normochromic, normocytic with a hemoglobin value of >2 g/100 ml below the lower limit of normal, or a hemoglobin value <10 g/100 ml Bone lesions: lytic lesions, severe osteopenia, or pathologic fractures.

Other plasma cell proliferative disorders that can be treated by the compositions and methods described herein include, but are not limited to, asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

Two staging systems are used in the staging of multiple myeloma: the International Staging System (ISS) (See Greipp et al. (2005), J. Clin. Oncol. 23 (15):3412-3420) and the Durie-Salmon Staging system (DSS) (See Durie et al. (1975), Cancer 36 (3): 842-854).

A third staging system for multiple myeloma is referred to as Revised International Staging System (R-ISS) (see Palumbo A, Avet-Loiseau H, Oliva S, et al. Journal of clinical oncology: official journal of the American Society of Clinical Oncology 2015; 33:2863-9, herein incorporated by reference in its entirety). R-ISS stage I includes ISS stage I (serum 02-microglobulin level <3.5 mg/L and serum albumin level ≥3.5 g/dL), no high-risk CA [del(17p) and/or t(4;14) and/or t(14;16)], and normal LDH level (less than the upper limit of normal range). R-ISS stage III includes ISS stage III (serum 02-microglobulin level >5.5 mg/L) and high-risk CA or high LDH level. R-ISS stage II includes all the other possible combinations.

The response of patients can be determined based on IMWG 2016 criteria, as disclosed in Kumar S, Paiva B, Anderson K C, et al. International Myeloma Working Group consensus criteria for response and minimal residual disease assessment in multiple myeloma. The Lancet Oncology; 17(8):e328-e346, herein incorporated by reference in its entirety.

Standard treatment for multiple myeloma and associated diseases includes chemotherapy, stem cell transplant (autologous or allogeneic), radiation therapy, and other drug therapies. Frequently used anti-myeloma drugs include alkylating agents (e.g., bendamustine, cyclophosphamide and melphalan), proteasome inhibitors (e.g., bortezomib), corticosteroids (e.g., dexamethasone and prednisone), and immunomodulators (e.g., thalidomide and lenalidomide or Revlimid®), or any combination thereof.

Biphosphonate drugs are also frequently administered in combination with the standard anti-MM treatments to prevent bone loss. Patients older than 65-70 years of age are unlikely candidates for stem cell transplant. In some cases, double-autologous stem cell transplants are options for patients less than 60 years of age with suboptimal response to the first transplant. The compositions and methods of the present invention may be administered in combination with any of the currently prescribed treatments for multiple myeloma.

Another example of a disease or disorder associated with BCMA is Hodgkin's lymphoma and non-Hodgkin's lymphoma (See Chiu et al., Blood. 2007, $10^9$(2):729-39; He et al., J Immunol. 2004, 172(5):3268-79).

Hodgkin's lymphoma (HL), also known as Hodgkin's disease, is a cancer of the lymphatic system that originates from white blood cells, or lymphocytes. The abnormal cells that comprise the lymphoma are called Reed-Sternberg cells. In Hodgkin's lymphoma, the cancer spreads from one lymph node group to another. Hodgkin's lymphoma can be subclassified into four pathologic subtypes based upon Reed-Sternberg cell morphology and the cell composition around the Reed-Sternberg cells (as determined through lymph node biopsy): nodular sclerosing HL, mixed-cellularity subtype, lymphocyte-rich or lymphocytic predominance, lymphocyte depleted. Some Hodgkin's lymphoma can also be nodular lymphocyte predominant Hodgkin's lymphoma, or can be unspecified. Symptoms and signs of Hodgkin's lymphoma include painless swelling in the lymph nodes in the neck, armpits, or groin, fever, night sweats, weight loss, fatigue, itching, or abdominal pain.

Non-Hodgkin's lymphoma (NHL) comprises a diverse group of blood cancers that include any kind of lymphoma other than Hodgkin's lymphoma. Subtypes of non-Hodgkin's lymphoma are classified primarily by cell morphology, chromosomal aberrations, and surface markers. NHL subtypes (or NHL-associated cancers) include B cell lymphomas such as, but not limited to, Burkitt's lymphoma, B-cell chronic lymphocytic leukemia (B-CLL), B-cell prolymphocytic leukemia (B-PLL), chronic lymphocytic leukemia (CLL), diffuse large B-cell lymphoma (DLBCL) (e.g., intravascular large B-cell lymphoma and primary mediastinal B-cell lymphoma), follicular lymphoma (e.g., follicle center lymphoma, follicular small cleaved cell), hair cell leukemia, high grade B-cell lymphoma (Burkitt's like), lymphoplasmacytic lymphoma (Waldenstrom's macroglublinemia), mantle cell lymphoma, marginal zone B-cell lymphomas (e.g., extranodal marginal zone B-cell lymphoma or mucosa-associated lymphoid tissue (MALT) lymphoma, nodal marginal zone B-cell lymphoma, and splenic marginal zone B-cell lymphoma), plasmacytoma/myeloma, precursor B-lymphoblastic leukemia/lymphoma (PB-LBL/L), primary central nervous system (CNS) lymphoma, primary intraocular lymphoma, small lymphocytic lymphoma (SLL); and T cell lymphomas, such as, but not limited to, anaplastic large cell lymphoma (ALCL), adult T-cell lymphoma/leukemia (e.g., smoldering, chronic, acute and lymphomatous), angiocentric lymphoma, angioimmunoblastic T-cell lymphoma, cutaneous T-cell lymphomas (e.g., mycosis fungoides, Sezary syndrome, etc.), extranodal natural killer/T-cell lymphoma (nasal-type), enteropathy type intestinal T-cell lymphoma, large granular lymphocyte leukemia, precursor T-lymphoblastic lymphoma/leukemia (T-LBL/L), T-cell chronic lymphocytic leukemia/prolymphocytic leukemia (T-CLL/PLL), and unspecified peripheral T-cell lymphoma. Symptoms and signs of Hodgkin's lymphoma include painless swelling in the lymph nodes in the neck, armpits, or groin, fever, night sweats, weight loss, fatigue, itching, abdominal pain, coughing, or chest pain.

The staging is the same for both Hodgkin's and non-Hodgkin's lymphoma, and refers to the extent of spread of the cancer cells within the body. In stage I, the lymphoma cells are in one lymph node group. In stage II, lymphoma cells are present in at least two lymph node groups, but both groups are on the same side of the diaphragm, or in one part of a tissue or organ and the lymph nodes near that organ on the same side of the diaphragm. In stage III, lymphoma cells are in lymph nodes on both sides of the diaphragm, or in one part of a tissue or organ near these lymph node groups or in the spleen. In stage IV, lymphoma cells are found in several parts of at least one organ or tissue, or lymphoma cells are in an organ and in lymph nodes on the other side of the diaphragm. In addition to the Roman numeral staging designation, the stages of can also be described by letters A, B, E, and S, wherein A refers to patients without symptoms, B refers to patients with symptoms, E refers to patients in which lymphoma is found in tissues outside the lymph system, and S refers to patients in which lymphoma is found in the spleen.

Hodgkin's lymphoma is commonly treated with radiation therapy, chemotherapy, or hematopoietic stem cell transplantation. The most common therapy for non-Hodgkin's lymphoma is R-CHOP, which consists of four different chemotherapies (cyclophosphamide, doxorubicin, vincristine, and prenisolone) and rituximab (Rituxan®). Other therapies commonly used to treat NHL include other chemotherapeutic agents, radiation therapy, stem cell transplantation (autologous or allogeneic bone marrow transplantation), or biological therapy, such as immunotherapy. Other examples of biological therapeutic agents include, but are not limited to, rituximab (Rituxan®), tositumomab (Bexxar®), epratuzumab (LymphoCide®), and alemtuzumab (MabCampath®). The compositions and methods of the present invention may be administered in combination with any of the currently prescribed treatments for Hodgkin's lymphoma or non-Hodgkin's lymphoma.

BCMA expression has also been associated Waldenstrom's macroglobulinemia (WM), also known as lymphoplasmacytic lymphoma (LPL). (See Elsawa et al., Blood. 2006, 107(7):2882-8). Waldenstrom's macroglobulinemia was previously considered to be related to multiple myeloma, but has more recently been classified as a subtype of non-Hodgkin's lymphoma. WM is characterized by uncontrolled B-cell lymphocyte proliferation, resulting in anemia and production of excess amounts of paraprotein, or immunoglobulin M (IgM), which thickens the blood and results in hyperviscosity syndrome. Other symptoms or signs of WM include fever, night sweats, fatigue, anemia, weight loss, lymphadenopathy or splenomegaly, blurred vision, dizziness, nose bleeds, bleeding gums, unusual bruises, renal impairment or failure, amyloidosis, or peripheral neuropathy.

Standard treatment for WM consists of chemotherapy, specifically with rituximab (Rituxan®). Other chemotherapeutic drugs can be used in combination, such as chlorambucil (Leukeran®), cyclophosphamide (Neosar®), fludarabine (Fludara®), cladribine (Leustatin®), vincristine, and/or thalidomide. Corticosteriods, such as prednisone, can also be administered in combination with the chemotherapy. Plasmapheresis, or plasma exchange, is commonly used throughout treatment of the patient to alleviate some symptoms by removing the paraprotein from the blood. In some cases, stem cell transplantation is an option for some patients.

Another example of a disease or disorder associated with BCMA is brain cancer. Specifically, expression of BCMA has been associated with astrocytoma or glioblastoma (See Deshayes et al, Oncogene. 2004, 23(17):3005-12, Pelekanou et al., PLoS One. 2013, 8(12):e83250). Astrocytomas are tumors that arise from astrocytes, which are a type of glial cell in the brain. Glioblastoma (also known as glioblastoma multiforme or GBM) is the most malignant form of astrocytoma, and is considered the most advanced stage of brain cancer (stage IV). There are two variants of glioblastoma: giant cell glioblastoma and gliosarcoma. Other astrocytomas include juvenile pilocytic astrocytoma (JPA), fibrillary astrocytoma, pleomorphic xantroastrocytoma (PXA), desembryoplastic neuroepithelial tumor (DNET), and anaplastic astrocytoma (AA).

Symptoms or signs associated with glioblastoma or astrocytoma include increased pressure in the brain, headaches, seizures, memory loss, changes in behavior, loss in movement or sensation on one side of the body, language dysfunction, cognitive impairments, visual impairment, nausea, vomiting, and weakness in the arms or legs.

Surgical removal of the tumor (or resection) is the standard treatment for removal of as much of the glioma as possible without damaging or with minimal damage to the normal, surrounding brain. Radiation therapy and/or chemotherapy are often used after surgery to suppress and slow recurrent disease from any remaining cancer cells or satellite lesions. Radiation therapy includes whole brain radiotherapy (conventional external beam radiation), targeted three-dimensional conformal radiotherapy, and targeted radionuclides. Chemotherapeutic agents commonly used to treat glioblastoma include temozolomide, gefitinib or erlotinib, and cisplatin. Angiogenesis inhibitors, such as Bevacizumab (Avastin®), are also commonly used in combination with chemotherapy and/or radiotherapy.

Supportive treatment is also frequently used to relieve neurological symptoms and improve neurologic function, and is administered in combination any of the cancer therapies described herein. The primary supportive agents include anticonvulsants and corticosteroids. Thus, the compositions and methods of the present invention may be used in combination with any of the standard or supportive treatments to treat a glioblastoma or astrocytoma.

Non-cancer related diseases and disorders associated with BCMA expression can also be treated by the compositions and methods disclosed herein. Examples of non-cancer related diseases and disorders associated with BCMA expression include, but are not limited to: viral infections; e.g., HIV, fungal infections, e.g., *C. neoformans*; irritable bowel disease; ulcerative colitis, and disorders related to mucosal immunity.

The CAR-modified immune effector cells (e.g., T cells or NK cells) of the present invention may be administered either alone, or as a pharmaceutical composition in combination with diluents and/or with other components such as IL-2 or other cytokines or cell populations.

The present invention provides for compositions and methods for treating cancer. In one aspect, the cancer is a hematologic cancer including but is not limited to hematological cancer is a leukemia or a lymphoma. In one aspect, the CAR-expressing cells (e.g., CART cells or CAR-expressing NK cells) of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with BCMA expression includes, but not limited to, e.g., atypical and/or non-classical cancers, malignancies, precancerous conditions or proliferative diseases expressing BCMA.

In embodiments, a composition described herein can be used to treat a disease including but not limited to a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

In embodiments, a composition described herein can be used to treat a disease including but not limited to a cancer, e.g., a cancer described herein, e.g., a prostate cancer (e.g., castrate-resistant or therapy-resistant prostate cancer, or metastatic prostate cancer), pancreatic cancer, or lung cancer.

The present invention also provides methods for inhibiting the proliferation or reducing a BCMA-expressing cell population, the methods comprising contacting a population of cells comprising a BMCA-expressing cell with an anti-BCMA CAR-expressing cell (e.g., BCMA CART cell or BCMA CAR-expressing NK cell) of the invention that binds to the BCMA-expressing cell. In a specific aspect, the present invention provides methods for inhibiting the proliferation or reducing the population of cancer cells expressing BCMA, the methods comprising contacting the BCMA-expressing cancer cell population with an anti-BCMA CAR-expressing cell (e.g., BCMA CART cell or BCMA CAR-expressing NK cell) of the invention that binds to the BCMA-expressing cell. In one aspect, the present invention provides methods for inhibiting the proliferation or reducing the population of cancer cells expressing BCMA, the methods comprising contacting the BMCA-expressing cancer cell population with an anti-BCMA CAR-expressing cell (e.g., BCMA CART cell or BCMA CAR-expressing NK cell) of the invention that binds to the BCMA-expressing cell. In some aspects, the anti-BCMA CAR-expressing cell (e.g., BCMA CART cell or BCMA CAR-expressing NK cell) of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with BCMA-expressing cells relative to a negative control. In one aspect, the subject is a human.

The present invention also provides methods for preventing, treating and/or managing a disease associated with BCMA-expressing cells (e.g., a hematologic cancer or atypical cancer expressing BCMA), the methods comprising administering to a subject in need an anti-BCMA CAR-expressing cell (e.g., BCMA CART cell or BCMA CAR-expressing NK cell) of the invention that binds to the BCMA-expressing cell. In one aspect, the subject is a human. Non-limiting examples of disorders associated with BCMA-expressing cells include viral or fungal infections, and disorders related to mucosal immunity.

The present invention also provides methods for preventing, treating and/or managing a disease associated with BCMA-expressing cells, the methods comprising administering to a subject in need an anti-BCMA CAR-expressing cell (e.g., BCMA CART cell or BCMA CAR-expressing NK cell) of the invention that binds to the BCMA-expressing cell. In one aspect, the subject is a human.

The present invention provides methods for preventing relapse of cancer associated with BCMA-expressing cells, the methods comprising administering to a subject in need thereof an anti-BCMA CAR-expressing cell (e.g., BCMA CART cell or BCMA CAR-expressing NK cell) of the invention that binds to the BCMA-expressing cell. In one aspect, the methods comprise administering to the subject in need thereof an effective amount of an anti-BCMA CAR-expressing cell (e.g., BCMA CART cell or BCMA CAR-expressing NK cell) described herein that binds to the BCMA-expressing cell in combination with an effective amount of another therapy.

Combination Therapies

A CAR-expressing cell described herein may be used in combination with other known agents and therapies. A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed. The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder. When administered in combination, the CAR therapy and the additional agent (e.g., second or third agent), or all, can be administered in an amount or dose that is higher, lower or the same than the amount or dosage of each agent used individually, e.g., as a monotherapy. In some embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect. In further aspects, a CAR-expressing cell described herein may be used in a treatment regimen in combination with surgery, chemotherapy, radiation, immunosuppressive agents. Exemplary agents and therapies that can be used in combination with a CAR-expressing cell described herein are disclosed on pages 266-313 of WO2016164731, herein incorporated by reference in its entirety.

Biomarkers for Evaluating CAR-Effectiveness

In some embodiments, disclosed herein is a method of evaluating or monitoring the effectiveness of a CAR-expressing cell therapy (for example, a CD19 or BCMA CAR therapy), in a subject (for example, a subject having a cancer, for example, a hematological cancer). The method includes acquiring a value of effectiveness to the CAR therapy, wherein said value is indicative of the effectiveness or suitability of the CAR-expressing cell therapy.

In embodiments, the value of effectiveness to the CAR therapy in a subject having CLL or SLL, comprises a measure of one, two, three, or all of the following parameters:

(i) a mutation in a gene encoding BTK in a sample (for example, an apheresis sample or a manufactured CAR-expressing cell product sample);

(ii) a mutation in a gene encoding PLCg2 in a sample (for example, an apheresis sample or a manufactured CAR-expressing cell product sample);

(iii) minimal residual disease, for example, as evaluated by the level and/or activity of CD8, CD4, CD3, CD5, CD19, CD20, CD22, CD43, CD79b, CD27, CD45RO, CD45RA, CCR7, CD95, Lag3, PD-1, Tim-3, and/or CD81; or as evaluated by immunoglobulin deep sequencing; in a sample (for example, an apheresis sample or tumor sample from the subject); or (iv) the level or activity of one, two, three, four, five, six, seven, eight, nine, ten or all of the cytokines chosen from IFN-g, IL-2, IL-4, IL-6, IL-8, IL-10, IL-15, TNF-$\alpha$, IP-10, MCP1, MIP1a, in a sample, for example, an apheresis sample from the subject.

In embodiments, the value of effectiveness to the CAR therapy in a subject having DLBCL, for example, relapsed and/or refractory DLBCL, comprises a measure of one or both the following parameters:

(i) minimal residual disease, for example, as evaluated by the level and/or activity of CD8, CD4, CAR19, CD3, CD27, CD45RO, CD45RA, CCR7, CD95, Lag3, PD-1, and/or Tim-3; or as evaluated by immunoglobulin deep sequencing; in a sample (for example, an apheresis sample or tumor sample from the subject); or (ii) the level or activity of one, two, three, four, five, six, seven, eight, nine, ten or all of the cytokines chosen from IFN-g, IL-2, IL-4, IL-6, IL-8, IL-10, IL-15, TNF-a, IP-10, MCP1, MIP1a, in a sample (for example, an apheresis sample from the subject).

In other embodiments, the value of effectiveness to the CAR therapy, further comprises a measure of one, two, three, four, five, six or more (all) of the following parameters:

(i) the level or activity of one, two, three, or more (for example, all) of resting $T_{EFF}$ cells, resting $T_{REG}$ cells, younger T cells (for example, naïve T cells (for example, naïve CD4 or CD8 T cells, naïve gamma/delta T cells), or stem memory T cells (for example, stem memory CD4 or CD8 T cells, or stem memory gamma/delta T cells), or early memory T cells, or a combination thereof, in a sample (for example, an apheresis sample or a manufactured CAR-expressing cell product sample);

(ii) the level or activity of one, two, three, or more (for example, all) of activated $T_{EFF}$ cells, activated $T_{REG}$ cells, older T cells (for example, older CD4 or CD8 cells), or late memory T cells, or a combination thereof, in a sample (for example, an apheresis sample or a manufactured CAR-expressing cell product sample);

(iii) the level or activity of an immune cell exhaustion marker, for example, one, two or more immune checkpoint inhibitors (for example, PD-1, PD-L1, TIM-3, TIGIT and/or LAG-3) in a sample (for example, an apheresis sample or a manufactured CAR-expressing cell product sample). In some embodiments, an immune cell has an exhausted phenotype, for example, co-expresses at least two exhaustion markers, for example, co-expresses PD-1 and TIM-3. In other embodiments, an immune cell has an exhausted phenotype, for example, co-expresses at least two exhaustion markers, for example, co-expresses PD-1 and LAG-3;

(iv) the level or activity of CD27 and/or CD45RO− (for example, CD27+CD45RO−) immune effector cells, for example, in a CD4+ or a CD8+ T cell population, in a sample (for example, an apheresis sample or a manufactured CAR-expressing cell product sample);

(v) the level or activity of one, two, three, four, five, six, seven, eight, nine, ten, eleven or all of the biomarkers chosen from CCL20, IL-17a, IL-6, PD-1, PD-L1, LAG-3, TIM-3, CD57, CD27, CD122, CD62L, KLRG1;

(vi) a cytokine level or activity (for example, quality of cytokine reportoire) in a CAR-expressing cell product sample, for example, CLL-1-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (for example, a population) of CAR-expressing immune effector cells, for example, a plurality (for example, a population) of T cells or NK cells, or a combination thereof. In some embodiments, the CAR-expressing cell therapy is a CD19 CAR therapy.

In some embodiments of any of the methods disclosed herein, the measure of one or more of the parameters disclosed herein is obtained from an apheresis sample acquired from the subject. The apheresis sample can be evaluated prior to infusion or re-infusion.

In some embodiments of any of the methods disclosed herein, the measure of one or more of the parameters disclosed herein is obtained from a tumor sample acquired from the subject.

In some embodiments of any of the methods disclosed herein, the measure of one or more of the parameters disclosed herein is obtained from a manufactured CAR-expressing cell product sample, for example, CD19 CAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of the parameters disclosed herein evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of the parameters disclosed herein.

In some embodiments of any of the methods disclosed herein, a responder, for example, complete responder has, or is identified as having, a greater, for example, a statistically significant greater, percentage of CD8+ T cells compared to a reference value, for example, a non-responder percentage of CD8+ T cells.

In some embodiments of any of the methods disclosed herein, a responder, for example, complete responder has, or is identified as having, a greater percentage of CD27+CD45RO− immune effector cells, for example, in the CD8+ population, compared to a reference value, for example, a non-responder number of CD27+CD45RO− immune effector cells.

In some embodiments of any of the methods disclosed herein, a responder, for example, complete responder or a partial responder has, or is identified as having, a greater, for example, a statistically significant greater, percentage of CD4+ T cells compared to a reference value, for example, a non-responder percentage of CD4+ T cells.

In some embodiments of any of the methods disclosed herein, a responder, for example, complete responder has, or is identified as having, a greater percentage of one, two, three, or more (for example, all) of resting $T_{EFF}$ cells, resting $T_{REG}$ cells, younger T cells, or early memory T cells, or a combination thereof, compared to a reference value, for example, a non-responder number of resting $T_{EFF}$ cells, resting $T_{REG}$ cells, younger T cells, or early memory T cells.

In some embodiments of any of the methods disclosed herein, a non-responder has, or is identified as having, a greater percentage of one, two, three, or more (for example, all) of activated $T_{EFF}$cells, activated $T_{REG}$ cells, older T cells (for example, older CD4 or CD8 cells), or late memory T cells, or a combination thereof, compared to a reference value, for example, a responder number of activated $T_{EFF}$ cells, activated $T_{REG}$ cells, older T cells (for example, older CD4 or CD8 cells), or late memory T cells.

In some embodiments of any of the methods disclosed herein, a non-responder has, or is identified as having, a greater percentage of an immune cell exhaustion marker, for example, one, two or more immune checkpoint inhibitors (for example, PD-1, PD-L1, TIM-3, TIGIT, and/or LAG-3). In some embodiments, a non-responder has, or is identified as having, a greater percentage of PD-1, PD-L1, or LAG-3 expressing immune effector cells (for example, CD4+ T cells and/or CD8+ T cells) (for example, CAR-expressing CD4+ cells and/or CD8+ T cells) compared to the percentage of PD-1 or LAG-3 expressing immune effector cells from a responder.

In some embodiments, a non-responder has, or is identified as having, a greater percentage of immune cells having an exhausted phenotype, for example, immune cells that co-express at least two exhaustion markers, for example, co-expresses PD-1, PD-L1 and/or TIM-3. In other embodiments, a non-responder has, or is identified as having, a greater percentage of immune cells having an exhausted phenotype, for example, immune cells that co-express at least two exhaustion markers, for example, co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population (for example, a CLL-1 CAR+ cell population) compared to a responder (for example, a complete responder) to the CAR-expressing cell therapy.

In some embodiments of any of the methods disclosed herein, the responder (for example, the complete or partial responder) has one, two, three or more (or all) of the following profile:

(i) has a greater number of CD27+ immune effector cells compared to a reference value, for example, a non-responder number of CD27+ immune effector cells;

(ii) has a greater number of CD8+ T cells compared to a reference value, for example, a non-responder number of CD8+ T cells;

(iii) has a lower number of immune cells expressing one or more checkpoint inhibitors, for example, a checkpoint inhibitor chosen from PD-1, PD-L1, LAG-3, TIM-3, or KLRG-1, or a combination, compared to a reference value, for example, a non-responder number of cells expressing one or more checkpoint inhibitors; or (iv) has a greater number of one, two, three, four or more (all) of resting $T_{EFF}$ cells, resting $T_{REG}$cells, naïve CD4 cells, unstimulated memory cells or early memory T cells, or a combination thereof, compared to a reference value, for example, a non-responder number of resting $T_{EFF}$ cells, resting $T_{REG}$cells, naïve CD4 cells, unstimulated memory cells or early memory T cells.

In embodiments, a subject who is a responder, a non-responder, a relapser or a non-relapser identified by the methods herein can be further evaluated according to clinical criteria. For example, a complete responder has, or is identified as, a subject having a disease, for example, a cancer, who exhibits a complete response, for example, a complete remission, to a treatment. A complete response may be identified, for example, using the NCCN Guidelines®, or the International Workshop on Chronic Lymphocytic Leukemia (iwCLL) 2018 guidelines as disclosed in Hallek M et al., Blood (2018) 131:2745-2760 "iwCLL guidelines for diagnosis, indications for treatment, response assessment, and supportive management of CLL," the entire contents of which are hereby incorporated by reference in its entirety. A partial responder has, or is identified as, a subject having a disease, for example, a cancer, who exhibits a partial response, for example, a partial remission, to a treatment. A partial response may be identified, for example, using the NCCN Guidelines®, or iwCLL 2018 criteria as described herein. A non-responder has, or is identified as, a subject having a disease, for example, a cancer, who does not exhibit a response to a treatment, for example, the patient has stable disease or progressive disease. A non-responder may be identified, for example, using the NCCN Guidelines®, or iwCLL 2018 criteria as described herein.

Alternatively, or in combination with the methods disclosed herein, responsive to said value, performing one, two, three four or more of:

administering for example, to a responder or a non-relapser, a CAR-expressing cell therapy;

administered an altered dosing of a CAR-expressing cell therapy;

altering the schedule or time course of a CAR-expressing cell therapy;

administering, for example, to a non-responder or a partial responder, an additional agent in combination with a CAR-expressing cell therapy, for example, a checkpoint inhibitor, for example, a checkpoint inhibitor described herein;

administering to a non-responder or partial responder a therapy that increases the number of younger T cells in the subject prior to treatment with a CAR-expressing cell therapy;

modifying a manufacturing process of a CAR-expressing cell therapy, for example, enriching for younger T cells prior to introducing a nucleic acid encoding a CAR, or increasing the transduction efficiency, for example, for a subject identified as a non-responder or a partial responder;

administering an alternative therapy, for example, for a non-responder or partial responder or relapser; or if the subject is, or is identified as, a non-responder or a relapser, decreasing the $T_{REG}$ cell population and/or $T_{REG}$ gene signature, for example, by one or more of CD25 depletion, administration of cyclophosphamide, anti-GITR antibody, or a combination thereof.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: In Vitro Characterization of Human BCMA CARs

A set of fully human single chain variable fragments (scFv) was cloned into lentiviral CAR expression vectors with the CD3zeta chain and the 4-1BB stimulatory molecules: R1B6, R1F2, R1G5, PI61, B61-10, B61-02, Hy03, and Hy52. The constructs were initially screened using automated cell reporter assay followed by selection for optimal clones based on expression on primary T cells as well as quantity and quality of effector T cell responses ("BCMA CART" or "BCMA CAR T cells") in response to BCMA expressing ("BCMA+" or "BCMA positive") targets. Effector T cell responses include, but are not limited to, cellular expansion, proliferation, doubling, cytokine production and target cell killing or cytolytic activity (degranulation).

Generation of BCMA CAR Lentivirus

All the above-mentioned scFv encoding lentiviral transfer vectors were used to produce the genomic material packaged into the VSVg pseudotyped lentiviral particles. Lentiviral transfer vector DNA encoding the CAR was mixed with the three packaging components VSVg, gag/pol and rev in combination with lipofectamine reagent to transfect Lenti-X 293T cells (Clontech), followed by medium replacement 12-18 h later. 30 hours after medium change, the media was collected, filtered and stored at −80° C.

BCMA CAR JNL and JNL Screening Reporter Assay Using Automated System

For the reporter assay, lentivirus encoding for BCMA CARs was generated in HEK293 cells at two different cell densities (40,000 cells (1×H293) or 80,000 cells (2×H293)) in an automated, small scale fashion in 96-well plates, where virus-containing supernatant was harvested 48 h after transfection and used fresh, without freezing, for the transduction of a Jurkat T cell reporter cell line. The Jurkat NFAT Luciferase (JNL) reporter cell line is based on the acute T cell leukemia line Jurkat. The line was modified to express luciferase under control of the Nuclear Factor of Activated T cells (NFAT) response element. For the transduction with BCMA CARs, 10,000 JNL cells/well of a 96-well plate were transduced with 50 μl of fresh, 45 pm-filtered virus-containing supernatant. The plates were cultured for 5 days before co-culturing with target cells.

To evaluate the functional ability of BCMA CARs to activate JNL cells, they were co-cultured with target cancer cells at different effector to target cell ratios (E:T ratio) to read out their activation by quantifying luciferase expression. The scFv-based CARs R1B6, R1F2, R1G5, PI61, B61-10, B61-02, Hy03, and Hy52 were assessed. The CD19 JNL CAR cells were used as a target specific control, and media alone without target cells served as a negative control.

Figure 1B:
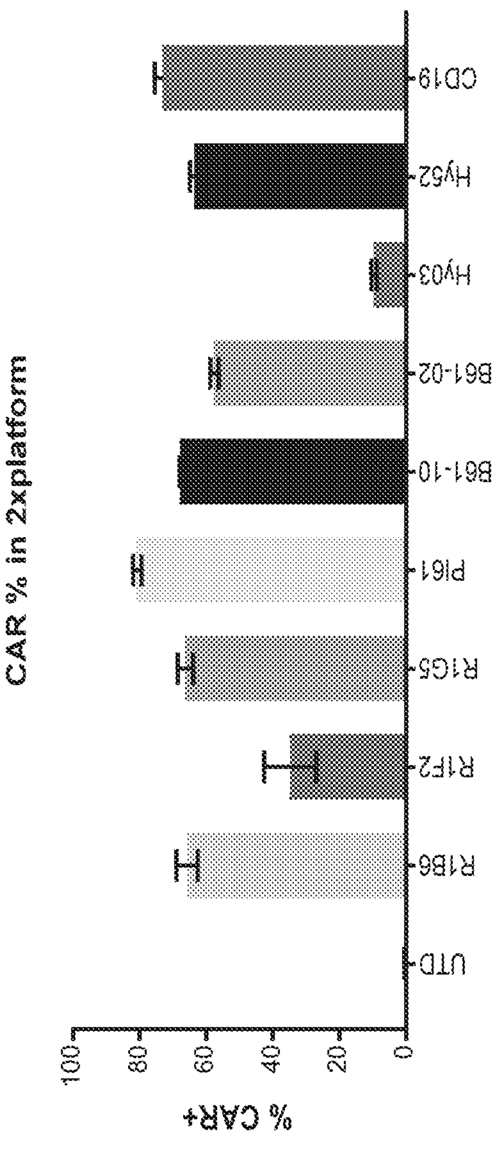
Figure 1C:
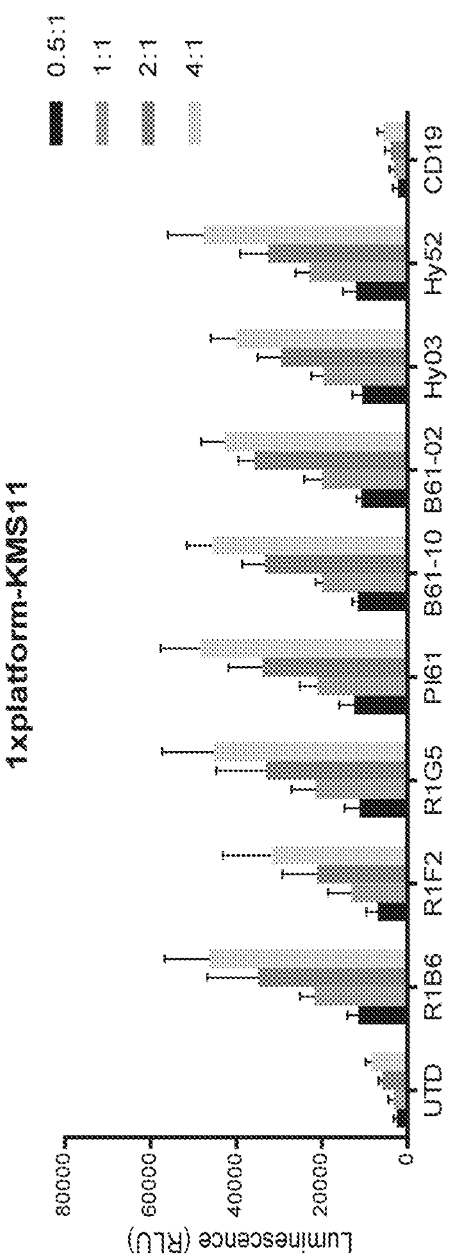
Figure 1D:
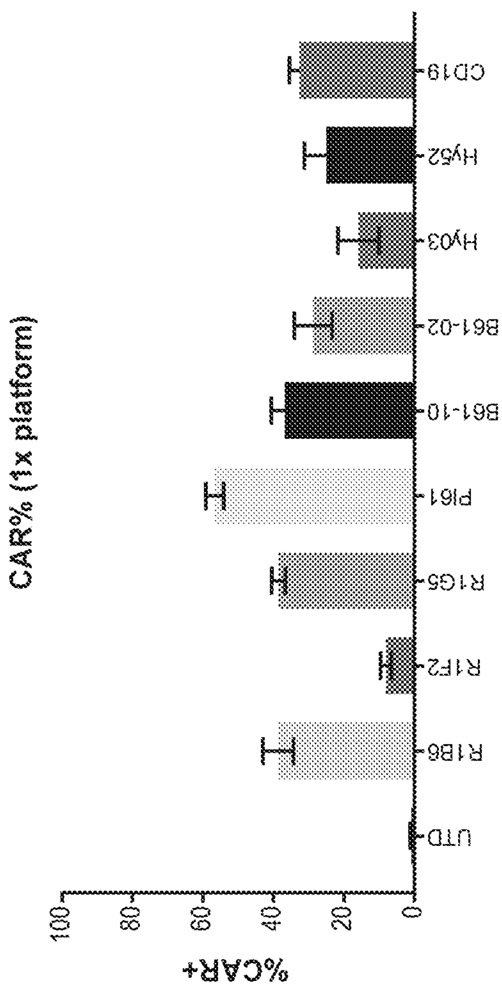
Figure 1E:
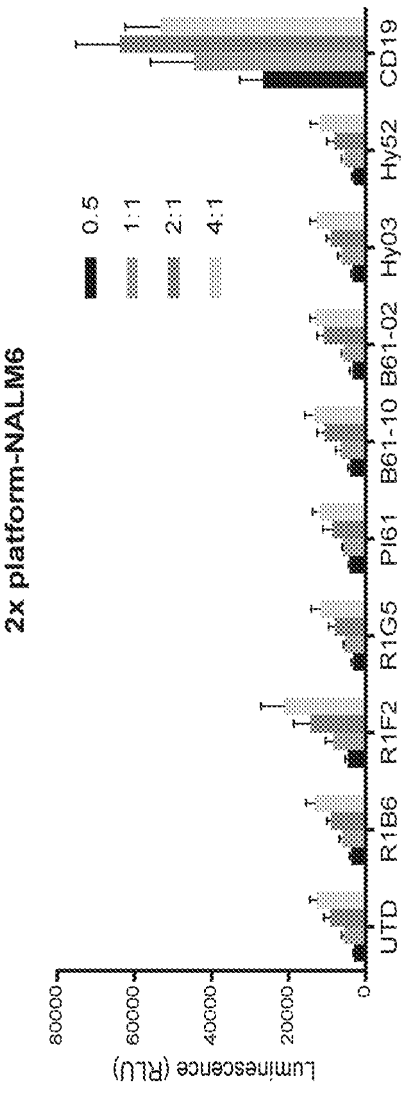
Figure 1F:
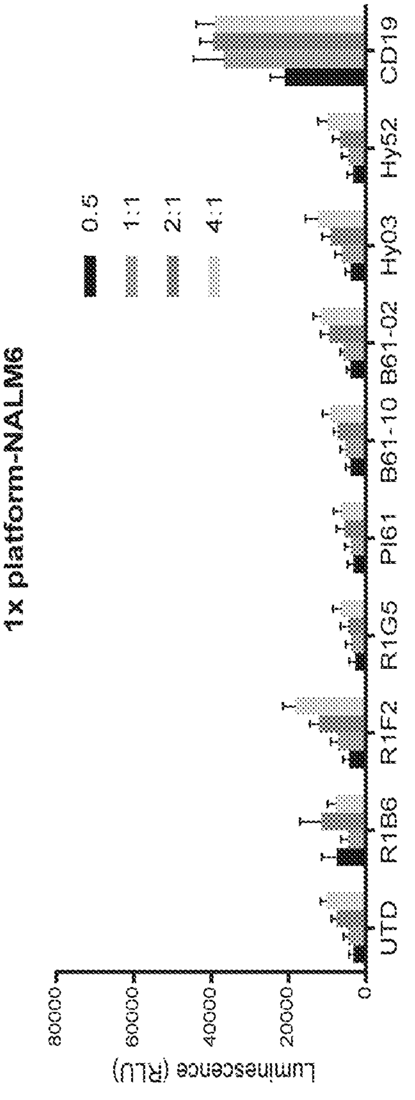
Figure 1G:
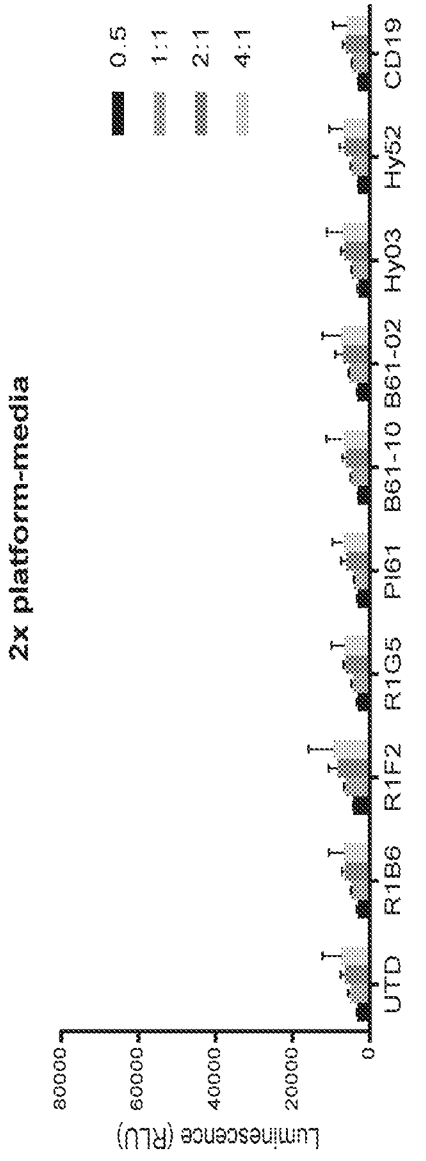
Figure 1H:
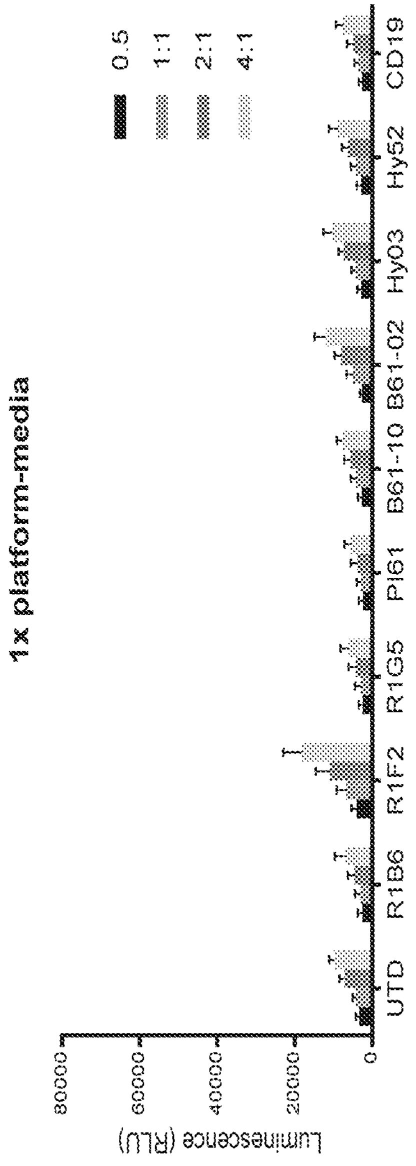

The above mentioned five-day transduced JNL CAR cells were co-cultured with the BCMA-positive multiple myeloma (MM) cell line KMS11, or NALM6, an acute lymphocytic leukemia cell line, served as a BCMA-negative control. Remaining JNL CAR T cells were evaluated for BCMA CAR expression by flow cytometry. Co-cultures were set up in 384-well plates at effector-to-target (E:T) ratios of 4:1, 2:1, 1:1 and 0.5:1 and incubated for 24h, after which the expression of luciferase by the activated JNL CAR T cells was quantified by Bright-Glo™ Luciferase Assay System (Promega, Madison, WI). The amount of light emitted from each well (luminescence) was a direct read-out of JNL activation by the respective CAR. JNL cells were considered to be activated when the level of luminescence was equal or more than twofold of UTD cells. The BCMA+ KMS11 cell line led to activation of the JNL cells expressing R1B6, R1F2, R1G5, PI61, B61-10, B61-02, Hy03, and Hy52 (FIGS. 1A and 1C). None of the BCMA CARs showed activation by the BCMA-negative line NALM6 (FIGS. 1E and 1F). Media alone, without target cells, did not activate any of the CAR transduced JNLs tested (FIGS. 1G and 1H). FACS analyses demonstrated that BCMA-CAR expression in transduced JNLs was detected to different degrees; CAR % is generally positively correlated with JNL activation by KMS11 cells in the most active JNL CARTs (FIGS. 1B and 1D).

Generation of BCMA CAR T Cells

The following 8 CARs were chosen for analysis of CAR expression, stability and efficacy in primary T cells: R1B6, R1F2, R1G5, PI61, B61-10, B61-02, Hy03, and Hy52. BCMA CAR T cells were generated by starting with blood from healthy apheresed donors whose T cells (CD4+ and CD8+ lymphocytes) were obtained by negative selection for CD3+ T cells. These cells were activated by the addition of CD3/CD28 beads (Dynabeads® Human T-Expander CD3/CD28, Thermo Fisher Scientific) at a ratio of 1:3 (T cell to bead) in T cell medium (RPMI1640, 10% heat-inactivated fetal calf serum (FCS), 2 mM L-glutamine, 1× Penicillin/Streptomycin, 100 μM non-essential amino acids, 1 mM Sodium Pyruvate, 10 mM Hepes, and 55 μM 2-mercaptoethanol). T cells were cultured at $0.5\times10^6$ T cells in 1 mL medium per well of a 24-well plate at 37° C., 5% $CO_2$. After 24 hours, when T cells were blasting, T cells were transduced with BCMA CAR virus at a multiplicity of infection (MOI) of 5. T cells began to divide in a logarithmic growth pattern, which was monitored by measuring the cell counts per mL, and T cells were diluted in fresh medium every two days and de-beaded and harvested for further analyses at day 9. Aliquots of T cells were stained to measure CAR expression by flow cytometry at day 5 and 9 on a FACS Fortessa (BD). All BCMA CAR T cells were produced under research grade (i.e., not clinical grade) manufacturing conditions.

Figure 2:
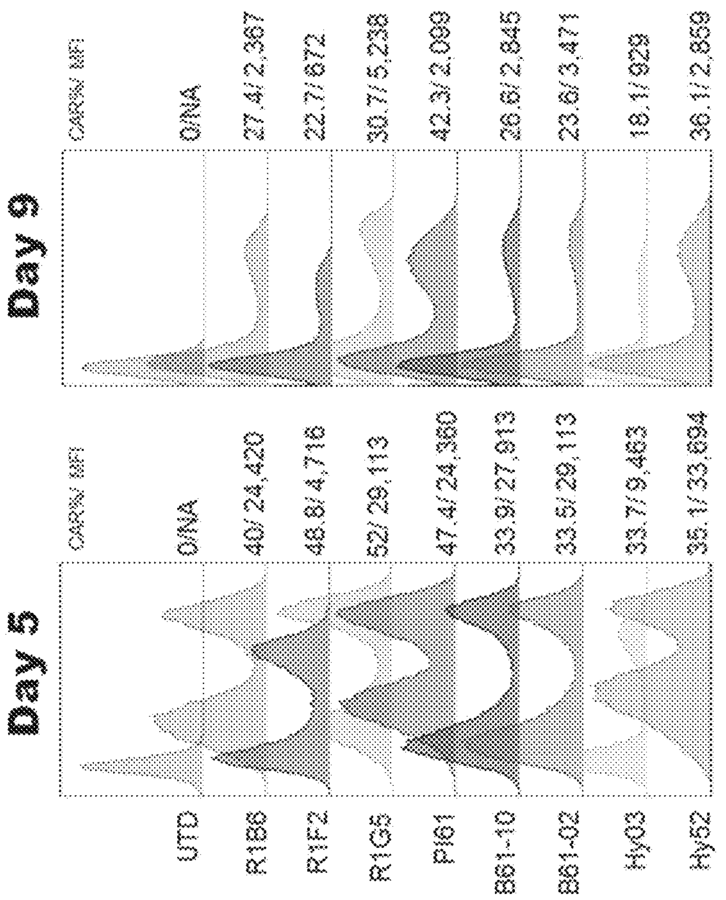
FIG. 2: Expression level of BCMA CARs on primary human T cells. Cells were stained with a human rBCMA_Fc-AF647 reagent and assayed by flow cytometry. The percentage of CAR+ cells and MFI are shown in the graph for day 5 and day 9 of cell culture. Data is summarized in Table 27, which includes the viral titer achieved for the respective CARs.

The BCMA-CAR surface expression and its stability was assessed by measuring CAR % and MFI (mean fluorescence intensity) at day 5 and day 9 using flow cytometry analyses of rBCMA_Fc-AF647 stained cells (FIG. 2 and Table 27). BCMA CAR expression in the final product at day 9 differs from construct to construct, ranging from 18% to 42.4%, and MFI from 672 to 5238. Constructs from PALLAS-derived clones R1F2, R1B6, and R1G5, and the hybridoma clone, Hy03 showed −30% to 50% CAR loss from day 5 to day 9, while PI61, B61-10 and -02, as well as Hy52 are relatively stable in terms of the percentage of CAR expression, though all the CAR constructs showed a decrease in MFI from day 5 to day 9, which was probably due to the smaller size of T cells at their resting stage on day 9. The cell counts of the CAR T cell cultures indicated that there is no detectable negative effect of the human scFv bearing BCMA CAR on the ability of the cells to expand normally when compared to the untransduced T cells ("UTD").

TABLE 27

| Analysis of CAR expression | | | | | |
|---|---|---|---|---|---|
| CAR | | CAR % on T cells | | CAR MFI on T cells | |
| Construct | Titer | Day 5 | Day 9 | Day 5 | Day 9 |
| R1B6 | 2.68E+08 | 40.0 | 27.4 | 24,420 | 2,367 |
| R1F2 | 3.60E+08 | 48.8 | 22.7 | 4,716 | 672 |
| R1G5 | 2.27E+08 | 52.0 | 30.7 | 29,113 | 5,238 |
| PI61 | 1.71E+08 | 47.4 | 42.3 | 24,360 | 2,099 |
| B61-10 | 7.06E+07 | 41.1 | 30.3 | 27,298 | 3,288 |
| B61-02 | 8.16E+07 | 33.5 | 23.6 | 29,113 | 3,471 |
| Hy03 | 4.96E+07 | 33.7 | 18.1 | 9,463 | 929 |
| Hy52 | 7.03E+07 | 35.1 | 36.1 | 33,694 | 2,859 |

Evaluating Functionality of BCMA CAR-Redirected T Cells

To evaluate the functional abilities of BCMA CAR−T cells, co-cultures were set up with BCMA-positive and -negative cancer lines. CAR−T cells were thawed, counted and co-cultured with target cells to read out their killing capabilities and secretion of cytokines. BCMA CAR-clones R1B6, R1F2, R1G5, B61-02, B61-10, PI61, Hy03, and Hy52 were tested. Non-transduced T cells (UTD) were used as non-targeting T cell controls.

Figure 3A:
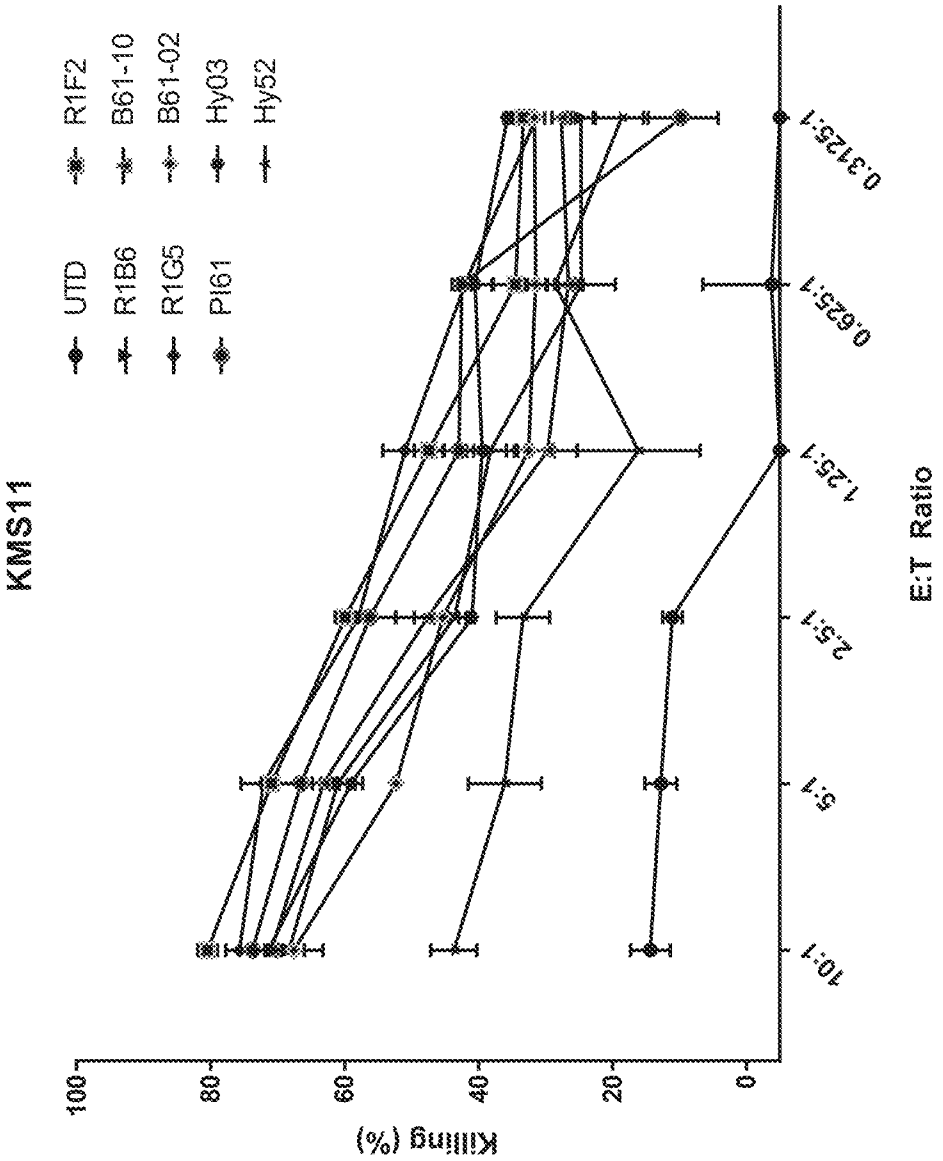
FIGS. 3A-3C: The ability of T cells expressing the indicated CARs to mediate cell lysis and cytokine production were evaluated against the KMS11 target cell line expressing firefly luciferase (KMS11-luc).
Figure 3B:
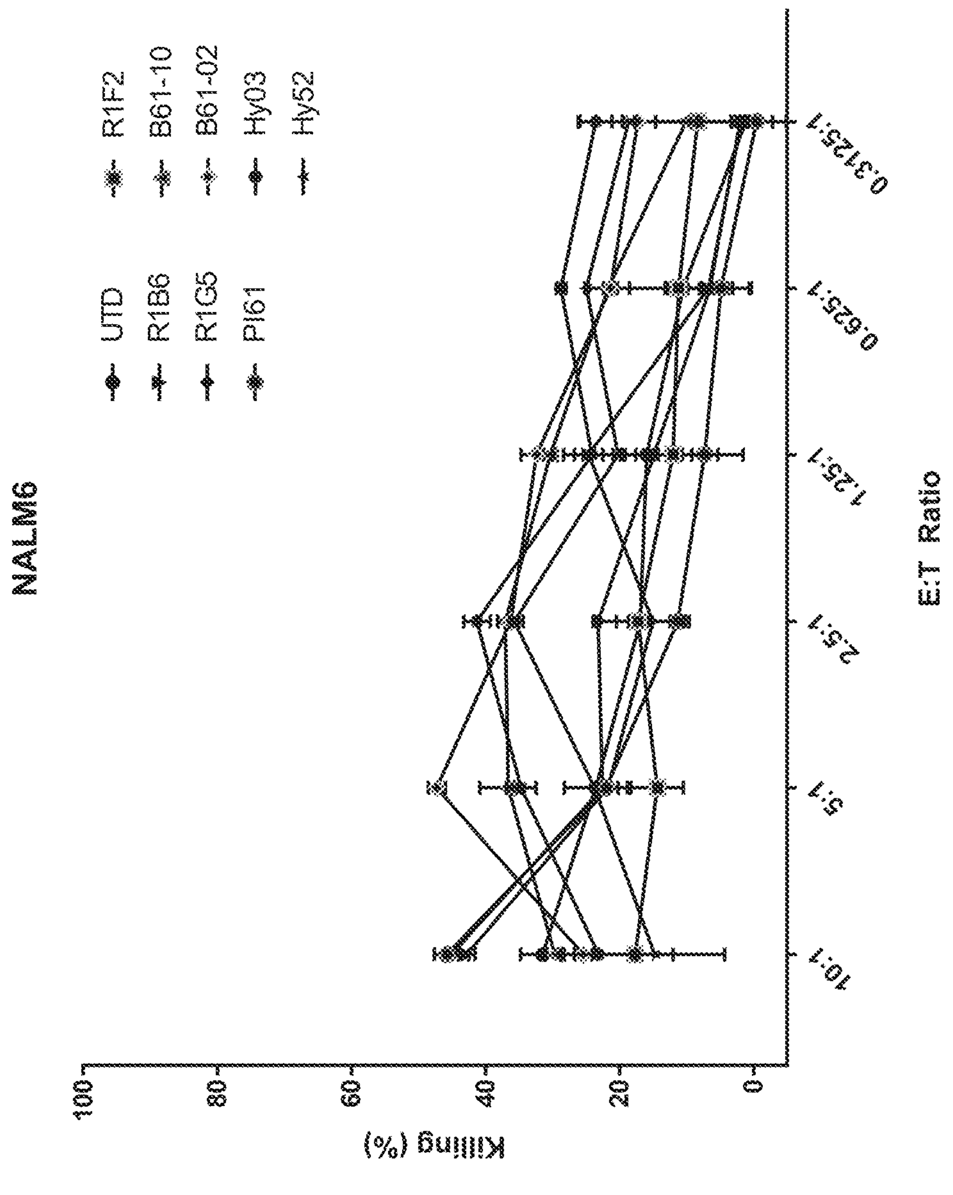
Figure 3C:
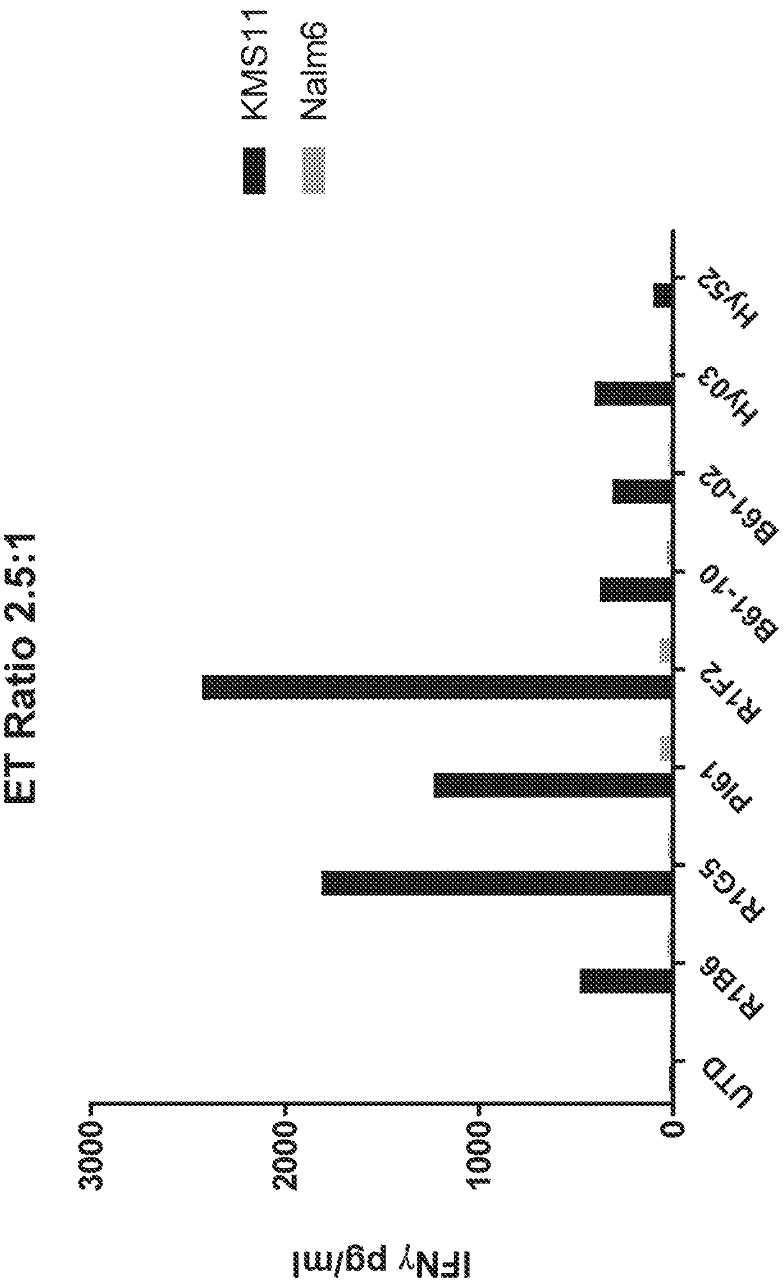

CART cell killing was performed by co-culturing CART cells with KMS11-Luc and NALM6-Luc target cells at different E:T ratios for 20 hours. CAR T cell populations were normalized to equivalent percentages of CAR-positive cells before plating. The cytokine IFNγ was measured in supernatants from 20 hour co-cultures of CAR−T cells with target cells at effector to target ratio of 2.5:1 using the Meso Scale Discovery (MSD; Gaithersburg, MD) and the results for each cytokine were calculated in pg/ml using known standards. All assays were performed in duplicate from a single source of donor cells. Killing data shows that all the BCMA CAR clones kill KMS11 cancer cells effectively (FIG. 3A). The control target cell NALM6 was not killed by any of these BCMA-specific CARs (FIG. 3B). The ability of these CARs to produce IFN-γ when cultured with KMS11 was also tested (FIG. 3C). BCMA CAR R1F2, R1G5 and PI61 led to the highest amounts of IFN-γ being produced. Levels of cytokine produced by BCMA CARTs after exposure to the control NALM6 cells were low (FIG. 3C), indicating no unspecific activation by BCMA CARs.

Conclusions

New BCMA-binding scFvs were tested in the context of CAR T cells. Eight CARs were assayed in a JNL reporter assay as well as in primary T cells: R1B6, R1F2, R1G5, B61-02, B61-10, PI61, Hy03, and Hy52. All eight CAR−T cells showed target-specific killing. T cells expressing R1F2, R1G5, or PI61 produced the highest amounts of IFN-γ in the presence of target cells. Overall, the transfer of BCMA CARs to primary T cells induced anti-BCMA CAR reactivity but no off-target function.

Example 2: Dual CAR Expression and In Vitro Activity of Anti-BCMA and Anti-CD19 Dual CARTs A set of bicistronic constructs comprising two full CAR (chimeric antigen receptor) chains, one directed to BCMA and the other to CD19, was engineered in a lentiviral vector (Table 28). CAR expression is driven by the EF1alpha promoter. Such CARs comprise a set of human single chain variable fragments (scFv) targeting BCMA (duBCMA.4, PI61, R1G5, and R1B6). The same humanized scFv targeting CD19 was engineered in all the constructs. At the N-terminus of each scFv, a signal peptide derived from CD8 alpha targets the CAR to the secretory pathway. Such a signal peptide is expected to be cleaved co-translationally and therefore be absent in the mature form of the CAR displayed at the cell surface. At the C-terminus of each scFv is the hinge and transmembrane domain of CD8 alpha, fused to the intracellular domain of 4-1BB, followed by the intracellular domain of CD3zeta. Between the two CARs, more precisely between the last amino acid of the first CD3zeta domain and the signal peptide of the subsequent CAR, is engineered a linker (GSG (SEQ ID NO: 206)) followed by 2A self-cleaving peptide from porcine teschovirus-1 2A (i.e., P2A sequence). Other linkers and/or self-cleaving peptides could be used as well. This design affords expression of two independent CARs, from a single mRNA transcript. The DNA sequences encoding the overlapping regions between the two CARs (signal peptide, hinge, transmembrane domain, 4-1BB, and CD3zeta) are distinct from one another in order to minimize potential recombination.

TABLE 28

| Summary of constructs. | |
|---|---|
| Construct NO. | Description |
| 234 | duCD19.1-duBCMA.4 |
| 235 | duBCMA.4-duCD19.1 |
| 236 | R1G5-duCD19.1 |
| 237 | R1B6-duCD19.1 |
| 238 | PI61-duCD19.1 |
| 244 | Mono-duCD19.1 |
| 245 | Mono-duBCMA.4 |

The constructs were used to make vector material, which was used to infect human primary T cells. CAR expression was assessed by flow cytometry. The quantity and quality of effector T cell responses ("BCMA-CD19 dual CART" or "T cells") in response to BCMA expressing ("BCMA+" or "BCMA positive") and CD19+ tumor targets were also measured. Effector T cell responses include, but are not limited to, cellular expansion, proliferation, doubling, cytokine production and target cell killing or cytolytic activity (degranulation).

Lentivirus Production and Titer Determination

The five constructs, encoding the dual BCMA/CD19 CARs, described above were used to produce genomic material packaged into VSVg pseudotyped lentiviral particles. Two constructs were used as controls: one encoding a mono CAR directed against BCMA (duBCMA.4) and another encoding a mono CAR directed against CD19. All seven constructs were engineered in the same plasmid backbone. Each of these DNAs was mixed with the three packaging components VSVg, gag/pol and rev in combination with lipofectamine reagent to transfect Lenti-X 293T cells (Clontech), followed by medium replacement 12-18 h later. 30 hours after medium change, the media was collected, filtered and stored at −80° C.

Lentiviral titer was determined by evaluating the surface expression of BCMA-CD19 dual CARs on transduced Sup-T1 cells using recombinant human Alexa-647-Fc-tagged BCMA protein (BCMA-Fc) and antiID-duCD19.1 antibody (PE). Sup-T1 cells were transduced with a 3-fold serial dilution of viral supernatants with a starting dilution of 1:3.

The percentage of cells expressing the CAR (CAR+ cells) was assessed four days later. Viral titer was calculated either using the upstream CAR positivity or dual positive CAR population according to the following formula:

(% CAR+)x(#Sup-T1 cells seeded)x(Dilution)/(Amount of Virus (mL))

Viral titer was calculated from the central most dilution point in the linear range giving between 5 and 25% CAR+ cells (Table 29).

TABLE 29 supT1 titers.

| Construct NO. | Based on CAR+ of the upstream CAR (a) | Based on the double+ CAR (b) |
|---|---|---|
| 234 | 5.39E+07 | 1.91E+07 |
| 235 | 4.41E+08 | 1.15E+08 |
| 236 | 2.14E+08 | 1.17E+08 |
| 237 | 1.97E+08 | 8.51E+07 |
| 238 | 1.85E+08 | 5.66E+07 |

Generation of BCMA-CD19 CAR T Cells Using Conventional 10-Day Production Process BCMA-CD19 dual or monoBCMA or monoCD19 CART cells were generated using human primary T cells (CD4+ and CD8+ lymphocytes) obtained by negative selection or positive selection via Prodigy upon processing blood from healthy apheresed donors. Before transduction, the T cells were activated using CD3/CD28 beads (Dynabeads® Human T-Expander CD3/CD28, Thermo Fisher Scientific) at a ratio of 1:3 (T cell to bead) in T cell medium (RPMI1640, 10% heat-inactivated fetal calf serum (FCS), 2 mM L-glutamine, 1× Penicillin/Streptomycin, 100 μM non-essential amino acids, 1 mM Sodium Pyruvate, 10 mM Hepes, and 55 μM 2-mercaptoethanol). The cells were cultured at a density of $0.5\times10^6$/mL medium per well in a 24-well plate at 37° C., 5% $CO_2$. After 24 hours, when T cells were blasting, they were transduced with viruses at a multiplicity of infection (MOI) of 5 based on the upstream CAR titer. T cells began to divide in a logarithmic growth pattern, which was monitored by measuring the cell counts per mL, and T cells were diluted in fresh medium every two days and de-beaded and harvested for further analyses on day 8 or beyond depending on the size of the cells. Aliquots of T cells were stained to measure CAR expression by flow cytometry on day 7 or 8 on a FACS Fortessa (BD).

Figure 4B:
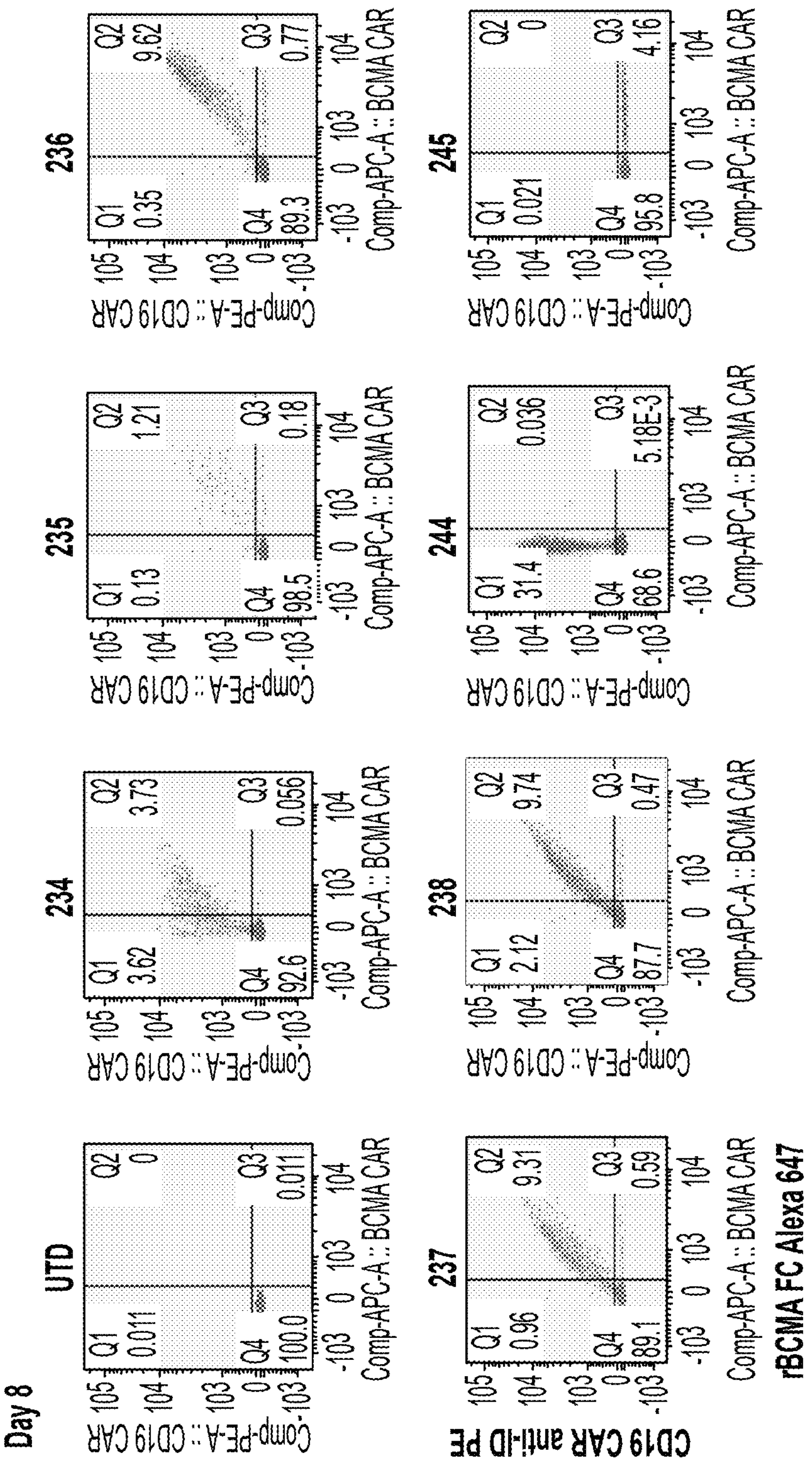
Figure 4C:
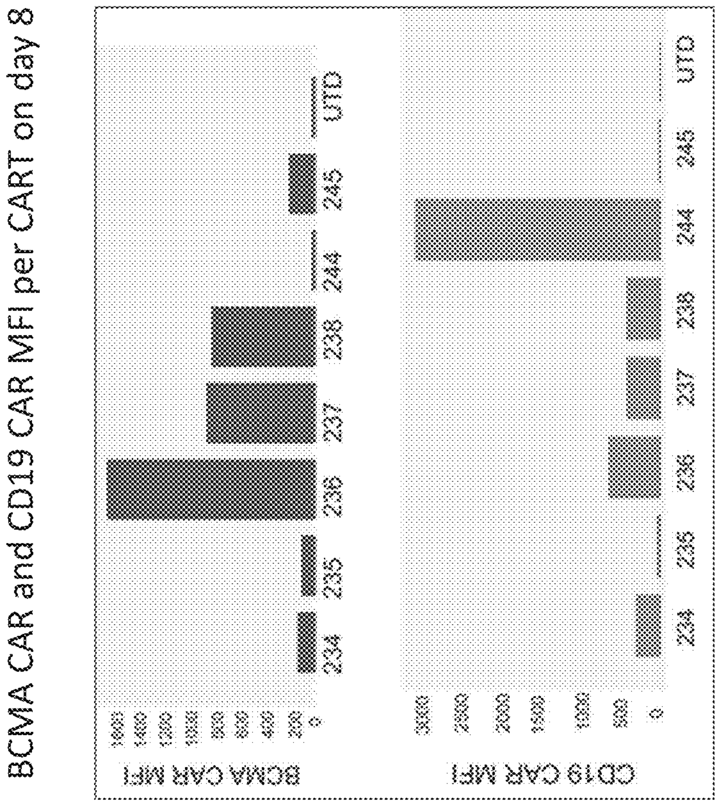

The BCMA-CAR and CD19-CAR surface expression was assessed by measuring CAR % and MFI (mean fluorescence intensity) at day 8 using flow cytometry analyses of rBCMA_Fc-AF647 and antiID-duCD19.1 (PE) stained cells (FIGS. 4A-4C). The three dual CAR vectors comprising R1G5, R1B6, or PI61 led to a similar percentage of double positive CARs (~10%), with construct 236 (R1G5/duCD19.1) displaying the highest MFI levels for BMCA and CD19 CARs (FIG. 4A). The mono duCD19.1 (construct 244) displays the highest MFI for CAR19 across the different constructs (FIG. 4B).

Evaluating Functionality of Dual BCMA-CD19 CAR-Redirected D8 T Cell Product In Vitro and In Vivo To evaluate the anti-tumor efficacy of each of the CARs within the dual BCMA-CD19 CART cells, co-cultures were set up with BCMA positive (KMS11), CD19 positive (NALM6) and BCMA/CD19 negative cancer lines (CD19KO; NALM6-derived). CART cells were thawed, counted and co-cultured with target cells to read out their killing capabilities and secretion of cytokine. Non-transduced T cells (UTD) were used as non-targeting T cell controls.

Figure 5A:
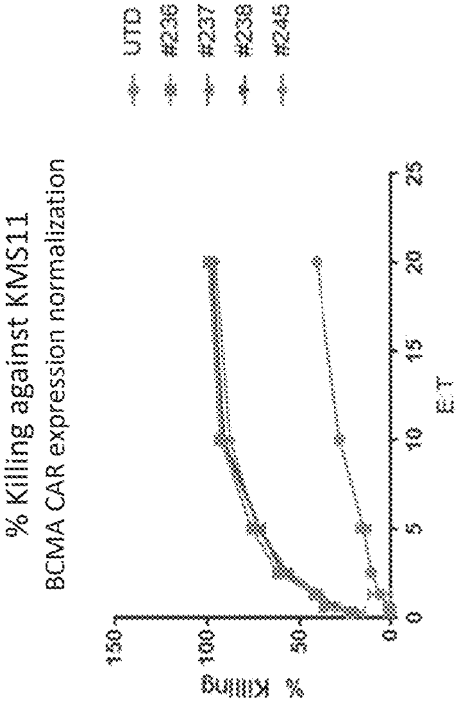
FIGS. 5A-5C: In vitro killing assay using Day 8 CART cells.
Figure 5B:
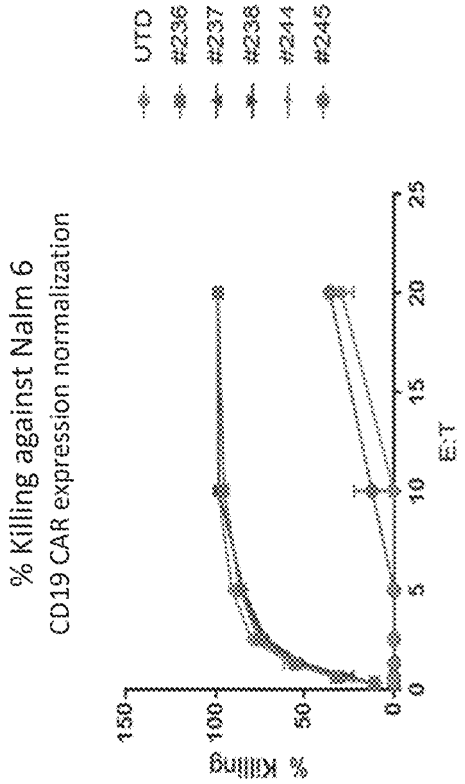
Figure 5C:
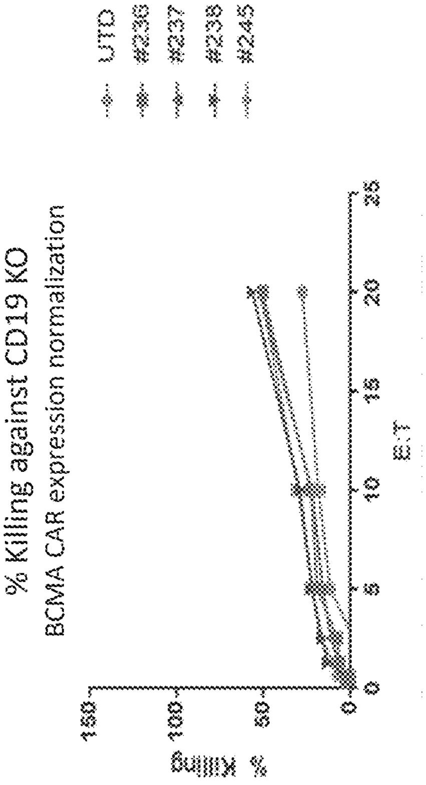

The in vitro cytotoxic assay was performed by co-culturing CART cells with target cells expressing luciferase at different E:T ratios for 20 hours. CART cell populations were normalized to equivalent percentages of CAR-positive cells before plating, according to the CAR directed to the respective tumor (i.e., normalization based on BCMA CAR when CARTs were co-cultured with KMS11 cells; and normalization based on CAR19 when CARTs were co-cultured with NALM6). The cytokine IFNγ was measured in the supernatants of the 20-hour co-cultures, corresponding to a target ratio of 1.25:1 or 2.5:1 (CAR–T cells: target cells), using the Meso Scale Discovery (MSD; Gaithersburg, MD). The results were calculated in pg/mL using known standards. All assays were performed in duplicate from a single source of donor cells. Killing data show that all dual CAR clones were effective against BCMA-positive KMS11 cells and CD19-positive Nalm6 cells (FIGS. 5A and 5B, respectively). Only background killing was observed against the BCMA/CD19 negative tumor cells (FIG. 5C). The ability of these dual CARs to produce IFN-γ when co-cultured with KMS11 or Nalm6 was similar as assessed using two different E:T ratios (FIGS. 6A-6D).

The in vivo anti-tumor activity of these D8 CARTs is analyzed using mixed xenograft tumor model (5% Nalm6 and 95% KMS11) in NSG mice.

Production and Measurement of Day 1 Anti BCMA-CD19 Dual CARTs with Activated Rapid Manufacturing (ARM) Process In some embodiments, this ARM process starts with a frozen or fresh leukapheresis product.

After a sample for counting and QC is obtained, the product is attached to a cell sorting machine (e.g., an installed CliniMACS Prodigy device kit) and the program begins. The cells are washed and incubated with microbeads that bind to desired surface markers, such as CD4 and CD8. The bead-labeled cells are selected by passing the cells through a magnetic column. Isolated cells are washed again and the separation buffer is exchanged for cell media. Purified T cells then either proceed to culture or are cryopreserved for later use. Purity of the isolated T cells will pass a QC step by flow cytometry assessment. Cryopreserved cells are thawed, washed in pre-warmed cell media, and resuspended in cell media. Fresh cells are added to culture directly. The cells are seeded into membrane bioreactors at 0.4-1.2e6 cells/$cm^2$ of membrane, an activating reagent such as anti-CD3/anti-CD28 beads/polymers, nanoparticles, or nanocolloids is added, and cell media is added to a final volume of 0.25-2 ml/$cm^2$ of membrane. For in vitro CAR expression kinetics study, a 24 well Grex is used. A Grex100, flask, or centricult is used to test whether this manufacturing process is scalable and to test in vivo anti-tumor efficacy. At the time of plating, the cells are transduced with a lentiviral vector encoding BCMA-CD19 dual CAR at a multiplicity of infection (MOI) of 1 or 2. MOI is determined based on the viral titer obtained in SupT1 cells, basing on the titer of the CAR that is engineered upstream of the 2A sequence. At 24 hours, the cells are washed to remove unnecessary reagents before staining to measure the CAR expression by flow cytometry and reformulated in cryopreservation media as “day 1 CART product” for in vivo study. In all cases, an aliquot of cells is harvested at 72 h post transduction for measuring CAR expression kinetics in vitro. The day 1 CART responses include, but are not limited to, in vivo cytolytic activity and expansion.

Figure 7A:
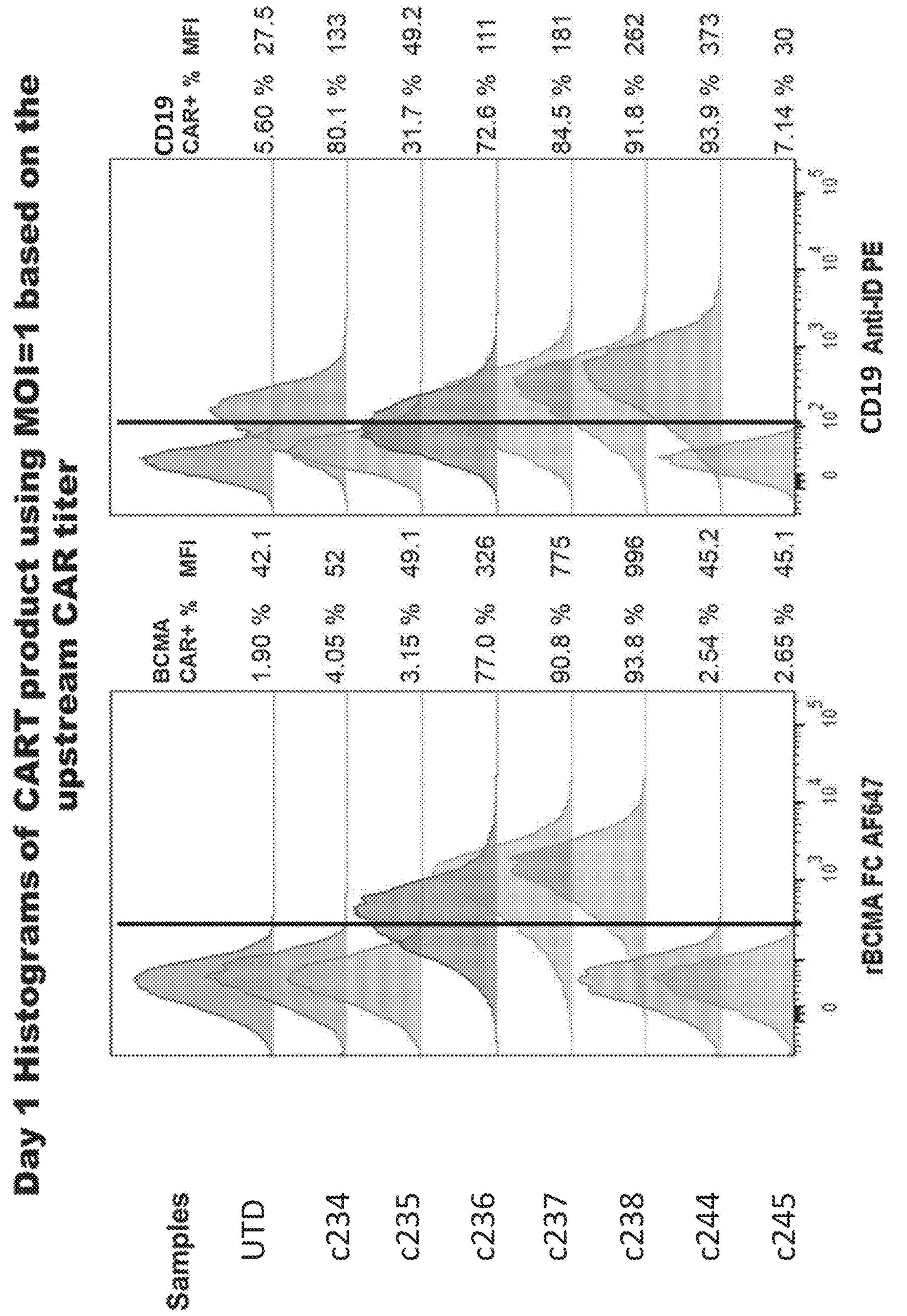
FIGS. 7A-7C: Individual CAR expression of cells manufactured using the ARM process.
Figure 7B:
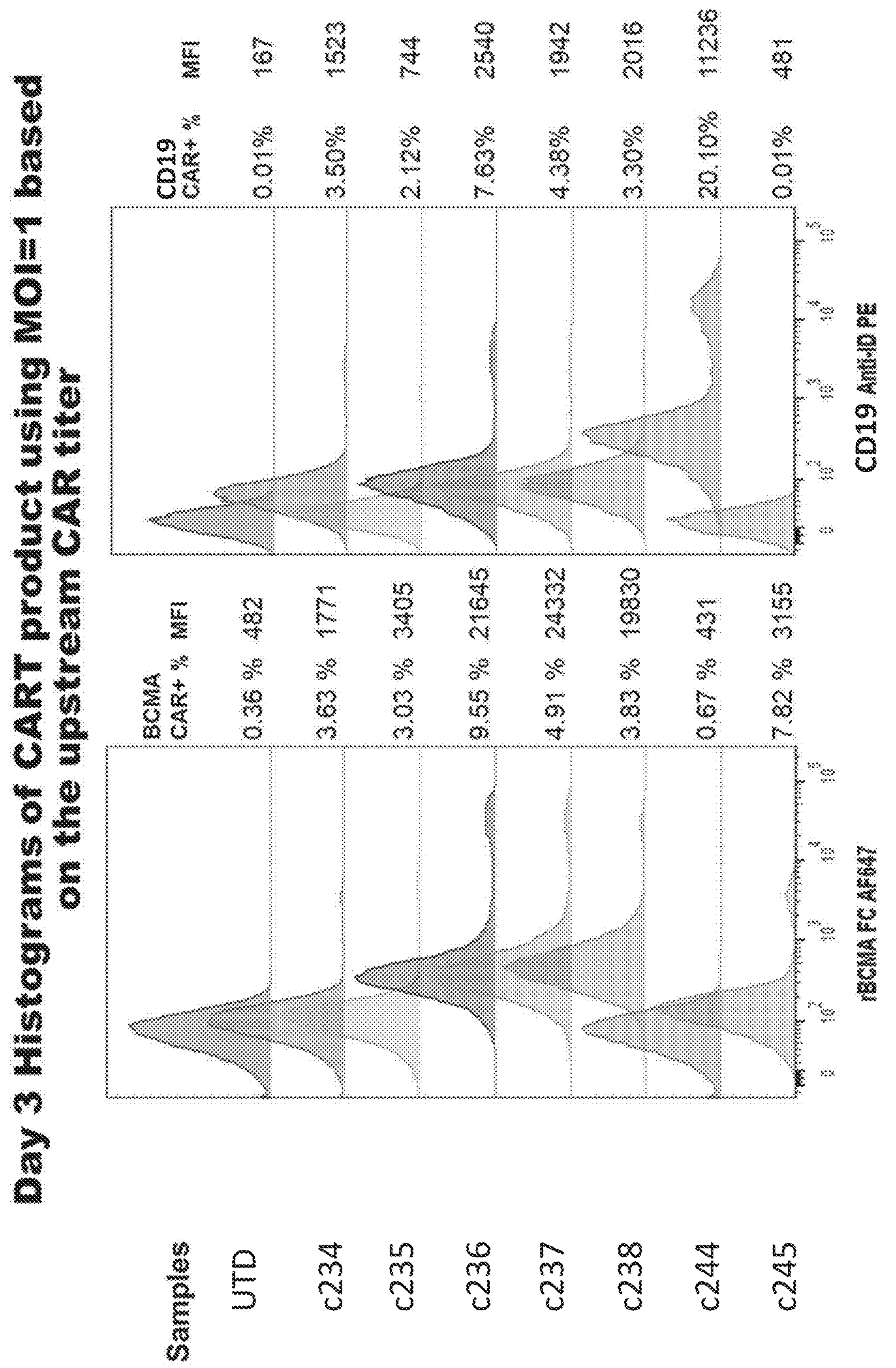
Figure 7C:
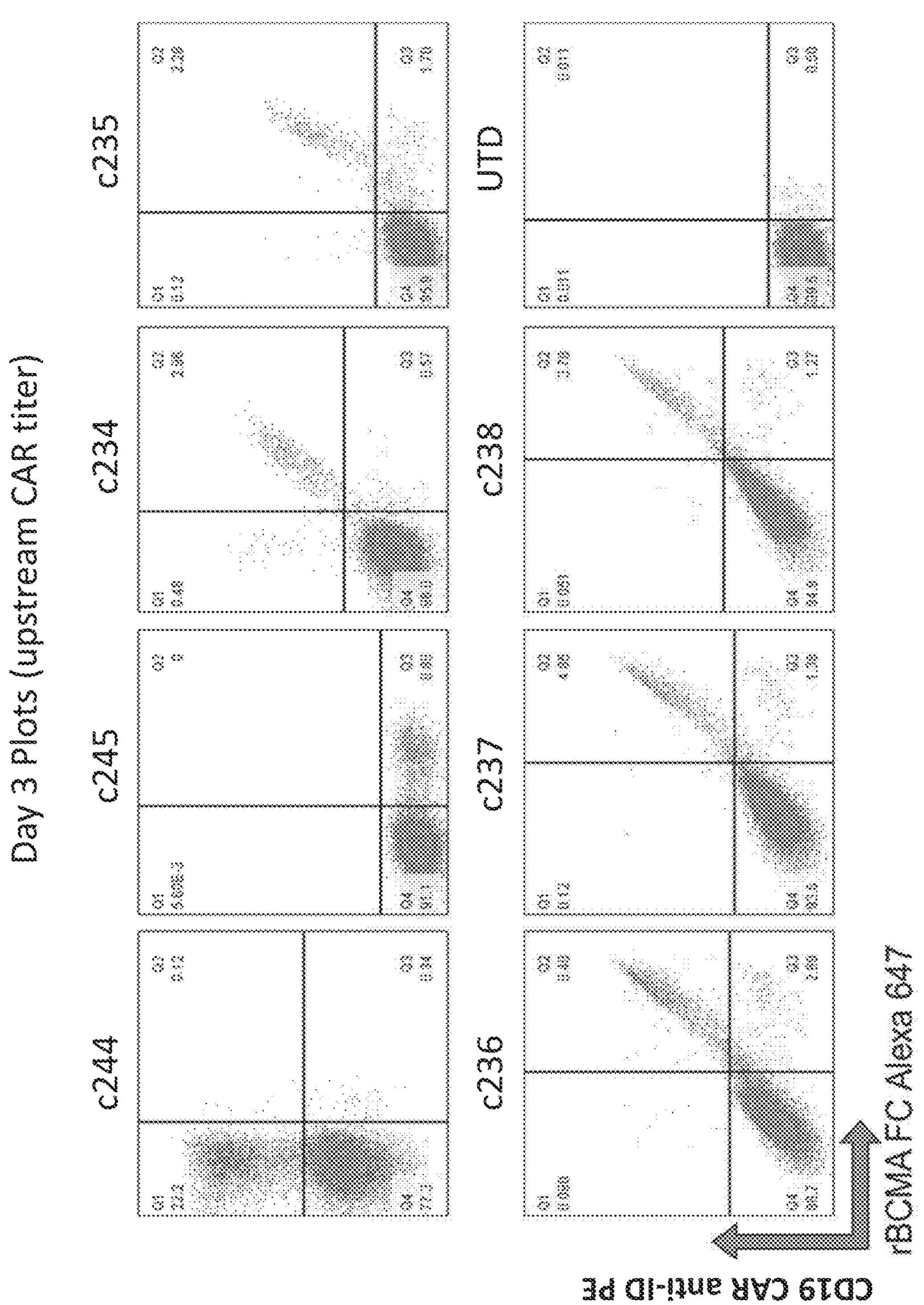

FIGS. 7A-7B show the expression pattern of both anti-BCMA and anti-CD19 CARs, at 24 h and 72 h post-transduction of human primary T cells manufactured using the ARM process, using a MOI of 1 based on the SupT1 titer determined by expression of the upstream CAR only. Twenty-four hours post-transduction, it was observed in a flow cytometry analysis that the whole population of live CD3+ T cells shifted to the right at different degrees (FIG. 7A). This expression pattern was different from a typical flow cytometry histogram of cells transduced to express a CAR, where a CAR positive population is clearly separated from a negative population. These data suggest "pseudo-transduction or transient expression" may be detected by the rBCMA_Fc flow cytometry staining reagent. It has been previously reported that lentiviral pseudotransduction was observed from the time of vector addition to 24 hours in CD34+ cells and up to 72 hours in 293 cells (Haas D L, et al. Mol Ther. 2000. 291: 71-80). Integrase-defective lentiviral vector caused transient eGFP expression for up to 10 days in CD34+ cells and for up to 14 days in 293 cells. Although the observed CAR expression on day 1 post T cell transduction may be potentially attributed to pseudotransduction, on day 3, however, two clear populations emerged, one that was rBCMA_Fc positive and the other anti-ID duCD19.1 positive (FIG. 7B and FIG. 7C). Furthermore, 20 to 30% of cells were monoBCMACAR positive (CD19CAR negative) in cells engineered using the dual constructs c235, c236, c237, and c238 (FIG. 7C). Altogether, these results demonstrate that both CARs were well expressed in the dual CART system when R1G5, R1B6, and PI61 were used in combination with duCD19.1. 72 h post viral transduction could serve as a surrogate time point for measuring CAR expression for in vivo dosing strategy.

Evaluating Functionality of the Day 1 ARM Processed BCMA CART In Vivo

The day 1 CARTs generated using the centricult or flask system were examined for their anti-tumor activity in vivo using three mouse models: a disseminated KMS-11-luc (BCMA+CD19−) multiple myeloma model, a Nalm6-Luc (CD19+BCMA−) xenograft mouse model, and a mixed model of 95% KMS-luc with 5% NALM6-Luc cells. The aims of this in vivo study was threefold: (1) demonstrating efficacy of both the BCMA and CD19 arms of the dual CARTs; (2) comparing the mixed model (comprising BCMA+ tumor cells and CD19+ tumor cells) to the KMS-11-luc multiple myeloma model (BCMA+CD19−) to understand potential activation of the dual CARTs through the CD19 target; and (3) testing the dual CARTs in the Nalm6 alone model (CD19+BCMA−) to examine the activity of the CD19 arm. BLI measurements were taken twice weekly. Peripheral blood was taken at days 6, 13, 20 and 27 for flow cytometry analysis. Plasma was collected on previously mentioned days along with day 2 for cytokine analysis. The study design and dose information are summarized in Table 30.

TABLE 30

In vivo study design and dose regime

| | KMS11 (BCMA) | Nalm6 (CD19) | Both Luc tagged KMS11 (BCMA) and Nalm6 (CD19) mix |
|---|---|---|---|
| c236 | 1e4, 5e4 | 1.5e5 | 1e4, 5e4 |
| c238 | 1e4, 5e4 | 1.5e5 | 1e4, 5e4 |
| Mono PI61 | 1e4, 5e4 | | 1e4, 5e4 |
| Mono CTL119 | | 1.5e5 | 1e4, 5e4 |

Figure 8A:
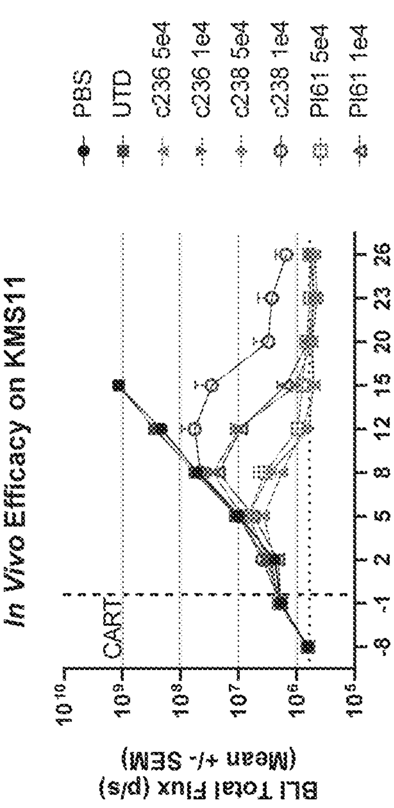
FIGS. 8A-8C: In vivo anti-tumor activity of construct #236 ("c236") and construct #238 ("c238") using three mouse models: a disseminated KMS-11 (BCMA+CD19−) multiple myeloma model, expressing a luciferase reporter gene (KMS11-Luc) (FIG. 8A), a Nalm6-Luc (CD19+ BCMA−) xenograft mouse model (FIG. 8B) and a mixed model of 95% KMS-luc with 5% NALM6-Luc cells (FIG. 8C). The tumor burden is expressed as total body luminescence (p/s), depicted as mean tumor burden+SEM. On day 7 or 8 post tumor inoculation, mice were treated with c236 and c238 at designated doses of BCMA CAR+ or CD19 CAR+ T cell (approximate number of viable CAR+ T cells), as shown in Table 30. Vehicle (PBS) and non-transduced T cells (UTD) served as negative controls. Mono anti-BCMA CAR PI61 and mono anti-CD19 CAR CTL119 were also used as controls.
Figure 8B:
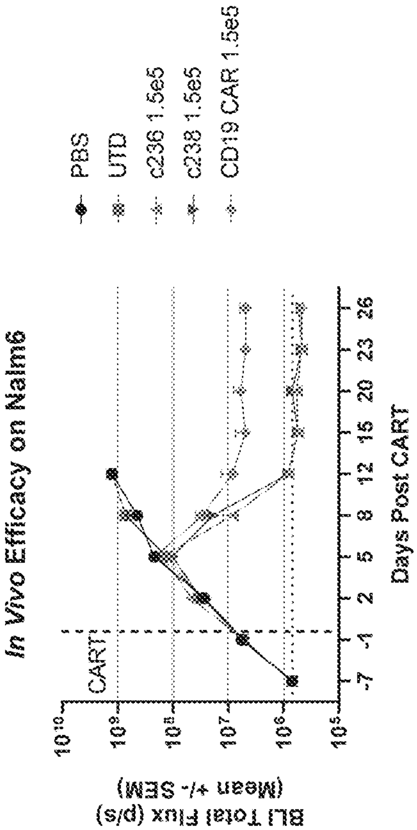
Figure 8C:
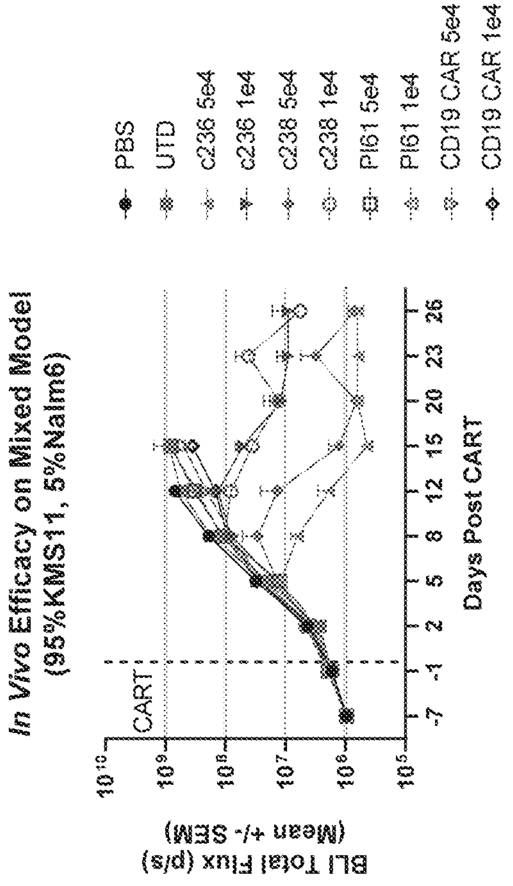
Figure 9B:
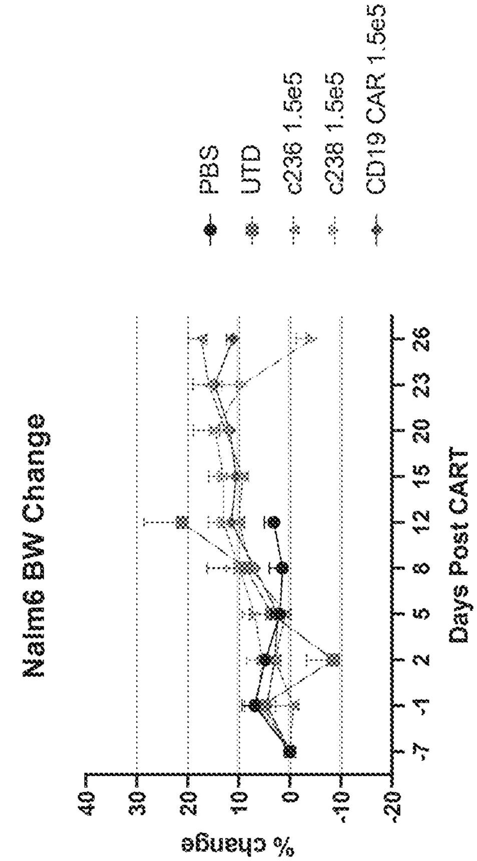
FIGS. 9A-9C: Body weight loss induced by graft-versus-host response. All mice were individually monitored for body weight loss, as a read-out for X-GvHD by measuring body weight over time. Body weight (BWT) is plotted as % change from baseline.
Figure 9A:
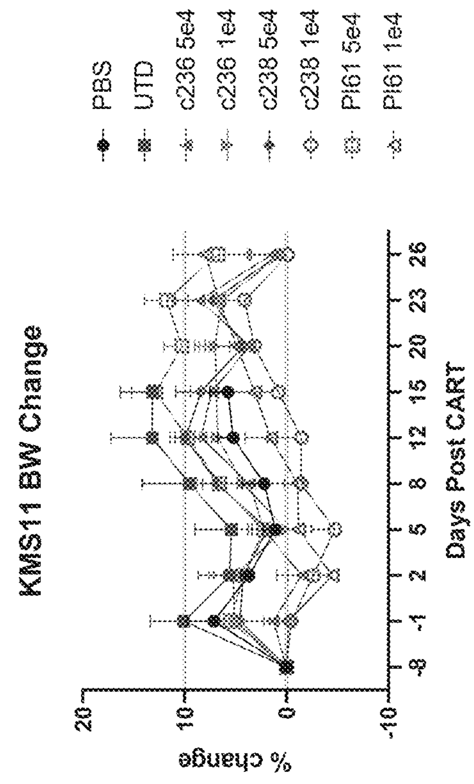
Figure 9C:
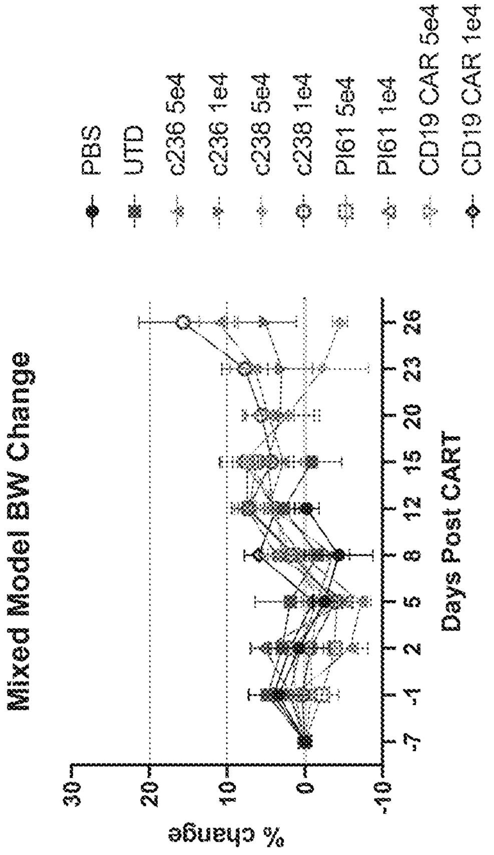

The dual CARTs cleared mixed tumors (BCMA+CD19+) at the dose of 5e4, and inhibited but not fully eliminated tumors at the dose of 1e4 over the course of the study (FIG. 8C). Neither PI61 nor CTL119 could control the mixed tumor (FIG. 8C). Both duals c236 and c238 exhibited similar or superior efficacy compared to the mono counterparts in the KMS11 and Nalm6 models (FIGS. 8A and 8B). Body weights increased during the study in all three models (FIGS. 9A-9C). There was a slight drop at the end of the KMS11 and NALM6 study possibly due to GVHD.

Figure 10B:
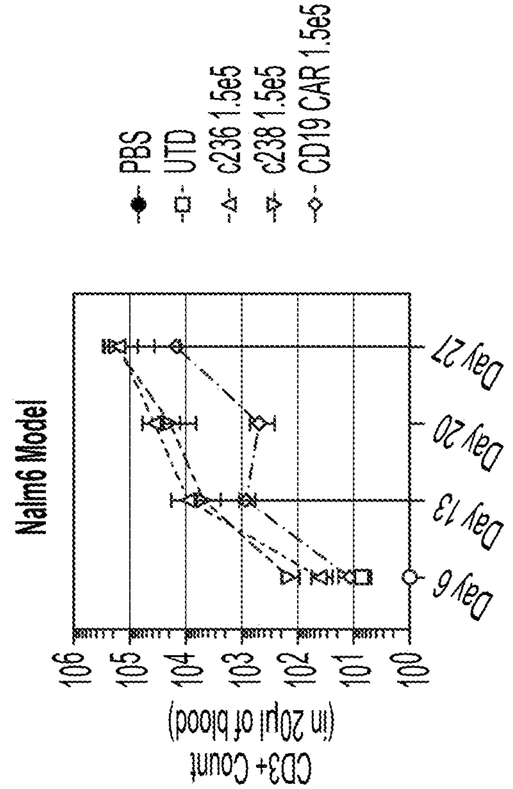
FIGS. 10A-10C: In vivo expansion of peripheral blood CD3+ T cells was analyzed by flow cytometry up to 4 weeks after infusion.
Figure 10A:
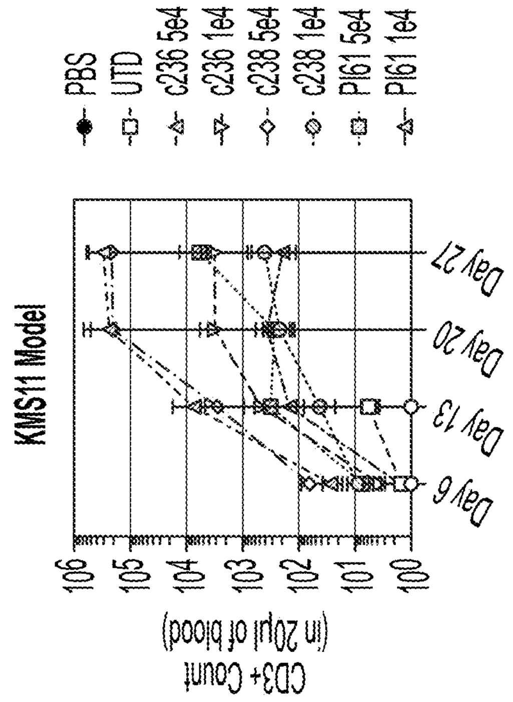
Figure 10C:
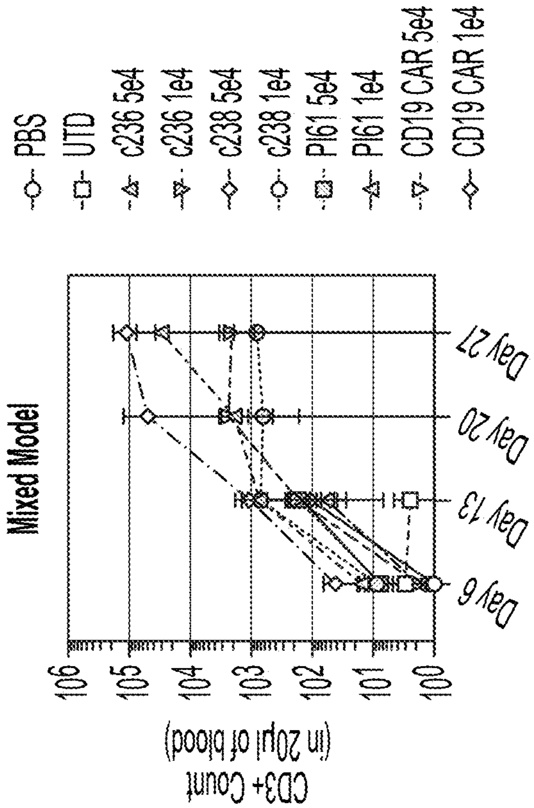
Figure 11B:
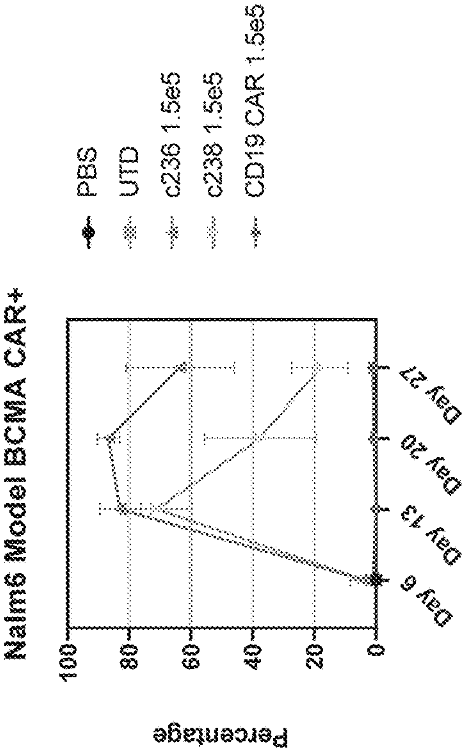
FIGS. 11A-11C: In vivo expansion of CAR+ T cells (BCMA CAR+ percentage) was analyzed by flow cytometry up to 4 weeks after infusion.
Figure 11A:
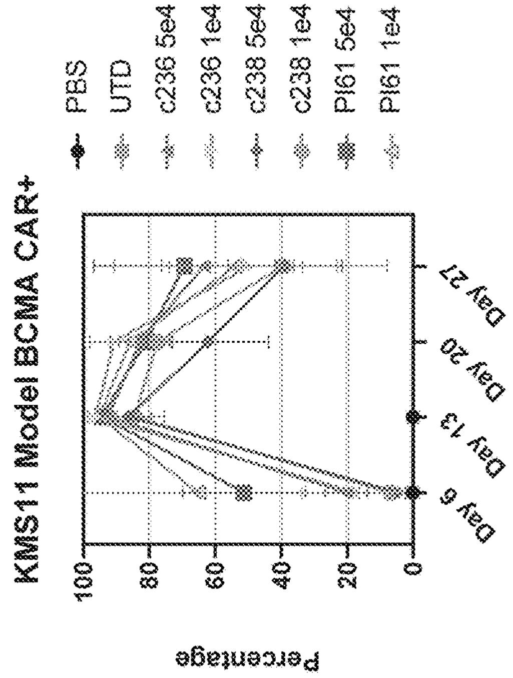
Figure 11C:
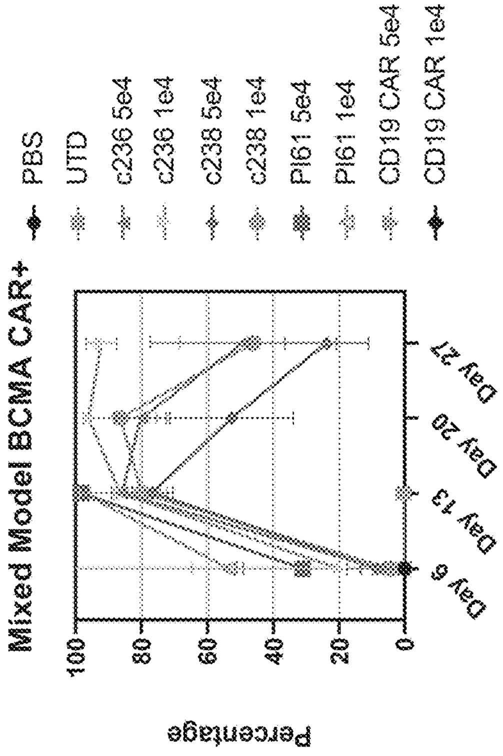

T cell expansion occurred from Day 6 to Day 20, and then evened out from Day 20 to Day 27 (FIGS. 10A-10C). Expansion was dose related across all three models (FIGS. 11A-11C). The KMS11 model showed 3-4 folds higher expansion compared to the mixed model in the higher doses (FIGS. 10A and 10C). Duals c236 and c238 showed higher expansion than mono CARTs (FIGS. 10A-10C).

Figure 12A:
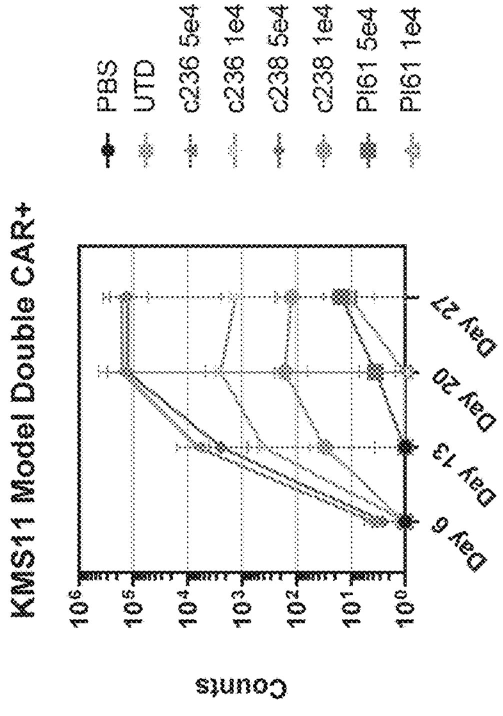
FIGS. 12A-12C: In vivo expansion of CAR+ T cells (double CAR+ counts) was analyzed by flow cytometry up to 4 weeks after infusion.
Figure 12B:
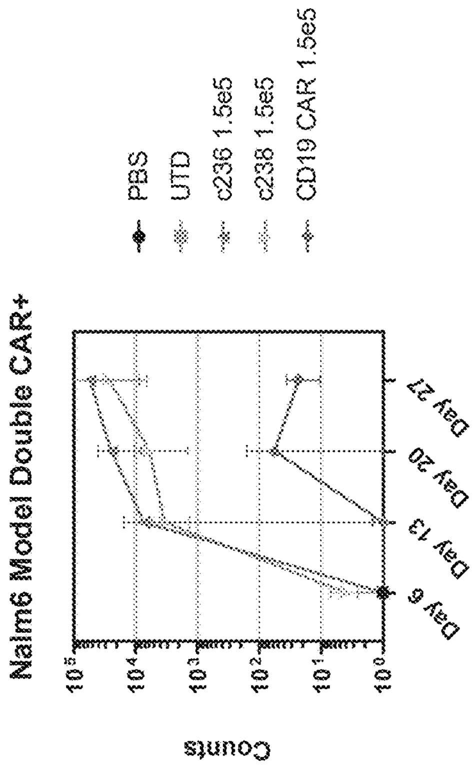
Figure 12C:
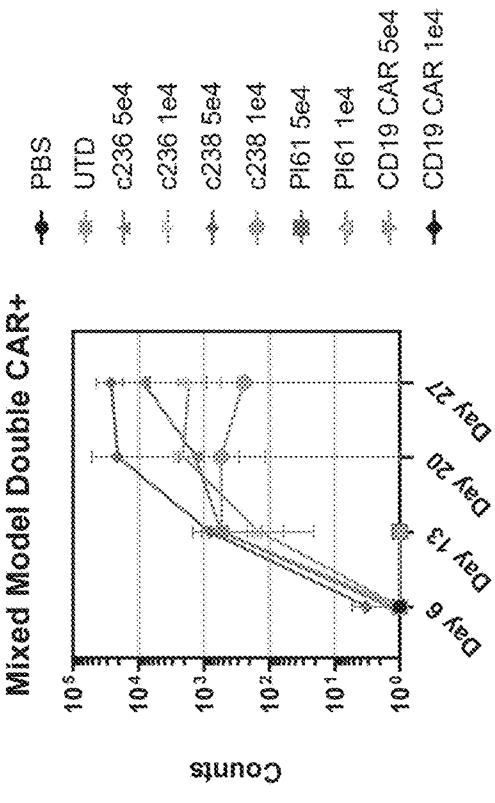

Total BCMA CAR+ percentage peaked at Day 13 and then began to decrease through Day 27 (FIGS. 11A-11C). In the mixed model, the 5e4 groups showed lower BCMA CAR+ percentages compared to the 1e4 groups after Day 13 (FIG. 11C). The double CAR+ percentage was related to an influx of total CD3+ cells, which could be a possible sign of GVHD. Double anti-BCMA and CD19 CAR+ T cell expansion was observed in c236 and c238 CART Rx groups in all three models (FIGS. 12A-12C).

Figure 13B:
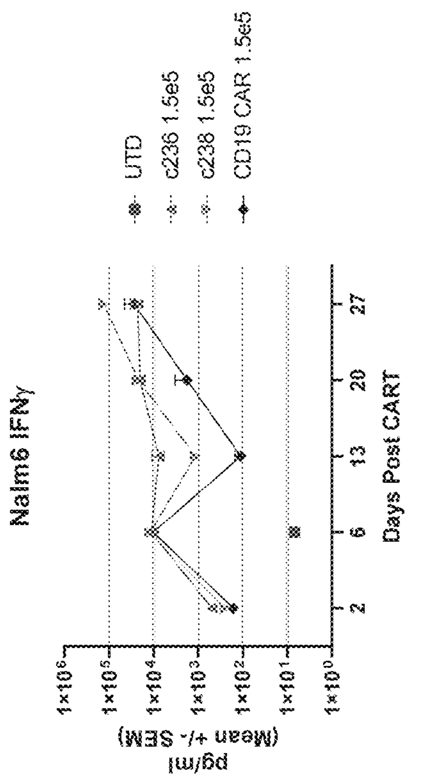
FIGS. 13A-13C: In vivo plasma IFN-γ kinetics. Plasma IFN-γ levels from all three mouse models treated with c236 and c238, as well as monoCAR controls, at respective CAR−T doses are plotted in the graphs. Mice were bled and plasma cytokine measured by MSD assay.
Figure 13A:
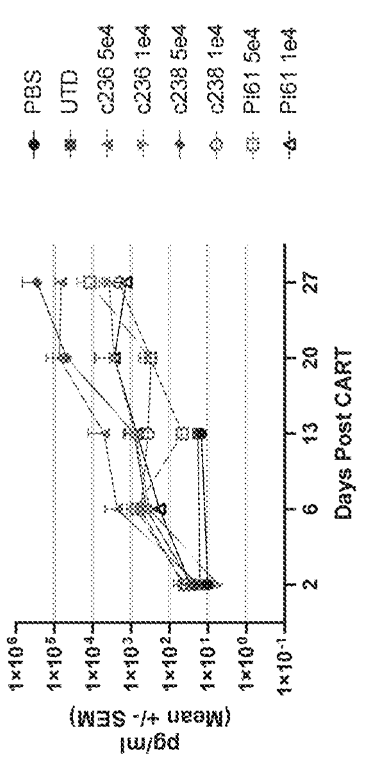
Figure 13C:
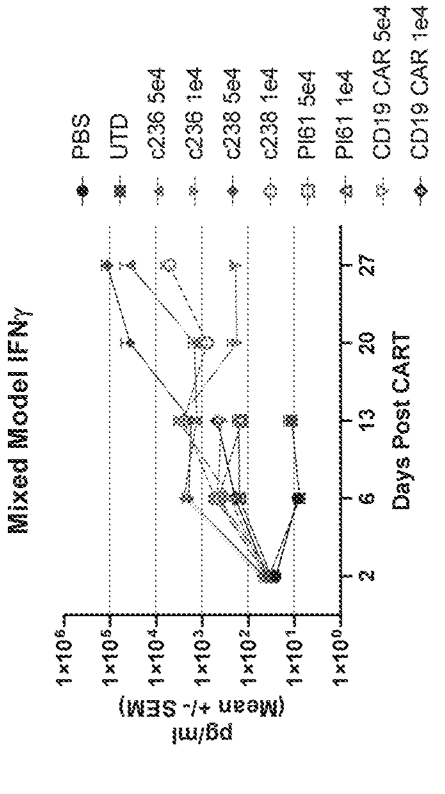

Induction of IFNγ was dose responsive across all the models (FIGS. 13A-13C). Duals at both doses produced ~3 to 4 folds more IFNγ at peak in the mixed model than that in the KMS11 alone model (FIGS. 13A and 13C). Peak induction was observed within 13 days in most of the groups in all the models (day 20 and day 27 peaks were most likely due to GVHD) (FIGS. 13A-13C).

Figure 14A:
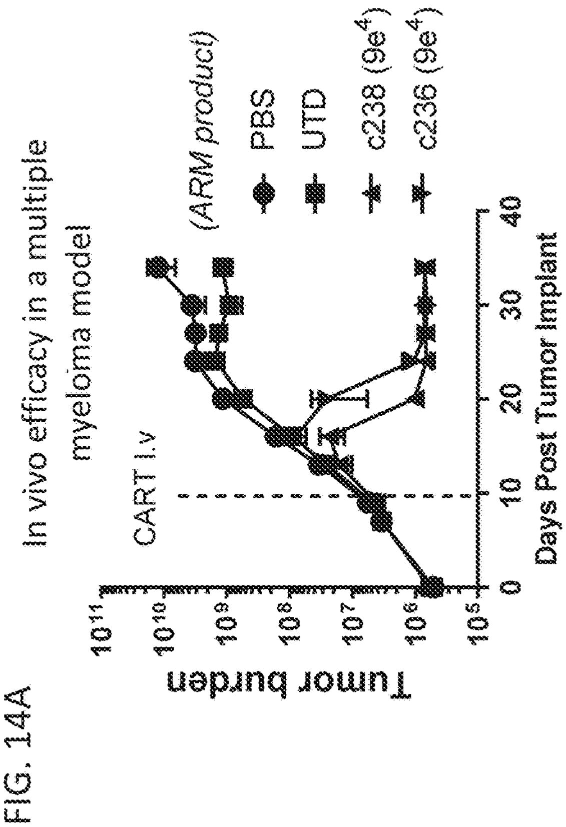
FIGS. 14A and 14B: In vivo efficacy and cellular expansion of cells generated using 236 and c238 in a multiple myeloma xenograft mouse model.
Figure 14B:
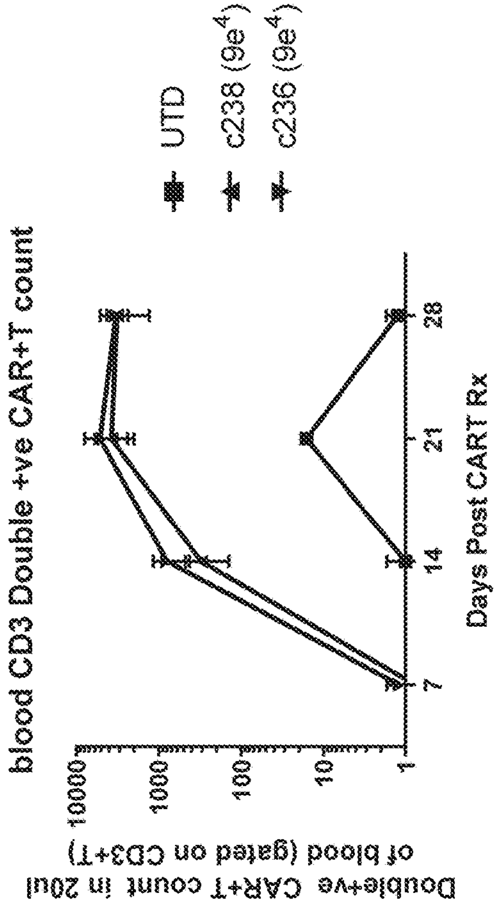

In a separate study, the day 1 CARTs generated using Grex100 and 6-well Grex system were examined for their anti-tumor activity in vivo using a disseminated KMS-11-luc multiple myeloma model. The luciferase reporter allows for monitoring of disease burden by quantitative bioluminescence imaging (BLI). Briefly, day 1 CARTs manufactured as described above were administered in tumor-bearing mice. Blood samples were taken weekly to measure peripheral blood CART expansion and analyzed by flow cytometry. T cells engineered with construct #236 and construct #238 displayed potent anti-tumor activity (FIG. 14A) and good CART expansion (FIG. 14B) in vivo towards a KMS11 (BCMA+CD19−) model.

Example 3: Characterization of Diabody CARTs

This example describes characterization of diabody CARs JL1 to JL10. JL1 to JL8 are PI61/CTL119 diabody constructs and JL9 to JL10 are R1G5/CTL119 diabody constructs. The sequence information of JL1 to JL10 is disclosed in Table 31.

Production and Measurement of Day 1 Anti BCMA-CD19 Diabody CARTs with Activated Rapid Manufacturing (ARM) Process In some embodiments, this ARM process starts with a frozen or fresh leukapheresis product. After a sample for counting and QC is obtained, the product is attached to a cell sorting machine (e.g., an installed CliniMACS Prodigy device kit) and the program begins. The cells are washed and incubated with microbeads that bind to desired surface markers, such as CD4 and CD8. The bead-labeled cells are selected by passing the cells through a magnetic column. Isolated cells are washed again and the separation buffer is exchanged for cell media. Purified T cells then either proceed to culture or are cryopreserved for later use. Purity of the isolated T cells will pass a QC step by flow cytometry assessment. Cryopreserved cells are thawed, washed in pre-warmed cell media, and resuspended in cell media. Fresh cells are added to culture directly. Aliquots of frozen Pan T isolated cells are thawed in a 37° C. water bath, put into Optimizer CM (Gibco Optimizer Media with Supplement +100U/mL human IL2) and spun for 5 minutes at 1500 rpm. Cells are counted and plated into a 24-well plate at 3e6/mL, 1 mL/well. TransAct is added to each well at 1/100 (10 μL/well).

For in vitro CAR expression kinetics study with the ARM process, a 24-well plate was used. At the time of plating, the cells were transduced with a lentiviral vector encoding BCMA-CD19 diabody CAR at a multiplicity of infection (MOI) of 2. MOI was determined based on the viral titer obtained in SupT1 cells based on the double positive CAR expression. After 24 hours in culture, cells were harvested and washed three times in PBS+1% HSA. Cells were then counted and re-plated at 1e6/mL final in a 24-well plate. 72 hours after re-plating, cells were harvested, counted and an aliquot of 5e5 cells from each sample was taken for flow cytometry analysis. This procedure was repeated 72 hours later for a day seven time point.

Figure 15A:
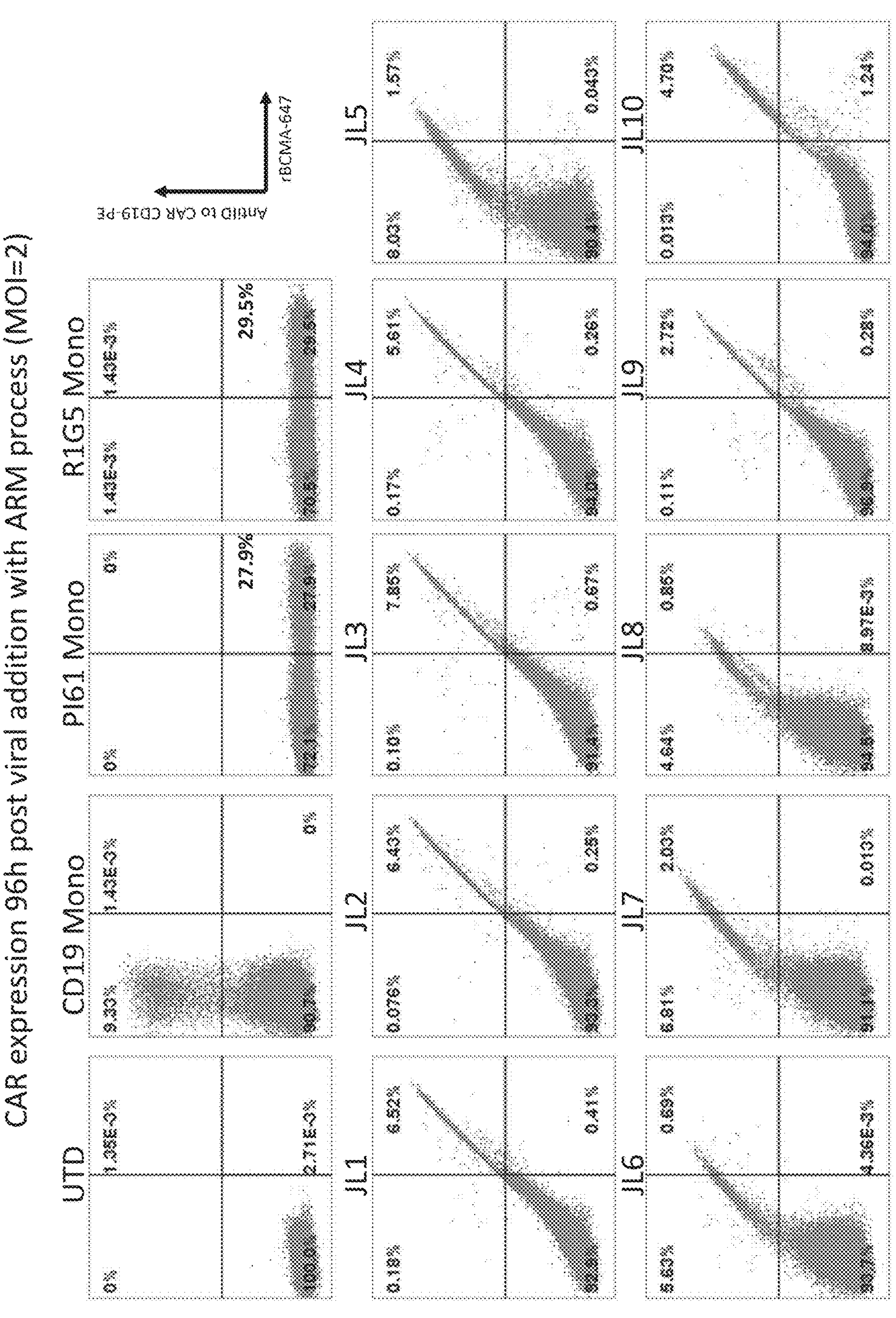
FIGS. 15A and 15B: CAR expression of cells manufactured using the ARM process. Flow cytometry plots showing the expression of double positive anti-BCMA and anti-CD19 CARs at 96h (FIG. 15A) and 7 days (FIG. 15B) post viral addition to human primary T cells manufactured using the ARM process. The studies used a MOI of 2 based on the SupT1 titer determined by expression of double CAR (positive for PI61 or R1G5 clones and CTL119) detected by anti-idiotype antibody that binds to CD19CAR and recombinant BCMA_Fc (AF647) that binds to PI61 or R1G5. Mono anti-BCMA CARTs PI61 and R1G5, and mono anti-CD19 CART CTL119 served as controls.
Figure 15B:
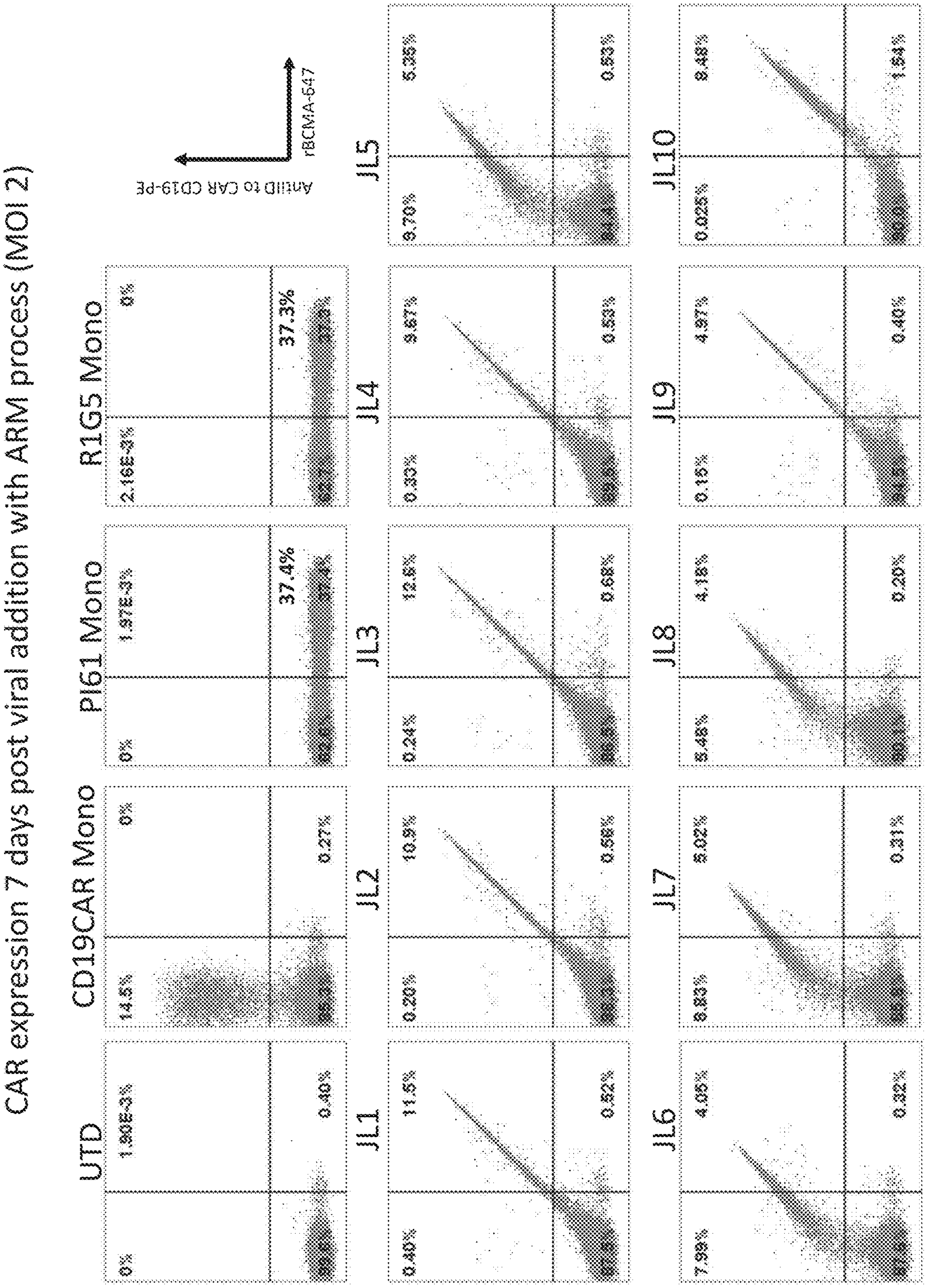

FIGS. 15A and 15B show the expression pattern of both anti-BCMA and anti-CD19 CARs, at 96 h (FIG. 15A) or 7 days (FIG. 15B) post-diabody viral addition to human primary T cells manufactured using the ARM process, using a MOI of 2. Altogether, these results demonstrate that both CARs were well expressed in the diabody CART system when R1G5 or PI61 was used in combination with duCD19.1 on day 4 (FIG. 15A) or day 7 (FIG. 15B) post viral addition. JL1-JL4, JL9, and JL10 showed linear expression of the double positive CAR, while JL5-JL8 showed a slight shift towards CD19+ population, which could be due to CAR binding differences to its respective detecting reagents. Data from one of two donors are shown here.

CAR−T cells production using Traditional manufacturing process Traditional manufacturing (TM) process is a process where T cells are expanded ex vivo for 8 to 9 days after activation and transduction prior to harvest. Prodigy processed T cells were resuspended in warm RPMI complete T cell medium (RPMI, 10% heat-inactivated FBS, 2 mM L-Glutamine, 100 U/mL Pen/Strep, 1×NEAA, 1 mM Sodium Pyruvate, 10 mM HEPES, and 55 μM P-Mercaptoethanol), and plated in 24-well plates at $0.5e^6$ cells/mL per well. T cells were incubated overnight at 37° C. with Human T-Expander CD3/CD28 beads at a 3:1 ratio of beads-to-cells.

On Day 1, lentiviruses were added at a MOI of 5, based on the SUP-T1titer. No virus was added to the untransduced control (UTD). The T cells were incubated overnight at 37° C. followed by the addition of 1 mL complete T cell medium per well, after which they were incubated overnight at 37° C. For the remaining six days of culture expansion, the T cells were transferred into tissue culture flasks and diluted with complete T cell medium every two days, targeting a concentration of $0.5e^6$ cells/mL. Typical split ratios ranged from 1:2 to 1:4 during the expansion phase.

On Day 7, the T cells were de-beaded, harvested and cryopreserved in CryoStor CS10 freezing medium, frozen at −80° C. in CoolCell Cell Freezing Containers (Biocision), and transferred to $LN_2$ the following day. Small aliquots of T cells were stained for CAR expression. Single color controls were included for compensation. Samples were measured on a flow cytometer (BD LSRFortessa), and data were analyzed with FlowJo software.

Figure 16:
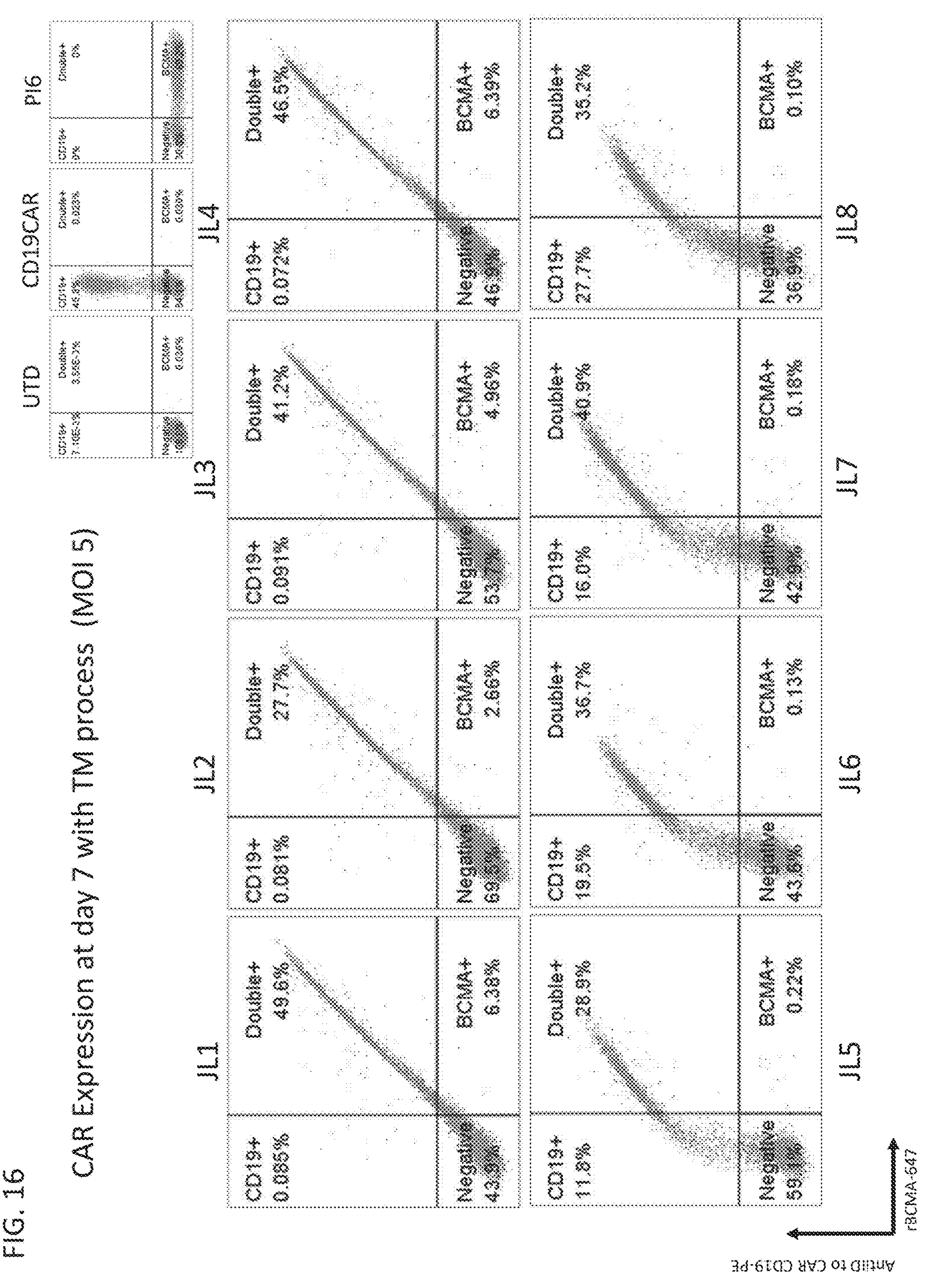
FIG. 16: CAR Expression at day 7 with TM process using MOI of 5. Flow cytometry plots showing the expression of double positive anti-BCMA and anti-CD19 CARs on day 7 post viral addition to human primary T cells manufactured using the TM process. The studies used a MOI of 5 based on the SupT1 titer determined by expression of double CAR (positive for PI61 or R1G5 clones and CTL119) detected by anti-idiotype antibody that binds to CD19CAR and recombinant BCMA_Fc (AF647) that binds to PI61 or R1G5.

FIG. 16 demonstrates CAR Expression at day 7 with TM process using MOI of 5. The TM products showed a similar expression pattern as the ARM products (FIGS. 15A, 15B, and 16).

In Vitro Killing Assay

The killing potential of T cells engineered with various diabody constructs in response to BCMA or CD19 expressing target cells was evaluated by incubating CART cells with target cells at 2-fold E:T ratio dilutions starting at 20:1. The number of target cells were fixed at $2.5\times10^5$ cells/well and cells were cultured in 96-well flat-bottom plates. Effector cells were CART cells generated using traditional manufacturing by transducing T cells with diabodies. Target cells include BCMA positive KMS11-luc cells or BCMA negative NALM6-luc cells. For this assay, the % transduction of CAR−T cells was normalized by addition of UTD to the BCMA CARTs. This allowed for the comparison of the same number of CARTs and same total T cell number in each sample.

Loss of luciferase signal resulting from cell killing was measured using Bright-Glo substrate 16h after cell seeding and specific lysis was calculated according to the following formula:

Specific lysis (%)=100−(sample luminescence/average maximal luminescence)*100

Figure 17B:
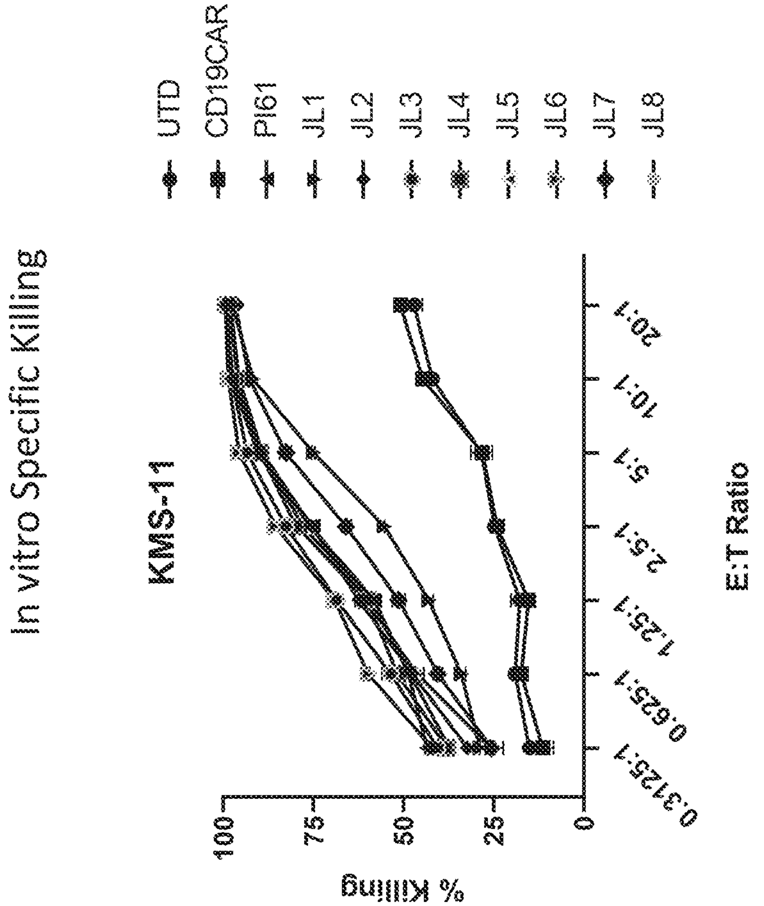
FIGS. 17A and 17B: In vitro specific killing of BCMA- or CD19-expressing tumor cells by T cells engineered with anti-BCMACAR and CD19CAR diabody constructs. The ability of T cells expressing PI61/CTL119 clones to mediate cell lysis was evaluated against the KMS11-Luc or NALM6-Luc target cell line. CART cells were co-cultured with BCMA+ KMS-11-luc or BCMA-NALM6-Luc target cells at the indicated E:T ratios for 20h, and % cell killing, determined by the difference in luciferase signal between target cells without effector T cells (control) and with effector T cells (experimental) expressed as a percent of the control, was measured as a surrogate for target cell lysis. UTD represents untransduced T cells. Mono PI61 or CTL119 served as controls.
Figure 17A:
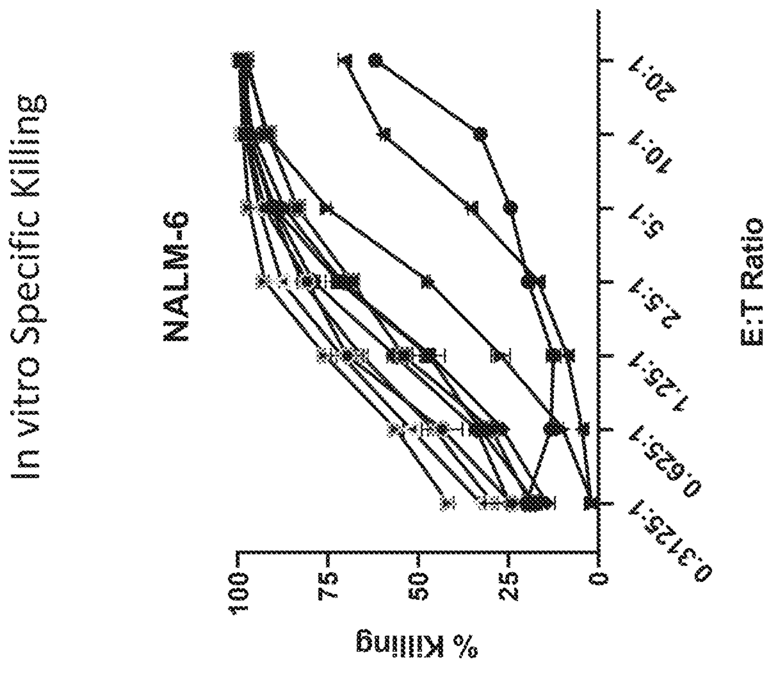

FIGS. 17A and 17B demonstrate the ability of different diabodies of PI61/CTL119 to effectively kill specific target cell lines NALM-6 (CD19+, BCMA−) (FIG. 17A) or KMS-11 (CD19−, BCMA+) (FIG. 17B). The data suggest that clones JL6, JL5, JL3, and JL8 equally killed both target cells.

Cytokine Secretion Assay

Figure 18B:
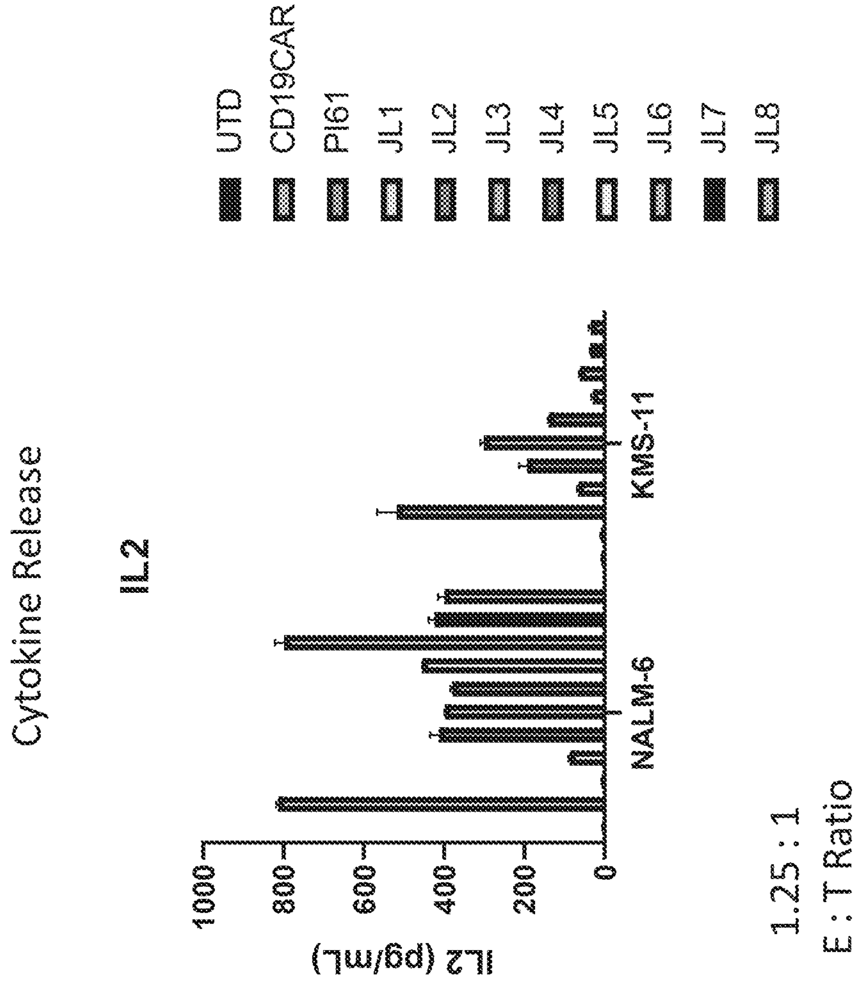
FIGS. 18A and 18B: Cytokine production of T cells engineered with anti-BCMACAR and CD19CAR diabody constructs in response to BCMA- or CD19-expressing tumor cells. IFN-γ(FIG. 18A) and IL-2 (FIG. 18B) were measured by MSD in the supernatants from the killing assay co-culture at a ratio of 1.25:1.
Figure 18A:
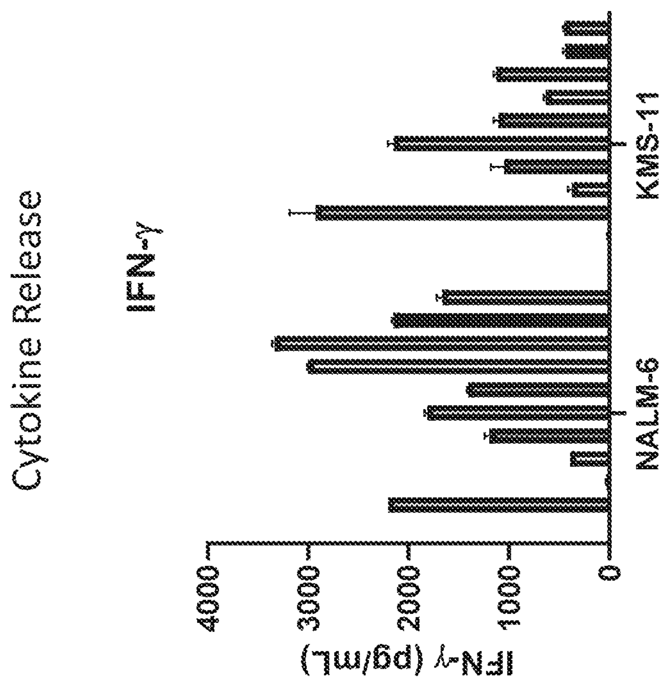

Supernatants were collected from the co-cultures (a ratio of 1.25:1) used in the killing assay above after 20 h incubation to be used in the MSD V-PLEX Human IFN-□□ and IL-2 analysis. Different magnitude of target-specific induction of IFN-□ or IL-2 by diabody transduced cells was observed in response to stimulation with KMS11 or NALM6 cells (FIGS. 18A and 18B). UTD cells did not show any unspecific IFN-□□ secretion in response to either target cells (FIG. 18A). In line with the results from the killing assay, clones JL6, JL5, JL3, and JL8 produced more cytokines in response to the target cells (FIGS. 18A and 18B).

Example 4: Co-Transduction of BCMA CAR and CD19 CAR

Aliquots of frozen Pan T isolated cells were thawed in a 37° C. water bath, put into Optimizer CM (Gibco Optimizer Media with Supplement+100U/mL human IL2) and spun for 5 minutes at 1500 rpm. Cells were counted and plated into a 24-well plate at 3e6/mL, 1 mL/well. TransAct was added to each well at 1/100 (10 μL/well). Virus was added at differing multiplicity of infections (MOIs) based on either the SupT1 titer for PI61 or the qPCR titer for CTL119. PI61 was used at a MOI of 2 or 1 and paired with three different CTL119 MOIs: 1, 0.5, and 0.25. Mono CARs were added at a MOI of 1 or 2 for PI61 and 1 for CTL119, and a UTD control was plated as well. After 24 hours in culture, cells were harvested and washed three times in PBS+1% HSA. Cells were then counted and re-plated at 1e6/mL final in a 24-well plate.

72 hours after re-plating, cells were harvested, counted and an aliquot of 5e5 cells from each sample was taken for flow cytometry analysis. Cells were stained with Live/Dead Aqua (BV510) for 15 minutes in 100 µl/well and were then washed twice. The antibody MM (Table 32) was then added at 50 µl/well for 25 minutes at 4° C. Cells were washed twice again and then fixed for 15 minutes in 1.6% PFA in PBS, 100 µl/well. After fixing, cells were washed as previously described and resuspended in a final volume of 150 µl/sample in flow cytometry buffer. 5e4 cells were acquired on the Live CD3 positive gate of each sample on a BD LSRFortessa (BD Biosciences, San Jose CA) and data was analyzed using FlowJo v.10 software (Ashland, OR). This procedure was repeated 72 hrs later for a day seven time point.

TABLE 32

| Antibody and other reagents. | | | | | |
|---|---|---|---|---|---|
| Marker | Clone | Fluorochrome | Vendor | Catalogue No. | Dilution |
| Live/Dead | | BV510 | Biolegend | 423102 | 1/500 |
| CD3 | SK7 | BUV395 | BD | 564001 | 1/200 |
| CAR19 | Anti-ID | PE | In House Reagent | | 1/160 |
| CD4 | SK3 | PerCP 5.5 | Biolegend | 344608 | 1/100 |
| CAR | rBCMA FC | AF 647 | In House Reagent | | 1/380 (3 ug/ml) |
| CD8 | SK1 | APC H7 | BD | 560179 | 1/200 |
| FACS Buffer | | | Miltenyi Biotec | 130-091-222 | |
| BSA Stock Solution | | | Miltenyi Biotec | 130-091-376 | |
| Phosphate Buffer Saline (PBS) | | | Gibco | 14190-144 | |
| Para formaldehyde (PFA) | | | Polysciences Inc. | 18814-10 | |

Figure 19:
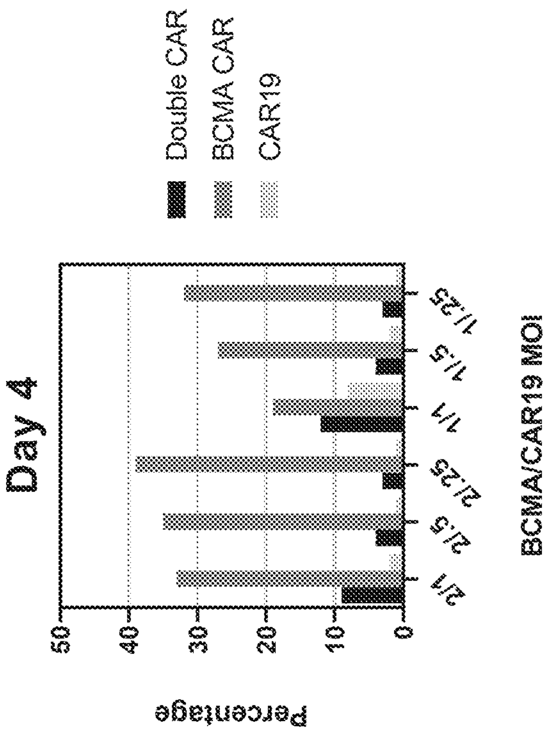
FIG. 19: Percentages of the double CAR positive population, BCMA CAR positive population, and CD19 CAR positive population on Day 4.
Figure 20:
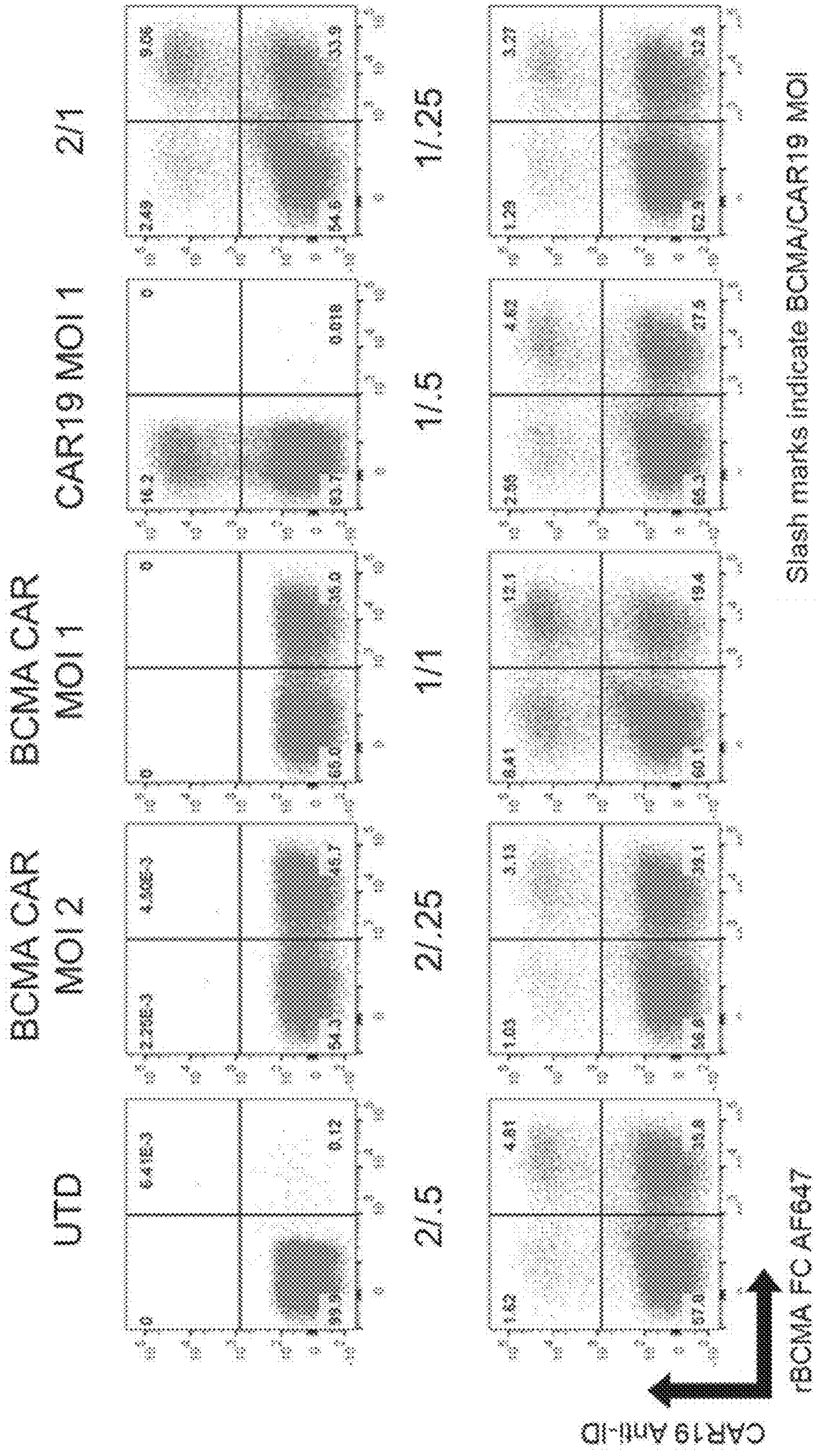
FIG. 20: Flow cytometry plots showing staining of cells with rBCMA-Fc and an anti-idiotype antibody that binds to CD19 CAR.
Figure 21:
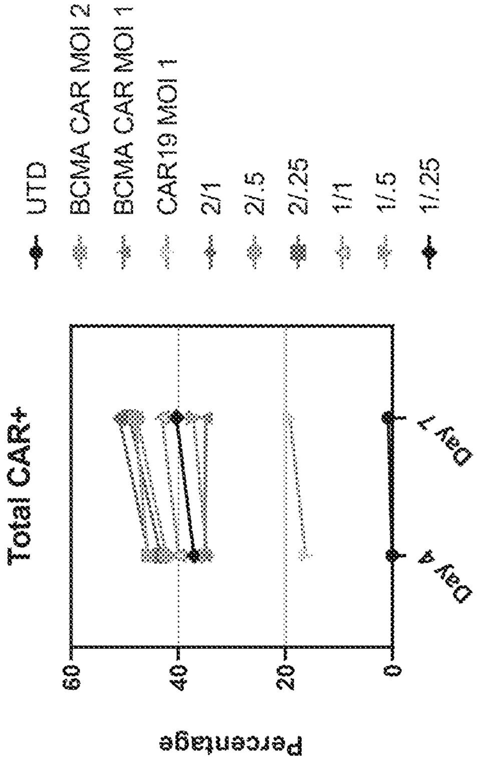
FIG. 21: Percentages of total CAR positive populations on Day 4 and Day 7 under the indicated conditions.
Figure 22:
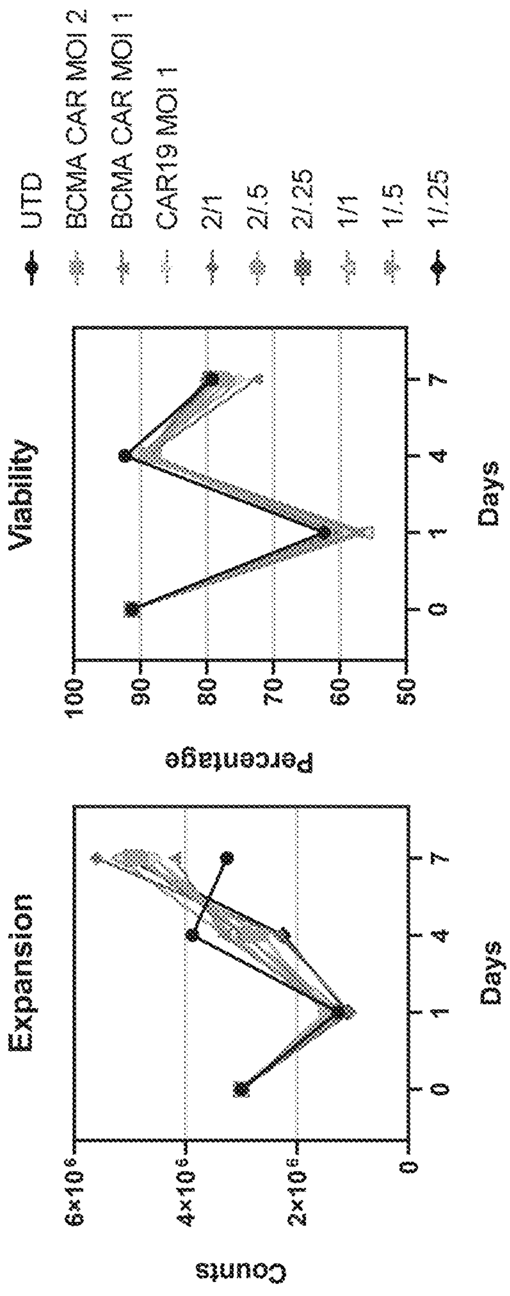
FIG. 22: Cell counts (left panel) and percentage of live cells (right panel) on Days 0, 1, 3, and 7 under the indicated conditions.

At Day four after viral addition, flow cytometry analysis showed significantly higher percentages of mono BCMA CAR+ population over the CAR19 positive population and the double CAR positive population in the BCMA CAR MOI 2 conditions (FIGS. 19 and 20). This was consistent across both donors. When PI61 was added at a MOI of 1, good titration of all the populations was observed (FIGS. 19 and 20). CAR19+ population as well as the double CAR+ population decreased as the CD19 CAR MOI decreased from 1 to 0.25 (FIG. 19). The BCMA CAR+ population increased when the CTL119-encoding virus was added at a lower amount (FIG. 19). Total CAR+ populations correlated in percentages with the total MOI added to each well (FIG. 21). Total BCMA CAR and CAR19 percentages correlated as well. All trends were stable from day four to day seven (FIG. 21). Viability and expansion rates were independent of the total MOI added (FIG. 22). Data from one of the four donors are shown here.

Example 5: Description of the Activated Rapid Manufacturing (ARM) Process

In some embodiments, CART cells are manufactured using a continuous Activated Rapid Manufacturing (ARM) process, over approximately 2 days, which will potentially allow for a greater number of less differentiated T cells (T naïve and $T_{SCM}$ (stem central memory T) cells) to be returned to a patient for in vivo cellular expansion. The short manufacturing time period allows the early differentiated T cells profile to proliferate in the body for their desired terminal differentiated state rather that in an ex vivo culture vessel.

In some embodiments, CART cells are manufactured using cryopreserved leukapheresis source material, for example, non-mobilized autologous peripheral blood leukapheresis (LKPK) material. Cryopreserved source material undergoes processing steps for T cell enrichment on the first day of production (Day 0) by means of anti-CD4/anti-CD8 immunomagnetic system. Positive fraction is then seeded in G-rex culture vessel, activated with an anti-CD3/CD28 system (TransACT) and on the same day transduced with a lentiviral vector (LV) encoding a CAR. On the following day, after 20-28 hours of transduction, the T cells are harvested, washed four times, formulated in freezing medium and then frozen by a Controlled Rate Freezer (CRF). From the start of the process on Day 0 to the initiation of harvest on the following day, cells are cultured for 20-28 hours with a target of 24 hours after Day 0 seeding.

Media for Day 0 were prepared according to Table 21.

TABLE 21

| Media type and point of use during CART manufacturing | | |
|---|---|---|
| Media/Buffer Type | Composition | Point of Use |
| Rapid Buffer (RB) | CliniMACS ® Buffer (+0.5% human serum albumin (HSA)) | Day 0 Processing on Cell Wash/Separator |
| Rapid Media (RM) | OpTmizer ™ Media, CTS ™, IL-2, Glutamax and ICSR | Day 0 for Processing on Cell Wash/Separator and Cell Seeding |
| Harvest Buffer (HB) (also called Harvest Buffer Solution) | PBS no EDTA and 2% HSA | Harvest Wash Buffer (Day 1) |
| Cryomedia | Cryostor10 (CS10) | Harvest Formulation |

The cryopreserved leukapheresis material is thawed. The thawed cells are diluted with the Rapid Buffer (Table 21) and washed on the CliniMACS® Prodigy® device. The T cells are selected by CliniMACS® CD4 and CD8 microbeads. Once the program is finished for T cell selection (approximately 3 h 40 min to 4 h 40 min), the reapplication bag containing the cells suspended in Rapid Media (Table 21) are transferred in a transfer pack. A sample is taken for viability and cell count. The cell count and viability data from the positive fraction bag is used to determine the cell concentration when seeding the culture vessel for activation and vector transduction.

ucts to obtain T cell percentage target for the apheresis. The results for the T cell percentage determine how many bags are thawed on Day 0 of the ARM process.

TABLE 25

Media and Buffer type and point of use during CART manufacturing

| Media Type | Source | Point of Use |
| --- | --- | --- |
| CliniMACS ® Buffer/human serum albumin (HSA) (0.5% in working concentration) | Prepared by operator on day 0 | Day 0 Processing on Cell Wash/Separator |
| Rapid Media | Prepared by operator on day 0 | Day 0 for Cell Seeding |
| PBS/HSA (1% or 2% in working concentration) | Prepared by operator on day 0 | Harvest and culture Wash Media (Day 1) |
| Cryostor10 (CS10) | Commercially available | Harvest Formulation |

Following positive selection of T cells via the CliniMACS® microbeads (CD4 and CD8), the cells are seeded in the culture vessel, G-Rex. Once the cells are seeded, the activation reagent (TransACT) is then added to the culture vessel. The cells are then transduced with a lentiviral vector encoding a CAR at a target MOI of 1.0 (0.8-1.2). Following the vector addition, the culture vessel is transported to an incubator where it is incubated for a target of 24 hours (operating range 20-28 hours) at a nominal temperature of 37° C. (operating range 36-38° C.) with nominal 5% $CO_2$ (operating range 4.5-5.5%). Following the incubation, the cells are washed with Harvest Wash Solution (Table 21) four times to remove any non-integrated vector and residual viral particles, as well as any other process related impurities. Then, the cells are eluted and a sample for cell count and viability is taken for testing and the results are used to determine the volume required to re-suspend the cells for final formulation with CryoStor® CS10. The cells are then centrifugated to remove the Harvest Wash Solution and proceed with cryopreservation.

In some embodiments, the CAR expressed in CART cells binds to CD19. In some embodiments, IL-2 used in the Rapid Media (RM) (Table 21) can be replaced with IL-15, hetIL-15 (IL-15/sIL-15Ra), IL-6, or IL-6/sIL-6Ra.

In some embodiments, the CAR expressed in CART cells binds to BCMA. In some embodiments, IL-2 used in the Rapid Media (RM) (Table 21) can be replaced with IL-15, hetIL-15 (IL-15/sIL-15Ra), IL-6, or IL-6/sIL-6Ra.

In some embodiments, the CART cells express dual CARs disclosed herein, e.g., anti-BCMA/anti-CD19 dual CARs disclosed herein. In some embodiments, the CART cells express a diabody CAR disclosed herein, e.g., an anti-BCMA/anti-CD19 diabody CAR disclosed herein. In some embodiments, the CART cells are engineered to express an anti-BCMA CAR and an anti-CD19 CAR using co-transduction as disclosed herein.

Example 6: Manufacturing CART Cells Using the Activated Rapid Manufacturing (ARM) Process The ARM process of CART cells initiates with the preparation of the media as outlined in Table 25.

Cryopreserved leukapheresis product is used as the starting material and is processed for T cell enrichment. When available, the apheresis paperwork is utilized to define the T cell percentage. In the absence of the T cell percentage data on the apheresis paperwork, the sentinel vial testing is performed on incoming cryopreserved leukapheresis prod- Cryopreserved leukapheresis is thawed, washed, and then undergoes T cell selection and enrichment using CliniMACS® microbead technology. Viable nucleated cells (VNCs) are activated with TransACT (Miltenyi) and transduced with a lentiviral vector encoding the CAR. The viable cells selected with the Miltenyi microbeads are seeded into the centricult on the Prodigy®, which is a non-humidified incubation chamber. While in culture, the cells are suspended in Rapid media, which is an OpTmizer™ CTS™ based medium that contains the CTS™ Supplement (ThermoFisher), Glutamax, IL-2 and 2% Immune cell serum replacement amongst its components to promote T cell activation and transduction. Lentiviral transduction is performed once on the day of seeding after the TransACT has been added to the diluted cells in the culture media. Lentiviral vector will be thawed immediately prior to use on day of seeding for up to 30 minutes at room temperature.

From the start of the process on Day 0 to the initiation of the culture wash and harvest, CART cells are cultured for 20-28 hours from seeding. Following culture, the cell suspension undergoes two culture washes and one harvest wash within the centricult chamber (Miltenyi Biotech).

After the harvest wash on the CliniMACS® Prodigy® on day 1, the cell suspension is sampled to determine viable cell count and viability. Cell suspension is then transferred to a centrifuge to be pelleted manually. The supernatant is removed, and the cell pellet is re-suspended in CS10 (BioLife Solution), resulting in a product formulation with a final DMSO concentration of ~10.0%. The viable cell count is formulated at the end of harvest for dosing. The doses are then distributed into individual cryobags and analytical sampling into cryovials.

Cryopreserved products are stored in monitored LN2 storage tanks, in a secure, limited access area until final release and shipping.

In some embodiments, the CART cells express dual CARs disclosed herein, e.g., anti-BCMA/anti-CD19 dual CARs disclosed herein. In some embodiments, the CART cells express a diabody CAR disclosed herein, e.g., an anti-BCMA/anti-CD19 diabody CAR disclosed herein. In some embodiments, the CART cells are engineered to express an anti-BCMA CAR and an anti-CD19 CAR using co-transduction as disclosed herein.

Example 7: Manufacture of CART Cells Expressing an Anti-BCMA CAR and an Anti-CD19 CAR The rapid manufacturing process of CART cells begins with the preparation of the media as outlined in Table 33.

TABLE 33

| Media type and point of use during CART manufacturing | | |
|---|---|---|
| Media/Buffer Type | Composition | Process Step |
| Rapid Media (RM) | OpTmizer CTS<br>CTS supplement<br>ICSR<br>GlutaMAX<br>Reconstituted IL-2 | Cell Seeding and activation |
| Rapid Buffer (RB) | CliniMACs Buffer (PBS with EDTA)<br>HSA | Cell Wash and T cell enrichment |
| Culture/Harvest Wash Solution | PBS (no Mg/Ca and EDTA)<br>HSA | Harvest Wash procedure |
| Cryomedia | CryoStor ® (CS10) with DMSO | Harvest Formulation |

Cryopreserved leukapheresis is thawed. The thawed cells are diluted with the Rapid Buffer (Table 33) and washed on the CliniMACS® Prodigy® device. The T cells are selected by CliniMACS® CD4 and CD8 microbeads. Once the program is finished for T cell selection (approximately 3 h 40 min to 4 h 40 min), the reapplication bag will contain the cells suspended in Rapid Buffer (Table 33). A sample is taken for viability and cell count. The cell count and viability data from the positive fraction bag is used to determine the cell concentration when seeding the culture vessel for activation and vector transduction.

Following positive selection of T cells via the CliniMACS® microbeads (CD4 and CD8), the cells are seeded in the culture vessel, CentriCult in the Prodigy®, at a target of $4.0\times10^8$-$1.0\times10^9$ total viable cells at a targeted concentration of about $4.0\times10^6$ viable cells/mL. Once the cells are seeded, the activation reagent (TransAct) is then added to the culture vessel.

The cells are then transduced with a lentiviral vector encoding an anti-BCMA CAR and a lentiviral vector encoding an anti-CD19 CAR. The vector volume to be used for transduction of T cells, following positive selection, is calculated based on a target Multiplicity of Infection (MOI) of 4.75 for the BCMA CAR lentiviral vector and a target MOI of 0.5 for the CD19 CAR lentiviral vector.

After a target of 24 hours (operating range 20-28 hours) of incubation at a temperature of 37° C. with nominal 5% $CO_2$, the cells are processed for harvest wash.

Following the incubation, the cells are washed with Harvest Wash Solution (Table 33) three times to remove any non-integrated vector and residual viral particles, as well as any other process related impurities. Then, the cells are eluted and a sample for cell count and viability is taken for testing and the results are used to determine the volume required to re-suspend the cells for final formulation with CryoStor® CS10. The cells are then centrifugated to remove the Harvest Wash Solution and proceed with cryopreservation.

Example 8: Gene Signature Analysis of CART Cells Manufactured Using the ARM Process Methods Single Cell RNAseq Single cell RNAseq libraries were generated using the 10× Genomics Chromium Controller instrument and supporting library construction kits.

Cryopreserved cells were thawed, counted and flow sorted (if required for study question), prior to being loaded on a 10× Genomics Instrument. Individual cells were loaded into droplets and RNA within individual droplets was barcoded via a GemCode bead. Barcoded RNA was released from droplets and converted into a whole transcriptome Illumina compatible sequencing library.

Generated libraries were sequenced on an Illumina HiSeq Instrument and analyzed using 10× Genomics analysis pipeline and Loupe Cell Browser software.

Single Cell Immune Cell Profiling

Whole transcriptome 10× Genomics single cell libraries were used as a template material to generate immune cell profiling and repertoire analysis. T cell receptor sequences were PCR amplified from Chromium Single Cell 5' Libraries and analyzed on an Illumina sequencing instrument.

Analysis Pipeline

Single cell RNAseq data was processed through the Cell Ranger analysis pipeline starting with FASTQ files. A detailed description of the Cell Ranger analysis pipeline can be found at: support.10xgenomics.com/single-cell-gene-expression/software/pipelines/latest/what-is-cell-ranger. The general pipeline included alignment, filtering, barcode counting, and UMI counting. Cellular barcodes were used to generate gene-barcode matrices, determine clusters, and perform gene expression analysis. Gene expression count data was normalized using the Seurat Bioconductor package. Cells were discarded from the analysis that had less than 200 expressed genes. Genes were discarded from the analysis that were only expressed in 2 cells or less. The remaining data was normalized with the Seurat log normalization method using a scale factor of 10,000. Data was scaled by regressing on the number of detected molecules per cell. The gene set score (GeneSetScore) was calculated by taking the mean log normalized gene expression value of all the genes in the gene set. Each gene is z-score normalized so that the mean expression of the gene across samples is 0 and standard deviation is 1. The gene set score is then calculated as the mean of the normalized values of the genes in the gene set. An exemplary gene set score calculation is described below.

For this example of gene set score calculation, the normalized gene expression of two (2) samples for six (6) genes is provided in Table 23. For the purposes of this exemplary calculation, the gene set consists of genes 1-4. Therefore, Sample 1 and 2 both have gene set scores of 0.

TABLE 23

| Exemplary dataset for gene set score calculation | | |
|---|---|---|
| | Sample 1 | Sample 2 |
| Gene 1 | −3 | 0 |
| Gene 2 | 3 | 0 |
| Gene 3 | 1 | 0 |

TABLE 23-continued

| Exemplary dataset for gene set score calculation | | |
|---|---|---|
| | Sample 1 | Sample 2 |
| Gene 4 | −1 | 0 |
| Gene 5 | 10 | 4 |
| Gene 6 | −5 | 3 |

The gene set "Up TEM vs. Down TSCM" includes the following genes: MXRA7, CLIC1, NAT13, TBC1D2B, GLCCI1, DUSP10, APOBEC3D, CACNB3, ANXA2P2, TPRG1, EOMES, MATK, ARHGAP10, ADAM8, MAN1A1, SLFN12L, SH2D2A, EIF2C4, CD58, MYO1F, RAB27B, ERN1, NPC1, NBEAL2, APOBEC3G, SYTL2, SLC4A4, PIK3AP1, PTGDR, MAF, PLEKHA5, ADRB2, PLXND1, GNAO1, THBS1, PPP2R2B, CYTH3, KLRF1, FLJ16686, AUTS2, PTPRM, GNLY, and GFPT2.

The gene set "Up Treg vs. Down Teff" includes the following genes: C12orf75, SELPLG, SWAP70, RGS1, PRR11, SPATS2L, SPATS2L, TSHR, C14orf145, CASP8, SYT11, ACTN4, ANXA5, GLRX, HLA-DMB, PMCH, RAB11FIP1, IL32, FAM160B1, SHMT2, FRMD4B, CCR3, TNFRSF13B, NTNG2, CLDND1, BARD1, FCER1G, TYMS, ATP1B1, GJB6, FGL2, TK1, SLC2A8, CDKN2A, SKAP2, GPR55, CDCA7, S100A4, GDPD5, PMAIP1, ACOT9, CEP55, SGMS1, ADPRH, AKAP2, HDAC9, IKZF4, CARD17, VAV3, OBFC2A, ITGB1, CIITA, SETD7, HLA-DMA, CCR10, KIAA0101, SLC14A1, PTTG3P, DUSP10, FAM164A, PYHINI, MYO1F, SLC1A4, MYBL2, PTTG1, RRM2, TP53INP1, CCR5, ST8SIA6, TOX, BFSP2, ITPRIPL1, NCAPH, HLA-DPB2, SYT4, NINJ2, FAM46C, CCR4, GBP5, C15orf53, LMCD1, MK167, NUSAP1, PDE4A, E2F2, CD58, ARHGEF12, LOC100188949, FAS, HLA-DPB1, SELP, WEE1, HLA-DPA1, FCRL1, ICA1, CNTNAP1, OAS1, METTL7A, CCR6, HLA-DRB4, ANXA2P3, STAM, HLA-DQB2, LGALS1, ANXA2, P116, DUSP4, LAYN, ANXA2P2, PTPLA, ANXA2P1, ZNF365, LAIR2, LOC541471, RASGRP4, BCAS1, UTS2, MIAT, PRDM1, SEMA3G, FAM129A, HPGD, NCF4, LGALS3, CEACAM4, JAKMIP1, TIGIT, HLA-DRA, IKZF2, HLA-DRB1, FANK1, RTKN2, TRIB1, FCRL3, and FOXP3.

The gene set "Down stemness" includes the following genes: ACE, BATF, CDK6, CHD2, ERCC2, HOXB4, MEOX1, SFRP1, SP7, SRF, TAL1, and XRCC5.

The gene set "Up hypoxia" includes the following genes: ABCB1, ACAT1, ADM, ADORA2B, AK2, AK3, ALDH1A1, ALDH1A3, ALDOA, ALDOC, ANGPT2, ANGPTL4, ANXA1, ANXA2, ANXA5, ARHGAP5, ARSE, ART1, BACE2, BATF3, BCL2L1, BCL2L2, BHLHE40, BHLHE41, BIK, BIRC2, BNIP3, BNIP3L, BPI, BTG1, C11orf2, C7orf68, CA12, CA9, CALD1, CCNG2, CCT6A, CD99, CDK1, CDKN1A, CDKN1B, CITED2, CLK1, CNOT7, COL4A5, COL5A1, COL5A2, COL5A3, CP, CTSD, CXCR4, D4S234E, DDIT3, DDIT4, 1-Dec, DKC1, DR1, EDN1, EDN2, EFNA1, EGF, EGR1, EIF4A3, ELF3, ELL2, ENG, ENO1, ENO3, ENPEP, EPO, ERRFI1, ETS1, F3, FABP5, FGF3, FKBP4, FLT1, FN1, FOS, FTL, GAPDH, GBE1, GLRX, GPI, GPRC5A, HAPI, HBP1, HDAC1, HDAC9, HERC3, HERPUD1, HGF, HIF1A, HK1, HK2, HLA-DQB1, HMOX1, HMOX2, HSPA5, HSPD1, HSPH1, HYOU1, ICAM1, ID2, IFI27, IGF2, IGFBP1, IGFBP2, IGFBP3, IGFBP5, IL6, IL8, INSIG1, IRF6, ITGA5, JUN, KDR, KRT14, KRT18, KRT19, LDHA, LDHB, LEP, LGALS1, LONP1, LOX, LRP1, MAP4, MET, MIF, MMP13, MMP2, MMP7, MPI, MT1L, MTL3P, MUC1, MXI1, NDRG1, NFIL3, NFKB1, NFKB2, NOS1, NOS2, NOS2P1, NOS2P2, NOS3, NR3C1, NR4A1, NT5E, ODC1, P4HA1, P4HA2, PAICS, PDGFB, PDK3, PFKFB1, PFKFB3, PFKFB4, PFKL, PGAM1, PGF, PGK1, PGK2, PGM1, PIM1, PIM2, PKM2, PLAU, PLAUR, PLIN2, PLOD2, PNN, PNP, POLM, PPARA, PPAT, PROK1, PSMA3, PSMD9, PTGS1, PTGS2, QSOX1, RBPJ, RELA, RIOK3, RNASEL, RPL36A, RRP9, SAT1, SERPINB2, SERPINE1, SGSM2, SIAH2, SIN3A, SIRPA, SLC16A1, SLC16A2, SLC20A1, SLC2A1, SLC2A3, SLC3A2, SLC6A10P, SLC6A16, SLC6A6, SLC6A8, SORL1, SPP1, SRSF6, SSSCA1, STC2, STRA13, SYT7, TBPL1, TCEAL1, TEK, TF, TFF3, TFRC, TGFA, TGFB1, TGFB3, TGFBI, TGM2, TH, THBS1, THBS2, TIMM17A, TNFAIP3, TP53, TPBG, TPD52, TPI1, TXN, TXNIP, UMPS, VEGFA, VEGFB, VEGFC, VIM, VPS11, and XRCC6.

The gene set "Up autophagy" includes the following genes: ABL1, ACBD5, ACIN1, ACTRT1, ADAMTS7, AKR1E2, ALKBH5, ALPK1, AMBRA1, ANXA5, ANXA7, ARSB, ASB2, ATG10, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATP13A2, ATP1B1, ATPAF1-AS1, ATPIF1, BECN1, BECN1P1, BLOC1S1, BMP2KL, BNIP1, BNIP3, BOC, C11orf2, C11orf41, C12orf44, C12orf5, Cl4orf133, C1orf210, C5, C6orf106, C7orf59, C7orf68, C8orf59, C9orf72, CA7, CALCB, CALCOCO2, CAPS, CCDC36, CD163L1, CD93, CDC37, CDKN2A, CHAF1B, CHMP2A, CHMP2B, CHMP3, CHMP4A, CHMP4B, CHMP4C, CHMP6, CHST3, CISD2, CLDN7, CLEC16A, CLN3, CLVS1, COX8A, CPA3, CRNKL1, CSPG5, CTSA, CTSB, CTSD, CXCR7, DAP, DKKL1, DNAAF2, DPF3, DRAM1, DRAM2, DYNLL1, DYNLL2, DZANK1, EI24, EIF2S1, EPG5, EPM2A, FABP1, FAM125A, FAM131B, FAM134B, FAM13B, FAM176A, FAM176B, FAM48A, FANCC, FANCF, FANCL, FBXO7, FCGR3B, FGF14, FGF7, FGFBP1, FIS1, FNBP1L, FOXO1, FUNDC1, FUNDC2, FXR2, GABARAP, GABARAPL1, GABARAPL2, GABARAPL3, GABRA5, GDF5, GMIP, HAPI, HAPLN1, HBXIP, HCAR1, HDAC6, HGS, HIST1H3A, HIST1H3B, HIST1H3C, HIST1H3D, HIST1H3E, HIST1H3F, HIST1H3G, HIST1H3H, HIST1H3I, HIST1H3J, HK2, HMGB1, HPR, HSF2BP, HSP90AA1, HSPA8, IFI16, IPPK, IRGM, IST1, ITGB4, ITPKC, KCNK3, KCNQ1, KIAA0226, KIAA1324, KRCC1, KRT15, KRT73, LAMPI, LAMP2, LAMTOR1, LAMTOR2, LAMTOR3, LARPIB, LENG9, LGALS8, LIX1, LIX1L, LMCD1, LRRK2, LRSAM1, LSM4, MAP1A, MAP1LC3A, MAP1LC3B, MAP1LC3B2, MAP1LC3C, MAP1S, MAP2K1, MAP3K12, MARK2, MBD5, MDH1, MEX3C, MFN1, MFN2, MLST8, MRPS10, MRPS2, MSTN, MTERFD1, MTMR14, MTMR3, MTOR, MTSS1, MYH11, MYLK, MYOM1, NBR1, NDUFB9, NEFM, NHLRC1, NME2, NPC1, NR2C2, NRBF2, NTHL1, NUP93, OBSCN, OPTN, P2RX5, PACS2, PARK2, PARK7, PDK1, PDK4, PEX13, PEX3, PFKP, PGK2, PHF23, PHYHIP, PI4K2A, PIK3C3, PIK3CA, PIK3CB, PIK3R4, PINK1, PLEKHM1, PLOD2, PNPO, PPARGC1A, PPY, PRKAA1, PRKAA2, PRKAB1, PRKAB2, PRKAG1, PRKAG2, PRKAG3, PRKD2, PRKG1, PSEN1, PTPN22, RAB12, RAB1A, RAB1B, RAB23, RAB24, RAB33B, RAB39, RAB7A, RB1CC1, RBM18, REEP2, REP15, RFWD3, RGS19, RHEB, RIMS3, RNF185, RNF41, RPS27A, RPTOR, RRAGA, RRAGB, RRAGC, RRAGD, S100A8, S100A9, SCN1A, SERPINB10, SESN2, SFRP4, SH3GLB1, SIRT2, SLC1A3, SLC1A4, SLC22A3, SLC25A19, SLC35B3, SLC35C1, SLC37A4, SLC6A1, SLCO1A2, SMURF1, SNAP29, SNAPIN, SNF8, SNRPB, SNRPB2, SNRPD1, SNRPF, SNTG1, SNX14, SPATA18, SQSTM1, SRPX, STAM, STAM2, STAT2, STBD1, STK11, STK32A, STOM, STX12, STX17, SUPT3H, TBC1D17, TBC1D25, TBC1D5, TCIRG1, TEAD4, TECPR1, TECPR2, TFEB, TM9SF1, TMBIM6, TMEM203, TMEM208, TMEM39A, TMEM39B, TMEM59, TMEM74, TMEM93, TNIK, TOLLIP, TOMM20, TOMM22, TOMM40, TOMM5, TOMM6, TOMM7, TOMM70A, TP53INP1, TP53INP2, TRAPPC8, TREM1, TRIM17, TRIMS, TSG101, TXLNA, UBA52, UBB, UBC, UBQLN1, UBQLN2, UBQLN4, ULK1, ULK2, ULK3, USP10, USP13, USP30, UVRAG, VAMP7, VAMP8, VDAC1, VMP1, VPS11, VPS16, VPS18, VPS25, VPS28, VPS33A, VPS33B, VPS36, VPS37A, VPS37B, VPS37C, VPS37D, VPS39, VPS41, VPS4A, VPS4B, VTA1, VTI1A, VTI1B, WDFY3, WDR45, WDR45L, WIPI1, WIPI2, XBP1, YIPF1, ZCCHC17, ZFYVE1, ZKSCAN3, ZNF189, ZNF593, and ZNF681.

The gene set "Up resting vs. Down activated" includes the following genes: ABCA7, ABCF3, ACAP2, AMT, ANKH, ATF7IP2, ATG14, ATP1A1, ATXN7, ATXN7L3B, BCL7A, BEX4, BSDC1, BTG1, BTG2, BTN3A1, C11orf21, C19orf22, C21orf2, CAMK2G, CARS2, CCNL2, CD248, CD5, CD55, CEP164, CHKB, CLK1, CLK4, CTSL1, DBP, DCUN1D2, DENND1C, DGKD, DLG1, DUSP1, EAPP, ECE1, ECHDC2, ERBB2IP, FAM117A, FAM134B, FAM134C, FAM169A, FAM190B, FAU, FLJ10038, FOXJ2, FOXJ3, FOXL1, FOXO1, FXYD5, FYB, HLA-E, HSPA1L, HYAL2, ICAM2, IFIT5, IFITM1, IKBKB, IQSEC1, IRS4, KIAA0664L3, KIAA0748, KLF3, KLF9, KRT18, LEF1, LINC00342, LIPA, LIPT1, LLGL2, LMBR1L, LPAR2, LTBP3, LYPD3, LZTFL1, MANBA, MAP2K6, MAP3K1, MARCH8, MAU2, MGEA5, MMP8, MPO, MSL1, MSL3, MYH3, MYLIP, NAGPA, NDST2, NISCH, NKTR, NLRP1, NOSIP, NPIP, NUMA1, PAIP2B, PAPD7, PBXIP1, PCIF1, PI4KA, PLCL2, PLEKHA1, PLEKHF2, PNISR, PPFIBP2, PRKCA, PRKCZ, PRKD3, PRMT2, PTP4A3, PXN, RASA2, RASA3, RASGRP2, RBM38, REPIN1, RNF38, RNF44, ROR1, RPL30, RPL32, RPLP1, RPS20, RPS24, RPS27, RPS6, RPS9, RXRA, RYK, SCAND2, SEMA4C, SETD1B, SETD6, SETX, SF3B1, SH2B1, SLC2A4RG, SLC35E2B, SLC46A3, SMAGP, SMARCE1, SMPD1, SNPH, SP140L, SPATA6, SPG7, SREK1IP1, SRSF5, STAT5B, SVIL, SYF2, SYNJ2BP, TAF1C, TBC1D4, TCF20, TECTA, TES, TMEM127, TMEM159, TMEM30B, TMEM66, TMEM8B, TP53TG1, TPCN1, TRIM22, TRIM44, TSC1, TSC22D1, TSC22D3, TSPYL2, TTC9, TTN, UBE2G2, USP33, USP34, VAMP1, VILL, VIPR1, VPS13C, ZBED5, ZBTB25, ZBTB40, ZC3H3, ZFPI61, ZFP36L1, ZFP36L2, ZHX2, ZMYM5, ZNF136, ZNF148, ZNF318, ZNF350, ZNF512B, ZNF609, ZNF652, ZNF83, ZNF862, and ZNF91.

The gene set "Progressively up in memory differentiation" includes the following genes: MTCH2, RAB6C, KIAA0195, SETD2, C2orf24, NRD1, GNA13, COPA, SELT, TNIP1, CBFA2T2, LRP10, PRKCI, BRE, ANKS1A, PNPLA6, ARL6IP1, WDFY1, MAPK1, GPR153, SHKBP1, MAP1LC3B2, PIP4K2A, HCN3, GTPBP1, TLN1, C4orf34, KIF3B, TCIRG1, PPP3CA, ATG4D, TYMP, TRAF6, C17orf76, WIPF1, FAM108A1, MYL6, NRM, SPCS2, GGT3P, GALKI, CLIP4, ARL4C, YWHAQ, LPCAT4, ATG2A, IDS, TBC1D5, DMPK, ST6GALNAC6, REEP5, ABHD6, KIAA0247, EMB, TSEN54, SPIRE2, PIWIL4, ZSCAN22, ICAM1, CHD9, LPIN2, SETD8, ZC3H12A, ULBP3, IL15RA, HLA-DQB2, LCP1, CHP, RUNX3, TMEM43, REEP4, MEF2D, ABL1, TMEM39A, PCBP4, PLCD1, CHST12, RASGRP1, C1orf58, C11orf63, C6orf129, FHOD1, DKFZp434F142, PIK3CG, ITPR3, BTG3, C4orf50, CNNM3, IFI16, AK1, CDK2AP1, REL, BCL2L1, MVD, TTC39C, PLEKHA2, FKBP11, EML4, FANCA, CDCA4, FUCA2, MFSD10, TBCD, CAPN2, IQGAP1, CHST11, PIK3R1, MYOSA, KIR2DL3, DLG3, MXD4, RALGD5, S1PR5, WSB2, CCR3, TIPARP, SP140, CD151, SOX13, KRTAP5-2, NF1, PEA15, PARP8, RNF166, UEVLD, LIMK1, CACNB1, TMX4, SLC6A6, LBA1, SV2A, LLGL2, IRF1, PPP2R5C, CD99, RAPGEF1, PPP4R1, OSBPL7, FOXP4, SLA2, TBC1D2B, ST7, JAZF1, GGA2, PI4K2A, CD68, LPGAT1, STX11, ZAK, FAM160B1, RORA, C8orf80, APOBEC3F, TGFBI, DNAJC1, GPR114, LRP8, CD69, CMIP, NAT13, TGFB1, FLJ00049, ANTXR2, NR4A3, IL12RB1, NTNG2, RDX, MLLT4, GPRIN3, ADCY9, CD300A, SCD5, ABI3, PTPN22, LGALS1, SYTL3, BMPR1A, TBK1, PMAIP1, RASGEF1A, GCNT1, GABARAPL1, STOM, CALHM2, ABCA2, PPP1R16B, SYNE2, PAM, C12orf75, CLCF1, MXRA7, APOBEC3C, CLSTN3, ACOT9, HIP1, LAG3, TNFAIP3, DCBLD1, KLF6, CACNB3, RNF19A, RAB27A, FADS3, DLG5, APOBEC3D, TNFRSF1B, ACTN4, TBKBP1, ATXN1, ARAP2, ARHGEF12, FAM53B, MAN1A1, FAM38A, PLXNC1, GRLF1, SRGN, HLA-DRB5, B4GALT5, WIPI1, PTPRJ, SLFN11, DUSP2, ANXA5, AHNAK, NEO1, CLIC1, EIF2C4, MAP3K5, IL2RB, PLEKHG1, MYO6, GTDC1, EDARADD, GALM, TARP, ADAM8, MSC, HNRPLL, SYT11, ATP2B4, NHSL2, MATK, ARHGAP18, SLFN12L, SPATS2L, RAB27B, PIK3R3, TP53INP1, MBOAT1, GYG1, KATNAL1, FAM46C, ZC3HAV1L, ANXA2P2, CTNNA1, NPC1, C3AR1, CRIM1, SH2D2A, ERN1, YPEL1, TBX21, SLC1A4, FASLG, PHACTR2, GALNT3, ADRB2, PIK3AP1, TLR3, PLEKHA5, DUSP10, GNAO1, PTGDR, FRMD4B, ANXA2, EOMES, CADM1, MAF, TPRG1, NBEAL2, PPP2R2B, PELO, SLC4A4, KLRF1, FOSL2, RGS2, TGFBR3, PRF1, MYO1F, GAB3, C17orf66, MICAL2, CYTH3, TOX, HLA-DRA, SYNE1, WEE1, PYHINI, F2R, PLD1, THBS1, CD58, FAS, NETO2, CXCR6, ST6GALNAC2, DUSP4, AUTS2, C1orf21, KLRG1, TNIP3, GZMA, PRR5L, PRDM1, ST8SIA6, PLXND1, PTPRM, GFPT2, MYBL1, SLAMF7, FLJ16686, GNLY, ZEB2, CST7, IL18RAP, CCL5, KLRD1, and KLRB1.

The gene set "Up TEM vs. Down TN" includes the following genes: MYOSA, MXD4, STK3, S1PR5, GLCCI1, CCR3, SOX13, KRTAP5-2, PEA15, PARP8, RNF166, UEVLD, LIMK1, SLC6A6, SV2A, KPNA2, OSBPL7, ST7, GGA2, PI4K2A, CD68, ZAK, RORA, TGFBI, DNAJC1, JOSD1, ZFYVE28, LRP8, OSBPL3, CMIP, NAT13, TGFB1, ANTXR2, NR4A3, RDX, ADCY9, CHN1, CD300A, SCD5, PTPN22, LGALS1, RASGEF1A, GCNT1, GLUL, ABCA2, CLDND1, PAM, CLCF1, MXRA7, CLSTN3, ACOT9, METRNL, BMPR1A, LRIG1, APOBEC3G, CACNB3, RNF19A, RAB27A, FADS3, ACTN4, TBKBP1, FAM53B, MAN1A1, FAM38A, GRLF1, B4GALT5, WIPI1, DUSP2, ANXA5, AHNAK, CLIC1, MAP3K5, ST8SIA1, TARP, ADAM8, MATK, SLFN12L, PIK3R3, FAM46C, ANXA2P2, CTNNA1, NPC1, SH2D2A, ERN1, YPEL1, TBX21, STOM, PHACTR2, GBP5, ADRB2, PIK3AP1, DUSP10, PTGDR, EOMES, MAF, TPRG1, NBEAL2, NCAPH, SLC4A4, FOSL2, RGS2, TGFBR3, MYO1F, C17orf66, CYTH3, WEE1, PYHINI, F2R, THBS1, CD58, AUTS2, FAM129A, TNIP3, GZMA, PRR5L, PRDM1, PLXND1, PTPRM, GFPT2, MYBL1, SLAMF7, ZEB2, CST7, CCL5, GZMK, and KLRB1.

Other gene sets describing similar processes and/or characteristics can also be used to characterize cell phenotypes described above.

Cell Ranger VDJ was used to generate single cell VDJ sequences and annotations for each single cell 5' library. Loupe Cell Browser software and Bioconductor packages were used for data analysis and visualization.

Results

This example aims to compare T cell states between purified T cells which served as input cells, CART cells manufactured using the ARM process (labeled as "Day 1" cells), and CART cells manufactured using the TM process (labeled as "Day 9" cells) using single-cell RNA-seq (scRNA-seq). In addition, single-cell TCR-seq (scTCR-seq) was performed to study clonality and track cell differentiation from input to post-manufacturing materials.

Figure 23C:
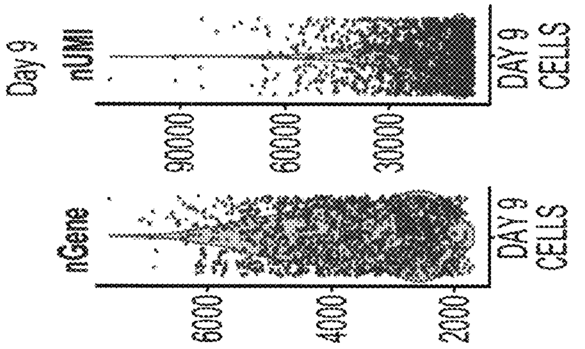
FIGS. 23A, 23B, and 23C: Single cell RNA-seq data for input cells (FIG. 23A), Day 1 cells (FIG. 23B), and Day 9 cells (FIG. 23C). The "nGene" graphs show the number of expressed genes per cell. The "nUMI" graphs show the number of unique molecular identifiers (UMIs) per cell.
Figure 23B:
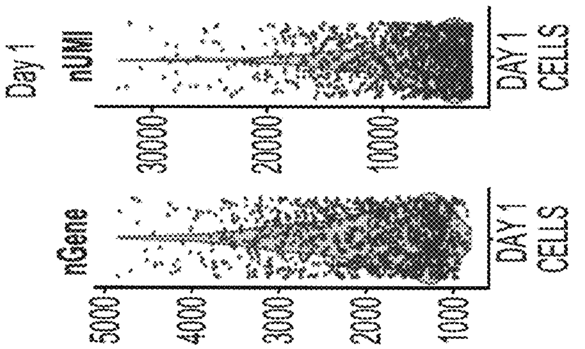
Figure 23A:
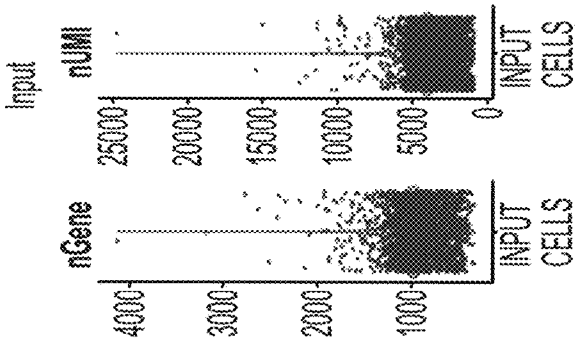
Figure 24A:
FIGS. 24A, 24B, 24C, and 24D: T-Distributed Stochastic Neighbor Embedding (TSNE) plots comparing input cells (FIG. 24A), Day 1 cells (FIG. 24B), and Day 9 cells (FIG. 24C) for a proliferation signature, which was determined based on expression of genes CCNB1, CCND1, CCNE1, PLK1, and MKI67. Each dot represents a cell in that sample. Cells shown as light grey do not express the proliferation genes whereas dark shaded cells express one or more of the proliferation genes.
Figure 24B:
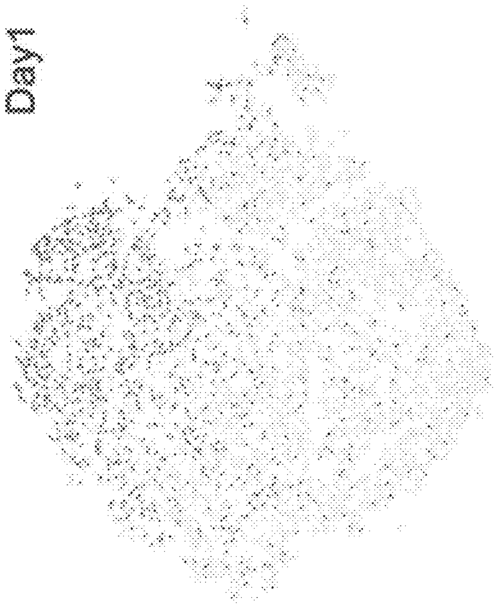
Figure 24C:
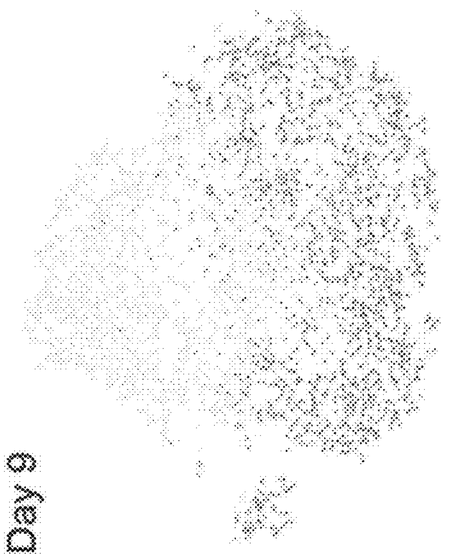
Figure 24D:
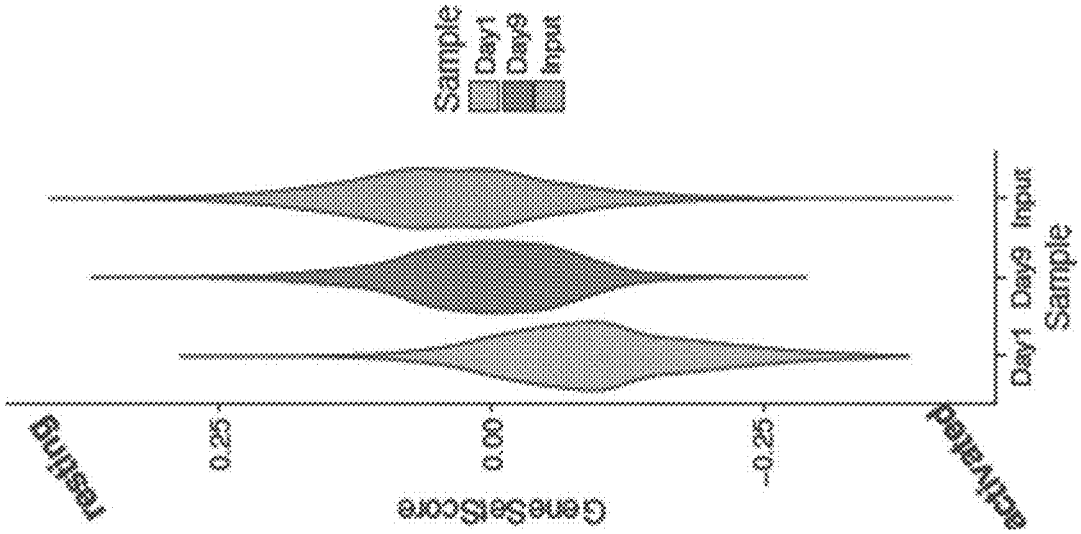

As shown in FIGS. 23A-23C, input cells had the fewest expressed genes and UMIs, suggesting these cells were not transcriptionally active and were in a resting state. Day 1 and Day 9 cells were expressing more genes, with Day 9 cells being the most transcriptionally active. Similar results are shown in FIGS. 24A-24D. Input cells were not expressing proliferation genes (FIGS. 24A and 24D).

Figure 25B:
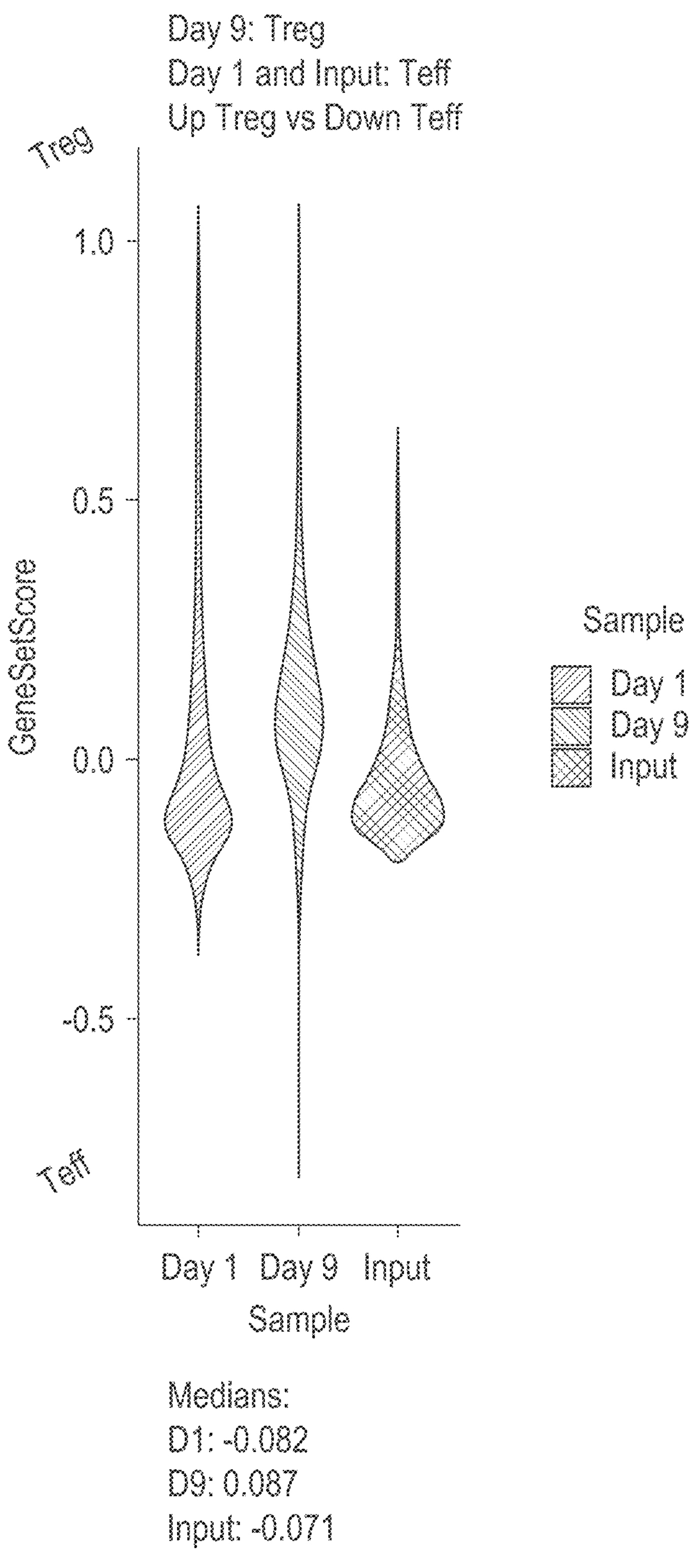
Figure 25C:
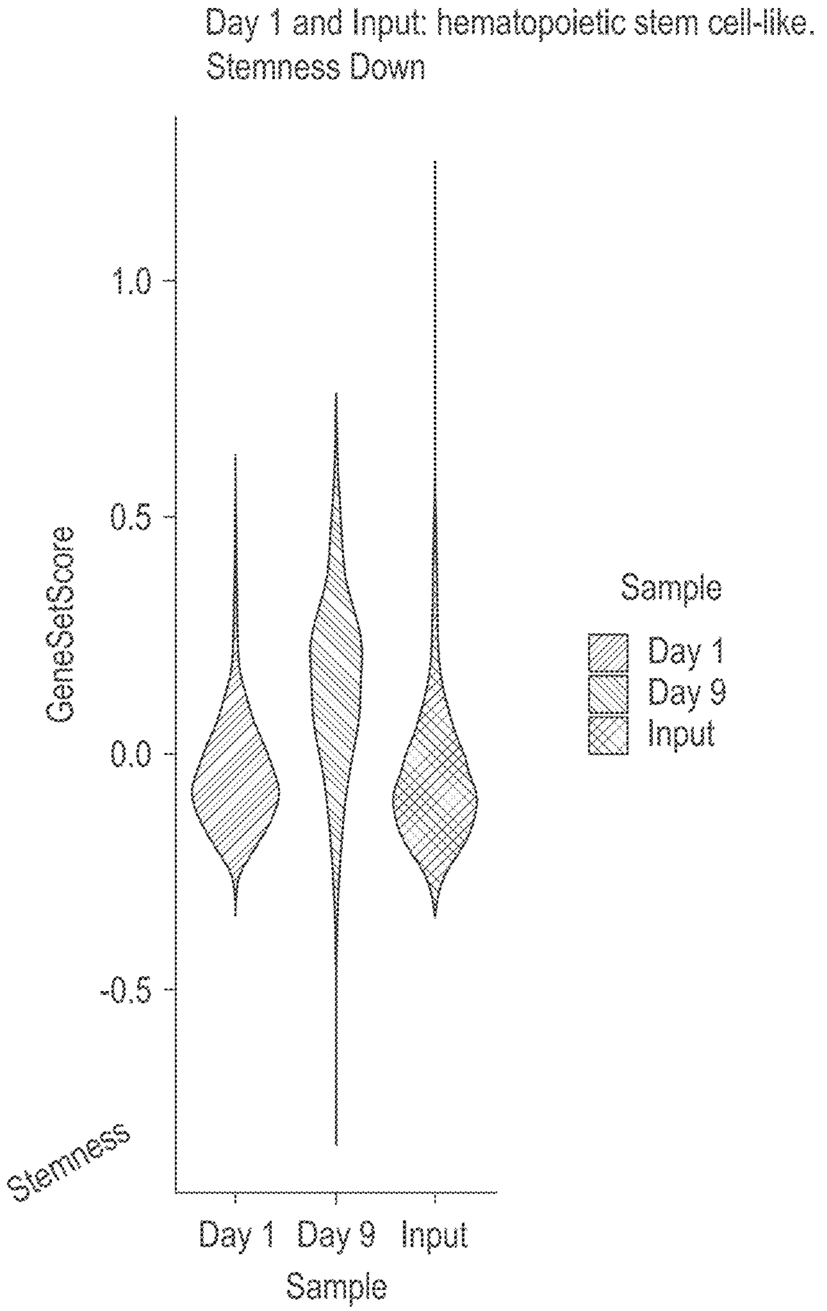

Additional gene set analysis data are shown in FIGS. 25A-25E. Different populations of cells were compared using the median gene set scores. Day 1 cells and input cells were in a younger, more stem-like memory state (FIGS. 25A-25C). In FIG. 25A, the median GeneSetScore (Up TEM vs. Down TSCM) values for Day 1 cells, Day 9 cells, and input cells are −0.084, 0.035, and −0.1, respectively. In FIG. 25B, the median GeneSetScore (Up Treg vs. Down Teff) values for Day 1 cells, Day 9 cells, and input cells are −0.082, 0.087, and −0.071, respectively. In FIG. 25C, the median GeneSetScore (Down stemness) values for Day 1 cells, Day 9 cells, and input cells are −0.062, 0.14, and −0.081, respectively.

Figure 25D:
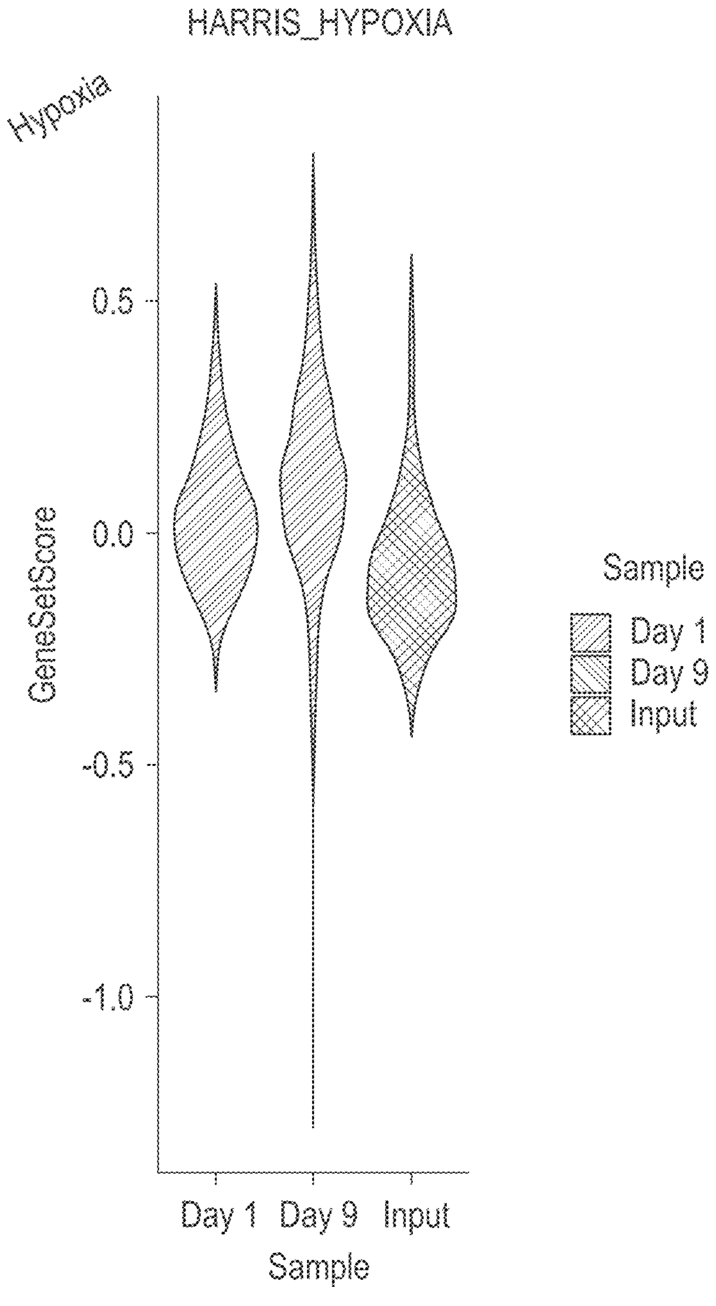
Figure 25E:
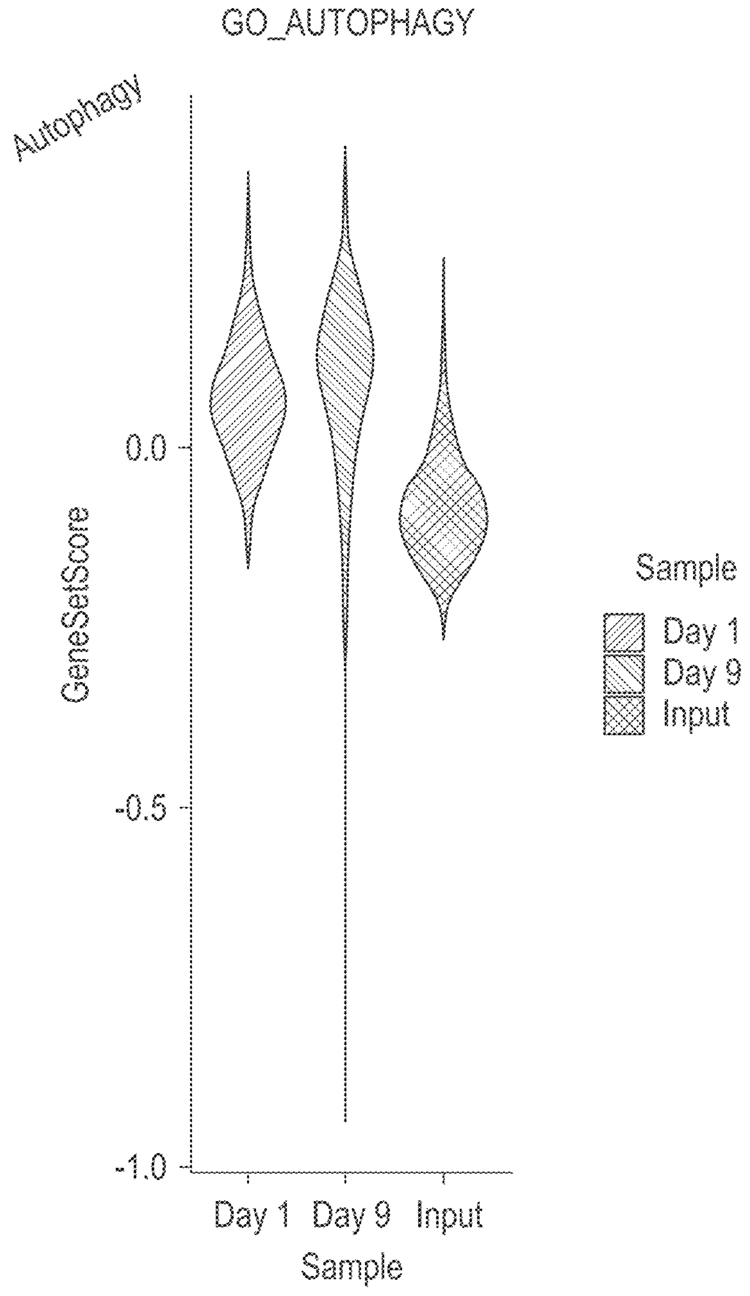

In addition, Day 1 cells were in a more ideal metabolic state compared to Day 9 cells (FIGS. 25D and 25E). In FIG. 25D, the median GeneSetScore (Up hypoxia) values for Day 1 cells, Day 9 cells, and input cells are 0.019, 0.11, and −0.096, respectively. In FIG. 25E, the median GeneSetScore (Up autophagy) values for Day 1 cells, Day 9 cells, and input cells are 0.066, 0.11, and −0.09, respectively.

Based on gene expression, the input cells contain four clusters. Cluster 0 is characterized by high expression of LMNA, S100A4, etc. Cluster 1 is characterized by high expression of RP913, PRKCQ-AS1, etc. Cluster 2 is characterized by high expression of PR11-291B21.2, CD8B, etc. Cluster 3 is characterized by high expression of NKG7, GZMH, CCL5, CST7, GNLY, FGFBP2, GZMA, CCL4, CTSW, CD8A, etc. In a T-Distributed Stochastic Neighbor Embedding (TSNE) plot for the input cells, Cluster 3 stood out from the other cells, and Cluster 1 and Cluster 2 were hard to differentiate.

Figure 26C:
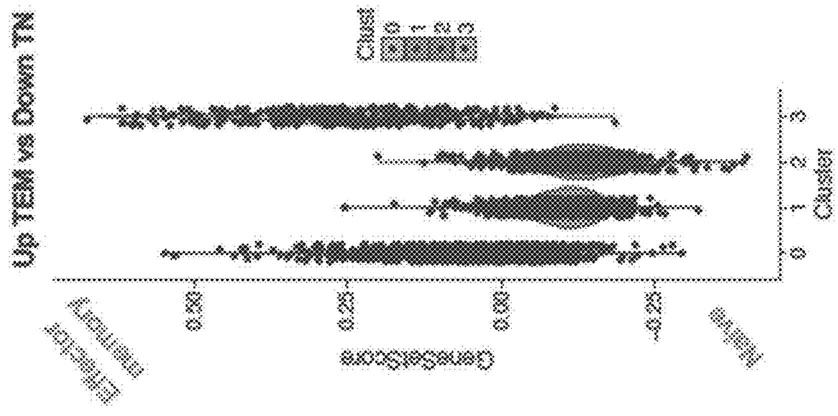
FIGS. 26A, 26B, and 26C: Gene cluster analysis for input cells.
Figure 26B:
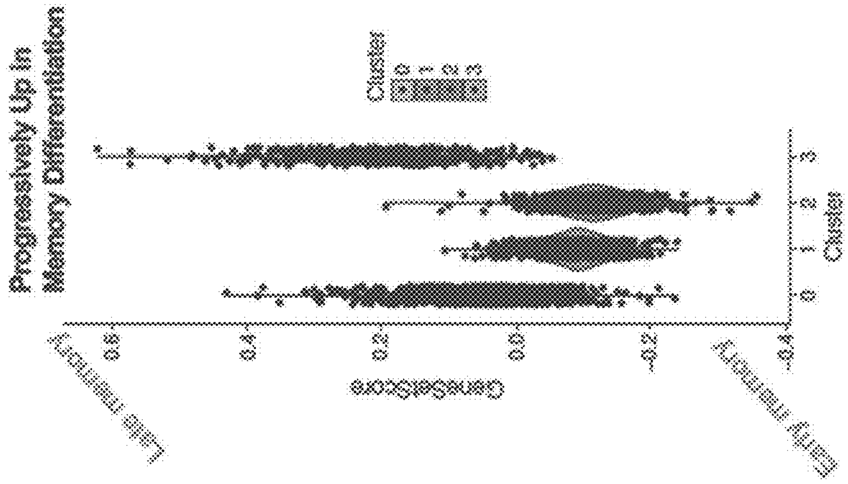
Figure 26A:
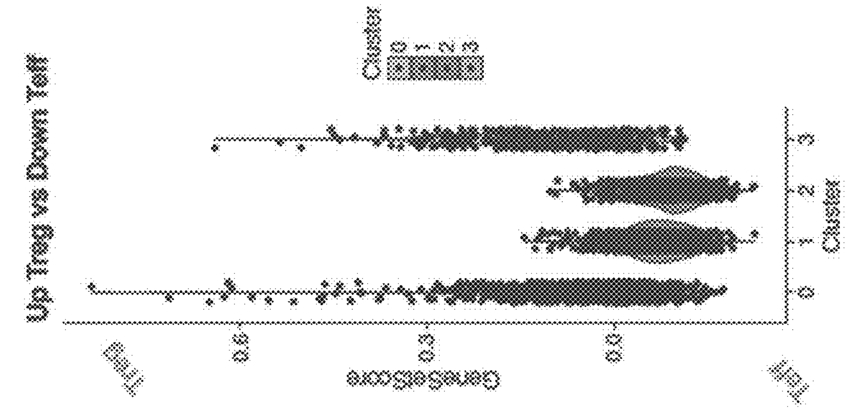

According to the gene set analysis shown in FIGS. 26A-26C, Cluster 0 and Cluster 3 were enriched for a T regulatory phenotype compared to Cluster 1 and Cluster 2 which were enriched for a T effector phenotype. Cluster 3 was dominated by late memory/effector memory (TEM) cells, Cluster 1 and Cluster 2 were early memory and naïve cells, and Cluster 0 is in the middle. The majority of the input cells were in an early memory, naïve state. Without wishing to be bound by theory, these cells may do the best during the manufacturing procedure.

Less transcriptional heterogeneity was seen in Day 1 cells and Day 9 cells (data not shown).

Like the input population, Day 1 cells showed a large cluster of early memory cells and a smaller cluster of late memory cells in a TSNE plot. Similar to what was seen with Cluster 3 of the input cells. In contrast, Day 9 cells did not show distinct clusters of early memory cells in a TSNE plot. This implies that by day 9, the cells had become more homogeneous.

Figure 27C:
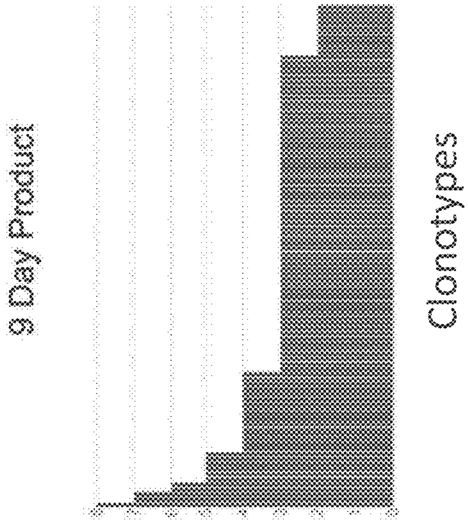
FIGS. 27A, 27B, and 27C: TCR sequencing and measuring clonotype diversity. Day 9 cells have flatter distribution of clonotype frequencies (higher diversity).
Figure 27B:
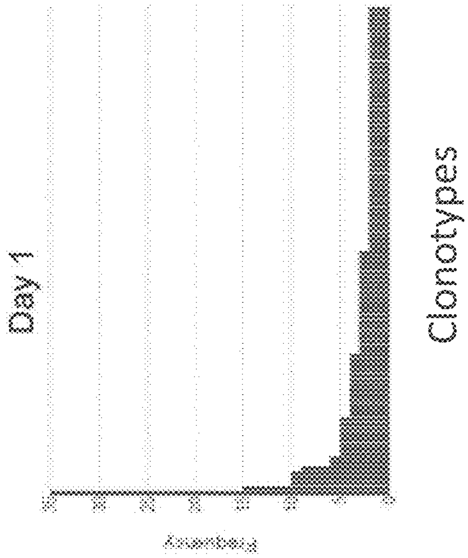
Figure 27A:
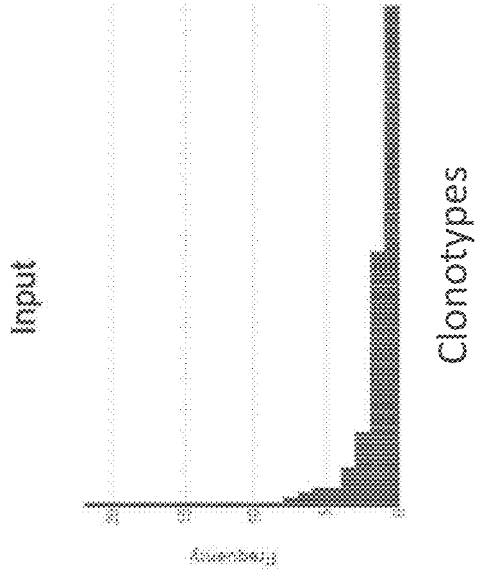

TCRs were sequenced and clonotype diversity was measured. Overall, the three clonotype profiles were very flat-most clones were only picked up once (FIGS. 27A-27C and Table 24). Shannon entropy in Table 24 measures the flatness of the distribution. The dominant clones in the input cells were late memory cells. Day 1 cells looked similar to the input cells but started to even out. By day 9, the dominate clones had substantially evened out and the distribution was much more flat. The diversity measurement was the highest at day 9 because there was a much more even and flat distribution in Day 9 cells than in the input cells or Day 1 cells.

TABLE 24

Measurements of TCR diversity

| | Input | Day 1 product | Day 9 product |
|---|---|---|---|
| Average clones per clonotype | 1.10 | 1.05 | 1.07 |
| Estimated number of cells | 7344 | 7687 | 7233 |
| Total number of clonotypes | 5325 | 7403 | 6736 |
| Diversity | 342.27 | 802.94 | 3382.62 |
| Normalized Shannon entropy | 9.98E−01 | 9.95E−01 | 9.96E−01 |

Summary

There were significant T cell state differences between Day 1 and Day 9 products. Day 1 cells were much more similar to input cells and had enrichment for stemness signatures, indicating a more efficacious product.

Example 9: Co-Transduction of BCMA CAR and CD19 CAR, Evaluation of MOI, and Efficacy Studies This example describes characterization of CART cells generated by co-transducing T cells with a lentiviral vector encoding a BCMA CAR and a lentiviral vector encoding a CD19 CAR. The BCMA CAR comprises the amino acid sequence of SEQ ID NO: 107 and the CD19 CAR comprises the amino acid sequence of SEQ ID NO: 225.

Cell Preparation and CAR Transduction

Four different MOI combinations of BCMA and CD19 CAR in transducing T cells were tested in a 24-well plate format. The BCMA CAR lentiviral vector and CD19 CAR lentiviral vector were used at MOIs of 5 and 1, respectively (5/1 in FIGS. 28A and 28B); 5 and 0.5, respectively (5/0.5 in FIGS. 28A and 28B); 2.5 and 1, respectively (2.5/1 in FIGS. 28A and 28B); or 2.5 and 0.5, respectively (2.5/0.5 in FIGS. 28A and 28B). T cells purified by Prodigy were seeded at $3e^6$/mL, 1 mL/well into 24-well plates and both BCMA and CD19 CAR vectors were added at different MOIs as indicated above. Upon seeding, TransAct (Miltenyi Biotec), a polymeric nanomatrix conjugated to anti-CD3 and anti-CD28 agonist, was added. Cells were incubated in OpTmizer complete T cell media containing 100 IU/mL human recombinant IL-2 (Prometheus, San Diego, CA) and 2% ICRS (Life Technologies) at 37° C. and 5% $CO_2$ for 24 hours prior to harvest.

Cells were then washed three times with 3× volume of PBS+1% HAS. After cultivation and harvest wash, viability and cell count were assessed to determine the impact of vector titration on the final product.

Cells were then re-cultured at $1\times10^6$ VNC/mL in a 24-well plate and incubated for 6 additional days. FACS analysis to assess anti-BCMA CAR expression was performed at days 4 and 7 post-transduction (3 and 6 days post-harvest).

CAR Expression Analysis

Samples were measured on a flow cytometer (BD LSR-Fortessa), and data were analyzed with FlowJo software. With ARM process, as CAR may not be fully integrated and expressed ex vivo within 24h, 96 h post viral addition could serve as a surrogate time point for in vitro and in vivo dosing strategy when the CAR is being stably expressed. The same strategy was adopted for dual targeting cocktail CAR measurements.

Figure 28A:
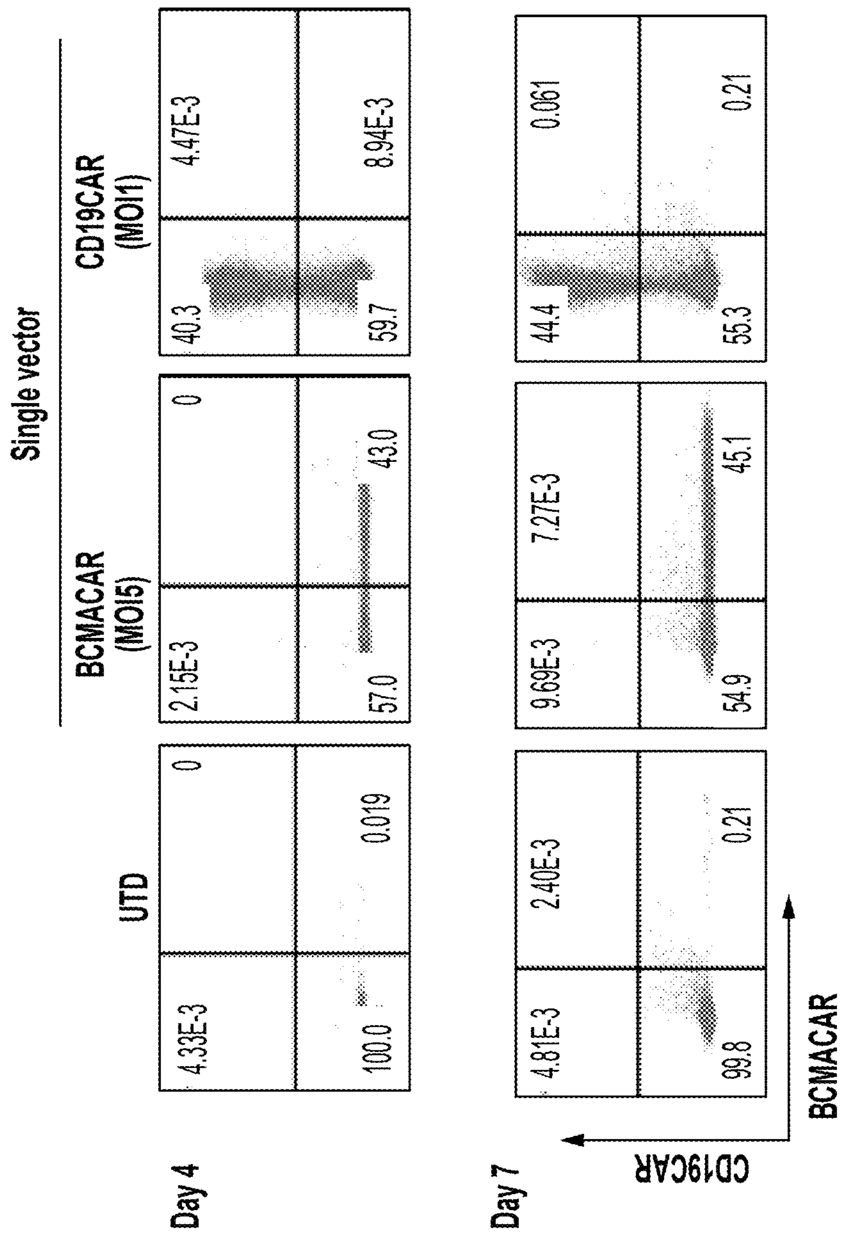
FIGS. 28A and 28B: Flow cytometry analyses for CAR expression on days 4 and 7 post-transduction. Flow cytometry analyses for CAR–T cells generated by co-transducing cells with BCMA and CD19CAR vectors at different combinations of MOIs with ARM process in a 24-well plate.
Figure 28A:
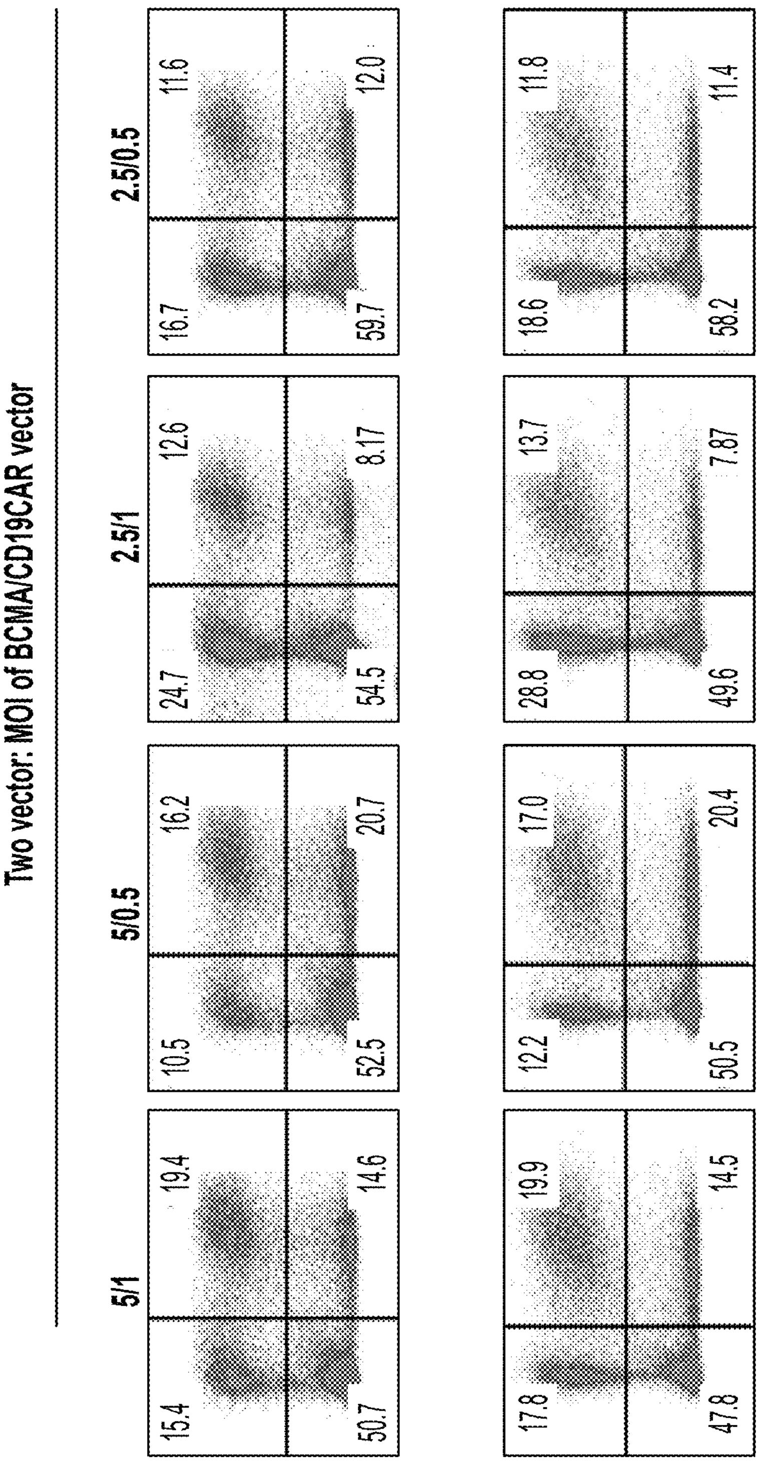
Figure 28B:
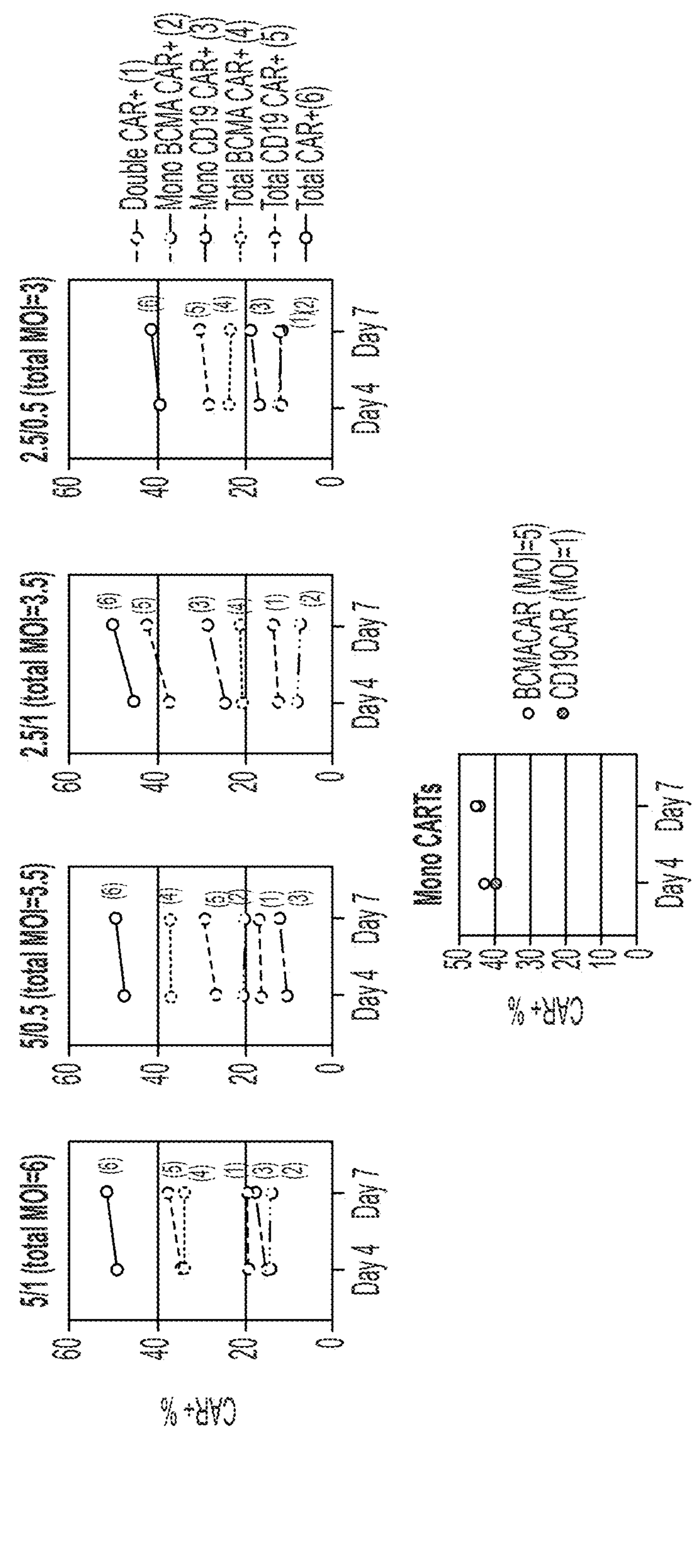

FACS analyses indicated that co-transduction of BCMA and CD19 CAR in T cells resulted in three distinct CAR+ subpopulations, and their proportions vary at the tested four different MOI combinations (FIG. 28A), indicating a cocktail CAR−T product could be successfully generated by co-transduction of BCMA and CD19 CAR. At an MOI of 5/0.5, mono anti-BCMA CAR+(anti-CD19 CAR negative) was highest with 20.7%, followed by double+ CAR at 16.2% and mono anti-CD19 CAR+at 10.5%. Total BCMA CAR+ calculated as double+ CAR % plus mono anti-BCMA CAR+ was 36.9%, while total CD19 CAR+ was 26.7% (FIGS. 28A and 28B). Both 2.5/0.5 and 2.5/1 MOI ratios resulted in much more mono CD19 CAR+% than double+% and mono anti-BCMA CAR+%. Moreover, double+ CAR % is positively correlated with total MOI usage (FIG. 28B). Total CAR+% is similar between MOI 5/1 and MOI 5/0.5. CAR expression in each population was observed to be relatively stable from day 4 to day 7 post-transduction, including BCMA or CD19 CAR transduced T cells (FIGS. 28A and 28B). Data was consistent among three donors. In some embodiments, a MOI 4-5 of BCMA CAR and a MOI 0.5 of CD19 CAR for co-transduction are used to generate dual targeting cocktail CART product.

In addition, large-scale run experiments were conducted entirely on the CliniMACS Prodigy from T cell enrichment, T cell seeding, activation, transduction and cultivation, to harvest washes in Centricult prior to formulation and cryopreservation. A MOI of 4/0.5 or 4.75/0.5 of BCMA/CD19CAR was used. This study used a seeding density of $3e^6$/mL in a total of 250 mL for $7.5e^8$ total cells. The cells were harvested at 24 hr, washed 3× with PBS+1% HAS and cryopreserved for downstream application. The remaining T cells were collected to generate respective control groups as UTD, BCMACART and CD19CART. An aliquot was taken and re-cultured at $1e^6$/mL in a 24 well plate for flow cytometry analyses to assess BCMA-CAR expression at day 4 post-transduction.

Figure 29:
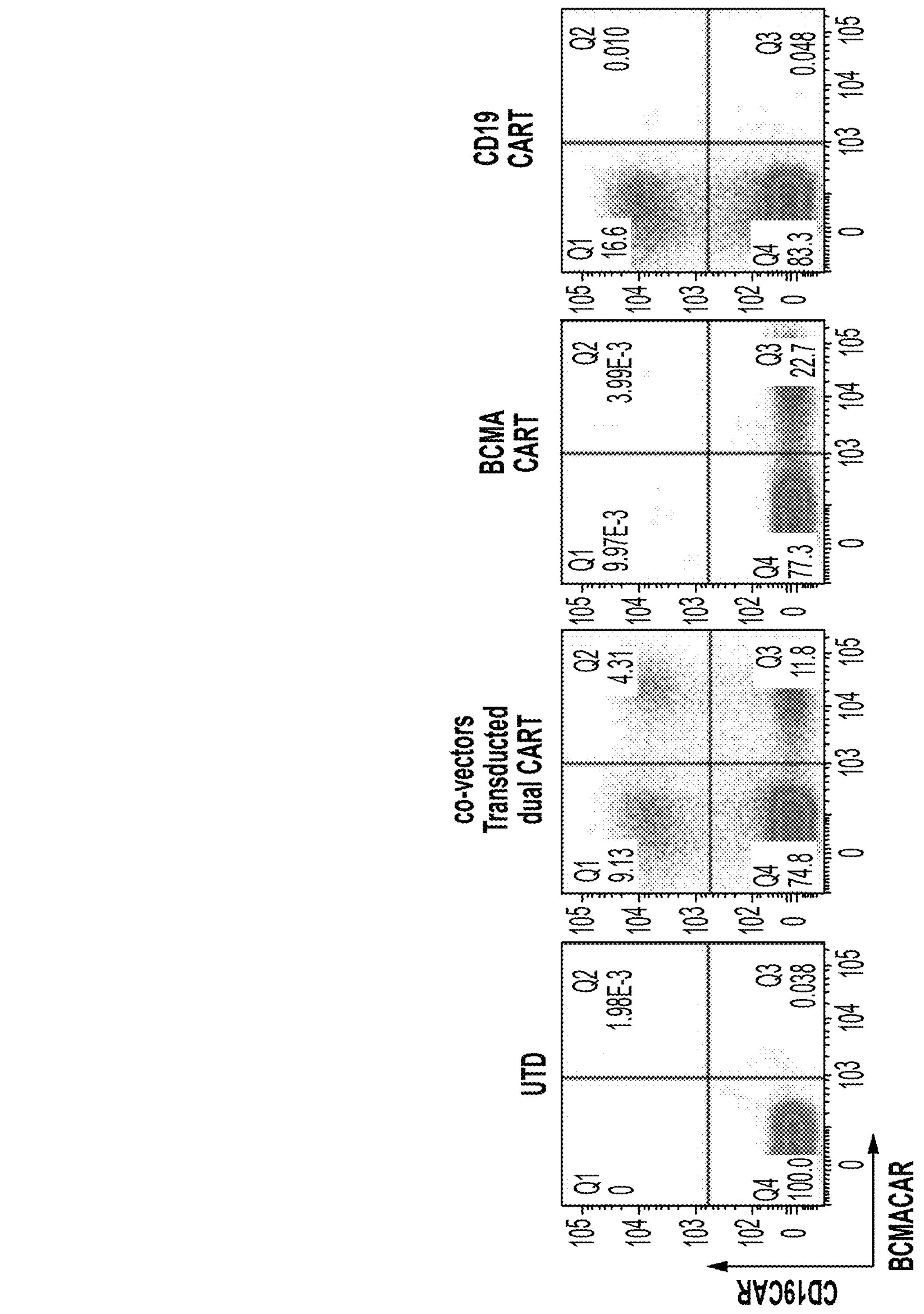
FIG. 29: Flow cytometry analyses for CAR expression on day 4 post-transduction. Flow cytometry analyses of final products of dual targeting cocktail CART, mono BCMACART and mono CD19CART for CAR expression on day 4 post-transduction. A small aliquots of each product at 24h harvest were re-cultured for three days prior to flow cytometry staining.

FIG. 29 showed that dual targeting cocktail CART contained 11.8% of mono anti-BCMA CART cells, 4.31% of double CART cells and ~9% of mono anti-CD19 CART cells on day 4 post-transduction. In this study, total anti-BCMA CAR+% calculated as double CAR+% plus mono anti-BCMA CAR+% was 16%; while total anti-CD19 CAR+% calculated as double CAR+% plus mono anti-CD19 CAR+% was 13.4%.

The dual cocktail CART in vivo activity was analyzed in three xenograft mouse models: 1) a KMS-11-luc model of multiple myeloma (this BCMA-expressing model is tagged with a luciferase reporter construct, which allows the disease to be monitored systemically in the bone marrow via bioluminescent imaging); 2) a mixed tumor model established by mixing 95% of KMS-11-luc myeloma cells with 5% of CD19+ tumors (e.g., Nalm-6-luc) to mimic heterogeneity of MM patients; and 3) a Nalm-6-luc model to evaluate the specificity of CD19 targeting and additional expansion of the double positive CART population of dual targeting cocktail CART. BCMACART and CD19CART served as controls for their respective models. For CAR−T cell dose calculation, the total anti-BCMA CAR+% was measured on day 4 post-transduction for models 1 and 2, while the total anti-CD19 CAR+% was measured on day 4 post-transduction for model 3. The UTD dose reflected the highest total T cell dose of the respective process.

Figure 30A:
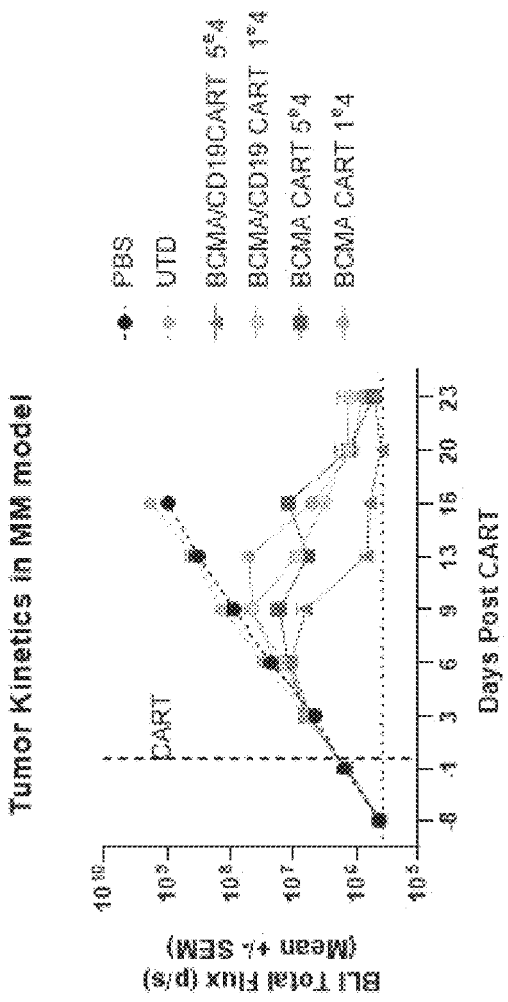
FIGS. 30A, 30B, 30C, 30D, and 30E: In vivo efficacy of dual CART compared to mono BCMA CART and CD19 CART in xenograft models. NSG mice were injected with cell lines expressing the luciferase reporter gene (KMS-11, or Nalm-6, or a mix of both with 5% of Nalm-6-luc). The tumor burden is expressed as total body luminescence (p/s), depicted as mean tumor burden+SEM. On day 7 or 8 post tumor inoculation, mice were treated with dual targeting cocktail CART, BCMA CART, or CD19 CART at the respective doses (approximate number of viable CAR+ T cells). Vehicle (PBS) and non-transduced T cells (UTD) served as negative controls. N=5 mice for all groups. BCMACART and CD19CART served as respective controls using the highest dose level. All experiments were terminated on day 23 after CAR–T administration.
Figure 30B:
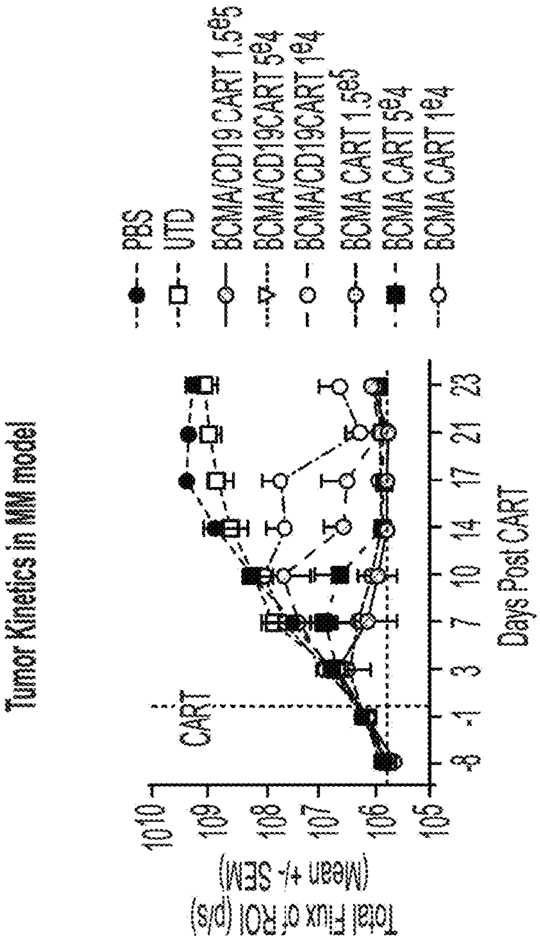

The tumor regression curves for all the groups in the three models are shown in FIGS. 30A-E. In the KMS-11-luc model, both dual targeting cocktail CART and BCMACART induced tumor regression in a dose-dependent manner as shown in FIG. 30A. At $1e^4$ dose, both dual targeting cocktail CART and BCMACART showed delayed tumor inhibition at similar pace, and both were able to clear tumor at the end of study. Dual targeting cocktail CART exhibited more effective tumor clearance than BCMACART at $5e^4$ dose, in which dual targeting cocktail CART cleared tumor by day 14 post CAR−T infusion, while BCMACART showed at least one-week delayed effect. In a repeated study by using the remaining cell products from the same batch, covering a wider dose ranges ($1e^4$, $5e^4$, $1.5e^5$) (FIG. 30B), dose dependency was confirmed in tumor regression by dual targeting cocktail CART. The regression curves of dual targeting cocktail CART at $1.5e^5$, $5e^4$ and BCMACART at $1.5e^5$ overlay. BCMACART at $5e^4$ was able to eliminate tumor by day 14 post CAR−T infusion in this cohort of mice, despite a slightly slower tumor regression than dual targeting cocktail CART at the same dose over the course of 14 days post CAR−T infusion. At $1e^4$ dose, dual targeting cocktail CART showed better efficacy than BCMACART. Briefly, using KMS-11-luc model, it was demonstrated that dual targeting cocktail CART was able to specifically target BCMA, shown to be as potent as BCMACART in killing BCMA+ multiple myeloma tumor, and was even more potent than BCMACART at lower doses.

Figure 30C:
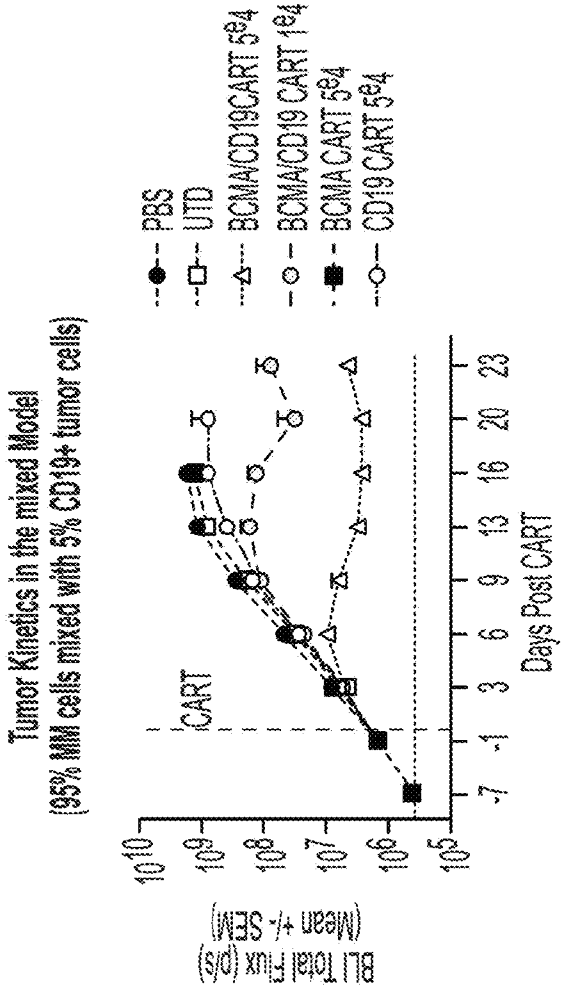
Figure 30D:
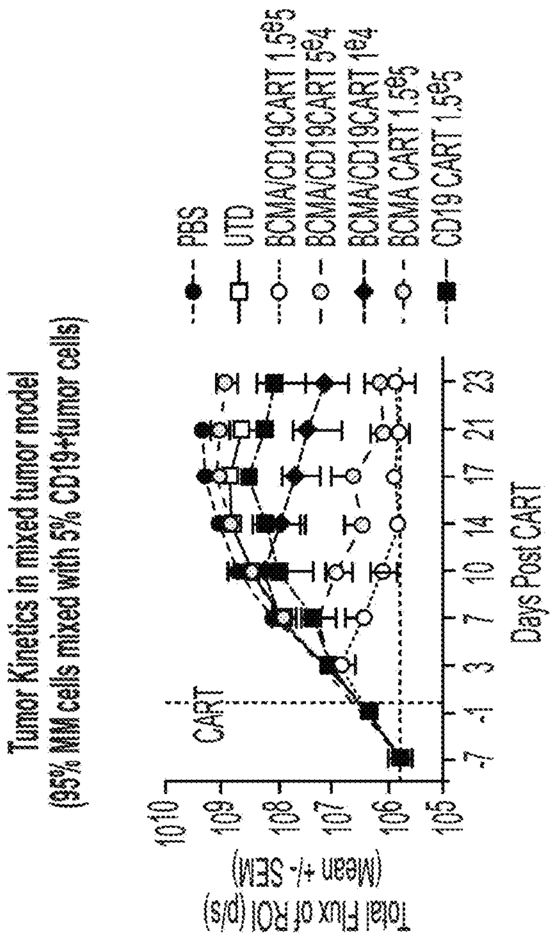

Next, the efficacy of dual targeting cocktail CART was evaluated when both BCMA and CD19 were present in a "mixed" model, where KMS-11-luc cells mixed with 5% of Naml-6-luc cells were implanted to mice. In the mixed tumor model as shown in FIG. 30C, only dual targeting cocktail CART at $5e^4$ and $1e^4$ demonstrated partial tumor inhibition in a dose dependent manner, while neither BCMACART nor CD19CART showed any effect at $5e^4$ dose. In a repeated study covering a higher dose group as shown in FIG. 30D, it was demonstrated that dual targeting cocktail CART at $1.5e^5$ was able to eliminate mixed tumors by day 14 post CAR−T infusion, and tumor suppression was dose dependent. In contrast, BCMACART and CD19CART at $1.5e^5$ only showed partial tumor inhibition in this mixed model when both BCMA and CD19 were present.

Figure 30E:
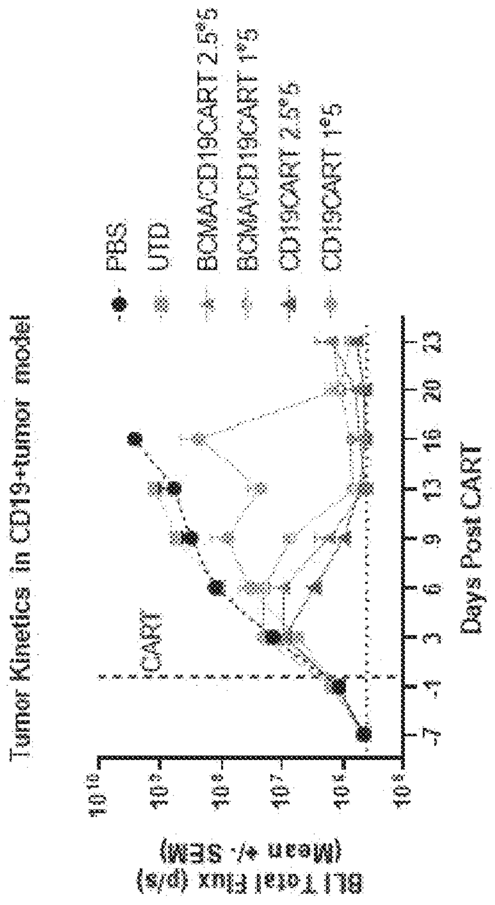

Last, Nalm-6-luc model was used to show if dual targeting cocktail CART could specifically target CD19+ tumor. As indicated in FIG. 30E, dual targeting cocktail CART was also able to eliminate Nalm-6-luc tumors in a dose dependent manner comparable to monoCD19CART at a higher dose and better than monoCD19CART at a lower dose.

Example 10: Evaluation of MOI for BCMA/CD19 CART Cellular Product Manufacturing

Figure 31:
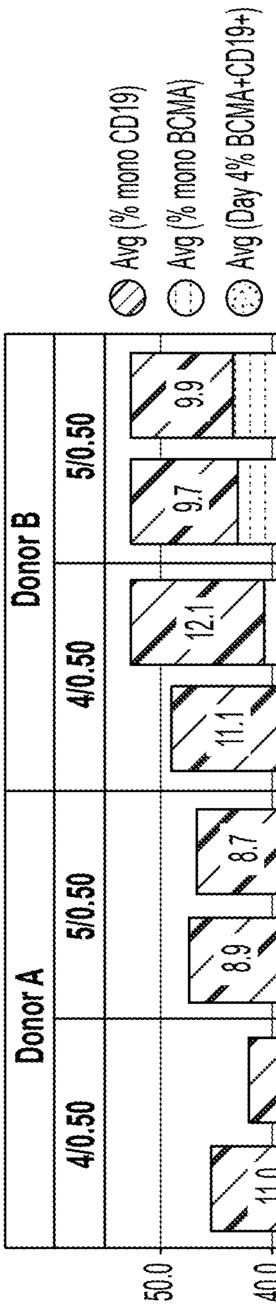
FIG. 31.

Based on the qPCR titer, a titration of the BCMA-CAR virus was performed to determine the optimum vector ratio of BCMA-CAR/CD19-CAR. Briefly, the T cells were thawed and resuspended at a density of $3\times10^6$ VNCs/mL or $6\times10^6$ VNCs/mL. For each MOI tested, 1 mL of the cell suspension was plated in a 24-well plate, transduced at time 0, and incubated for 20-24 hours. Each 1 mL culture was then manually washed with 3×2 mL of PBS+1% HSA. After cultivation and harvest wash, viability and cell count were assessed to determine the impact of the vector titration on final product. Harvested cells were then placed into culture at $1\times10^6$VNCs/mL and CAR (BCMA and CD19) expression were measured 72 hours and 144 hours post-harvest (Day 3 and Day 6 post-harvest (PH) (Day 4 and Day 7 post transduction) Table 34 and FIG. 31).

TABLE 34

Transduction of BCMA/CD19 dual CART cellular product GMP Vector Titration

| Donor ID | Day 0 seeding density (VNC/mL) | MOI (TU/cell) BCMA-CAR/ CD19-CAR | % CAR (Total BCMA-CAR = mono BCMA population + double BCMA/CD19 CAR population) Day 3 PH | Day 6 PH | % mono CD19 CAR Day 3 PH | Day 6 PH |
|---|---|---|---|---|---|---|
| Donor A | 3e6 | 4/0.5 | 34.4 | 40.6 | 11.0 | 14.4 |
| | | 5/0.5 | 38.3 | 49.1 | 8.9 | 12.1 |
| | 6e6 | 4/0.5 | 32.6 | 40.7 | 9.4 | 13.3 |
| | | 5/0.5 | 38.1 | 47.8 | 8.7 | 11.7 |
| Donor B | 3e6 | 4/0.5 | 38.0 | 47.9 | 11.1 | 14.9 |
| | | 5/0.5 | 40.6 | 52.9 | 9.7 | 12.6 |
| | 6e6 | 4/0.5 | 40.6 | 51.2 | 12.1 | 16.7 |
| | | 5/0.5 | 43.0 | 55.9 | 9.9 | 13.6 |

In some embodiments, the total number of BCMA CAR+ viable T cells, measured by flow cytometry, 4 days post transduction (or 3 days post-harvest) is used for dose related calculations. In some embodiments, T cells are seeded at a density of about 4e6 VNC/mL in CentriCult. In some embodiments, the BCMA CAR vector is used at a MOI of 4.75 and the CD19 CAR vector is used at a MOI of 0.5.

Figure 32:
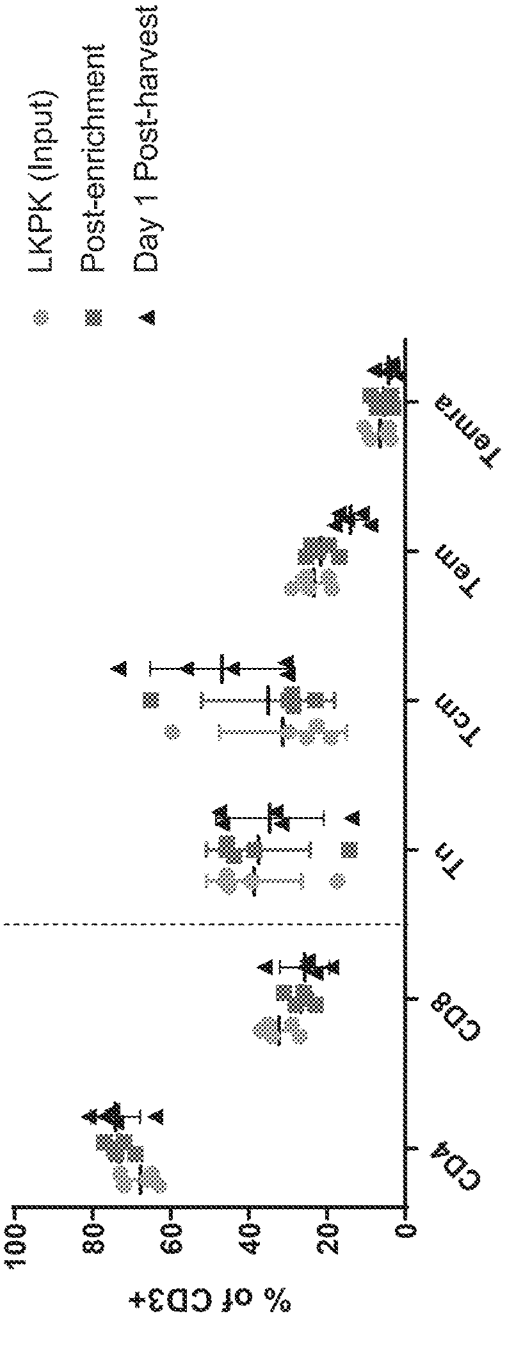
FIG. 32: Characterization of T cell subsets.

In a separate study, BCMA/CD19 CART cells were manufactured using the co-transduction rapid manufacturing approach described above at a large scale on an automated-closed system device, the CliniMACS Prodigy. Briefly, the process begins with the selection of T cells from a cryopreserved leukopak. T cells are positively selected using CD4 and CD8 microbeads. Post-selection, the T-cells are eluted into the reapplication bag and a sample is removed to assess cell concentration, viability and purity. T cells are than activated and transduced with a lentiviral vector encoding an anti-BCMA CAR and a lentiviral vector encoding an anti-CD19 CAR. As shown in FIG. 32, the T cell subsets from the output of the Prodigy did not differ from the input for the apheresis.

Example 11: Further Characterization of T Cells Engineered to Express an Anti-BCMA CAR and an Anti-CD19 CAR This example describes further characterization of the BCMA/CD19 CART cellular product that was generated as described in Example 9. This cellular product contains three different CAR+ populations: mono anti-BCMA CAR−T cells, mono anti-CD19 CAR−T cells, and double-positive anti-BCMA/anti-CD19 CAR−T cells. In addition, this cellular product also contains a population of untransduced T cells.

Plasma IFN-γ in BCMA/CD19 Dual CART Cellular Product Treated Mice

Figure 33A:
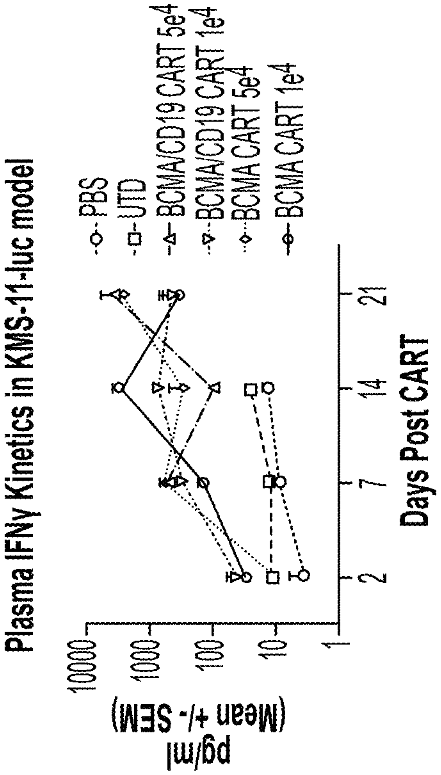
FIGS. 33A and 33B: Plasma IFN-γ Kinetics of BCMA/CD19 dual CART cellular product, BCMA CART, and CD19 CART treated mice. Animals were treated with PBS, UTD, BCMA/CD19 dual CART cellular product, BCMA CART, or CD19 CART at respective CAR–T doses. Mice were bled and plasma cytokine measured by MSD assay.
Figure 33B:
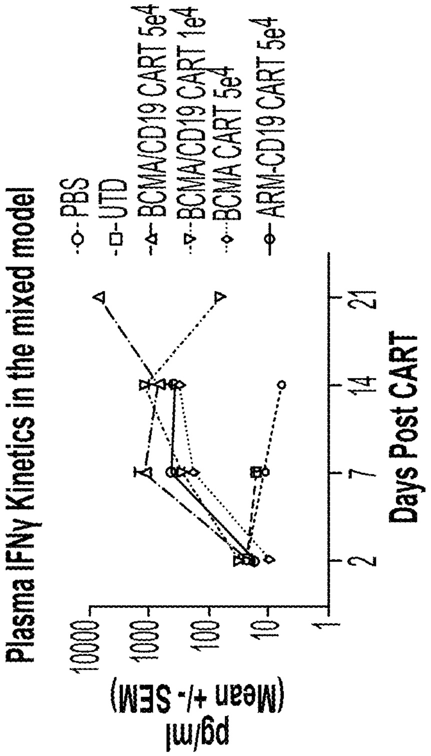

IFN-γ is a hallmark of CAR−T cell activation in response to target engagement. The kinetics of plasma IFN-γ was analyzed in the in vivo studies described in Example 9. As shown in FIGS. 33A and 33B, all CAR−T treated groups showed low levels of circulating IFN-γ (10-50 pg/ml) at day 2 and continued increasing IFN-γ secretion afterward.

Non-Clinical Pharmacokinetics and Metabolism

The expansion of the BCMA/CD19 dual CART cellular product in peripheral blood (including mono anti-BCMA, mono anti-CD19, or double-positive anti-BCMA/anti-CD19 CAR−T cells) was analyzed by flow cytometry up to 3 weeks after infusion, and compared to the benchmarked BCMA CART in the KMS-11-luc model. Both CD3+ T cell and CAR+ T cell expansion were observed in all CAR−T treatment groups. Dose-dependent cellular expansion was observed for the BCMA/CD19 dual CART cellular product in dual or mono CAR+ T cell populations. Based on data from two studies, the BCMA/CD19 dual CART cellular product showed slightly higher expansion of BCMA targeting CAR+ T cells and total CAR+ T cells as compared to BCMA CART.

Antigen dependent expansion of the BCMA/CD19 dual CART cellular product was demonstrated by assessing expansion of CAR+ T cells in three models (KMS-11, Nalm-6, and mixed). In the BCMA expressing KMS-11 xenograft model, double-positive anti-BCMA/anti-CD19 and mono anti-BCMA CAR+ T cells expanded extensively, while in CD19 expressing Nalm-6 xenograft model, double-positive anti-BCMA/anti-CD19 and mono anti-CD19 CAR+ T cells expanded extensively. The double-positive CAR−T cell population was able to expand with activation from either BCMA or CD19 antigen alone. The initial expansion rates of double-positive anti-BCMA/anti-CD19 and mono anti-BCMA CAR+ T cells were comparable in the KMS-11 model, as were those of the double-positive CAR and mono anti-CD19 CAR+ T cells in the Nalm-6 model.

Conclusions

The BCMA/CD19 dual CART cellular product is a novel anti-BCMA and anti-CD19 dual-targeting CAR−T cell product generated using a rapid manufacturing process, which preserves T-cell stemness.

In the three xenograft mice models (KMS-11, Nalm-6, and mixed), the BCMA/CD19 dual CART cellular product demonstrated potent in vivo pharmacology by controlling tumor growth, inducing CAR−T expansion and cytokine production, in an antigen-dependent and dose-dependent manner.

Tumor elimination in the mixed model was achieved by using the dual-targeting BCMA/CD19 CART cellular product, with increased tumor regression in a dose dependent fashion. Neither mono BCMA CART nor mono CD19 CART showed tumor regression in the mixed model. In addition, the BCMA/CD19 dual CART cellular product showed extended CAR−T expansion in vivo while the double-positive CAR population expanded with activation from either BCMA or CD19 alone. In the KMS-11-luc-model for multiple myeloma, the BCMA/CD19 dual CART cellular product showed improvement in tumor growth control at the higher dose levels tested and better tumor growth control at the lower dose level tested compared with BCMA CART.

These results support the BCMA/CD19 dual CART cellular product as a dual-targeting CAR-T that may change clinical outcomes by addressing the potential contribution of BCMA-/CD19+ stem/progenitor cells to multiple myeloma relapse, potentially providing deeper and more durable responses than traditionally manufactured or single antigen BCMA-targeting CAR-T.

Example 12: Phase I Clinical Trial of Anti-BCMA CART Cells Manufactured Using the ARM Process This example describes an open-label, phase I study to assess the safety and tolerability of an anti-BCMA CART cell therapy that is manufactured using the ARM process in adult patients with relapsed and/or refractory multiple myeloma.

Primary outcome measures include: incidence and nature of Dose Limiting Toxicities (DLTs) during the first 28 days after anti-BCMA CAR-T cell administration, as well as incidence and severity of adverse events (AEs) and serious adverse events (SAEs), including changes in laboratory values, ECGs, and vital signs after anti-BCMA CAR-T cell administration.

Secondary outcome measures include: manufacture success rate (defined as number of subjects treated with planned target dose divided by total number of subjects treated), ORR (proportion of subjects with the best overall response (BOR) of sCR+CR+ VGPR+PR at Months 3 and 6, as determined by local investigator using the IMWG Criteria (Kumar et al., Lancet Oncol. 2016 August; 17(8):e328-e346, herein incorporated by reference in its entirety)), CRR (proportion of subjects with the BOR of sCR+CR at Month 3, as determined by local investigator using the IMWG Criteria), DOR as assessed by local investigator (the time from achievement of sCR+CR+ VGPR+PR to relapse or death due to MM), qPCR-detected transgene of CART concentrations over time in peripheral blood and bone marrow, as well as summary of pre-existing and treatment induced immunogenicity (cellular and humoral) of BCMA CAR-T cell therapy.

Inclusion Criteria are as Follows:

- subjects with MM who are relapsed and/or refractory to at least 2 prior treatment regimens, including an IMiD (e.g. lenalidomide or pomalidomide), a proteasome inhibitor (e.g. bortezomib, carfilzomib), and an approved anti-CD38 antibody (e.g. daratumumab), if available, and have documented evidence of disease progression (IMWG criteria);
- measurable disease as defined by the protocol;
- ECOG performance status that is either 0 or 1 at screening;
- adequate hematological values; and
- must have a leukapheresis material of nonmobilized cells accepted for manufacturing.

Exclusion Criteria are as Follows:

- prior administration of a genetically modified cellular product including prior BCMA CAR-T therapy. Patients who have received prior BCMA-directed bispecific antibodies or antibody-drug conjugates (ADC) are not excluded;
- autologous HSCT within 6 weeks prior to enrollment or any prior history of allogeneic hematopoietic stem cell transplant (HSCT);
- chemotherapy or any concomitant anti-cancer therapies (other than protocol prescribed lymphodepletion (LD) chemotherapy) within 2 weeks prior to apheresis;
- treatment with small molecule targeted antineoplastics within 2 weeks of apheresis collection or 5 half-lives whichever is shorter; and
- have received antibodies or immunotherapies (other than daratumumab) within 4 weeks prior to apheresis collection. Daratumumab within 3 weeks prior to apheresis collection.

Example 13: Evaluation of BCMA/CD19 Diabody CART

The efficacy of the CD19 antigen responsive element in the novel single chain diabody CARTs is evaluated using the NALM-6 luciferized model. $1\times10^6$ NALM-6 Luc cells are implanted through lateral tail vein injection on day −7 from CART dosing. Body weight is taken, and in vivo bioluminescent imaging (BLI) is performed to evaluate tumor progression twice a week. Animals are measured twice a week, and once tumor burden reaches $3\times10^6$ photon flux (photons/second), animals are randomized to their particular group (day−1). On day 0, the diabody CAR-Ts are removed from liquid nitrogen and defrosted for injection. $1\times10^6$ double CAR positive cells are injected through the lateral tail vein. Experimental evaluation is conducted over the course of several weeks to determine which construct has the best functional efficacy by evaluating the decrease in BLI over time.

EQUIVALENTS

The disclosures of each and every patent, patent application, and publication cited herein are hereby incorporated herein by reference in their entirety. While this invention has been disclosed with reference to certain embodiments, it is apparent that further embodiments and variations of this invention may be devised by others skilled in the art without departing from the true spirit and scope of the invention. The appended claims are intended to be construed to include all such embodiments and equivalent variations.

What is claimed is:

1. An isolated cell or a population of cells comprising a polypeptide comprising:

(a) a first chimeric antigen receptor (CAR) comprising a first antigen-binding domain which binds to BCMA (a BCMA CAR) and a first transmembrane domain; a first intracellular signaling domain comprising a co-stimulatory signaling domain and a first primary signaling domain;

and (b) a second CAR comprising a second antigen-binding domain which binds to CD19 (a CD19 CAR) and a second transmembrane domain; a second intracellular signaling domain comprising a second co-stimulatory signaling domain; and a second primary signaling domain;

wherein the first CAR and the second CAR each comprise an HCDR1, HCDR2, HCDR3, LCDR1, LCDR2, and LCDR3 as recited in one of SEQ ID NO: 214, 216, 218, 220, or 222.

2. The isolated cell or population of cells of claim 1, wherein the first CAR is encoded by a first nucleic acid sequence and the second CAR is encoded by a second nucleic acid sequence, wherein the first and second nucleic acid sequences are disposed on a single nucleic acid molecule.

3. The isolated cell or population of cells of claim 2, wherein:

(a) the single nucleic acid molecule comprises the following configuration in a 5' to 3' orientation:

(i) a nucleic acid sequence encoding the first antigen-binding domain-a nucleic acid sequence encoding a first transmembrane domain-a nucleic acid sequence encoding a first intracellular signaling domain-a nucleic acid sequence encoding a linker-a nucleic acid sequence encoding the second antigen-binding domain-a nucleic acid sequence encoding a second transmembrane domain-a nucleic acid sequence encoding a second intracellular signaling domain; or (ii) a nucleic acid sequence encoding the second antigen-binding domain-a nucleic acid sequence encoding a second transmembrane domain-a nucleic acid sequence encoding a second intracellular signaling domain-a nucleic acid sequence encoding a linker-a nucleic acid sequence encoding the first antigen-binding domain-a nucleic acid sequence encoding a first transmembrane domain-a nucleic acid sequence encoding a first intracellular signaling domain;

(b) the single nucleic acid molecule comprises the nucleic acid sequence of SEQ ID NO: 215, 217, 219, 221, or 223, or a nucleic acid sequence having at least about 85%, 90%, 95%, or 99% sequence identity thereto; or (c) the single nucleic acid molecule encodes the amino acid sequence of SEQ ID NO: 214, 216, 218, 220, or 222, or an amino acid sequence having at least about 95%, or 99% sequence identity thereto.

4. The isolated cell or population of cells of claim 1, wherein the first antigen-binding domain or second antigen-binding domain comprises a VH and a VL, wherein the VH and VL are connected by a linker, and wherein the linker comprises the amino acid sequence of SEQ ID NO: 5, or an amino acid sequence having at least about 85%, 90%, 95%, or 99% sequence identity thereto.

5. The isolated cell or population of cells of claim 2, wherein:

(ii) the first transmembrane domain or second transmembrane domain comprises the amino acid sequence of SEQ ID NO: 6, or an amino acid sequence having at least about 85%, 90%, 95%, or 99% sequence identity thereto;

(iii) the first transmembrane domain or second transmembrane domain is encoded by the nucleic acid sequence of SEQ ID NO: 17, or a nucleic acid sequence having at least about 85%, 90%, 95%, or 99% sequence identity thereto;

(iv) the first antigen-binding domain is connected to the first transmembrane domain by a first hinge region or the second antigen-binding domain is connected to the second transmembrane domain by a second hinge region;

(v) the primary signaling domain comprises a functional signaling domain derived from a CD3 zeta, wherein;

(a) the primary signaling domain comprises the amino acid sequence of SEQ ID NO: 9 or 10, or an amino acid sequence having at least about 85%, 90%, 95%, or 99% sequence identity thereto; or (b) the primary signaling domain is encoded by the nucleic acid sequence of SEQ ID NO: 20, 21, or 205, or a nucleic acid sequence having at least about 85%, 90%, 95%, or 99% sequence identity thereto;

(vi) the costimulatory signaling domain comprises a functional signaling domain derived from 4-1BB (CD137); wherein:

(a) the costimulatory signaling domain comprises the amino acid sequence of SEQ ID NO: 7, or an amino acid sequence having at least about 85%, 90%, 95%, or 99% sequence identity thereto; or (b) the costimulatory signaling domain is encoded by the nucleic acid sequence of SEQ ID NO: 18 or 204, or a nucleic acid sequence having at least about 85%, 90%, 95%, or 99% sequence identity thereto;

(vii) the first intracellular signaling domain or second intracellular signaling domain comprises a functional signaling domain derived from 4-1BB and a functional signaling domain derived from CD3 zeta, wherein:

(a) the first intracellular signaling domain or second intracellular signaling domain comprises the amino acid sequence of SEQ ID NO: 7 (or an amino acid sequence having at least about 85%, 90%, 95%, or 99% sequence identity thereto) and the amino acid sequence of SEQ ID NO: 9 or 10 (or an amino acid sequence having at least about 85%, 90%, 95%, or 99% sequence identity thereto), or (b) the first intracellular signaling domain or second intracellular signaling domain comprises the amino acid sequence of SEQ ID NO: 7 and the amino acid sequence of SEQ ID NO: 9 or 10; or (viii) the first CAR further comprises a first leader sequence or second CAR further comprises a second leader sequence, wherein:

(a) the first or second leader sequence comprises the amino acid sequence of SEQ ID NO: 1, or an amino acid sequence having at least about 85%, 90%, 95%, or 99% sequence identity thereto; or (b) the first or second leader sequence is encoded by the nucleic acid sequence of SEQ ID NO: 199 or 210, or a nucleic acid sequence having at least about 85%, 90%, 95%, or 99% sequence identity thereto.

6. The isolated cell or population of cells of claim 2, wherein:

(a):

(i) the first leader sequence and the second leader sequence are encoded by different nucleic acid sequences;

(ii) the first hinge region and the second hinge region are encoded by different nucleic acid sequences;

(iii) the first transmembrane domain and the second transmembrane domain are encoded by different nucleic acid sequences; and/or (iv) the first intracellular signaling domain and the second intracellular signaling domain are encoded by different nucleic acid sequences;

(b):

(i) the first leader sequence and the second leader sequence comprise the same amino acid sequence, or comprise different amino acid sequences;

(ii) the first hinge region and the second hinge region comprise the same amino acid sequence, or comprise different amino acid sequences;

(iii) the first transmembrane domain and the second transmembrane domain comprise the same amino acid sequence, or comprise different amino acid sequences; and/or (iv) the first intracellular signaling domain and the second intracellular signaling domain comprise the same amino acid sequence, or comprise different amino acid sequences;

(c):

(i) the first leader sequence and the second leader sequence are encoded by nucleic acid sequences comprising SEQ ID NOs: 199 and 210, respectively, or a nucleic acid sequence having at least about 85%, 90%, 95%, or 99% sequence identity thereto, or SEQ ID NOs: 210 and 199, respectively, or a nucleic acid sequence having at least about 85%, 90%, 95%, or 99% sequence identity thereto;

(ii) the first hinge region and the second hinge region are encoded by nucleic acid sequences comprising SEQ ID NOs: 337 and 13, respectively, or a nucleic acid sequence having at least about 85%, 90%, 95%, or 99% sequence identity thereto; or SEQ ID NOs: 13 and 337, respectively, or a nucleic acid sequence having at least about 85%, 90%, 95%, or 99% sequence identity thereto;

(iii) the first transmembrane domain and the second transmembrane domain are encoded by nucleic acid sequences comprising SEQ ID NOs: 338 and 17, respectively, or a nucleic acid sequence having at least about 85%, 90%, 95%, or 99% sequence identity thereto; or SEQ ID NOs: 17 and 338, respectively, or a nucleic acid sequence having at least about 85%, 90%, 95%, or 99% sequence identity thereto;

(iv) the first costimulatory signaling domain and the second costimulatory signaling domain are encoded by nucleic acid sequences comprising SEQ ID NOs: 204 and 18, respectively, or a nucleic acid sequence having at least about 85%, 90%, 95%, or 99% sequence identity thereto; or SEQ ID NOs: 18 and 204, respectively, or a nucleic acid sequence having at least about 85%, 90%, 95%, or 99% sequence identity thereto; and/or (v) the first primary signaling domain and the second primary signaling domain are encoded by nucleic acid sequences comprising SEQ ID NOs: 205 and 21, respectively, or a nucleic acid sequence having at least about 85%, 90%, 95%, or 99% sequence identity thereto; or SEQ ID NOs: 21 and 205, respectively, or a nucleic acid sequence having at least about 85%, 90%, 95%, or 99% sequence identity thereto; or (d): the first CAR or second CAR is encoded by a nucleic acid molecule comprising a woodchuck hepatitis post-transcriptional regulatory element (WPRE).

7. An isolated nucleic acid molecule encoding a polypeptide, said nucleic acid molecule comprising:

(a) a first nucleic acid sequence encoding a first CAR comprising a first antigen-binding domain which binds to BCMA (a BCMA CAR) and a first transmembrane domain; a first intracellular signaling domain comprising a co-stimulatory signaling domain and a first primary signaling domain; and (b) a second nucleic acid sequence encoding a second CAR comprising a second antigen-binding domain which binds to CD19 (a CD19 CAR) and a second transmembrane domain; a second intracellular signaling domain comprising a second co-stimulatory signaling domain; and a second primary signaling domain;

wherein the first CAR and the second CAR each comprise an HCDR1, HCDR2, HCDR3, LCDR1, LCDR2, and LCDR3 as recited in one of SEQ ID NO: 214, 216, 218, 220, or 222;

and wherein the first nucleic acid sequence and the second nucleic acid sequence are disposed on a single nucleic acid molecule.

8. An isolated polypeptide, wherein the polypeptide comprises:

(a) a first CAR comprising a first antigen-binding domain which binds to BCMA (a BCMA CAR) and a first transmembrane domain; a first intracellular signaling domain comprising a co-stimulatory signaling domain and a first primary signaling domain; and (b) a second CAR comprising a second antigen-binding domain which binds to CD19 (a CD19 CAR) and a second transmembrane domain; a second intracellular signaling domain comprising a second co-stimulatory signaling domain; and a second primary signaling domain; and wherein the first CAR and the second CAR each comprise an HCDR1, HCDR2, HCDR3, LCDR1, LCDR2, and LCDR3 as recited in one of SEQ ID NO: 214, 216, 218, 220, or 222.

9. A vector comprising the nucleic acid molecule claim 7.

10. An isolated cell or a population of cells comprising the nucleic acid molecule of claim 7.

11. A method of making a cell comprising transducing a cell with the vector of claim 9.

12. A method of making an RNA-engineered cell comprising introducing an in vitro transcribed RNA or synthetic RNA into a cell, wherein the RNA comprises the nucleic acid molecule of claim 7.

13. A pharmaceutical composition comprising the cell or population of cells of claim 1, and a pharmaceutically acceptable carrier.

14. A population of cells engineered to express the polypeptide of claim 8, wherein the population comprises a cell comprising a nucleic acid molecule encoding the first CAR and the second CAR, and wherein:

the nucleic acid molecule comprises a first nucleic acid sequence encoding the first CAR and a second nucleic acid sequence encoding the second CAR, or the first and second nucleic acid sequences are disposed on a single nucleic acid molecule, wherein the first nucleic acid sequence and the second nucleic acid sequence are separated by a third nucleic acid sequence encoding a self-cleavage site.

15. The isolated cell of claim 3, wherein the linker comprises a self-cleavage site, and wherein the self-cleavage site comprises a P2A site, a T2A site, an E2A site, or an F2A site.

16. The isolated cell of claim 15, wherein:

(a) the linker is encoded by the nucleic acid sequence of SEQ ID NO: 209, or a nucleic acid sequence having at least about 85%, 90%, 95%, or 99% sequence identity thereto; or (b) the linker comprises the amino acid sequence of SEQ ID NO: 208, or an amino acid sequence having at least about 85%, 90%, 95%, or 99% sequence identity thereto.

17. The isolated cell of claim 5, wherein:

(a) the first hinge region or the second hinge region comprises the amino acid sequence of SEQ ID NO: 2, or an amino acid sequence having at least about 85%, 90%, 95%, or 99% sequence identity thereto;

(b) the first hinge region or the second hinge region is encoded by the nucleic acid sequence of SEQ ID NO: 13, or a nucleic acid sequence having at least about 85%, 90%, 95%, or 99% sequence identity thereto;

(c) the first hinge region and the first transmembrane domain or the second hinge region and the second transmembrane domain and the transmembrane domain comprise the amino acid sequence of SEQ ID NO: 202, or an amino acid sequence having at least about 85%, 90%, 95%, or 99% sequence identity thereto; or (d) the first hinge region and the first transmembrane domain or the second hinge region and the second transmembrane domain and the transmembrane domain are encoded by the nucleic acid sequence of SEQ ID NO: 203 or 213, or a nucleic acid sequence having at least about 85%, 90%, 95%, or 99% sequence identity thereto.

18. The isolated cell of claim 6, wherein:

(a) the first primary signaling domain and the second primary signaling domain are encoded by different nucleic acid sequences;

(b) the first costimulatory signaling domain and the second costimulatory signaling domain are encoded by different nucleic acid sequences;

(c) the first leader sequence and the second leader sequence comprise the amino acid sequence of SEQ ID NO: 1, or an amino acid sequence having at least about 85%, 90%, 95%, or 99% sequence identity thereto;

(d) the first hinge region and the second hinge region comprise the amino acid sequence of SEQ ID NO: 2, or an amino acid sequence having at least about 85%, 90%, 95%, or 99% sequence identity thereto;

(e) the first transmembrane domain and the second transmembrane domain comprise the amino acid sequence of SEQ ID NO: 6, or an amino acid sequence having at least about 85%, 90%, 95%, or 99% sequence identity thereto;

(f) the first primary signaling domain and the second primary signaling domain comprise the amino acid sequence of SEQ ID NO: 10, or an amino acid sequence having at least about 85%, 90%, 95%, or 99% sequence identity thereto; or (g) the first costimulatory signaling domain and the second costimulatory signaling domain comprise the amino acid sequence of SEQ ID NO: 7, or an amino acid sequence having at least about 85%, 90%, 95%, or 99% sequence identity thereto.

19. The vector of claim 9, wherein the vector is chosen from a DNA vector, a RNA vector, a plasmid, a lentivirus vector, an adenoviral vector, or a retrovirus vector.

20. The isolated nucleic acid molecule of claim 7, wherein the encoded polypeptide comprising the first CAR and the second CAR comprises the amino acid sequence of SEQ ID NO: 214, 216, 218, 220, 222, or an amino acid having at least 95%, 96%, 97%, 98%, or 99% identity thereto.

21. The isolated polypeptide of claim 8, wherein the polypeptide comprises the amino acid sequence of SEQ ID NO: 214, 216, 218, 220, 222, or an amino acid having at least 95%, 96%, 97%, 98%, or 99% identity thereto.

* * * * *